United States Patent
Abrignani et al.

(10) Patent No.: US 12,247,982 B2
(45) Date of Patent: Mar. 11, 2025

(54) MARKERS SELECTIVELY DEREGULATED IN TUMOR-INFILTRATING REGULATORY T CELLS

(71) Applicant: CheckMab S.R.L., Milan (IT)

(72) Inventors: Sergio Abrignani, Rapolano Terme (IT); Massimiliano Pagani, Trescore Balneario (IT)

(73) Assignee: CheckMab S.R.L., Milan (IT)

( * ) Notice: Subject to any disclaimer, the term of this patent is extended or adjusted under 35 U.S.C. 154(b) by 0 days.

(21) Appl. No.: 18/295,965

(22) Filed: Apr. 5, 2023

(65) Prior Publication Data

US 2023/0375555 A1 Nov. 23, 2023

Related U.S. Application Data

(63) Continuation of application No. 16/301,805, filed as application No. PCT/EP2017/061642 on May 15, 2017, now abandoned.

(30) Foreign Application Priority Data

May 16, 2016 (EP) .................................. 16169791
Nov. 14, 2016 (EP) .................................. 16198724

(51) Int. Cl.
| | | |
|---|---|---|
| *G01N 33/574* | (2006.01) | |
| *A61K 35/17* | (2015.01) | |
| *A61K 45/06* | (2006.01) | |
| *C07K 14/47* | (2006.01) | |
| *C07K 16/28* | (2006.01) | |
| *C07K 16/30* | (2006.01) | |
| *C12N 5/0783* | (2010.01) | |
| *C12N 15/113* | (2010.01) | |

(52) U.S. Cl.
CPC ....... *G01N 33/57492* (2013.01); *A61K 35/17* (2013.01); *A61K 45/06* (2013.01); *C07K 14/4748* (2013.01); *C07K 16/2866* (2013.01); *C07K 16/30* (2013.01); *C12N 5/0637* (2013.01); *C12N 15/1135* (2013.01); *C12N 15/1138* (2013.01); *C07K 2317/732* (2013.01); *C07K 2317/76* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| | | |
|---|---|---|
| 2008/0182250 A1 | 7/2008 | Zhao et al. |
| 2010/0292303 A1 | 11/2010 | Birrer et al. |
| 2019/0391152 A1 | 12/2019 | Abrignani et al. |

FOREIGN PATENT DOCUMENTS

| | | |
|---|---|---|
| WO | WO 1999/006561 A2 | 2/1999 |
| WO | WO 2004/003545 A1 | 1/2004 |
| WO | WO 2007/044756 A2 | 4/2007 |
| WO | WO 2009/100035 A2 | 8/2009 |
| WO | WO 2013/131010 A2 | 9/2013 |
| WO | WO 2015/017537 A2 | 2/2015 |

OTHER PUBLICATIONS

Bhairavabhotla et al., Transcriptome Profiling of Human FoxP3+ Regulatory T Cells. Hum Immunol. Feb. 2016; 77(2): 201-213. EPub Dec. 10, 2015. doi: 10.1016/j.humimm.2015.12.004.
Chan et al., Therapeutic antibodies for autoimmunity and inflammation. Nat Rev Immunol. May 2010;10(5):301-16. doi: 10.1038/nri2761.
Chen et al., Down-regulation of layilin, a novel hyaluronan receptor, via RNA interference, inhibits invasion and lymphatic metastasis of human lung A549 cells. Biotechnol Appl Biochem. Jun. 2008;50(Pt 2):89-96. doi: 10.1042/BA20070138.
De Simone et al., Transcriptional Landscape of Human Tissue Lymphocytes Unveils Uniqueness of Tumor-Infiltrating T Regulatory Cells. Immunity. Nov. 15, 2016;45(5):1135-1147. doi: 10.1016/j.immuni.2016.10.021.
Dixon et al., Functional Anti-TIGIT Antibodies Regulate Development of Autoimmunity and Antitumor Immunity. J Immunol. Apr. 15, 2018;200(8):3000-3007. doi: 10.4049/jimmunol.1700407. Epub Mar. 2, 2018.
Fehrenbacher et al., Atezolizumab versus docetaxel for patients with previously treated non-small-cell lung cancer (POPLAR): a multicentre, open-label, phase 2 randomised controlled trial. Lancet. Apr. 30, 2016;387(10030):1837-46. doi: 10.1016/S0140-6736(16)00587-0. Epub Mar. 10, 2016.
Guay et al., Stable inhibition of interleukin 1 receptor type II in Ishikawa cells augments secretion of matrix metalloproteinases: possible role in endometriosis pathophysiology. Reproduction. Sep. 2007;134(3):525-34. doi: 10.1530/REP-06-0377.
Janeway et al., The generation of diversity in immunoglobulins. Immunobiology: The Immune System in Health and Disease. 5th Editio. New York. Garland Science. 2001.
Lee et al., A Comprehensive Review on Current Advances in Peptide Drug Development and Design. Int J Mol Sci. May 14, 2019;20(10):2383. doi: 10.3390/ijms20102383.

(Continued)

*Primary Examiner* — Amy E Juedes
(74) *Attorney, Agent, or Firm* — Wolf, Greenfield & Sacks, P.C.

(57) ABSTRACT

The present invention discloses a number of markers selectively deregulated in tumor-infiltrating regulatory T cells. The invention relates to molecules able to modulate the expression and/or function of at least one such marker for use in the prevention and/or treatment of the tumor. Preferably the molecule specifically binds to the marker and induces antibody-dependent cell-mediated cytotoxicity (ADCC). The invention further relates to a molecule able to modulate the expression and/or function of at least one such marker for use in a method for in vivo depleting tumor-infiltrating regulatory T cell in a subject, or for use in a method to enhance tumor immunity in a subject. Corresponding pharmaceutical compositions are also contemplated.

1 Claim, 22 Drawing Sheets

Figure 1:
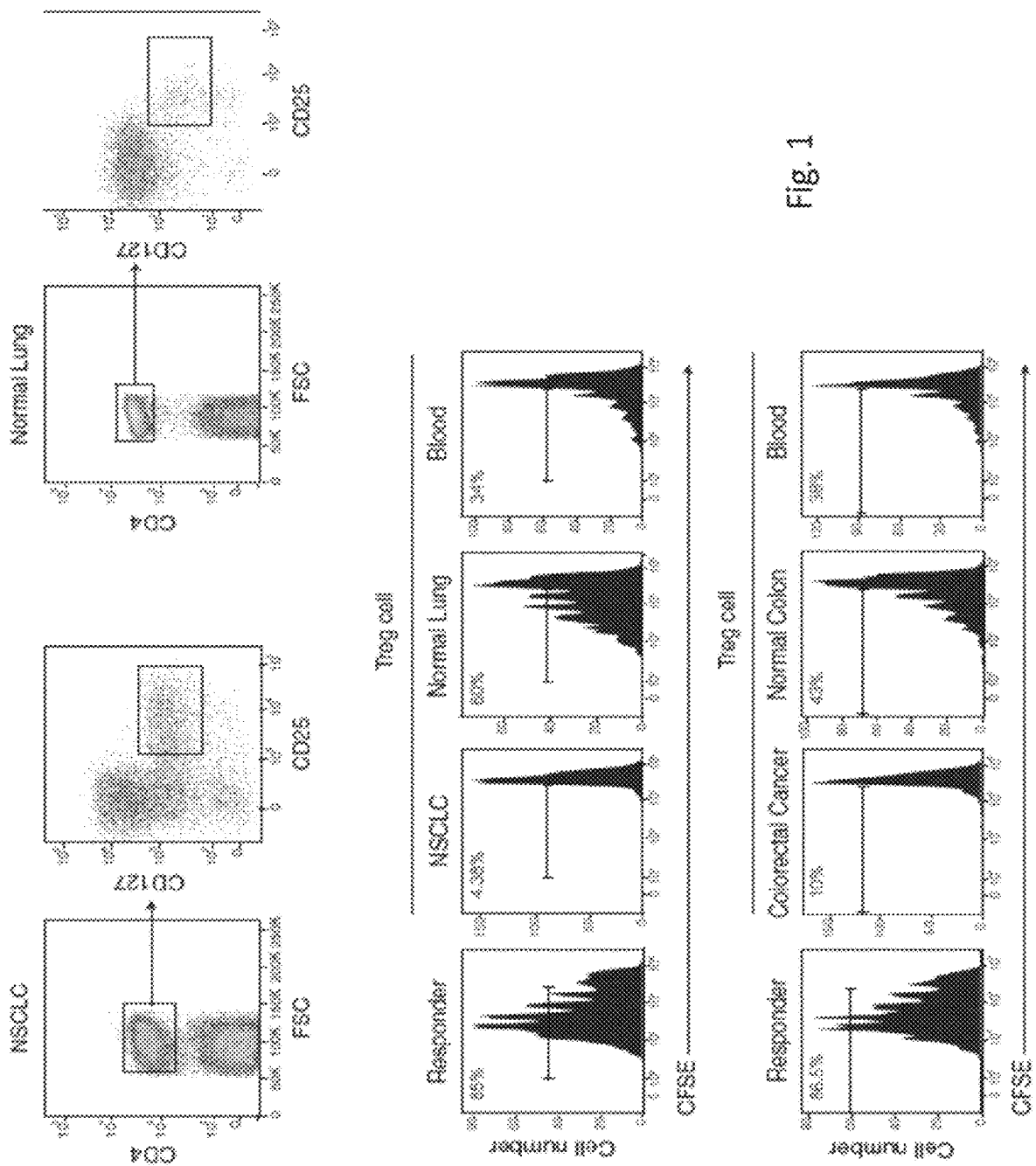
Figure 1:
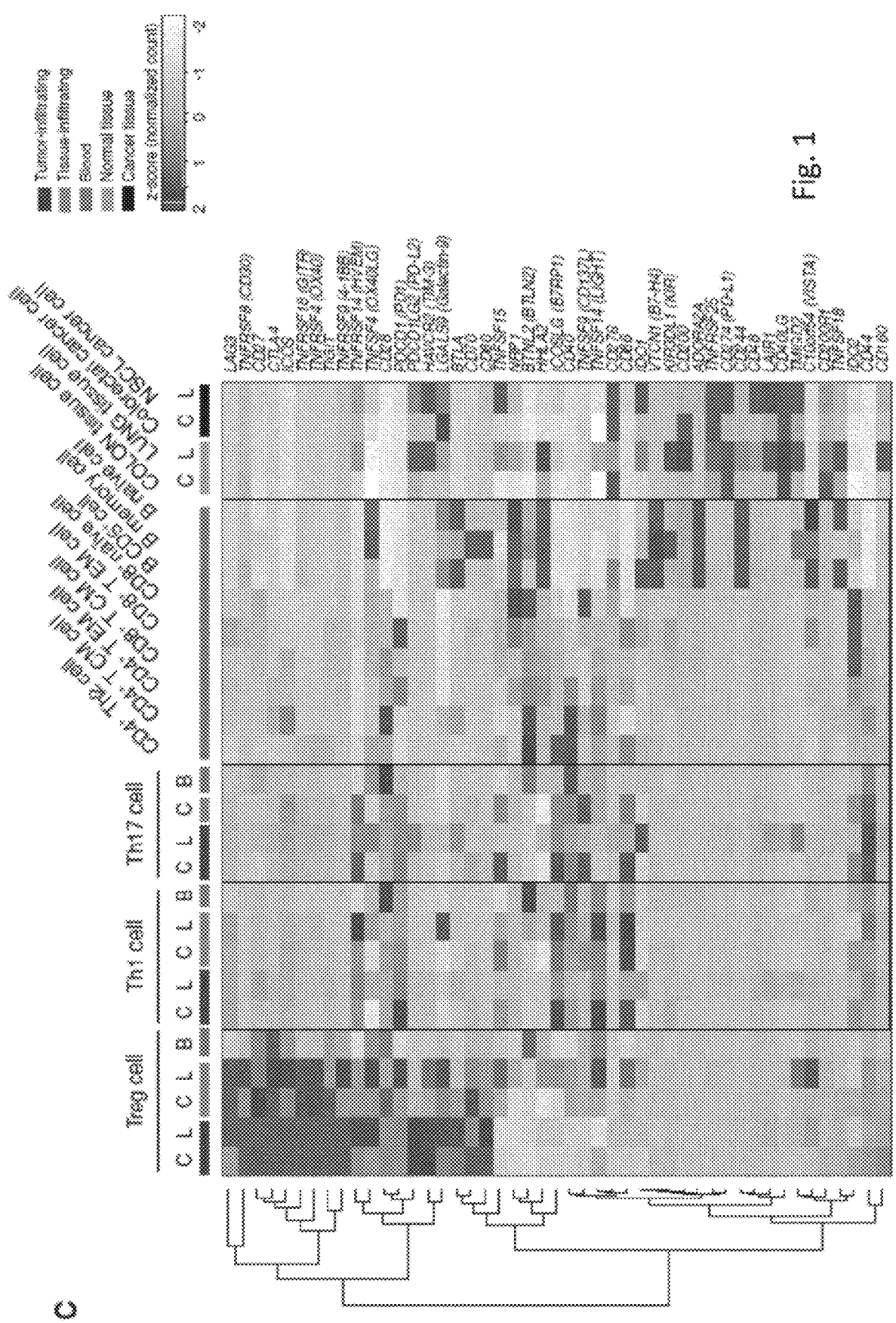

Specification includes a Sequence Listing.

(56) References Cited

OTHER PUBLICATIONS

Mahuron et al., Layilin augments integrin activation to promote antitumor immunity. J Exp Med. Sep. 7, 2020;217(9):e20192080. doi: 10.1084/jem.20192080.
Mar et al., Interleukin-1 Receptor Type 2 Acts with c-Fos to Enhance the Expression of Interleukin-6 and Vascular Endothelial Growth Factor A in Colon Cancer Cells and Induce Angiogenesis. J Biol Chem. Sep. 4, 2015;290(36):22212-24. doi: 10.1074/jbc.M115.644823. Epub Jul. 24, 2015.
Marabelle et al., Depleting tumor-specific Tregs at a single site eradicates disseminated tumors. J Clin Invest. Jun. 2013;123(6):2447-63. doi: 10.1172/JCI64859. Erratum in: J Clin Invest. Nov. 2013;123(11):4980.
Plitas et al., Abstract P4-04-11: Preferential expression of the chemokine receptor 8 (CCR8) on regulatory T cells (Treg) infiltrating human breast cancers represents a novel immunotherapeutic target. Cancer Res. Feb. 2016;76(4 Suppl):Abstract. doi: 10.1158/1538-7445.SABCS15-P4-04-11.
Plitas et al., Regulatory T Cells Exhibit Distinct Features in Human Breast Cancer. Immunity. Nov. 15, 2016;45(5):1122-1134. doi: 10.1016/j.immuni.2016.10.032.
Rabia et al., Understanding and overcoming trade-offs between antibody affinity, specificity, stability and solubility. Biochem Eng J. Sep. 15, 2018;137:365-374. doi: 10.1016/j.bej.2018.06.003. Epub Jun. 5, 2018.
Scott et al., Antibody therapy of cancer. Nat Rev Cancer. Mar. 22, 2012;12(4):278-87. doi: 10.1038/nrc3236.
Selby et al., Anti-CTLA-4 antibodies of IgG2a isotype enhance antitumor activity through reduction of intratumoral regulatory T cells. Cancer Immunol Res. Jul. 2013;1(1):32-42. doi: 10.1158/2326-6066.CIR-13-0013. Epub Apr. 7, 2013.
Sheng et al., Structure-based DNA-targeting strategies with small molecule ligands for drug discovery. Med Res Rev. Sep. 2013;33(5):1119-73. doi: 10.1002/med.21278. Epub Apr. 30, 2013.
Takeuchi et al., Roles of regulatory T cells in cancer immunity. Int Immunol. Aug. 2016;28(8):401-9. doi: 10.1093/intimm/dxw025. Epub May 9, 2016.
Tosolini et al., Clinical Impact of Different Classes of Infiltrating T Cytotoxic and Helper Cells (Th1, Th2, Treg, Th17) in Patients with Colorectal Cancer. Cancer Res. Feb. 2011;71(4):1263-1271. doi: 10.1158/0008-5472.CAN-10-2907.
Vargas et al., Fc-Optimized Anti-CD25 Depletes Tumor-Infiltrating Regulatory T Cells and Synergizes with PD-1 Blockade to Eradicate Established Tumors. Immunity. Apr. 18, 2017;46(4):577-586. doi: 10.1016/j.immuni.2017.03.013. Epub Apr. 11, 2017.
Whisstock et al., Prediction of protein function from protein sequence and structure. Q Rev Biophys. Aug. 2003;36(3):307-40. doi: 10.1017/s0033583503003901.
Arpaia et al., Distinct Function of Regulatory T Cells in Tissue Protection. Cell. Aug. 27, 2015;162(5):1078-89. doi: 10.1016/j.cell.2015.08.021.
Asano et al., Secretion of inflammatory factors from chondrocytes by layilin signaling. Biochem Biophys Res Commun. Sep. 12, 2014;452(1):85-90. doi: 10.1016/j.bbrc.2014.08.053. Epub Aug. 19, 2014.
Bindea et al., CluePedia Cytoscape plugin: pathway insights using integrated experimental and in silico data. Bioinformatics. Mar. 1, 2013;29(5):661-3. doi: 10.1093/bioinformatics/btt019. Epub Jan. 16, 2013.
Bindea et al., Spatiotemporal dynamics of intratumoral immune cells reveal the immune landscape in human cancer. Immunity. Oct. 17, 2013;39(4):782-95. doi: 10.1016/j.immuni.2013.10.003.
Bolger et al., Trimmomatic: a flexible trimmer for Illumina sequence data. Bioinformatics. Aug. 1, 2014;30(15):2114-20. doi: 10.1093/bioinformatics/btu170. Epub Apr. 1, 2014.
Borowsky et al., Layilin, a novel talin-binding transmembrane protein homologous with C-type lectins, is localized in membrane ruffles. J Cell Biol. Oct. 19, 1998;143(2):429-42. doi: 10.1083/jcb.143.2.429.

Boussiotis et al., Biochemical signaling of PD-1 on T cells and its functional implications. Cancer J. Jul. 2014-Aug.20(4):265-71. doi: 10.1097/PPO.0000000000000059.
Briesemeister et al., Going from where to why—interpretable prediction of protein subcellular localization. Bioinformatics. May 1, 2010;26(9):1232-8. doi: 10.1093/bioinformatics/btq115. Epub Mar. 17, 2010.
Burzyn et al., A special population of regulatory T cells potentiates muscle repair. Cell. Dec. 5, 2013;155(6):1282-95. doi: 10.1016/j.cell.2013.10.054.
Campbell et al., Phenotypical and functional specialization of FOXP3+ regulatory T cells. Nat Rev Immunol. Feb. 2011;11(2):119-30. doi: 10.1038/nri2916.
Carthon et al., Preoperative CTLA-4 blockade: tolerability and immune monitoring in the setting of a presurgical clinical trial. Clin Cancer Res. May 15, 2010;16(10):2861-71. doi: 10.1158/1078-0432.CCR-10-0569. Epub May 11, 2010.
Chen et al., CCL18 from tumor-associated macrophages promotes breast cancer metastasis via PITPNM3. Cancer Cell. Apr. 12, 2011;19(4):541-55. doi: 10.1016/j.ccr.2011.02.006. Erratum in: Cancer Cell. Jun. 14, 2011;19(6):814-6.
Cipolletta et al., PPAR-γ is a major driver of the accumulation and phenotype of adipose tissue Treg cells. Nature. Jun. 28, 2012;486(7404):549-53. doi: 10.1038/nature11132.
Duhen et al., Functionally distinct subsets of human FOXP3+ Treg cells that phenotypically mirror effector Th cells. Blood. May 10, 2012;119(19):4430-40. doi: 10.1182/blood-2011-11-392324. Epub Mar. 21, 2012. Erratum in: Blood. Nov. 22, 2012;120(22):4447.
Fridman et al., The immune contexture in human tumours: impact on clinical outcome. Nat Rev Cancer. Mar. 15, 2012;12(4):298-306. doi: 10.1038/nrc3245.
Galluzzi et al., Immunological Effects of Conventional Chemotherapy and Targeted Anticancer Agents. Cancer Cell. Dec. 14, 2015;28(6):690-714. doi: 10.1016/j.ccell.2015.10.012.
Geginat et al., Plasticity of human CD4 T cell subsets. Front Immunol. Dec. 16, 2014;5:630. doi: 10.3389/fimmu.2014.00630.
Gentles et al., The prognostic landscape of genes and infiltrating immune cells across human cancers. Nat Med. Aug. 2015;21(8):938-945. doi: 10.1038/nm.3909. Epub Jul. 20, 2015.
Gonzalez-Pons et al., Colorectal Cancer Biomarkers: Where Are We Now? Biomed Res Int. 2015;2015:149014. doi: 10.1155/2015/149014. Epub May 27, 2015.
Hodi et al., Improved survival with ipilimumab in patients with metastatic melanoma. N Engl J Med. Aug. 19, 2010;363(8):711-23. doi: 10.1056/NEJMoa1003466. Epub Jun. 5, 2010. Erratum in: N Engl J Med. Sep. 23, 2010;363(13):1290.
Huang et al., Systematic and integrative analysis of large gene lists using DAVID bioinformatics resources. Nat Protoc. 2009;4(1):44-57. doi: 10.1038/nprot.2008.211.
Islam et al., Identification of human CCR8 as a CCL18 receptor. J Exp Med. Sep. 23, 2013;210(10):1889-98. doi: 10.1084/jem.20130240. Epub Sep. 2, 2013.
Jacobs et al., Immune Checkpoint Modulation in Colorectal Cancer: What's New and What to Expect. J Immunol Res. 2015;2015:158038. doi: 10.1155/2015/158038. Epub Oct. 29, 2015.
Jamal-Hanjani et al., Tumour heterogeneity and immune-modulation. Curr Opin Pharmacol. Aug. 2013;13(4):497-503. doi: 10.1016/j.coph.2013.04.006. Epub May 7, 2013.
Joller et al., Treg cells expressing the coinhibitory molecule TIGIT selectively inhibit proinflammatory Th1 and Th17 cell responses. Immunity. Apr. 17, 2014;40(4):569-81. doi: 10.1016/j.immuni.2014.02.012.
Josefowicz et al., Regulatory T cells: mechanisms of differentiation and function. Annu Rev Immunol. 2012;30:531-64. doi: 10.1146/annurev.immunol.25.022106.141623. Epub Jan. 6, 2012.
Käll et al., Advantages of combined transmembrane topology and signal peptide prediction—the Phobius web server. Nucleic Acids Res. Jul. 2007;35(Web Server issue): W429-32. doi: 10.1093/nar/gkm256. Epub May 5, 2007.
Kharchenko et al., Bayesian approach to single-cell differential expression analysis. Nat Methods. Jul. 2014;11(7):740-2. doi: 10.1038/nmeth.2967. Epub May 18, 2014.

(56) References Cited

OTHER PUBLICATIONS

Kroemer et al., Colorectal cancer: the first neoplasia found to be under immunosurveillance and the last one to respond to immunotherapy? Oncoimmunology. Jun. 5, 2015;4(7):e1058597. doi: 10.1080/2162402X.2015.1058597.

Le et al., PD-1 Blockade in Tumors with Mismatch-Repair Deficiency. N Engl J Med. Jun. 25, 2015;372(26):2509-20. doi: 10.1056/NEJMoa1500596. Epub May 30, 2015.

Lesterhuis et al., PD-L2 is predominantly expressed by Th2 cells. Mol Immunol. Oct. 2011;49(1-2):1-3. doi: 10.1016/j.molimm.2011.09.014. Epub Oct. 13, 2011.

Löffler-Wirth et al., oposSOM: R-package for high-dimensional portraying of genome-wide expression landscapes on bioconductor. Bioinformatics. Oct. 1, 2015;31(19):3225-7. doi: 10.1093/bioinformatics/btv342. Epub Jun. 10, 2015.

Messal et al., PD-L2 is expressed on activated human T cells and regulates their function. Mol Immunol. Sep. 2011;48(15-16):2214-9. doi: 10.1016/j.molimm.2011.06.436. Epub Jul. 12, 2011.

Munn et al., Immune suppressive mechanisms in the tumor microenvironment. Curr Opin Immunol. Apr. 2016;39:1-6. doi: 10.1016/j.coi.2015.10.009. Epub Nov. 21, 2015.

Murphy et al., Specificity through cooperation: BATF-IRF interactions control immune-regulatory networks. Nat Rev Immunol. Jul. 2013; 13(7):499-509. doi: 10.1038/nri3470. Epub Jun. 21, 2013.

Nishikawa et al., Regulatory T cells in tumor immunity. Int J Cancer. Aug. 1,5 2010;127(4):759-67. doi: 10.1002/ijc.25429.

Panduro et al., Tissue Tregs. Annu Rev Immunol. May 20, 2016;34:609-33. doi: 10.1146/annurev-immunol-032712-095948.

Pardoll, The blockade of immune checkpoints in cancer immunotherapy. Nat Rev Cancer. Mar. 22, 2012;12(4):252-64. doi: 10.1038/nrc3239.

Peggs et al., Blockade of CTLA-4 on both effector and regulatory T cell compartments contributes to the antitumor activity of anti-CTLA-4 antibodies. J Exp Med. Aug. 3, 2009;206(8):1717-25. doi: 10.1084/jem.20082492. Epub Jul. 6, 2009.

Ranzani et al., The long intergenic noncoding RNA landscape of human lymphocytes highlights the regulation of T cell differentiation by linc-MAF-4. Nat Immunol. Mar. 2015;16(3):318-325. doi: 10.1038/ni.3093. Epub Jan. 26, 2015.

Sakaguchi et al., Regulatory T cells and immune tolerance. Cell. May 30, 2008;133(5):775-87. doi: 10.1016/j.cell.2008.05.009.

Sato et al., Human lung epithelial cells progressed to malignancy through specific oncogenic manipulations. Mol Cancer Res. Jun. 2013;11(6):638-50. doi: 10.1158/1541-7786.MCR-12-0634-T. Epub Feb. 28, 2013.

Schoenbrunn et al., A converse 4-1BB and CD40 ligand expression pattern delineates activated regulatory T cells (Treg) and conventional T cells enabling direct isolation of alloantigen-reactive natural Foxp3+ Treg. J Immunol. Dec. 15, 2012;189(12):5985-94. doi: 10.4049/jimmunol.1201090. Epub Nov. 16, 2012.

Schutyser et al., Involvement of CC chemokine ligand 18 (CCL18) in normal and pathological processes. J Leukoc Biol. Jul. 2005;78(1):14-26. doi: 10.1189/jlb.1204712. Epub Mar. 22, 2005.

Sharma et al., Immune checkpoint targeting in cancer therapy: toward combination strategies with curative potential. Cell. Apr. 9, 2015;161(2):205-14. doi: 10.1016/j.cell.2015.03.030.

Simpson et al., Fc-dependent depletion of tumor-infiltrating regulatory T cells co-defines the efficacy of anti-CTLA-4 therapy against melanoma. J Exp Med. Aug. 26, 2013;210(9):1695-710. doi: 10.1084/jem.20130579. Epub Jul. 29, 2013.

Sledzinska et al., Negative immune checkpoints on T lymphocytes and their relevance to cancer immunotherapy. Mol Oncol. Dec. 2015;9(10):1936-65. doi: 10.1016/j.molonc.2015.10.008. Epub Oct. 26, 2015.

Smith et al., Experimentally derived metastasis gene expression profile predicts recurrence and death in patients with colon cancer. Gastroenterology. Mar. 2010; 138(3):958-68. doi: 10.1053/j.gastro.2009.11.005. Epub Nov. 13, 2009.

Sobin et al., TNM Classification of Malignant Tumors. Wiley-Blackwell. UICC International Union Against Cancer. 2009. 7th ed. pp. 100-105, 138-46.

Teng et al., Conditional regulatory T-cell depletion releases adaptive immunity preventing carcinogenesis and suppressing established tumor growth. Cancer Res. Oct. 15, 2010;70(20):7800-9. doi: 10.1158/0008-5472.CAN-10-1681. Epub Oct. 5, 2010. Erratum in: Cancer Res. Dec. 1, 2010;70(23):10014.

Therneau, A package for survival analysis in S. R package version 2.37-4. 2013. 113 pages.

Topalian et al., Immune checkpoint blockade: a common denominator approach to cancer therapy. Cancer Cell. Apr. 13, 2015;27(4):450-61. doi: 10.1016/j.ccell.2015.03.001. Epub Apr. 6, 2015.

Torre et al., Global cancer statistics, 2012. CA Cancer J Clin. Mar. 2015;65(2):87-108. doi: 10.3322/caac.21262. Epub Feb. 4, 2015.

Twyman-Saint Victor et al., Radiation and dual checkpoint blockade activate non-redundant immune mechanisms in cancer. Nature. Apr. 16, 2015;520(7547):373-7. doi: 10.1038/nature14292. Epub Mar. 9, 2015.

Van Den Eertwegh et al., Combined immunotherapy with granulocyte-macrophage colony-stimulating factor-transduced allogeneic prostate cancer cells and ipilimumab in patients with metastatic castration-resistant prostate cancer: a phase 1 dose-escalation trial. Lancet Oncol. May 2012;13(5):509-17. doi: 10.1016/S1470-2045(12)70007-4. Epub Feb. 10, 2012.

Voo et al., Antibodies targeting human OX40 expand effector T cells and block inducible and natural regulatory T cell function. J Immunol. Oct. 1, 2013;191(7):3641-50. doi: 10.4049/jimmunol.1202752. Epub Sep. 6, 2013.

Walter et al., Multipeptide immune response to cancer vaccine IMA901 after single-dose cyclophosphamide associates with longer patient survival. Nat Med. Aug. 2012;18(8):1254-61. doi: 10.1038/nm.2883. Epub Jul. 29, 2012.

Weon et al., The MAGE protein family and cancer. Curr Opin Cell Biol. Dec. 2015;37:1-8. doi: 10.1016/j.ceb.2015.08.002. Epub Sep. 3, 2015.

Wirth et al., Mining SOM expression portraits: feature selection and integrating concepts of molecular function. BioData Min. Oct. 8, 2012;5(1):18. doi: 10.1186/1756-0381-5-18.

Xin et al., A Critical Role of IL-21-Induced BATF in Sustaining CD8-T-Cell-Mediated Chronic Viral Control. Cell Rep. Nov. 10, 2015;13(6):1118-1124. doi: 10.1016/j.celrep.2015.09.069. Epub Oct. 29, 2015.

Yang et al., Ipilimumab (anti-CTLA4 antibody) causes regression of metastatic renal cell cancer associated with enteritis and hypophysitis. J Immunother. Nov. 2007-Dec. 30(8):825-30. doi: 10.1097/CJI.0b013e318156e47e.

Zitvogel et al., Mechanism of action of conventional and targeted anticancer therapies: reinstating immunosurveillance. Immunity. Jul. 25, 2013;39(1):74-88. doi: 10.1016/j.immuni.2013.06.014.

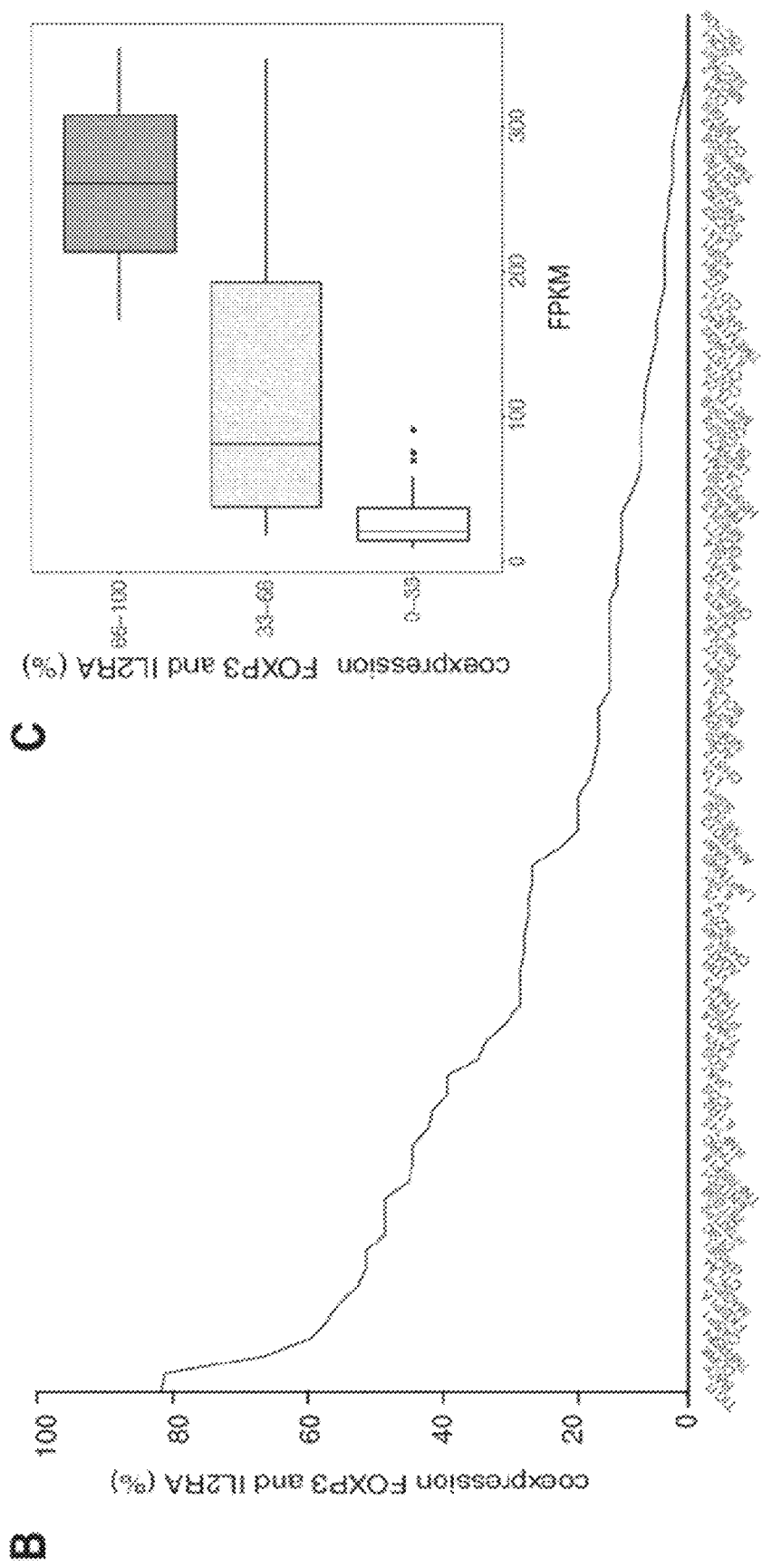

C

SEQUENCE LISTING

```
Sequence total quantity: 791
SEQ ID NO: 1             moltype = AA  length = 374
FEATURE                  Location/Qualifiers
source                   1..374
                         mol_type = protein
                         organism = Homo sapiens
SEQUENCE: 1
MRPGTALQAV LLAVLLVGLR AATGRLLSGQ PVCRGGTQRP CYKVIYFHDT SRRLNFEEAK   60
EACRRDGGQL VSIESEDEQK LIEKFIENLL PSDGDFWIGL RRREEKQSNS TACQDLYAWT  120
DGSISQFRNW YVDEPSCGSE VCVVMYHQPS APAGIGGPYM FQWNDDRCNM KNNFICKYSD  180
EKPAVPSREA EGEETELTTP VLPEETQEED AKKTFKESRE AALNLAYILI PSIPLLLLLV  240
VTTVVCWVWI CRKRKREQPD PSTKKQHTIW PSPHQGNSPD LEVYNVIRKQ SEADLAETRP  300
DLKNISFRVC SGEATPDDMS CDYDNMAVNP SESGFVTLVS VESGFVTNDI YEFSPDQMGR  360
SKESGWVENE IYGY                                                   374

SEQ ID NO: 2             moltype = AA  length = 382
FEATURE                  Location/Qualifiers
source                   1..382
                         mol_type = protein
                         organism = Homo sapiens
SEQUENCE: 2
MRPGTALQAV LLAVLLVGLR AATGRLLSAS DLDLRGGQPV CRGGTQRPCY KVIYFHDTSR   60
RLNFEEAKEA CRRDGGQLVS IESEDEQKLI EKFIENLLPS DGDFWIGLRR REEKQSNSTA  120
CQDLYAWTDG SISQFRNWYV DEPSCGSEVC VVMYHQPSAP AGIGGPYMFQ WNDDRCNMKN  180
NFICKYSDEK PAVPSREAEG EETELTTPVL PEETQEEDAK KTFKESREAA LNLAYILIPS  240
IPLLLLLVVT TVVCWVWICR KRKREQPDPS TKKQHTIWPS PHQGNSPDLE VYNVIRKQSE  300
ADLAETRPDL KNISFRVCSG EATPDDMSCD YDNMAVNPSE SGFVTLVSVE SGFVTNDIYE  360
FSPDQMGRSK ESGWVENEIY GY                                          382

SEQ ID NO: 3             moltype = AA  length = 229
FEATURE                  Location/Qualifiers
source                   1..229
                         mol_type = protein
                         organism = Homo sapiens
```

```
SEQUENCE: 3
MVTSGLGSGG VRRNKAIAQP ARTFMLGLMA AYHNLEKPAV PSREAEGEET ELTTPVLPEE    60
TQEEDAKKTF KESREAALNL AYILIPSIPL LLLLVVTTVV CWVWICRKRK REQPDPSTKK   120
QHTIWPSPHQ GNSPDLEVYN VIRKQSEADL AETRPDLKNI SFRVCSGEAT PDDMSCDYDN   180
MAVNPSESGF VTLVSVESGF VTNDIYEFSP DQMGRSKESG WVENEIYGY               229

SEQ ID NO: 4           moltype = AA   length = 270
FEATURE                Location/Qualifiers
source                 1..270
                       mol_type = protein
                       organism = Homo sapiens
SEQUENCE: 4
MRPGTALQAV LLAVLLVGLR AATGRLLSAS DLDLRGGQPV CRGGTQRPCY KVIYFHDTSR    60
RLNFEEAKEA CRRDGGQLVS IESEDEQKLI EKFIENLLPS DGDFWIGLRR REEKQSNSTA   120
CQDLYAWTDG SISQFRNWYV DEPSCGSEVC VVMYHQPSAP AGIGGPYMFQ WNDDRCNMKN   180
NFICKYSDEK PAVPSREAEG EETELTTPVL PEETQEEDAK KTFKESREAA LNLAYILIPS   240
IPLLLLLVVT TVVCWVWICR KRQKTGAARP                                    270

SEQ ID NO: 5           moltype = AA   length = 134
FEATURE                Location/Qualifiers
source                 1..134
                       mol_type = protein
                       organism = Homo sapiens
SEQUENCE: 5
MRPGTALQAV LLAVLLVGLR AATGRLLSGQ PVCRGGTQRP CYKVIYFHDT SRRLNFEEAK    60
EACRRDGGQL VSIESEDEQK LIEKFIENLL PSDGDFWIGL RRREEKQSNS TACQDLYAWT   120
DGSISQFRET SSSF                                                     134

SEQ ID NO: 6           moltype = AA   length = 108
FEATURE                Location/Qualifiers
source                 1..108
                       mol_type = protein
                       organism = Homo sapiens
SEQUENCE: 6
MVTSGLGSGG VRRNKAIAQP ARTFMLGLMA AYHNLEKPAV PSREAEGEET ELTTPVLPEE    60
TQEEDAKKTF KESREAALNL AYILIPSIPL LLLLVVTTVV CWVWICRK                108

SEQ ID NO: 7           moltype = AA   length = 109
FEATURE                Location/Qualifiers
source                 1..109
                       mol_type = protein
                       organism = Homo sapiens
SEQUENCE: 7
MYHQPSAPAG IGGPYMFQWN DDRCNMKNNF ICKYSDEKPA VPSREAEGEE TELTTPVLPE    60
ETQEEDAKKT FKESREAALN LAYILIPSIP LLLLLVVTTV VCWVWICRK               109

SEQ ID NO: 8           moltype = AA   length = 262
FEATURE                Location/Qualifiers
source                 1..262
                       mol_type = protein
                       organism = Homo sapiens
SEQUENCE: 8
MRPGTALQAV LLAVLLVGLR AATGRLLSGQ PVCRGGTQRP CYKVIYFHDT SRRLNFEEAK    60
EACRRDGGQL VSIESEDEQK LIEKFIENLL PSDGDFWIGL RRREEKQSNS TACQDLYAWT   120
DGSISQFRNW YVDEPSCGSE VCVVMYHQPS APAGIGGPYM FQWNDDRCNM KNNFICKYSD   180
EKPAVPSREA EGEETELTTP VLPEETQEED AKKTFKESRE AALNLAYILI PSIPLLLLLV   240
VTTVVCWVWI CRKRQKTGAA RP                                            262

SEQ ID NO: 9           moltype = AA   length = 49
FEATURE                Location/Qualifiers
source                 1..49
                       mol_type = protein
                       organism = Homo sapiens
SEQUENCE: 9
MYHQPSAPAG IGGPYMFQWN DDRCNMKNNF ICKYSDEKPA VPSREAEGE                49

SEQ ID NO: 10          moltype = AA   length = 355
FEATURE                Location/Qualifiers
source                 1..355
                       mol_type = protein
                       organism = Homo sapiens
SEQUENCE: 10
MDYTLDLSVT TVTDYYYPDI FSSPCDAELI QTNGKLLLAV FYCLLFVFSL LGNSLVILVL    60
VVCKKLRSIT DVYLLNLALS DLLFVFSFPF QTYYLLDQWV FGTVMCKVVS GFYYIGFYSS   120
MFFITLMSVD RYLAVVHAVY ALKVRTIRMG TTLCLAVWLT AIMATIPLLV FYQVASEDGV   180
LQCYSFYNQQ TLKWKIFTNF KMNILGLLIP FTIFMFCYIK ILHQLKRCQN HNKTAIRLV    240
LIVVIASLLF WVPFNVVLFL TSLHSMHILD GCSISQQLTY ATHVTEIISF THCCVNPVIY   300
AFVGEKFKKH LSEIFQKSCS QIFNYLGRQM PRESCEKSSS CQQHSSRSSS VDYIL        355
```

```
SEQ ID NO: 11              moltype = AA   length = 118
FEATURE                    Location/Qualifiers
source                     1..118
                           mol_type = protein
                           organism = Homo sapiens
SEQUENCE: 11
MDYTLDLSVT TVTDYYYPDI FSSPCDAELI QTNDLLSAGP VGVWDCNVQS GVWLLLHWLL    60
QQHVFHHPHE CGQVPGCCPC RVCPKGEDDQ DGHNAVPGSM ANRHYGYHPI ASVLPSGL     118

SEQ ID NO: 12              moltype = AA   length = 538
FEATURE                    Location/Qualifiers
source                     1..538
                           mol_type = protein
                           organism = Homo sapiens
SEQUENCE: 12
MPRGWAAPLL LLLLQGGWGC PDLVCYTDYL QTVICILEMW NLHPSTLTLT WQDQYEELKD    60
EATSCSLHRS AHNATHATYT CHMDVFHFMA DDIFSVNITD QSGNYSQECG SFLLAESIKP   120
APPFNVTVTF SGQYNISWRS DYEDPAFYML KGKLQYELQY RNRGDPWAVS PRRKLISVDS   180
RSVSLLPLEF RKDSSYELQV RAGPMPGSSY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SGLEDPLLD    420
AGTTVLSCGC VSAGSPGLGG PLGSLLDRLK PPLADGEDWA GGLPWGGRSP GGVSESEAGS   480
PLAGLDMDTF DSGFVGSDCS SPVECDFTSP GDEGPPRSYL RQWVVIPPPL SSPGPQAS     538

SEQ ID NO: 13              moltype = AA   length = 538
FEATURE                    Location/Qualifiers
source                     1..538
                           mol_type = protein
                           organism = Homo sapiens
SEQUENCE: 13
MPRGWAAPLL LLLLQGGWGC PDLVCYTDYL QTVICILEMW NLHPSTLTLT WQDQYEELKD    60
EATSCSLHRS AHNATHATYT CHMDVFHFMA DDIFSVNITD QSGNYSQECG SFLLAESIKP   120
APPFNVTVTF SGQYNISWRS DYEDPAFYML KGKLQYELQY RNRGDPWAVS PRRKLISVDS   180
RSVSLLPLEF RKDSSYELQV RAGPMPGSSY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SGLEDPLLD    420
AGTTVLSCGC VSAGSPGLGG PLGSLLDRLK PPLADGEDWA GGLPWGGRSP GGVSESEAGS   480
PLAGLDMDTF DSGFVGSDCS SPVECDFTSP GDEGPPRSYL RQWVVIPPPL SSPGPQAS     538

SEQ ID NO: 14              moltype = AA   length = 538
FEATURE                    Location/Qualifiers
source                     1..538
                           mol_type = protein
                           organism = Homo sapiens
SEQUENCE: 14
MPRGWAAPLL LLLLQGGWGC PDLVCYTDYL QTVICILEMW NLHPSTLTLT WQDQYEELKD    60
EATSCSLHRS AHNATHATYT CHMDVFHFMA DDIFSVNITD QSGNYSQECG SFLLAESIKP   120
APPFNVTVTF SGQYNISWRS DYEDPAFYML KGKLQYELQY RNRGDPWAVS PRRKLISVDS   180
RSVSLLPLEF RKDSSYELQV RAGPMPGSSY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SGLEDPLLD    420
AGTTVLSCGC VSAGSPGLGG PLGSLLDRLK PPLADGEDWA GGLPWGGRSP GGVSESEAGS   480
PLAGLDMDTF DSGFVGSDCS SPVECDFTSP GDEGPPRSYL RQWVVIPPPL SSPGPQAS     538

SEQ ID NO: 15              moltype = AA   length = 467
FEATURE                    Location/Qualifiers
source                     1..467
                           mol_type = protein
                           organism = Homo sapiens
SEQUENCE: 15
MRPQELPRLA FPLLLLLLLL LPPPPCPAHS ATRFDPTWES LDARQLPAWF DQAKFGIFIH    60
WGVFSVPSFG SEWFWWYWQK EKIPKYVEFM KDNYPPSFKY EDFGPLFTAK FFNANQWADI   120
FQASGAKYIV LTSKHHEGFT LWGSEYSWNW NAIDEGPKRD IVKELEVAIR NRTDLRFGLY   180
YSLFEWFHPL FLEDESSSFH KRQFPVSKTL PELYELVNNY QPEVLWSDGD GGAPDQYWNS   240
TGFLAWLYNE SPVRGTVVTN DRWGAGSICK HGGFYTCSIR HGGHLLPHK WENCMTIDKL   300
SWGYRREAGI SDYLTIEELV KQLVETVSCG GNLLMNIGPT LDGTISVVFE ERLRQMGSWL   360
KVNGEAIYET HTWRSQNDTV TPDVWYTSKP KEKLVYAIFL KWPTSGQLFL GHPKAILGAT   420
EVKLLGHGQP LNWISLEQNG IMVELPQLTI HQMPCKWGWA LALTNVI                467

SEQ ID NO: 16              moltype = AA   length = 109
FEATURE                    Location/Qualifiers
source                     1..109
                           mol_type = protein
                           organism = Homo sapiens
SEQUENCE: 16
QLVETVSCGG NLLMNIGPTL DGTISVVFEE RLRQMGSWLK VNGEAIYETH TWRSQNDTVT    60
```

```
PDVWYTSKPK EKLVYAIFLK WPTSGQLFLG HPKAILGATE VRGNFTLFL            109

SEQ ID NO: 17           moltype = AA  length = 350
FEATURE                 Location/Qualifiers
source                  1..350
                        mol_type = protein
                        organism = Homo sapiens
SEQUENCE: 17
MSGHKCSYPW DLQDRYAQDK SVVNKMQQKY WETKQAFIKA TGKKEDEHVV ASDADLDAKL   60
ELFHSIQRTC LDLSKAIVLY QKRICFLSQE ENELGKFLRS QGFQDKTRAG KMMQATGKAL  120
CFSSQQRLAL RNPLCRFHQE VETFRHRAIS DTWLTVNRME QCRTEYRGAL LWMKDVSQEL  180
DPDLYKQMEK FRKVQTQVRL AKKNFDKLKM DVCQKVDLLG ASRCNLLSHM LATYQTTLLH  240
FWEKTSHTMA AIHESFKGYQ PYEFTTLKVW KLEGPLENLE KSKVLFISQA KSIAESIIIP  300
GLRMLKRELC PQQSLFLSFF LSFFFFFFFF TASGFNTMRI YCNPKARIEP            350

SEQ ID NO: 18           moltype = AA  length = 443
FEATURE                 Location/Qualifiers
source                  1..443
                        mol_type = protein
                        organism = Homo sapiens
SEQUENCE: 18
MAASPHTLSS RLLTGCVGGS VWYLERRTIQ DSPHKFLHLL RNVNKQWITF QHFSFLKRMY   60
VTQLNRSHNQ QVRPKPEPVA SPFLEKTSSG QAKAEIYEMR PLSPPSLSLS RKPNEKELIE  120
LEPDSVIEDS IDVGKETKEE KRWKEMKLQV YDLPGILARL SKIKLTALVV STTAAGFALA  180
PGPFDWPCFL LTSVGTGLAS CAANSINQFF EVPFDSNMNR TKNRPLVRGQ ISPLLAVSFA  240
TCCAVPGVAI LTLGVNPLTG ALGLFNIFLY TCCYTPLKRI SIANTWVGAV VGAIPPVMGW  300
TAATGSLDAG AFLLGGILYS WQFPHFNALS WGLREDYSRG GYCMMSVTHP GLCRRVALRH  360
CLALLVLSAA APVLDITTWT FPIMALPINA YISYLGFRFY VDADRRSSRR LFFCSLWHLP  420
LLLLLMLTCK RPSGGGDAGP PPS                                        443

SEQ ID NO: 19           moltype = AA  length = 168
FEATURE                 Location/Qualifiers
source                  1..168
                        mol_type = protein
                        organism = Homo sapiens
SEQUENCE: 19
MCFPKVLSDD MKKLKARMVM SSLAELEDDF KEGYLETVAA YYEEQHPELT PLLEKERDGL   60
RCRGNRSPVP DVEDPATEEP GESFCDKVMR WFQAMLQRLQ TWWHGVLAWV KEKVVALVHA  120
VQALWKQFQS FCCSLSELFM SSFQSYGAPR GDKEELTPQK CSEPQSSK              168

SEQ ID NO: 20           moltype = AA  length = 234
FEATURE                 Location/Qualifiers
source                  1..234
                        mol_type = protein
                        organism = Homo sapiens
SEQUENCE: 20
MCFPKVLSDD MKKLKARMVM LLPTSAQGLG AWVSACDTED TVGHLGPWRD KDPALWCQLC   60
LSSQHQAIER FYDKMQNAES GRGQVMSSLA ELEDDFKEGY LETVAAYYEE QHPELTPLLE  120
KERDGLRCRG NRSPVPDVED PATEEPGESF CDKVMRWFQA MLQRLQTWWH GVLAWVKEKV  180
VALVHAVQAL WKQFQSFCCS LSELFMSSFQ SYGAPRGDKE ELTPQKCSEP QSSK        234

SEQ ID NO: 21           moltype = AA  length = 131
FEATURE                 Location/Qualifiers
source                  1..131
                        mol_type = protein
                        organism = Homo sapiens
SEQUENCE: 21
MCFPKVLSDD MKKLKARMDD FKEGYLETVA AYYEEQHPEL TPLLEKERDG LRCRGNRSPV   60
PDVEDPATEE PGESFCDKVM RWFQAMLQRL QTWWHGVLAW VKEKVVALVH AVQALWKQFQ  120
SFCCSLSELF M                                                      131

SEQ ID NO: 22           moltype = AA  length = 442
FEATURE                 Location/Qualifiers
source                  1..442
                        mol_type = protein
                        organism = Homo sapiens
SEQUENCE: 22
MCFPKVLSDD MKKLKARMVM LLPTSAQGLG AWVSACDTED TVGHLGPWRD KDPALWCQLC   60
LSSQHQAIER FYDKMQNAES GRGQVMSSLA ELEDDFKEGY LETVAAYYEE QHPELTPLLE  120
KERDGLRCRG NRSPVPDVED PATEEPGESF CDKVMRWFQA MLQRLQTWWH GVLAWVKEKV  180
VALVHAVQAL WKQFQSFCCS LSELFMSSFQ SYGATRGARR SMCFPKVLSD DMKKLKARMV  240
MLLPTSAQGL GAWVSACDTE DTVGHLGPWR DKDPALWCQL CLSSQHQAIE RFYDKMQNAE  300
SGRGQVMSSL AELEDDFKEG YLETVAAYYE EQHPELTPLL EKERDGLRCR GNRSPVPDVE  360
DPATEEPGES FCDKVMRWFQ AMLQRLQTWW HGVLAWVKEK VVALVHAVQA LWKQFQSFCC  420
SLSELFMSSF QSYGATRGAR RS                                          442

SEQ ID NO: 23           moltype = AA  length = 168
FEATURE                 Location/Qualifiers
source                  1..168
```

```
                              mol_type =  protein
                              organism =  Homo sapiens
SEQUENCE: 23
MCFPKVLSDD  MKKLKARMVM  SSLAELEDDF  KEGYLETVAA  YYEEQHPELT  PLLEKERDGL   60
RCRGNRSPVP  DVEDPATEEP  GESFCDKVMR  WFQAMLQRLQ  TWWHGVLAWV  KEKVVALVHA  120
VQALWKQFQS  FCCSLSELFM  SSFQSYGAPR  GDKEELTPQK  CSEPQSSK                168

SEQ ID NO: 24                 moltype =  AA   length =  234
FEATURE                       Location/Qualifiers
source                        1..234
                              mol_type =  protein
                              organism =  Homo sapiens
SEQUENCE: 24
MCFPKVLSDD  MKKLKARMVM  LLPTSAQGLG  AWVSACDTED  TVGHLGPWRD  KDPALWCQLC   60
LSSQHQAIER  FYDKMQNAES  GRGQVMSSLA  ELEDDFKEGY  LETVAAYYEE  QHPELTPLLE  120
KERDGLRCRG  NRSPVPDVED  PATEEPGESF  CDKVMRWFQA  MLQRLQTWWH  GVLAWVKEKV  180
VALVHAVQAL  WKQFQSFCCS  LSELFMSSFQ  SYGAPRGDKE  ELTPQKCSEP  QSSK        234

SEQ ID NO: 25                 moltype =  AA   length =  148
FEATURE                       Location/Qualifiers
source                        1..148
                              mol_type =  protein
                              organism =  Homo sapiens
SEQUENCE: 25
MCFPKVLSDD  MKKLKARMVM  SSLAELEELT  PLLEKERDGL  RCRGNRSPVP  DVEDPATEEP   60
GESFCDKVMR  WFQAMLQRLQ  TWWHGVLAWV  KEKVVALVHA  VQALWKQFQS  FCCSLSELFM  120
SSFQSYGAPR  GDKEELTPQK  CSEPQSSK                                        148

SEQ ID NO: 26                 moltype =  AA   length =  234
FEATURE                       Location/Qualifiers
source                        1..234
                              mol_type =  protein
                              organism =  Homo sapiens
SEQUENCE: 26
MCFPKVLSDD  MKKLKARMVM  LLPTSAQGLG  AWVSACDTED  TVGHLGPWRD  KDPALWCQLC   60
LSSQHQAIER  FYDKMQNAES  GRGQVMSSLA  ELEDDFKEGY  LETVAAYYEE  QHPELTPLLE  120
KERDGLRCRG  NRSPVPDVED  PATEEPGESF  CDKVMRWFQA  MLQRLQTWWH  GVLAWVKEKV  180
VALVHAVQAL  WKQFQSFCCS  LSELFMSSFQ  SYGAPRGDKE  ELTPQKCSEP  QSSK        234

SEQ ID NO: 27                 moltype =  AA   length =  225
FEATURE                       Location/Qualifiers
source                        1..225
                              mol_type =  protein
                              organism =  Homo sapiens
SEQUENCE: 27
MCFPKVLSDD  MKKLKARMVM  LLPTSAQGLG  AWVSACDTED  TVGHLGPWRD  KDPALWCQLC   60
LSSQHQAIER  FYDKMQNAES  GRGQVMSSLA  ELEDDFKEGY  LETVAAYYEE  QHPELTPLLE  120
KERDGLRCRG  NRSPVPDVED  PATEEPGESF  CDKVMRWFQA  MLQRLQTWWH  GVLAWVKEKV  180
VALVHAVQAL  WKQFQSFCCS  LSELFMSSFQ  SYGAPRGDKE  ELTPQ                   225

SEQ ID NO: 28                 moltype =  AA   length =  225
FEATURE                       Location/Qualifiers
source                        1..225
                              mol_type =  protein
                              organism =  Homo sapiens
SEQUENCE: 28
MCFPKVLSDD  MKKLKARMVM  LLPTSAQGLG  AWVSACDTED  TVGHLGPWRD  KDPALWCQLC   60
LSSQHQAIER  FYDKMQNAES  GRGQDDFKEG  YLETVAAYYE  EQHPELTPLL  EKERDGLRCR  120
GNRSPVPDVE  DPATEEPGES  FCDKVMRWFQ  AMLQRLQTWW  HGVLAWVKEK  VVALVHAVQA  180
LWKQFQSFCC  SLSELFMSSF  QSYGAPRGDK  EELTPQKCSE  PQSSK                   225

SEQ ID NO: 29                 moltype =  AA   length =  168
FEATURE                       Location/Qualifiers
source                        1..168
                              mol_type =  protein
                              organism =  Homo sapiens
SEQUENCE: 29
MCFPKVLSDD  MKKLKARMVM  SSLAELEDDF  KEGYLETVAA  YYEEQHPELT  PLLEKERDGL   60
RCRGNRSPVP  DVEDPATEEP  GESFCDKVMR  WFQAMLQRLQ  TWWHGVLAWV  KEKVVALVHA  120
VQALWKQFQS  FCCSLSELFM  SSFQSYGAPR  GDKEELTPQK  CSEPQSSK                168

SEQ ID NO: 30                 moltype =  AA   length =  212
FEATURE                       Location/Qualifiers
source                        1..212
                              mol_type =  protein
                              organism =  Homo sapiens
SEQUENCE: 30
MCFPKGLGAW  VSACDTEDTV  GHLGPWRDKD  PALWCQLCLS  SQHQAIERFY  DKMQNAESGR   60
GQVMSSLAEL  EDDFKEGYLE  TVAAYYEEQH  PELTPLLEKE  RDGLRCRGNR  SPVPDVEDPA  120
```

```
TEEPGESFCD KVMRWFQAML QRLQTWWHGV LAWVKEKVVA LVHAVQALWK QFQSFCCSLS   180
ELFMSSFQSY GAPRGDKEEL TPQKCSEPQS SK                                212

SEQ ID NO: 31           moltype = AA  length = 317
FEATURE                 Location/Qualifiers
source                  1..317
                        mol_type = protein
                        organism = Homo sapiens
SEQUENCE: 31
MQEGELAISP ISPVAAMPPL GTHVQARCEA QINLLGEGGI CKLPGRLRIQ PALWSREDVL    60
HWLRWAEQEY SLPCTAEHGF EMNGRALCIL TKDDFRHRAP SSGDVLYELL QYIKTQRRAL   120
VCGPFFGGIF RLKTPTQHSP VPPEEVTGPS QMDTRRGHLL QPPDPGLTSN FGHLDDPGLA   180
RWTPGKEESL NLCHCAELGC RTQGVCSFPA MPQAPIDGRI ADCRLLWDYV YQLLLDTRYE   240
PYIKWEDKDA KIFRVVDPNG LARLWGNHKN RVNMTYEKMS RALRHYYKLN IIKKEPGQKL   300
LFRNGLQLIF IFIWSFQ                                                 317

SEQ ID NO: 32           moltype = AA  length = 262
FEATURE                 Location/Qualifiers
source                  1..262
                        mol_type = protein
                        organism = Homo sapiens
SEQUENCE: 32
MQEGELAISP ISPVAAMPPL GTHVQARCEA QINLLGEGGI CKLPGRLRDV LYELLQYIKT    60
QRRALVCGPF FGGIFRLKTP TQHSPVPPEE VTGPSQMDTR RGHLLQPPDP GLTSNFGHLD   120
DPGLARWTPG KEESLNLCHC AELGCRTQGV CSFPAMPQAP IDGRIADCRL LWDYVYQLLL   180
DTRYEPYIKW EDKDAKIFRV VDPNGLARLW GNHKNRVNMT YEKMSRALRH YYKLNIIKKE   240
PGQKLLFRNG LQLIFIFIWS FQ                                           262

SEQ ID NO: 33           moltype = AA  length = 888
FEATURE                 Location/Qualifiers
source                  1..888
                        mol_type = protein
                        organism = Homo sapiens
SEQUENCE: 33
MKVARFQKIP NGENETMIPV LTSKKASELP VSEVASILQA DLQNGLNKCE VSHRRAFHGW    60
NEFDISEDEP LWKKYISQFK NPLIMLLLAS AVISVLMHQF DDAVSITVAI LIVVTVAFVQ   120
EYRSEKSLEE LSKLVPPECH CVREGKLEHT LARDLVPGDT VCLSVGDRVP ADLRLFEAVD   180
LSIDESSLTG ETTPCSKVTA PQPAATNGDL ASRSNIAFMG TLVRCGKAKG VVIGTGENSE   240
FGEVFKMMQA EEAPKTPLQK SMDLLGKQLS FYSFGIIGII MLVGWLLGKD ILEMFTISVS   300
LAVAAIPEGL PIVVTVTLAL GVMRMVKKRA IVKKLPIVET LGCCNVICSD KTGTLTKNEM   360
TVTHIFTSDG LHAEVTGVGY NQFGEVIVDG DVVHGFYNPA VSRIVEAGCV CNDAVIRNNT   420
LMGKPTEGAL IALAMKMGLD GLQQDYIRKA EYPFSSEQKW MAVKCVHRTQ QDRPEICFMK   480
GAYEQVIKYC TTYQSKGQTL TLTQQQRDVY QQEKARMGSA GLRVLALASG PELGQLTFLG   540
LVGIIDPPRT GVKEAVTTLI ASGVSIKMIT GDSQETAVAI ASRLGLYSKT SQSVSGEEID   600
AMDVQQLSQI VPKVAVFYRA SPRHKMKIIK SLQKNGSVVA MTGDGVNDAV ALKAADIGVA   660
MGQTGTDVCK EAADMILVDD DFQTIMSAIE EGKIYNNIK NFVRFQLSTS IAALTLISLA   720
TLMNFPNPLN AMQILWINII MDGPPAQSLG VEPVDKDVIR KPPRNWKDSI LTKNLILKIL   780
VSSIIIVCGT LFVFWRELRD NVITPRDTTM TFTCFVFFDM FNALSSRSQT KSVFEIGLCS   840
NRMFCYAVLG SIMGQLLVIY FPPLQKVFQT ESLSILGLAL GEEWTAAG               888

SEQ ID NO: 34           moltype = AA  length = 949
FEATURE                 Location/Qualifiers
source                  1..949
                        mol_type = protein
                        organism = Homo sapiens
SEQUENCE: 34
MKVARFQKIP NGENETMIPV LTSKKASELP VSEVASILQA DLQNGLNKCE VSHRRAFHGW    60
NEFDISEDEP LWKKYISQFK NPLIMLLLAS AVISVLMHQF DDAVSITVAI LIVVTVAFVQ   120
EYRSEKSLEE LSKLVPPECH CVREGKLEHT LARDLVPGDT VCLSVGDRVP ADLRLFEAVD   180
LSIDESSLTG ETTPCSKVTA PQPAATNGDL ASRSNIAFMG TLVRCGKAKG VVIGTGENSE   240
FGEVFKMMQA EEAPKTPLQK SMDLLGKQLS FYSFGIIGII MLVGWLLGKD ILEMFTISVS   300
LAVAAIPEGL PIVVTVTLAL GVMRMVKKRA IVKKLPIVET LGCCNVICSD KTGTLTKNEM   360
TVTHIFTSDG LHAEVTGVGY NQFGEVIVDG DVVHGFYNPA VSRIVEAGCV CNDAVIRNNT   420
LMGKPTEGAL IALAMKMGLD GLQQDYIRKA EYPFSSEQKW MAVKCVHRTQ QDRPEICFMK   480
GAYEQVIKYC TTYQSKGQTL TLTQQQRDVY QQEKARMGSA GLRVLALASG PELGQLTFLG   540
LVGIIDPPRT GVKEAVTTLI ASGVSIKMIT GDSQETAVAI ASRLGLYSKT SQSVSGEEID   600
AMDVQQLSQI VPKVAVFYRA SPRHKMKIIK SLQKNGSVVA MTGDGVNDAV ALKAADIGVA   660
MGQTGTDVCK EAADMILVDD DFQTIMSAIE EGKIYNNIK NFVRFQLSTS IAALTLISLA   720
TLMNFPNPLN AMQILWINII MDGPPAQSLG VEPVDKDVIR KPPRNWKDSI LTKNLILKIL   780
VSSIIIVCGT LFVFWRELRD NVITPRDTTM TFTCFVFFDM FNALSSRSQT KSVFEIGLCS   840
NRMFCYAVLG SIMGQLLVIY FPPLQKVFQT ESLSILDLLF LLGLTSSVCI VAEIIKKVER   900
SREKIQKHVS STSSSFLEVW LWERSGQQLV EIHPHLETGL PLTEDVSCV              949

SEQ ID NO: 35           moltype = AA  length = 939
FEATURE                 Location/Qualifiers
source                  1..939
                        mol_type = protein
                        organism = Homo sapiens
SEQUENCE: 35
```

```
MKVARFQKIP NGENETMIPV LTSKKASELP VSEVASILQA DLQNGLNKCE VSHRRAFHGW    60
NEFDISEDEP LWKKYISQFK NPLIMLLLAS AVISVLMHQF DDAVSITVAI LIVVTVAFVQ   120
EYRSEKSLEE LSKLVPPECH CVREGKLEHT LARDLVPGDT VCLSVGDRVP ADLRLFEAVD   180
LSIDESSLTG ETTPCSKVTA PQPAATNGDL ASRSNIAFMG TLVRCGKAKG VVIGTGENSE   240
FGEVFKMMQA EEAPKTPLQK SMDLLGKQLS FYSFGIIGII MLVGWLLGKD ILEMFTISVS   300
LAVAAIPEGL PIVVTVTLAL GVMRMVKKRA IVKKLPIVET LGCCNVICSD KTGTLTKNEM   360
TVTHIFTSDG LHAEVTGVGY NQFGEVIVDG DVVHGFYNPA VSRIVEAGCV CNDAVIRNNT   420
LMGKPTEGAL IALAMKMGLD GLQQDYIRKA EYPFSSEQKW MAVKCVHRTQ QDRPEICFMK   480
GAYEQVIKYC TTYQSKGQTL TLTQQQRDVY QQEKARMGSA GLRVLALASG PELGQLTFLG   540
LVGIIDPPRT GVKEAVTTLI ASGVSIKMIT GDSQETAVAI ASRLGLYSKT SQSVSGEEID   600
AMDVQQLSQI VPKVAVFYRA SPRHKMKIIK SLQKNGSVVA MTGDGVNDAV ALKAADIGVA   660
MGQTGTDVCK EAADMILVDD DFQTIMSAIE EGKGIYNNIK NFVRFQLSTS IAALTLISLA   720
TLMNFPNPLN AMQILWINII MDGPPAQSLG VEPVDKDVIR KPPRNWKDSI LTKNLILKIL   780
VSSIIIVCGT LFVFWRELRD NVITPRDTTM TFTCFVFFDM FNALSSRSQT KSVFEIGLCS   840
NRMFCYAVLG SIMGQLLVIY FPPLQKVFQT ESLSILDLLF LLGLTSSVCI VAEIIKKVER   900
SREKIQKHVW LWERSGQQLV EIHPHLETGL PLTEDVSCV                          939

SEQ ID NO: 36           moltype = AA  length = 919
FEATURE                 Location/Qualifiers
source                  1..919
                        mol_type = protein
                        organism = Homo sapiens
SEQUENCE: 36
MKVARFQKIP NGENETMIPV LTSKKASELP VSEVASILQA DLQNGLNKCE VSHRRAFHGW    60
NEFDISEDEP LWKKYISQFK NPLIMLLLAS AVISVLMHQF DDAVSITVAI LIVVTVAFVQ   120
EYRSEKSLEE LSKLVPPECH CVREGKLEHT LARDLVPGDT VCLSVGDRVP ADLRLFEAVD   180
LSIDESSLTG ETTPCSKVTA PQPAATNGDL ASRSNIAFMG TLVRCGKAKG VVIGTGENSE   240
FGEVFKMMQA EEAPKTPLQK SMDLLGKQLS FYSFGIIGII MLVGWLLGKD ILEMFTISVS   300
LAVAAIPEGL PIVVTVTLAL GVMRMVKKRA IVKKLPIVET LGCCNVICSD KTGTLTKNEM   360
TVTHIFTSDG LHAEVTGVGY NQFGEVIVDG DVVHGFYNPA VSRIVEAGCV CNDAVIRNNT   420
LMGKPTEGAL IALAMKMGLD GLQQDYIRKA EYPFSSEQKW MAVKCVHRTQ QDRPEICFMK   480
GAYEQVIKYC TTYQSKGQTL TLTQQQRDVY QQEKARMGSA GLRVLALASG PELGQLTFLG   540
LVGIIDPPRT GVKEAVTTLI ASGVSIKMIT GDSQETAVAI ASRLGLYSKT SQSVSGEEID   600
AMDVQQLSQI VPKVAVFYRA SPRHKMKIIK SLQKNGSVVA MTGDGVNDAV ALKAADIGVA   660
MGQTGTDVCK EAADMILVDD DFQTIMSAIE EGKGIYNNIK NFVRFQLSTS IAALTLISLA   720
TLMNFPNPLN AMQILWINII MDGPPAQSLG VEPVDKDVIR KPPRNWKDSI LTKNLILKIL   780
VSSIIIVCGT LFVFWRELRD NVITPRDTTM TFTCFVFFDM FNALSSRSQT KSVFEIGLCS   840
NRMFCYAVLG SIMGQLLVIY FPPLQKVFQT ESLSILDLLF LLGLTSSVCI VAEIIKKVER   900
SREKIQKHVS STSSSFLEV                                                919

SEQ ID NO: 37           moltype = AA  length = 944
FEATURE                 Location/Qualifiers
source                  1..944
                        mol_type = protein
                        organism = Homo sapiens
SEQUENCE: 37
MDSLLPPSRF SYFKKYPLHA IRRYLSTLRN QRAEEQVARF QKIPNGENET MIPVLTSKKA    60
SELPVSEVAS ILQFKNPLIM LLLASAVISV LMHQFDDAVS ITVAILIVVT VAFVQEYRSE   120
KSLEELSKLV PPECHCVREG KLEHTLARDL VPGDTVCLSV GDRVPADLRL FEAVDLSIDE   180
SSLTGETTPC SKVTAPQPAA TNGDLASRSN IAFMGTLVRC GKAKGVVIGT GENSEFGEVF   240
KMMQAEEAPK TPLQKSMDLL GKQLSFYSFG IIGIIMLVGW LLGKDILEMF TISVSLAVAA   300
IPEGLPIVVT VTLALGVMRM VKKRAIVKKL PIVETLGCCN VICSDKTGTL TKNEMTVTHI   360
FTSDGLHAEV TGVGYNQFGE VIVDGDVVHG FYNPAVSRIV EAGCVCNDAV IRNNTLMGKP   420
TEGALIALAM KMGLDGLQQD YIRKAEYPFS SEQKWMAVKC VHRTQQDRPE ICFMKGAYEQ   480
VIKYCTTYQS KGQTLTLTQQ QRDVYQQEKA RMGSAGLRVL ALASGPELGQ LTFLGLVGII   540
DPPRTGVKEA VTTLIASGVS IKMITGDSQE TAVAIASRLG LYSKTSQSVS GEEIDAMDVQ   600
QLSQIVPKVA VFYRASPRHK MKIIKSLQKN GSVVAMTGDG VNDAVALKAA DIGVAMGQTG   660
TDVCKEAADM ILVDDDFQTI MSAIEEGKGI YNNIKNFVRF QLSTSIAALT LISLATLMNF   720
PNPLNAMQIL WINIIMDGPP AQSLGVEPVD KDVIRKPPRN WKDSILTKNL ILKILVSSII   780
IVCGTLFVFW RELRDNVITP RDTTMTFTCF VFFDMFNALS SRSQTKSVFE IGLCSNRMFC   840
YAVLGSIMGQ LLVIYFPPLQ KVFQTESLSI LDLLFLLGLT SSVCIVAEII KKVERSREKI   900
QKHVSSTSSS FLEVWLWERS GQQLVEIHPH LETGLPLTED VSCV                    944

SEQ ID NO: 38           moltype = AA  length = 215
FEATURE                 Location/Qualifiers
source                  1..215
                        mol_type = protein
                        organism = Homo sapiens
SEQUENCE: 38
VTVTLALGVM RMVKKRAIVK KLPIVETLGC CNVICSDKTG TLTKNEMTVT HIFTSDGLHA    60
EVTGVGYNQF GEVIVDGDVV HGFYNPAVSR IVEAGCVCND AVIRNNTLMG KPTEGALIAL   120
AMKMGLDGLQ QDYIRKAEYP FSSEQKWMAV KCVHRTQQDR PEICFMKGAY EQVIKYCTTY   180
QSKGQTLTLT QQQRDVYQQE KARMGSAGLR VYLVF                              215

SEQ ID NO: 39           moltype = AA  length = 903
FEATURE                 Location/Qualifiers
source                  1..903
                        mol_type = protein
                        organism = Homo sapiens
```

```
SEQUENCE: 39
XKCEVSHRRA FHGWNEFDIS EDEPLWKKYI SQFKNPLIML LLASAVISVL MHQFDDAVSI    60
TVAILIVVTV AFVQEYRSEK SLEELSKLVP PECHCVREGK LEHTLARDLV PGDTVCLSVG   120
DRVPADLRLF EAVDLSIDES SLTGETTPCS KVTAPQPAAT NGDLASRSNI AFMGTLVRCG   180
KAKGVVIGTG ENSEFGEVFK MMQAEEAPKT PLQKSMDLLG KQLSFYSFGI IGIIMLVGWL   240
LGKDILEMFT ISVSLAVAAI PEGLPIVVTV TLALGVMRMV KKRAIVKKLP IVETLGCCNV   300
ICSDKTGTLT KNEMTVTHIF TSDGLHAEVT GVGYNQFGEV IVDGDVVHGF YNPAVSRIVE   360
AGCVCNDAVI RNNTLMGKPT EGALIALAMK MGLDGLQQDY IRKAEYPFSS EQKWMAVKCV   420
HRTQQDRPEI CFMKGAYEQV IKYCTTYQSK GQTLTLTQQQ RDVYQQEKAR MGSAGLRVLA   480
LASGPELGQL TFLGLVGIID PPRTGVKEAV TTLIASGVSI KMITGDSQET AVAIASRLGL   540
YSKTSQSVSG EEIDAMDVQQ LSQIVPKVAV FYRASPRHKM KIIKSLQKNG SVVAMTGDGV   600
NDAVALKAAD IGVAMGQTGT DVCKEAADMI LVDDDFQTIM SAIEEGKGIY NNIKNFVRFQ   660
LSTSIAALTL ISLATLMNFP NPLNAMQILW INIIMDGPPA QSLGVEPVDK DVIRKPPRNW   720
KDSILTKNLI LKILVSSIII VCGTLFVFWR ELRDNVITPR DTTMTFTCFV FFDMFNALSS   780
RSQTKSVFEI GLCSNRMFCY AVLGSIMGQL LVIYFPPLQK VFQTESLSIL DLLFLLGLTS   840
SVCIVAEIIK KVERSREKIQ KHVSSTSSSF LEVWLWERSG QQLVEIHPHL ETGLPLTEDV   900
SCV                                                                903

SEQ ID NO: 40        moltype = AA  length = 903
FEATURE              Location/Qualifiers
source               1..903
                     mol_type = protein
                     organism = Homo sapiens
SEQUENCE: 40
MIPVLTSKKA SELPVSEVAS ILQADLQNGL NKCEVSHRRA FHGWNEFDIS EDEPLWKKYI    60
SQFKNPLIML LLASAVISVL MHQFDDAVSI TVAILIVVTV AFVQEYRSEK SLEELSKLVP   120
PECHCVREGK LEHTLARDLV PGDTVCLSVG DRVPADLRLF EAVDLSIDES SLTGETTPCS   180
KVTAPQPAAT NGDLASRSNI AFMGTLVRCG KAKGVVIGTG ENSEFGEVFK MMQAEEAPKT   240
PLQKSMDLLG KQLSFYSFGI IGIIMLVGWL LGKDILEMFT ISVSLAVAAI PEGLPIVVTV   300
TLALGVMRMV KKRAIVKKLP IVETLGCCNV ICSDKTGTLT KNEMTVTHIF TSDGLHAEVT   360
GVGYNQFGEV IVDGDVVHGF YNPAVSRIVE AGCVCNDAVI RNNTLMGKPT EGALIALAMK   420
MGLDGLQQDY IRKAEYPFSS EQKWMAVKCV HRTQQDRPEI CFMKGAYEQV IKYCTTYQSK   480
GQTLTLTQQQ RDVYQQEKAR MGSAGLRVLA LASGPELGQL TFLGLVGIID PPRTGVKEAV   540
TTLIASGVSI KMITGDSQET AVAIASRLGL YSKTSQSVSG EEIDAMDVQQ LSQIVPKVAV   600
FYRASPRHKM KIIKSLQKNG SVVAMTGDGV NDAVALKAAD IGVAMGQTGT DVCKEAADMI   660
LVDDDFQTIM SAIEEGKGIY NNIKNFVRFQ LSTSIAALTL ISLATLMNFP NPLNAMQILW   720
INIIMDGPPA QSLGVEPVDK DVIRKPPRNW KDSILTKNLI LKILVSSIII VCGTLFVFWR   780
ELRDNVITPR DTTMTFTCFV FFDMFNALSS RSQTKSVFEI GLCSNRMFCY AVLGSIMGQL   840
LVIYFPPLQK VFQTESLSIL DLLFLLGLTS SVCIVAEIIK KVERSREKIQ KHVSSTSSSF   900
LEV                                                                903

SEQ ID NO: 41        moltype = AA  length = 120
FEATURE              Location/Qualifiers
source               1..120
                     mol_type = protein
                     organism = Homo sapiens
SEQUENCE: 41
MKVARFQKIP NGENETMIPV LTSKKASELP VSEVASILQA DLQNGLNKCE VSHRRAFHGW    60
NEFDISEDEP LWKKYISQFK NPLIMLLLAS AVISVLMHQF DDAVSITVAI LIVVTVAFVQ   120

SEQ ID NO: 42        moltype = AA  length = 953
FEATURE              Location/Qualifiers
source               1..953
                     mol_type = protein
                     organism = Homo sapiens
SEQUENCE: 42
MDSLLPPSRF SYFKKYPLHA IRRYLSTLRN QRAEEQVARF QKIPNGENET MIPVLTSKKA    60
SELPVSEVAS ILQADLQNGL NKCEVSHRRA FHGWNEFDIS EDEPLWKKYI SQFKNPLIML   120
LLASAVISVL MHQFDDAVSI TVAILIVVTV AFVQEYRSEK SLEELSKLVP PECHCVREGK   180
LEHTLARDLV PGDTVCLSVG DRVPADLRLF EAVDLSIDES SLTGETTPCS KVTAPQPAAT   240
NGDLASRSNI AFMGTLVRCG KAKGVVIGTG ENSEFGEVFK MMQAEEAPKT PLQKSMDLLG   300
KQLSFYSFGI IGIIMLVGWL LGKDILEMFT ISVSLAVAAI PEGLPIVVTV TLALGVMRMV   360
KKRAIVKKLP IVETLGCCNV ICSDKTGTLT KNEMTVTHIF TSDGLHAEVT GVGYNQFGEV   420
IVDGDVVHGF YNPAVSRIVE AGCVCNDAVI RNNTLMGKPT EGALIALAMK MGLDGLQQDY   480
IRKAEYPFSS EQKWMAVKCV HRTQQDRPEI CFMKGAYEQV IKYCTTYQSK GQTLTLTQQQ   540
RDVYQQEKAR MGSAGLRVLA LASGPELGQL TFLGLVGIID PPRTGVKEAV TTLIASGVSI   600
KMITGDSQET AVAIASRLGL YSKTSQSVSG EEIDAMDVQQ LSQIVPKVAV FYRASPRHKM   660
KIIKSLQKNG SVVAMTGDGV NDAVALKAAD IGVAMGQTGT DVCKEAADMI LVDDDFQTIM   720
SAIEEGKGIY NNIKNFVRFQ LSTSIAALTL ISLATLMNFP NPLNAMQILW INIIMDGPPA   780
QSLGVEPVDK DVIRKPPRNW KDSILTKNLI LKILVSSIII VCGTLFVFWR ELRDNVITPR   840
DTTMTFTCFV FFDMFNALSS RSQTKSVFEI GLCSNRMFCY AVLGSIMGQL LVIYFPPLQK   900
VFQTESLSIL DLLFLLGLTS SVCIVAEIIK KVERSREKIQ KHVSSTSSSF LEV          953

SEQ ID NO: 43        moltype = AA  length = 50
FEATURE              Location/Qualifiers
source               1..50
                     mol_type = protein
                     organism = Homo sapiens
SEQUENCE: 43
```

```
LVDDDFQTIM SAIEEGKGIY NNIKNFVRFQ LSTFCGSILL WMDPQLRALE           50

SEQ ID NO: 44            moltype = AA  length = 973
FEATURE                  Location/Qualifiers
source                   1..973
                         mol_type = protein
                         organism = Homo sapiens
SEQUENCE: 44
MDSLLPPSRF SYFKKYPLHA IRRYLSTLRN QRAEEQVARF QKIPNGENET MIPVLTSKKA  60
SELPVSEVAS ILQADLQNGL NKCEVSHRRA FHGWNEFDIS EDEPLWKKYI SQFKNPLIML 120
LLASAVISVL MHQFDDAVSI TVAILIVVTV AFVQEYRSEK SLEELSKLVP PECHCVREGK 180
LEHTLARDLV PGDTVCLSVG DRVPADLRLF EAVDLSIDES SLTGETTPCS KVTAPQPAAT 240
NGDLASRSNI AFMGTLVRCG KAKGVVIGTG ENSEFGEVFK MMQAEEAPKT PLQKSMDLLG 300
KQLSFYSFGI IGIIMLVGWL LGKDILEMFT ISVSLAVAAI PEGLPIVVTV TLALGVMRMV 360
KKRAIVKKLP IVETLGCCNV ICSDKTGTLT KNEMTVTHIF TSDGLHAEVT GVGYNQFGEV 420
IVDGDVVHGF YNPAVSRIVE AGCVCNDAVI RNNTLMGKPT EGALIALAMK MGLDGLQQDY 480
IRKAEYPFSS EQKWMAVKCV HRTQQDRPEI CFMKGAYEQV IKYCTTYQSK GQTLTLTQQQ 540
RDVYQQEKAR MGSAGLRVLA LASGPELGQL TFLGLVGIID PPRTGVKEAV TTLIASGVSI 600
KMITGDSQET AVAIASRLGL YSKTSQSVSG EEIDAMDVQQ LSQIVPKVAV FYRASPRHKM 660
KIIKSLQKNG SVVAMTGDGV NDAVALKAAD IGVAMGQTGT DVCKEAADMI LVDDDFQTIM 720
SAIEEGKGIY NNIKNFVRFQ LSTSIAALTL ISLATLMNFP NPLNAMQILW INIIMDGPPA 780
QSLGVEPVDK DVIRKPPRNW KDSILTKNLI LKILVSSIII VCGTLFVFWR ELRDNVITPR 840
DTTMTFTCFV FFDMFNALSS RSQTKSVFEI GLCSNRMFCY AVLGSIMGQL LVIYFPPLQK 900
VFQTESLSIL DLLFLLGLTS SVCIVAEIIK KVERSREKIQ KHVWLWERSG QQLVEIHPHL 960
ETGLPLTEDV SCV                                                   973

SEQ ID NO: 45            moltype = AA  length = 82
FEATURE                  Location/Qualifiers
source                   1..82
                         mol_type = protein
                         organism = Homo sapiens
SEQUENCE: 45
MIPVLTSKKA SELPVSEVAS ILQADLQNGL NKCEVSHRRA FHGWNEFDIS EDEPLWKKYI  60
SQFKNPLIML LLASAVISVL MH                                          82

SEQ ID NO: 46            moltype = AA  length = 919
FEATURE                  Location/Qualifiers
source                   1..919
                         mol_type = protein
                         organism = Homo sapiens
SEQUENCE: 46
MKVARFQKIP NGENETMIPV LTSKKASELP VSEVASILQA DLQNGLNKCE VSHRRAFHGW  60
NEFDISEDEP LWKKYISQFK NPLIMLLLAS AVISVLMHQF DDAVSITVAI LIVVTVAFVQ 120
EYRSEKSLEE LSKLVPPECH CVREGKLEHT LARDLVPGDT VCLSVGDRVP ADLRLFEAVD 180
LSIDESSLTG ETTPCSKVTA PQPAATNGDL ASRSNIAFMG TLVRCGKAKG VVIGTGENSE 240
FGEVFKMMQA EEAPKTPLQK SMDLLGKQLS FYSFGIIGII MLVGWLLGKD ILEMFTISVS 300
LAVAAIPEGL PIVVTVTLAL GVMRMVKKRA IVKKLPIVET LGCCNVICSD KTGTLTKNEM 360
TVTHIFTSDG LHAEVTGVGY NQFGEVIVDG DVVHGFYNPA VSRIVEAGCV CNDAVIRNNT 420
LMGKPTEGAL IALAMKMGLD GLQQDYIRKA EYPFSSEQKW MAVKCVHRTQ QDRPEICFMK 480
GAYEQVIKYC TTYQSKGQTL TLTQQQRDVY QQEKARMGSA GLRVLALASG PELGQLTFLG 540
LVGIIDPPRT GVKEAVTTLI ASGVSIKMIT GDSQETAVAI ASRLGLYSKT SQSVSGEEID 600
AMDVQQLSQI VPKVAVFYRA SPRHKMKIIK SLQKNGSVVA MTGDGVNDAV ALKAADIGVA 660
MGQTGTDVCK EAADMILVDD DFQTIMSAIE EGKGIYNNIK NFVRFQLSTS IAALTLISLA 720
TLMNFPNPLN AMQILWINII MDGPPAQSLG VEPVDKDVIR KPPRNWKDSI LTKNLILKIL 780
VSSIIIVCGT LFVFWRELRD NVITPRDTTM TFTCFVFFDM FNALSSRSQT KSVFEIGLCS 840
NRMFCYAVLG SIMGQLLVIY FPPLQKVFQT ESLSILDLLF LLGLTSSVCI VAEIIKKVER 900
SREKIQKHVS STSSSFLEV                                             919

SEQ ID NO: 47            moltype = AA  length = 314
FEATURE                  Location/Qualifiers
source                   1..314
                         mol_type = protein
                         organism = Homo sapiens
SEQUENCE: 47
XEGALIALAM KMGLDGLQQD YIRKAEYPFS SEQKWMAVKC VHRTQQDRPE ICFMKGAYEQ  60
VIKYCTTYQS KGQTLTLTQQ QRDVYQQEKA RMGSAGLRAS RLGLYSKTSQ SVSGEEIDAM 120
DVQQLSQIVP KVAVFYRASP RHKMKIIKSL QKNGSVVAMT GDGVNDAVAL KAADIGVAMG 180
QTGTDVCKEA ADMILVDDDF QTIMSAIEEG KGIYNNIKNF VRFQLSTSIA ALTLISLATL 240
MNFPNPLNAM QILWINIIMD GPPAQSLGVE PVDKDVIRKP PRNWKDSILT KNLILKILVS 300
SIIIVCGTLF VFWR                                                  314

SEQ ID NO: 48            moltype = AA  length = 102
FEATURE                  Location/Qualifiers
source                   1..102
                         mol_type = protein
                         organism = Homo sapiens
SEQUENCE: 48
MKVARFQKIP NGENETMIPV LTSKKASELP VSEVASILQA DLQNGLNKCE VSHRRAFHGW  60
NEFDISEDEP LWKKYISQFK NPLIMLLLAS AVISVLMHQF DD                   102
```

```
SEQ ID NO: 49            moltype = AA  length = 919
FEATURE                  Location/Qualifiers
source                   1..919
                         mol_type = protein
                         organism = Homo sapiens
SEQUENCE: 49
MKVARFQKIP NGENETMIPV LTSKKASELP VSEVASILQA DLQNGLNKCE VSHRRAFHGW   60
NEFDISEDEP LWKKYISQFK NPLIMLLLAS AVISVLMHQF DDAVSITVAI LIVVTVAFVQ  120
EYRSEKSLEE LSKLVPPECH CVREGKLEHT LARDLVPGDT VCLSVGDRVP ADLRLFEAVD  180
LSIDESSLTG ETTPCSKVTA PQPAATNGDL ASRSNIAFMG TLVRCGKAKG VVIGTGENSE  240
FGEVFKMMQA EEAPKTPLQK SMDLLGKQLS FYSFGIIGII MLVGWLLGKD ILEMFTISVS  300
LAVAAIPEGL PIVVTVTLAL GVMRMVKKRA IVKKLPIVET LGCCNVICSD KTGTLTKNEM  360
TVTHIFTSDG LHAEVTGVGY NQFGEVIVDG DVVHGFYNPA VSRIVEAGCV CNDAVIRNNT  420
LMGKPTEGAL IALAMKMGLD GLQQDYIRKA EYPFSSEQKW MAVKCVHRTQ QDRPEICFMK  480
GAYEQVIKYC TTYQSKGQTL TLTQQQRDVY QQEKARMGSA GLRVLALASG PELGQLTFLG  540
LVGIIDPPRT GVKEAVTTLI ASGVSIKMIT GDSQETAVAI ASRLGLYSKT SQSVSGEEID  600
AMDVQQLSQI VPKVAVFYRA SPRHKMKIIK SLQKNGSVVA MTGDGVNDAV ALKAADIGVA  660
MGQTGTDVCK EAADMILVDD DFQTIMSAIE EGKGIYNNIK NFVRFQLSTS IAALTLISLA  720
TLMNFPNPLN AMQILWINII MDGPPAQSLG VEPVDKDVIR KPPRNWKDSI LTKNLILKIL  780
VSSIIIVCGT LFVFWRELRD NVITPRDTTM TFTCFVFFDM FNALSRSQT KSVFEIGLCS  840
NRMFCYAVLG SIMGQLLVIY FPPLQKVFQT ESLSILDLLF LLGLTSSVCI VAEIIKKVER  900
SREKIQKHVS STSSSPLEV                                              919

SEQ ID NO: 50            moltype = AA  length = 923
FEATURE                  Location/Qualifiers
source                   1..923
                         mol_type = protein
                         organism = Homo sapiens
SEQUENCE: 50
MIPVLTSKKA SELPVSEVAS ILQADLQNGL NKCEVSHRRA FHGWNEFDIS EDEPLWKKYI   60
SQFKNPLIML LLASAVISVL MHQFDDAVSI TVAILIVVTV AFVQEYRSEK SLEELSKLVP  120
PECHCVREGK LEHTLARDLV PGDTVCLSVG DRVPADLRLF EAVDLSIDES SLTGETTPCS  180
KVTAPQPAAT NGDLASRSNI AFMGTLVRCG KAKGVVIGTG ENSEFGEVFK MMQAEEAPKT  240
PLQKSMDLLG KQLSFYSFGI IGIIMLVGWL LGKDILEMFT ISVSLAVAAI PEGLPIVVTV  300
TLALGVMRMV KKRAIVKKLP IVETLGCCNV ICSDKTGTLT KNEMTVTHIF TSDGLHAEVT  360
GVGYNQFGEV IVDGDVVHGF YNPAVSRIVE AGCVCNDAVI RNNTLMGKPT EGALIALAMK  420
MGLDGLQQDY IRKAEYPFSS EQKWMAVKCV HRTQQDRPEI CFMKGAYEQV IKYCTTYQSK  480
GQTLTLTQQQ RDVYQQEKAR MGSAGLRVLA LASGPELGQL TFLGLVGIID PPRTGVKEAV  540
TTLIASGVSI KMITGDSQET AVAIASRLGL YSKTSQSVSG EEIDAMDVQQ LSQIVPKVAV  600
FYRASPRHKM KIIKSLQKNG SVVAMTGDGV NDAVALKAAD IGVAMGQTGT DVCKEAADMI  660
LVDDDFQTIM SAIEEGKGIY NNIKNFVRFQ LSTSIAALTL ISLATLMNFP NPLNAMQILW  720
INIIMDGPPA QSLGVEPVDK DVIRKPPRNW KDSILTKNLI LKILVSSIII VCGTLFVFWR  780
ELRDNVITPR DTTMTFTCFV FFDMFNALSS RSQTKSVFEI GLCSNRMFCY AVLGSIMGQL  840
LVIYFPPLQK VFQTESLSIL DLLFLLGLTS SVCIVAEIIK KVERSREKIQ KHVWLWERSG  900
QQLVEIHPHL ETGLPLTEDV SCV                                         923

SEQ ID NO: 51            moltype = AA  length = 131
FEATURE                  Location/Qualifiers
source                   1..131
                         mol_type = protein
                         organism = Homo sapiens
SEQUENCE: 51
MDLLGKQLSF YSFGIIGIIM LVGWLLGKDI LEMFTISVSL AVAAIPEGLP IVVTVTLALG   60
VMRMVKKRAI VKKLPIVETL GCCNVICSDK TGTLTKNEMT VTHIFTSDGL HAEVTGVGYN  120
QFGEVIVDGD V                                                      131

SEQ ID NO: 52            moltype = AA  length = 888
FEATURE                  Location/Qualifiers
source                   1..888
                         mol_type = protein
                         organism = Homo sapiens
SEQUENCE: 52
MKVARFQKIP NGENETMIPV LTSKKASELP VSEVASILQA DLQNGLNKCE VSHRRAFHGW   60
NEFDISEDEP LWKKYISQFK NPLIMLLLAS AVISVLMHQF DDAVSITVAI LIVVTVAFVQ  120
EYRSEKSLEE LSKLVPPECH CVREGKLEHT LARDLVPGDT VCLSVGDRVP ADLRLFEAVD  180
LSIDESSLTG ETTPCSKVTA PQPAATNGDL ASRSNIAFMG TLVRCGKAKG VVIGTGENSE  240
FGEVFKMMQA EEAPKTPLQK SMDLLGKQLS FYSFGIIGII MLVGWLLGKD ILEMFTISVS  300
LAVAAIPEGL PIVVTVTLAL GVMRMVKKRA IVKKLPIVET LGCCNVICSD KTGTLTKNEM  360
TVTHIFTSDG LHAEVTGVGY NQFGEVIVDG DVVHGFYNPA VSRIVEAGCV CNDAVIRNNT  420
LMGKPTEGAL IALAMKMGLD GLQQDYIRKA EYPFSSEQKW MAVKCVHRTQ QDRPEICFMK  480
GAYEQVIKYC TTYQSKGQTL TLTQQQRDVY QQEKARMGSA GLRVLALASG PELGQLTFLG  540
LVGIIDPPRT GVKEAVTTLI ASGVSIKMIT GDSQETAVAI ASRLGLYSKT SQSVSGEEID  600
AMDVQQLSQI VPKVAVFYRA SPRHKMKIIK SLQKNGSVVA MTGDGVNDAV ALKAADIGVA  660
MGQTGTDVCK EAADMILVDD DFQTIMSAIE EGKGIYNNIK NFVRFQLSTS IAALTLISLA  720
TLMNFPNPLN AMQILWINII MDGPPAQSLG VEPVDKDVIR KPPRNWKDSI LTKNLILKIL  780
VSSIIIVCGT LFVFWRELRD NVITPRDTTM TFTCFVFFDM FNALSRSQT KSVFEIGLCS  840
NRMFCYAVLG SIMGQLLVIY FPPLQKVFQT ESLSILGLAL GEEWTAAG               888
```

```
SEQ ID NO: 53              moltype = AA  length = 233
FEATURE                    Location/Qualifiers
source                     1..233
                           mol_type = protein
                           organism = Homo sapiens
SEQUENCE: 53
MLGIWTLLPL VLTSVARLSS KSVNAQVTDI NSKGLELRKT VTTVETQNLE GLHHDGQFCH    60
KPCPPGERKA RDCTVNGDEP DCVPCQEGKE YTDKAHFSSK CRRCRLCDEG HGLEVEINCT   120
RTQNTKCRCK PNFFCNSTVC EHCDPCTKCE HGIIKECTLT SNTKCKEEGS RSNLGWLCLL   180
LLPIPLIVWV KRKEVQKTCR KHRKENQGSH ESPTLNPETV AINLSDYFLF FRC          233

SEQ ID NO: 54              moltype = AA  length = 220
FEATURE                    Location/Qualifiers
source                     1..220
                           mol_type = protein
                           organism = Homo sapiens
SEQUENCE: 54
MLGIWTLLPL VLTSVARLSS KSVNAQVTDI NSKGLELRKT VTTVETQNLE GLHHDGQFCH    60
KPCPPGERKA RDCTVNGDEP DCVPCQEGKE YTDKAHFSSK CRRCRLCDEG HGLEVEINCT   120
RTQNTKCRCK PNFFCNSTVC EHCDPCTKCE HGIIKECTLT SNTKCKEEGS RSNLGWLCLL   180
LLPIPLIVWV KRKEVQKTCR KHRKENQGSH ESPTLNPMLT                         220

SEQ ID NO: 55              moltype = AA  length = 335
FEATURE                    Location/Qualifiers
source                     1..335
                           mol_type = protein
                           organism = Homo sapiens
SEQUENCE: 55
MLGIWTLLPL VLTSVARLSS KSVNAQVTDI NSKGLELRKT VTTVETQNLE GLHHDGQFCH    60
KPCPPGERKA RDCTVNGDEP DCVPCQEGKE YTDKAHFSSK CRRCRLCDEG HGLEVEINCT   120
RTQNTKCRCK PNFFCNSTVC EHCDPCTKCE HGIIKECTLT SNTKCKEEGS RSNLGWLCLL   180
LLPIPLIVWV KRKEVQKTCR KHRKENQGSH ESPTLNPETV AINLSDVDLS KYITTIAGVM   240
TLSQVKGFVR KNGVNEAKID EIKNDNVQDT AEQKVQLLRN WHQLHGKKEA YDTLIKDLKK   300
ANLCTLAEKI QTIILKDITS DSENSNFRNE IQSLV                              335

SEQ ID NO: 56              moltype = AA  length = 314
FEATURE                    Location/Qualifiers
source                     1..314
                           mol_type = protein
                           organism = Homo sapiens
SEQUENCE: 56
MLGIWTLLPL VLTSVARLSS KSVNAQVTDI NSKGLELRKT VTTVETQNLE GLHHDGQFCH    60
KPCPPGERKA RDCTVNGDEP DCVPCQEGKE YTDKAHFSSK CRRCRLCDEG HGLEVEINCT   120
RTQNTKCRCK PNFFCNSTVC EHCDPCTKCE HGIIKECTLT SNTKCKEEVK RKEVQKTCRK   180
HRKENQGSHE SPTLNPETVA INLSDVDLSK YITTIAGVMT LSQVKGFVRK NGVNEAKIDE   240
IKNDNVQDTA EQKVQLLRNW HQLHGKKEAY DTLIKDLKKA NLCTLAEKIQ TIILKDITSD   300
SENSNFRNEI QSLV                                                     314

SEQ ID NO: 57              moltype = AA  length = 86
FEATURE                    Location/Qualifiers
source                     1..86
                           mol_type = protein
                           organism = Homo sapiens
SEQUENCE: 57
MLGIWTLLPL VLTSVARLSS KSVNAQVTDI NSKGLELRKT VTTVETQNLE GLHHDGQFCH    60
KPCPPDVNME SSRNAHSPAT PSAKRK                                         86

SEQ ID NO: 58              moltype = AA  length = 103
FEATURE                    Location/Qualifiers
source                     1..103
                           mol_type = protein
                           organism = Homo sapiens
SEQUENCE: 58
MLGIWTLLPL VLTSVARLSS KSVNAQVTDI NSKGLELRKT VTTVETQNLE GLHHDGQFCH    60
KPCPPDVNME SSRNAHSPAT PSAKRKDPDL TWGGFVFFFC QFH                     103

SEQ ID NO: 59              moltype = AA  length = 149
FEATURE                    Location/Qualifiers
source                     1..149
                           mol_type = protein
                           organism = Homo sapiens
SEQUENCE: 59
MLGIWTLLPL VLTSVARLSS KSVNAQVTDI NSKGLELRKT VTTVETQNLE GLHHDGQFCH    60
KPCPPGERKA RDCTVNGDEP DCVPCQEGKE YTDKAHFSSK CRRCRLCDEG HDVNMESSRN   120
AHSPATPSAK RKDPDLTWGG FVFFFCQFH                                     149

SEQ ID NO: 60              moltype = AA  length = 132
FEATURE                    Location/Qualifiers
source                     1..132
```

```
                          mol_type = protein
                          organism = Homo sapiens
SEQUENCE: 60
MLGIWTLLPL VLTSVARLSS KSVNAQVTDI NSKGLELRKT VTTVETQNLE GLHHDGQFCH    60
KPCPPGERKA RDCTVNGDEP DCVPCQEGKE YTDKAHFSSK CRRCRLCDEG HDVNMESSRN   120
AHSPATPSAK RK                                                      132

SEQ ID NO: 61             moltype = AA  length = 149
FEATURE                   Location/Qualifiers
source                    1..149
                          mol_type = protein
                          organism = Homo sapiens
SEQUENCE: 61
MLGIWTLLPL VLTSVARLSS KSVNAQVTDI NSKGLELRKT VTTVETQNLE GLHHDGQFCH    60
KPCPPGERKA RDCTVNGDEP DCVPCQEGKE YTDKAHFSSK CRRCRLCDEG HDVNMESSRN   120
AHSPATPSAK RKDPDLTWGG FVFFFCQFH                                    149

SEQ ID NO: 62             moltype = AA  length = 244
FEATURE                   Location/Qualifiers
source                    1..244
                          mol_type = protein
                          organism = Homo sapiens
SEQUENCE: 62
MLGIWTLLPL VLTSVARLSS KSVNAQVTDI NSKGLELRKT VTTVETQNLE GLHHDGQFCH    60
KPCPPGERKA RDCTVNGDEP DCVPCQEGKE YTDKAHFSSK CRRCRLCDEG HGLEVEINCT   120
RTQNTKCRCK PNFFCNSTVC EHCDPCTKCE HGIIKECTLT SNTKCKEEGS RSNLGWLCLL   180
LLPIPLIVWV KRKEVQKTCR KHRKENQGSH ESPTLNPMES CSIAQAGVQG CNHGSLQPQS   240
PGLK                                                               244

SEQ ID NO: 63             moltype = AA  length = 373
FEATURE                   Location/Qualifiers
source                    1..373
                          mol_type = protein
                          organism = Homo sapiens
SEQUENCE: 63
MLRSVWNFLK RHKKKCIFLG TVLGGVYILG KYGQKKIREI QEREAAEYIA QARRQYHFES    60
NQRTCNMTVL SMLPTLREAL MQQLNSESLT ALLKNRPSNK LEIWEDLKII SFTRSTVAVY   120
STCMLVVLLR VQLNIIGGYI YLDNAAVGKN GTTILAPPDV QQQYLSSIQH LLGDGLTELI   180
TVIKQAVQKV LGSVSLKHSL SLLDLEQKLK EIRNLVEQHK SSSWINKDGS KPLLCHYMMP   240
DEETPLAVQA CGLSPRDITT IKLLNETRDM LESPDFSTVL NTCLNRGFSR LLDNMAEFFR   300
PTEQDLQHGN SMNSLSSVSL PLAKIIPIVN GQIHSVCSET PSHFVQDLLT MEQVKDFAAN   360
VYEAFSTPQQ LEK                                                     373

SEQ ID NO: 64             moltype = AA  length = 182
FEATURE                   Location/Qualifiers
source                    1..182
                          mol_type = protein
                          organism = Homo sapiens
SEQUENCE: 64
MLRSVWNFLK RHKKKCIFLG TVLGVLSMLP TLREALMQQL NSESLTALLK NRPSNKLEIW    60
EDLKIISFTR STVAVYSTCM LVVLLRVQLN IIGGYIYLDN AAVGKNGTTI LAPPDVQQQY   120
LSSIQHLLGD GLTELITVIK QAVQKVLGSV SLKHSLSLLD LEQKLKEIRN LVEQHKSSSW   180
IN                                                                 182

SEQ ID NO: 65             moltype = AA  length = 188
FEATURE                   Location/Qualifiers
source                    1..188
                          mol_type = protein
                          organism = Homo sapiens
SEQUENCE: 65
MPGKHQHFQE PEVGCCGKYF LFGFNIVFWF SVFLGLIFFL ELATGILAFV FKDWIRDQLN    60
LFINNNVKAY RDDIDLQNLI DFAQEYEDVL NTQCGYDVRL KLELEQQGFI HTKGCVGQFE   120
KWLQDNLIVV AGVFMGIALL QVPLWPHVPL PLPGPPSLSP HLSSVLQIFG ICLAQNLVSD   180
IKAVKANW                                                           188

SEQ ID NO: 66             moltype = AA  length = 332
FEATURE                   Location/Qualifiers
source                    1..332
                          mol_type = protein
                          organism = Homo sapiens
SEQUENCE: 66
MPGKHQHFQE PEVGCCGKYF LFGFNIVFWV LGALFLAIGL WAWGEKGVLS NISALTDLGG    60
LDPVWLFVVV GGVMSVLGFA GCIGALRENT FLLKFFSVFL GLIFFLELAT GILAFVFKDW   120
IRDQLNLFIN NNVKAYRDDI DLQNLIDFAQ EYWSCCGARG PNDWNLNIYF NCTDLNPSRE   180
RCGVPFSCCV RDPAEDVLNT QCGYDVRLKL VRGELEQQGF IHTKGCVGQF EKWLQDNLIV   240
VAGVFMGIAL LQIFGICLAQ NLVSDIKAVK ANWSKWNDDF ENHWLTPTIS EVLSTAGPQQ   300
NSLTGAPGPA PPSRHVFFGL GGLYPEPTFK NW                                332

SEQ ID NO: 67             moltype = AA  length = 58
```

```
FEATURE                 Location/Qualifiers
source                  1..58
                        mol_type = protein
                        organism = Homo sapiens
SEQUENCE: 67
MPGKHQHFQE PEVGCCGKYF LFGFNIVFWV SAGCWEPCSW LSASGPGVRR AFSRTSQR    58

SEQ ID NO: 68           moltype = AA  length = 309
FEATURE                 Location/Qualifiers
source                  1..309
                        mol_type = protein
                        organism = Homo sapiens
SEQUENCE: 68
MPGKHQHFQE PEVGCCGKYF LFGFNIVFWV LGALFLAIGL WAWGEKGVLS NISALTDLGG   60
LDPVWLFVVV GGVMSVLGFA GCIGALRENT FLLKFDWIRD QLNLFINNNV KAYRDDIDLQ  120
NLIDFAQEYW SCCGARGPND WNLNIYFNCT DLNPSRERCG VPFSCCVRDP AEDVLNTQCG  180
YDVRLKLVRG ELEQQGFIHT KGCVGQFEKW LQDNLIVVAG VFMGIALLQI FGICLAQNLV  240
SDIKAVKANW SKWNDDFENH WLTPTISEVL STAGPQQNSL TGAPGPAPPS RHVFFGLGGL  300
YPEPTFKNW                                                          309

SEQ ID NO: 69           moltype = AA  length = 257
FEATURE                 Location/Qualifiers
source                  1..257
                        mol_type = protein
                        organism = Homo sapiens
SEQUENCE: 69
MPGKHQHFQE PEVGCCGKYF LFGFNIVFWV LGALFLAIGL WAWGEKGVLS NISALTDLGG   60
LDPVWLFVVV GGVMSVLGFA GCIGALRENT FLLKFLATGI LAFVFKDWIR DQLNLFINNN  120
VKAYRDDIDL QNLIDFAQEY WSCCGARGPN DWNLNIYFNC TDLNPSRERC GVPFSCCVRD  180
PAEDVLNTQC GYDVRLKLEL EQQGFIHTKG CVGQFEKWLQ DNLIVVAGVF MGIALLQIFG  240
ICLAQNLVSD IKAVKAN                                                 257

SEQ ID NO: 70           moltype = AA  length = 203
FEATURE                 Location/Qualifiers
source                  1..203
                        mol_type = protein
                        organism = Homo sapiens
SEQUENCE: 70
XGKHQHFQEP EVGCCGKYFL FGFNIVFWFS VFLGLIFFLE LATGILAFVF KDWIRDQLNL   60
FINNNVKAYR DDIDLQNLID FAQEYWSCCG ARGPNDWNLN IYFNCTDLNP SRERCGVPFS  120
CCVRDPAEDV LNTQCGYDVR LKLELEQQGF IHTKGCVGQF EKWLQDNLIV VAGVFMGIAL  180
LQIFGICLAQ NLVSDIKAVK ANW                                          203

SEQ ID NO: 71           moltype = AA  length = 329
FEATURE                 Location/Qualifiers
source                  1..329
                        mol_type = protein
                        organism = Homo sapiens
SEQUENCE: 71
MPGKHQHFQE PEVGCCGKYF LFGFNIVFWV LGALFLAIGL WAWGEKGVLS NISALTDLGG   60
LDPVWLFVVV GGVMSVLGFA GCIGALRENT FLLKFFSVFL GLIFFLELAT GILAFVFKDW  120
IRDQLNLFIN NNVKAYRDDI DLQNLIDFAQ EYWSCCGARG PNDWNLNIYF NCTDLNPSRE  180
RCGVPFSCCV RDPAEDVLNT QCGYDVRLKL ELEQQGFIHT KGCVGQFEKW LQDNLIVVAG  240
VFMGIALLQI FGICLAQNLV SDIKAVKANW SKWNDDFENH WLTPTISEVL STAGPQQNSL  300
TGAPGPAPPS RHVFFGLGGL YPEPTFKNW                                    329

SEQ ID NO: 72           moltype = AA  length = 263
FEATURE                 Location/Qualifiers
source                  1..263
                        mol_type = protein
                        organism = Homo sapiens
SEQUENCE: 72
MPGKHQHFQE PEVGCCGKYF LFGFNIVFWV LGALFLAIGL WAWGEKGVLS NISALTDLGG   60
LDPVWLFVVV GGVMSVLGFA GCIGALRENT FLLKFFSVFL GLIFFLELAT GILAFVFKDW  120
IRDQLNLFIN NNVKAYRDDI DLQNLIDFAQ EYWSCCGARG PNDWNLNIYF NCTDLNPSRE  180
RCGVPFSCCV RDPAEDVLNT QCGYDVRLKL ELEQQGFIHT KGCVGQFEKW LQDNLIVVAG  240
VFMGIALLQI FGICLAQNLE QME                                          263

SEQ ID NO: 73           moltype = AA  length = 83
FEATURE                 Location/Qualifiers
source                  1..83
                        mol_type = protein
                        organism = Homo sapiens
SEQUENCE: 73
MAAATASPRS LLVLLQVVVL ALAQIRGPPG ERGPPGPPGP PGVPGSDGID GPPGPVGLPG   60
EIGIRGPKGD PGPDGPSGPP GPP                                           83

SEQ ID NO: 74           moltype = AA  length = 689
FEATURE                 Location/Qualifiers
```

```
                              -continued source                  1..689
                        mol_type = protein
                        organism = Homo sapiens
SEQUENCE: 74
MAAATASPRS LLVLLQVVVL ALAQIRGPPG ERGPPGPPGP PGVPGSDGID GDNGPPGKAG      60
PPGPKGEPGK AGPDGPDGKP GIDGLTGAKG EPGPMGIPGV KGQPGLPGPP GLPGPGFAGP     120
PGPPGPVGLP GEIGIRGPKG DPGPDGPSGP PGPPGKPGRP GTIQGLEGSA DFLCPTNCPP     180
GMKGPPGLQG VKGHAGKRGI LGDPGHQGKP GPKGDVGASG EQGIPGPPGP QGIRGYPGMA     240
GPKGETGPHG YKGMVGAIGA TGPPGEEGPR GPPGRAGEKG DEGSPGIRGP QGITGPKGAT     300
GPPGINGKDG TPGTPGMKGS AGQAGQPGSP GHQGLAGVPG QPGTKGGPGD QGEPGPQGLP     360
GFSGPPGKEG EPGPRGEIGP QGIMGQKGDQ GERGPVGQPG PQGRQGPKGE QGPPGIPGPQ     420
GLPGVKGDKG SPGKTGPRGK VGDPGVAGLP GEKGEKGESG EPGPKGQQGV RGEPGYPGPS     480
GDAGAPGVQG YPGPPGPRGL AGNRGVPGQP GRQGVEGRDA TDQHIVDVAL KMLQEQLAEV     540
AVSAKREALG AVGMMGPPGP PGPPGYPGKQ GPHGHPGPRG VPGIVGAVGQ IGNTGPKGKR     600
GEKGDPGEVG RGHPGMPGPP GIPGLPGRPG QAINGKDGDR GSPGAPGEAG RPGLPGPVGL     660
PGFCEPAACL GASAYASARL TEPGSIKGP                                      689

SEQ ID NO: 75           moltype = AA   length = 226
FEATURE                 Location/Qualifiers
source                  1..226
                        mol_type = protein
                        organism = Homo sapiens
SEQUENCE: 75
XSPFRGPPGA AGARRGPPGE RGPPGPPGPP GVPGSDGIDG DNGPPGKAGP PGPKGEPGKA      60
GPDGPDGKPG IDGLTGAKGE PGPMGIPGVK GQPGLPGPPG LPGPGFAGPP GPPGPVGLPG     120
EIGIRGPKGD PGPDGPSGPP GPPGKPGRPG TIQGLEGSAD FLCPTNCPPG MKGPPGLQGV     180
KGHAGKRGIL GDPGHQGKPG PKGDVGASGE QGIPGPPGPQ GIRGYP                   226

SEQ ID NO: 76           moltype = AA   length = 694
FEATURE                 Location/Qualifiers
source                  1..694
                        mol_type = protein
                        organism = Homo sapiens
SEQUENCE: 76
MKHLKRWWSA GGGLLHLTLL LSLAGLRVDL DLYLLLPPPT LLQDELLFLG GPASSAYALS      60
PFSASGGWGR AGHLHPKGRE LDPAAPPEGQ LLREVRALGV PFVPRTSVDA WLVHSVAAGS     120
ADEAHGLLGA AAASSTGGAG ASVDGGSQAV QGGGGDPRAA RSGPLDAGEE EKAPAEPTAQ     180
VPDAGGCASE ENGVLREKHE AVDHSSQHEE NEERVSAQKE NSLQQNDDDE NKIAEKPDWE     240
AEKTTESRNE RHLNGTDTSF SLEDLFQLLS SQPENSLEGI SLGQDIPLPGS ISDGMNSSAH     300
YHVNFSQAIS QDVNLHEAIL LCPNNTFRRD PTARTSQSQE PFLQLNSHTT NPEQTLPGTN     360
LTGFLSPVDN HMRNLTSQDL LYDLDINIFD EINLMSLATE DNFDPIDVSQ LFDEPDSDSG     420
LSLDSSHNNT SVIKSNSSHS VCDEGAIGYC TDHESSSHHD LEGAVGGYYP EPSKLCHLDQ     480
SDSDFHGDLT FQHVFHNHTY HLQPTAPEST SEPPFPWPGKS QKIRSRYLED TDRNLSRDEQ     540
RAKALHIPFS VDEIVGMPVD SFNSMLSRYY LTDLQVSLIR DIRRRGKNKV AAQNCRKRKL     600
DIILNLEDDV CNLQAKKETL KREQAQCNKA INIMKQKLHD LYHDIFSRLR DDQGRPVNPN     660
HYALQCTHDG SILIVPKELV ASGHKKETQK GKRK                                694

SEQ ID NO: 77           moltype = AA   length = 86
FEATURE                 Location/Qualifiers
source                  1..86
                        mol_type = protein
                        organism = Homo sapiens
SEQUENCE: 77
CNCGLVFHLQ DPWVPTGPGA VQKQREHPPD YQWYALDQLP PDVQHKANES AILSTACFYG      60
LVRPPRSGLY KLSYNQNPTS ILIKYT                                          86

SEQ ID NO: 78           moltype = AA   length = 1722
FEATURE                 Location/Qualifiers
source                  1..1722
                        mol_type = protein
                        organism = Homo sapiens
SEQUENCE: 78
MRTGWATPRR PAGLLMLLFW FFDLAEPSGR AANDPFTIVH GNTGKCIKPV YGWIVADDCD      60
ETEDKLWKWV SQHRLFHLHS QKCLGLDITK SVNELRMFSC DSSAMLWWKC EHHSLYGAAR     120
YRLALKDGHG TAISNASDVW KKGGSEESLC DQPYHEIYTR DGNSYGRPCE FPFLIDGTWH     180
HDCILDEDHS GPWCATTLNY EYDRKWGICL KPENGCEDNW EKNEQFGSCY QFNTQTALSW     240
KEAYVSCQNQ GADLLSINSA AELTYLKEKE GIAKIFWIGL NQLYSARGWE WSDHKPLNFL     300
NWDPDRPSAP TIGGSSCARM DAESGLWQSF SCEAQLPYVC RKPLNNTVEL TDVWTYSDTR     360
CDAGWLPNNG FCYLLVNESN SWDKAHACKC AFSSDLISIH SLADVEVVVT KLHNEDIKEE     420
VWIGLKNINI PTLFQWSDGT EVTLTYWDEN EPNVPYNKTP NCVSYLGELG QWKVQSCEEK     480
LKYVCKRKGE KLNDASSDKM CPPDEGWKRH GETCYKIYED EVPFGTNCNL TITSRFEQEY     540
LNDLMKKYDK SLRKYFWTGL RDVDSCGEYN WATVGGRRRA VTFSNWNFLE PASPGGCVAM     600
STGKSVGKWE VKDCRSFKAL SICKKMSGPL GPEEASPKPD DPCPEGWQSF PASLSCYKVF     660
HAERIVRKRN WEEAERFCQA LGAHLSSFSH VDEIKEFLHF LTDQFSGQHW LWIGLNKRSP     720
DLQGSWQWSD RTPVSTIIMP NEFQQDYDIR DCAAVKVFHR PWRRGWHFYD DREFIYLRPF     780
ACDTKLEWVC QIPKGRTPKT PDWYNPDRAG IHGPPLIIEG SEYWFVADLH LNYEEAVLYC     840
ASNHSFLATI TSFVGLKAIK NKIANISGDG QKWWIRISEW PIDDHFTYSR YPWHRFPVTF     900
GEECLYMSAK TWLIDLGKPT DCSTKLPFIC EKYNVSSLEK YSPDSAAKVQ CSEQWIPFQN     960
KCFLKIKPVS LTFSQASDTC HSYGGTLPSV LSQIEQDFIT SLLPDMEATL WIGLRWTAYE    1020
```

```
KINKWTDNRE LTYSNFHPLL VSGRLRIPEN FFEEESRYHC ALILNLQKSP FTGTWNFTSC  1080
SERHFVSLCQ KYSEVKSRQT LQNASETVKY LNNLYKIIPK TLTWHSAKRE CLKSNMQLVS  1140
ITDPYQQAFL SVQALLHNSS LWIGLFSQDD ELNFGWSDGK RLHFSRWAET NGQLEDCVVL  1200
DTDGFWKTVD CNDNQPGAIC YYSGNETEKE VKPVDSVKCP SPVLNTPWIP FQNCCYNFII  1260
TKNRHMATTQ DEVHTKCQKL NPKSHILSIR DEKENNFVLE QLLYFNYMAS WVMLGITYRN  1320
KSLMWFDKTP LSYTHWRAGR PTIKNEKFLA GLSTDGFWDI QTFKVIEEAV YFHQHSILAC  1380
KIEMVDYKEE YNTTLPQFMP YEDGIYSVIQ KKVTWYEALN MCSQSGGHLA SVHNQNGQLF  1440
LEDIVKRDGF PLWVGLSSHD GSESSFEWSD GSTFDYIPWK GQTSPGNCVL LDPKGTWKHE  1500
KCNSVKDGAI CYKPTKSKKL SRLTYSSRCP AAKENGSRWI QYKGHCYKSD QALHSFSEAK  1560
KLCSKHDHSA TIVISIKDEDE NKFVSRLMRE NNNITMRVWL GLSQHSVDQS WSWLDGSEVT  1620
FVKWENKSKS GVGRCSMLIA SNETWKKVEC EHGFGRVVCK VPLGPDYTAI AIIVATLSIL  1680
VLMGGLIWFL FQRHRLHLAG FSSVRYAQGV NEDEIMLPSF HD                    1722

SEQ ID NO: 79           moltype = AA   length = 306
FEATURE                 Location/Qualifiers
source                  1..306
                        mol_type = protein
                        organism = Homo sapiens
SEQUENCE: 79
MAAVDDLQFE EFGNAATSLT ANPDATTVNI EDPGETPKHQ PGSPRGSGRE EDDELLGNDD   60
SDKTELLAGQ KKSSPFWTFE YYQTFFDVDT YQVFDRIKGS LLPIPGKNFV RLYIRSNPDL  120
YGPFWICATL VFAIAISGNL SNFLIHLGEK TYHVPEFRK VSIAATIIYA YAWLVPLALW   180
GFLMWRNSKV MNIVSYSFLE IVCVYGYSLF IYIPTAILWI IPQKAVRWIL VMIALGISGS  240
LLAMTFWPAV REDNRRVALA TIVTIVLLHM LLSVGCLAYF FDAPEMDHLP TTTATPNQTV  300
AAAKSS                                                             306

SEQ ID NO: 80           moltype = AA   length = 123
FEATURE                 Location/Qualifiers
source                  1..123
                        mol_type = protein
                        organism = Homo sapiens
SEQUENCE: 80
MWRNSKVMNI VSYSFLEIVC VYGYSLFIYI PTAILWIIPQ KAVRWILVMI ALGISGSLLA   60
MTFWPAVRED NRRVALATIV TIVLLHMLLS VGCLAYFFDA PEMDHLPTTT ATPNQTVAAA  120
KSS                                                                123

SEQ ID NO: 81           moltype = AA   length = 217
FEATURE                 Location/Qualifiers
source                  1..217
                        mol_type = protein
                        organism = Homo sapiens
SEQUENCE: 81
MAAVDDLQFE EFGNAATSLT ANPDATTVNI EDPGETPKHQ PGSPRGSGRE EDDELLGNDD   60
SDKTELLAGQ KKSSPFWTFE YYQTFFDVDT YQVFDRIKGS LLPIPGKNFV RLYIRSNPDL  120
YGPFWICATL VFAIAISGNL SNFLIHLGEK TYHVPEFRK VSIAATIIYA YAWLVPLALW   180
GFLMWRNSKV MNIVSYSFLE IVCVYGYSLF IYIPTAV                            217

SEQ ID NO: 82           moltype = AA   length = 306
FEATURE                 Location/Qualifiers
source                  1..306
                        mol_type = protein
                        organism = Homo sapiens
SEQUENCE: 82
MAAVDDLQFE EFGNAATSLT ANPDATTVNI EDPGETPKHQ PGSPRGSGRE EDDELLGNDD   60
SDKTELLAGQ KKSSPFWTFE YYQTFFDVDT YQVFDRIKGS LLPIPGKNFV RLYIRSNPDL  120
YGPFWICATL VFAIAISGNL SNFLIHLGEK TYHVPEFRK VSIAATIIYA YAWLVPLALW   180
GFLMWRNSKV MNIVSYSFLE IVCVYGYSLF IYIPTAILWI IPQKAVRWIL VMIALGISGS  240
LLAMTFWPAV REDNRRVALA TIVTIVLLHM LLSVGCLAYF FDAPEMDHLP TTTATPNQTV  300
AAAKSS                                                             306

SEQ ID NO: 83           moltype = AA   length = 298
FEATURE                 Location/Qualifiers
source                  1..298
                        mol_type = protein
                        organism = Homo sapiens
SEQUENCE: 83
MAAAEPAVLA LPNSGAGGAG APSGTVPVLF CFSVFARPSS VPHGAGYELL IQKFLSLYGD   60
QIDMHRKFVV QLFAEEWGQY VDLPKGFAVS ERCKVRLVPL QIQLTTLGNL TPSSTVFFCC  120
DMQERFRPAI KYFGDIISVG QRLLQGARIL GIPVIVTEQY PKGLGSTVQE IDLTGVKLVL  180
PKTKFSMVLP EVEAALAEIP GVRSVVLFGV ETHVCIQQTA LELVGRGVEV HIVADATSSR  240
SMMDRMFALE RLARTGIIVT TSEAVLLQLV ADKDHPKFKE IQNLIKASAP ESGLLSKV    298

SEQ ID NO: 84           moltype = AA   length = 188
FEATURE                 Location/Qualifiers
source                  1..188
                        mol_type = protein
                        organism = Homo sapiens
SEQUENCE: 84
MAAAEPAVLA LPNSGAGGAG APSGTVPVLF CFSVFARPSS VPHGAGYELL IQKFLSLYGD   60
```

```
QIDMHRKFVV QLFAEEWGQY VDLPKGFAVS ERCKLTTLGN LTPSSTVFFC CDMQERFRPA    120
IKYFGDIISV GQRLLQGARI LGIPVIVTEQ YPKGLGSTVQ EIDLTGVKLV LPKTKFSMVL    180
PEVEAALA                                                             188

SEQ ID NO: 85          moltype = AA   length = 711
FEATURE                Location/Qualifiers
source                 1..711
                       mol_type = protein
                       organism = Homo sapiens
SEQUENCE: 85
MKLKLNVLTI ILLPVHLLIT IYSALIFIPW YFLTNAKKKN AMAKRIKAKP TSDKPGSPYR    60
SVTHFDSLAV IDIPGADTLD KLFDHAVSKF GKKDSLGTRE ILSEENEMQP NGKVFKKLIL    120
GNYKWMNYLE VNRRVNNFGS GLTALGLKPK NTIAIFCETR AEWMIAAQTC FKYNFPLVTL    180
YATLGKEAVV HGLNESEASY LITSVELLES KLKTALLDIS CVKHIIYVDN KAINKAEYPE    240
GFEIHSMQSV EELGSNPENL GIPPSRPTPS DMAIVMYTSG STGRPKGVMM HHSNLIAGMT    300
GQCERIPGLG PKDTYIGYLP LAHVLELTAE ISCFTYGCRI GYSSPLTLSD QSSKIKKGSK    360
GDCTVLKPTL MAAVPEIMDR IYKNVMSKVQ EMNYIQKTLF KIGYDYKLEQ IKKGYDAPLC    420
NLLLFKKVKA LLGGNVRMML SGGAPLSPQT HRFMNVCFCC PIGQGYGLTE SCGAGTVTEV    480
TDYTTGRVGA PLICCEIKLK DWQEGGYTIN DKPNPRGEIV IGGQNISMGY FKNEEKTAED    540
YSVDENGQRW FCTGDIGEFH PDGCLQIIDR KKDLVKLQAG EYVSLGKVEA ALKNCPLIDN    600
ICAFAKSDQS YVISFVVPNQ KRLTLLAQQK GVEGTWVDIC NNPAMEAEIL KEIREAANAM    660
KLERFEIPIK VRLSPEPWTP ETGLVTDAFK LKRKELRNHY LKDIERMYGG K             711

SEQ ID NO: 86          moltype = AA   length = 711
FEATURE                Location/Qualifiers
source                 1..711
                       mol_type = protein
                       organism = Homo sapiens
SEQUENCE: 86
MKLKLNVLTI ILLPVHLLIT IYSALIFIPW YFLTNAKKKN AMAKRIKAKP TSDKPGSPYR    60
SVTHFDSLAV IDIPGADTLD KLFDHAVSKF GKKDSLGTRE ILSEENEMQP NGKVFKKLIL    120
GNYKWMNYLE VNRRVNNFGS GLTALGLKPK NTIAIFCETR AEWMIAAQTC FKYNFPLVTL    180
YATLGKEAVV HGLNESEASY LITSVELLES KLKTALLDIS CVKHIIYVDN KAINKAEYPE    240
GFEIHSMQSV EELGSNPENL GIPPSRPTPS DMAIVMYTSG STGRPKGVMM HHSNLIAGMT    300
GQCERIPGLG PKDTYIGYLP LAHVLELTAE ISCFTYGCRI GYSSPLTLSD QSSKIKKGSK    360
GDCTVLKPTL MAAVPEIMDR IYKNVMSKVQ EMNYIQKTLF KIGYDYKLEQ IKKGYDAPLC    420
NLLLFKKVKA LLGGNVRMML SGGAPLSPQT HRFMNVCFCC PIGQGYGLTE SCGAGTVTEV    480
TDYTTGRVGA PLICCEIKLK DWQEGGYTIN DKPNPRGEIV IGGQNISMGY FKNEEKTAED    540
YSVDENGQRW FCTGDIGEFH PDGCLQIIDR KKDLVKLQAG EYVSLGKVEA ALKNCPLIDN    600
ICAFAKSDQS YVISFVVPNQ KRLTLLAQQK GVEGTWVDIC NNPAMEAEIL KEIREAANAM    660
KLERFEIPIK VRLSPEPWTP ETGLVTDAFK LKRKELRNHY LKDIERMYGG K             711

SEQ ID NO: 87          moltype = AA   length = 54
FEATURE                Location/Qualifiers
source                 1..54
                       mol_type = protein
                       organism = Homo sapiens
SEQUENCE: 87
MKLKLNVLTI ILLPVHLLIT IYSALIFIPW YFLTNAKKKN AMAKRIKAKP TSDK          54

SEQ ID NO: 88          moltype = AA   length = 145
FEATURE                Location/Qualifiers
source                 1..145
                       mol_type = protein
                       organism = Homo sapiens
SEQUENCE: 88
MKLKLNVLTI ILLPVHLLIT IYSALIFIPW YFLTNAKKKN AMAKRIKAKP TSDKPGSPYR    60
SVTHFDSLAV IDIPGADTLD KLFDHAVSKF GKKDSLGTRE ILSEENEMQP NGKVFKKLIL    120
GNYKWMNYLE VNRRVNNFGS GLTAL                                          145

SEQ ID NO: 89          moltype = AA   length = 126
FEATURE                Location/Qualifiers
source                 1..126
                       mol_type = protein
                       organism = Homo sapiens
SEQUENCE: 89
MKLKLNVLTI ILLPVHLLIT IYSALIFIPW YFLTNAKKKN AMAKRIKAKP TSDKPGSPYR    60
SVTHFDSLAV IDIPGADTLD KLFDHAVSKF GKKDSLGTRE ILSEENEMQP NGKVFKKLIL    120
GNYKWM                                                               126

SEQ ID NO: 90          moltype = AA   length = 128
FEATURE                Location/Qualifiers
source                 1..128
                       mol_type = protein
                       organism = Homo sapiens
SEQUENCE: 90
MKLKLNVLTI ILLPVHLLIT IYSALIFIPW YFLTNAKKKN AMAKRIKAKP TSDKPGSPYR    60
SVTHFDSLAV IDIPGADTLD KLFDHAVSKF GKKDSLGTRE ILSEENEMQP NGKVFKKLIL    120
GNYKWMNY                                                             128
```

```
SEQ ID NO: 91            moltype = AA   length = 80
FEATURE                  Location/Qualifiers
source                   1..80
                         mol_type = protein
                         organism = Homo sapiens
SEQUENCE: 91
NLVRMRSQAL GQSAPSLTAS LKELSLPRRG SLIDSQKWNC LVKRSLSPTP SSPGSPCSPL    60
LAFHFWSPVC PNAGRTSPLG                                                80

SEQ ID NO: 92            moltype = AA   length = 58
FEATURE                  Location/Qualifiers
source                   1..58
                         mol_type = protein
                         organism = Homo sapiens
SEQUENCE: 92
MAKVAKDLNP GVKKMSLGQL QSARGVACLG CKGTCSGFEP HSWRDCSTWS SSPRRSSQ      58

SEQ ID NO: 93            moltype = AA   length = 760
FEATURE                  Location/Qualifiers
source                   1..760
                         mol_type = protein
                         organism = Homo sapiens
SEQUENCE: 93
MMDQARSAFS NLFGGEPLSY TRFSLARQVD GDNSHVEMKL AVDEEENADN NTKANVTKPK    60
RCSGSICYGT IAVIVFFLIG FMIGYLGYCK GVEPKTECER LAGTESPVRE EPGEDFPAAR   120
RLYWDDLKRK LSEKLDSTDF TGTIKLLNEN SYVPREAGSQ KDENLALYVE NQFREFKLSK   180
VWRDQHFVKI QVKDSAQNSV IIVDKNGRLV YLVENPGGYV AYSKAATVTG KLVHANFGTK   240
KDFEDLYTPV NGSIVIVRAG KITFAEKVAN AESLNAIGVL IYMDQTKFPI VNAELSFFGH   300
AHLGTGDPYT PGFPSFNHTQ FPPSRSSGLP NIPVQTISRA AAEKLFGNME GDCPSDWKTD   360
STCRMVTSES KNVKLTVSNV LKEIKILNIF GVIKGFVEPD HYVVVGAQRD AWGPGAAKSG   420
VGTALLLKLA QMFSDMVLKD GFQPSRSIIF ASWSAGDFGS VGATEWLEGY LSSLHLKAFT   480
YINLDKAVLG TSNFKVSASP LLYTLIEKTM QNVKHPVTGQ FLYQDSNWAS KVEKLTLDNA   540
APPFLAYSGI PAVSFCFCED TDYPYLGTTM DTYKELIERI PELNKVARAA AEVAGQFVIK   600
LTHDVELNLD YERYNSQLLS FVRDLNQYRA DIKEMGLSLQ WLYSARGDFF RATSRLTTDF   660
GNAEKTDRFV MKKLNDRVMR VEYHFLSPYV SPKESPFRHV FWGSGSHTLP ALLENLKLRK   720
QNNGAFNETL FRNQLALATW TIQGAANALS GDVWDIDNEF                         760

SEQ ID NO: 94            moltype = AA   length = 760
FEATURE                  Location/Qualifiers
source                   1..760
                         mol_type = protein
                         organism = Homo sapiens
SEQUENCE: 94
MMDQARSAFS NLFGGEPLSY TRFSLARQVD GDNSHVEMKL AVDEEENADN NTKANVTKPK    60
RCSGSICYGT IAVIVFFLIG FMIGYLGYCK GVEPKTECER LAGTESPVRE EPGEDFPAAR   120
RLYWDDLKRK LSEKLDSTDF TGTIKLLNEN SYVPREAGSQ KDENLALYVE NQFREFKLSK   180
VWRDQHFVKI QVKDSAQNSV IIVDKNGRLV YLVENPGGYV AYSKAATVTG KLVHANFGTK   240
KDFEDLYTPV NGSIVIVRAG KITFAEKVAN AESLNAIGVL IYMDQTKFPI VNAELSFFGH   300
AHLGTGDPYT PGFPSFNHTQ FPPSRSSGLP NIPVQTISRA AAEKLFGNME GDCPSDWKTD   360
STCRMVTSES KNVKLTVSNV LKEIKILNIF GVIKGFVEPD HYVVVGAQRD AWGPGAAKSG   420
VGTALLLKLA QMFSDMVLKD GFQPSRSIIF ASWSAGDFGS VGATEWLEGY LSSLHLKAFT   480
YINLDKAVLG TSNFKVSASP LLYTLIEKTM QNVKHPVTGQ FLYQDSNWAS KVEKLTLDNA   540
APPFLAYSGI PAVSFCFCED TDYPYLGTTM DTYKELIERI PELNKVARAA AEVAGQFVIK   600
LTHDVELNLD YERYNSQLLS FVRDLNQYRA DIKEMGLSLQ WLYSARGDFF RATSRLTTDF   660
GNAEKTDRFV MKKLNDRVMR VEYHFLSPYV SPKESPFRHV FWGSGSHTLP ALLENLKLRK   720
QNNGAFNETL FRNQLALATW TIQGAANALS GDVWDIDNEF                         760

SEQ ID NO: 95            moltype = AA   length = 81
FEATURE                  Location/Qualifiers
source                   1..81
                         mol_type = protein
                         organism = Homo sapiens
SEQUENCE: 95
MMDQARSAFS NLFGGEPLSY TRFSLARQVD GDNSHVEMKL AVDEEENADN NTKANVTKPK    60
RCSGSICYGT IAVIVFFLIG C                                              81

SEQ ID NO: 96            moltype = AA   length = 118
FEATURE                  Location/Qualifiers
source                   1..118
                         mol_type = protein
                         organism = Homo sapiens
SEQUENCE: 96
AAAEVAGQFV IKLTHDVELN LDYERYNSQL LSFVRDLNQY RADIKEMGLS LQWLYSARGD    60
FFRATSRLTT DFGNAEKTDR FVMKKLNDRV MREGPQMMLL LTDARPSNHF LSPLLSLH     118

SEQ ID NO: 97            moltype = AA   length = 643
FEATURE                  Location/Qualifiers
source                   1..643
```

```
                        mol_type = protein
                        organism = Homo sapiens
SEQUENCE: 97
MHHLLEQSAD MATALLAGEK LRELILPGAQ DDKAGALAAL LLQLKLELPF DRVVTIGTVL    60
VPILLVTLVF TKNFAEEPIY CYTPHNFTRD QALYARGYCW TELRDALPGV DASLWPSLFE   120
HKFLPYALLA FAAIMYVPAL GWEFLASTRL TSELNFLLQE IDNCYHRAAE GRAPKIEKQI   180
QSKGPGITER EKREIIENAE KEKSPEQNLF EKYLERRGRS NFLAKLYLAR HVLILLLSAV   240
PISYLCTYYA TQKQNEFTCA LGASPDGAAG AGPAVRVSCK LPSVQLQRII AGVDIVLLCV   300
MNLIILVNLI HLFIFRKSNF IFDKLHKVGI KTRRQWRRSQ FCDINILAMF CNENRDHIKS   360
LNRLDFITNE SDLMYDNVVR QLLAALAQSN HDATPTVRDS GVQTVDPSAN PAEPDGAAEP   420
PVVKRPRKKM KWIPTSNPLP QPFKEPLAIM RVENSKAEKP KPARRKTATD TLIAPLLDRS   480
AHHYKGGGGD PGPGPAPAPA PPPAPDKKHA RHFSLDVHPY ILGTKKAKAE AVPAALPASR   540
SQEGGFLSQA EDCGLGLAPA PIKDAPLPEK EIPYPTEPAR AGLPSGGPFH VRSPPAAPAV   600
APLTPASLGK AEPLTILSRN ATHPLLHINT LSSSPPSTSR ERS                    643

SEQ ID NO: 98           moltype = AA   length = 677
FEATURE                 Location/Qualifiers
source                  1..677
                        mol_type = protein
                        organism = Homo sapiens
SEQUENCE: 98
MHHLLEQSAD MATALLAGEK LRELILPGAQ DDKAGALAAL LLQLKLELPF DRVVTIGTVL    60
VPILLVTLVF TKNFAEEPIY CYTPHNFTRD QALYARGYCW TELRDALPGV DASLWPSLFE   120
HKFLPYALLA FAAIMYVPAL GWEFLASTRL TSELNFLLQE IDNCYHRAAE GRAPKIEKQI   180
QSKGPGITER EKREIIENAE KEKSPEQNLF EKYLERRGRS NFLAKLYLAR HVLILLLSAV   240
PISYLCTYYA TQKQNEFTCA LGASPDGAAG AGPAVRVSCK LPSVQLQRII AGVDIVLLCV   300
MNLIILVNLI HLFIFRKSNF IFDKLHKVGI KTRRQWRRSQ FCDINILAMF CNENRDHIKS   360
LNRLDFITNE SDLMYDNVVR QLLAALAQSN HDATPTVRDS GVQTVDPSAN PAEPDGAAEP   420
PVVKRPRKKM KWIPTSNPLP QPFKEPLAIM RVENSKAEKP KPARRKTATD TLIAPLLDRS   480
AHHYKGGGGD PGPGPAPAPA PPPAPDKKHA RHFSLDVHPY ILGTKKAKAE AVPAALPASR   540
SQEGGFLSQA EDCGLGLAPA PIKDAPLPEK EIPYPTEPAR AGLPSGGPFH VRSPPAAPAV   600
APLTPASLGK AEPLTILSRN ATHPLLHINT LYEAREEEDG GPRLPQDVGD LIAIPAPQQI   660
LIATFDEPRT VVSTVEF                                                 677

SEQ ID NO: 99           moltype = AA   length = 77
FEATURE                 Location/Qualifiers
source                  1..77
                        mol_type = protein
                        organism = Homo sapiens
SEQUENCE: 99
MATALLAGEK LRELILPGAQ DDKAGALAAL LLQLKLELPF DRVVTIGTVL VPILLVTLVF    60
TKNFAGWTLF SGSWDWL                                                  77

SEQ ID NO: 100          moltype = AA   length = 1204
FEATURE                 Location/Qualifiers
source                  1..1204
                        mol_type = protein
                        organism = Homo sapiens
SEQUENCE: 100
MYVTMMMTDQ IPLELPPLLN GEVAMMPHLV NGDAAQQVIL VQVNPGETFT IRAEDGTLQC    60
IQGPAEVPMM SPNGSIPPIH VPPGYISQVI EDSTGVRRVV VTPQSPECYP PSYPSAMSPT   120
HHLPPYLTHH PHFIHNSHTA YYPPVTGPGD MPPQFFPQHH LPHTIYGEQE IIPFYGMSTY   180
ITREDQYSKP PHKKLKDRQI DRQNRLNSPP SSIYKSSCTT VYNGYGKGHS GGSGGGGSGS   240
GPGIKKTERR ARSSPKSNDS DLQEYELEVK RVQDILSGIE KPQVSNIQAR AVVLSWAPPV   300
GLSCGPHSGL SFPYSYEVAL SDKGRDGKYK IIYSGEELEC NLKDLRPATD YHVRVYAMYN   360
SVKGSCSEPV SFTTHSCAPE CPFPPKLAHR SKSSLTLQWK APIDNGSKIT NYLLEWDEGK   420
RNSGFRQCFF GSQKHCKLTK LCPAMGYTFR LAARNDIGTS GYSQEVVCYT LGNIPQMPSA   480
PRLVRAGITW VTLQWSKPEG CSPEEVITYT LEIQEDENDN LFHPKYTGED LTCTVKNLKR   540
STQYKFRLTA SNTEGKSCPS EVLVCTTSPD RPGPPTRPLV KGPVTSHGFS VKWDPPKDNG   600
GSEILKYLLE ITDGNSEANQ WEVAYSGSAT EYTFTHLKPG TLYKLRACCI STGGHSQCSE   660
SLPVRTLSIA PGQCRPPRVL GRPKHKEVHL EWDVPASESG CEVSEYSVEM TEPEDVASEV   720
YHGPELECTV GNLLPGTVYR FRVRALNDGG YGPYSDVSEI TTAAGPPGQC KAPCISCTPD   780
GCVLVGWESP DSSGADISEY RLEWGEDEES LELIYHGTGT RFEIRDLLPA AQYCCRLQAF   840
NQAGAGPYSE LVLCQTPASA PDPVSTLCVL EEEPLDAYPD SPSACLVLNW EEPCNNGSEI   900
LAYTIDLGDT SITVGNTTMH VMKDLLPETT YRIRIQAINE IGAGPFSQFI KAKTRPLPPL   960
PPRLECAAAG PQSLKLKWGD SNSKTHAAED IVYTLQLEDR NKRFISIYRG PSHTYKVQRL  1020
TEFTCYSFRI QAASEAGEGP FSETYTFSTT KSVPPTIKAP RVTQLEGNSC EILWETVPSM  1080
KGDPVNYILQ VLVGRESEYK QVYKGEEATF QISGLQTNTD YRFRVCACRR CLDTSQELSG  1140
AFSPSAAFVL QRSEVMLTGD MGSLDDPKMK SMMPTDEQFA AIIVLGFATL SILFAFILQY  1200
FLMK                                                              1204

SEQ ID NO: 101          moltype = AA   length = 1204
FEATURE                 Location/Qualifiers
source                  1..1204
                        mol_type = protein
                        organism = Homo sapiens
SEQUENCE: 101
MYVTMMMTDQ IPLELPPLLN GEVAMMPHLV NGDAAQQVIL VQVNPGETFT IRAEDGTLQC    60
IQGPAEVPMM SPNGSIPPIH VPPGYISQVI EDSTGVRRVV VTPQSPECYP PSYPSAMSPT   120
```

```
HHLPPYLTHH PHFIHNSHTA YYPPVTGPGD MPPQFFPQHH LPHTIYGEQE IIPFYGMSTY    180
ITREDQYSKP PHKKLKDRQI DRQNRLNSPP SSIYKSSCTT VYNGYGKGHS GGSGGGGSGS    240
GPGIKKTERR ARSSPKSNDS DLQEYELEVK RVQDILSGIE KPQVSNIQAR AVVLSWAPPV    300
GLSCGPHSGL SFPYSYEVAL SDKGRDGKYK IIYSGEELEC NLKDLRPATD YHVRVYAMYN    360
SVKGSCSEPV SFTTHSCAPE CPFPPKLAHR SKSSLTLQWK APIDNGSKIT NYLLEWDEGK    420
RNSGFRQCFF GSQKHCKLTK LCPAMGYTFR LAARNDIGTS GYSQEVVCYT LGNIPQMPSA    480
PRLVRAGITW VTLQWSKPEG CSPEEVITYT LEIQEDENDN LFHPKYTGED LTCTVKNLKR    540
STQYKFRLTA SNTEGKSCPS EVLVCTTSPD RPGPPTRPLV KGPVTSHGFS VKWDPPKDNG    600
GSEILKYLLE ITDGNSEANQ WEVAYSGSAT EYTFTHLKPG TLYKLRACCI STGGHSQCSE    660
SLPVRTLSIA PGQCRPPRVL GRPKHKEVHL EWDVPASESG CEVSEYSVEM TEPEDVASEV    720
YHGPELECTV GNLLPGTVYR FRVRALNDGG YGPYSDVSEI TTAAGPPGQC KAPCISCTPD    780
GCVLVGWESP DSSGADISEY RLEWGEDEES LELIYHGTDT RFEIRDLLPA AQYCCRLQAF    840
NQAGAGPYSE LVLCQTPASA PDPVSTLCVL EEEPLDAYPD SPSACLVLNW EEPCNNGSEI    900
LAYTIDLGDT SITVGNTTMH VMKDLLPETT YRIRIQAINE IGAGPFSQFI KAKTRPLPPL    960
PPRLECAAAG PQSLKLKWGD SNSKTHAAED IVYTLQLEDR NKRFISIYRG PSHTYKVQRL   1020
TEFTCYSFRI QAASEAGEGP FSETYTFSTT KSVPPTIKAP RVTQLEGNSC EILWETVPSM   1080
KGDPVNYILQ VLVGRESEYK QVYKGEEATF QISGLQTNTD YRFRVCACRR CLDTSQELSG   1140
AFSPSAAFVL QRSEVMLTGD MGSLDDPKMK SMMPTDEQFA AIIVLGFATL SILFAFILQY   1200
FLMK                                                                1204

SEQ ID NO: 102         moltype = AA  length = 1204
FEATURE                Location/Qualifiers
source                 1..1204
                       mol_type = protein
                       organism = Homo sapiens
SEQUENCE: 102
MYVTMMMTDQ IPLELPPLLN GEVAMMPHLV NGDAAQQVIL VQVNPGETFT IRAEDGTLQC     60
IQGPAEVPMM SPNGSIPPIH VPPGYISQVI EDSTGVRRVV VTPQSPECYP PSYPSAMSPT    120
HHLPPYLTHH PHFIHNSHTA YYPPVTGPGD MPPQFFPQHH LPHTIYGEQE IIPFYGMSTY    180
ITREDQYSKP PHKKLKDRQI DRQNRLNSPP SSIYKSSCTT VYNGYGKGHS GGSGGGGSGS    240
GPGIKKTERR ARSSPKSNDS DLQEYELEVK RVQDILSGIE KPQVSNIQAR AVVLSWAPPV    300
GLSCGPHSGL SFPYSYEVAL SDKGRDGKYK IIYSGEELEC NLKDLRPATD YHVRVYAMYN    360
SVKGSCSEPV SFTTHSCAPE CPFPPKLAHR SKSSLTLQWK APIDNGSKIT NYLLEWDEGK    420
RNSGFRQCFF GSQKHCKLTK LCPAMGYTFR LAARNDIGTS GYSQEVVCYT LGNIPQMPSA    480
PRLVRAGITW VTLQWSKPEG CSPEEVITYT LEIQEDENDN LFHPKYTGED LTCTVKNLKR    540
STQYKFRLTA SNTEGKSCPS EVLVCTTSPD RPGPPTRPLV KGPVTSHGFS VKWDPPKDNG    600
GSEILKYLLE ITDGNSEANQ WEVAYSGSAT EYTFTHLKPG TLYKLRACCI STGGHSQCSE    660
SLPVRTLSIA PGQCRPPRVL GRPKHKEVHL EWDVPASESG CEVSEYSVEM TEPEDVASEV    720
YHGPELECTV GNLLPGTVYR FRVRALNDGG YGPYSDVSEI TTAAGPPGQC KAPCISCTPD    780
GCVLVGWESP DSSGADISEY RLEWGEDEES LELIYHGTDT RFEIRDLLPA AQYCCRLQAF    840
NQAGAGPYSE LVLCQTPASA PDPVSTLCVL EEEPLDAYPD SPSACLVLNW EEPCNNGSEI    900
LAYTIDLGDT SITVGNTTMH VMKDLLPETT YRIRIQAINE IGAGPFSQFI KAKTRPLPPL    960
PPRLECAAAG PQSLKLKWGD SNSKTHAAED IVYTLQLEDR NKRFISIYRG PSHTYKVQRL   1020
TEFTCYSFRI QAASEAGEGP FSETYTFSTT KSVPPTIKAP RVTQLEGNSC EILWETVPSM   1080
KGDPVNYILQ VLVGRESEYK QVYKGEEATF QISGLQTNTD YRFRVCACRR CLDTSQELSG   1140
AFSPSAAFVL QRSEVMLTGD MGSLDDPKMK SMMPTDEQFA AIIVLGFATL SILFAFILQY   1200
FLMK                                                                1204

SEQ ID NO: 103         moltype = AA  length = 71
FEATURE                Location/Qualifiers
source                 1..71
                       mol_type = protein
                       organism = Homo sapiens
SEQUENCE: 103
MYVTMMMTDQ IPLELPPLLN GEVAMMPHLV NGDAAQQVIL VQVNPGETFT IRAEDGTLQC     60
IQDEVVKRAC D                                                         71

SEQ ID NO: 104         moltype = AA  length = 71
FEATURE                Location/Qualifiers
source                 1..71
                       mol_type = protein
                       organism = Homo sapiens
SEQUENCE: 104
MYVTMMMTDQ IPLELPPLLN GEVAMMPHLV NGDAAQQVIL VQVNPGETFT IRAEDGTLQC     60
IQDEVVKRAC D                                                         71

SEQ ID NO: 105         moltype = AA  length = 862
FEATURE                Location/Qualifiers
source                 1..862
                       mol_type = protein
                       organism = Homo sapiens
SEQUENCE: 105
MAHTFRGCSL AFMFIITWLL IKAKIDACKR GDVTVKPSHV ILLGSTVNIT CSLKPRQGCF     60
HYSRRNKLIL YKFDRRINFH HGHSLNSQVT GLPLGTTLFV CKLACINSDE IQICGAEIFV    120
GVAPEQPQNL SCIQKGEQGT VACTWERGRD THLYTEYTLQ LSGPKNLTWQ KQCKDIYCDY    180
LDFGINLTPE SPESNFTAKV TAVNSLGSSS SLPSTFTFLD IVRPLPPWDI RIKFQKASVS    240
RCTLYWRDEG LVLLNRLRYR PSNSRLWNMV NVTKAKGRHD LLDLKPFTEY EFQISSKLHL    300
YKGSWSDWSE SLRAQTPEEE PTGMLDVWYM KRHIDYSRQQ ISLFWKNLSV SEARGKILHY    360
QVTLQELTGG KAMTQNITGH TSWTTVIPRT GNWAVAVSAA NSKGSSLPTR INIMNLCEAG   420
```

```
LLAPRQVSAN SEGMDNILVT WQPPRKDPSA VQEYVVEWRE LHPGGDTQVP LNWLRSRPYN  480
VSALISENIK SYICYEIRVY ALSGDQGGCS SILGNSKHKA PLSGPHINAI TEEKGSILIS  540
WNSIPVQEQM GCLLHYRIYW KERDSNSQPQ LCEIPYRVSQ NSHPINSLQP RVTYVLWMTA  600
LTAAGESSHG NEREFCLQGK ANWMAFVAPS ICIAIIMVGI FSTHYFQQKV FVLLAALRPQ  660
WCSREIPDPA NSTCAKKYPI AEEKTQLPLD RLLIDWPTPE DPEPLVISEV LHQVTPVFRH  720
PPCSNWPQRE KGIQGHQASE KDMMHSASSP PPPRALQAES RQLVDLYKVL ESRGSDPKPE  780
NPACPWTVLP AGDLPTHDGY LPSNIDDLPS HEAPLADSLE ELEPQHISLS VFPSSSLHPL  840
TFSCGDKLTL DQLKMRCDSL ML                                          862

SEQ ID NO: 106           moltype = AA   length = 659
FEATURE                  Location/Qualifiers
source                   1..659
                         mol_type = protein
                         organism = Homo sapiens
SEQUENCE: 106
MAHTFRGCSL AFMFIITWLL IKAKIDACKR GDVTVKPSHV ILLGSTVNIT CSLKPRQGCF   60
HYSRRNKLIL YKFDRRINFH HGHSLNSQVT GLPLGTTLFV CKLACINSDE IQICGAEIFV  120
GVAPEQPQNL SCIQKGEQGT VACTWERGRD THLYTEYTLQ LSGPKNLTWQ KQCKDIYCDY  180
LDFGINLTPE SPESNFTAKV TAVNSLGSSS SLPSTFTFLD IVRPLPPWDI RIKFQKASVS  240
RCTLYWRDEG LVLLNRLRYR PSNSRLWNMV NVTKAKGRHD LLDLKPFTEY EFQISSKLHL  300
YKGSWSDWSE SLRAQTPEEE PTGMLDVWYM KRHIDYSRQQ ISLFWKNLSV SEARGKILHY  360
QVTLQELTGG KAMTQNITGH TSWTTVIPRT GNWAVAVSAA NSKGSSLPTR INIMNLCEAG  420
LLAPRQVSAN SEGMDNILVT WQPPRKDPSA VQEYVVEWRE LHPGGDTQVP LNWLRSRPYN  480
VSALISENIK SYICYEIRVY ALSGDQGGCS SILGNSKHKA PLSGPHINAI TEEKGSILIS  540
WNSIPVQEQM GCLLHYRIYW KERDSNSQPQ LCEIPYRVSQ NSHPINSLQP RVTYVLWMTA  600
LTAAGESSHG NEREFCLQGK ANWMAFVAPS ICIAIIMVGI FSTHYFQQKR RHSCPWTGS   659

SEQ ID NO: 107           moltype = AA   length = 230
FEATURE                  Location/Qualifiers
source                   1..230
                         mol_type = protein
                         organism = Homo sapiens
SEQUENCE: 107
XQKGEQGTVA CTWERGRDTH LYTEYTLQLS GPKNLTWQKQ CKDIYCDYLD FGINLTPESP   60
ESNFTAKVTA VNSLGSSSSL PSTFTFLDIV RPLPPWDIRI KFQKASVSRC TLYWRDEGLV  120
LLNRLRYRPS NSRLWNMVNV TKAKGRHDLL DLKPFTEYEF QISSKLHLYK GSWSDWSESL  180
RAQTPEEEPT GMLDVWYMKR HIDYSRQQIS LFWKVSFKRQ LKTQGNKTEG            230

SEQ ID NO: 108           moltype = AA   length = 635
FEATURE                  Location/Qualifiers
source                   1..635
                         mol_type = protein
                         organism = Homo sapiens
SEQUENCE: 108
MAHTFRGCSL AFMFIITWLL IKAKIDACKR GDVTVKPSHV ILLGSTVNIT CSLKPRQGCF   60
HYSRRNKLIL YKFDRRINFH HGHSLNSQVT GLPLGTTLFV CKLACINSDE IQICGAEIFV  120
GVAPEQPQNL SCIQKGEQGT VACTWERGRD THLYTEYTLQ LSGPKNLTWQ KQCKDIYCDY  180
LDFGINLTPE SPESNFTAKV TAVNSLGSSS SLPSTFTFLD IVRPLPPWDI RIKFQKASVS  240
RCTLYWRDEG LVLLNRLRYR PSNSRLWNMV NVTKAKGRHD LLDLKPFTEY EFQISSKLHL  300
YKGSWSDWSE SLRAQTPEEE PTGMLDVWYM KRHIDYSRQQ ISLFWKNLSV SEARGKILHY  360
QVTLQELTGG KAMTQNITGH TSWTTVIPRT GNWAVAVSAA NSKGSSLPTR INIMNLCEAG  420
LLAPRQVSAN SEGMDNILVT WQPPRKDPSA VQEYVVEWRE LHPGGDTQVP LNWLRSRPYN  480
VSALISENIK SYICYEIRVY ALSGDQGGCS SILGNSKHKA PLSGPHINAI TEEKGSILIS  540
WNSIPVQEQM GCLLHYRIYW KERDSNSQPQ LCEIPYRVSQ NSHPINSLQP RVTYVLWMTA  600
LTAAGESSHG NEREFCLQGE DTAALGQAPD RLAHA                             635

SEQ ID NO: 109           moltype = AA   length = 776
FEATURE                  Location/Qualifiers
source                   1..776
                         mol_type = protein
                         organism = Homo sapiens
SEQUENCE: 109
MAHTFRGCSL AFMFIITWLL IKAKIDACKR GDVTVKPSHV ILLGSTVNIT CSLKPRQGCF   60
HYSRRNKLIL YKFDRRINFH HGHSLNSQVT GLPLGTTLFV CKLACINSDE IQICGAEIFV  120
GVAPEQPQNL SCIQKGEQGT VACTWERGRD THLYTEYTLQ LSGPKNLTWQ KQCKDIYCDY  180
LDFGINLTPE SPESNFTAKV TAVNSLGSSS SLPSTFTFLD IVRPLPPWDI RIKFQKASVS  240
RCTLYWRDEG LVLLNRLRYR PSNSRLWNMV NVTKAKGRHD LLDLKPFTEY EFQISSKLHL  300
YKGSWSDWSE SLRAQTPEEE PTGMLDVWYM KRHIDYSRQQ ISLFWKNLSV SEARGKILHY  360
QVTLQELTGG KAMTQNITGH TSWTTVIPRT GNWAVAVSAA NSKGSSLPTR INIMNLCEAG  420
LLAPRQVSAN SEGMDNILVT WQPPRKDPSA VQEYVVEWRE LHPGGDTQVP LNWLRSRPYN  480
VSALISEIPY RVSQNSHPIN SLQPRVTYVL WMTALTAAGE SSHGNEREFC LQGKANWMAF  540
VAPSICIAII MVGIFSTHYF QQKVFVLLAA LRPQWCSREI PDPANSTCAK KYPIAEEKTQ  600
LPLDRLLIDW PTPEDPEPLV ISEVLHQVTP VFRHPPCSNW PQREKGIQGH QASEKDMMHS  660
ASSPPPPRAL QAESRQLVDL YKVLESRGSD PKPENPACPW TVLPAGDLPT HDGYLPSNID  720
DLPSHEAPLA DSLEELEPQH ISLSVFPSSS LHPLTFSCGD KLTLDQLKMR CDSLML      776

SEQ ID NO: 110           moltype = AA   length = 370
FEATURE                  Location/Qualifiers
source                   1..370
```

```
                           mol_type = protein
                           organism = Homo sapiens
SEQUENCE: 110
MLPRRLLAAW LAGTRGGGLL ALLANQCRFV TGLRVRRAQQ IAQLYGRLYS ESSRRVLLGR    60
LWRRLHGRPG HASALMAALA GVFVWDEERI QEEELQRSIN EMKRLEEMSN MFQSSGVQHH   120
PPEPKAQTEG NEDSEGKEQR WEMVMDKKHF KLWRRPITGT HLYQYRVFGT YTDVTPRQFF   180
NVQLDTEYRK KWDALVIKLE VIERDVVSGS EVLHWVTHFP YPMYSRDYVY VRRYSVDQEN   240
NMMVLVSRAV EHPSVPESPE FVRVRSYESQ MVIRPHKSFD ENGFDYLLTY SDNPQTVFPR   300
YCVSWMVSSG MPDFLEKLHM ATLKAKNMEI KVKDYISAKP LEMSSEAKAT SQSSERKNEG   360
SCGPARIEYA                                                         370

SEQ ID NO: 111             moltype = AA  length = 154
FEATURE                    Location/Qualifiers
source                     1..154
                           mol_type = protein
                           organism = Homo sapiens
SEQUENCE: 111
MVSKAKVIVN GWLFPACLGF CLSESFFMVK GAALFLQQGS SPQGQRSLQH PHKHAGDLPQ    60
HLQVMINLLR CEDRIKLAVR LESAWADRVR YMVVVYSSGR QDTEENILLG VDFSSKESKS   120
CTIGMVLRLW SDTKIHLDGD GGFSVSTAGR MHIF                              154

SEQ ID NO: 112             moltype = AA  length = 37
FEATURE                    Location/Qualifiers
source                     1..37
                           mol_type = protein
                           organism = Homo sapiens
SEQUENCE: 112
MALVTLQRSP TPSAASSSAS NSELEAGSEE DRKLNLR                            37

SEQ ID NO: 113             moltype = AA  length = 147
FEATURE                    Location/Qualifiers
source                     1..147
                           mol_type = protein
                           organism = Homo sapiens
SEQUENCE: 113
MAGNSILLAA VSILSACQQS YFALQVGKAR LKYKVTPPAV TGSPEFERVF RAQQNCVEFY    60
PIFIITLWMA GWYFNQVFAT CLGLVYIYGR HLYFWGYSEA AKKRITGFRL SLGILALLTL   120
LGALGIANSF LDEYLDLNIA KKLRRQF                                      147

SEQ ID NO: 114             moltype = AA  length = 147
FEATURE                    Location/Qualifiers
source                     1..147
                           mol_type = protein
                           organism = Homo sapiens
SEQUENCE: 114
MAGNSILLAA VSILSACQQS YFALQVGKAR LKYKVTPPAV TGSPEFERVF RAQQNCVEFY    60
PIFIITLWMA GWYFNQVFAT CLGLVYIYGR HLYFWGYSEA AKKRITGFRL SLGILALLTL   120
LGALGIANSF LDEYLDLNIA KKLRRQF                                      147

SEQ ID NO: 115             moltype = AA  length = 77
FEATURE                    Location/Qualifiers
source                     1..77
                           mol_type = protein
                           organism = Homo sapiens
SEQUENCE: 115
MAGNSILLAA VSILSACQQS YFALQVGKAR LKYKVTPPAV TGSPEFERVF RAHFCYLSGS    60
GVHIWPSPIL LGIFRSC                                                  77

SEQ ID NO: 116             moltype = AA  length = 147
FEATURE                    Location/Qualifiers
source                     1..147
                           mol_type = protein
                           organism = Homo sapiens
SEQUENCE: 116
MAGNSILLAA VSILSACQQS YFALQVGKAR LKYKVTPPAV TGSPEFERVF RAQQNCVEFY    60
PIFIITLWMA GWYFNQVFAT CLGLVYIYGR HLYFWGYSEA AKKRITGFRL SLGILALLTL   120
LGALGIANSF LDEYLDLNIA KKLRRQF                                      147

SEQ ID NO: 117             moltype = AA  length = 110
FEATURE                    Location/Qualifiers
source                     1..110
                           mol_type = protein
                           organism = Homo sapiens
SEQUENCE: 117
MPFKSPLKVPA LIQCLGMYDS SLAAKYLLHS LVFGSAVYSS GSERHLTYIQ KIFRMEIFGC    60
FALTELSHGS NTKAIRTTAH YDPATEEFII HSPDFEAAKF WVGNMGKTAT               110

SEQ ID NO: 118             moltype = AA  length = 121
FEATURE                    Location/Qualifiers
```

```
source                       1..121
                             mol_type = protein
                             organism = Homo sapiens
SEQUENCE: 118
XGHQNVFPNH ISVGTNRKRC LEDSEDFGVK KARTEAQSLD SAVPLTNGDT EDDADKMHVD    60
REFAVVTGGS GQFPVSCNNN PMVEDTKQQE SGSVGPKEIE IYTVSAMQTP CRCRNQYAYY   120
F                                                                   121

SEQ ID NO: 119               moltype = AA   length = 37
FEATURE                      Location/Qualifiers
source                       1..37
                             mol_type = protein
                             organism = Homo sapiens
SEQUENCE: 119
MGVQVETISP GDGRTFPKRG QTCVVHYTGG DCILVNE                             37

SEQ ID NO: 120               moltype = AA   length = 129
FEATURE                      Location/Qualifiers
source                       1..129
                             mol_type = protein
                             organism = Homo sapiens
SEQUENCE: 120
MGVQVETISP GDGRTFPKRG QTCVVHYTGM LEDGKKFDSS RDRNKPFKFM LGKQEVIRGW    60
EEGVAQVCSL ICFVLLSSIY LLYFFIGGIF IRFKNKKSEK SHPHAIPSDQ YPHKKLLLLM   120
FLVLWFKHI                                                           129

SEQ ID NO: 121               moltype = AA   length = 97
FEATURE                      Location/Qualifiers
source                       1..97
                             mol_type = protein
                             organism = Homo sapiens
SEQUENCE: 121
MGVQVETISP GDGRTFPKRG QTCVVHYTDE CGSESQTDYI SRLCLWCHWA PRHHPTTCHS    60
RLRCGASKTG MTGMASSLSS LFLDLPWRDL VPPDMCT                             97

SEQ ID NO: 122               moltype = AA   length = 276
FEATURE                      Location/Qualifiers
source                       1..276
                             mol_type = protein
                             organism = Homo sapiens
SEQUENCE: 122
MPVPASWPHP PGPFLLLTLL LGLTEVAGEE ELQMIQPEKL LLVTVGKTAT LHCTVTSLLP    60
VGPVLWFRGV GPGRELIYNQ KEGHFPRVTT VSDLTKRNNM DFSIRISSIT PADVGTYYCV   120
KFRKGSPENV EFKSGPGTEM ALGAKPSAPV VLGPAARTTP EHTVSFTCES HGFSPRDITL   180
KWFKNGNELS DFQTNVDPTG QSVAYSIRST ARVVLDPWDV RSQVICEVAH VTLQGDPLRG   240
TANLSEAIRG PASSLTALLL IAVLLGPIYV PWKQKT                             276

SEQ ID NO: 123               moltype = AA   length = 387
FEATURE                      Location/Qualifiers
source                       1..387
                             mol_type = protein
                             organism = Homo sapiens
SEQUENCE: 123
MPVPASWPHP PGPFLLLTLL LGLTEVAGEE ELQMIQPEKL LLVTVGKTAT LHCTVTSLLP    60
VGPVLWFRGV GPGRELIYNQ KEGHFPRVTT VSDLTKRNNM DFSIRISSIT PADVGTYYCV   120
KFRKGSPENV EFKSGPGTEM ALGAKPSAPV VLGPAARTTP EHTVSFTCES HGFSPRDITL   180
KWFKNGNELS DFQTNVDPTG QSVAYSIRST ARVVLDPWDV RSQVICEVAH VTLQGDPLRG   240
TANLSEAIRV PPTLEVTQQP MRVGNQVNVT CQVRKFYPQS LQLTWSENGN VCQRETASTL   300
TENKDGTYNW TSWFLVNISD QRDDVVLTCQ VKHDGQLAVS KRLALEVTVH QKDQSSDATP   360
GPASSLTALL LIAVLLGPIY VPWKQKT                                       387

SEQ ID NO: 124               moltype = AA   length = 170
FEATURE                      Location/Qualifiers
source                       1..170
                             mol_type = protein
                             organism = Homo sapiens
SEQUENCE: 124
MPVPASWPHP PGPFLLLTLL LGLTEVAGEE ELQMIQPEKL LLVTVGKTAT LHCTVTSLLP    60
VGPVLWFRGV GPGRELIYNQ KEGHFPRVTT VSDLTKRNNM DFSIRISSIT PADVGTYYCV   120
KFRKGSPENV EFKSGPGTEM ALGGPASSLT ALLLIAVLLG PIYVPWKQKT               170

SEQ ID NO: 125               moltype = AA   length = 354
FEATURE                      Location/Qualifiers
source                       1..354
                             mol_type = protein
                             organism = Homo sapiens
SEQUENCE: 125
MIQPEKLLLV TVGKTATLHC TVTSLLPVGP VLWFRGVGPG RELIYNQKEG HFPRVTTVSD    60
LTKRNNMDFS IRISSITPAD VGTYYCVKFR KGSPENVEFK SGPGTEMALG AKPSAPVVLG   120
```

```
PAARTTPEHT VSFTCESHGF SPRDITLKWF KNGNELSDFQ TNVDPTGQSV AYSIRSTARV    180
VLDPWDVRSQ VICEVAHVTL QGDPLRGTAN LSEAIRVPPT LEVTQQPMRV GNQVNVTCQV    240
RKFYPQSLQL TWSENGNVCQ RETASTLTEN KDGTYNWTSW FLVNISDQRD DVVLTCQVKH    300
DGQLAVSKRL ALEVTVHQKD QSSDATPGPA SSLTALLLIA VLLGPIYVPW KQKT          354

SEQ ID NO: 126           moltype = AA   length = 276
FEATURE                  Location/Qualifiers
source                   1..276
                         mol_type = protein
                         organism = Homo sapiens
SEQUENCE: 126
MPVPASWPHP PGPFLLLTLL LGLTEVAGEE ELQMIQPEKL LLVTVGKTAT LHCTVTSLLP     60
VGPVLWFRGV GPGRELIYNQ KEGHFPRVTT VSDLTKRNNM DFSIRISSIT PADVGTYYCV    120
KFRKGSPENV EFKSGPGTEM ALGAKPSAPV VLGPAARTTP EHTVSFTCES HGFSPRDITL    180
KWFKNGNELS DFQTNVDPTG QSVAYSIRST ARVVLDPWDV RSQVICEVAH VTLQGDPLRG    240
TANLSEAIRG PASSLTALLL IAVLLGPIYV PWKQKT                              276

SEQ ID NO: 127           moltype = AA   length = 556
FEATURE                  Location/Qualifiers
source                   1..556
                         mol_type = protein
                         organism = Homo sapiens
SEQUENCE: 127
MHGSLEALLF LPQVTLSLAH AHLICSNAQL EMCVFPHRFL GDLTTEGINK PGFYKGPAGS     60
QVTLSSLGNQ TRVLLEEQAR HLLNEQEHAT MAYYLDEYRG GSVSVEALVM ALFKLLNTHA    120
KFSLLSEVRG TISPQDLERF DHLVLRRREIE SMKARQPGP GAGDTYSMVS YSDTGSSTGS    180
HGTSTTVSSA RNTLDLEETG EAVQGNINAL PDVSVDDVRS TSQGLSSFKP LPRPPPLAQG    240
NDLPLGQPRK LGREDLQPPS SMPSCSGTVF SAPQNRSPPA GTAPTPGTSS AQDLPSSPIY    300
ASVSPANPSS KRPLDAHLAL VNQHPIGPFP RVQSPPHLKS PSAEATVAGG CLLPPSPSGH    360
PDQTGTNQHF VMVEVHRPDS EPDVNEVRAL PQTRTASTLS QLSDSGQTLS EDSGVDAGEA    420
EASAPGRGRQ SVSTKSRSSK ELPRNERPTD GANKPPGLLE PTSTLVRVKK SAATLGIAIE    480
GGANTRQPLP RIVTIQRGGS AHNCGQLKVG HVILEVNGLT LRGKEHREAA RIIAEAFKTK    540
DRDYIDFLVT EFNVML                                                   556

SEQ ID NO: 128           moltype = AA   length = 180
FEATURE                  Location/Qualifiers
source                   1..180
                         mol_type = protein
                         organism = Homo sapiens
SEQUENCE: 128
MSVLRPLDKL PGLNTATILL VGTEDALLQQ LADSMLKEDC ASELKVHLAK SLPLPSSVNR     60
PRIDLIVFVV NLHSKYSLQN TEESLRHVDA SFFLGKVCFL ATGAGRESHC SIHRHTVVKL    120
AHTYQSPLLY CDLEVEGFRA TMAQRLVRVL QICAGHVPGV SALNLLSLLR SSEGPSLEDL    180

SEQ ID NO: 129           moltype = AA   length = 146
FEATURE                  Location/Qualifiers
source                   1..146
                         mol_type = protein
                         organism = Homo sapiens
SEQUENCE: 129
MLKEDCASEL KVHLAKSLPL PSSVNRPRID LIVFVVNLHS KYSLQNTEES LRHVDASFFL     60
GKVCFLATGA GRESHCSIHR HTVVKLAHTY QSPLLYCDLE VEGFRATMAQ RLVRVLQICA    120
GHVPGVSALN LLSLLRSSEG PSLEDL                                         146

SEQ ID NO: 130           moltype = AA   length = 125
FEATURE                  Location/Qualifiers
source                   1..125
                         mol_type = protein
                         organism = Homo sapiens
SEQUENCE: 130
MLKEDCASEL KVHLAKSLPL PSSVNRPRID LIVFVVNLHS KYRIREARTS AFSVVKFCSL     60
VCFLTLAWPP QSPEHRGVPA PCGCQLLLGE GVFPRHRCWA GEPLQHSPAH RGEAGPHLSK    120
PPALL                                                                125

SEQ ID NO: 131           moltype = AA   length = 73
FEATURE                  Location/Qualifiers
source                   1..73
                         mol_type = protein
                         organism = Homo sapiens
SEQUENCE: 131
MLKEDCASEL KVHLAKSLPL PSSVNRPRID LIVFVVNLHS KYSLQNTEES LRHVDASFFL     60
GKVCFLATGG GRL                                                        73

SEQ ID NO: 132           moltype = AA   length = 107
FEATURE                  Location/Qualifiers
source                   1..107
                         mol_type = protein
                         organism = Homo sapiens
SEQUENCE: 132
```

```
MSVLRPLDKL PGLNTATILL VGTEDALLQQ LADSMLKEDC ASELKVHLAK SLPLPSSVNR   60
PRIDLIVFVV NLHSKYSLQN TEESLRHVDA SFFLGKVCFL ATGGGRL               107

SEQ ID NO: 133            moltype = AA   length = 166
FEATURE                   Location/Qualifiers
source                    1..166
                          mol_type = protein
                          organism = Homo sapiens
SEQUENCE: 133
MRIPALNAYM KSLLSLPVWV LMDEDVRIFF YQSPYDSEQV PQALRRLRPR TRKVKSVSPQ   60
GNSVDRMAAP RAEALFDFTG NSKLELNFKA GDVIFLLSRI NKDWLEGTVR GATGIFPLSF  120
VKILKDFPEE DDPTNWLRCY YYEDTISTIK SVAWEGGACP AFLPSL                166

SEQ ID NO: 134            moltype = AA   length = 889
FEATURE                   Location/Qualifiers
source                    1..889
                          mol_type = protein
                          organism = Homo sapiens
SEQUENCE: 134
MVLAQGLLSM ALLALCWERS LAGAEETIPL QTLRCYNDYT SHITCRWADT QDAQRLVNVT   60
LIRRVNEDLL EPVSCDLSDD MPWSACPHPR CVPRRCVIPC QSFVVTDVDY FSFQPDRPLG  120
TRLTVTLTQH VQPPEPRDLQ ISTDQDHFLL TWSVALGSPQ SHWLMSPGDLE FEVVYKRLQD  180
SWEDAAILLS NTSQATLGPE HLMPSSTYVA RVRTRLAPGS RLSGRPSKWS PEVCWDSQPG  240
DEAQPQNLEC FFDGAAVLSC SWEVRKEVAS SVSFGLFYKP SPDAGEEECS PVLREGLGSL  300
HTRHHCQIPV PDPATHGQYI VSVQPRRAEK HIKSSVNIQM APPSLNVTKD GDSYSLRWET  360
MKMRYEHIDH TFEIQYRKDT ATWKDSKTET LQNAHSMALP ALEPSTRYWA RVRVRTSRTG  420
YNGIWSEWSE ARSWDTESVL PMWVLALIVI FLTIAVLLAL RFCGIYGYRL RRKWEEKIPN  480
PSKSHLFQNG SAELWPPGSM SAFTSGSPPH QGPWGSRFPE LEGVFPVGFG DSEVSPLTIE  540
DPKHVCDPPS GPDTTPAASD LPTEQPPSPQ PGPPAASHTP EKQASSFDFN GPYLGPPHSR  600
SLPDILGQPE PPQEGGSQKS PPPGSLEYLC LPAGGQVQLV PLAQAMGPGQ AVEVERRPSQ  660
GAAGSPSLES GGGPAPPALG PRVGGQDQKD SPVAIPMSSG DTEDPGVASG YVSSADLVFT  720
PNSGASSVSL VPSLGLPSDQ TPSLCPGLAS GPPGAPGPVK SGFEGYVELP PIEGRSPRSP  780
RNNPVPPEAK SPVLNPGERP ADVSPTSPQP EGLLVLQQVG DYCFLPGLGP GPLSLRSKPS  840
SPGPGPEIKN LDQAFQVKKP PGQAVPQVPV IQLFKALVVS VMSVGPPVP             889

SEQ ID NO: 135            moltype = AA   length = 897
FEATURE                   Location/Qualifiers
source                    1..897
                          mol_type = protein
                          organism = Homo sapiens
SEQUENCE: 135
MVLAQGLLSM ALLALCWERS LAGAEETIPL QTLRCYNDYT SHITCRWADT QDAQRLVNVT   60
LIRRVNEDLL EPVSCDLSDD MPWSACPHPR CVPRRCVIPC QSFVVTDVDY FSFQPDRPLG  120
TRLTVTLTQH VQPPEPRDLQ ISTDQDHFLL TWSVALGSPQ SHWLSPGDLE FEVVYKRLQD  180
SWEDAAILLS NTSQATLGPE HLMPSSTYVA RVRTRLAPGS RLSGRPSKWS PEVCWDSQPG  240
DEAQPQNLEC FFDGAAVLSC SWEVRKEVAS SVSFGLFYKP SPDAGEEECS PVLREGLGSL  300
HTRHHCQIPV PDPATHGQYI VSVQPRRAEK HIKSSVNIQM APPSLNVTKD GDSYSLRWET  360
MKMRYEHIDH TFEIQYRKDT ATWKDSKTET LQNAHSMALP ALEPSTRYWA RVRVRTSRTG  420
YNGIWSEWSE ARSWDTESVL PMWVLALIVI FLTIAVLLAL RFCGIYGYRL RRKWEEKIPN  480
PSKSHLFQNG SAELWPPGSM SAFTSGSPPH QGPWGSRFPE LEGVFPVGFG DSEVSPLTIE  540
DPKHVCDPPS GPDTTPAASD LPTEQPPSPQ PGPPAASHTP EKQASSFDFN GPYLGPPHSR  600
SLPDILGQPE PPQEGGSQKS PPPGSLEYLC LPAGGQVQLV PLAQAMGPGQ AVEVERRPSQ  660
GAAGSPSLES GGGPAPPALG PRVGGQDQKD SPVAIPMSSG DTEDPGVASG YVSSADLVFT  720
PNSGASSVSL VPSLGLPSDQ TPSLCPGLAS GPPGAPGPVK SGFEGYVELP PIEGRSPRSP  780
RNNPVPPEAK SPVLNPGERP ADVSPTSPQP EGLLVLQQVG DYCFLPGLGP GPLSLRSKPS  840
SPGPGPEIKN LDQAFQVKKP PGQAVPQVPV IQLFKALKQQ DYLSLPPWEV NKPGEVC     897

SEQ ID NO: 136            moltype = AA   length = 903
FEATURE                   Location/Qualifiers
source                    1..903
                          mol_type = protein
                          organism = Homo sapiens
SEQUENCE: 136
MVLAQGLLSM ALLALCWERS LAGAEETIPL QTLRCYNDYT SHITCRWADT QDAQRLVNVT   60
LIRRVNEDLL EPVSCDLSDD MPWSACPHPR CVPRRCVIPC QSFVVTDVDY FSFQPDRPLG  120
TRLTVTLTQH VQPPEPRDLQ ISTDQDHFLL TWSVALGSPQ SHWLSPGDLE FEVVYKRLQD  180
SWEDAAILLS NTSQATLGPE HLMPSSTYVA RVRTRLAPGS RLSGRPSKWS PEVCWDSQPG  240
DEAQPQNLEC FFDGAAVLSC SWEVRKEVAS SVSFGLFYKP SPDAGSAVLL REEECSPVLR  300
EGLGSLHTRH HCQIPVPDPA THGQYIVSVQ PRRAEKHIKS SVNIQMAPPS LNVTKDGDSY  360
SLRWETMKMR YEHIDHTFEI QYRKDTATWK DSKTETLQNA HSMALPALEP STRYWARVRV  420
RTSRTGYNGI WSEWSEARSW DTESVLPMWV LALIVIFLTI AVLLALRFCG IYGYRLRRKW  480
EEKIPNPSKS HLFQNGSAEL WPPGSMSAFT SGSPPHQGPW GSRFPELEGV FPVGFGDSEV  540
SPLTIEDPKH VCDPPSGPDT TPAASDLPTE QPPSPQPGPP AASHTPEKQA SSFDFNGPYL  600
GPPHSRSLPD ILGQPEPPQE GGSQKSPPPG SLEYLCLPAG GQVQLVPLAQ AMGPGQAVEV  660
ERRPSQGAAG SPSLESGGGP APPALGPRVG GQDQKDSPVA IPMSSGDTED PGVASGYVSS  720
ADLVFTPNSG ASSVSLVPSL GLPSDQTPSL CPGLASGPPG APGPVKSGFE GYVELPPIEG  780
RSPRSPRNNP VPPEAKSPVL NPGERPADVS PTSPQPEGLL VLQQVGDYCF LPGLGPGPLS  840
LRSKPSSPGP GPEIKNLDQA FQVKKPPGQA VPQVPVIQLF KALKQQDYLS LPPWEVNKPG  900
EVC                                                               903
```

```
SEQ ID NO: 137          moltype = AA  length = 229
FEATURE                 Location/Qualifiers
source                  1..229
                        mol_type = protein
                        organism = Homo sapiens
SEQUENCE: 137
MPWSACPHPR CVPRRCVIPC QSFVVTDVDY FSFQPDRPLG TRLTVTLTQH VQPPEPRDLQ    60
ISTDQDHFLL TWSVALGSPQ SHWLSPGDLE FEVVYKRLQD SWEDAAILLS NTSQATLGPE   120
HLMPSSTYVA RVRTRLAPGS RLSGRPSKWS PEVCWDSQPG DEAQPQNLEC FFDGAAVLSC   180
SWEVRKEVAS SVSFGLFYKP SPDAGEEECS PVLREGLGSL HTRHHCQIP              229

SEQ ID NO: 138          moltype = AA  length = 144
FEATURE                 Location/Qualifiers
source                  1..144
                        mol_type = protein
                        organism = Homo sapiens
SEQUENCE: 138
MAFTFAAFCY MLALLLTAAL IFFAIWHIIA FDELKTDYKN PIDQCNTLNP LVLPEYLIHA    60
FFCVMFLCAA EWLTLGLNMP LLAYHIWRYM SRPVMSGPGL YDPTTIMNAD ILAYCQKEGW   120
CKLAFYLLAF FYYLYGMIYV LVSS                                         144

SEQ ID NO: 139          moltype = AA  length = 96
FEATURE                 Location/Qualifiers
source                  1..96
                        mol_type = protein
                        organism = Homo sapiens
SEQUENCE: 139
MAFTFAAFCY MLALLLTAAL IFFAIWHIIA FDELKTDYKN PIDQCNTLNP LVLPEYLIHA    60
FFCVMFLCAA EWLTLGLNMP LLAYHIWSMI YVLVSS                             96

SEQ ID NO: 140          moltype = AA  length = 121
FEATURE                 Location/Qualifiers
source                  1..121
                        mol_type = protein
                        organism = Homo sapiens
SEQUENCE: 140
MAFTFAAFCY MLALLLTAAL IFFAIWHLVL PEYLIHAFFC VMFLCAAEWL TLGLNMPLLA    60
YHIWRYMSRP VMSGPGLYDP TTIMNADILA YCQKEGWCKL AFYLLAFFYY LYGMIYVLVS   120
S                                                                  121

SEQ ID NO: 141          moltype = AA  length = 33
FEATURE                 Location/Qualifiers
source                  1..33
                        mol_type = protein
                        organism = Homo sapiens
SEQUENCE: 141
MAFTFAAFCY MLALLLTAAL IFFAIWHDKE EFG                                33

SEQ ID NO: 142          moltype = AA  length = 136
FEATURE                 Location/Qualifiers
source                  1..136
                        mol_type = protein
                        organism = Homo sapiens
SEQUENCE: 142
MAFTFAAFCY MLALLLTAAL IFFAIWHIIA FDELKTDYKN PIDQCNTLNP LVLPEYLIHA    60
FFCVMFLCAA EWLTLGLNMP LLAYHIWRYM SRPVMSGPGL YDPTTIMNAD ILAYCQKEGW   120
CKLAFYLLAF FYYLYG                                                  136

SEQ ID NO: 143          moltype = AA  length = 53
FEATURE                 Location/Qualifiers
source                  1..53
                        mol_type = protein
                        organism = Homo sapiens
SEQUENCE: 143
MAFTFAAFCY MLALLLTAAL IFFAIWHIIA FDELKTDYKN PIDQCNTLNP VYE           53

SEQ ID NO: 144          moltype = AA  length = 160
FEATURE                 Location/Qualifiers
source                  1..160
                        mol_type = protein
                        organism = Homo sapiens
SEQUENCE: 144
MAFTFAAFCY MLALLLTAAL IFFAIWHIIA FDELKTDYKN PIDQCNTLNP TVEKVKKIKR    60
VKIALKLVLP EYLIHAFFCV MFLCAAEWLT LGLNMPLLAY HIWRYMSRPV MSGPGLYDPT   120
TIMNADILAY CQKEGWCKLA FYLLAFFYYL YGMIYVLVSS                        160

SEQ ID NO: 145          moltype = AA  length = 435
FEATURE                 Location/Qualifiers
```

```
source                  1..435
                        mol_type = protein
                        organism = Homo sapiens
SEQUENCE: 145
MAAPLVLVLV VAVTVRAALF RSSLAEFISE RVEVVSPLSS WKRVVEGLSL LDLGVSPYSG    60
AVFHETPLII YLFHFLIDYA ELVFMITDAL TAIALYFAIQ DFNKVVFKKQ KLLLELDQYA   120
PDVAELIRTP MEMRYIPLKV ALFYLLNPYT ILSCVAKSTC AINNTLIAFF ILTTIKGSAF   180
LSAIFLALAT YQSLYPLTLF VPGLLYLLQR QYIPVKMKSK AFWIFSWEYA MMYVGSLVVI   240
ICLSFFLLSS WDFIPAVYGF ILSVPDLTPN IGLFWYFFAE MFEHFSLFFV CVFQINVFFY   300
TIPLAIKLKE HPIFFMFIQI AVIAIFKSYP TVGDVALYMA FFPVWNHLYR FLRNIFVLTC   360
IIIVCSLLFP VLWHLWIYAG SANSNFFYAI TLTFNVGQIL LISDYFYAFL RREYYLTHGL   420
YLTAKDGTEA MLVLK                                                   435

SEQ ID NO: 146          moltype = AA  length = 415
FEATURE                 Location/Qualifiers
source                  1..415
                        mol_type = protein
                        organism = Homo sapiens
SEQUENCE: 146
MAAPLVLVLV VAVTVRAALF RSSLAEFISE RVEVVSPLSS WKRVVEGLSL LDLGVSPYSG    60
AVFHEITDAL TAIALYFAIQ DFNKVVFKKQ KLLLELDQYA PDVAELIRTP MEMRYIPLKV   120
ALFYLLNPYT ILSCVAKSTC AINNTLIAFF ILTTIKGSAF LSAIFLALAT YQSLYPLTLF   180
VPGLLYLLQR QYIPVKMKSK AFWIFSWEYA MMYVGSLVVI ICLSFFLLSS WDFIPAVYGF   240
ILSVPDLTPN IGLFWYFFAE MFEHFSLFFV CVFQINVFFY TIPLAIKLKE HPIFFMFIQI   300
AVIAIFKSYP TVGDVALYMA FFPVWNHLYR FLRNIFVLTC IIIVCSLLFP VLWHLWIYAG   360
SANSNFFYAI TLTFNVGQIL LISDYFYAFL RREYYLTHGL YLTAKDGTEA MLVLK        415

SEQ ID NO: 147          moltype = AA  length = 170
FEATURE                 Location/Qualifiers
source                  1..170
                        mol_type = protein
                        organism = Homo sapiens
SEQUENCE: 147
VSVPTHLVCP RTPLSPPAAV HTCENEEQSL LDLFLGVCHD INVFFYTIPL AIKLKEHPIF    60
FMFIQIAVIA IFKSYPTVGD VALYMAFFPV WNHLYRFLRN IFVLTCIIIV CSLLFPVLWH   120
LWIYAGSANS NFFYAITLTF NVGQILLISD YFYAFLRREY YLTHGLYLTA              170

SEQ ID NO: 148          moltype = AA  length = 336
FEATURE                 Location/Qualifiers
source                  1..336
                        mol_type = protein
                        organism = Homo sapiens
SEQUENCE: 148
MARRRSQRVC ASGPSMLNSA RGAPELLRGT ATNAEVSAAA AGATGSEELP PGDRGCRNGG    60
GRGPAATTSS TGVAVGAEHG EDSLSRKPDP EPGRMDHHQP GTGRYQVLLN EEDNSESSAI   120
EQPPTSNPAP QIVQAASSAP ALETDSSPPP YSSITVEVPT TSDTEVYGEF YPVPPPYSVA   180
TSLPTYDEAE KAKAAAMAAA AAETSQRIQE EECPPRDDFS DADQLRVGND GIFMLAFFMA   240
FIFNWLGFCL SFCITNTIAG RYGAICGFGL SLIKWILIVR FSDYFTGYFN GQYWLWWIFL   300
VLGLLLFFRG FVNYLKVRNM SESMAAAHRT RYFFLL                            336

SEQ ID NO: 149          moltype = AA  length = 222
FEATURE                 Location/Qualifiers
source                  1..222
                        mol_type = protein
                        organism = Homo sapiens
SEQUENCE: 149
MDHHQPGTGR YQVLLNEEDN SESSAIEQPP TSNPAPQIVQ AASSAPALET DSSPPPYSSI    60
TVEVPTTSDT EVYGEFYPVP PPYSVATSLP TYDEAEKAKA AAMAAAAAET SQRIQEEECP   120
PRDDFSDADQ LRVGNDGIFM LAFFTGRYGA ICGFGLSLIK WILIVRFSDY FTGYFNGQYW   180
LWWIFLVLGL LLFFRGFVNY LKVRNMSESM AAAHRTRYFF LL                      222

SEQ ID NO: 150          moltype = AA  length = 336
FEATURE                 Location/Qualifiers
source                  1..336
                        mol_type = protein
                        organism = Homo sapiens
SEQUENCE: 150
MARRRSQRVC ASGPSMLNSA RGAPELLRGT ATNAEVSAAA AGATGSEELP PGDRGCRNGG    60
GRGPAATTSS TGVAVGAEHG EDSLSRKPDP EPGRMDHHQP GTGRYQVLLN EEDNSESSAI   120
EQPPTSNPAP QIVQAASSAP ALETDSSPPP YSSITVEVPT TSDTEVYGEF YPVPPPYSVA   180
TSLPTYDEAE KAKAAAMAAA AAETSQRIQE EECPPRDDFS DADQLRVGND GIFMLAFFMA   240
FIFNWLGFCL SFCITNTIAG RYGAICGFGL SLIKWILIVR FSDYFTGYFN GQYWLWWIFL   300
VLGLLLFFRG FVNYLKVRNM SESMAAAHRT RYFFLL                            336

SEQ ID NO: 151          moltype = AA  length = 242
FEATURE                 Location/Qualifiers
source                  1..242
                        mol_type = protein
                        organism = Homo sapiens
```

```
SEQUENCE: 151
MDHHQPGTGR YQVLLNEEDN SESSAIEQPP TSNPAPQIVQ AASSAPALET DSSPPPYSSI    60
TVEVPTTSDT EVYGEFYPVP PPYSVATSLP TYDEAEKAKA AAMAAAAAET SQRIQEEECP   120
PRDDFSDADQ LRVGNDGIFM LAFFMAFIFN WLGFCLSFCI TNTIAGRYGA ICGFGLSLIK   180
WILIVRFSDY FTGYFNGQYW LWWIFLVLGL LLFFRGFVNY LKVRNMSESM AAAHRTRYFF   240
LL                                                                 242

SEQ ID NO: 152        moltype = AA  length = 325
FEATURE               Location/Qualifiers
source                1..325
                      mol_type = protein
                      organism = Homo sapiens
SEQUENCE: 152
MDMWTALLIL QALLLPSLAD GATPALRFVA VGDWGGVPNA PFHTAREMAN AKEIARTVQI    60
LGADFILSLG DNFYFTGVQD INDKRFQETF EDVFSDRSLR KVPWYVLAGN HDHLGNVSAQ   120
IAYSKISKRW NFPSPFYRLH FKIPQTNVSV AIFMLDTVTL CGNSDDFLSQ QPERPRDVKL   180
ARTQLSWLKK QLAAAREDYV LVAGHYPVWS IAEHGPTHCL VKQLRPLLAT YGVTAYLCGH   240
DHNLQYLQDE NGVGYVLSGA GNFMDPSKRH QRKVPNGYLR FHYGTEDSLG GFAYVEISSK   300
EMTVTYIEAS GKSLFKTRLP RRARP                                        325

SEQ ID NO: 153        moltype = AA  length = 325
FEATURE               Location/Qualifiers
source                1..325
                      mol_type = protein
                      organism = Homo sapiens
SEQUENCE: 153
MDMWTALLIL QALLLPSLAD GATPALRFVA VGDWGGVPNA PFHTAREMAN AKEIARTVQI    60
LGADFILSLG DNFYFTGVQD INDKRFQETF EDVFSDRSLR KVPWYVLAGN HDHLGNVSAQ   120
IAYSKISKRW NFPSPFYRLH FKIPQTNVSV AIFMLDTVTL CGNSDDFLSQ QPERPRDVKL   180
ARTQLSWLKK QLAAAREDYV LVAGHYPVWS IAEHGPTHCL VKQLRPLLAT YGVTAYLCGH   240
DHNLQYLQDE NGVGYVLSGA GNFMDPSKRH QRKVPNGYLR FHYGTEDSLG GFAYVEISSK   300
EMTVTYIEAS GKSLFKTRLP RRARP                                        325

SEQ ID NO: 154        moltype = AA  length = 325
FEATURE               Location/Qualifiers
source                1..325
                      mol_type = protein
                      organism = Homo sapiens
SEQUENCE: 154
MDMWTALLIL QALLLPSLAD GATPALRFVA VGDWGGVPNA PFHTAREMAN AKEIARTVQI    60
LGADFILSLG DNFYFTGVQD INDKRFQETF EDVFSDRSLR KVPWYVLAGN HDHLGNVSAQ   120
IAYSKISKRW NFPSPFYRLH FKIPQTNVSV AIFMLDTVTL CGNSDDFLSQ QPERPRDVKL   180
ARTQLSWLKK QLAAAREDYV LVAGHYPVWS IAEHGPTHCL VKQLRPLLAT YGVTAYLCGH   240
DHNLQYLQDE NGVGYVLSGA GNFMDPSKRH QRKVPNGYLR FHYGTEDSLG GFAYVEISSK   300
EMTVTYIEAS GKSLFKTRLP RRARP                                        325

SEQ ID NO: 155        moltype = AA  length = 74
FEATURE               Location/Qualifiers
source                1..74
                      mol_type = protein
                      organism = Homo sapiens
SEQUENCE: 155
MDMWTALLIL QALLLPSLAD GATPALRFVA VGDWGGVPNA PFHTAREMAN AKEIARTVQI    60
LGADFILSLG DNFY                                                     74

SEQ ID NO: 156        moltype = AA  length = 59
FEATURE               Location/Qualifiers
source                1..59
                      mol_type = protein
                      organism = Homo sapiens
SEQUENCE: 156
MDMWTALLIL QALLLPSLGI SWTPQSGTSA RSPTAICAST MGLKTHWVAL PMWRSAPKR     59

SEQ ID NO: 157        moltype = AA  length = 124
FEATURE               Location/Qualifiers
source                1..124
                      mol_type = protein
                      organism = Homo sapiens
SEQUENCE: 157
MDMWTALLIL QALLLPSLAD GATPALRFVA VGDWGGVPNA PFHTAREMAN AKEIARTVQI    60
LGADFILSLG DNFYFTGVQD INDKRFQETF EDVFSDRSLR KVPWYVLAGN HDHLGNVSAQ   120
IAYS                                                               124

SEQ ID NO: 158        moltype = AA  length = 52
FEATURE               Location/Qualifiers
source                1..52
                      mol_type = protein
                      organism = Homo sapiens
SEQUENCE: 158
```

```
MDMWTALLIL QALLLPSLAD GATPALRFVA VGDWGGVPNA PFHTAREMAN AK              52

SEQ ID NO: 159           moltype = AA  length = 325
FEATURE                  Location/Qualifiers
source                   1..325
                         mol_type = protein
                         organism = Homo sapiens
SEQUENCE: 159
MDMWTALLIL QALLLPSLAD GATPALRFVA VGDWGGVPNA PFHTAREMAN AKEIARTVQI      60
LGADFILSLG DNFYFTGVQD INDKRFQETF EDVFSDRSLR KVPWYVLAGN HDHLGNVSAQ     120
IAYSKISKRW NFPSPFYRLH FKIPQTNVSV AIFMLDTVTL CGNSDDFLSQ QPERPRDVKL     180
ARTQLSWLKK QLAAAREDYV LVAGHYPVWS IAEHGPTHCL VKQLRPLLAT YGVTAYLCGH     240
DHNLQYLQDE NGVGYVLSGA GNFMDPSKRH QRKVPNGYLR FHYGTEDSLG GFAYVEISSK     300
EMTVTYIEAS GKSLFKTRLP RRARP                                          325

SEQ ID NO: 160           moltype = AA  length = 119
FEATURE                  Location/Qualifiers
source                   1..119
                         mol_type = protein
                         organism = Homo sapiens
SEQUENCE: 160
MPSDFISLLS ADLDLESPKS LYSRDSLKLH PSQNFHRAGL LEESVYDLLP KELQLPPSRE      60
TSVASMSQTS GGEAGSPPPA VVAAGIPEMF ILCILMCMIL RFKKGFASEA GSVCIKNDL     119

SEQ ID NO: 161           moltype = AA  length = 150
FEATURE                  Location/Qualifiers
source                   1..150
                         mol_type = protein
                         organism = Homo sapiens
SEQUENCE: 161
MSGSMATAEA SGSDGKGQEV ETSVTYYRLE EVAKRNSLKE LWLVIHGRVY DVTRFLNEHP      60
GGEEVLLEQA GVDASESFED VGHSSDAREM LKQYYIGDIH PSDLKPESGS KDPSKNDTCK     120
SCWAYWILPI IGAVLLGFLY RYYTSESKSS                                     150

SEQ ID NO: 162           moltype = AA  length = 146
FEATURE                  Location/Qualifiers
source                   1..146
                         mol_type = protein
                         organism = Homo sapiens
SEQUENCE: 162
MATAEASGSD GKGQEVETSV TYYRLEEVAK RNSLKELWLV IHGRVYDVTR FLNEHPGGEE      60
VLLEQAGVDA SESFEDVGHS SDAREMLKQY YIGDIHPSDL KPESGSKDPS KNDTCKSCWA     120
YWILPIIGAV LLGFLYRYYT SESKSS                                         146

SEQ ID NO: 163           moltype = AA  length = 64
FEATURE                  Location/Qualifiers
source                   1..64
                         mol_type = protein
                         organism = Homo sapiens
SEQUENCE: 163
KRNSLKELWL VIHGRVYDVT RFLNEDPSKN DTCKSCWAYW ILPIIGAVLL GFLYRYYTSE      60
SKSS                                                                  64

SEQ ID NO: 164           moltype = AA  length = 317
FEATURE                  Location/Qualifiers
source                   1..317
                         mol_type = protein
                         organism = Homo sapiens
SEQUENCE: 164
MTSRTRVTWP SPPRPLPVPA AAVAFGAKG TDPAEARSSR GIEEAGPRAH GRAGREPERR       60
RSRQQRRGGL QARRSTLLKT CARARATAPG AMKMVAPWTR FYSNSCCLCC HVRTGTILLG     120
VWYLIINAVV LLILLSALAD PDQYNFSSSE LGGDFEFMDD ANMCIAIAIS LLMILICAMA     180
TYGAYKQRAA WIIPFFCYQI FDFALNMLVA ITVLIYPNSI QEYIRQLPPN FPYRDDVMSV     240
NPTCLVLIIL LFISIILTFK GYLISCVWNC YRYINGRNSS DVLVYVTSND TTVLLPPYDD     300
ATVNGAAKEP PPPYVSA                                                   317

SEQ ID NO: 165           moltype = AA  length = 152
FEATURE                  Location/Qualifiers
source                   1..152
                         mol_type = protein
                         organism = Homo sapiens
SEQUENCE: 165
MKMVAPWTRF YSNSCCLCCH VRTGTILLGV WYLIINAVVL LILLSALADP DQYNFSSSEL      60
GGDFEFMDDA KILFNLSADM CIAIAISLLM ILICAMATYG AYKQRAAWII PFFCYQIFDF     120
ALNMLVAITV LIYPNSIQEY IRQLPPNFPY RD                                  152

SEQ ID NO: 166           moltype = AA  length = 226
FEATURE                  Location/Qualifiers
source                   1..226
```

```
                         mol_type = protein
                         organism = Homo sapiens
SEQUENCE: 166
MKMVAPWTRF YSNSCCLCCH VRTGTILLGV WYLIINAVVL LILLSALADP DQYNFSSSEL    60
GGDFEFMDDA NMCIAIAISL LMILICAMAT YGAYKQRAAW IIPFFCYQIF DPALNMLVAI   120
TVLIYPNSIQ EYIRQLPPNF PYRDDVMSVN PTCLVLIILL FISIILTFKG YLISCVWNCY   180
RYINGRNSSD VLVYVTSNDT TVLLPPYDDA TVNGAAKEPP PPYVSA                  226

SEQ ID NO: 167           moltype = AA  length = 317
FEATURE                  Location/Qualifiers
source                   1..317
                         mol_type = protein
                         organism = Homo sapiens
SEQUENCE: 167
MTSRTRVTWP SPPRPLPVPA AAAVAFGAKG TDPAEARSSR GIEEAGPRAH GRAGREPERR    60
RSRQQRRGGL QARRSTLLKT CARARATAPG AMKMVAPWTR FYSNSCCLCC HVRTGTILLG   120
VWYLIINAVV LLILLSALAD PDQYNFSSSE LGGDFEFMDD ANMCIAIAIS LLMILICAMA   180
TYGAYKQRAA WIIPFFCYQI FDFALNMLVA ITVLIYPNSI QEYIRQLPPN FPYRDDVMSV   240
NPTCLVLIIL LFISIILTFK GYLISCVWNC YRYINGRNSS DVLVYVTSND TTVLLPPYDD   300
ATVNGAAKEP PPYVSA                                                  317

SEQ ID NO: 168           moltype = AA  length = 177
FEATURE                  Location/Qualifiers
source                   1..177
                         mol_type = protein
                         organism = Homo sapiens
SEQUENCE: 168
MFHVSFRYIF GLPPLILVLL PVASSDCDIE GKDGKQYESV LMVSIDQLLD SMKEIGSNCL    60
NNEFNFFKRH ICDANKEGMF LFRAARKLRQ FLKMNSTGDF DLHLLKVSEG TTILLNCTGQ   120
VKGRKPAALG EAQPTKSLEE NKSLKEQKKL NDLCFLKRLL QEIKTCWNKI LMGTKEH      177

SEQ ID NO: 169           moltype = AA  length = 115
FEATURE                  Location/Qualifiers
source                   1..115
                         mol_type = protein
                         organism = Homo sapiens
SEQUENCE: 169
MFHVSFRYIF GLPPLILVLL PVASSDCDIE GKDGKQYESV LMVSIDQLLD SMKEIGSNCL    60
NNEFNFFKRH ICDANKEENK SLKEQKKLND LCFLKRLLQE IKTCWNKILM GTKEH        115

SEQ ID NO: 170           moltype = AA  length = 71
FEATURE                  Location/Qualifiers
source                   1..71
                         mol_type = protein
                         organism = Homo sapiens
SEQUENCE: 170
MFHVSFRYIF GLPPLILVLL PVASSDCDIE GKDGKQYESV LMVSIDQLLN QPYKKKEKRT    60
ERKQQSAMSN N                                                        71

SEQ ID NO: 171           moltype = AA  length = 37
FEATURE                  Location/Qualifiers
source                   1..37
                         mol_type = protein
                         organism = Homo sapiens
SEQUENCE: 171
MFHVSFRYIF GLPPLILVLL PVASSDCDIE GQHERNW                             37

SEQ ID NO: 172           moltype = AA  length = 133
FEATURE                  Location/Qualifiers
source                   1..133
                         mol_type = protein
                         organism = Homo sapiens
SEQUENCE: 172
MFHVSFRYIF GLPPLILVLL PVASSDCDIE GKDGKQYESV LMVSIDQLLD SMKEIGSNCL    60
NNEFNFFKRH ICDANKVKGR KPAALGEAQP TKSLEENKSL KEQKKLNDLC FLKRLLQEIK   120
TCWNKILMGT KEH                                                     133

SEQ ID NO: 173           moltype = AA  length = 37
FEATURE                  Location/Qualifiers
source                   1..37
                         mol_type = protein
                         organism = Homo sapiens
SEQUENCE: 173
MFHVSFRYIF GLPPLILVLL PVASSDCDIE GQHERNW                             37

SEQ ID NO: 174           moltype = AA  length = 159
FEATURE                  Location/Qualifiers
source                   1..159
                         mol_type = protein
```

```
                            organism = Homo sapiens
SEQUENCE: 174
MPHVSFRYIF GLPPLILVLL PVASSDCDIE GKDGKQYESV LMVSIDQLLD SMKEIGSNCL    60
NNEFNFFKRH ICDANKEGMF LFRAARKLRQ FLKMNSTGDF DLHLLKVSEG TTILLNCTGQ   120
EENKSLKEQK KLNDLCFLKR LLQEIKTCWN KILMGTKEH                          159

SEQ ID NO: 175              moltype = AA   length = 229
FEATURE                     Location/Qualifiers
source                      1..229
                            mol_type = protein
                            organism = Homo sapiens
SEQUENCE: 175
MTPQLLLALV LWASCPPCSG RKGPPAALTL PRVQCRASRY PIAVDCSWTL PPAPNSTSPV    60
SFIATYRLGM AARGHSWPCL QQTPTSTSCT ITDVQLFSMA PYVLNVTAVH PWGSSSSFVP   120
FITEHIIKPD PPEGVRLSPL AERQLQVQWE PPGSWPFPEI FSLKYWIRYK RQGAARFHRV   180
GPIEATSFIL RAVRPRARYY VQVAAQDLTD YGELSDWSLP ATATMSLGK               229

SEQ ID NO: 176              moltype = AA   length = 130
FEATURE                     Location/Qualifiers
source                      1..130
                            mol_type = protein
                            organism = Homo sapiens
SEQUENCE: 176
XMLENWTRTS LEKQEQPHED PERKGSLSNL MDFVKKTGIC ASKWEWGTTH NFLYKHGGIR    60
DKIMSSRKHL HLVDAGLAIN TPFPLVLPPT REVHLILSFD FSAGDPFEHP RSATSNELLC   120
MSVSSAVKLG                                                          130

SEQ ID NO: 177              moltype = AA   length = 36
FEATURE                     Location/Qualifiers
source                      1..36
                            mol_type = protein
                            organism = Homo sapiens
SEQUENCE: 177
MRTRPRPRLR LECNGMISAH WHLHLLSSSD SPPSAS                              36

SEQ ID NO: 178              moltype = AA   length = 47
FEATURE                     Location/Qualifiers
source                      1..47
                            mol_type = protein
                            organism = Homo sapiens
SEQUENCE: 178
MKEQGLLDAV TYLAGVSGST WAISSLYTND GDMEALEADL KHRFTRQ                  47

SEQ ID NO: 179              moltype = AA   length = 43
FEATURE                     Location/Qualifiers
source                      1..43
                            mol_type = protein
                            organism = Homo sapiens
SEQUENCE: 179
MRTRPRPRLR VSLLLPRLEC NGMISAHWHL HLLSSSDSPP SAS                      43

SEQ ID NO: 180              moltype = AA   length = 194
FEATURE                     Location/Qualifiers
source                      1..194
                            mol_type = protein
                            organism = Homo sapiens
SEQUENCE: 180
AAAAPAEQAP RAKGRPRRSP ESHRRSSSPE RRSPGSPVCR ADKAKSQQVR TSSTIRRTSS    60
LDTITGPYLT GQWPRDPHVH YPSCMKDKAT QTPSCWAEEG AEKRSHQRSA SWGSADQLKE   120
QIAKLRQQLQ RSKQSSRHSK EKDRQSPLHG NHITISHTQA TGSSRWTYQM VEELHFLLIT   180
GAVVLAALTL RLLL                                                     194

SEQ ID NO: 181              moltype = AA   length = 312
FEATURE                     Location/Qualifiers
source                      1..312
                            mol_type = protein
                            organism = Homo sapiens
SEQUENCE: 181
MLRAPGCLLR TSVAPAAALA AALLSSLARC SLLEPRDPVA SSLSPYFGTK TRYEDVNPVL    60
LSGPEAPWRD PELLEGTCTP VQLVALIRHG TRYPTVKQIR KLRQLHGLLQ ARGSRDGGAS   120
STGSRDLGAA LADWPLWYAD WMDGQLVEKG RQDMRQLALR LASLFPALFS RENYGRLRLI   180
TSSKHRCMDS SAAFLQGLWQ HYHPGLPPPD VADMEFGPPT VNDKLMRFFD HCEKFLTEVE   240
KNATALYHVE AFKTGPEMQN ILKKVAATLQ VPVNDLNAGL SQFLLQSSSS LVMQRLFFHC   300
FLSWATSKTR NP                                                       312

SEQ ID NO: 182              moltype = AA   length = 487
FEATURE                     Location/Qualifiers
source                      1..487
                            mol_type = protein
```

```
                        organism = Homo sapiens
SEQUENCE: 182
MLRAPGCLLR TSVAPAAALA AALLSSLARC SLLEPRDPVA SSLSPYFGTK TRYEDVNPVL    60
LSGPEAPWRD PELLEGTCTP VQLVALIRHG TRYPTVKQIR KLRQLHGLLQ ARGSRDGGAS   120
STGSRDLGAA LADWPLWYAD WMDGQLVEKG RQDMRQLALR LASLFPALFS RENYGRLRLI   180
TSSKHRCMDS SAAFLQGLWQ HYHPGLPPPD VADMEFGPPT VNDKLMRFFD HCEKFLTEVE   240
KNATALYHVE AFKTGPEMQN ILKKVAATLQ VPVNDLNADL IQVAFFTCSF DLAIKGVKSP   300
WCDVFDIDDA KVLEYLNDLK QYWKRGYGYT INSRSSCTLF QDIFQHLDKA VEQKQRSQPI   360
SSPVILQFGH AETLLPLLSL MGYFKDKEPL TAYNYKKQMH RKFRSGLIVP YASNLIFVLY   420
HCENAKTPKE QFRVQMLLNE KVLPLAYSQE TVSFYEDLKN HYKDILQSCQ TSEECELARA   480
NSTSDEL                                                            487

SEQ ID NO: 183          moltype = AA  length = 286
FEATURE                 Location/Qualifiers
source                  1..286
                        mol_type = protein
                        organism = Homo sapiens
SEQUENCE: 183
MCLFQLCGLV RYMEFGPPTV NDKLMRFFDH CEKFLTEVEK NATALYHVEA FKTGPEMQNI    60
LKKVAATLQV PVNDLNADLI QVAFFTCSFD LAIKGVKSPW CDVFDIDDAK VLEYLNDLKQ   120
YWKRGYGYTI NSRSSCTLFQ DIFQHLDKAV EQKQRSQPIS SPVILQFGHA ETLLPLLSLM   180
GYFKDKEPLT AYNYKKQMHR KFRSGLIVPY ASNLIFVLYH CENAKTPKEQ FRVQMLLNEK   240
VLPLAYSQET VSFYEDLKNH YKDILQSCQT SEECELARAN STSDEL                  286

SEQ ID NO: 184          moltype = AA  length = 207
FEATURE                 Location/Qualifiers
source                  1..207
                        mol_type = protein
                        organism = Homo sapiens
SEQUENCE: 184
MASFPPRVNE KEIVFLFFLL VRLRTIGELL APAAPFDKKC GRENWTVAFA PDGSYFAWSQ    60
GHRTVKLVPW SQCLQNFLLH GTKNVTNSSS LRLPRQNSDG GQKNKPREHI IDCGDIVWSL   120
AFGSSVPEKQ SRCVNIEWHR FRFGQDQLLL ATGLNNGRIK IWDVYTGKLL LNLVDHTEVV   180
RDLTFAPDGS LILVSASRDK TLRVWDL                                      207

SEQ ID NO: 185          moltype = AA  length = 74
FEATURE                 Location/Qualifiers
source                  1..74
                        mol_type = protein
                        organism = Homo sapiens
SEQUENCE: 185
MASFPPRVNE KEIVRLRTIG ELLAPAAPFD KKCGRENWTV AFAPDGSYFA WSQGHRTVKL    60
VPWSQCLQNL KTPP                                                    74

SEQ ID NO: 186          moltype = AA  length = 54
FEATURE                 Location/Qualifiers
source                  1..54
                        mol_type = protein
                        organism = Homo sapiens
SEQUENCE: 186
MASFPPRVNE KEIGNMMKVL RGHQNWVYSC AFSPDSSMLC SVGASKAVVA AILV          54

SEQ ID NO: 187          moltype = AA  length = 78
FEATURE                 Location/Qualifiers
source                  1..78
                        mol_type = protein
                        organism = Homo sapiens
SEQUENCE: 187
MASFPPRVNE KEIAPAAPFD KKCGRENWTV AFAPDGSYFA WSQGHRTVKL VPWSQCLQNF    60
LLHGTKNVTN SSSLRLPR                                                78

SEQ ID NO: 188          moltype = AA  length = 276
FEATURE                 Location/Qualifiers
source                  1..276
                        mol_type = protein
                        organism = Homo sapiens
SEQUENCE: 188
MAGPAALSAA AAAALAAALL LLRREDPGPG AGPSMAETEA LSKLREDFRM QNKSVFILGA    60
SGETGRVLLK EILEQGLFSK VTLIGRRKLT FDEEAYKNVN QEVVDFEKLD DYASAFQGHD   120
VGFCCLGTTR GKAGAEGFVR VDRDYVLKSA ELAKAGGCKH FNLLSSKGAD KSSNFLYLQV   180
KGEVEAKVEE LKFDRYSVFR PGVLLCDRQE SRPGEWLVRK FFGSLPDSWA SGHSVPVVTV   240
VRAMLNNVVR PRDKQMELLE NKAIHDLGKA HGSLKP                            276

SEQ ID NO: 189          moltype = AA  length = 133
FEATURE                 Location/Qualifiers
source                  1..133
                        mol_type = protein
                        organism = Homo sapiens
SEQUENCE: 189
```

```
MAETEALSKL REDFRMQNKS VFILGASGET GRVLLKEILE QGLFSKVTLI GRRKLTFDEE    60
AYKNVNQEVV DFEKLDDYAS AFQGHDVGFC CLGTTRGKAG AVRKAYALFP FCWPVISRIL   120
FLLTLFLCAC CNA                                                     133

SEQ ID NO: 190          moltype = AA   length = 133
FEATURE                 Location/Qualifiers
source                  1..133
                        mol_type = protein
                        organism = Homo sapiens
SEQUENCE: 190
MAETEALSKL REDFRMQNKS VFILGASGET GRVLLKEILE QGLFSKVTLI GRRKLTFDEE    60
AYKNVNQEVV DFEKLDDYAS AFQGHDVGFC CLGTTRGKAG AVRKAYALFP FCWPVISRIL   120
FLLTLFLCAC CNA                                                     133

SEQ ID NO: 191          moltype = AA   length = 133
FEATURE                 Location/Qualifiers
source                  1..133
                        mol_type = protein
                        organism = Homo sapiens
SEQUENCE: 191
MAETEALSKL REDFRMQNKS VFILGASGET GRVLLKEILE QGLFSKVTLI GRRKLTFDEE    60
AYKNVNQEVV DFEKLDDYAS AFQGHDVGFC CLGTTRGKAG AVRKAYALFP FCWPVISRIL   120
FLLTLFLCAC CNA                                                     133

SEQ ID NO: 192          moltype = AA   length = 463
FEATURE                 Location/Qualifiers
source                  1..463
                        mol_type = protein
                        organism = Homo sapiens
SEQUENCE: 192
MGAGPSLLLA ALLLLLSGDG AVRCDTPANC TYLDLLGTWV FQVGSSGSQR DVNCSVMGPQ    60
EKKVVVYLQK LDTAYDDLGN SGHFTIIYNQ GFEIVLNDYK WFAFFKYKEE GSKVTTYCNE   120
TMTGWVHDVL GRNWACFTGK KVGTASENVY VNIAHLKNSQ EKYSNRLYKY DHNFVKAINA   180
IQKSWTATTY MEYETLTLGD MIRRSGGHSR KIPRPKPAPL TAEIQQKILH LPTSWDWRNV   240
HGINFVSPVR NQASCGSCYS FASMGMLEAR IRILTNNSQT PILSPQEVVS CSQYAQGCEG   300
GFPYLIAGKY AQDFGLVEEA CFPYTGTDSP CKMKEDCFRY YSSEYHYVGG FYGGCNEALM   360
KLELVHHGPM AVAFEVYDDF LHYKKGIYHH TGLRDPFNPF ELTNHAVLLV GYGTDSASGM   420
DYWIVKNSWG TGWGENGYFR IRRGTDECAI ESIAVAATPI PKL                    463

SEQ ID NO: 193          moltype = AA   length = 137
FEATURE                 Location/Qualifiers
source                  1..137
                        mol_type = protein
                        organism = Homo sapiens
SEQUENCE: 193
MGAGPSLLLA ALLLLLSGDG AVRCDTPANC TYLDLLGTWV FQVGSSGSQR DVNCSVMGPQ    60
EKKVVVYLQK LDTAYDDLGN SGHFTIIYNQ GFEIVLNDYK WFAFFKDVTD FISHLFMQLG   120
TVGIYDLPHL RNKLVIK                                                 137

SEQ ID NO: 194          moltype = AA   length = 245
FEATURE                 Location/Qualifiers
source                  1..245
                        mol_type = protein
                        organism = Homo sapiens
SEQUENCE: 194
XVVDSPLARS ARLPGPQEKK VVVYLQKLDT AYDDLGNSGH FTIIYNQGFE IVLNDYKWFA    60
FFKYKEEGSK VTTYCNETMT GWVHDVLGRN WACFTGKKVG TASENVYVNI AHLKNSQEKY   120
SNRLYKYDHN FVKAINAIQK SWTATTYMEY ETLTLGDMIR RSGGHSRKIP RPKPAPLTAE   180
IQQKILHLPT SWDWRNVHGI NFVSPVRNQA SCGSCYSFAS MGMLEARIRI LTNNSQTPIL   240
SPQEV                                                              245

SEQ ID NO: 195          moltype = AA   length = 36
FEATURE                 Location/Qualifiers
source                  1..36
                        mol_type = protein
                        organism = Homo sapiens
SEQUENCE: 195
XDVTDFISHL FMQLGTVGIY DLPHLRNKLA MNRRWG                             36

SEQ ID NO: 196          moltype = AA   length = 141
FEATURE                 Location/Qualifiers
source                  1..141
                        mol_type = protein
                        organism = Homo sapiens
SEQUENCE: 196
MGAGPSLLLA ALLLLLSGDG AVRCDTPANC TYLDLLGTWV FQVGSSGSQR DVNCSVMGPQ    60
EKKVVVYLQK LDTAYDDLGN SGHFTIIYNQ GFEIVLNDYK WFAFFKDVTD FISHLFMQLG   120
TVGIYDLPHL RNKLAMNRRW G                                            141
```

```
SEQ ID NO: 197          moltype = AA   length = 431
FEATURE                 Location/Qualifiers
source                  1..431
                        mol_type = protein
                        organism = Homo sapiens
SEQUENCE: 197
MSSVCDMSFL QKSCITMVHF CGLLTLHREP VPLKSISVSV NIYEFVAGVS ATLNYENEEK    60
VPLEAFFVFP MDEDSAVYSF EALVDGKKIV AELQDKMKAR TNYEKAISQG HQAFLLEGDS   120
SSRDVFSCNV GNLQPGSKAA VTLKYVQELP LEADGALRFV LPAVLNPRYQ FSGSSKDSCL   180
NVKTPIVPVE DLPYTLSMVA TIDSQHGIEK VQSNCPLSPT EYLGEDKTSA QVSLAAGHKF   240
DRDVELLIYY NEVHTPSVVL EMGMPNMKPG HLMGDPSAMV SFYPNIPEDQ PSNTCGEFIF   300
LMDRSGSMQS PMSSQDTSQL RIQAAKETLI LLLKSLPIGC YFNIYGFGSS YEACFPESVK   360
YTQQTMEEAL GRVKLMQADL GGTEILAPLQ NIYRGPSIPG HPLQLFVFTD GEVTDTFSVI   420
KEVRINRQKH R                                                       431

SEQ ID NO: 198          moltype = AA   length = 786
FEATURE                 Location/Qualifiers
source                  1..786
                        mol_type = protein
                        organism = Homo sapiens
SEQUENCE: 198
MVHFCGLLTL HREPVPLKSI SVSVNIYEFV AGVSATLNYE NEEKVPLEAF FVFPMDEDSA    60
VYSFEALVDG KKIVAELQDK MKARTNYEKA ISQGHQAFLL EGDSSRDVF SCNVGNLQPG   120
SKAAVTLKYV QELPLEADGA LRFVLPAVLN PRYQFSGSSK DSCLNVKTPI VPVEDLPYTL   180
SMVATIDSQH GIEKVQSNCP LSPTEYLGED KTSAQVSLAA GHKFDRDVEL LIYYNEVHTP   240
SVVLEMGMPN MKPGHLMGDP SAMVSFYPNI PEDQPSNTCG EFIFLMDRSG SMQSPMSSQD   300
TSQLRIQAAK ETLILLLKSL PIGCYFNIYG FGSSYEACFP ESVKYTQQTM EEALGRVKLM   360
QADLGGTEIL APLQNIYRGP SIPGHPLQLF VFTDGEVTDT FSVIKEVRIN RQKHRCFSFG   420
IGEGTSTSLI KGIARASGGT SEFITGKDRM QSKALRTLKR SLQPVVEDVS LSWHLPPGLS   480
AKMLSPEQTV IFRGQRLISY AQLTGRMPAA ETTGEVCLKY TLQGKTFEDK VTFPLQPKPD   540
VNLTIHRLAA KSLLQTKDMG LRETPASDKK DALNLSLESG VISSFTAFIA INKELNKPVQ   600
GPLAHRDVPR PILLGASAPL KIKCQSGFRK ALHSDRPPSA SQPRGELMCY KAKTFQMDDY   660
SLCGLISHKD QHSPGFGENH LVQLIYHQNA NGSWDLNEDL AKILGMSLEE IMAAQPAELV   720
DSSGWATILA VIWLHSNGKD LKCEWELLER KAVAWMRAHA GSTMPSVVKA AITFLKSSVD   780
PAIFAF                                                             786

SEQ ID NO: 199          moltype = AA   length = 786
FEATURE                 Location/Qualifiers
source                  1..786
                        mol_type = protein
                        organism = Homo sapiens
SEQUENCE: 199
MVHFCGLLTL HREPVPLKSI SVSVNIYEFV AGVSATLNYE NEEKVPLEAF FVFPMDEDSA    60
VYSFEALVDG KKIVAELQDK MKARTNYEKA ISQGHQAFLL EGDSSRDVF SCNVGNLQPG   120
SKAAVTLKYV QELPLEADGA LRFVLPAVLN PRYQFSGSSK DSCLNVKTPI VPVEDLPYTL   180
SMVATIDSQH GIEKVQSNCP LSPTEYLGED KTSAQVSLAA GHKFDRDVEL LIYYNEVHTP   240
SVVLEMGMPN MKPGHLMGDP SAMVSFYPNI PEDQPSNTCG EFIFLMDRSG SMQSPMSSQD   300
TSQLRIQAAK ETLILLLKSL PIGCYFNIYG FGSSYEACFP ESVKYTQQTM EEALGRVKLM   360
QADLGGTEIL APLQNIYRGP SIPGHPLQLF VFTDGEVTDT FSVIKEVRIN RQKHRCFSFG   420
IGEGTSTSLI KGIARASGGT SEFITGKDRM QSKALRTLKR SLQPVVEDVS LSWHLPPGLS   480
AKMLSPEQTV IFRGQRLISY AQLTGRMPAA ETTGEVCLKY TLQGKTFEDK VTFPLQPKPD   540
VNLTIHRLAA KSLLQTKDMG LRETPASDKK DALNLSLESG VISSFTAFIA INKELNKPVQ   600
GPLAHRDVPR PILLGASAPL KIKCQSGFRK ALHSDRPPSA SQPRGELMCY KAKTFQMDDY   660
SLCGLISHKD QHSPGFGENH LVQLIYHQNA NGSWDLNEDL AKILGMSLEE IMAAQPAELV   720
DSSGWATILA VIWLHSNGKD LKCEWELLER KAVAWMRAHA GSTMPSVVKA AITFLKSSVD   780
PAIFAF                                                             786

SEQ ID NO: 200          moltype = AA   length = 327
FEATURE                 Location/Qualifiers
source                  1..327
                        mol_type = protein
                        organism = Homo sapiens
SEQUENCE: 200
MLSLCICGTA ITSQYLAERY KVNTPMLQSF INYCLLFLIY TVMLAFRSGS DNLLVILKRK    60
WWKYILLGLA DVEANYVIVR AYQYTTLTSV QLLDCFGIPV LMALSWFILH ARYRVIHFIA   120
VAVCLLGVGT MVGADILAGR EDNSGSDVLI GDILVLLGAS LYAISNVCEE YIVKKLSRQE   180
FLGMVGLFGT IISGIQLLIV EYKDIASIHW DWKIALLFVA FALCMFCLYS FMPLVIKVTS   240
ATSVNLGILT ADLYSLFVGL FLFGYKFSGL YILSFTVIMV GFILYCSTPT RTAEPAESSV   300
PPVTSIGIDN LGLKLEENLQ ETHSAVL                                      327

SEQ ID NO: 201          moltype = AA   length = 357
FEATURE                 Location/Qualifiers
source                  1..357
                        mol_type = protein
                        organism = Homo sapiens
SEQUENCE: 201
MEADSPAGPG APEPLAEGAA AEFSSLLRRI KGKLFTWNIL KTIALGQMLS LCICGTAITS    60
QYLAERYKVN TPMLQSFINY CLLFLIYTVM LAFRSGSDNL LVILKRKWWK YILLGLADVE   120
ANYVIVRAYQ YTTLTSVQLL DCFGIPVLMA LSWFILHARY RVIHFIAVAV CLLGVGTMVG   180
```

```
ADILAGREDN SGSDVLIGDI LVLLGASLYA ISNVCEEYIV KKLSRQEFLG MVGLFGTIIS    240
GIQLLIVEYK DIASIHWDWK IALLFVAFAL CMFCLYSFMP LVIKVTSATS VNLGILTADL    300
YSLFVGLFLF GYKDSTSCPS LSSWWGLSCT APPLLARPSR LKAACLQSPA LGLTTWG       357

SEQ ID NO: 202              moltype = AA   length = 374
FEATURE                     Location/Qualifiers
source                      1..374
                            mol_type = protein
                            organism = Homo sapiens
SEQUENCE: 202
MEADSPAGPG APEPLAEGAA AEFSSLLRRI KGKLFTWNIL KTIALGQMLS LCICGTAITS     60
QYLAERYKVN TPMLQSFINY CLLFLIYTVM LAFRSGSDNL LVILKRKWWK YILLGLADVE    120
ANYVIVRAYQ YTTLTSVQLL DCFGIPVLMA LSWFILHARY RVIHFIAVAV CLLGVGTMVG    180
ADILAGREDN SGSDVLIGDI LVLLGASLYA ISNVCEEYIV KKLSRQEFLG MVGLFGTIIS    240
GIQLLIVEYK DIASIHWDWK IALLFVAFAL CMFCLYSFMP LVIKVTSATS VNLGILTADL    300
YSLFVGLFLF GYKFSGLYIL SFTVIMVGFI LYCSTPTRTA EPAESSVPPV TSIGIDNLGL    360
KLEENLQETH SAVL                                                      374

SEQ ID NO: 203              moltype = AA   length = 265
FEATURE                     Location/Qualifiers
source                      1..265
                            mol_type = protein
                            organism = Homo sapiens
SEQUENCE: 203
MEADSPAGPG APEPLAEGAA AEFSSLLRRI KGKLFTWNIL KTIALGQMLS LCICGTAITS     60
QYLAERYKVN TPMLQSFINY CLLFLIYTVM LAFRSGSDNL LVILKRKWWK YILLGLADVE    120
ANYVIVRAYQ YTTLTSVQLL DCFGIPVLMA LSWFILHARY RVIHFIAVAV CLLGVGTMVG    180
ADILAGREDN SGSDVLIGDI LVLLGASLYA ISNVCEEYIV KKLSRQEFLG MVGLFGTIIS    240
GIQLPAVRGI CPVYVLPVQL HAIGD                                          265

SEQ ID NO: 204              moltype = AA   length = 49
FEATURE                     Location/Qualifiers
source                      1..49
                            mol_type = protein
                            organism = Homo sapiens
SEQUENCE: 204
MEAMAASTSL PDPGDFDRNV PRICGVCGDR ATGFHFNAMT CEGCKGFFR                  49

SEQ ID NO: 205              moltype = AA   length = 1093
FEATURE                     Location/Qualifiers
source                      1..1093
                            mol_type = protein
                            organism = Homo sapiens
SEQUENCE: 205
MSQPGIPASG GAPASLQAQN GAALASGSPY TNGPVQNALL SSQESVSQGY NFQLPGSYPH     60
PIPAKTLNPV SGQSNYGGSQ GSGQTLNRPP VASNPVTPSL HSGPAPRMPL PASQNPATTG    120
MPSSSFLPEA NLPPPLNWQY NYPSTASQTN HCPRASSQNT VSGNTSLTTN HQYVSSGYPS    180
LQNSFIKSGP SVPPLVNPPL PTTFQPGAPH GPPPAGGPPP VRALTPLTSS YRDVPQPLFN    240
SAVNQEGITS NTNNGSMVVH SSYDEIEGGG LLATPQLTNK NPKMSRSVGY SYPSLPPGYQ    300
NTTPPGATGV PPSSLNYPSG PQAFTQTPLG ANHLTTSMSG LSLQPEGLRV VNLLQERNML    360
PSTPLKPPVP NLHEDIQKLN CNPELFRCTL TSIPQTQALL NKAKLPLGLL LHPFKDLVQL    420
PVVTSSTIVR CRSCRTYINP FVSFLDQRRW KCNLCYRVND VPEEFLYNPL TRVYGEPHRR    480
PEVQNATIEF MAPSEYMLRP PQPPVYLFVF DVSHNAVETG YLNSVCQSLL DNLDLLPGNT    540
RTKIGFITFD STIHFYGLQE SLSQPQMLIV SDIEDVFIPM PENLLVNLNE SKELVQDLLK    600
TLPQMFTKTL ETQSALGPAL QAAFKLMSPT GGRMSVFQTQ LPTLGVGALK PREEPNHRSS    660
AKDIHMTPST DFYKKLALDC SGQQVAVDLF LLSGQYSDLA SLGCISRYSA GSVYYYPSYH    720
HQHNPVQVQK LQKELQRYLT RKIGFEAVMR IRCTKGLSIH TPHGNFFVRS TDLLSLPNVN    780
PDAGYAVQMS VEESLTDTQL VSFQSALLYT SSKGERRIRV HTLCLPVVST LNDVFLGADV    840
QAISGLLANM AVDRSMTASL SDARDALVNA VIDSLSAYRS SVLSNQQPGL MVPFSLRLFP    900
LFVLALLKQK SFQTGTNARL DERIFAMCQV KNQPLVYLML TTHPSLYRVD NLSDEGALNI    960
SDRTIPQPPI LQLSVEKLSR DGAFLMDAGS VLMLWVGKNC TQNFLSQVLG VQNYASIPQP   1020
MTDLPELDTP ESARIIAFIS WLREQRPFFP ILYVIRDESP MKANFLQNMI EDRTESALSY   1080
YEFLLHIQQQ VNK                                                      1093

SEQ ID NO: 206              moltype = AA   length = 398
FEATURE                     Location/Qualifiers
source                      1..398
                            mol_type = protein
                            organism = Homo sapiens
SEQUENCE: 206
MLRLYVLVMG VSAFTLQPAA HTGAARSCRF RGRHYKREFR LEGEPVALRC PQVPYWLWAS     60
VSPRINLTWH KNDSARTVPG EEETRMWAQD GALWLLPALQ EDSGTYVCTT RNASYCDKMS    120
IELRVFENTD AFLPFISYPQ ILTLSTSGVL VCPDLSEFTR DKTDVKIQWY KDSLLLDKDN    180
EKFLSVRGTT HLLVHDVALE DAGYYRCVLT FAHEGQQYNI TRSIELRIKK KKEETIPVII    240
SPLKTISASL GSRLTIPCKV FLGTGTPLTT MLWWTANDTH IESAYPGGRV TEGPRQEYSE    300
NNENYIEVPL IFDPVTREDL HMDFKCVVHN TLSFQTLRTT VKEASSTFSW GIVLAPLSLA    360
FLVLGGIWMH RRCKHRTGKA DGLTVLWPHH QDFQSYPK                            398

SEQ ID NO: 207              moltype = AA   length = 398
```

```
FEATURE                 Location/Qualifiers
source                  1..398
                        mol_type = protein
                        organism = Homo sapiens
SEQUENCE: 207
MLRLYVLVMG VSAFTLQPAA HTGAARSCRF RGRHYKREFR LEGEPVALRC PQVPYWLWAS    60
VSPRINLTWH KNDSARTVPG EEETRMWAQD GALWLLPALQ EDSGTYVCTT RNASYCDKMS   120
IELRVFENTD AFLPFISYPQ ILTLSTSGVL VCPDLSEFTR DKTDVKIQWY KDSLLLDKDN   180
EKFLSVRGTT HLLVHDVALE DAGYYRCVLT FAHEGQQYNI TRSIELRIKK KKEETIPVII   240
SPLKTISASL GSRLTIPCKV FLGTGTPLTT MLWWTANDTH IESAYPGGRV TEGPRQEYSE   300
NNENYIEVPL IFDPVTREDL HMDFKCVVHN TLSFQTLRTT VKEASSTFSW GIVLAPLSLA   360
FLVLGGIWMH RRCKHRTGKA DGLTVLWPHH QDFQSYPK                           398

SEQ ID NO: 208          moltype = AA  length = 296
FEATURE                 Location/Qualifiers
source                  1..296
                        mol_type = protein
                        organism = Homo sapiens
SEQUENCE: 208
MLRLYVLVMG VSAFTLQPAA HTGAARSCRF RGRHYKREFR LEGEPVALRC PQVPYWLWAS    60
VSPRINLTWH KNDSARTVPG EEETRMWAQD GALWLLPALQ EDSGTYVCTT RNASYCDKMS   120
IELRVFENTD AFLPFISYPQ ILTLSTSGVL VCPDLSEFTR DKTDVKIQWY KDSLLLDKDN   180
EKFLSVRGTT HLLVHDVALE DAGYYRCVLT FAHEGQQYNI TRSIELRIKK KKEETIPVII   240
SPLKTISASL GSRLTIPCKV FLGTGTPLTT MLWWTANDTH IESAYPGGRV TEGPRQ       296

SEQ ID NO: 209          moltype = AA  length = 229
FEATURE                 Location/Qualifiers
source                  1..229
                        mol_type = protein
                        organism = Homo sapiens
SEQUENCE: 209
MLRLYVLVMG VSAFTLQPAA HTGAARSCRF RGRHYKREFR LEGEPVALRC PQVPYWLWAS    60
VSPRINLTWH KNDSARTVPG EEETRMWAQD GALWLLPALQ EDSGTYVCTT RNASYCDKMS   120
IELRVFENTD AFLPFISYPQ ILTLSTSGVL VCPDLSEFTR DKTDVKIQWY KDSLLLDKDN   180
EKFLSVRGTT HLLVHDVALE DAGYYRCVLT FAHEGQQYNI TRSIELRIK              229

SEQ ID NO: 210          moltype = AA  length = 447
FEATURE                 Location/Qualifiers
source                  1..447
                        mol_type = protein
                        organism = Homo sapiens
SEQUENCE: 210
MKVLLRLICF IALLISSLEA DKCKEREEKI ILVSSANEID VRPCPLNPNE HKGTITWYKD    60
DSKTPVSTEQ ASRIHQHKEK LWFVPAKVED SGHYYCVVRN SSYCLRIKIS AKFVENEPNL   120
CYNAQAIFKQ KLPVAGDGGL VCPYMEFFKN ENNELPKLQW YKDCKPLLLD NIHFSGVKDR   180
LIVMNVAEKH RGNYTCHASY TYLGKQYPIT RVIEFITLEE NKPTRPVIVS PANETMEVDL   240
GSQIQLICNV TGQLSDIAYW KWNGSVIDED DPVLGEDYYS VENPANKRRS TLITVLNISE   300
IESRFYKHPF TCFAKNTHGI DAAYIQLIYP VTNFQKHMIG ICVTLTVIIV CSVFIYKIFK   360
IDIVLWYRDS CYDFLPIKAS DGKTYDAYIL YPKTVGEGST SDCDIFVFKV LPEVLEKQCG   420
YKLFIYGRDD YVGEGMCVME QSKGLLL                                      447

SEQ ID NO: 211          moltype = AA  length = 447
FEATURE                 Location/Qualifiers
source                  1..447
                        mol_type = protein
                        organism = Homo sapiens
SEQUENCE: 211
MKVLLRLICF IALLISSLEA DKCKEREEKI ILVSSANEID VRPCPLNPNE HKGTITWYKD    60
DSKTPVSTEQ ASRIHQHKEK LWFVPAKVED SGHYYCVVRN SSYCLRIKIS AKFVENEPNL   120
CYNAQAIFKQ KLPVAGDGGL VCPYMEFFKN ENNELPKLQW YKDCKPLLLD NIHFSGVKDR   180
LIVMNVAEKH RGNYTCHASY TYLGKQYPIT RVIEFITLEE NKPTRPVIVS PANETMEVDL   240
GSQIQLICNV TGQLSDIAYW KWNGSVIDED DPVLGEDYYS VENPANKRRS TLITVLNISE   300
IESRFYKHPF TCFAKNTHGI DAAYIQLIYP VTNFQKHMIG ICVTLTVIIV CSVFIYKIFK   360
IDIVLWYRDS CYDFLPIKAS DGKTYDAYIL YPKTVGEGST SDCDIFVFKV LPEVLEKQCG   420
YKLFIYGRDD YVGEGMCVME QSKGLLL                                      447

SEQ ID NO: 212          moltype = AA  length = 173
FEATURE                 Location/Qualifiers
source                  1..173
                        mol_type = protein
                        organism = Homo sapiens
SEQUENCE: 212
MKVLLRLICF IALLISSLEA DKCKEREEKI ILVSSANEID VRPCPLNPNE HKGTITWYKD    60
DSKTPVSTEQ ASRIHQHKEK LWFVPAKVED SGHYYCVVRN SSYCLRIKIS AKFVENEPNL   120
CYNAQAIFKQ KLPVAGDGGL VCPYMEFFKN ENNELPKLQW YKVAVSRVWA TAL          173

SEQ ID NO: 213          moltype = AA  length = 538
FEATURE                 Location/Qualifiers
source                  1..538
```

```
                          mol_type = protein
                          organism = Homo sapiens
SEQUENCE: 213
MKVLLRLICF IALLISSLEA DKCKEREEKI ILVSSANEID VRPCPLNPNE HKGTITWYKD    60
DSKTPVSTEQ ASRIHQHKEK LWFVPAKVED SGHYYCVVRN SSYCLRIKIS AKFVENEPNL   120
CYNAQAIFKQ KLPVAGDGGL VCPYMEFFKN ENNELPKLQW YKDCKPLLLD NIHFSGVKDR   180
LIVMNVAEKH RGNYTCHASY TYLGKQYPIT RVIEFITLEE NKPTRPVIVS PANETMEVDL   240
GSQIQLICNV TGQLSDIAYW KWNGSVIDED DPVLGEDYYS VENPANKRRS TLITVLNISE   300
IESRFYKHPF TCFAKNTHGI DAAYIQLIYP VTNFQKHMIG ICVTLTVIIV CSVFIYKIFK   360
IDIVLWYRDS CYDFLPIKVL PEVLEKQCGY KLFIYGRDDY VGEDIVEVIN ENVKKSRRLI   420
IILVRETSGF SWLGGSSEEQ IAMYNALVQD GIKVVLLELE KIQDYEKMPE SIKFIKQKHG   480
AIRWSGDFTQ GPQSAKTRFW KNVRYHMPVQ RRSPSSKHQL LSPATKEKLQ REAHVPLG    538

SEQ ID NO: 214            moltype = AA    length = 569
FEATURE                   Location/Qualifiers
source                    1..569
                          mol_type = protein
                          organism = Homo sapiens
SEQUENCE: 214
MKVLLRLICF IALLISSLEA DKCKEREEKI ILVSSANEID VRPCPLNPNE HKGTITWYKD    60
DSKTPVSTEQ ASRIHQHKEK LWFVPAKVED SGHYYCVVRN SSYCLRIKIS AKFVENEPNL   120
CYNAQAIFKQ KLPVAGDGGL VCPYMEFFKN ENNELPKLQW YKDCKPLLLD NIHFSGVKDR   180
LIVMNVAEKH RGNYTCHASY TYLGKQYPIT RVIEFITLEE NKPTRPVIVS PANETMEVDL   240
GSQIQLICNV TGQLSDIAYW KWNGSVIDED DPVLGEDYYS VENPANKRRS TLITVLNISE   300
IESRFYKHPF TCFAKNTHGI DAAYIQLIYP VTNFQKHMIG ICVTLTVIIV CSVFIYKIFK   360
IDIVLWYRDS CYDFLPIKAS DGKTYDAYIL YPKTVGEGST SDCDIFVFKV LPEVLEKQCG   420
YKLFIYGRDD YVGEDIVEVI NENVKKSRRL IIILVRETSG FSWLGGSSEE QIAMYNALVQ   480
DGIKVVLLEL EKIQDYEKMP ESIKFIKQKH GAIRWSGDFT QGPQSAKTRF WKNVRYHMPV   540
QRRSPSSKHQ LLSPATKEKL QREAHVPLG                                    569

SEQ ID NO: 215            moltype = AA    length = 119
FEATURE                   Location/Qualifiers
source                    1..119
                          mol_type = protein
                          organism = Homo sapiens
SEQUENCE: 215
MKVLLRLICF IALLISSLEA DKCKEREEKI ILVSSANEID VRPCPLNPNE HKGTITWYKD    60
DSKTPVSTEQ ASRIHQHKEK LWFVPAKVED SGHYYCVVRI ANLYFLTIYT LVESKIGSS   119

SEQ ID NO: 216            moltype = AA    length = 124
FEATURE                   Location/Qualifiers
source                    1..124
                          mol_type = protein
                          organism = Homo sapiens
SEQUENCE: 216
XKCKEREEKI ILVSSANEID VRPCPLNPNE HKGTITWYKD DSKTPVSTEQ ASRIHQHKEK    60
LWFVPAKVED SGHYYCVETE DLCALIWSFL KMKIMSYLNY SGIRIANLYF LTIYTLVESK   120
IGSS                                                                124

SEQ ID NO: 217            moltype = AA    length = 447
FEATURE                   Location/Qualifiers
source                    1..447
                          mol_type = protein
                          organism = Homo sapiens
SEQUENCE: 217
MKVLLRLICF IALLISSLEA DKCKEREEKI ILVSSANEID VRPCPLNPNE HKGTITWYKD    60
DSKTPVSTEQ ASRIHQHKEK LWFVPAKVED SGHYYCVVRN SSYCLRIKIS AKFVENEPNL   120
CYNAQAIFKQ KLPVAGDGGL VCPYMEFFKN ENNELPKLQW YKDCKPLLLD NIHFSGVKDR   180
LIVMNVAEKH RGNYTCHASY TYLGKQYPIT RVIEFITLEE NKPTRPVIVS PANETMEVDL   240
GSQIQLICNV TGQLSDIAYW KWNGSVIDED DPVLGEDYYS VENPANKRRS TLITVLNISE   300
IESRFYKHPF TCFAKNTHGI DAAYIQLIYP VTNFQKHMIG ICVTLTVIIV CSVFIYKIFK   360
IDIVLWYRDS CYDFLPIKAS DGKTYDAYIL YPKTVGEGST SDCDIFVFKV LPEVLEKQCG   420
YKLFIYGRDD YVGEGMCVME QSKGLLL                                      447

SEQ ID NO: 218            moltype = AA    length = 298
FEATURE                   Location/Qualifiers
source                    1..298
                          mol_type = protein
                          organism = Homo sapiens
SEQUENCE: 218
MEFFKNENNE LPKLQWYKDC KPLLLDNIHF SGVKDRLIVM NVAEKHRGNY TCHASYTYLG    60
KQYPITRVIE FITLEENKPT RPVIVSPANE TMEVDLGSQI QLICNVTGQL SDIAYWKWNG   120
SVIDEDDPVL GEDYYSVENP ANKRRSTLIT VLNISEIESR FYKHPFTCFA KNTHGIDAAY   180
IQLIYPVTNF QKHMIGICVT LTVIIVCSVF IYKIFKIDIV LWYRDSCYDF LPIKASDGKT   240
YDAYILYPKT VGEGSTSDCD IFVFKVLPEV LEKQCGYKLF IYGRDDYVGE DIVEVINE     298

SEQ ID NO: 219            moltype = AA    length = 182
FEATURE                   Location/Qualifiers
source                    1..182
```

```
                        mol_type = protein
                        organism = Homo sapiens
SEQUENCE: 219
MKVLLRLICF IALLISSLEA DKCKEREEKI ILVSSANEID VRPCPLNPNE HKGTITWYKD    60
DSKTPVSTEQ ASRIHQHKEK LWFVPAKVED SGHYYCVVRN SSYCLRIKIS AKFVENEPNL   120
CYNAQAIFKQ KLPVAGDGGL VCPYMEFFKN ENNELPKLQW YKDCKPLLLD NIHFSGVKDR   180
LI                                                                 182

SEQ ID NO: 220          moltype = AA  length = 114
FEATURE                 Location/Qualifiers
source                  1..114
                        mol_type = protein
                        organism = Homo sapiens
SEQUENCE: 220
MKVLLRLICF IALLISSLEA DKCKEREEKI ILVSSANEID VRPCPLNPNE HKGTITWYKD    60
DSKTPVSTEQ ASRIHQHKEK LWFVPAKVED SGHYYCVVRN SSYCLRIKIS AKFV         114

SEQ ID NO: 221          moltype = AA  length = 106
FEATURE                 Location/Qualifiers
source                  1..106
                        mol_type = protein
                        organism = Homo sapiens
SEQUENCE: 221
MKVLLRLICF IALLISSLEA DKCKEREEKI ILVSSANEID VRPCPLNPNE HKGTITWYKD    60
DSKTPVSTEQ ASRIHQHKEK LWFVPAKVED SGHYYCVVRN SSYCLR                  106

SEQ ID NO: 222          moltype = AA  length = 80
FEATURE                 Location/Qualifiers
source                  1..80
                        mol_type = protein
                        organism = Homo sapiens
SEQUENCE: 222
MKVLLRLICF IALLISSLEA DKCKEREEKI ILVSSANEID VRPCPLNPNE HKGTITWYKD    60
DSKTPVSTEQ ASRIHQHKEK                                                80

SEQ ID NO: 223          moltype = AA  length = 575
FEATURE                 Location/Qualifiers
source                  1..575
                        mol_type = protein
                        organism = Homo sapiens
SEQUENCE: 223
MWSLLLCGLS IALPLSVTAD GCKDIFMKNE ILSASQPFAF NCTFPPITSG EVSVTWYKNS    60
SKIPVSKIIQ SRIHQDETWI LFLPMEWGDS GVYQCVIKGR DSCHRIHVNL TVFEKHWCDT   120
SIGGLPNLSD EYKQILHLGK DDSLTCHLHF PKSCVLGPIK WYKDCNEIKG ERFTVLETRL   180
LVSNVSAEDR GNYACQAILT HSGKQYEVLN GITVSITERA GYGGSVPKII YPKNHSIEVQ   240
LGTTLIVDCN VTDTKDNTNL RCWRVNNTLV DDYYDESKRI REGVETHVSF REHNLYTVNI   300
TFLEVKMEDY GLPFMCHAGV STAYIILQLP APDFRAYLIG GLIALVAVAV SVVYIYNIFK   360
IDIVLWYRSA FHSTETIVDG KLYDAYVLYP KPHKESQRHA VDALVLNILP EVLERQCGYK   420
LFIFGRDEFP GQAVANVIDE NVKLCRRLIV IVVPESLGFG LLKNLSEEQI AVYSALIQDG   480
MKVILIELEK IEDYTVMPES IQYIKQKHGA IRWHGDFTEQ SQCMKTKFWK TVRYHMPPRR   540
CRPFPPVQLL QHTPCYRTAG PELGSRRKKC TLTTG                              575

SEQ ID NO: 224          moltype = AA  length = 172
FEATURE                 Location/Qualifiers
source                  1..172
                        mol_type = protein
                        organism = Homo sapiens
SEQUENCE: 224
MWSLLLCGLS IALPLSVTAD GCKDIFMKNE ILSASQPFAF NCTFPPITSG EVSVTWYKNS    60
SKIPVSKIIQ SRIHQDETWI LFLPMEWGDS GVYQCVIKGR DSCHRIHVNL TVFEKHWCDT   120
SIGGLPNLSD EYKQILHLGK DDSLTCHLHF PKSCVLGPIK WYKDCNEIKG ER           172

SEQ ID NO: 225          moltype = AA  length = 457
FEATURE                 Location/Qualifiers
source                  1..457
                        mol_type = protein
                        organism = Homo sapiens
SEQUENCE: 225
MTGLVSLSYF PLSTRSCALQ SCSPVWGCGP CCSAGCPSPF HCLSQQDCNE IKGERFTVLE    60
TRLLVSNVSA EDRGNYACQA ILTHSGKQYE VLNGITVSIK RAGYGGSVPK IIYPKNHSIE   120
VQLGTTLIVD CNVTDTKDNT NLRCWRVNNT LVDDYYDESK RIREGVETHV SFREHNLYTV   180
NITFLEVKME DYGLPFMCHA GVSTAYIILQ LPAPDFRAYL IGGLIALVAV AVSVVYIYNI   240
FKIDIVLWYR SAFHSTETIV DGKLYDAYVL YPKPHKESQR HAVDALVLNI LPEVLERQCG   300
YKLFIFGRDE FPGQAVANVI DENVKLCRRL IVIVVPESLG FGLLKNLSEE QIAVYSALIQ   360
DGMKVILIEL EKIEDYTVMP ESIQYIKQKH GAIRWHGDFT EQSQCMKTKF WKTVRYHMPP   420
RRCRPFPPVQ LLQHTPCYRT AGPELGSRRK KCTLTTG                            457

SEQ ID NO: 226          moltype = AA  length = 556
FEATURE                 Location/Qualifiers
```

```
source                  1..556
                        mol_type = protein
                        organism = Homo sapiens
SEQUENCE: 226
MGFWILAILT ILMYSTAAKF SKQSWGLENE ALIVRCPRQG KPSYTVDWYY SQTNKSIPTQ   60
ERNRVFASGQ LLKFLPAAVA DSGIYTCIVR SPTFNRTGYA NVTIYKKQSD CNVPDYLMYS  120
TVSGSEKNSK IYCPTIDLYN WTAPLEWFKN CQALQGSRYR AHKSFLVIDN VMTEDAGDYT  180
CKFIHNENGA NYSVTATRSF TVKDEQGFSL FPVIGAPAQN EIKEVEIGKN ANLTCSACFG  240
KGTQFLAAVL WQLNGTKITD FGEPRIQQEE GQNQSFSNGL ACLDMVLRIA DVKEEDLLLQ  300
YDCLALNLHG LRRHTVRLSR KNPIDHHSIY CIIAVCSVFL MLINVLVIIL KMFWIEATLL  360
WRDIAKPYKT RNDGKLYDAY VVYPRNYKSS TDGASRVEHF VHQILPDVLE NKCGYTLCIY  420
GRDMLPGEDV VTAVETNIRK SRRHIFILTP QITHNKEFAY EQEVALHCAL IQNDAKVILI  480
EMEALSELDM LQAEALQDSL QHLMKVQGTI KWREDHIANK RSLNSKFWKH VRYQMPVPSK  540
IPRKASSLTP LAAQKQ                                                  556

SEQ ID NO: 227          moltype = AA  length = 328
FEATURE                 Location/Qualifiers
source                  1..328
                        mol_type = protein
                        organism = Homo sapiens
SEQUENCE: 227
MGFWILAILT ILMYSTAAKF SKQSWGLENE ALIVRCPRQG KPSYTVDWYY SQTNKSIPTQ   60
ERNRVFASGQ LLKFLPAAVA DSGIYTCIVR SPTFNRTGYA NVTIYKKQSD CNVPDYLMYS  120
TVSGSEKNSK IYCPTIDLYN WTAPLEWFKN CQALQGSRYR AHKSFLVIDN VMTEDAGDYT  180
CKFIHNENGA NYSVTATRSF TVKDEQGFSL FPVIGAPAQN EIKEVEIGKN ANLTCSACFG  240
KGTQFLAAVL WQLNGTKITD FGEPRIQQEE GQNQSFSNGL ACLDMVLRIA DVKEEDLLLQ  300
YDCLALNLHG LRRHTVRLSR KNPSKECF                                     328

SEQ ID NO: 228          moltype = AA  length = 211
FEATURE                 Location/Qualifiers
source                  1..211
                        mol_type = protein
                        organism = Homo sapiens
SEQUENCE: 228
MYSTVSGSEK NSKIYCPTID LYNWTAPLEW FKNCQALQGS RYRAHKSFLV IDNVMTEDAG   60
DYTCKFIHNE NGANYSVTAT RSFTVKDEQG FSLFPVIGAP AQNEIKEVEI GKNANLTCSA  120
CFGKGTQFLA AVLWQLNGTK ITDFGEPRIQ QEEGQNQSFS NGLACLDMVL RIADVKEEDL  180
LLQYDCLALN LHGLRRHTVR LSRKNPSKEC F                                 211

SEQ ID NO: 229          moltype = AA  length = 314
FEATURE                 Location/Qualifiers
source                  1..314
                        mol_type = protein
                        organism = Homo sapiens
SEQUENCE: 229
MGFWILAILT ILMYSTAAKF SKQSWGLENE ALIVRCPRQG KPSYTVDWYY SQTNKSIPTQ   60
ERNRVFASGQ LLKFLPAAVA DSGIYTCIVR SPTFNRTGYA NVTIYKKQSD CNVPDYLMYS  120
TVSGSEKNSK IYCPTIDLYN WTAPLEWFKN CQALQGSRYR AHKSFLVIDN VMTEDAGDYT  180
CKFIHNENGA NYSVTATRSF TVKDEQGFSL FPVIGAPAQN EIKEVEIGTQ FLAAVLWQLN  240
GTKITDFGEP RIQQEEGQNQ SFSNGLACLD MVLRIADVKE EDLLLQYDCL ALNLHGLRRH  300
TVRLSRKNPS KECF                                                    314

SEQ ID NO: 230          moltype = AA  length = 259
FEATURE                 Location/Qualifiers
source                  1..259
                        mol_type = protein
                        organism = Homo sapiens
SEQUENCE: 230
MGFWILAILT ILMYSTAAKF SKQSWGLENE ALIVRCPRQG KPSYTVDWYY SQTNKSIPTQ   60
ERNRVFASGQ LLKFLPAAVA DSGIYTCIVR SPTFNRTGYA NVTIYKKQSD CNVPDYLMYS  120
TVSGSEKNSK IYCPTIDLYN WTAPLEWFKN CQALQGSRYR AHKSFLVIDN VMTEDAGDYT  180
CKFIHNENGA NYSVTATRSF TVKVWCQSFC KLKKSLIFSN THWIQSLMRG FVMVYYGVHK  240
CCRVVFNLCL QYFQHHQWP                                               259

SEQ ID NO: 231          moltype = AA  length = 38
FEATURE                 Location/Qualifiers
source                  1..38
                        mol_type = protein
                        organism = Homo sapiens
SEQUENCE: 231
MGFWILAILT ILMYSTAAKF SKQSWGLENE ALIVRCPR                           38

SEQ ID NO: 232          moltype = AA  length = 425
FEATURE                 Location/Qualifiers
source                  1..425
                        mol_type = protein
                        organism = Homo sapiens
SEQUENCE: 232
MVSKALLRLV SAVNRRRMKL LLGIALLAYV ASVWGNFVNM SFLLNRSIQE NGELKIESKI   60
```

```
EEMVEPLREK IRDLEKSFTQ KYPPVKFLSE KDRKRILITG GAGFVGSHLT DKLMMDGHEV    120
TVVDNFFTGR KRNVEHWIGH ENFELINHDV VEPLYIEVDQ IYHLASPASP PNYMYNPIKT    180
LKTNTIGTLN MLGLAKRVGA RLLLASTSEV YGDPEVHPQS EDYWGHVNPI GPRACYDEGK    240
RVAETMCYAY MKQEGVEVRV ARIFNTFGPR MHMNDGRVVS NFILQALQGE PLTVYGSGSQ    300
TRAFQYVSDL VNGLVALMNS NVSSPVNLGN PEEHTILEFA QLIKNLVGSG SEIQFLSEAQ    360
DDPQKRKPDI KKAKLMLGWE PVVPLEEGLN KAIHYFRKEL EYQANNQYIP KPKPARIKKG    420
RTRHS                                                                425

SEQ ID NO: 233           moltype = AA   length = 420
FEATURE                  Location/Qualifiers
source                   1..420
                         mol_type = protein
                         organism = Homo sapiens
SEQUENCE: 233
MVSKALLRLV SAVNRRRMKL LLGIALLAYV ASVWGNFVNM RSIQENGELK IESKIEEMVE     60
PLREKIRDLE KSFTQKYPPV KFLSEKDRKR ILITGGAGFV GSHLTDKLMM DGHEVTVVDN    120
FFTGRKRNVE HWIGHENFEL INHDVVEPLY IEVDQIYHLA SPASPPNYMY NPIKTLKTNT    180
IGTLNMLGLA KRVGARLLLA STSEVYGDPE VHPQSEDYWG HVNPIGPRAC YDEGKRVAET    240
MCYAYMKQEG VEVRVARIFN TFGPRMHMND GRVVSNFILQ ALQGEPLTVY GSGSQTRAFQ    300
YVSDLVNGLV ALMNSNVSSP VNLGNPEEHT ILEFAQLIKN LVGSGSEIQF LSEAQDDPQK    360
RKPDIKKAKL MLGWEPVVPL EEGLNKAIHY FRKELEYQAN NQYIPKPKPA RIKKGRTRHS    420

SEQ ID NO: 234           moltype = AA   length = 171
FEATURE                  Location/Qualifiers
source                   1..171
                         mol_type = protein
                         organism = Homo sapiens
SEQUENCE: 234
MVSKALLRLV SAVNRRRMKL LLGIALLAYV AWLAKRVGAR LLLASTSEVY GDPEVHPQSE     60
DYWGHVNPIG PRACYDEGKR VAETMCYAYM KQEGVEVRVA RIFNTFGPRM HMNDGRVVSN    120
FILQALQGEP LTVYGSGSQT RAFQYVSDLV NGLVALMNSN VSSPVNLSA P              171

SEQ ID NO: 235           moltype = AA   length = 190
FEATURE                  Location/Qualifiers
source                   1..190
                         mol_type = protein
                         organism = Homo sapiens
SEQUENCE: 235
MVEPLREKIR DLEKSFTQKY PPVKFLSEKD RKRILITGGA GFVGSHLTDK LMMDGHEVTV     60
VDNFFTGRKR NVEHWIGHEN FELINHDVVE PLYIEVDQIY HLASPASPPN YMYNPIKTLK    120
TNTIGTLNML GLAKRVGARL LLASTSEVYG DPEVHPQSED YWGHVNPIGP RACYDEGKRV    180
AETMCYAYMK                                                           190

SEQ ID NO: 236           moltype = AA   length = 210
FEATURE                  Location/Qualifiers
source                   1..210
                         mol_type = protein
                         organism = Homo sapiens
SEQUENCE: 236
MAVKVQTTKR GDPHELRNIF LQYASTEVDG ERYMTPEDFV QRYLGLYNDP NSNPKIVQLL     60
AGVADQTKDG LISYQEFLAF ESVLCAPDSM FIVAFQLFDK SGNGEVTFGG VLWPHRWYSS    120
SFQAHSWNRH GGSLGEECQP RSEKMSKKFL DRLLFIIISL TGIVNLSDC ILGITGRSIL    180
TTQNSRSFSR SCNWNMQDKP LHSKTKAKVA                                     210

SEQ ID NO: 237           moltype = AA   length = 870
FEATURE                  Location/Qualifiers
source                   1..870
                         mol_type = protein
                         organism = Homo sapiens
SEQUENCE: 237
MGVKKKKEMQ VAALTICHQD LETLKSFADV EGKNLASLLL HCVQLTDGVS QIHYIKQIVP     60
LLEKADKNGM CDPTIQSCLD ILAGIYLSLS LKNPLKKVLA SSLNSLPDFF LPEAMHRFTS    120
RLQEELNTTD LYSYRKVTDN ISSCMENFNL GRASVNNLLK NVLHFLQKSL IEILEENRKC    180
AGNHIIQTQL MNDLLVGIRV SMMLVQKVQD FQGNLWKTSD SPIWQNMCGL LSIFTKVLSD    240
DDLLQTVQST SGLAIIILFIK TMFHPSEKIP HLISSVLLRS VDCTSVPEWF MSSCRSLCCG    300
DISQSAVLFL CQGTLAMLDW QNGSMGRSGE ALLLDTAHVL FTLSSQIKEP TLEMFLSRIL    360
ASWTNSAIQV LESSSPSLTD SLNGNSSIVG RLLEYVYTHW EHPLDALRHQ TKIMFKNLLQ    420
MHRLTVEGAD FVPDPPFVEL TESLLRLEWH IKGKYTCLGC LVECIGVEHI LAIDKTIPSQ    480
ILEVMGDQSL VPYASDLLET MFRNHKSHLR SQTAESSWID QWHETWVSPL LFILCEGNLD    540
QKSYVIDYYL PKLLSYSPES LQYMVKILQT SIDAKTGQEQ SFPSLGSCNS RGALGALMAC    600
LRIARAHGHL QSATDTWENL VSDARIKQGL IHQHCQVRID TLGLLCESNR STEIVSMEEM    660
QWIQFFITYN LNSQSPGVRQ QICSLLKKLF CRIQESSQVL YKLEQSKSKR EPENELTKQH    720
PSVSLQQYKN FMSSICNSLF EALFPGSSYS TRFSALTILG SIAEVFHVPE GKCLIMLGEV    780
IFVFFQNILI LHFALFEVSV LLPFFEVSFL PYNSCLYIMK FASKGQKRKK LSPFSLIIIC    840
QPQSIIFMDY AYYGKSSSYY LTNLFVAVLR                                      870

SEQ ID NO: 238           moltype = AA   length = 906
FEATURE                  Location/Qualifiers
source                   1..906
```

```
                        mol_type  = protein
                        organism  = Homo sapiens
SEQUENCE: 238
MICQKFCVVL LHWEFIYVIT AFNLSYPITP WRFKLSCMPP NSTYDYFLLP AGLSKNTSNS    60
NGHYETAVEP KFNSSGTHFS NLSKTTFHCC FRSEQDRNCS LCADNIEGKT FVSTVNSLVF   120
QQIDANWNIQ CWLKGDLKLF ICYVESLFKN LFRNYNYKVH LLYVLPEVLE DSPLVPQKGS   180
FQMVHCNCSV HECCECLVPV PTAKLNDTLL MCLKITSGGV IFQSPLMSVQ PINMVKPDPP   240
LGLHMEITDD GNLKISWSSP PLVPFPLQYQ VKYSENSTTV IREADKIVSA TSLLVDSILP   300
GSSYEVQVRG KRLDGPGIWS DWSTPRVFTT QDVIYFPPKI LTSVGSNVSF HCIYKKENKI   360
VPSKEIVWWM NLAEKIPQSQ YDVVSDHVSK VTFFNLNETK PRGKFTYDAV YCCNEHECHH   420
RYAELYVIDV NINISCETDG YLTKMTCRWS TSTIQSLAES TLQLRYHRSS LYCSDIPSIH   480
PISEPKDCYL QSDGFYECIF QPIFLLSGYT MWIRINHSLG SLDSPPTCVL PDSVVKPLPP   540
SSVKAEITIN IGLLKISWEK PVFPENNLQF QIRYGLSGKE VQWKMYEVYD AKSKSVSLPV   600
PDLCAVYAVQ VRCKRLDGLG YWSNWSNPAY TVVMDIKVPM RGPEFWRIIN GDTMKKEKNV   660
TLLWKPLMKN DSLCSVQRYV INHHTSCNGT WSEDVGNHTK FTFLWTEQAH TVTVLAINSI   720
GASVANFNLT FSWPMSKVNI VQSLSAYPLN SSCVIVSWIL SPSDYKLMYF IIEWKNLNED   780
GEIKWLRISS SVKKYYIHDH FIPIEKYQFS LYPIFMEGVG KPKIINSFTQ DDIEKHQSDA   840
GLYVIVPVII SSSILLLGTL LISHQRMKKL FWEDVPNPKN CSWAQGLNFQ KKMPGTKELL   900
GGGWLT                                                              906

SEQ ID NO: 239          moltype = AA  length = 1165
FEATURE                 Location/Qualifiers
source                  1..1165
                        mol_type  = protein
                        organism  = Homo sapiens
SEQUENCE: 239
MICQKFCVVL LHWEFIYVIT AFNLSYPITP WRFKLSCMPP NSTYDYFLLP AGLSKNTSNS    60
NGHYETAVEP KFNSSGTHFS NLSKTTFHCC FRSEQDRNCS LCADNIEGKT FVSTVNSLVF   120
QQIDANWNIQ CWLKGDLKLF ICYVESLFKN LFRNYNYKVH LLYVLPEVLE DSPLVPQKGS   180
FQMVHCNCSV HECCECLVPV PTAKLNDTLL MCLKITSGGV IFQSPLMSVQ PINMVKPDPP   240
LGLHMEITDD GNLKISWSSP PLVPFPLQYQ VKYSENSTTV IREADKIVSA TSLLVDSILP   300
GSSYEVQVRG KRLDGPGIWS DWSTPRVFTT QDVIYFPPKI LTSVGSNVSF HCIYKKENKI   360
VPSKEIVWWM NLAEKIPQSQ YDVVSDHVSK VTFFNLNETK PRGKFTYDAV YCCNEHECHH   420
RYAELYVIDV NINISCETDG YLTKMTCRWS TSTIQSLAES TLQLRYHRSS LYCSDIPSIH   480
PISEPKDCYL QSDGFYECIF QPIFLLSGYT MWIRINHSLG SLDSPPTCVL PDSVVKPLPP   540
SSVKAEITIN IGLLKISWEK PVFPENNLQF QIRYGLSGKE VQWKMYEVYD AKSKSVSLPV   600
PDLCAVYAVQ VRCKRLDGLG YWSNWSNPAY TVVMDIKVPM RGPEFWRIIN GDTMKKEKNV   660
TLLWKPLMKN DSLCSVQRYV INHHTSCNGT WSEDVGNHTK FTFLWTEQAH TVTVLAINSI   720
GASVANFNLT FSWPMSKVNI VQSLSAYPLN SSCVIVSWIL SPSDYKLMYF IIEWKNLNED   780
GEIKWLRISS SVKKYYIHDH FIPIEKYQFS LYPIFMEGVG KPKIINSFTQ DDIEKHQSDA   840
GLYVIVPVII SSSILLLGTL LISHQRMKKL FWEDVPNPKN CSWAQGLNFQ KPETFEHLFI   900
KHTASVTCGP LLLEPETISE DISVDTSWKN KDEMMPTTVV SLLSTTDLEK GSVCISDQFN   960
SVNFSEAEGT EVTYEDESQR QPFVKYATLI SNSKPSETGE EQGLINSSVT KCFSSKNSPL  1020
KDSFSNSSWE IEAQAFFILS DQHPNIISPH LTFSEGLDEL LKLEGNFPEE NNDKKSIYYL  1080
GVTSIKKRES GVLLTDKSRV SCPFPAPCLF TDIRVLQDSC SHFVENNINL GTSSKKTFAS  1140
YMPQFQTCST QTHKIMENKM CDLTV                                       1165

SEQ ID NO: 240          moltype = AA  length = 906
FEATURE                 Location/Qualifiers
source                  1..906
                        mol_type  = protein
                        organism  = Homo sapiens
SEQUENCE: 240
MICQKFCVVL LHWEFIYVIT AFNLSYPITP WRFKLSCMPP NSTYDYFLLP AGLSKNTSNS    60
NGHYETAVEP KFNSSGTHFS NLSKTTFHCC FRSEQDRNCS LCADNIEGKT FVSTVNSLVF   120
QQIDANWNIQ CWLKGDLKLF ICYVESLFKN LFRNYNYKVH LLYVLPEVLE DSPLVPQKGS   180
FQMVHCNCSV HECCECLVPV PTAKLNDTLL MCLKITSGGV IFQSPLMSVQ PINMVKPDPP   240
LGLHMEITDD GNLKISWSSP PLVPFPLQYQ VKYSENSTTV IREADKIVSA TSLLVDSILP   300
GSSYEVQVRG KRLDGPGIWS DWSTPRVFTT QDVIYFPPKI LTSVGSNVSF HCIYKKENKI   360
VPSKEIVWWM NLAEKIPQSQ YDVVSDHVSK VTFFNLNETK PRGKFTYDAV YCCNEHECHH   420
RYAELYVIDV NINISCETDG YLTKMTCRWS TSTIQSLAES TLQLRYHRSS LYCSDIPSIH   480
PISEPKDCYL QSDGFYECIF QPIFLLSGYT MWIRINHSLG SLDSPPTCVL PDSVVKPLPP   540
SSVKAEITIN IGLLKISWEK PVFPENNLQF QIRYGLSGKE VQWKMYEVYD AKSKSVSLPV   600
PDLCAVYAVQ VRCKRLDGLG YWSNWSNPAY TVVMDIKVPM RGPEFWRIIN GDTMKKEKNV   660
TLLWKPLMKN DSLCSVQRYV INHHTSCNGT WSEDVGNHTK FTFLWTEQAH TVTVLAINSI   720
GASVANFNLT FSWPMSKVNI VQSLSAYPLN SSCVIVSWIL SPSDYKLMYF IIEWKNLNED   780
GEIKWLRISS SVKKYYIHDH FIPIEKYQFS LYPIFMEGVG KPKIINSFTQ DDIEKHQSDA   840
GLYVIVPVII SSSILLLGTL LISHQRMKKL FWEDVPNPKN CSWAQGLNFQ KKMPGTKELL   900
GGGWLT                                                              906

SEQ ID NO: 241          moltype = AA  length = 958
FEATURE                 Location/Qualifiers
source                  1..958
                        mol_type  = protein
                        organism  = Homo sapiens
SEQUENCE: 241
MICQKFCVVL LHWEFIYVIT AFNLSYPITP WRFKLSCMPP NSTYDYFLLP AGLSKNTSNS    60
NGHYETAVEP KFNSSGTHFS NLSKTTFHCC FRSEQDRNCS LCADNIEGKT FVSTVNSLVF   120
QQIDANWNIQ CWLKGDLKLF ICYVESLFKN LFRNYNYKVH LLYVLPEVLE DSPLVPQKGS   180
```

```
FQMVHCNCSV HECCECLVPV PTAKLNDTLL MCLKITSGGV IFQSPLMSVQ PINMVKPDPP    240
LGLHMEITDD GNLKISWSSP PLVPFPLQYQ VKYSENSTTV IREADKIVSA TSLLVDSILP    300
GSSYEVQVRG KRLDGPGIWS DWSTPRVFTT QDVIYFPPKI LTSVGSNVSF HCIYKKENKI    360
VPSKEIVWWM NLAEKIPQSQ YDVVSDHVSK VTFFNLNETK PRGKFTYDAV YCCNEHECHH    420
RYAELYVIDV NINISCETDG YLTKMTCRWS TSTIQSLAES TLQLRYHRSS LYCSDIPSIH    480
PISEPKDCYL QSDGFYECIF QPIFLLSGYT MWIRINHSLG SLDSPPTCVL PDSVVKPLPP    540
SSVKAEITIN IGLLKISWEK PVFPENNLQF QIRYGLSGKE VQWKMYEVYD AKSKSVSLPV    600
PDLCAVYAVQ VRCKRLDGLG YWSNWSNPAY TVVMDIKVPM RGPEFWRIIN GDTMKKEKNV    660
TLLWKPLMKN DSLCSVQRYV INHHTSCNGT WSEDVGNHTK FTFLWTEQAH TVTVLAINSL    720
GASVANFNLT FSWPMSKVNI VQSLSAYPLN SSCVIVSWIL SPSDYKLMYF IIEWKNLNED    780
GEIKWLRISS SVKKYYIHDH FIPIEKYQFS LYPIFMEGVG KPKIINSFTQ DDIEKHQSDA    840
GLYVIVPVII SSSILLLGTL LISHQRMKKL FWEDVPNPKN CSWAQGLNFQ KMLEGSMFVK    900
SHHHSLISST QGHKHCGRPQ GPLHRKTRDL CSLVYLLTLP PLLSYDPAKS PSVRNTQE     958

SEQ ID NO: 242         moltype = AA  length = 896
FEATURE                Location/Qualifiers
source                 1..896
                       mol_type = protein
                       organism = Homo sapiens
SEQUENCE: 242
MICQKFCVVL LHWEFIYVIT AFNLSYPITP WRFKLSCMPP NSTYDYFLLP AGLSKNTSNS     60
NGHYETAVEP KFNSSGTHFS NLSKTTFHCC FRSEQDRNCS LCADNIEGKT FVSTVNSLVF    120
QQIDANWNIQ CWLKGDLKLF ICYVESLFKN LFRNYNYKVH LLYVLPEVLE DSPLVPQKGS    180
FQMVHCNCSV HECCECLVPV PTAKLNDTLL MCLKITSGGV IFQSPLMSVQ PINMVKPDPP    240
LGLHMEITDD GNLKISWSSP PLVPFPLQYQ VKYSENSTTV IREADKIVSA TSLLVDSILP    300
GSSYEVQVRG KRLDGPGIWS DWSTPRVFTT QDVIYFPPKI LTSVGSNVSF HCIYKKENKI    360
VPSKEIVWWM NLAEKIPQSQ YDVVSDHVSK VTFFNLNETK PRGKFTYDAV YCCNEHECHH    420
RYAELYVIDV NINISCETDG YLTKMTCRWS TSTIQSLAES TLQLRYHRSS LYCSDIPSIH    480
PISEPKDCYL QSDGFYECIF QPIFLLSGYT MWIRINHSLG SLDSPPTCVL PDSVVKPLPP    540
SSVKAEITIN IGLLKISWEK PVFPENNLQF QIRYGLSGKE VQWKMYEVYD AKSKSVSLPV    600
PDLCAVYAVQ VRCKRLDGLG YWSNWSNPAY TVVMDIKVPM RGPEFWRIIN GDTMKKEKNV    660
TLLWKPLMKN DSLCSVQRYV INHHTSCNGT WSEDVGNHTK FTFLWTEQAH TVTVLAINSI    720
GASVANFNLT FSWPMSKVNI VQSLSAYPLN SSCVIVSWIL SPSDYKLMYF IIEWKNLNED    780
GEIKWLRISS SVKKYYIHDH FIPIEKYQFS LYPIFMEGVG KPKIINSFTQ DDIEKHQSDA    840
GLYVIVPVII SSSILLLGTL LISHQRMKKL FWEDVPNPKN CSWAQGLNFQ KRTDIL        896

SEQ ID NO: 243         moltype = AA  length = 232
FEATURE                Location/Qualifiers
source                 1..232
                       mol_type = protein
                       organism = Homo sapiens
SEQUENCE: 243
MMPTTVVSLL STTDLEKGSV CISDQFNSVN FSEAEGTEVT YEDESQRQPF VKYATLISNS     60
KPSETGEEQG LINSSVTKCF SSKNSPLKDS FSNSSWEIEA QAFFILSDQH PNIISPHLTF    120
SEGLDELLKL EGNFPEENND KKSIYYLGVT SIKKRESGVL LTDKSRVSCP FPAPCLFTDI    180
RVLQDSCSHF VENNINLGTS SKKTFASYMP QFQTCSTQTH KIMENKMCDL TV            232

SEQ ID NO: 244         moltype = AA  length = 896
FEATURE                Location/Qualifiers
source                 1..896
                       mol_type = protein
                       organism = Homo sapiens
SEQUENCE: 244
MICQKFCVVL LHWEFIYVIT AFNLSYPITP WRFKLSCMPP NSTYDYFLLP AGLSKNTSNS     60
NGHYETAVEP KFNSSGTHFS NLSKTTFHCC FRSEQDRNCS LCADNIEGKT FVSTVNSLVF    120
QQIDANWNIQ CWLKGDLKLF ICYVESLFKN LFRNYNYKVH LLYVLPEVLE DSPLVPQKGS    180
FQMVHCNCSV HECCECLVPV PTAKLNDTLL MCLKITSGGV IFQSPLMSVQ PINMVKPDPP    240
LGLHMEITDD GNLKISWSSP PLVPFPLQYQ VKYSENSTTV IREADKIVSA TSLLVDSILP    300
GSSYEVQVRG KRLDGPGIWS DWSTPRVFTT QDVIYFPPKI LTSVGSNVSF HCIYKKENKI    360
VPSKEIVWWM NLAEKIPQSQ YDVVSDHVSK VTFFNLNETK PRGKFTYDAV YCCNEHECHH    420
RYAELYVIDV NINISCETDG YLTKMTCRWS TSTIQSLAES TLQLRYHRSS LYCSDIPSIH    480
PISEPKDCYL QSDGFYECIF QPIFLLSGYT MWIRINHSLG SLDSPPTCVL PDSVVKPLPP    540
SSVKAEITIN IGLLKISWEK PVFPENNLQF QIRYGLSGKE VQWKMYEVYD AKSKSVSLPV    600
PDLCAVYAVQ VRCKRLDGLG YWSNWSNPAY TVVMDIKVPM RGPEFWRIIN GDTMKKEKNV    660
TLLWKPLMKN DSLCSVQRYV INHHTSCNGT WSEDVGNHTK FTFLWTEQAH TVTVLAINSI    720
GASVANFNLT FSWPMSKVNI VQSLSAYPLN SSCVIVSWIL SPSDYKLMYF IIEWKNLNED    780
GEIKWLRISS SVKKYYIHDH FIPIEKYQFS LYPIFMEGVG KPKIINSFTQ DDIEKHQSDA    840
GLYVIVPVII SSSILLLGTL LISHQRMKKL FWEDVPNPKN CSWAQGLNFQ KRTDIL        896

SEQ ID NO: 245         moltype = AA  length = 214
FEATURE                Location/Qualifiers
source                 1..214
                       mol_type = protein
                       organism = Homo sapiens
SEQUENCE: 245
MGLRDWLRTV CCCCGCECLE ERALPEKEPL VSDNNPYSSF GATLVRDDEK NLWSMPHDVS     60
HTEADDDRTL YNLIVIRNQQ AKDSEEWQKL NYDIHTLRQV RREVRNRWKC ILEDLGFQKE    120
ADSLLSVTKL STISDSKNTR KAREMLLKLA EETNIFPTSW ELSERYLFVV DRLIALDAAE    180
EFFKLARRTY PKKPGVPCLA DGQKELHYLP FPSP                               214
```

```
SEQ ID NO: 246          moltype = AA  length = 214
FEATURE                 Location/Qualifiers
source                  1..214
                        mol_type = protein
                        organism = Homo sapiens
SEQUENCE: 246
MGLRDWLRTV CCCCGCECLE ERALPEKEPL VSDNNPYSSF GATLVRDDEK NLWSMPHDVS    60
HTEADDDRTL YNLIVIRNQQ AKDSEEWQKL NYDIHTLRQV RREVRNRWKC ILEDLGFQKE   120
ADSLLSVTKL STISDSKNTR KAREMLLKLA EETNIFPTSW ELSERYLFVV DRLIALDAAE   180
EFFKLARRTY PKKPGVPCLA DGQKELHYLP FPSP                              214

SEQ ID NO: 247          moltype = AA  length = 526
FEATURE                 Location/Qualifiers
source                  1..526
                        mol_type = protein
                        organism = Homo sapiens
SEQUENCE: 247
MVNEGPNQEE SDDTPVPESA LQADPSVSVH PSVSVHPSVS INPSVSVHPS SSAHPSALAQ    60
PSGLAHPSSS GPEDLSVIKV SRRRWAVVLV FSCYSMCNSF QWIQYGSINN IFMHFYGVSA   120
FAIDWLSMCY MLTYIPLLLP VAWLLEKFGL RTIALTGSAL NCLGAWVKLG SLKPHLFPVT   180
VVGQLICSVA QVFILGMPSR IASVWFGANE VSTACSVAVF GNQLGIAIGF LVPPVLVPNI   240
EDRDELAYHI SIMFYIIGGV ATLLLILVII VFKEKPKYPP SRAQSLSYAL TSPDASYLGS   300
IARLFKNLNF VLLVITYGLN AGAFYALSTL LNRMVIWHYP GEEVNAGRIG LTIVIAGMLG   360
AVISGIWLDR SKTYKETTLV VYIMTLVGMV VYTFTLNLGH LWVVFITAGT MGFFMTGYLP   420
LGFEFAVELT YPESEGISSG LLNISAQVFG IIFTISQGQI IDNYGTKPGN IFLCVFLTLG   480
AALTAFIKAD LRRQKANKET LENKLQEEEE ESNTSKVPTA VSEDHL                 526

SEQ ID NO: 248          moltype = AA  length = 321
FEATURE                 Location/Qualifiers
source                  1..321
                        mol_type = protein
                        organism = Homo sapiens
SEQUENCE: 248
MSADNSSTIC VCRSVRQELG IAIGFLVPPV LVPNIEDRDE LAYHISIMFY IIGGVATLLL    60
ILVIIVFKEK PKYPPSRAQS LSYALTSPDA SYLGSIARLF KNLNFVLLVI TYGLNAGAFY   120
ALSTLLNRMV IWHYPGEEVN AGRIGLTIVI AGMLGAVISG IWLDRSKTYK ETTLVVYIMT   180
LVGMVVYTFT LNLGHLWVVF ITAGTMGFFM TGYLPLGFEF AVELTYPESE GISSGLLNIS   240
AQVFGIIFTI SQGQIIDNYG TKPGNIFLCV FLTLGAALTA FIKADLRRQK ANKETLENKL   300
QEEEEESNTS KVPTAVSEDH L                                            321

SEQ ID NO: 249          moltype = AA  length = 203
FEATURE                 Location/Qualifiers
source                  1..203
                        mol_type = protein
                        organism = Homo sapiens
SEQUENCE: 249
MFYIIGGVAT LLLILVIIGL NAGAFYALST LLNRMVIWHY PGEEVNAGRI GLTIVIAGML    60
GAVISGIWLD RSKTYKETTL VVYIMTLVGM VVYTFTLNLG HLWVVFITAG TMGFFMTGYL   120
PLGFEFAVEL TYPESEGISS GLLNISAQVF GIIFTISQGQ IIDNYGTKPG NIFLCVFLTL   180
GAALTAFIKA DLRRQKANKE TLE                                          203

SEQ ID NO: 250          moltype = AA  length = 133
FEATURE                 Location/Qualifiers
source                  1..133
                        mol_type = protein
                        organism = Homo sapiens
SEQUENCE: 250
MFYIIGGVAT LLLILVIIVF KEKPKYPPSR AQSLSYALTS PDASYLGSIA RLFKNLNFVL    60
LVITYGLNAG AFYALSTLLN RMVIWHYPGE EVNAGRIGLT IVIAGMLGAV ISGIWLDRSK   120
TYKNLCHPNC LIQ                                                     133

SEQ ID NO: 251          moltype = AA  length = 203
FEATURE                 Location/Qualifiers
source                  1..203
                        mol_type = protein
                        organism = Homo sapiens
SEQUENCE: 251
MSPYGISSLG NGLSKWLSLN AGAFYALSTL LNRMVIWHYP GEEVNAGRIG LTIVIAGMLG    60
AVISGIWLDR SKTYKETTLV VYIMTLVGMV VYTFTLNLGH LWVVFITAGT MGFFMTGYLP   120
LGFEFAVELT YPESEGISSG LLNISAQVFG IIFTISQGQI IDNYGTKPGN IFLCVFLTLG   180
AALTAFIKAD LRRQKANKET LEN                                          203

SEQ ID NO: 252          moltype = AA  length = 241
FEATURE                 Location/Qualifiers
source                  1..241
                        mol_type = protein
                        organism = Homo sapiens
SEQUENCE: 252
```

```
MCPDLHPSKY VQPPLSSSSS PLKGGQEAFS PLGLNAGAFY ALSTLLNRMV IWHYPGEEVN    60
AGRIGLTIVI AGMLGAVISG IWLDRSKTYK ETTLVVYIMT LVGMVVYTFT LNLGHLWVVF   120
ITAGTMGFFM TGYLPLGFEF AVELTYPESE GISSGLLNIS AQVFGIIFTI SQGQIIDNYG   180
TKPGNIFLCV FLTLGAALTA FIKADLRRQK ANKETLENKL QEEEEESNTS KVPTAVSEDH   240
L                                                                  241

SEQ ID NO: 253          moltype = AA  length = 88
FEATURE                 Location/Qualifiers
source                  1..88
                        mol_type = protein
                        organism = Homo sapiens
SEQUENCE: 253
MFYIIGGVAT LLLILVIIVF KEKPKYPPSR AQSLSYALTS PDASYLGSIA RLFKNLNFVL    60
LVITYGLNAG AFYALSTLLN RMVIWHYP                                      88

SEQ ID NO: 254          moltype = AA  length = 93
FEATURE                 Location/Qualifiers
source                  1..93
                        mol_type = protein
                        organism = Homo sapiens
SEQUENCE: 254
MFYIIGGVAT LLLILVIIVF KEKPKYPPSR AQSLSYALTS PDASYLGSIA RLFKNLNFVL    60
LVITYETPRG GGGEQHQQSA HCCVRGSSLR GRW                                93

SEQ ID NO: 255          moltype = AA  length = 102
FEATURE                 Location/Qualifiers
source                  1..102
                        mol_type = protein
                        organism = Homo sapiens
SEQUENCE: 255
MTLRCLEPSG NGGEGTRSQW GTAGSAEEPS PQAARLAKAL RELGQTGREP IGRDACGRER    60
LPKEAARKRG RGGKQRIRWK YVPCFQGTAE STLAGSWVLG NA                     102

SEQ ID NO: 256          moltype = AA  length = 46
FEATURE                 Location/Qualifiers
source                  1..46
                        mol_type = protein
                        organism = Homo sapiens
SEQUENCE: 256
XAPSLQHLCR LTINKCTGAI WGLPLPTRLK DYLEEYKFQP AVFYPG                   46

SEQ ID NO: 257          moltype = AA  length = 341
FEATURE                 Location/Qualifiers
source                  1..341
                        mol_type = protein
                        organism = Homo sapiens
SEQUENCE: 257
MNIVVEFFVV TFKVLWAFVL AAARWLVRPK EKSVAGQVCL ITGAGSGLGR LFALEFARRR    60
ALLVLWDINT QSNEETAGMV RHIYRDLEAA DAAALQAGNG EEEILPHCNL QVFTYTCDVG   120
KRENVYLTAE RVRKEVGEVS VLVNNAGVVS GHHLLECPDE LIERTMMVNC HAHFWTTKAF   180
LPTMLEINHG HIVTVASSLG LFSTAGVEDY CASKFGVVGF HESLSHELKA AEKDGIKTTL   240
VCPYLVDTGM FRGCRIRKEI EPFLPPLKPD YCVKQAMKAI LTDQPMICTP RLMYIVTFMK   300
SILPFEAVVC MYRFLGADKC MYPFIAQRKQ ATNNNEAKNG I                       341

SEQ ID NO: 258          moltype = AA  length = 176
FEATURE                 Location/Qualifiers
source                  1..176
                        mol_type = protein
                        organism = Homo sapiens
SEQUENCE: 258
MMVNCHAHFW TTKAFLPTML EINHGHIVTV ASSLGLFSTA GVEDYCASKF GVVGFHESLS    60
HELKAAEKDG IKTTLVCPYL VDTGMFRGCR IRKEIEPFLP PLKPDYCVKQ AMKAILTDQP   120
MICTPRLMYI VTFMKSILPF EAVVCMYRFL GADKCMYPFI AQRKQATNNN EAKNGI       176

SEQ ID NO: 259          moltype = AA  length = 62
FEATURE                 Location/Qualifiers
source                  1..62
                        mol_type = protein
                        organism = Homo sapiens
SEQUENCE: 259
MMVNCHAHFW TTKAFLPTML EINHGHIVTV ASSLGLFSTA GVEDYCASKF GVVGFHESLS    60
HE                                                                  62

SEQ ID NO: 260          moltype = AA  length = 382
FEATURE                 Location/Qualifiers
source                  1..382
                        mol_type = protein
                        organism = Homo sapiens
SEQUENCE: 260
```

```
MRSHFLQWAL ATSRNKDQIT NIFSGFAGLL AILLVVAVFC ILWNWNKRKK RQVPYLRVTV    60
MPLLTLPQTR QRAKNIYDIL PWRQEDLGRH ESRSMRIFST ESLLSRNSES PEHVPSQAGN   120
APQEHTAHIH ATEYAVGIYD NAMVPQMCGN LTPSAHCINV RASRDCASIS SEDSHDYVNV   180
PTAEEIAETL ASTKSPSRNL FVLPSTQKLE FTEERDEGCG DAGDCTSLYS PGAEDSDSLS   240
NGEGSSQISN DYVNMTGLDL SAIQERQLWV AFQCCRDYEN VPAADPSGSQ QQAEKDVPSS   300
NIGHVEDKTD DPGTHVQCVK RTFLASGDYA DFQPFTQSED SQMKHREEMS NEDSSDYENV   360
LTAKLGGRDS EQGPGTQLLP DE                                           382

SEQ ID NO: 261             moltype = AA   length = 398
FEATURE                    Location/Qualifiers
source                     1..398
                           mol_type = protein
                           organism = Homo sapiens
SEQUENCE: 261
MDGVTPTLST IRGRTLESST LHVTPRSLDR NKDQITNIFS GFAGLLAILL VVAVFCILWN    60
WNKRKKRQVP YLRVTVMPLL TLPQTRQRAK NIYDILPWRQ EDLGRHESRS MRIFSTESLL   120
SRNSESPEHV PSQAGNAFQE HTAHIHATEY AVGIYDNAMV PQMCGNLTPS AHCINVRASR   180
DCASISSEDS HDYVNVPTAE EIAETLASTK SPSRNLFVLP STQKLEFTEE RDEGCGDAGD   240
CTSLYSPGAE DSDSLSNGEG SSQISNDYVN MTGLDLSAIQ ERQLWVAFQC CRDYENVPAA   300
DPSGSQQQAE KDVPSSNIGH VEDKTDDPGT HVQCVKRTFL ASGDYADFQP FTQSEDSQMK   360
HREEMSNEDS SDYENVLTAK LGGRDSEQGP GTQLLPDE                          398

SEQ ID NO: 262             moltype = AA   length = 48
FEATURE                    Location/Qualifiers
source                     1..48
                           mol_type = protein
                           organism = Homo sapiens
SEQUENCE: 262
MEAAETEAEA AALEVLAEVA GILEPVGLQE EAELPAKILV EFVVVCTR                 48

SEQ ID NO: 263             moltype = AA   length = 439
FEATURE                    Location/Qualifiers
source                     1..439
                           mol_type = protein
                           organism = Homo sapiens
SEQUENCE: 263
MRRAALRLCA LGKGQLTPGR GLTQGPQNPK KQGIFHIHEV RDKLREIVGA STNWRDHVKA    60
MEERKLLHSF LAKSQDGLPP RRMKDSYIEV LLPLGSEPEL REKYLTVQNT VRFGRILEDL   120
DSLGVLICYM HNKIHSAKMS PLSIVTALVD KIDMCKKSLS PEQDIKFSGH VSWVGKTSME   180
VKMQMFQLHG DEFCPVLDAT FVMVARDSEN KGPAFVNPLI PESPEEEELF RQGELNKGRR   240
IAFSSTSLLK MAPSAEERTT IHEMFLSTLD PKTISFRSRV LPSNAVWMEN SKLKSLEICH   300
PQERNIFNRI FGGFLMRKAY ELAWATACSF GGSRPFVVAV DDIMFQKPVE VGSLLFLSSQ   360
VCFTQNNYIQ VRVHSEVASL QEKQHTTTNV FHFTFMSEKE VPLVFPKTYG ESMLYLDGQR   420
HFNSMSGPAT LRKDYLVEP                                               439

SEQ ID NO: 264             moltype = AA   length = 448
FEATURE                    Location/Qualifiers
source                     1..448
                           mol_type = protein
                           organism = Homo sapiens
SEQUENCE: 264
MRRAALRLCA LGKGQLTPGR GLTQGPQNPK KQGIFHIHEA CSSIHVNHVR DKLREIVGAS    60
TNWRDHVKAM EERKLLHSFL AKSQDGLPPR RMKDSYIEVL LPLGSEPELR EKYLTVQNTV   120
RFGRILEDLD SLGVLICYMH NKIHSAKMSP LSIVTALVDK IDMCKKSLSP EQDIKFSGHV   180
SWVGKTSMEV KMQMFQLHGD EFCPVLDATF VMVARDSENK GPAFVNPLIP ESPEEEELFR   240
QGELNKGRRI AFSSTSLLKM APSAEERTTI HEMFLSTLDP KTISFRSRVL PSNAVWMENS   300
KLKSLEICHP QERNIFNRIF GGFLMRKAYE LAWATACSFG GSRPFVVAVD DIMFQKPVEV   360
GSLLFLSSQV CFTQNNYIQV RVHSEVASLQ EKQHTTTNVF HFTFMSEKEV PLVFPKTYGE   420
SMLYLDGQRH FNSMSGPATL RKDYLVEP                                     448

SEQ ID NO: 265             moltype = AA   length = 46
FEATURE                    Location/Qualifiers
source                     1..46
                           mol_type = protein
                           organism = Homo sapiens
SEQUENCE: 265
MRRAALRLCA LGKGQLTPGR GLTQGPQNPK KQGIFHIHEG KHGVSV                   46

SEQ ID NO: 266             moltype = AA   length = 663
FEATURE                    Location/Qualifiers
source                     1..663
                           mol_type = protein
                           organism = Homo sapiens
SEQUENCE: 266
MSARLPVLSP PRWPRLLLLS LLLLGAVPGP RRSGAFYLPG LAPVNFCDEE KKSDECKAEI    60
ELFVNRLDSV ESVLPYEYTA FDFCQASEGK RPSENLGQVL FGERIEPSPY KPTFNKKETC   120
KLVCTKTYHT EKAEDKQKLE FLKKSMLLNY QHHWIVDNMP VTWCYDVEDG QRFCNPGFPI   180
GCYITDKGHA KDACVISSDF HERDTFYIFN HVDIKIYYHV VETGSMGARL VAAKLEPKSF   240
KHTHIDKPDC SGPPMDISNK ASGEIKIAYT YSVSFEEDDK IRWASRWDYI LESMPHTHIQ   300
```

```
WFSIMNSLVI VLFLSGMVAM IMLRTLHKDI ARYNQMDSTE DAQEEFGWKL VHGDIFRPPR    360
KGMLLSVFLG SGTQILIMTF VTLFFACLGF LSPANRGALM TCAVVLWVLL GTPAGYVAAR    420
FYKSFGGEKW KTNVLLTSFL CPGIVFADFF IMNLILWGEG SSAAIPFGTL VAILALWFCI    480
SVPLTFIGAY FGFKKNAIEH PVRTNQIPRQ IPEQSFYTKP LPGIIMGGIL PFGCIFIQLF    540
FILNSIWSHQ MYYMFGFLPL VFIILVITCS EATILLCYPH LCAEDYHWQW RSFLTSGFTA    600
VYFLIYAVHY FFSKLQITGT ASTILYFGYT MIMVLIFFLF TGTIGFFACF WFVTKIYSVV    660
KVD                                                                  663

SEQ ID NO: 267              moltype = AA   length = 390
FEATURE                     Location/Qualifiers
source                      1..390
                            mol_type = protein
                            organism = Homo sapiens
SEQUENCE: 267
MGQRLSGGRS CLDVPGRLLP QPPPPPPPVR RKLALLFAML CVWLYMFLYS CAGSCAAAPG    60
LLLLGSGSRA AHDPPALATA PDGTPPRLPF RAPPATPLAS GKEMAEGAAS PEEQSPEVPD    120
SPSPISSFFS GSGSKQLPQA IIIGVKKGGT RALLEFLRVH PDVRAVGAEP HFFDRSYDKG    180
LAWYRDLMPR TLDGQITMEK TPSYFVTREA PARISAMSKD TKLIVVVRDP VTRAISDYTQ    240
TLSKRPDIPT FESLTFKNRT AGLIDTSWSA IQIGIYAKHL EHWLRHFPIR QMLFVSGERL    300
ISDPAGELGR VQDFLGLKRI ITDKHFYFNK TKGFPCLKKA EGSSRPHCLG KTKGRTHPEI    360
DREVVRRLRE FYRPFNLKFY QMTGHDFGWD                                     390

SEQ ID NO: 268              moltype = AA   length = 390
FEATURE                     Location/Qualifiers
source                      1..390
                            mol_type = protein
                            organism = Homo sapiens
SEQUENCE: 268
MGQRLSGGRS CLDVPGRLLP QPPPPPPPVR RKLALLFAML CVWLYMFLYS CAGSCAAAPG    60
LLLLGSGSRA AHDPPALATA PDGTPPRLPF RAPPATPLAS GKEMAEGAAS PEEQSPEVPD    120
SPSPISSFFS GSGSKQLPQA IIIGVKKGGT RALLEFLRVH PDVRAVGAEP HFFDRSYDKG    180
LAWYRDLMPR TLDGQITMEK TPSYFVTREA PARISAMSKD TKLIVVVRDP VTRAISDYTQ    240
TLSKRPDIPT FESLTFKNRT AGLIDTSWSA IQIGIYAKHL EHWLRHFPIR QMLFVSGERL    300
ISDPAGELGR VQDFLGLKRI ITDKHFYFNK TKGFPCLKKA EGSSRPHCLG KTKGRTHPEI    360
DREVVRRLRE FYRPFNLKFY QMTGHDFGWD                                     390

SEQ ID NO: 269              moltype = AA   length = 649
FEATURE                     Location/Qualifiers
source                      1..649
                            mol_type = protein
                            organism = Homo sapiens
SEQUENCE: 269
MSSFGAGKTK EVIFSVEDGS VKMFLRGRPV PMMIPDELAP TYSLDTRSEL PSCRLKLEWV    60
YGYRGRDCRA NLYLLPTGEI VYFVASVAVL YSVEEQRQRH YLGHNDDIKC LAIHPDMVTI    120
ATGQVAGTTK EGKPLPPHVR IWDSVSLSTL HVLGLGVFDR AVCCVGFSKS NGGNLLCAVD    180
ESNDHMLSVW DWAKETKVVD VKCSNEAVLV ATFHPTDPTV LITCGKSHIY FWTLEGGSLS    240
KRQGLFEKHE KPKYVLCVTF LEGGDVVTGD SGGNLYVWGK GGNRITQAVL GAHDGGVFGL    300
CALRDGTLVS GGGRDRRVVL WGSDYSKLQE VEVPEDFGPV RTVAEGHGDT LYVGTTRNSI    360
LQGSVHTGFS LLVQGHVEEL WGLATHPSRA QFVTCGQDKL VHLWSSDSHQ PLWSRIIEDP    420
ARSAGFHPSG SVLAVGTVTG RWLLLDTETH DLVAIHTDGN EQISVVSFSP DGAYLAVGSH    480
DNLVYVYTVD QGGRKVSRLG KCSGHSSFIT HLDWAQDSSC FVTNSGDYEI LYWDPATCKQ    540
ITSADAVRNM EWATATCVLG FGVFGIWSEG ADGTDINAVA RSHDGKLLAS ADDFGKVHLF    600
SYPCCQPRAL SHKYGGHSSH VTNVAFLWDD SMALTTGGKD TSVLQWRVV                649

SEQ ID NO: 270              moltype = AA   length = 145
FEATURE                     Location/Qualifiers
source                      1..145
                            mol_type = protein
                            organism = Homo sapiens
SEQUENCE: 270
MSSFGAGKTK EVIFSVAWPS TQIWSPSPRD RWREPLRKGS RCRPTCASGT QFPSPPYTCW    60
AWGCLTEPCA VWASPNLMEA TCCVQWMNPM ITCSRCGTGP RRPRWWMSSA PMRLYWWPPS    120
TPRTPLCLSP AGNLTSTSGP WRGAA                                          145

SEQ ID NO: 271              moltype = AA   length = 76
FEATURE                     Location/Qualifiers
source                      1..76
                            mol_type = protein
                            organism = Homo sapiens
SEQUENCE: 271
XGRKVSRLGK CSGHSSFITH LDWAQDSSCF VTNSGDYEIL YLEMGFHHLG QAGLELLTSG    60
DPARCCGSCC LLGLQT                                                    76

SEQ ID NO: 272              moltype = AA   length = 225
FEATURE                     Location/Qualifiers
source                      1..225
                            mol_type = protein
                            organism = Homo sapiens
SEQUENCE: 272
```

```
MFLRGRPVPM MIPDELAPTY SLDTRSELPS CRLKLEWVYG YRGRDCRANL YLLPTGEIVY    60
FVASVAVLYS VEEQRQRHYL GHNDDIKCLA IHPDMVTIAT GQVAGTTKEG KPLPPHVRIW   120
DSVSLSTLHV LGLGVFDRAV CCVGFSKSNG GNLLCAVDES NDHMLSVWDW AKETKVVDVK   180
CSNEAVLVAT FHPTDPTVLI TCGKSHIYFW TLEGGSLSKR QGLFE                  225

SEQ ID NO: 273            moltype = AA  length = 850
FEATURE                   Location/Qualifiers
source                    1..850
                          mol_type = protein
                          organism = Homo sapiens
SEQUENCE: 273
MLERRALLWQ REAGPGWGDR ARAGTGGAGG GCGGAMAERG PAFCGLYDTS SLLRYCNDDN    60
LSGTSGMEVD DRVSALEQRL QLQEDELAVL KAALADALRR LRACEEQGAA LRARGTPKGR   120
APPRLGTTAS VCQLLKGLPT RTPLNGSGPP RRVGGYATSP SSPKKEATSG RSSVRRYLSP   180
ERLASVRRED PRSRTTSSSS NCSAKKEGKT KEVIFSVEDG SVKMFLRGRP VPMMIPDELA   240
PTYSLDTRSE LPSCRLKLEW VYGYRGRDCR ANLYLLPTGE IVYFVASVAV LYSVEEQRQR   300
HYLGHNDDIK CLAIHPDMVT IATGQVAGTT KEGKPLPPHV RIWDSVSLST LHVLGLGVFD   360
RAVCCVGFSK SNGGNLLCAV DESNDHMLSV WDWAKETKVV DVKCSNEAVL VATFHPTDPT   420
VLITCGKSHI YFWTLEGGSL SKRQGLFEKH EKPKYVLCVT FLEGGDVVTG DSGGNLYVWG   480
KGGNRITQAV LGAHDGGVFG LCALRDGTLV SGGGRDRRVV LWGSDYSKLQ EVEVPEDFGP   540
VRTVAEGHGD TLYVGTTRNS ILQGSVHTGF SLLVQGHVEE LWGLATHPSR AQFVTCGQDK   600
LVHLWSSDSH QPLWSRIIED PARSAGFHPS GSVLAVGTVT GRWLLLDTET HDLVAIHTDG   660
NEQISVVSFS PDGAYLAVGS HDNLVYYTV DQGGRKVSRL GKCSGHSSFI THLDWAQDSS    720
CFVTNSGDYE ILYWDPATCK QITSADAVRN MEWATATCVL GFGVFGIWSE GADGTDINAV   780
ARSHDGKLLA SADDFGKVHL FSYPCCQPRA LSHKYGGHSS HVTNVAFLWD DSMALTTGGK   840
DTSVLQWRVV                                                         850

SEQ ID NO: 274            moltype = AA  length = 73
FEATURE                   Location/Qualifiers
source                    1..73
                          mol_type = protein
                          organism = Homo sapiens
SEQUENCE: 274
XHQPLWSRII EDPARSAGFH PSGSVLAVGT VTGRWLLLDT ETHDLVAIHT DGNEQISVVS    60
FSPGPFQFYH PPG                                                      73

SEQ ID NO: 275            moltype = AA  length = 121
FEATURE                   Location/Qualifiers
source                    1..121
                          mol_type = protein
                          organism = Homo sapiens
SEQUENCE: 275
XLCAVDESND HMLSVWDWAK ETKVVDVKVP EDFGPVRTVA EGHGDTLYVG TTRNSILQGS    60
VHTGFSLLVQ GHVEELWGLA THPSRAQFVT CGQDKLVHLW SSDSHQPLWS RIIEDPARSA   120
G                                                                  121

SEQ ID NO: 276            moltype = AA  length = 427
FEATURE                   Location/Qualifiers
source                    1..427
                          mol_type = protein
                          organism = Homo sapiens
SEQUENCE: 276
MSSFGAGKTK EVIFSVEDGS VKMFLRGRPV PMMIPDELAP TYSLDTRSEL PSCRLKLEWV    60
YGYRGRDCRA NLYLLPTGEI VYFVASVAVL YSVEEQRQRH YLGHNDDIKC LAIHPDMVTI   120
ATGQVAGTTK EGKPLPPHVR IWDSVSLSTL HVLGLGVFDR AVCCVGFSKS NGGNLLCAVD   180
ESNDHMLSVW DWAKETKVVD VKCSNEAVLV ATFHPTDPTV LITCGKSHIY FWTLEGGSLS   240
KRQGLFEKHE KPKYVLCVTF LEGGDVVTGD SGGNLYVWGK GGNRITQAVL GAHDGGVFGL   300
CALRDGTLVS GGGRDRRVVL WGSDYSKLQE VEVPEDFGPV RTVAEGHGDT LYVGTTRNSI   360
LQGSVHTGFS LLVQGHVEEL WGLATHPSRA QFVTCGQDKL VHLWSSDSHQ PLWSRIIEMA   420
AAGHGDP                                                            427

SEQ ID NO: 277            moltype = AA  length = 773
FEATURE                   Location/Qualifiers
source                    1..773
                          mol_type = protein
                          organism = Homo sapiens
SEQUENCE: 277
MSSFGAGKTK EVIFSVEDGS VKMFLRGRPV PMMIPDELAP TYSLDTRSEL PSCRLKLEWV    60
YGYRGRDCRA NLYLLPTGEI VYFVASVAVL YSVEEQRQRH YLGHNDDIKC LAIHPDMVTI   120
ATGQVAGTTK EGKPLPPHVR IWDSVSLSTL HVLGLGVFDR AVCCVGFSKS NGGNLLCAVD   180
ESNDHMLSVW DWAKETKVVD VKCSNEAVLV ATFHPTDPTV LITCGKSHIY FWTLEGGSLS   240
KRQGLFEKHE KPKYVLCVTF LEGGDVVTGD SGGNLYVWGK GGNRITQAVL GAHDGGVFGL   300
CALRDGTLVS GGGRDRRVVL WGSDYSKLQE VEVPEDFGPV RTVAEGHGDT LYVGTTRNSI   360
LQGSVHTGFS LLVQGHVEEL WGLATHPSRA QFVTCGQDKL VHLWSSDSHQ PLWSRIIEDP   420
ARSAGFHPSG SVLAVGTVTG RWLLLDTETH DLVAIHTDGN EQISVVSFSP DGAYLAVGSH   480
DNLVYYTVD QGGRKVSRLG KCSGHSSFIT HLDWAQDSSC FVTNSGDYEI LYWDPATCKQ    540
ITSADAVRNM EWATATCVLG FGVFGIWSEG ADGTDINAVA RSHDGKLLAS ADDFGKVHLF   600
SYPCCQPRVL GKWPSAAEAA LSSGIRVLFR PLVASLGPAW KNVPRKFCWK SAGDSPRDPP   660
PRPQGHSQPS FPSSGPWETA VCKFYRQGRW REVRVFASWA PPCIPHSQWL WFPSSEPQFL   720
```

```
WELELSLETG NRLPPCPFCP RLAMASCPLR MVPWGRPILC GFLHSAHPSI NCP          773

SEQ ID NO: 278            moltype = AA   length = 98
FEATURE                   Location/Qualifiers
source                    1..98
                          mol_type = protein
                          organism = Homo sapiens
SEQUENCE: 278
MFLRGRPVPM MIPDELAPTY SLDTRSELPS CRLKLEWVYG YRGRDCRANL YLLPTGEIVY   60
FVASVAVLYS VEEQRQRHYL GHNDDIKCLA IHPDMVTI                           98

SEQ ID NO: 279            moltype = AA   length = 111
FEATURE                   Location/Qualifiers
source                    1..111
                          mol_type = protein
                          organism = Homo sapiens
SEQUENCE: 279
MFLRGRPVPM MIPDELAPTY SLDTRSELPS CRLKLEWVYG YRGRDCRANL YLLPTGEIVY   60
FVASVAVLYS VEEQRQRHYL GHNDDIKCLA IHPDMVTIAT GQVAGTTKEG K            111

SEQ ID NO: 280            moltype = AA   length = 51
FEATURE                   Location/Qualifiers
source                    1..51
                          mol_type = protein
                          organism = Homo sapiens
SEQUENCE: 280
WTLEGGSLSK RQGLFEKHEK PKYVLCVTFL EGGDVVTGDS GGNLYVWGKG P            51

SEQ ID NO: 281            moltype = AA   length = 148
FEATURE                   Location/Qualifiers
source                    1..148
                          mol_type = protein
                          organism = Homo sapiens
SEQUENCE: 281
MFLRGRPVPM MIPDELAPTY SLDTRSELPS CRLKLEWVYG YRGRDCRANL YLLPTGEIVY   60
FVASVAVLYS VEEQRQRHYL GHNDDIKCLA IHPDMVTIAT GQVAGTTKEG KPLPPHVRIW   120
DSVSLSTLHV LGLGVFDRAV CCVGFSKS                                      148

SEQ ID NO: 282            moltype = AA   length = 91
FEATURE                   Location/Qualifiers
source                    1..91
                          mol_type = protein
                          organism = Homo sapiens
SEQUENCE: 282
PLPPHVRIWD SVSLSTLHVL GLGVFDRAVC CVGFSKSNGG NLLCAVDESN DHMLSVWDWA   60
KETKVVDVKA GVQWHNLGSL QPPPPRFQRF S                                  91

SEQ ID NO: 283            moltype = AA   length = 133
FEATURE                   Location/Qualifiers
source                    1..133
                          mol_type = protein
                          organism = Homo sapiens
SEQUENCE: 283
MFLRGRPVPM MIPDELAPTY SLDTRSELPS CRLKLEWVYG YRGRDCRANL YLLPTGEIVY   60
FVASVAVLYS VEEQRQRHYL GHNDDIKCLA IHPDMVTIAT GQVAGTTKEG KPLPPHVRIW   120
DSVSLSTLHV LGL                                                      133

SEQ ID NO: 284            moltype = AA   length = 252
FEATURE                   Location/Qualifiers
source                    1..252
                          mol_type = protein
                          organism = Homo sapiens
SEQUENCE: 284
MKMKLFQTIC RQLRSSKFSV ESAALVAFST SSYSCGRKKK VNPYEEVDQE KYSNLVQSVL   60
SSRGVAQTPG SVEEDALLCG PVSKHKLPNQ GEDRRVPQNW FPIFNPERSD KPNASDPSVP   120
LKIPLQRNVI PSVTRVLQQT MTKQQVFLLE RWKQRMILEL GEDGFKEYTS SSMWLNCGGL   180
QRWITCPPTF HGCRALFPVL DQVASSTRRI YGKEKEPEYS ETRIFRIGSK LLFGNIQHLL   240
TVWEHILLFT PV                                                       252

SEQ ID NO: 285            moltype = AA   length = 264
FEATURE                   Location/Qualifiers
source                    1..264
                          mol_type = protein
                          organism = Homo sapiens
SEQUENCE: 285
MKMKLFQTIC RQLRSSKFSV ESAALVAFST SSYSCGRKKK VNPYEEVDQE KYSNLVQSVL   60
SSRGVAQTPG SVEEDALLCG PVSKHKLPNQ DVFLQGKRFH EALESILSPQ ETLKERDENL   120
LKSGYIESVQ HILKDVSGVR ALESAVQHET LNYIGLLDCV AEYQGKLCVI DWKTSEKPKP   180
FIQSTFDNPL QVVAYMGAMN HDTNYSFQVQ CGLIVVAYKD GSPAHPHFMD AELCSQYWTK   240
```

```
WLLRLEEYTE KKKNQNIQKP EYSE                                                264

SEQ ID NO: 286           moltype = AA  length = 344
FEATURE                  Location/Qualifiers
source                   1..344
                         mol_type = protein
                         organism = Homo sapiens
SEQUENCE: 286
MKMKLFQTIC RQLRSSKFSV ESAALVAFST SSYSCGRKKK VNPYEEVDQE KYSNLVQSVL          60
SSRGVAQTPG SVEEDALLCG PVSKHKLPNQ GEDRRVPQNW FPIFNPERSD KPNASDPSVP         120
LKIPLQRNVI PSVTRVLQQT MTKQQVFLLE RWKQRMILEL GEDGFKEYTS NVFLQGKRFH         180
EALESILSPQ ETLKERDENL LKSGYIESVQ HILKDVSGVR ALESAVQHET LNYIGLLDCV         240
AEYQGKLCVI DWKTSEKPKP FIQSTFDNPL QVVAYMGAMN HDTNYSFQVQ CGLIVVAYKD         300
GSPAHPHFMD AELCSQYWTK WLLRLEEYTE KKKNQNIQKP EYSE                          344

SEQ ID NO: 287           moltype = AA  length = 355
FEATURE                  Location/Qualifiers
source                   1..355
                         mol_type = protein
                         organism = Homo sapiens
SEQUENCE: 287
MGPGRCLLTA LLLLALAPPP EASQYCGRLE YWNPDNKCCS SCLQRFGPPP CPDYEFRENC          60
GLNDHGDFVT PPFRKCSSGQ CNPDGAELCS PCGGGAVTPT PAAGGGRTPW RCRERPVPAK         120
GHCPLTPGNP GAPSSQERSS PASSIAWRTP EPVPQQAWPN FLPLVVVLLL LTLAVIAILL         180
FILLWHLCWP KEKADPYPYP GLVCGVPNTH TPSSSHLSSP GALETGDTWK EASLLPLLSR         240
ELSSLASQPL SRLLDELEVL EELIVLLDPE PGPGGGMAHG TTRHLAARYG LPAAWSTFAY         300
SLRPSRSPLR ALIEMVVARE PSASLGQLGT HLAQLGRADA LRVLSKLGSS GVCWA              355

SEQ ID NO: 288           moltype = AA  length = 132
FEATURE                  Location/Qualifiers
source                   1..132
                         mol_type = protein
                         organism = Homo sapiens
SEQUENCE: 288
MGPGRCLLTA LLLLALAPPP EASQYCGRLE YWNPDNKCCS SCLQRFGPPP CPDYEFRENC          60
GLNDHGDFVT PPFRKCSSGQ CNPDGAELCS PCGGGAVTPT PAAGGGRTPW RCREAGPCQG         120
ALPPHTWKPR RP                                                            132

SEQ ID NO: 289           moltype = AA  length = 187
FEATURE                  Location/Qualifiers
source                   1..187
                         mol_type = protein
                         organism = Homo sapiens
SEQUENCE: 289
MGPGRCLLTA LLLLALAPPP EASQYCGRLE YWNPDNKCCS SCLQRFGPPP CPGALETGDT          60
WKEASLLPLL SRELSSLASQ PLSRLLDELE VLEELIVLLD PEPGPGGGMA HGTTRHLAAR         120
YGLPAAWSTF AYSLRPSRSP LRALIEMVVA REPSASLGQL GTHLAQLGRA DALRVLSKLG         180
SSGVCWA                                                                  187

SEQ ID NO: 290           moltype = AA  length = 138
FEATURE                  Location/Qualifiers
source                   1..138
                         mol_type = protein
                         organism = Homo sapiens
SEQUENCE: 290
MGPGRCLLTA LLLLALAPPP EASQYCGRLE YWNPDNKCCS SCLQRFGPPP CPDYEFRENC          60
GLNDHGDFVT PPFRKCSSGQ CNPDGAELCS PCGGGAVTPT PAAGGGRTPW RCRERPVPAK         120
GHCPLTPGNP GAPSSQER                                                      138

SEQ ID NO: 291           moltype = AA  length = 74
FEATURE                  Location/Qualifiers
source                   1..74
                         mol_type = protein
                         organism = Homo sapiens
SEQUENCE: 291
XNCGLNDHGD FVTPPFRKCS SGQCNPDGAE LCSPCGGGAV TPTPAAGGGR TPWRCREAPW          60
RQGTHGRRPH YFHS                                                           74

SEQ ID NO: 292           moltype = AA  length = 355
FEATURE                  Location/Qualifiers
source                   1..355
                         mol_type = protein
                         organism = Homo sapiens
SEQUENCE: 292
MGPGRCLLTA LLLLALAPPP EASQYCGRLE YWNPDNKCCS SCLQRFGPPP CPDYEFRENC          60
GLNDHGDFVT PPFRKCSSGQ CNPDGAELCS PCGGGAVTPT PAAGGGRTPW RCRERPVPAK         120
GHCPLTPGNP GAPSSQERSS PASSIAWRTP EPVPQQAWPN FLPLVVVLLL LTLAVIAILL         180
FILLWHLCWP KEKADPYPYP GLVCGVPNTH TPSSSHLSSP GALETGDTWK EASLLPLLSR         240
ELSSLASQPL SRLLDELEVL EELIVLLDPE PGPGGGMAHG TTRHLAARYG LPAAWSTFAY         300
```

```
SLRPSRSPLR ALIEMVVARE PSASLGQLGT HLAQLGRADA LRVLSKLGSS GVCWA        355

SEQ ID NO: 293             moltype = AA   length = 60
FEATURE                    Location/Qualifiers
source                     1..60
                           mol_type = protein
                           organism = Homo sapiens
SEQUENCE: 293
XGRLEYWNPD NKCCSSCLQR FGPPPCPGEN PRPSLAWAEL AEAGPCQGAL PPHTWKPRRP   60

SEQ ID NO: 294             moltype = AA   length = 167
FEATURE                    Location/Qualifiers
source                     1..167
                           mol_type = protein
                           organism = Homo sapiens
SEQUENCE: 294
MGPGRCLLTA LLLLALAPPP EASQYCGRLE YWNPDNKCCS SCLQRFGPPP CPELSSLASQ   60
PLSRLLDELE VLEELIVLLD PEPGPGGGMA HGTTRHLAAR YGLPAAWSTF AYSLRPSRSP   120
LRALIEMVVA REPSASLGQL GTHLAQLGRA DALRVLSKLG SSGVCWA                167

SEQ ID NO: 295             moltype = AA   length = 1742
FEATURE                    Location/Qualifiers
source                     1..1742
                           mol_type = protein
                           organism = Homo sapiens
SEQUENCE: 295
MAVAELYTQY NRVWIPDPEE VWKSAEIAKD YRVGDKVLRL LLEDGTELDY SVNPESLPPL   60
RNPDILVGEN DLTALSYLHE PAVLHNLRIR FAESKLIYTY SGIILVAMNP YKQLPIYGDA   120
IIHAYSGQNM GDMDPHIFAV AEEAYKQMAR NNRNQSIIVS GESGAGKTVS ARYAMRYFAT   180
VSKSGSNAHV EDKVLASNPI TEAVGNAKTT RNDNSSRFGK YTEISFDEQN QIIGANMSTY   240
LLEKSRVVFQ SENERNYHIF YQLCASAQQS EFKHLKLGSA EEFNYTRMGG NTVIEGVNDR   300
AEMVETQKTF TLLGFKEDFQ MDVFKILAAI LHLGNVQITA VGNERSSVSE DDSHLKVFCE   360
LLGLESGRVA QWLCNRKIVT SSETVVKPMT RPQAVNARDA LAKKIYAHLF DFIVERINQA   420
LQFSGKQHTF IGVLDIYGFE TFDVNSFEQF CINYANEKLQ QQFNMHVFKL EQEEYMKEDI   480
PWTLIDFYDN QPVIDLIEAK MGILELLDEE CLLPHGTDEN WLQKLYNNFV NRNPLFEKPR   540
MSNTSFVIQH FADKVEYKCE GFLEKNRDTV YDMLVEILRA SKFHLCANFF QENPTPPSPF   600
GSMITVKSAK QVIKPNSKHF RTTVGSKFRS SYLLMETLN ATTPHYVRCI KPNDEKLPFE   660
FDSKRIVQQL RACGVLETIR ISAQSYPSRW TYIEFYSRYG ILMTKQELSF SDKKEVCKVV   720
LHRLIQDSNQ YQFGKTKIFF RAGQVAYLEK LRLDKLRQSC VMVQKHMRGW LQRKKFLRER   780
RAALIIQQYF RGQQTVRKAI TAVALKEAWA AIIIQKHCRG YLVRSLYQLI RMATITMQAY   840
SRGFLARRRY RKMLEEHKAV ILQKYARAWL ARRRFQSIRR FVLNIQLTYR VQRLQKKLED   900
QNKENHGLVE KLTSLAALRA GDVEKIQKLE AELEKAATHR RNYEEKGKRY RDAVEEKLAK   960
LQKHNSELET QKEQIQLKLQ EKTEELKEKM DNLTKQLFDD VQKEERQRML LEKSFELKTQ   1020
DYEKQIQSLK EEIKALKDEK MQLQHLVEGE HVTSDGLKAE VARLSKQVKT ISEFEKEIEL   1080
LQAQKIDVEK HVQSQKREMR EKMSEITKQL LESYDIEDVR SRLVSEDLEH LNEDGELWFA   1140
YEGLKKATRV LESHFQSQKD CYEKEIEALN FKVVHLSQEI NHLQKLFREE NDINESIRHE   1200
VTRLTSENMM IPDFKQQISE LEKQKQDLEI RLNEQAEKMK GKLEELSNQL HRSQEEEGTQ   1260
RKALEAQNEI HTKEKEKLID KIQEMQEASD HLKKQFETES EVKCNFRQEA SRLTLENRDL   1320
EEELDMKDRV IKKLQDQVKT LSKTIGKAND VHSSSGPKEY LGMLQYKRED EAKLIQNLIL   1380
DLKPRGVVVN MIPGLPAHIL FMCVRYADSL NDANMLKSLM NSTINGIKQV VKEHLEDFEM   1440
LSFWLSNTCH FLNCLKQYSG EEEFMKHNSP QQNKNCLNNF DLSEYRQILS DVAIRIYHQP   1500
IIIMEKNIQP IIVPGMLEYE SLQGISGLKP TGFRKRSSSI DDTDGYTMTS VLQQLSYFYT   1560
TMCQNGLDPE LVRQAVKQLF FLIGAVTLNS LFLRKDMCSC RKGMQIRCNI SYLEEWLKDK   1620
NLQNSLAKET LEPLSQAAWL LQVKKTTDSD AKEIYERCTS LSAVQIIKIL NSYTPIDDFE   1680
KRVTPSFVRK VQALLNSRED SSQLMLDTKY LFQVTFPFTP SPHALEMIQI PSSFKLGFLN   1740
RL                                                                 1742

SEQ ID NO: 296             moltype = AA   length = 612
FEATURE                    Location/Qualifiers
source                     1..612
                           mol_type = protein
                           organism = Homo sapiens
SEQUENCE: 296
MAAAGRLPSS WALFSPLLAG LALLGVGPVP ARALHNVTAE LFGAEAWGTL AAFGDLNSDK   60
QTDLFVLRER NDLIVPLADQ NAPYFKPKVK VSFKNHSALI TSVVPGDYDG DSQMDVLLTY   120
LPKNYAKSEL GAVIFWGQNQ TLDPNNMTIL NRTFQDEPLI MDFNGDLIPD IFGITNESNQ   180
PQILLGGNLS WHPALTTTSK MRIPHSHAFI DLTEDFTADL FLTTLNATTS TFQFEIWENL   240
DGNFSVSTIL EKPQNMMVVG QSAFADFDGD GHMDHLLPGC EDKNCQKSTI YLVRSGMKQW   300
VPVLQDFSNK GTLWGFVPFV DEQQPTEIPI PITLHIGDYN MDGYPDALVI LKNTSGSNQQ   360
AFLLENVPCN NASCEEARRM FKVYWELTDL NQIKDAMVAT FFDIYEDGIL DIVVLSKGYT   420
KNDFAIHTLK NNFEADAYFV KVIVLSGLCS NDCPRKITPF GVNQPGPYIM YTTVDANGYL   480
KNGSAGQLSQ SAHLALQLPY NVLGLGRSAN FLDHLYVGIP RPSGEKSIRK QEWTAIIPNS   540
QLIVIPYPHN VPRSWSAKLY LTPSNIVLLT AIALIGVCVF ILAIIGILHW QEKKADDREK   600
RQEAHRFHFD AM                                                      612

SEQ ID NO: 297             moltype = AA   length = 464
FEATURE                    Location/Qualifiers
source                     1..464
                           mol_type = protein
```

```
                        organism = Homo sapiens
SEQUENCE: 297
MDVLLTYLPK NYAKSELGAV IFWGQNQTLD PNNMTILNRT FQDEPLIMDF NGDLIPDIFG   60
ITNESNQPQI LLGGNLSWHP ALTTTSKMRI PHSHAFIDLT EDFTADLFLT TLNATTSTFQ  120
FEIWENLDGN FSVSTILEKP QNMMVVGQSA FADFDGDGHM DHLLPGCEDK NCQKSTIYLV  180
RSGMKQWVPV LQDFSNKGTL WGFVPFVDEQ QPTEIPIPIT LHIGDYNMDG YPDALVILKN  240
TSGSNQQAFL LENVPCNNAS CEEARRMFKV YWELTDLNQI KDAMVATFFD IYEDGILDIV  300
VLSKGYTKND FAIHTLKNNF EADAYFVKVI VLSGLCSNDC PRKITPFGVN QPGPYIMYTT  360
VDANGYLKNG SAGQLSQSAH LALQLPYNVL GLGRSANFLD HLYVGIPRPS GEKSIRKQEW  420
TAIIPNSQLI VIPYPHNVPR SSHRCLCFHL GNNWHFTLAG KESR                  464

SEQ ID NO: 298          moltype = AA  length = 74
FEATURE                 Location/Qualifiers
source                  1..74
                        mol_type = protein
                        organism = Homo sapiens
SEQUENCE: 298
MDVLLTYLPK NYAKSELGAV IFWGQNQTLD PNNMTILNRT FQDEPLIMDF NGDLIPDIFG   60
ITNESNQPQI LLGG                                                    74

SEQ ID NO: 299          moltype = AA  length = 178
FEATURE                 Location/Qualifiers
source                  1..178
                        mol_type = protein
                        organism = Homo sapiens
SEQUENCE: 299
VLSKGYTKND FAIHTLKNNF EADAYFVKVI VLSGLCSNDC PRKITPFGVN QPGPYIMYTT   60
VDANGYLKNG SGRSANFLDH LYVGIPRPSG EKSIRKQEWT AIIPNSQLIV IPYPHNVPRS  120
WSAKLYLTPS NIVLLTAIAL IGVCVFILAI IGILHWQEKK ADDREKRQEA HRFHFDAM    178

SEQ ID NO: 300          moltype = AA  length = 113
FEATURE                 Location/Qualifiers
source                  1..113
                        mol_type = protein
                        organism = Homo sapiens
SEQUENCE: 300
XKPKVKVSFK NHSALITSVV PGDYDGDSQM DVLLTYLPKN YAKSELGAVI FWGQNQTLDP   60
NNMTILNRTF QDEPLIMDFN GDLIPDIFGI TNESNQPQIL LGGHTTLNAP HLF         113

SEQ ID NO: 301          moltype = AA  length = 431
FEATURE                 Location/Qualifiers
source                  1..431
                        mol_type = protein
                        organism = Homo sapiens
SEQUENCE: 301
MAEITNIRPS FDVSPVVAGL IGASVLVVCV SVTVFVWSCC HQQAEKKQKN PPYKFIHMLK   60
GISIYPETLS NKKKIIKVRR DKDGPGREGG RRNLLVDAAE AGLLSRDKDP RGPSSGSCID  120
QLPIKMDYGE ELRSPITSLT PGESKTTSPS SPEEDVMLGS LTFSVDYNFP KKALVVTIQE  180
AHGLPVMDDQ TQGSDPYIKM TILPDKRHRV KTRVLRKTLD PVFDETFTFY GIPYSQLQDL  240
VLHFLVLSFD RFSRDDVIGE VMVPLAGVDP STGKVQLTRD IIKRNIQKCI SRGELQVSLS  300
YQPVAQRMTV VVLKARHLPK MDITGLSGNP YVKVNVYYGR KRIAKKKTHV KKCTLNPIFN  360
ESFIYDIPTD LLPDISIEFL VIDFDRTTKN EVVGRLILGA HSVTASGAEH WREVCESPRK  420
PVAKWHSLSE Y                                                      431

SEQ ID NO: 302          moltype = AA  length = 513
FEATURE                 Location/Qualifiers
source                  1..513
                        mol_type = protein
                        organism = Homo sapiens
SEQUENCE: 302
MSSKPEPKDV HQLNGTGPSA SPCSSDGPGR EPLAGTSEFL GPDGAGVEVV IESRANAKGV   60
REEDALLENG SQSNESDDVS TDRGPAPPSP LKETSFSIGL QVLFPFLLAG FGTVAAGMVL  120
DIVQHWEVFQ KVTEVFILVP ALLGLKGNLE MTLASRLSTA ANIGHMDTPK ELWRMITGNM  180
ALIQVQATVV GFLASIAAVV FGWIPDGHFS IPHAFLLCAS SVATAFIASL VLGMIMIGVI  240
IGSRKIGINP DNVATPIAAS LGDLITLALL SGISWGLYLE LNHWRYIYPL VCAFFVALLP  300
VWVVLARRSP ATREVLYSGW EPVIIAMAIS SVGGLILDKT VSDPNFAGMA VFTPVINGVG  360
GNLVAVQASR ISTFLHMNGM PGENSEQAPR RCPSPCTTFF SPDVNSRSAR VLFLLVVPGH  420
LVFLYTISCM QGGHTTLTLI FIIFYMTAAL LQVLILLYIA DWMVHWMWGR GLDPDNFSIP  480
YLTALGDLLG TGLLALSFHV LWLIGDRDTD VGD                              513

SEQ ID NO: 303          moltype = AA  length = 1226
FEATURE                 Location/Qualifiers
source                  1..1226
                        mol_type = protein
                        organism = Homo sapiens
SEQUENCE: 303
MDREERKTIN QGQEDEMEIY GYNLSRWKLA IVSLGVICSG GFLLLLLYWM PEWRVKATCV   60
RAAIKDCEVV LLRTTDEFKM WFCAKIRVLS LETYPVSSPK SMSNKLSNGH AVCLIENPTE  120
ENRHRISKYS QTESQQIRYF THHSVKYFWN DTIHNFDFLK GLDEGVSCTS IYEKHSAGLT  180
```

```
KGMHAYRKLL YGVNEIAVKV PSVFKLLIKE VLNPFYIFQL FSVILWSTDE YYYYALAIVV    240
MSIVSIVSSL YSIRKQYVML HDMVATHSTV RVSVCRVNEE IEEIFSTDLV PGDVMVIPLN    300
GTIMPCDAVL INGTCIVNES MLTGESVPVT KTNLPNPSVD VKGIGDELYN PETHKRHTLF    360
CGTTVIQTRF YTGELVKAIV VRTGFSTSKG QLVRSILYPK PTDFKLYRDA YLFLLCLVAV    420
AGIGFIYTII NSILNEVQVG VIIIESLDII TITVPPALPA AMTAGIVYAQ RRLKKIGIFC    480
ISPQRINICG QLNLVCFDKT GTLTEDGLDL WGIQRVENAR FLSPEENVCN EMLVKSQFVA    540
CMATCHSLTK IEGVLSGDPL DLKMFEAIGW ILEEATEEET ALHNRIMPTV VRPPKQLLPE    600
STPAGNQEME LFELPATYEI GIVRQFPFSS ALQRMSVVAR VLGDRKMDAY MKGAPEAIAG    660
LCKPETVPVD FQNVLEDFTK QGFRVIALAH RKLESKLTWH KVQNISRDAI ENNMDFMGLI    720
IMQNKLKQET PAVLEDLHKA NIRTVMVTGD SMLTAVSVAR DCGMILPQDK VIIAEALPPK    780
DGKVAKINWH YADSLTQCSH PSAIDPEAIP VKLVHDSLED LQMTRYHFAM NGKSFSVILE    840
HFQDLVPKLM LHGTVFARMA PDQKTQLIEA LQNVDYFVGM CGDGANDCGA LKRAHGGISL    900
SELEASVASP FTSKTPSISC VPNLIREGRA ALITSFCVFK FMALYSIIQY FSVTLLYSIL    960
SNLGDFQFLF IDLAIILVVV FTMSLNPAWK ELVAQRPPSG LISGALLFSV LSQIIICIGF    1020
QSLGFFWVKQ QPWYEVWHPK SDACNTTGSG FWNSSHVDNE TELDEHNIQN YENTTVFFIS    1080
SFQYLIVAIA FSKGKPFRQP CYKNYFFVFS VIFLYIFILF IMLYPVASVD QVLQIVCVPY    1140
QWRVTMLIIV LVNAFVSITV EESVDRWGKC CLPWALGCRK KTPKAKYMYL AQELLVDPEW    1200
PPKPQTTTEA KALVKENGSC QIITIT                                        1226

SEQ ID NO: 304         moltype = AA  length = 162
FEATURE                Location/Qualifiers
source                 1..162
                       mol_type = protein
                       organism = Homo sapiens
SEQUENCE: 304
XPFRQPCYKN YFFVFSVIFL YIFILFIMLY PVASVDQVLQ IVCVPYQWRV TMLIIVLVNA    60
FVSITVENFF LDMVLWKVVF NRDKQGEYRF STTQPPQESV DRWGKCCLPW ALGCRKKTPK    120
AKYMYLAQEL LVDPEWPPKP QTTTEAKALV KENGSCQIIT IT                      162

SEQ ID NO: 305         moltype = AA  length = 1226
FEATURE                Location/Qualifiers
source                 1..1226
                       mol_type = protein
                       organism = Homo sapiens
SEQUENCE: 305
MDREERKTIN QGQEDEMEIY GYNLSRWKLA IVSLGVICSG GFLLLLLYWM PEWRVKATCV    60
RAAIKDCEVV LLRTTDEFKM WFCAKIRVLS LETYPVSSPK SMSNKLSNGH AVCLIENPTE    120
ENRHRISKYS QTESQQIRYF THHSVKYFWN DTIHNFDFLK GLDEGVSCTS IYEKHSAGLT    180
KGMHAYRKLL YGVNEIAVKV PSVFKLLIKE VLNPFYIFQL FSVILWSTDE YYYYALAIVV    240
MSIVSIVSSL YSIRKQYVML HDMVATHSTV RVSVCRVNEE IEEIFSTDLV PGDVMVIPLN    300
GTIMPCDAVL INGTCIVNES MLTGESVPVT KTNLPNPSVD VKGIGDELYN PETHKRHTLF    360
CGTTVIQTRF YTGELVKAIV VRTGFSTSKG QLVRSILYPK PTDFKLYRDA YLFLLCLVAV    420
AGIGFIYTII NSILNEVQVG VIIIESLDII TITVPPALPA AMTAGIVYAQ RRLKKIGIFC    480
ISPQRINICG QLNLVCFDKT GTLTEDGLDL WGIQRVENAR FLSPEENVCN EMLVKSQFVA    540
CMATCHSLTK IEGVLSGDPL DLKMFEAIGW ILEEATEEET ALHNRIMPTV VRPPKQLLPE    600
STPAGNQEME LFELPATYEI GIVRQFPFSS ALQRMSVVAR VLGDRKMDAY MKGAPEAIAG    660
LCKPETVPVD FQNVLEDFTK QGFRVIALAH RKLESKLTWH KVQNISRDAI ENNMDFMGLI    720
IMQNKLKQET PAVLEDLHKA NIRTVMVTGD SMLTAVSVAR DCGMILPQDK VIIAEALPPK    780
DGKVAKINWH YADSLTQCSH PSAIDPEAIP VKLVHDSLED LQMTRYHFAM NGKSFSVILE    840
HFQDLVPKLM LHGTVFARMA PDQKTQLIEA LQNVDYFVGM CGDGANDCGA LKRAHGGISL    900
SELEASVASP FTSKTPSISC VPNLIREGRA ALITSFCVFK FMALYSIIQY FSVTLLYSIL    960
SNLGDFQFLF IDLAIILVVV FTMSLNPAWK ELVAQRPPSG LISGALLFSV LSQIIICIGF    1020
QSLGFFWVKQ QPWYEVWHPK SDACNTTGSG FWNSSHVDNE TELDEHNIQN YENTTVFFIS    1080
SFQYLIVAIA FSKGKPFRQP CYKNYFFVFS VIFLYIFILF IMLYPVASVD QVLQIVCVPY    1140
QWRVTMLIIV LVNAFVSITV EESVDRWGKC CLPWALGCRK KTPKAKYMYL AQELLVDPEW    1200
PPKPQTTTEA KALVKENGSC QIITIT                                        1226

SEQ ID NO: 306         moltype = AA  length = 47
FEATURE                Location/Qualifiers
source                 1..47
                       mol_type = protein
                       organism = Homo sapiens
SEQUENCE: 306
MDREERKTIN QGQEDEMEIY GYNLSRWKLA IVSLGVICSG GFLLLLL                  47

SEQ ID NO: 307         moltype = AA  length = 103
FEATURE                Location/Qualifiers
source                 1..103
                       mol_type = protein
                       organism = Homo sapiens
SEQUENCE: 307
MDREERKTIN QGQEDEMEIY GYNLSRWKLA IVSLGVICSG GFLLLLLYWM PEWRVKATCV    60
RAAIKDCEVV LLRTTDEFKM WFCAKIRVLS LETYPVSSPK SMS                      103

SEQ ID NO: 308         moltype = AA  length = 701
FEATURE                Location/Qualifiers
source                 1..701
                       mol_type = protein
                       organism = Homo sapiens
```

```
SEQUENCE: 308
ISEIEEIFST DLVPGDVMVI PLNGTIMPCD AVLINGTCIV NESMLTGESV PVTKTNLPNP      60
SVDVKGIGDE LYNPETHKRH TLFCGTTVIQ TRFYTGELVK AIVVRTGFST SKGQLVRSIL     120
YPKPTDFKLY RDAYLFLLCL VAVAGIGFIY TIINSILNEV QVGVIIIESL DIIITITVPPA    180
LPAAMTAGIV YAQRRLKKIG IFCISPQRIN ICGQLNLVCF DKTGTLTEDG LDLWGIQRVE     240
NARFLSPEEN VCNEMLVKSQ FVACMATCHS LTKIEGVLSG DPLDLKMFEA IGWILEEATE     300
EETALHNRIM PTVVRPPKQL LPESTPAGNQ EMELFELPAT YEIGIVRQFP FSSALQRMSV     360
VARVLGDRKM DAYMKGAPEA IAGLCKPETV PVDFQNVLED FTKQGFRVIA LAHRKLESKL     420
TWHKVQNISR DAIENNMDFM GLIIMQNKLK QETPAVLEDL HKANIRTVMV TGDSMLTAVS     480
VARDCGMILP QDKVIIAEAL PPKDGKVAKI NWHYADSLTQ CSHPSAIDPE AIPVKLVHDS    540
LEDLQMTRYH FAMNGKSFSV ILEHFQDLVP KLMLHGTVFA RMAPDQKTQL IEALQNVDYF    600
VGMCGDGAND CGALKRAHGG ISLSELEASV ASPFTSKTPS ISCVPNLIRE GRAALITSFC    660
ELALFSIVTY SLDHFIISIL ISNMLVLFFS DFHNCAFYSL V                        701

SEQ ID NO: 309          moltype = AA   length = 976
FEATURE                 Location/Qualifiers
source                  1..976
                        mol_type = protein
                        organism = Homo sapiens
SEQUENCE: 309
MGENEDEKQA QAGQVFENFV QASTCKGTLQ AFNILTRHLD LDPLDHRNFY SKLKSKVTTW      60
KAKALWYKLD KRGSHKEYKR GKSCTNTKCL IVGGGPCGLR TAIELAYLGA KVVVVEKRDS    120
FSRNNVLHLW PFTIHDLRGL GAKKFYGKFC AGSIDHISIR QLQLILFKVA LMLGVEIHVN    180
VEFVKVLEPP EDQENQKIGW RAEFLPTDHS LSEFEFDVII GADGRRNTLE GFRRKEFRGK    240
LAIAITANFI NRNSTAEAKV EEISGVAFIF NQKFFQDLKE ETGIDLENIV YYKDCTHYFV    300
MTAKKQSLLD KGVIINDYID TEMLLCAENV NQDNLLSYAR EAADFATNYQ LPSLDFAMNH    360
YGQPDVAMFD FTCMYASENA ALVRERQAHQ LLVALVGDSL LEPFWPMGTG CARGFLAAFD    420
TAWMVKSWNQ GTPPLELLAE RESLYRLLPQ TTPENINKNF EQYTLDPGTR YPNLNSHCVR    480
PHQVKHLYIT KELEHYPLER LGSVRRSVNL SRKESDIRPS KLLTWCQQQT EGYQHVNVTD    540
LTTSWRSGLA LCAIIHRFRP ELINFDSLNE DDAVENNQLA FDVAEREFGI PPVTTGKEMA    600
SAQEPDKLSM VMYLSKFYEL FRGTPLRPVD SWRKNYGENA DLSLAKSSIS NNYLNLTFPR    660
KRTPRVDGQT GENDMNKRRR KGFTNLDEPS NFSSRSLGSN QECGSSKEGG NQNKVKSMAN    720
QLLAKFEEST RNPSLMKQEK KSPSGFHFHP SHLRTVHPQE SMRKSFPLNL GGSDTCYFCK    780
KRVYVMERLS AEGHFFHREC FRCSICATTL RLAAYTFDCD KGFKYCKPHF IHCKTNSKQR    840
KRRAELKQQR EEEATWQEQE APRRDTPTES SCAVAAIGTL EGSPPGISTS FFRKVLGWPL    900
RLPRDLCNWM QGLLQAAGLH IRDNAYNYCY MYELLSLGLP LLWAFSEVLA AMYRESEGSL    960
ESICNWVLRC FPVKLR                                                    976

SEQ ID NO: 310          moltype = AA   length = 633
FEATURE                 Location/Qualifiers
source                  1..633
                        mol_type = protein
                        organism = Homo sapiens
SEQUENCE: 310
MAAAAAATT AACSSGSAGT DAAGASGLQQ PPPQPQPQPA AAAPAQPPPE PPRKPRMDPR       60
RRQAALSFLT NISLDGRLPP QDAEWGGGEE GGAAKPGAGG ACGARTRFSL LAAAERGGCI    120
ALAAPGTPAA GLAAGSGPCL PQPSSLPPLI PGGHATVSGP GVARGFASPL GAGRASGEQW    180
QPPRPAPLAA CAQLQLLDGS GAAGQEELEE DDAFISVQVP AAAFLGSGTP GSGSGSRGRL    240
NSFTQGILPI AFSRPTSQNY CSLEQPGQGG STSAFEQLQR SRRRLISQRS SLETLEDIEE    300
NAPLRRCRTL SGSPRPKNFK KIHFIKNMRQ HDTRNGRIVL ISGRRSFCSI FSVLPYRDST    360
QVGDLKLDGG RQSTGAVSLK EIIGLEGVEL GADGKTVSYT QFLLPTNAFG ARRNTIDSTS    420
SFSQFRNLSH RSLSIGRASG TQGSLDTGSD LGDFMDYDPN LLDDPQWPCG KHKRVLIFPS    480
YMTTVIDYVK PSDLKKDMNE TFKEKFPHIK LTLSKIRSLK REMRKLAQED CGLEEPTVAM    540
AFVYFEKLAL KGKLNKQNRK LCAGACVLLA AKIGSDLKKH EVKHLIDKLE EKFRLNRREL    600
IAFEFPVLVA LEFALHLPEH EVMPHYRRLV QSS                                 633

SEQ ID NO: 311          moltype = AA   length = 38
FEATURE                 Location/Qualifiers
source                  1..38
                        mol_type = protein
                        organism = Homo sapiens
SEQUENCE: 311
MRQHDTRNGR IVLISGRRSF CSIFSVLPYR DSTQVGQQ                             38

SEQ ID NO: 312          moltype = AA   length = 301
FEATURE                 Location/Qualifiers
source                  1..301
                        mol_type = protein
                        organism = Homo sapiens
SEQUENCE: 312
MFSHLPFDCV LLLLLLLLTR SSEVEYRAEV GQNAYLPCFY TPAAPGNLVP VCWGKGACPV      60
FECGNVVLRT DERDVNYWTS RYWLNGDFRK GDVSLTIENV TLADSGIYCC RIQIPGIMND    120
EKFNLKLVIK PAKVTPAPTR QRDFTAAFPR MLTTRGHGPA ETQTLGSLPD INLTQISTLA    180
NELRDSRLAN DLRDSGATIR IGIYIGAGIC AGLALALIFG ALIFKWYSHS KEKIQNLSLI    240
SLANLPPSGL ANAVAEGIRS EENIYTIEEN VYEVEEPNEY YCYVSSRQQP SQPLGCRFAM    300
P                                                                    301

SEQ ID NO: 313          moltype = AA   length = 273
FEATURE                 Location/Qualifiers
```

```
source                   1..273
                         mol_type = protein
                         organism = Homo sapiens
SEQUENCE: 313
MFSHLPFDCV LLLLLLLLTR SSEVEYRAEV GQNAYLPCFY TPAAPGNLVP VCWGKGACPV    60
FECGNVVLRT DERDVNYWTS RYWLNGDFRK GDVSLTIENV TLADSGIYCC RIQIPGIMND   120
EKFNLKLVIK PAETQTLGSL PDINLTQIST LANELRDSRL ANDLRDSGAT IRIGIYIGAG   180
ICAGLALALI FGALIFKWYS HSKEKIQNLS LISLANLPPS GLANAVAEGI RSEENIYTIE   240
ENVYEVEEPN EYYCYVSSRQ QPSQPLGCRF AMP                                273

SEQ ID NO: 314           moltype = AA   length = 116
FEATURE                  Location/Qualifiers
source                   1..116
                         mol_type = protein
                         organism = Homo sapiens
SEQUENCE: 314
MQLSFWSHCR CFCMFSIPLL MCRVRDQICD CPECTLQENP FFSQPGAPIL QCMGCCFSRA    60
YPTPLRSKKT MLVQKNVTSE STCCVAKSYN RVTVMGGFKV ENHTACHCST CYYHKS       116

SEQ ID NO: 315           moltype = AA   length = 147
FEATURE                  Location/Qualifiers
source                   1..147
                         mol_type = protein
                         organism = Homo sapiens
SEQUENCE: 315
MDYYRKYAAI FLVTLSVFLH VLHSAPDVQE TGFHHVAQAA LKLLSSSNPP TKASQSARIT    60
DCPECTLQEN PFFSQPGAPI LQCMGCCFSR AYPTPLRSKK TMLVQKNVTS ESTCCVAKSY   120
NRVTVMGGFK VENHTACHCS TCYYHKS                                       147

SEQ ID NO: 316           moltype = AA   length = 62
FEATURE                  Location/Qualifiers
source                   1..62
                         mol_type = protein
                         organism = Homo sapiens
SEQUENCE: 316
MDYYRKYAAI FLVTLSVFLH VLHSAPDVQD CPECTLQENP FFSQPGAPIL QCMGCCFSRA    60
YP                                                                   62

SEQ ID NO: 317           moltype = AA   length = 116
FEATURE                  Location/Qualifiers
source                   1..116
                         mol_type = protein
                         organism = Homo sapiens
SEQUENCE: 317
MDYYRKYAAI FLVTLSVFLH VLHSAPDVQD CPECTLQENP FFSQPGAPIL QCMGCCFSRA    60
YPTPLRSKKT MLVQKNVTSE STCCVAKSYN RVTVMGGFKV ENHTACHCST CYYHKS       116

SEQ ID NO: 318           moltype = AA   length = 101
FEATURE                  Location/Qualifiers
source                   1..101
                         mol_type = protein
                         organism = Homo sapiens
SEQUENCE: 318
MDYYRKYAAI FLVTLSVFLH VLHSAPDVQD CPECTLQENP FFSQPGAPIL QCMGCCFSRA    60
YPTPLRSKKT MLVQKNVTSE STCCVAKSYN RVRTSRSPEA F                       101

SEQ ID NO: 319           moltype = AA   length = 316
FEATURE                  Location/Qualifiers
source                   1..316
                         mol_type = protein
                         organism = Homo sapiens
SEQUENCE: 319
MTQGKLSVAN KAPGTEGQQQ VHGEKKEAPA VPSAPPSYEE ATSGEGMKAG AFPPAPTAVP    60
LHPSWAYVDP SSSSSYDNGF PTGDHELFTT FSWDDQKVRR VFVRKVYTIL LIQLLVTLAV   120
VALFTFCDPV KDYVQANPGW YWASYAVFFA TYLTLACCSG PRRHFPWNLI LLTVFTLSMA   180
YLTGMLSSYY NTTSVLLCLG ITALVCLSVT VFSFQTKFDF TSCQGVLFVL LMTLFFSGLI   240
LAILLPFQYV PWLHAVYAAL GAGVFTLFLA LDTQLLMGNR RHSLSPEEYI FGALNIYLDI   300
IYIFTFFLQL FGTNRE                                                   316

SEQ ID NO: 320           moltype = AA   length = 111
FEATURE                  Location/Qualifiers
source                   1..111
                         mol_type = protein
                         organism = Homo sapiens
SEQUENCE: 320
MKAGAFPPAP TAVPLHPSWA YVDPSSSSSY DNGFPTGDHE LFTTFSWDDQ KVRRVFVRKV    60
YTILLIQLLV TLAVVALFTF CDPVKDYVQA NPGWYWASYA VFFATYLTLA C            111

SEQ ID NO: 321           moltype = AA   length = 208
```

```
FEATURE                 Location/Qualifiers
source                  1..208
                        mol_type = protein
                        organism = Homo sapiens
SEQUENCE: 321
MTQGKLSVAN KAPGTEGQQQ VHGEKKEAPA VPSAPPSYEE ATSGEGMKAG AFPPAPTAVP    60
LHPSWAYVDP SSSSSYDNGF PTGDHELFTT FSWDDQKVRR VFVRKNPSHP QVYTILLIQL   120
LVTLAVVALF TFCDPVKDYV QANPGWYWAS YAVFFATYLT LACCSGPRRH FPWNLILLTV   180
FTLSMAYLTG MLSSSTSPPA RACSSCFS                                     208

SEQ ID NO: 322          moltype = AA  length = 248
FEATURE                 Location/Qualifiers
source                  1..248
                        mol_type = protein
                        organism = Homo sapiens
SEQUENCE: 322
MTQGKLSVAN KAPGTEGQQQ VHGEKKEAPA VPSAPPSYEE ATSGEGMKAG AFPPAPTAVP    60
LHPSWAYVDP SSSSSYDNGF PTGDHELFTT FSWDDQKVRR VFVRKVYTIL LIQLLVTLAV   120
VALFTFCDPV KDYVQANPGW YWASYAVFFA TYLTLACCSG PRRHFPWNLI LLTVFTLSMA   180
YLTGMLSSYY NTTSVLLCLG ITALVCLSVT VFSFQTKFDF TSCQGVLFVL LMTLFFSGLI   240
LAILLPFQ                                                           248

SEQ ID NO: 323          moltype = AA  length = 270
FEATURE                 Location/Qualifiers
source                  1..270
                        mol_type = protein
                        organism = Homo sapiens
SEQUENCE: 323
MKAGAFPPAP TAVPLHPSWA YVDPSSSSSY DNGFPTGDHE LFTTFSWDDQ KVRRVFVRKV    60
YTILLIQLLV TLAVVALFTF CDPVKDYVQA NPGWYWASYA VFFATYLTLA CCSGPRRHFP   120
WNLILLTVFT LSMAYLTGML SSYYNTTSVL LCLGITALVC LSVTVFSFQT KFDFTSCQGV   180
LFVLLMTLFF SGLILAILLP FQYVPWLHAV YAALGAGVFT LFLALDTQLL MGNRRHSLSP   240
EEYIFGALNI YLDIIYIFTF FLQLFGTNRE                                   270

SEQ ID NO: 324          moltype = AA  length = 266
FEATURE                 Location/Qualifiers
source                  1..266
                        mol_type = protein
                        organism = Homo sapiens
SEQUENCE: 324
MVYTSHYKSP GRRPLKTHPT VTYWRVNEGS SSSYDNGFPT GDHELFTTFS WDDQKVRRVF    60
VRKVYTILLI QLLVTLAVVA LFTFCDPVKD YVQANPGWYW ASYAVFFATY LTLACCSGPR   120
RHFPWNLILL TVFTLSMAYL TGMLSSYYNT TSVLLCLGIT ALVCLSVTVF SFQTKFDFTS   180
CQGVLFVLLM TLFFSGLILA ILLPFQYVPW LHAVYAALGA GVFTLFLALD TQLLMGNRRH   240
SLSPEEYIFG ALNIYLDIIY IFTFFL                                       266

SEQ ID NO: 325          moltype = AA  length = 145
FEATURE                 Location/Qualifiers
source                  1..145
                        mol_type = protein
                        organism = Homo sapiens
SEQUENCE: 325
XYVQANPGWY WASYAVFFAT YLTLACCSGP RRHFPWNLIL LTVFTLSMAY LTGMLSSYYN    60
TTSVLLCLGI TALVCLSVTV FSFQTKFDFT SCQGVLFVLL MTLFFSGLIL AILLPFQYFL   120
ALDTQLLMGN RRHSLSPEEY IFGAL                                        145

SEQ ID NO: 326          moltype = AA  length = 695
FEATURE                 Location/Qualifiers
source                  1..695
                        mol_type = protein
                        organism = Homo sapiens
SEQUENCE: 326
XEGGQGPRGL GTVPWLRDLP GSENHMPWEE PAGEKPSCSH SQKAFHMEPA QKPCFTTDMV    60
TWALLCISAE TVRGEAPSQP RGIPHRSPVS VDDLWLEKTQ RKKLQKQAHV ERRLHIGAVH   120
KDGVKCWRKT IITSPESLNL PRRSHPLSQS APTGLNHMGW PEHTPGTAMP DGALDTAVCA   180
DEVGSEEDLY DDLHSSSHHY SHPGGGGEQL AINELISDGS VVCAEALWDH VTMDDQELGF   240
KAGDVIEVMD ATNREWWWGR VADGEGWFPA SFVRLRVNQD EPADDDAPLA GNSGAEDGGA   300
EAQSSKDQMR TNVINEILST ERDYIKHLRD ICEGYVRQCR KRADMFSEEQ LRTIFGNIED   360
IYRCQKAFVK ALEQRFNRER PHLSELGACF LEHQADFQIY SEYCNNHPNA CVELSRLTKL   420
SKYVYFFEAC RLLQKMIDIS LDGFLLTPVQ KICKYPLQLA ELLKYTHPQH RDFKDVEAAL   480
HAMKNVAQLI NERKRRLENI DKIAQWQSSI EDWEGEDLLV RSSELIYSGE LTRVTQPQAK   540
SQQRMFFLFD HQLIYCKKDL LRRDVLYYKG RLDMDGLEVV DLEDGKDRDL HVSIKNAFRL   600
HRGATGDSHL LCTRKPEQKQ RWLKAFARER EQVQLDQETG FSITELQRKQ AMLNASKQQV   660
TGKPKGRRTA APPPRLPGPY PADIIPFSEP QSQAS                             695

SEQ ID NO: 327          moltype = AA  length = 573
FEATURE                 Location/Qualifiers
source                  1..573
                        mol_type = protein
```

```
                               organism = Homo sapiens
SEQUENCE: 327
MTNSKGRSIT DKTSGGPSSG GGFVDWTLRL NTIQSDKFLN LLLSMVPVIY QKNQEDRHKK    60
ANGIWQDGLS TAVQTFSNRS EQHMEYHSFS EQSFHANNGH ASSSCSQKYD DYANYNYCDG   120
RETSETTAML QDEDISSDGD EDAIVEVTPK LPKESSGIMA LQILVPFLLA GFGTVSAGMV   180
LDIVQHWEVF RKVTEVFILV PALLGLKGNL EMTLASRLST AVNIGKMDSP IEKWNLIIGN   240
LALKQVQATV VGFLAAVAAI ILGWIPEGKY YLDHSILLCS SSVATAFIAS LLQGIIMVGV   300
IVGSKKTGIN PDNVATPIAA SFGDLITLAI LAWISQGLYS CLETYYYISP LVGVFFLALT   360
PIWIIIAAKH PATRTVLHSG WEPVITAMVI SSIGGLILDT TVSDPNLVGI VVYTPVINGI   420
GGNLVAIQAS RISTYLHLHS IPGELPDEPK GCYYPFRTFF GPGVNNKSAQ VLLLLVIPGH   480
LIFLYTIHLM KSGHTSLTII FIVVYLFGAV LQVFTLLWIA DWMVHHFWRK GKDPDSFSIP   540
YLTALGDLLG TALLALSFHF LWLIGDRDGD VGD                                573

SEQ ID NO: 328             moltype = AA    length = 149
FEATURE                    Location/Qualifiers
source                     1..149
                           mol_type = protein
                           organism = Homo sapiens
SEQUENCE: 328
XDDYANYNYC DGRETSETTA MLQDEDISSD GDEDAIVEVT PKLPKESSGI MALQILVPFL    60
LAGFGTVSAG MVLDIVQVNI GKMDSPIEKW NLIIGNLALK QVQATVVGFL AAVAAIILGW   120
IPEGKYYLDH SILLCSSSVA TAFIASLLQ                                     149

SEQ ID NO: 329             moltype = AA    length = 68
FEATURE                    Location/Qualifiers
source                     1..68
                           mol_type = protein
                           organism = Homo sapiens
SEQUENCE: 329
XLKALKGYIK HEARKGNENQ DSSTSKRKTL CGFYSHQPTT LARPVLWPCK SEYLGSEGVT    60
QALCYLCS                                                             68

SEQ ID NO: 330             moltype = AA    length = 76
FEATURE                    Location/Qualifiers
source                     1..76
                           mol_type = protein
                           organism = Homo sapiens
SEQUENCE: 330
MIIPSLEELD SLKYSDLQNL AKSLGLRANL RATKLLKALK GYIKHEARKG NENQFHSCCP    60
GWSAMTRSRL TATSTS                                                    76

SEQ ID NO: 331             moltype = AA    length = 748
FEATURE                    Location/Qualifiers
source                     1..748
                           mol_type = protein
                           organism = Homo sapiens
SEQUENCE: 331
MVLLRVLILL LSWAAGMGGQ YGNPLNKYIR HYEGLSYNVD SLHQKHQRAK RAVSHEDQFL    60
RLDFHAHGRH FNLRMKRDTS LFSDEFKVET SNKVLDYDTS HIYTGHIYGE EGSFSHGSVI   120
DGRFEGFIQT RGGTFYVEPA ERYIKDRTLP FHSVIYHEDD INYPHKYGPQ GGCADHSVFE   180
RMRKYQMTGV EEVTQIPQEE HAANGPELLR KKRTTSAEKN TCQLYIQTDH LFFKYYGTRE   240
AVIAQISSHV KAIDTIYQTT DFSGIRNISF MVKRIRINTT ADEKDPTNPF RFPNIGVEKF   300
LELNSEQNHD DYCLAYVFTD RDFDDGVLGL AWVGAPSGSS GGICEKSKLY SDGKKKSLNT   360
GIITVQNYGS HVPPKVSHIT FAHEVGHNFG SPHDSGTECT PGESKNLGQK ENGNYIMYAR   420
ATSGDKLNNN KFSLCSIRNI SQVLEKKRNN CFVESGQPIC GNGMVEQGEE CDCGYSDQCK   480
DECCFDANQP EGRKCKLKPG KQCSPSQGPC CTAQCAFKSK SEKCRDDSDC AREGICNGFT   540
ALCPASDKKP NFTDCNRHTQ VCINGQCAGS ICEKYGLEEC TCASSDGKDD KELCHVCCMK   600
KMDPSTCAST GSVQWSRHFS GRTITLQPGS PCNDFRGYCD VFMRCRLVDA DGPLARLKKA   660
IFSPELYENI AEWIVAHWWA VLLMGIALIM LMAGFIKICS VHTPSSNPKL PPPKPLPGTL   720
KRRRPPPQPIQ QPQRQRPRES YQMGHMRR                                     748

SEQ ID NO: 332             moltype = AA    length = 58
FEATURE                    Location/Qualifiers
source                     1..58
                           mol_type = protein
                           organism = Homo sapiens
SEQUENCE: 332
XEEGSFSHGS VIDGRFEGFI QTRGGTFYVE PAERYIKDRT LPFHSVIYHE DDISEGLN      58

SEQ ID NO: 333             moltype = AA    length = 71
FEATURE                    Location/Qualifiers
source                     1..71
                           mol_type = protein
                           organism = Homo sapiens
SEQUENCE: 333
MVLLRVLILL LSWAAGMGDR DFDDGVLGLA WVGAPSGSSG GICEKSKLYS DVPTMGKLHS    60
KEKPIKSSSP N                                                         71

SEQ ID NO: 334             moltype = AA    length = 125
```

```
FEATURE                 Location/Qualifiers
source                  1..125
                        mol_type = protein
                        organism = Homo sapiens
SEQUENCE: 334
MVLLRVLILL LSWAAGMGGQ YGNPLNKYIR HYEGLSYNVD SLHQKHQRAK RAVSHEDQFL    60
RLDFHAHGRH FNLRMKRDTS LFSDEFKVET SNKVLDYDTS HIYTGHIYDY PHKYGPQGGC   120
ADHSV                                                               125

SEQ ID NO: 335          moltype = AA   length = 59
FEATURE                 Location/Qualifiers
source                  1..59
                        mol_type = protein
                        organism = Homo sapiens
SEQUENCE: 335
MVLLRVLILL LSWAAGMGAP ARWRIPKSSP PPRPAAQTRG KLCCLQLGSC IVLYPARRS     59

SEQ ID NO: 336          moltype = AA   length = 115
FEATURE                 Location/Qualifiers
source                  1..115
                        mol_type = protein
                        organism = Homo sapiens
SEQUENCE: 336
MVLLRVLILL LSWAAGMGGQ YGNPLNKYIR HYEGLSYNVD SLHQKHQRAK RAVSHEDQFL    60
RLDFHAHGRD GVLPCCPGWS QTPGLKRSTC LSLPQCWDYR CEPSPMISVF DYPHK         115

SEQ ID NO: 337          moltype = AA   length = 148
FEATURE                 Location/Qualifiers
source                  1..148
                        mol_type = protein
                        organism = Homo sapiens
SEQUENCE: 337
MVLLRVLILL LSWAAGMGDR DFDDGVLGLA WVGAPSGSSG GICEKSKLYS DGKKKSLNTG    60
IITVQNYGSH VPPKVSHITF AHEVGHNFGS PHDSGTECTP GESKNLGQKE NGNYIMYARA   120
TSGDKLNNNK FSLCSIRNIS QVLEKKRN                                      148

SEQ ID NO: 338          moltype = AA   length = 38
FEATURE                 Location/Qualifiers
source                  1..38
                        mol_type = protein
                        organism = Homo sapiens
SEQUENCE: 338
MVLLRVLILL LSWAAGMGVP TMGKLHSKEK PIKSSSPN                            38

SEQ ID NO: 339          moltype = AA   length = 452
FEATURE                 Location/Qualifiers
source                  1..452
                        mol_type = protein
                        organism = Homo sapiens
SEQUENCE: 339
MTLVSGWLLY GWIIAVQTKT KKTLAKPNIR NVVVVDGVRT PFLLSGTSYK DLMPHDLARA    60
ALTGLLHRTS VPKEVVDYII FGTVIQEVKT SNVAREAALG AGFSDKTPAH TVTMACISAN   120
QAMTTGVGLI ASGQCDVIVA GGVELMSDVP IRHSRKMRKL MLDDLNKAKSM GQRLSLISKF  180
RFNFLAPELP AVSEFSTSET MGHSADRLAA AFAVSRLEQD EYALRSHSLA KKAQDEGLLS   240
DVVPFKVPGK DTVTKDNGIR PSSLEQMAKL KPAFIKPYGT VTAANSSFLT DGASAMLIMA   300
EEKALAMGYK PKAYLRDFMY VSQDPKDQLL LGPTYATPKV LEKAGLTMND IDAFEFHEAF   360
SGQILANFKA MDSDWFAENY MGRKTKVGLP PLEKFNNWGG SLSLGHPFGA TGCRLVMAAA   420
NRLRKEGGQY GLVAACAAGG QGHAMIVEAY PK                                 452

SEQ ID NO: 340          moltype = AA   length = 260
FEATURE                 Location/Qualifiers
source                  1..260
                        mol_type = protein
                        organism = Homo sapiens
SEQUENCE: 340
MARPHPWWLC VLGTLVGLSA TPAPKSCPER HYWAQGKLCC QMCEPGTFLV KDCDQHRKAA    60
QCDPCIPGVS FSPDHHTRPH CESCRHCNSG LLVRNCTITA NAECACRNGW QCRDKECTEC   120
DPLPNPSLTA RSSQALSPHP QPTHLPYVSE MLEARTAGHM QTLADFRQLP ARTLSTHWPP   180
QRSLCSSDFI RILVIFSGMF LVFTLAGALF LHQRRKYRSN KGESPVEPAE PCHYSCPREE   240
EGSTIPIQED YRKPEPACSP                                               260

SEQ ID NO: 341          moltype = AA   length = 819
FEATURE                 Location/Qualifiers
source                  1..819
                        mol_type = protein
                        organism = Homo sapiens
SEQUENCE: 341
MWGLVRLLLA WLGGWGCMGR LAAPARAWAG SREHPGPALL RTRRSWVWNQ FFVIEEYAGP    60
EPVLIGKLHS DVDRGEGRTK YLLTGEGAGT VFVIDEATGN IHVTKSLDRE EKAQYVLLAQ   120
```

```
AVDRASNRPL EPPSEFIIKV QDINDNPPIF PLGPYHATVP EMSNVGTSVI QVTAHDADDP  180
SYGNSAKLVY TVLDGLPFFS VDPQTGVVRT AIPNMDRETQ EEFLVVIQAK DMGGHMGGLS  240
GSTTVTVTLS DVNDNPPKFP QSLYQFSVVE TAGPGTLVGR LRAQDPDLGD NALMAYSILD  300
GEGSEAFSIS TDLQGRDGLL TVRKPLDFES QRSYSFRVEA TNTLIDPAYL RRGPFKDVAS  360
VRVAVQDAPE PPAFTQAAYH LTVPENKAPG TLVGQISAAD LDSPASPIRY SILPHSDPER  420
CFSIQPEEGT IHTAAPLDRE ARAWHNLTVL ATELGWSWGP ERGWVPLLVA EWSAPAAPPQ  480
RSPVGSAVGI PQDSSAQASR VQVAIQTLDE NDNAPQLAEP YDTFVCDSAA PGQLIQVIRA  540
LDRDEVGNSS HVSFQGPLGP DANFTVQDNR DGSASLLLPS RPAPPRHAPY LVPIELWDWG  600
QPALSSTATV TVSVCRCQPD GSVASCWPEA HLSAAGLSTG ALLAIITCVG ALLALVVLFV  660
ALRRQKQEAL MVLEEEDVRE NIITYDDEGG GEEDTEAFDI TALQNPDGAA PPAPGPPARR  720
DVLPRARVSR QPRPPGPADV AQLLALRLRE ADEDPGVPPY DSVQVYGYEG RGSSCGSLSS  780
LGSGSEAGGA PGPAEPLDDW GPLFRTLAEL YGAKEPPAP                        819

SEQ ID NO: 342         moltype = AA  length = 819
FEATURE                Location/Qualifiers
source                 1..819
                       mol_type = protein
                       organism = Homo sapiens
SEQUENCE: 342
MWGLVRLLLA WLGGWGCMGR LAAPARAWAG SREHPGPALL RTRRSWVWNQ FFVIEEYAGP  60
EPVLIGKLHS DVDRGEGRTK YLLTGEGAGT VFVIDEATGN IHVTKSLDRE EKAQYVLLAQ  120
AVDRASNRPL EPPSEFIIKV QDINDNPPIF PLGPYHATVP EMSNVGTSVI QVTAHDADDP  180
SYGNSAKLVY TVLDGLPFFS VDPQTGVVRT AIPNMDRETQ EEFLVVIQAK DMGGHMGGLS  240
GSTTVTVTLS DVNDNPPKFP QSLYQFSVVE TAGPGTLVGR LRAQDPDLGD NALMAYSILD  300
GEGSEAFSIS TDLQGRDGLL TVRKPLDFES QRSYSFRVEA TNTLIDPAYL RRGPFKDVAS  360
VRVAVQDAPE PPAFTQAAYH LTVPENKAPG TLVGQISAAD LDSPASPIRY SILPHSDPER  420
CFSIQPEEGT IHTAAPLDRE ARAWHNLTVL ATELGWSWGP ERGWVPLLVA EWSAPAAPPQ  480
RSPVGSAVGI PQDSSAQASR VQVAIQTLDE NDNAPQLAEP YDTFVCDSAA PGQLIQVIRA  540
LDRDEVGNSS HVSFQGPLGP DANFTVQDNR DGSASLLLPS RPAPPRHAPY LVPIELWDWG  600
QPALSSTATV TVSVCRCQPD GSVASCWPEA HLSAAGLSTG ALLAIITCVG ALLALVVLFV  660
ALRRQKQEAL MVLEEEDVRE NIITYDDEGG GEEDTEAFDI TALQNPDGAA PPAPGPPARR  720
DVLPRARVSR QPRPPGPADV AQLLALRLRE ADEDPGVPPY DSVQVYGYEG RGSSCGSLSS  780
LGSGSEAGGA PGPAEPLDDW GPLFRTLAEL YGAKEPPAP                        819

SEQ ID NO: 343         moltype = AA  length = 781
FEATURE                Location/Qualifiers
source                 1..781
                       mol_type = protein
                       organism = Homo sapiens
SEQUENCE: 343
MWGLVRLLLA WLGGWGCMGR LAAPARAWAG SREHPGPALL RTRRSWVWNQ FFVIEEYAGP  60
EPVLIGKLHS DVDRGEGRTK YLLTGEGAGT VFVIDEATGN IHVTKSLDRE EKAQYVLLAQ  120
AVDRASNRPL EPPSEFIIKV QDINDNPPIF PLGPYHATVP EMSNVGTSVI QVTAHDADDP  180
SYGNSAKLVY TVLDGLPFFS VDPQTGVVRT AIPNMDRETQ EEFLVVIQAK DMGGHMGGLS  240
GSTTVTVTLS DVNDNPPKFP QSLYQFSVVE TAGPGTLVGR LRAQDPDLGD NALMAYSILD  300
GEGSEAFSIS TDLQGRDGLL TVRKPLDFES QRSYSFRVEA TNTLIDPAYL RRGPFKDVAS  360
VRVAVQDAPE PPAFTQAAYH LTVPENKAPG TLVGQISAAD LDSPASPIRY SILPHSDPER  420
CFSIQPEEGT IHTAAPLDRE ARAWHNLTVL ATELDSSAQA SRVQVAIQTL DENDNAPQLA  480
EPYDTFVCDS AAPGQLIQVI RALDRDEVGN SSHVSFQGPL GPDANFTVQD NRDGSASLLL  540
PSRPAPPRHA PYLVPIELWD WGQPALSSTA TVTVSVCRCQ PDGSVASCWP EAHLSAAGLS  600
TGALLAIITC VGALLALVVL FVALRRQKQE ALMVLEEEDV RENIITYDDE GGGEEDTEAF  660
DITALQNPDG AAPPAPGPPA RRDVLPRARV SRQPRPPGPA DVAQLLALRL READEDPGVP  720
PYDSVQVYGY EGRGSSCGSL SSLGSGSEAG GAPGPAEPLD DWGPLFRTLA ELYGAKEPPA  780
P                                                                781

SEQ ID NO: 344         moltype = AA  length = 781
FEATURE                Location/Qualifiers
source                 1..781
                       mol_type = protein
                       organism = Homo sapiens
SEQUENCE: 344
MWGLVRLLLA WLGGWGCMGR LAAPARAWAG SREHPGPALL RTRRSWVWNQ FFVIEEYAGP  60
EPVLIGKLHS DVDRGEGRTK YLLTGEGAGT VFVIDEATGN IHVTKSLDRE EKAQYVLLAQ  120
AVDRASNRPL EPPSEFIIKV QDINDNPPIF PLGPYHATVP EMSNVGTSVI QVTAHDADDP  180
SYGNSAKLVY TVLDGLPFFS VDPQTGVVRT AIPNMDRETQ EEFLVVIQAK DMGGHMGGLS  240
GSTTVTVTLS DVNDNPPKFP QSLYQFSVVE TAGPGTLVGR LRAQDPDLGD NALMAYSILD  300
GEGSEAFSIS TDLQGRDGLL TVRKPLDFES QRSYSFRVEA TNTLIDPAYL RRGPFKDVAS  360
VRVAVQDAPE PPAFTQAAYH LTVPENKAPG TLVGQISAAD LDSPASPIRY SILPHSDPER  420
CFSIQPEEGT IHTAAPLDRE ARAWHNLTVL ATELDSSAQA SRVQVAIQTL DENDNAPQLA  480
EPYDTFVCDS AAPGQLIQVI RALDRDEVGN SSHVSFQGPL GPDANFTVQD NRDGSASLLL  540
PSRPAPPRHA PYLVPIELWD WGQPALSSTA TVTVSVCRCQ PDGSVASCWP EAHLSAAGLS  600
TGALLAIITC VGALLALVVL FVALRRQKQE ALMVLEEEDV RENIITYDDE GGGEEDTEAF  660
DITALQNPDG AAPPAPGPPA RRDVLPRARV SRQPRPPGPA DVAQLLALRL READEDPGVP  720
PYDSVQVYGY EGRGSSCGSL SSLGSGSEAG GAPGPAEPLD DWGPLFRTLA ELYGAKEPPA  780
P                                                                781

SEQ ID NO: 345         moltype = AA  length = 314
FEATURE                Location/Qualifiers
source                 1..314
```

```
                        mol_type = protein
                        organism = Homo sapiens
SEQUENCE: 345
MWGLVRLLLA WLGGWGCMGR LAAPARAWAG SREHPGPALL RTRRSWVWNQ FFVIEEYAGP    60
EPVLIGKLHS DVDRGEGRTK YLLTGEGAGT VFVIDEATGN IHVTKSLDRE EKAQYVLLAQ   120
AVDRASNRPL EPPSEFIIKI ITCVGALLAL VVLFVALRRQ KQEALMVLEE EDVRENIITY   180
DDEGGGEEDT EAFDITALQN PDGAAPPAPG PPARRDVLPR ARVSRQPRPP GPADVAQLLA   240
LRLREADEDP GVPPYDSVQV YGYEGRGSSC GSLSSLGSGS EAGGAPGPAE PLDDWGPLFR   300
TLAELYGAKE PPAP                                                    314

SEQ ID NO: 346          moltype = AA   length = 45
FEATURE                 Location/Qualifiers
source                  1..45
                        mol_type = protein
                        organism = Homo sapiens
SEQUENCE: 346
MFRAAAPGQL RRARRGFPML PRLVSNSCPQ VIHLPRPPKV LELQA                    45

SEQ ID NO: 347          moltype = AA   length = 45
FEATURE                 Location/Qualifiers
source                  1..45
                        mol_type = protein
                        organism = Homo sapiens
SEQUENCE: 347
MFRAAAPGQL RRARRGFPML PRLVSNSCPQ VIHLPRPPKV LELQA                    45

SEQ ID NO: 348          moltype = AA   length = 46
FEATURE                 Location/Qualifiers
source                  1..46
                        mol_type = protein
                        organism = Homo sapiens
SEQUENCE: 348
MNEAKVKETL RRCGASGDEC GRLQYALTCL RKVTGLGGEH KEDSSW                   46

SEQ ID NO: 349          moltype = AA   length = 248
FEATURE                 Location/Qualifiers
source                  1..248
                        mol_type = protein
                        organism = Homo sapiens
SEQUENCE: 349
MQTCPLAFPG HVSQALGTLL FLAASLSAQN EGWDSPICTE GVVSVSWGEN TVMSCNISNA    60
FSHVNIKLRA HGQESAIFNE VAPGYFSRDG WQLQVQGGVA QLVIKGARDS HAGLYMWHLV   120
GHQRNNRQVT LEVSGAEPQS APDTGFWPVP AVVTAVFILL VALVMFAWYR CRCSQQRREK   180
KFFLLEPQMK VAALRAGAQQ GLSRASAELW TPDSEPTPRP LALVFKPSPL GALELLSPQP   240
LFPYAADP                                                           248

SEQ ID NO: 350          moltype = AA   length = 149
FEATURE                 Location/Qualifiers
source                  1..149
                        mol_type = protein
                        organism = Homo sapiens
SEQUENCE: 350
MQTCPLAFPG HVSQALGTLL FLAASLSAQN EGWDSPICTE GVVSVSWGEN TVMSCNISNA    60
FSHVNIKLRA HGQESAIFNE VAPGYFSRDG WQLQVQGGVA QLVIKGARDS HAGLYMWHLV   120
GHQRNNRQVT LEVSGAAVPS NAGRRSSSS                                    149

SEQ ID NO: 351          moltype = AA   length = 178
FEATURE                 Location/Qualifiers
source                  1..178
                        mol_type = protein
                        organism = Homo sapiens
SEQUENCE: 351
MQTCPLAFPG HVSQALGTLL FLAASLSAQN EGWDSPICTE GVVSVSWGEN TVMSCNISNA    60
FSHVNIKLRA HGQESAIFNE VAPGYFSRDG WQLQVQGGVA QLVIKGARDS HAGLYMWHLV   120
GHQRNNRQVT LEVSGAEPQS APDTGFWPVP AVVTAVFILL VALVMFAWYR CRCSQQRR    178

SEQ ID NO: 352          moltype = AA   length = 43
FEATURE                 Location/Qualifiers
source                  1..43
                        mol_type = protein
                        organism = Homo sapiens
SEQUENCE: 352
MQTCPLAFPG HVSQALGTLL FLAASLSAQN EAACPRAGER HLQ                     43

SEQ ID NO: 353          moltype = AA   length = 44
FEATURE                 Location/Qualifiers
source                  1..44
                        mol_type = protein
                        organism = Homo sapiens
```

```
SEQUENCE: 353
MQTCPLAFPG HVSQALGTLL FLAASLSAQN EGWDSPICTE GVVS                      44

SEQ ID NO: 354          moltype = AA  length = 85
FEATURE                 Location/Qualifiers
source                  1..85
                        mol_type = protein
                        organism = Homo sapiens
SEQUENCE: 354
MQTCPLAFPG HVSQALGTLL FLAASLSAQN EGWDSPICTE GVVSVSWGEN TVMSCNISNA    60
FSHVNIKLRA HGQESAIFNE VAPGY                                          85

SEQ ID NO: 355          moltype = AA  length = 170
FEATURE                 Location/Qualifiers
source                  1..170
                        mol_type = protein
                        organism = Homo sapiens
SEQUENCE: 355
MQTCPLAFPG HVSQALGTLL FLAASLSAQN EGWDSPICTE GVVSVSWGEN TVMSCNISNA    60
FSHVNIKLRA HGQESAIFNE VAPGYFSRDG WQLQVQGGVA QLVIKGARDS HAGLYMWHLV   120
GHQRNNRQVT LEVSEPRGLK DRASAQLLGP GTSRGAEPQS APDTGFWPVP              170

SEQ ID NO: 356          moltype = AA  length = 147
FEATURE                 Location/Qualifiers
source                  1..147
                        mol_type = protein
                        organism = Homo sapiens
SEQUENCE: 356
MQTCPLAFPG HVSQALGTLL FLAASLSAQN EGWDSPICTE GVVSVSWGEN TVMSCNISNA    60
FSHVNIKLRA HGQESAIFNE VAPGYFSRDG WQLQVQGGVA QLVIKGARDS HAGLYMWHLV   120
GHQRNNRQVT LEVSEPRGLK DRASAQL                                       147

SEQ ID NO: 357          moltype = AA  length = 165
FEATURE                 Location/Qualifiers
source                  1..165
                        mol_type = protein
                        organism = Homo sapiens
SEQUENCE: 357
MDAPRRDMEL LSNSLAAYAH IRANPESFGL YFVLGVCFGL LLTLCLLVIS ISWAPRPRPR    60
GPAQRRDPRS STLEPEDDDE DEEDTVTRLG PDDTLPGPEL SAEPDGPLNV NVFTSAEELE   120
RAQRLEERER ILREIWRTGQ PDLLGTGTLG PSPTATGTLG RMHYY                   165

SEQ ID NO: 358          moltype = AA  length = 639
FEATURE                 Location/Qualifiers
source                  1..639
                        mol_type = protein
                        organism = Homo sapiens
SEQUENCE: 358
MNLEKLSKPE LLTLFSILEG ELEARDLVIE ALKAQHRDTF IEERYGKYNI SDPLMALQRD    60
FETLKEKNDG EKQPVCTNPL SILKVVMKQC KNMQERMLSQ LAAAESRHRK VILDLEEERQ   120
RHAQDTAEGD DVTYMLEKER ERLTQQLEFE KSQVKKFEKE QKKLSSQLEE ERSRHKQLSS   180
MLVLECKKAT NKAAEEGQKA GELSLKLEKE KSRVSKLEEE LAAERKRGLQ TEAQVEKQLS   240
EFDIEREQLR AKLNREENRT KTLKEEMESL KKIVKDLEAS HQHSSPNEQL KKPVTVSKGT   300
ATEPLMLMSV FCQTESFPAE RTHGSNIAKM TNTGLPGPAT PAYSYAKTNG HCDPEIQTTR   360
ELTAGNNVEN QVPPREKSVA LAQEKPVENG GCPVGIETPV PMPSPLSSSG SSLSPSSTAS   420
SSLTSSPCSS PVLTKRLLGS SASSPGYQSS YQVGINQRFH AARHKFQSQA DQDQQASGLQ   480
SPPSRDLSPT LIDNSAAKQL ARNTVQVLS RFTSQQGPIK PVSPNSSPFG TDYRNLANTA    540
NPRGDTSHSP TPGKVSSPLS PLSPGIKSPT IPRAERGNPP PIPPKKPGLT PSPSATTPLT   600
KTHSQAASLT TAEDLASSCS SNTVVANGKD VELLLPTSS                          639

SEQ ID NO: 359          moltype = AA  length = 271
FEATURE                 Location/Qualifiers
source                  1..271
                        mol_type = protein
                        organism = Homo sapiens
SEQUENCE: 359
MNLEKLSKPE LLTLFSILEG ELEARDLVIE ALKAQHRDTF IEERYGKYNI SDPLMALQRD    60
FETLKEKNDG EKQPVCTNPL SILKVVMKQC KNMQERMLSQ LAAAESRHRK VILDLEEERQ   120
RHAQDTAEGD DVTYMLEKER ERLTQQLEFE KSQVKKFEKE QKKLSSQLEE ERSRHKQLSS   180
MLVLECKKAT NKAAEEGQKA GELSLKLEKE KSRVSKLEEE LAAERKRGLQ TEAQVEKQLS   240
EFDIEREQLR AKLNREENRT KTLKEEMESL K                                  271

SEQ ID NO: 360          moltype = AA  length = 396
FEATURE                 Location/Qualifiers
source                  1..396
                        mol_type = protein
                        organism = Homo sapiens
SEQUENCE: 360
MSATDRMGPR AVPGLRLALL LLLVLGTPKS GVQGQEGLDF PEYDGVDRVI NVNAKNYKNV    60
```

```
FKKYEVLALL  YHEPPEDDKA  SQRQFEMEEL  ILELAAQVLE  DKGVGFGLVD  SEKDAAVAKK   120
LGLTEVDSMY  VFKGDEVIEY  DGEFSADTIV  EFLLDVLEDP  VELIEGEREL  QAFENIEDEI   180
KLIGYFKSKD  SEHYKAFEDA  AEEFHPYIPF  FATFDSKVAK  KLTLKLNEID  FYEAFMEEPV   240
TIPDKPNSEE  EIVNFVEEHR  RSTLRKLKPE  SMYETWEDDM  DGIHIVAFAE  EADPDGFEFL   300
ETLKAVAQDN  TENPDLSIIW  IDPDDFPLLV  PYWEKTFDID  LSAPQIGVVN  VTDADSVWME   360
MDDEEDLPSA  EELEDWLEDV  LEGEINTEDD  DDDDDD                               396

SEQ ID NO: 361           moltype = AA   length = 188
FEATURE                  Location/Qualifiers
source                   1..188
                         mol_type = protein
                         organism = Homo sapiens
SEQUENCE: 361
MDVNIAPLRA  WDDFFPGSDR  FARPDFRDIS  KWNNRVVSNL  LYYQTNYLVV  AAMMISIVGF    60
LSPFNMILGG  IVVVLVFTGF  VWAAHNKDVL  RRMKKRYPTT  FVMVVMLASY  FLISMFGGVM   120
VFVFGITFPL  LLMFIHASLR  LRNLKNKLEN  KMEGIGLKRT  PMGIVLDALE  QQEEGINRLT   180
DYISKVKE                                                                 188

SEQ ID NO: 362           moltype = AA   length = 88
FEATURE                  Location/Qualifiers
source                   1..88
                         mol_type = protein
                         organism = Homo sapiens
SEQUENCE: 362
MDVNIAPLRA  WDDFFPGSDR  FARPDFRDIS  KWNNRVVSNL  LYYQTNYLVV  AAMMISIVGF    60
LSPFNPPIVS  EVSRVFMKSN  GKWITRFL                                          88

SEQ ID NO: 363           moltype = AA   length = 93
FEATURE                  Location/Qualifiers
source                   1..93
                         mol_type = protein
                         organism = Homo sapiens
SEQUENCE: 363
MDVNIAPLRA  WDDFFPGSDR  FARPDFRDIS  KWNNRVVSNL  LYYQTNYLVV  AAMMISIVGL    60
ECNGVISAHC  NLHLLSSSDS  PASASQVAGI  TGF                                   93

SEQ ID NO: 364           moltype = AA   length = 59
FEATURE                  Location/Qualifiers
source                   1..59
                         mol_type = protein
                         organism = Homo sapiens
SEQUENCE: 364
MDVNIAPLRA  WDDFFPGSDR  FARPDFRDIS  KWNNRVVSNL  LYYQTNYLVV  AAMMISIVG     59

SEQ ID NO: 365           moltype = AA   length = 357
FEATURE                  Location/Qualifiers
source                   1..357
                         mol_type = protein
                         organism = Homo sapiens
SEQUENCE: 365
MEKYVAAMVL  SAAGDALGYY  NGKWEFLQDG  EKIHRQLAQL  GGLDALDVGR  WRVSDDTVMH    60
LATAEALVEA  GKAPKLTQLY  YLLAKHYQDC  MEDMDGRAPG  GASVHNAMQL  KPGKPNGWRI   120
PFNSHEGGCG  AAMRAMCIGL  RFPHHSQLDT  LIQVSIESGR  MTHHHPTGYL  GALASALFTA   180
YAVNSRPPLQ  WGKGLMELLP  EAKKYIVQSG  YFVEENLQHW  SYFQTKWENY  LKLRGILDGE   240
SAPTFPESFG  VKERDQFYTS  LSYSGWGGSS  GHDAPMIAYD  AVLAAGDSWK  ELAHRAFFHG   300
GDSDSTAAIA  GCWWGVMYGF  KGVSPSNYEK  LEYRNRLEET  ARALYSLGSK  EDTVISL      357

SEQ ID NO: 366           moltype = AA   length = 357
FEATURE                  Location/Qualifiers
source                   1..357
                         mol_type = protein
                         organism = Homo sapiens
SEQUENCE: 366
MEKYVAAMVL  SAAGDALGYY  NGKWEFLQDG  EKIHRQLAQL  GGLDALDVGR  WRVSDDTVMH    60
LATAEALVEA  GKAPKLTQLY  YLLAKHYQDC  MEDMDGRAPG  GASVHNAMQL  KPGKPNGWRI   120
PFNSHEGGCG  AAMRAMCIGL  RFPHHSQLDT  LIQVSIESGR  MTHHHPTGYL  GALASALFTA   180
YAVNSRPPLQ  WGKGLMELLP  EAKKYIVQSG  YFVEENLQHW  SYFQTKWENY  LKLRGILDGE   240
SAPTFPESFG  VKERDQFYTS  LSYSGWGGSS  GHDAPMIAYD  AVLAAGDSWK  ELAHRAFFHG   300
GDSDSTAAIA  GCWWGVMYGF  KGVSPSNYEK  LEYRNRLEET  ARALYSLGSK  EDTVISL      357

SEQ ID NO: 367           moltype = AA   length = 357
FEATURE                  Location/Qualifiers
source                   1..357
                         mol_type = protein
                         organism = Homo sapiens
SEQUENCE: 367
MEKYVAAMVL  SAAGDALGYY  NGKWEFLQDG  EKIHRQLAQL  GGLDALDVGR  WRVSDDTVMH    60
LATAEALVEA  GKAPKLTQLY  YLLAKHYQDC  MEDMDGRAPG  GASVHNAMQL  KPGKPNGWRI   120
PFNSHEGGCG  AAMRAMCIGL  RFPHHSQLDT  LIQVSIESGR  MTHHHPTGYL  GALASALFTA   180
```

```
YAVNSRPPLQ WGKGLMELLP EAKKYIVQSG YFVEENLQHW SYFQTKWENY LKLRGILDGE    240
SAPTFPESFG VKERDQFYTS LSYSGWGGSS GHDAPMIAYD AVLAAGDSWK ELAHRAFFHG    300
GDSDSTAAIA GCWWGVMYGF KGVSPSNYEK LEYRNRLEET ARALYSLGSK EDTVISL       357

SEQ ID NO: 368            moltype = AA   length = 357
FEATURE                   Location/Qualifiers
source                    1..357
                          mol_type = protein
                          organism = Homo sapiens
SEQUENCE: 368
MEKYVAAMVL SAAGDALGYY NGKWEFLQDG EKIHRQLAQL GGLDALDVGR WRVSDDTVMH    60
LATAEALVEA GKAPKLTQLY YLLAKHYQDC MEDMDGRAPG GASVHNAMQL KPGKPNGWRI    120
PFNSHEGGCG AAMRAMCIGL RFPHHSQLDT LIQVSIESGR MTHHHPTGYL GALASALFTA    180
YAVNSRPPLQ WGKGLMELLP EAKKYIVQSG YFVEENLQHW SYFQTKWENY LKLRGILDGE    240
SAPTFPESFG VKERDQFYTS LSYSGWGGSS GHDAPMIAYD AVLAAGDSWK ELAHRAFFHG    300
GDSDSTAAIA GCWWGVMYGF KGVSPSNYEK LEYRNRLEET ARALYSLGSK EDTVISL       357

SEQ ID NO: 369            moltype = AA   length = 125
FEATURE                   Location/Qualifiers
source                    1..125
                          mol_type = protein
                          organism = Homo sapiens
SEQUENCE: 369
MEKYVAAMVL SAAGDALGYY NGKWEFLQDG EKIHRQLAQL GGLDALDVGR WRVSDDTVMH    60
LATAEALVEA GKAPKLTQLY YLLAKHYQDC MEDMDGRAPG GASVHNAMQL KPGKPNGWRI    120
PFNSH                                                                125

SEQ ID NO: 370            moltype = AA   length = 974
FEATURE                   Location/Qualifiers
source                    1..974
                          mol_type = protein
                          organism = Homo sapiens
SEQUENCE: 370
MAGRVPSLLV LLVFPSSCLA FRSPLSVFKR FKETTRPFSN ECLGTTRPVV PIDSSDFALD    60
IRMPGVTPKQ SDTYFCMSMR IPVDEEAFVI DFKPRASMDT VHHMLLFGCN MPSSTGSYWF    120
CDEGTCTDKA NILYAWARNA PPTRLPKGVG FRVGGETGSK YFVLQVHYGD ISAFRDNNKD    180
CSGVSLHLTR LPQPLIAGMY LMMSVDTVIP AGEKVVNSDI SCHYKNYPMH VFAYRVHTHH    240
LGKVVSGYRV RNGQWTLIGR QSPQLPQAFY PVGHPVDVSF GDLLAARCVF TGEGRTEATH    300
IGGTSSDEMC NLYIMYYMEA KHAVSFMTCT QNVAPDMFRT IPPEANIPIP VKSDMVMMHE    360
HHKETEYKDK IPLLQQPKRE EEEVLDQGDF YSLLSKLLGE REDVVHVHKY NPTEKAESES    420
DLVAEIANVV QKKDLGRSDA REGAEHERGN AILVRDRIHK FHRLVSTLRP PESRVFSLQQ    480
PPPGEGTWEP EHTGDFHMEE ALDWPGVYLL PGQVSGVALD PKNNLVIFHR GDHVWDGNSF    540
DSKFVYQQIG LGPIEEDTIL VIDPNNAAVL QSSGKNLFYL PHGLSIDKDG NYWVTDVALH    600
QVFKLDPNNK EGPVLILGRS MQPGSDQNHF CQPTDVAVDP GTGAIYVSDG YCNSRIVQFS    660
PSGKFITQWG EESSGSSPLP GQFTVPHSLA LVPLLGQLCV ADRENGRIQC FKTDTKEFVR    720
EIKHSSFGRN VFAISYIPGL LFAVNGKPHF GDQEPVQGFV MNFSNGEIID IFKPVRKHFD    780
MPHDIVASED GTVYIGDAHT NTVWKFTLTE KLEHRSVKKA GIEVQEIKEA EAVVETKMEN    840
KPTSSELQKM QEKQKLIKEP GSGVPVVLIT TLLVIPVVVL LAIAIFIRWK KSRAFGADSE    900
HKLETSSGRV LGRFRGKGSG GLNLGNFFAS RKGYSRKGFD RLSTEGSDQE KEDDGSESEE    960
EYSAPLPALA PSSS                                                      974

SEQ ID NO: 371            moltype = AA   length = 175
FEATURE                   Location/Qualifiers
source                    1..175
                          mol_type = protein
                          organism = Homo sapiens
SEQUENCE: 371
MAGRVPSLLV LLVFPSSCLA FRSPLSVFKR FKETTRPFSN ECLGTTRPVV PIDSSDFALD    60
IRMPGVTPKQ LTSSLEPAWI LSITCYFLDA ICLHPLEVTG FVMKEPVQIK PIFCMPGREM    120
LPLPGSPKVL DSELEERLEV NTLYYRYTMG ILVLLEIITR TVLVCPYTSH VCHSL          175

SEQ ID NO: 372            moltype = AA   length = 887
FEATURE                   Location/Qualifiers
source                    1..887
                          mol_type = protein
                          organism = Homo sapiens
SEQUENCE: 372
MAGRVPSLLV LLVFPSSCLA FRSPLSVFKR FKETTRPFSN ECLGTTRPVV PIDSSDFALD    60
IRMPGVTPKQ SDTYFCMSMR IPVDEEAFVI DFKPRASMDT VHHMLLFGCN MPSSTGSYWF    120
CDEGTCTDKA NILYAWARNA PPTRLPKGVG FRVGGETGSK YFVLQVHYGD ISAFRDNNKD    180
CSGVSLHLTR LPQPLIAGMY LMMSVDTVIP AGEKVVNSDI SCHYKNYPMH VFAYRVHTHH    240
LGKVVSGYRV RNGQWTLIGR QSPQLPQAFY PVGHPVDVSF GDLLAARCVF TGEGRTEATH    300
IGGTSSDEMC NLYIMYYMEA KHAVSFMTCT QNVAPDMFRT IPPEANIPIP VKSDMVMMHE    360
HHKETEYKDK IPLLQQPKRE EEEVLDQGDF YSLLSKLLGE REDVVHVHKY NPTEKAESES    420
DLVAEIANVV QKKDLGRSDA REGAEHERGN AILVRDRIHK FHRLVSTLRP PESRVFSLQQ    480
PPPGEGTWEP EHTGDFHMEE ALDWPGVYLL PGQVSGVALD PKNNLVIFHR GDHVWDGNSF    540
DSKFVYQQIG LGPIEEDTIL VIDPNNAAVL QSSGKNLFYL PHGLSIDKDG NYWVTDVALH    600
QVFKLDPNNK EGPVLILGRS MQPGSDQNHF CQPTDVAVDP GTGAIYVSDG YCNSRIVQFS    660
PSGKFITQWG EESSGSSPLP GQFTVPHSLA LVPLLGQLCV ADRENGRIQC FKTDTKEFVR    720
```

```
EIKHSSFGRN VFAISYIPGL LFAVNGKPHF GDQEPVQGFV MNFSNGEIID IFKPVRKHFD   780
MPHDIVASED GTVYIGDAHT NTVWKFTLTE KLEHRSVKKA GIEVQEIKGK GSGGLNLGNF   840
FASRKGYSRK GFDRLSTEGS DQEKEDDGSE SEEEYSAPLP ALAPSSS                887

SEQ ID NO: 373           moltype = AA  length = 866
FEATURE                  Location/Qualifiers
source                   1..866
                         mol_type = protein
                         organism = Homo sapiens
SEQUENCE: 373
MAGRVPSLLV LLVFPSSCLA FRSPLSVFKR FKETTRPFSN ECLGTTRPVV PIDSSDFALD    60
IRMPGVTPKQ SDTYFCMSMR IPVDEEAFVI DFKPRASMDT VHHMLLFGCN MPSSTGSYWF   120
CDEGTCTDKA NILYAWARNA PPTRLPKGVG FRVGGETGSK YFVLQVHYGD ISAFRDNNKD   180
CSGVSLHLTR LPQPLIAGMY LMMSVDTVIP AGEKVVNSDI SCHYKNYPMH VFAYRVHTHH   240
LGKVVSGYRV RNGQWTLIGR QSPQLPQAFY PVGHPVDVSF GDLLAARCVF TGEGRTEATH   300
IGGTSSDEMC NLYIMYYMEA KHAVSFMTCT QNVAPDMFRT IPPEANIPIP VKSDMVMMHE   360
HHKETEYKDK IPLLQQPKRE EEEVLDQDFH MEEALDWPGV YLLPGQVSGV ALDPKNNLVI   420
FHRGDHVWDG NSFDSKFVYQ QIGLGPIEED TILVIDPNNA AVLQSSGKNL FYLPHGLSID   480
KDGNYWVTDV ALHQVFKLDP NNKEGPVLIL GRSMQPGSDQ NHFCQPTDVA VDPGTGAIYV   540
SDGYCNSRIV QFSPSGKFIT QWGEESSGSS PLPGQFTVPH SLALVPLLGQ LCVADRENGR   600
IQCFKTDTKE FVREIKHSSF GRNVFAISYI PGLLFAVNGK PHFGDEPVQ GFVMNFSNGE   660
IIDIFKPVRK HFDMPHDIVA SEDGTVYIGD AHTNTVWKFT LTEKLEHRSV KKAGIEVQEI   720
KEAEAVVETK MENKPTSSEL QKMQEKQKLI KEPGSGVPVV LITTLLVIPV VVLLAIAIFI   780
RWKKSRAFGD SEHKLETSSG RVLGRFRGKG SGGLNLGNFF ASRKGYSRKG FDRLSTEGSD   840
QEKEDDGSES EEEYSAPLPA LAPSSS                                       866

SEQ ID NO: 374           moltype = AA  length = 973
FEATURE                  Location/Qualifiers
source                   1..973
                         mol_type = protein
                         organism = Homo sapiens
SEQUENCE: 374
MAGRVPSLLV LLVFPSSCLA FRSPLSVFKR FKETTRPFSN ECLGTTRPVV PIDSSDFALD    60
IRMPGVTPKQ SDTYFCMSMR IPVDEEAFVI DFKPRASMDT VHHMLLFGCN MPSSTGSYWF   120
CDEGTCTDKA NILYAWARNA PPTRLPKGVG FRVGGETGSK YFVLQVHYGD ISAFRDNNKD   180
CSGVSLHLTR LPQPLIAGMY LMMSVDTVIP AGEKVVNSDI SCHYKNYPMH VFAYRVHTHH   240
LGKVVSGYRV RNGQWTLIGR QSPQLPQAFY PVGHPVDVSF GDLLAARCVF TGEGRTEATH   300
IGGTSSDEMC NLYIMYYMEA KHAVSFMTCT QNVAPDMFRT IPPEANIPIP VKSDMVMMHE   360
HHKETEYKDK IPLLQQPKRE EEEVLDQGDF YSLLSKLLGE REDVVHVHKY NPTEKAESES   420
DLVAEIANVV QKKDLGRSDA REGAEHERGN AILVRDRIHK FHRLVSTLRP PESRVFSLQQ   480
PPPGEGTWEP EHTGDFHMEE ALDWPGVYLL PGQVSGVALD PKNNLVIFHR GDHVWDGNSF   540
DSKFVYQQIG LGPIEEDTIL VIDPNNAAVL QSSGKNLFYL PHGLSIDKDG NYWVTDVALH   600
QVFKLDPNNK EGPVLILGRS MQPGSDQNHF CQPTDVAVDP GTGAIYVSDG YCNSRIVQFS   660
PSGKFITQWG EESSGSSPLP GQFTVPHSLA LVPLLGQLCV ADRENGRIQC FKTDTKEFVR   720
EIKHSSFGRN VFAISYIPGL LFAVNGKPHF GDQEPVQGFV MNFSNGEIID IFKPVRKHFD   780
MPHDIVASED GTVYIGDAHT NTVWKFTLTE KLEHRSVKKA GIEVQEIKEA EAVVETKMEN   840
KPTSSELQKM QEKQKLIKEP GSGVPVVLIT TLLVIPVVVL LAIAIFIRWK KSRAFGDSEH   900
KLETSSGRVL GRFRGKGSGG LNLGNFFASR KGYSRKGFDR LSTEGSDQEK EDDGSESEEE   960
YSAPLPALAP SSS                                                     973

SEQ ID NO: 375           moltype = AA  length = 905
FEATURE                  Location/Qualifiers
source                   1..905
                         mol_type = protein
                         organism = Homo sapiens
SEQUENCE: 375
MAGRVPSLLV LLVFPSSCLA FRSPLSVFKR FKETTRPFSN ECLGTTRPVV PIDSSDFALD    60
IRMPGVTPKQ SDTYFCMSMR IPVDEEAFVI DFKPRASMDT VHHMLLFGCN MPSSTGSYWF   120
CDEGTCTDKA NILYAWARNA PPTRLPKGVG FRVGGETGSK YFVLQVHYGD ISAFRDNNKD   180
CSGVSLHLTR LPQPLIAGMY LMMSVDTVIP AGEKVVNSDI SCHYKNYPMH VFAYRVHTHH   240
LGKVVSGYRV RNGQWTLIGR QSPQLPQAFY PVGHPVDVSF GDLLAARCVF TGEGRTEATH   300
IGGTSSDEMC NLYIMYYMEA KHAVSFMTCT QNVAPDMFRT IPPEANIPIP VKSDMVMMHE   360
HHKETEYKDK IPLLQQPKRE EEEVLDQGDF YSLLSKLLGE REDVVHVHKY NPTEKAESES   420
DLVAEIANVV QKKDLGRSDA REGAEHERGN AILVRDRIHK FHRLVSTLRP PESRVFSLQQ   480
PPPGEGTWEP EHTGDFHMEE ALDWPGVYLL PGQVSGVALD PKNNLVIFHR GDHVWDGNSF   540
DSKFVYQQIG LGPIEEDTIL VIDPNNAAVL QSSGKNLFYL PHGLSIDKDG NYWVTDVALH   600
QVFKLDPNNK EGPVLILGRS MQPGSDQNHF CQPTDVAVDP GTGAIYVSDG YCNSRIVQFS   660
PSGKFITQWG EESSGSSPLP GQFTVPHSLA LVPLLGQLCV ADRENGRIQC FKTDTKEFVR   720
EIKHSSFGRN VFAISYIPGL LFAVNGKPHF GDQEPVQGFV MNFSNGEIID IFKPVRKHFD   780
MPHDIVASED GTVYIGDAHT NTVWKFTLTE KLEHRSVKKA GIEVQEIKDS EHKLETSSGR   840
VLGRFRGKGS GGLNLGNFFA SRKGYSRKGF DRLSTEGSDQ EKEDDGSESE EEYSAPLPAL   900
APSSS                                                              905

SEQ ID NO: 376           moltype = AA  length = 250
FEATURE                  Location/Qualifiers
source                   1..250
                         mol_type = protein
                         organism = Homo sapiens
SEQUENCE: 376
```

```
XRIQCFKTDT KEFVREIKHS SFGRNVFAIS YIPGLLFAVN GKPHFGDQEP VQGFVMNFSN    60
GEIIDIFKPV RKHFDMPHDI VASEDGTVYI GDAHTNTVWK FTLTEKLEHR SVKKAGIEVQ   120
EIKEAEAVVE TKMENKPTSS ELQKMQEKQK LIKEPGSGVP VVLITTLLVI PVVVLLAIAI   180
FIRWKKSRAF GGKGSGGLNL GNFFASRKGY SRKGFDRLST EGSDQEKEDD GSESEEEYSA   240
PLPALAPSSS                                                         250

SEQ ID NO: 377        moltype = AA  length = 29
FEATURE               Location/Qualifiers
source                1..29
                      mol_type = protein
                      organism = Homo sapiens
SEQUENCE: 377
MAGRVPSLLV LLVFPSSCLA FRSPLSVFK                                     29

SEQ ID NO: 378        moltype = AA  length = 28
FEATURE               Location/Qualifiers
source                1..28
                      mol_type = protein
                      organism = Homo sapiens
SEQUENCE: 378
MAGRVPSLLV LLVFPSSCLA FRSPLSVF                                      28

SEQ ID NO: 379        moltype = AA  length = 53
FEATURE               Location/Qualifiers
source                1..53
                      mol_type = protein
                      organism = Homo sapiens
SEQUENCE: 379
MAGRVPSLLV LLVFPSSCLA FRSPLSVFKR FKETTRPFSN ECLGTTRPVV PID          53

SEQ ID NO: 380        moltype = AA  length = 42
FEATURE               Location/Qualifiers
source                1..42
                      mol_type = protein
                      organism = Homo sapiens
SEQUENCE: 380
MAGRVPSLLV LLVFPSSCLA FRSPLSVFKR FKETTRPFSN EC                      42

SEQ ID NO: 381        moltype = AA  length = 68
FEATURE               Location/Qualifiers
source                1..68
                      mol_type = protein
                      organism = Homo sapiens
SEQUENCE: 381
MAGRVPSLLV LLVFPSSCLA FRSPLSVFKR FKETTRPFSN ECLGTTRPVV PIDSSDFALD   60
IRMPGVTP                                                            68

SEQ ID NO: 382        moltype = AA  length = 25
FEATURE               Location/Qualifiers
source                1..25
                      mol_type = protein
                      organism = Homo sapiens
SEQUENCE: 382
MAGRVPSLLV LLVFPSSCLA FRSPL                                         25

SEQ ID NO: 383        moltype = AA  length = 691
FEATURE               Location/Qualifiers
source                1..691
                      mol_type = protein
                      organism = Homo sapiens
SEQUENCE: 383
MMRNHRIASS LCGDQVFSKK KKKKKNNMA AKEKLEAVLN VALRVPSIML LDVLYRWDVS     60
SFFQQIQRSS LSNNPLFQYK YLALNMHYVG YILSVVLLTL PRQHLVQLYL YPLTALLLYA   120
GHQISRDYVR SELEFAYEGP MYLEPLSMNR FTTALIGQLV VCTLCSCVMK TKQIWLFSAH   180
MLPLLARLCL VPLETIVIIN KFAMIFTGLE VLYFLGSNLL VPYNLAKSAY RELVQVVEVY   240
GLLALGMSLW NQLVVPVLFM VFWLVLFALQ IYSYFSTRDQ PASRERLLFL PLTSIAECCS   300
TPYSLLGLVF TVSFVALGVL TLCKFYLQGY RAFMNDPAMN RGMTEGVTLL ILAVQTGLIE   360
LQVVHRAFLL SIILFIVVAS ILQSMLEIAD PIVLALGASR DKSLWKHFRA VSLCLFLLVF   420
PAYMAYMICQ FFHMDFWLLI IISSSILTSL QVLGTLFIYV LFMVEEFRKE PVENMDDVIY   480
YVNGTYRLLE FLVALCVVAY GVSETIFGEW TVMGSMIIFI HSYYNVWLRA QLGWKSFLLR   540
RDAVNKIKSL PIATKEQLEK HNDICAICYQ DMKSAVITPC SHFFHAGCLK KWLYVQETCP   600
LCHCHLKNSS QLPGLGTEPV LQPHAGAEQN VMFQEGTEPP GQEHTPGTRI QEGSRDNNEY   660
IARRPDNQEG AFDPKEYPHS AKDEAHPVES A                                 691

SEQ ID NO: 384        moltype = AA  length = 663
FEATURE               Location/Qualifiers
source                1..663
                      mol_type = protein
                      organism = Homo sapiens
```

```
SEQUENCE: 384
MAAKEKLEAV LNVALRVPSI MLLDVLYRWD VSSFFQQIQR SSLSNNPLFQ YKYLALNMHY    60
VGYILSVVLL TLPRQHLVQL YLYFLTALLL YAGHQISRDY VRSELEFAYE GPMYLEPLSM   120
NRFTTALIGQ LVVCTLCSCV MKTKQIWLFS AHMLPLLARL CLVPLETIVI INKFAMIFTG   180
LEVLYFLGSN LLVPYNLAKS AYRELVQVVE VYGLLALGMS LWNQLVVPVL FMVFWLVLFA   240
LQIYSYFSTR DQPASRERLL FLFLTSIAEC CSTPYSLLGL VFTVSFVALG VLTLCKFYLQ   300
GYRAFMNDPA MNRGMTEGVT LLILAVQTGL IELQVVHRAF LLSIILFIVV ASILQSMLEI   360
ADPIVLALGA SRDKSLWKHF RAVSLCLFLL VFPAYMAYMI CQFFHMDFWL LIIISSSILT   420
SLQVLGTLFI YVLFMVEEFR KEPVENMDDV IYYVNGTYRL LEFLVALCVV AYGVSETIFG   480
EWTVMGSMII FIHSYYNVWL RAQLGWKSFL LRRDAVNKIK SLPIATKEQL EKHNDICAIC   540
YQDMKSAVIT PCSHFFHAGC LKKWLYVQET CPLCHCHLKN SSQLPGLGTE PVLQPHAGAE   600
QNVMFQEGTE PPGQEHTPGT RIQEGSRDNN EYIARRPDNQ EGAFDPKEYP HSAKDEAHPV   660
ESA                                                                663

SEQ ID NO: 385          moltype = AA  length = 693
FEATURE                 Location/Qualifiers
source                  1..693
                        mol_type = protein
                        organism = Homo sapiens
SEQUENCE: 385
MHRDRISPSN SPTWSLQVFS KKKKKKKKNN MAAKEKLEAV LNVALRVPSI MLLDVLYRWD    60
VSSFFQQIQR SSLSNNPLFQ YKYLALNMHY VGYILSVVLL TLPRQHLVQL YLYFLTALLL   120
YAGHQISRDY VRSELEFAYE GPMYLEPLSM NRFTTALIGQ LVVCTLCSCV MKTKQIWLFS   180
AHMLPLLARL CLVPLETIVI INKFAMIFTG LEVLYFLGSN LLVPYNLAKS AYRELVQVVE   240
VYGLLALGMS LWNQLVVPVL FMVFWLVLFA LQIYSYFSTR DQPASRERLL FLFLTSIAEC   300
CSTPYSLLGL VFTVSFVALG VLTLCKFYLQ GYRAFMNDPA MNRGMTEGVT LLILAVQTGL   360
IELQVVHRAF LLSIILFIVV ASILQSMLEI ADPIVLALGA SRDKSLWKHF RAVSLCLFLL   420
VFPAYMAYMI CQFFHMDFWL LIIISSSILT SLQVLGTLFI YVLFMVEEFR KEPVENMDDV   480
IYYVNGTYRL LEFLVALCVV AYGVSETIFG EWTVMGSMII FIHSYYNVWL RAQLGWKSFL   540
LRRDAVNKIK SLPIATKEQL EKHNDICAIC YQDMKSAVIT PCSHFFHAGC LKKWLYVQET   600
CPLCHCHLKN SSQLPGLGTE PVLQPHAGAE QNVMFQEGTE PPGQEHTPGT RIQEGSRDNN   660
EYIARRPDNQ EGAFDPKEYP HSAKDEAHPV ESA                                693

SEQ ID NO: 386          moltype = AA  length = 663
FEATURE                 Location/Qualifiers
source                  1..663
                        mol_type = protein
                        organism = Homo sapiens
SEQUENCE: 386
MAAKEKLEAV LNVALRVPSI MLLDVLYRWD VSSFFQQIQR SSLSNNPLFQ YKYLALNMHY    60
VGYILSVVLL TLPRQHLVQL YLYFLTALLL YAGHQISRDY VRSELEFAYE GPMYLEPLSM   120
NRFTTALIGQ LVVCTLCSCV MKTKQIWLFS AHMLPLLARL CLVPLETIVI INKFAMIFTG   180
LEVLYFLGSN LLVPYNLAKS AYRELVQVVE VYGLLALGMS LWNQLVVPVL FMVFWLVLFA   240
LQIYSYFSTR DQPASRERLL FLFLTSIAEC CSTPYSLLGL VFTVSFVALG VLTLCKFYLQ   300
GYRAFMNDPA MNRGMTEGVT LLILAVQTGL IELQVVHRAF LLSIILFIVV ASILQSMLEI   360
ADPIVLALGA SRDKSLWKHF RAVSLCLFLL VFPAYMAYMI CQFFHMDFWL LIIISSSILT   420
SLQVLGTLFI YVLFMVEEFR KEPVENMDDV IYYVNGTYRL LEFLVALCVV AYGVSETIFG   480
EWTVMGSMII FIHSYYNVWL RAQLGWKSFL LRRDAVNKIK SLPIATKEQL EKHNDICAIC   540
YQDMKSAVIT PCSHFFHAGC LKKWLYVQET CPLCHCHLKN SSQLPGLGTE PVLQPHAGAE   600
QNVMFQEGTE PPGQEHTPGT RIQEGSRDNN EYIARRPDNQ EGAFDPKEYP HSAKDEAHPV   660
ESA                                                                663

SEQ ID NO: 387          moltype = AA  length = 677
FEATURE                 Location/Qualifiers
source                  1..677
                        mol_type = protein
                        organism = Homo sapiens
SEQUENCE: 387
MVFSKKKKKK KKNNMAAKEK LEAVLNVALR VPSIMLLDVL YRWDVSSFFQ QIQRSSLSNN    60
PLFQYKYLAL NMHYVGYILS VVLLTLPRQH LVQLYLYFLT ALLLYAGHQI SRDYVRSELE   120
FAYEGPMYLE PLSMNRFTTA LIGQLVVCTL CSCVMKTKQI WLFSAHMPLL LARLCLVPLE   180
TIVIINKFAM IFTGLEVLYF LGSNLLVPYN LAKSAYRELV QVVEVYGLLA LGMSLWNQLV   240
VPVLFMVFWL VLFALQIYSY FSTRDQPASR ERLLFLFLTS IAECCSTPYS LLGLVFTVSF   300
VALGVLTLCK FYLQGYRAFM NDPAMNRGMT EGVTLLILAV QTGLIELQVV HRAFLLSIIL   360
FIVVASILQS MLEIADPIVL ALGASRDKSL WKHFRAVSLC LFLLVFPAYM AYMICQFFHM   420
DFWLLIIISS SILTSLQVLG TLFIYVLFMV EEFRKEPVEN MDDVIYYVNG TYRLLEFLVA   480
LCVVAYGVSE TIFGEWTVMG SMIIFIHSYY NVWLRAQLGW KSFLLRRDAV NKIKSLPIAT   540
KEQLEKHNDI CAICYQDMKS AVITPCSHFF HAGCLKKWLY VQETCPLCHC HLKNSSQLPG   600
LGTEPVLQPH AGAEQNVMFQ EGTEPPGQEH TPGTRIQEGS RDNNEYIARR PDNQEGAFDP   660
KEYPHSAKDE AHPVESA                                                 677

SEQ ID NO: 388          moltype = AA  length = 680
FEATURE                 Location/Qualifiers
source                  1..680
                        mol_type = protein
                        organism = Homo sapiens
SEQUENCE: 388
MAEVVFSKKK KKKKKNNMAA KEKLEAVLNV ALRVPSIMLL DVLYRWDVSS FFQQIQRSSL    60
SNNPLFQYKY LALNMHYVGY ILSVVLLTLP RQHLVQLYLY FLTALLLYAG HQISRDYVRS   120
```

```
ELEFAYEGPM YLEPLSMNRF TTALIGQLVV CTLCSCVMKT KQIWLFSAHM LPLLARLCLV    180
PLETIVIINK FAMIFTGLEV LYFLGSNLLV PYNLAKSAYR ELVQVVEVYG LLALGMSLWN    240
QLVVPVLFMV FWLVLFALQI YSYFSTRDQP ASRERLLFLF LTSIAECCST PYSLLGLVFT    300
VSFVALGVLT LCKFYLQGYR AFMNDPAMNR GMTEGVTLLI LAVQTGLIEL QVVHRAFLLS    360
IILFIVVASI LQSMLEIADP IVLALGASRD KSLWKHFRAV SLCLFLLVFP AYMAYMICQF    420
FHMDFWLLII ISSSILTSLQ VLGTLFIYVL FMVEEFRKEP VENMDDVIYY VNGTYRLLEF    480
LVALCVVAYG VSETIFGEWT VMGSMIIFIH SYYNVWLRAQ LGWKSFLLRR DAVNKIKSLP    540
IATKEQLEKH NDICAICYQD MKSAVITPCS HFFHAGCLKK WLYVQETCPL CHCHLKNSSQ    600
LPGLGTEPVL QPHAGAEQNV MFQEGTEPPG QEHTPGTRIQ EGSRDNNEYI ARRPDNQEGA    660
FDPKEYPHSA KDEAHPVESA                                                680

SEQ ID NO: 389           moltype = AA  length = 663
FEATURE                  Location/Qualifiers
source                   1..663
                         mol_type = protein
                         organism = Homo sapiens
SEQUENCE: 389
MAAKEKLEAV LNVALRVPSI MLLDVLYRWD VSSFFQQIQR SSLSNNPLFQ YKYLALNMHY    60
VGYILSVVLL TLPRQHLVQL YLYFLTALLL YAGHQISRDY VRSELEFAYE GPMYLEPLSM   120
NRFTTALIGQ LVVCTLCSCV MKTKQIWLFS AHMLPLLARL CLVPLETIVI INKFAMIFTG   180
LEVLYFLGSN LLVPYNLAKS AYRELVQVVE VYGLLALGMS LWNQLVVPVL FMVFWLVLFA   240
LQIYSYFSTR DQPASRERLL FLFLTSIAEC CSTPYSLLGL VFTVSFVALG VLTLCKFYLQ   300
GYRAFMNDPA MNRGMTEGVT LLILAVQTGL IELQVVHRAF LLSIILFIVV ASILQSMLEI   360
ADPIVLALGA SRDKSLWKHF RAVSLCLFLL VFPAYMAYMI CQFFHMDFWL LIIISSSILT   420
SLQVLGTLFI YVLFMVEEFR KEPVENMDDV IYYVNGTYRL LEFLVALCVV AYGVSETIFG   480
EWTVMGSMII FIHSYYNVWL RAQLGWKSFL LRRDAVNKIK SLPIATKEQL EKHNDICAIC   540
YQDMKSAVIT PCSHFFHAGC LKKWLYVQET CPLCHCHLKN SSQLPGLGTE PVLQPHAGAE   600
QNVMFQEGTE PPGQEHTPGT RIQEGSRDNN EYIARRPDNQ EGAFDPKEYP HSAKDEAHPV   660
ESA                                                                  663

SEQ ID NO: 390           moltype = AA  length = 185
FEATURE                  Location/Qualifiers
source                   1..185
                         mol_type = protein
                         organism = Homo sapiens
SEQUENCE: 390
MAGPRPRWRD QLLFMSIIVL VIVVICLMFY ALLWEAGNLT DLPNLRIGFY NFCLWNEDTS    60
TLQCHQFPEL EALGVPRVGL GLARLGVYGS LVLTLFAPQP LLLAQCNSDE RAWRLAVGFL   120
AVSSVLLAGG LGLFLSYVWK WVRLSLPGPG FLALGSAQAL LILLLIAMAV FPLRAERAES   180
KLESC                                                                185

SEQ ID NO: 391           moltype = AA  length = 486
FEATURE                  Location/Qualifiers
source                   1..486
                         mol_type = protein
                         organism = Homo sapiens
SEQUENCE: 391
MKGRRRRRRE YCKFALLLVL YTLVLLLVPS VLDGGRDGDK GAEHCPGLQR SLGVWSLEAA    60
AAGEREQGAE ARAAEEGGAN QSPRFPSNLS GAVGEAVSRE KQHIYVHATW RTGSSFLGEL   120
FNQHPDVFYL YEPMWHLWQA LYPGDAESLQ GALRDMLRSL FRCDFSVRL YAPPGDPAAR   180
APDTALFRWR TNKV ICSPPLCPGA PRARAEVGLV EDTACERSCP PVAIRALEAE          240
CRKYPVVVIK DVRLLDLGVL VPLLRDPGLN LKVVQLFRDP RAVHNSRLKS RQGLLRESIQ   300
VLRTRQRGDR FHRVLLAHGV GARPGGQSRA LPAAPRADFF LTGALEVICE AWLRDLLFAR   360
GAPAWLRRRY LRLRYEDLVR QPRAQLRRLL RFSGLRALAA LDAFALNMTR GAAYGADRPF   420
HLSARDAREA VHAWRERLSR EQVRQVEAAC APAMRLLAYP RSGEEGDAEQ PREGETPLEM   480
DADGAT                                                               486

SEQ ID NO: 392           moltype = AA  length = 494
FEATURE                  Location/Qualifiers
source                   1..494
                         mol_type = protein
                         organism = Homo sapiens
SEQUENCE: 392
MLTSKGQGFL HGGLCLWLCV FTPFFKGCVG CATEERLFHK LFSHYNQFIR PVENVSDPVT    60
VHFEVAITQL ANVDEVNQIM ETNLWLRHIW NDYKLRWDPM EYDGIETLRV PADKIWKPDI   120
VLYNNAVGDF QVEGKTKALL KYNGMITWTP PAIFKSSCPM DITFFPFDHQ NCSLKFGSWT   180
YDKAEIDLLI IGSKVDMNDF WENSEWEIID ASGYKHDIKY NCCEEIYTDI TYSFYIRRLP   240
MFYTINLIIP CLFISFLTVL VFYLPSDCGE KVTLCISVLL SLTVFLLVIT ETIPSTSLVP   300
PLVGEYLLFT MIFVTLSIVV TVFVLNIHYR TPTTHTMPRW VKTVFLKLLP QVLLMRWPLD   360
KTRGTGSDAV PRGLARRPAK GKLASHGEPR HLKECFHCHK SNELATSKRR LSHQPLQWVV   420
ENSEHSPEVE DVINSVQFIA ENMKSHNETK EVEDDWKYVA MVVDRVFLWV FIIVCVFGTA   480
GLFLQPLLGN TGKS                                                      494

SEQ ID NO: 393           moltype = AA  length = 111
FEATURE                  Location/Qualifiers
source                   1..111
                         mol_type = protein
                         organism = Homo sapiens
SEQUENCE: 393
```

```
METNLWLRHI WNDYKLRWDP MEYDGIETLR VPADKIWKPD IVLYNNAVGD FQVEGKTKAL    60
LKYNGMITWT PPAIFKSSCP MDITFFPFDH QNCSLKFGSW TYDKAEIDLL I            111

SEQ ID NO: 394           moltype = AA  length = 479
FEATURE                  Location/Qualifiers
source                   1..479
                         mol_type = protein
                         organism = Homo sapiens
SEQUENCE: 394
MLTSKGQGFL HGGLCLWLCV FTPFFKGCVG CATEERLFHK LFSHYNQFIR PVENVSDPVT    60
VHFEVAITQL ANVIWNDYKL RWDPMEYDGI ETLRVPADKI WKPDIVLYNN AVGDFQVEGK   120
TKALLKYNGM ITWTPPAIFK SSCPMDITFF PFDHQNCSLK FGSWTYDKAE IDLLIIGSKV   180
DMNDFWENSE WEIIDASGYK HDIKYNCCEE IYTDITYSFY IRRLPMFYTI NLIIPCLFIS   240
FLTVLVFYLP SDCGEKVTLC ISVLLSLTVF LLVITETIPS TSLVVPLVGE YLLFTMIFVT   300
LSIVVTVFVL NIHYRTPTTH TMPRWVKTVF LKLLPQVLLM RWPLDKTRGT GSDAVPRGLA   360
RRPAKGKLAS HGEPRHLKEC FHCHKSNELA TSKRRLSHQP LQWVVENSEH SPEVEDVINS   420
VQFIAENMKS HNETKEVEDD WKYVAMVVDR VFLWVFIIVC VFGTAGLFLQ PLLGNTGKS    479

SEQ ID NO: 395           moltype = AA  length = 1337
FEATURE                  Location/Qualifiers
source                   1..1337
                         mol_type = protein
                         organism = Homo sapiens
SEQUENCE: 395
MKPAAREARL PPRSPGLRWA LPLLLLLLRL GQILCAGGTP SPIPDPSVAT VATGENGITQ    60
ISSTAESFHK QNGTGTPQVE TNTSEDGESS GANDSLRTPE QGSNGTDGAS QKTPSSTGPS   120
PVFDIKAVSI SPTNVILTWK SNDTAASEYK YVVKHKMENE KTITVVHQPW CNITGLRPAT   180
SYVFSITPGI GNETWGDPRV IKVITEPIPV SDLRVALTGV RKAALSWSNG NGTASCRVLL   240
ESIGSHEELT QDSRLQVNIS GLKPGVQYNI NPYLLQSNKT KGDPLGTEGG LDASNTERSR   300
AGSPTAPVHD ESLVGPVDPS SGQQSRDTEV LLVGLEPGTR YNATVYSQAA NGTEGQPQAI   360
EFRTNAIQVF DVTAVNISAT SLTLIWKVSD NESSSNYTYK IHVAGETDSS NLNVSEPRAV   420
IPGLRSSTFY NITVCPVLGD IEGTPGFLQV HTPPVPVSDF RVTVVSTTEI GLAWSSHDAE   480
SFQMHITQEG AGNSRVEITT NQSIIIGGLF PGTKYCFEIV PKGPNGTEGA SRTVCNRTVP   540
SAVFDIHVVY VTTTEMWLDW KSPDGASEYV YHLVIESKHG SNHTSTYDKA ITLQGLIPGT   600
LYNITISPEV DHVWGDPNST AQYTRPSNVS NIDVSTNTTA ATLSWQNFDD ASPTYSYCLL   660
IEKAGNSSNA TQVVTDIGIT DATVTELIPG SSYTVEIFAQ VGDGIKSLEP GRKSFCTDPA   720
SMASFDCEVV PKEPALVLKW TCPPGANAGF ELEVSSGAWN NATHLESCSS ENGTEYRTEV   780
TYLNFSTSYN ISITTVSCGK MAAPTRNTCT TGITDPPPPD GSPNITSVSH NSVKVKFSGF   840
EASHGPIKAY AVILTTGEAG HPSADVLKYT YEDFKKGASD TYVTYLIRTE EKGRSQSLSE   900
VLKYEIDVGN ESTTLGYYNG KLEPLGSYRA CVAGFTNITF HPQNKGLIDG AESYVSFSRY   960
SDAVSLPQDP GVICGAVFGC IFGALVIVTV GGFIFWRKKR KDAKNNEVSF SQIKPKKSKL  1020
IRVENFEAYF KKQQADSNCG FAEEYEDLKL VGISQPKYAA ELAENRGKNR YNNVLPYDIS  1080
RVKLSVQTHS TDDYINANYM PGYHSKKDFI ATQGPLPNTL KDFWRMVWEK NVYAIIMLTK  1140
CVEQGRTKCE EYWPSKQAQD YGDITVAMTS EIVLPEWTIR DFTVKNIQTS ESHPLRQFHF  1200
TSWPDHGVPD TTDLLINFRY LVRDYMKQSP PESPILVHCS AGVGRTGTFI AIDRLIYQIE  1260
NENTVDVYGI VYDLRMHRPL MVQTEDQYVF LNQCVLDIVR SQKDSKVDLI YQNTTAMTIY  1320
ENLAPVTTFG KTNGYIA                                                 1337

SEQ ID NO: 396           moltype = AA  length = 539
FEATURE                  Location/Qualifiers
source                   1..539
                         mol_type = protein
                         organism = Homo sapiens
SEQUENCE: 396
MKPAAREARL PPRSPGLRWA LPLLLLLLRL GQILCAGGTP SPIPDPSVAT VATGENGITQ    60
ISSTAESFHK QNGTGTPQVE TNTSEDGESS GANDSLRTPE QGSNGTDGAS QKTPSSTGPS   120
PVFDIKAVSI SPTNVILTWK SNDTAASEYK YVVKHKMENE KTITVVHQPW CNITGLRPAT   180
SYVFSITPGI GNETWGDPRV IKVITEPIPV SDLRVALTGV RKAALSWSNG NGTASCRVLL   240
ESIGSHEELT QDSRLQVNIS GLKPGVQYNI NPYLLQSNKT KGDPLGTEGG LDASNTERSR   300
AGSPTAPVHD ESLVGPVDPS SGQQSRDTEV LLVGLEPGTR YNATVYSQAA NGTEGQPQAI   360
EFRTNAIQVF DVTAVNISAT SLTLIWKVSD NESSSNYTYK IHVAGETDSS NLNVSEPRAV   420
IPGLRSSTFY NITVCPVLGD IEGTPGFLQV HTPPVPVSDF RVTVVSTTEI GLAWSSHDAE   480
SFQMHITQEG AGNSRVEITT NQSIIIGGLF PGTKYCFEIV PKGPNGTEGA SRTVCNRTG    539

SEQ ID NO: 397           moltype = AA  length = 147
FEATURE                  Location/Qualifiers
source                   1..147
                         mol_type = protein
                         organism = Homo sapiens
SEQUENCE: 397
MKPAAREARL PPRSPGLRWA LPLLLLLLRL GQILCAGGTP SPIPDPSVAT VATGENGITQ    60
ISSTAESFHK QNGTGTPQVE TNTSEDGESS GANDSLRTPE QGSNGTDGAS QKTPSSTEPI   120
PVSDLRVALT GVRKAALSWS NGNGTAS                                       147

SEQ ID NO: 398           moltype = AA  length = 120
FEATURE                  Location/Qualifiers
source                   1..120
                         mol_type = protein
                         organism = Homo sapiens
```

```
SEQUENCE: 398
MKPAAREARL PPRSPGLRWA LPLLLLLLRL GQILCAGGRP SPVFDIKAVS ISPTNVILTW    60
KSNDTAASEY KYVVKHKMEN EKTITVVHQP WCNITGLRPA TSYVFSITPG IGNETWGDPR   120

SEQ ID NO: 399           moltype = AA   length = 1338
FEATURE                  Location/Qualifiers
source                   1..1338
                         mol_type = protein
                         organism = Homo sapiens
SEQUENCE: 399
MKPAAREARL PPRSPGLRWA LPLLLLLLRL GQILCAGGTP SPIPDPSVAT VATGENGITQ    60
ISSTAESFHK QNGTGTPQVE TNTSEDGESS GANDSLRTPE QGSNGTDGAS QKTPSSTGPS   120
PVFDIKAVSI SPTNVILTWK SNDTAASEYK YVVKHKMENE KTITVVHQPW CNITGLRPAT   180
SYVFSITPGI GNETWGDPRV IKVITEPIPV SDLRVALTGV RKAALSWSNG NGTASCRVLL   240
ESIGSHEELT QDSRLQVNIS GLKPGVQYNI NPYLLQSNKT KGDPLGTEGG LDASNTERSR   300
AGSPTAPVHD ESLVGPVDPS SGQQSRDTEV LLVGLEPGTR YNATVYSQAA NGTEGQPQAI   360
EFRTNAIQVF DVTAVNISAT SLTLIWKVSD NESSSNYTYK IHVAGETDSS NLNVSEPRAV   420
IPGLRSSTFY NITVCPVLGD IEGTPGFLQV HTPPVPVSDF RVTVVSTTEI GLAWSSHDAE   480
SFQMHITQEG AGNSRVEITT NQSIIIGGLF PGTKYCFEIV PKGPNGTEGA SRTVCNRTVP   540
SAVFDIHVVY VTTTEMWLDW KSPDGASEYV YHLVIESKHG SNHTSTYDKA ITLQGLIPGT   600
LYNITISPEV DHVWGDPNST AQYTRPSNVS NIDVSTNTTA ATLSWQNFDD ASPTYSYCLL   660
IEKAGNSSNA TQVVTDIGIT DATVTELIPG SSYTVEIFAQ VGDGIKSLEP GRKSFCTDPA   720
SMASFDCEVV PKEPALVLKW TCPPGANAGF ELEVSSGAWN NATHLESCSS ENGTEYRTEV   780
TYLNFSTSYN ISITTVSCGK MAAPTRNTCT TGITDPPPPD GSPNITSVSH NSVKVKFSGF   840
EASHGPIKAY AVILTTGEAG HPSADVLKYT YEDFKKGASD TYVTYLIRTE EKGRSQSLSE   900
VLKYEIDVGN ESTTLGYYNG KLEPLGSYRA CVAGFTNITF HPQNKGLIDG AESYVSFSRY   960
SDAVSLPQDP GVICGAVFGC IFGALVIVTV GGFIFWRKKR KDAKNNEVSF SQIKSLKRSK  1020
LIRVENFEAY FKKQQADSNC GFAEEYEDLK LVGISQPKYA AELAENRGKN RYNNVLPYDI  1080
SRVKLSVQTH STDDYINANY MPGYHSKKDF IATQGPLPNT LKDFWRMVWE KNVYAIIMLT  1140
KCVEQGRTKC EEYWPSKQAQ DYGDITVAMT SEIVLPEWTI RDFTVKNIQT SESHPLRQFH  1200
FTSWPDHGVP DTTDLLINFR YLVRDYMKQS PPESPILVHC SAGVGRTGTF IAIDRLIYQI  1260
ENENTVDVYG IVYDLRMHRP LMVQTEDQYV FLNQCVLDIV RSQKDSKVDL IYQNTTAMTI  1320
YENLAPVTTF GKTNGYIA                                                1338

SEQ ID NO: 400           moltype = AA   length = 1342
FEATURE                  Location/Qualifiers
source                   1..1342
                         mol_type = protein
                         organism = Homo sapiens
SEQUENCE: 400
MKPAAREARL PPRSPGLRWA LPLLLLLLRL GQILCAGGTP SPIPDPSVAT VATGENGITQ    60
ISSTAESFHK QNGTGTPQVE TNTSEDGESS GANDSLRTPE QGSNGTDGAS QKTPSSTGPS   120
PVFDIKAVSI SPTNVILTWK SNDTAASEYK YVVKHKMENE KTITVVHQPW CNITGLRPAT   180
SYVFSITPGI GNETWGDPRV IKVITEPIPV SDLRVALTGV RKAALSWSNG NGTASCRVLL   240
ESIGSHEELT QDSRLQVNIS GLKPGVQYNI NPYLLQSNKT KGDPLGTEGG LDASNTERSR   300
AGSPTAPVHD ESLVGPVDPS SGQQSRDTEV LLVGLEPGTR YNATVYSQAA NGTEGQPQAI   360
EFRTNAIQVF DVTAVNISAT SLTLIWKVSD NESSSNYTYK IHVAGETDSS NLNVSEPRAV   420
IPGLRSSTFY NITVCPVLGD IEGTPGFLQV HTPPVPVSDF RVTVVSTTEI GLAWSSHDAE   480
SFQMHITQEG AGNSRVEITT NQSIIIGGLF PGTKYCFEIV PKGPNGTEGA SRTVCNRTVP   540
SAVFDIHVVY VTTTEMWLDW KSPDGASEYV YHLVIESKHG SNHTSTYDKA ITLQGLIPGT   600
LYNITISPEV DHVWGDPNST AQYTRPSNVS NIDVSTNTTA ATLSWQNFDD ASPTYSYCLL   660
IEKAGNSSNA TQVVTDIGIT DATVTELIPG SSYTVEIFAQ VGDGIKSLEP GRKSFCTDPA   720
SMASFDCEVV PKEPALVLKW TCPPGANAGF ELEVSSGAWN NATHLESCSS ENGTEYRTEV   780
TYLNFSTSYN ISITTVSCGK MAAPTRNTCT TGITDPPPPD GSPNITSVSH NSVKVKFSGF   840
EASHGPIKAY AVILTTGEAG HPSADVLKYT YEDFKKGASD TYVTYLIRTE EKGRSQSLSE   900
VLKYEIDVGN ESTTLGYYNG KLEPLGSYRC LLRACVAGFT NITFHPQNKG LIDGAESYVS   960
FSRYSDAVSL PQDPGVICGA VFGCIFGALV IVTGGFIFW RKKRKDAKNN EVSFSQIKSL  1020
KRSKLIRVEN FEAYFKKQQA DSNCGFAEEY EDLKLVGISQ PKYAAELAEN RGKNRYNNVL  1080
PYDISRVKLS VQTHSTDDYI NANYMPGYHS KKDFIATQGP LPNTLKDFWR MVWEKNVYAI  1140
IMLTKCVEQG RTKCEEYWPS KQAQDYGDIT VAMTSEIVLP EWTIRDFTVK NIQTSESHPL  1200
RQFHFTSWPD HGVPDTTDLL INFRYLVRDY MKQSPPESPI LVHCSAGVGR TGTFIAIDRL  1260
IYQIENENTV DVYGIVYDLR MHRPLMVQTE DQYVFLNQCV LDIVRSQKDS KVDLIYQNTT  1320
AMTIYENLAP VTTFGKTNGY IA                                           1342

SEQ ID NO: 401           moltype = AA   length = 858
FEATURE                  Location/Qualifiers
source                   1..858
                         mol_type = protein
                         organism = Homo sapiens
SEQUENCE: 401
MLQTKDLIWT LFFLGTAVSL QVDIVPSQGE ISVGESKFFL CQVAGDAKDK DISWFSPNGE    60
KLTPNQQRIS VVWNDDSSST LTIYNANIDD AGIYKCVVTG EDGSESEATV NVKIFQKLMF   120
KNAPTPQEFR EGEDAVIVCD VVSSLPPTII WKHKGRDVIL KKDVRFIVLS NNYLQIRGIK   180
KTDEGTYRCE GRILARGEIN FKDIQVIVNV PPTIQARQNI VNATANLGQS VTLVCDAEGF   240
PEPTMSWTKD GEQIEQEEDD EKYIFSDDSS QLTIKKVDKN DEAEYICIAE NKAGEQDATI   300
HLKVFAKPKI TYVENQTAME LEEQVTLTCE ASGDPIPSIT WRTSTRNISS EEKASWTRPE   360
KQETLDGHMV VRSHARVSSL TLKSIQYTDA GEYICTASNT IGQDSQSMYL EVQYAPKLQG   420
PVAVYTWEGN QVNITCEVFA YPSATISWFR DGQLLPSSNI KIYNTPS ASYLEVTPDS   480
ENDFGNYNCT AVNRIGQESL EFILVQADTP SSPSIDQVEP YSSTAQVQFD EPEATGGVPI   540
```

```
LKYKAEWRAV GEEVWHSKWY DAKEASMEGI VTIVGLKPET TYAVRLAALN GKGLGEISAA   600
SEFKTQPVQG EPSAPKLEGQ MGEDGNSIKV NLIKQDDGGS PIRHYLVRYR ALSSEWKPEI   660
RLPSGSDHVM LKSLDWNAEY EVYVVAENQQ GKSKAAHFVF RTSAQPTAIP ANGSPTSGLS   720
TGAIVGILIV IFVLLLVVVD ITCYFLNKCG LFMCIAVNLC GKAGPGAKGK DMEEGKAAFS   780
KDESKEPIVE VRTEEERTPN HDGGKHTEPN ETTPLTEPEK GPVEAKPECQ ETETKPAPAE   840
VKTVPNDATQ TKENESKA                                                858

SEQ ID NO: 402          moltype = AA  length = 725
FEATURE                 Location/Qualifiers
source                  1..725
                        mol_type = protein
                        organism = Homo sapiens
SEQUENCE: 402
MLQTKDLIWT LFFLGTAVSL QVDIVPSQGE ISVGESKFFL CQVAGDAKDK DISWFSPNGE    60
KLTPNQQRIS VVWNDDSSST LTIYNANIDD AGIYKCVVTG EDGSESEATV NVKIFQKLMF   120
KNAPTPQEFR EGEDAVIVCD VVSSLPPTII WKHKGRDVIL KKDVRFIVLS NNYLQIRGIK   180
KTDEGTYRCE GRILARGEIN FKDIQVIVNV PPTIQARQNI VNATANLGQS VTLVCDAEGF   240
PEPTMSWTKD GEQIEQEEDD EKYIFSDDSS QLTIKKVDKN DEAEYICIAE NKAGEQDATI   300
HLKVFAKPKI TYVENQTAME LEEQVTLTCE ASGDPIPSIT WRTSTRNISS EEKTLDGHMV   360
VRSHARVSSL TLKSIQYTDA GEYICTASNT IGQDSQSMYL EVQYAPKLQG PVAVYTWEGN   420
QVNITCEVFA YPSATISWFR DGQLLPSSNY SNIKIYNTPS ASYLEVTPDS ENDFGNYNCT   480
AVNRIGQESL EFILVQADTP SSPSIDQVEP YSSTAQVQFD EPEATGGVPI LKYKAEWRAV   540
GEEVWHSKWY DAKEASMEGI VTIVGLKPET TYAVRLAALN GKGLGEISAA SEFKTQPVRE   600
PSAPKLEGQM GEDGNSIKVN LIKQDDGGSP IRHYLVRYRA LSSEWKPEIR LPSGSDHVML   660
KSLDWNAEYE VYVVAENQQG KSKAAHFVFR TSAQPTAIPA TLGGNSASYT FVSLLFSAVT   720
LLLLC                                                              725

SEQ ID NO: 403          moltype = AA  length = 84
FEATURE                 Location/Qualifiers
source                  1..84
                        mol_type = protein
                        organism = Homo sapiens
SEQUENCE: 403
XQDDGGSPIR HYLVRYRALS SEWKPEIRLP SGSDHVMLKS LDWNAEYEVY VVAENQQGKS    60
KAAHFVFRTS AQPTAIPVTL LLLC                                          84

SEQ ID NO: 404          moltype = AA  length = 305
FEATURE                 Location/Qualifiers
source                  1..305
                        mol_type = protein
                        organism = Homo sapiens
SEQUENCE: 404
YNTPSASYLE VTPDSENDFG NYNCTAVNRI GQESLEFILV QADTPSSPSI DQVEPYSSTA    60
QVQFDEPEAT GGVPILKYKA EWRAVGEEVW HSKWYDAKEA SMEGIVTIVG LKPETTYAVR   120
LAALNGKGLG EISAASEFKT QPVHSPPPPA SASSSTPVPL SPPDTTWPLP ALATTEPARE   180
PSAPKLEGQM GEDGNSIKVN LIKQDDGGSP IRHYLVRYRA LSSEWKPEIR LPSGSDHVML   240
KSLDWNAEYE VYVVAENQQG KSKAAHFVFR TSAQPTAIPA TLGGNSASYT FVSLLFSAVT   300
LLLLC                                                              305

SEQ ID NO: 405          moltype = AA  length = 468
FEATURE                 Location/Qualifiers
source                  1..468
                        mol_type = protein
                        organism = Homo sapiens
SEQUENCE: 405
XSGSDHVMLK SLDWNAEYEV YVVAENQQGK SKAAHFVFRT SAQPTAIPAN GSPTSGLSTG    60
AIVGILIVIF VLLLVVVDIT CYFLNKCGLF MCIAVNLCGK AGPGAKGKDM EEGKAAFSKD   120
ESKEPIVEVR TEEERTPNHD GGKHTEPNET TPLTEPELPA DTTATVEDML PSVTTVTTNS   180
DTITETFATA QNSPTSETTT LTSSIAPPAT ATPDSNSVPA GQATPSKGPS ASAPSPAPAS   240
APKVAPLVDL SDTPTSTPAA SNLSSSVLAN QGAVLSPSAP AGVGEASKAP PASKPTPAPV   300
PTPTGAASPL AAAAAPATEA PQAKQEAPST KGPDPEPTQP GAAKSPAEAA TALASPKSEA   360
ASVSTTNPSQ GEDFKMDEGN FKTPDIDLAK DVFAALGSPA PAAGASGQAP ELAPSTADSS   420
VSPAPAKTEK GPVEAKPECQ ETETKPAPAE VKTVPNDATQ TKENESKA                468

SEQ ID NO: 406          moltype = AA  length = 372
FEATURE                 Location/Qualifiers
source                  1..372
                        mol_type = protein
                        organism = Homo sapiens
SEQUENCE: 406
XTPSSPSIDQ VEPYSSTAQV QFDEPEATGG VPILKYKAEW RAVGEEVWHS KWYDAKEASM    60
EGIVTIVGLK PETTYAVRLA ALNGKGLGEI SAASEFKTQP VHSPPPPASA SSSTPVPLSP   120
PDKGEPSAPK LEGQMGEDGN SIKVNLIKQD DGGSPIRHYL VRYRALSSEW KPEIRLPSGS   180
DHVMLKSLDW NAEYEVYVVA ENQQGKSKAA HFVFRTSAQP TAIPANGSPT SGLSTGAIVG   240
ILIVIFVLLL VVVDITCYFL NKCGLFMCIA VNLCGKAGPG AKGKDMEEGK AAFSKDESKE   300
PIVEVRTEEE RTPNHDGGKH TEPNETTPLT EPEKGPVEAK PECQETETKP APAEVKTVPN   360
DATQTKENES KA                                                      372

SEQ ID NO: 407          moltype = AA  length = 364
```

```
FEATURE             Location/Qualifiers
source              1..364
                    mol_type = protein
                    organism = Homo sapiens
SEQUENCE: 407
MLQTKDLIWT LFFLGTAVSL QVDIVPSQGE ISVGESKFFL CQVAGDAKDK DISWFSPNGE    60
KLTPNQQRIS VVWNDDSSST LTIYNANIDD AGIYKCVVTG EDGSESEATV NVKIFQKLMF   120
KNAPTPQEFR EGEDAVIVCD VVSSLPPTII WKHKGRDVIL KKDVRFIVLS NNYLQIRGIK   180
KTDEGTYRCE GRILARGEIN FKDIQVIVNV PPTIQARQNI VNATANLGQS VTLVCDAEGF   240
PEPTMSWTKD GEQIEQEEDD EKYIFSDDSS QLTIKKVDKN DEAEYICIAE NKAGEQDATI   300
HLKVFAKPKI TYVENQTAME LEEQVTLTCE ASGDPIPSIT WRTSTRNISS EEKASWTRPE   360
KQEV                                                                364

SEQ ID NO: 408      moltype = AA  length = 848
FEATURE             Location/Qualifiers
source              1..848
                    mol_type = protein
                    organism = Homo sapiens
SEQUENCE: 408
MLQTKDLIWT LFFLGTAVSL QVDIVPSQGE ISVGESKFFL CQVAGDAKDK DISWFSPNGE    60
KLTPNQQRIS VVWNDDSSST LTIYNANIDD AGIYKCVVTG EDGSESEATV NVKIFQKLMF   120
KNAPTPQEFR EGEDAVIVCD VVSSLPPTII WKHKGRDVIL KKDVRFIVLS NNYLQIRGIK   180
KTDEGTYRCE GRILARGEIN FKDIQVIVNV PPTIQARQNI VNATANLGQS VTLVCDAEGF   240
PEPTMSWTKD GEQIEQEEDD EKYIFSDDSS QLTIKKVDKN DEAEYICIAE NKAGEQDATI   300
HLKVFAKPKI TYVENQTAME LEEQVTLTCE ASGDPIPSIT WRTSTRNISS EEKTLDGHMV   360
VRSHARVSSL TLKSIQYTDA GEYICTASNT IGQDSQSMYL EVQYAPKLQG PVAVYTWEGN   420
QVNITCEVFA YPSATISWFR DGQLLPSSNY SNIKIYNTPS ASYLEVTPDS ENDFGNYNCT   480
AVNRIGQESL EFILVQADTP SSPSIDQVEP YSSTAQVQFD EPEATGGVPI LKYKAEWRAV   540
GEEVWHSKWY DAKEASMEGI VTIVGLKPET TYAVRLAALN GKGLGEISAA SEFKTQPVQG   600
EPSAPKLEGQ MGEDGNSIKV NLIKQDDGGS PIRHYLVRYR ALSSEWKPEI RLPSGSDHVM   660
LKSLDWNAEY EVYVVAENQQ GKSKAAHFVF RTSAQPTAIP ANGSPTSGLS TGAIVGILIV   720
IFVLLLVVVD ITCYFLNKCG LFMCIAVNLC GKAGPGAKGK DMEEGKAAFS KDESKEPIVE   780
VRTEEERTPN HDGGKHTEPN ETTPLTEPEK GPVEAKPECQ ETETKPAPAE VKTVPNDATQ   840
TKENESKA                                                            848

SEQ ID NO: 409      moltype = AA  length = 165
FEATURE             Location/Qualifiers
source              1..165
                    mol_type = protein
                    organism = Homo sapiens
SEQUENCE: 409
EFILVQADTP SSPSIDQVEP YSSTAQVQFD EPEATGGVPI LKYKAEWRAV GEEVWHSKWY    60
DAKEASMEGI VTIVGLKPET TYAVRLAALN GKGLGEISAA SEFKTQPVHS PPPPASASSS   120
TPVPLSPPDT TWPLPALATT EPAKNIAQNH CCNMFQAGLH NALMK                   165

SEQ ID NO: 410      moltype = AA  length = 357
FEATURE             Location/Qualifiers
source              1..357
                    mol_type = protein
                    organism = Homo sapiens
SEQUENCE: 410
XFILVQADTP SSPSIDQVEP YSSTAQVQFD EPEATGGVPI LKYKAEWRAV GEEVWHSKWY    60
DAKEASMEGI VTIVGLKPET TYAVRLAALN GKGLGEISAA SEFKTQPVRE PSAPKLEGQM   120
GEDGNSIKVN LIKQDDGGSP IRHYLVRYRA LSSEWKPEIR LPSGSDHVML KSLDWNAEYE   180
VYVVAENQQG KSKAAHFVFR TSAQPTAIPA NGSPTSGLST GAIVGILIVI FVLLLVVVDI   240
TCYFLNKCGL FMCIAVNLCG KAGPGAKGKD MEEGKAAFSK DESKEPIVEV RTEEERTPNH   300
DGGKHTEPNE TTPLTEPEKG PVEAKPECQE TETKPAPAEV KTVPNDATQT KENESKA      357

SEQ ID NO: 411      moltype = AA  length = 133
FEATURE             Location/Qualifiers
source              1..133
                    mol_type = protein
                    organism = Homo sapiens
SEQUENCE: 411
MLQTKDLIWT LFFLGTAAKP KITYVENQTA MELEEQVTLT CEASGDPIPS ITWRTSTRNI    60
SSEEKTLDGH MVVRSHARVS SLTLKSIQYT DAGEYICTAS NTIGQDSQSM YLEVQYAPKL   120
QGPVAVYTWE GNQ                                                      133

SEQ ID NO: 412      moltype = AA  length = 858
FEATURE             Location/Qualifiers
source              1..858
                    mol_type = protein
                    organism = Homo sapiens
SEQUENCE: 412
MLQTKDLIWT LFFLGTAVSL QVDIVPSQGE ISVGESKFFL CQVAGDAKDK DISWFSPNGE    60
KLTPNQQRIS VVWNDDSSST LTIYNANIDD AGIYKCVVTG EDGSESEATV NVKIFQKLMF   120
KNAPTPQEFR EGEDAVIVCD VVSSLPPTII WKHKGRDVIL KKDVRFIVLS NNYLQIRGIK   180
KTDEGTYRCE GRILARGEIN FKDIQVIVNV PPTIQARQNI VNATANLGQS VTLVCDAEGF   240
PEPTMSWTKD GEQIEQEEDD EKYIFSDDSS QLTIKKVDKN DEAEYICIAE NKAGEQDATI   300
```

```
HLKVFAKPKI TYVENQTAME LEEQVTLTCE ASGDPIPSIT WRTSTRNISS EEKASWTRPE    360
KQETLDGHMV VRSHARVSSL TLKSIQYTDA GEYICTASNT IGQDSQSMYL EVQYAPKLQG    420
PVAVYTWEGN QVNITCEVFA YPSATISWFR DGQLLPSSNY SNIKIYNTPS ASYLEVTPDS    480
ENDFGNYNCT AVNRIGQESL EFILVQADTP SSPSIDQVEP YSSTAQVQFD EPEATGGVPI    540
LKYKAEWRAV GEEVWHSKWY DAKEASMEGI VTIVGLKPET TYAVRLAALN GKGLGEISAA    600
SEFKTQPVPG EPSAPKLEGQ MGEDGNSIKV NLIKQDDGGS PIRHYLVRYR ALSSEWKPEI    660
RLPSGSDHVM LKSLDWNAEY EVYVVAENQQ GKSKAAHFVF RTSAQPTAIP ANGSPTSGLS    720
TGAIVGILIV IFVLLLVVVD ITCYFLNKCG LFMCIAVNLC GKAGPGAKGK DMEEGKAAFS    780
KDESKEPIVE VRTEEERTPN HDGGKHTEPN ETTPLTEPEK GPVEAKPECQ ETETKPAPAE    840
VKTVPNDATQ TKENESKA                                                  858

SEQ ID NO: 413          moltype = AA  length = 884
FEATURE                 Location/Qualifiers
source                  1..884
                        mol_type = protein
                        organism = Homo sapiens
SEQUENCE: 413
MLQTKDLIWT LFFLGTAVSL QVDIVPSQGE ISVGESKFFL CQVAGDAKDK DISWFSPNGE     60
KLTPNQQRIS VVWNDDSSST LTIYNANIDD AGIYKCVVTG EDGSESEATV NVKIFQKLMF    120
KNAPTPQEFR EGEDAVIVCD VVSSLPPTII WKHKGRDVIL KKDVRFIVLS NNYLQIRGIK    180
KTDEGTYRCE GRILARGEIN FKDIQVIVNV PPTIQARQNI VNATANLGQS VTLVCDAEGF    240
PEPTMSWTKD GEQIEQEEDD EKYIFSDDSS QLTIKKVDKN DEAEYICIAE NKAGEQDATI    300
HLKVFAKPKI TYVENQTAME LEEQVTLTCE ASGDPIPSIT WRTSTRNISS EEKASWTRPE    360
KQEVHAPWNW QVGRQKGQAG SAGFPGSHET LDGHMVVRSH ARVSSLTLKS IQYTDAGEYI    420
CTASNTIGQD SQSMYLEVQY APKLQGPVAV YTWEGNQVNI TCEVFAYPSA TISWFRDGQL    480
LPSSNYSNIK IYNTPSASYL EVTPDSENDF GNYNCTAVNR IGQESLEFIL VQADTPSSPS    540
IDQVEPYSST AQVQFDEPEA TGGVPILKYK AEWRAVGEEV WHSKWYDAKE ASMEGIVTIV    600
GLKPETTYAV RLAALNGKGL GEISAASEFK TQPVPGEPSA PKLEGQMGED GNSIKVNLIK    660
QDDGGSPIRH YLVRYRALSS EWKPEIRLPS GSDHVMLKSL DWNAEYEVYV VAENQQGKSK    720
AAHFVFRTSA QPTAIPANGS PTSGLSTGAI VGILIVIFVL LLVVVDITCY FLNKCGLFMC    780
IAVNLCGKAG PGAKGKDMEE GKAAFSKDES KEPIVEVRTE EERTPNHDGG KHTEPNETTP    840
LTEPEKGPVE AKPECQETET KPAPAEVKTV PNDATQTKEN ESKA                    884

SEQ ID NO: 414          moltype = AA  length = 848
FEATURE                 Location/Qualifiers
source                  1..848
                        mol_type = protein
                        organism = Homo sapiens
SEQUENCE: 414
MLQTKDLIWT LFFLGTAVSL QVDIVPSQGE ISVGESKFFL CQVAGDAKDK DISWFSPNGE     60
KLTPNQQRIS VVWNDDSSST LTIYNANIDD AGIYKCVVTG EDGSESEATV NVKIFQKLMF    120
KNAPTPQEFR EGEDAVIVCD VVSSLPPTII WKHKGRDVIL KKDVRFIVLS NNYLQIRGIK    180
KTDEGTYRCE GRILARGEIN FKDIQVIVNV PPTIQARQNI VNATANLGQS VTLVCDAEGF    240
PEPTMSWTKD GEQIEQEEDD EKYIFSDDSS QLTIKKVDKN DEAEYICIAE NKAGEQDATI    300
HLKVFAKPKI TYVENQTAME LEEQVTLTCE ASGDPIPSIT WRTSTRNISS EEKTLDGHMV    360
VRSHARVSSL TLKSIQYTDA GEYICTASNT IGQDSQSMYL EVQYAPKLQG PVAVYTWEGN    420
QVNITCEVFA YPSATISWFR DGQLLPSSNY SNIKIYNTPS ASYLEVTPDS ENDFGNYNCT    480
AVNRIGQESL EFILVQADTP SSPSIDQVEP YSSTAQVQFD EPEATGGVPI LKYKAEWRAV    540
GEEVWHSKWY DAKEASMEGI VTIVGLKPET TYAVRLAALN GKGLGEISAA SEFKTQPVPG    600
EPSAPKLEGQ MGEDGNSIKV NLIKQDDGGS PIRHYLVRYR ALSSEWKPEI RLPSGSDHVM    660
LKSLDWNAEY EVYVVAENQQ GKSKAAHFVF RTSAQPTAIP ANGSPTSGLS TGAIVGILIV    720
IFVLLLVVVD ITCYFLNKCG LFMCIAVNLC GKAGPGAKGK DMEEGKAAFS KDESKEPIVE    780
VRTEEERTPN HDGGKHTEPN ETTPLTEPEK GPVEAKPECQ ETETKPAPAE VKTVPNDATQ    840
TKENESKA                                                             848

SEQ ID NO: 415          moltype = AA  length = 884
FEATURE                 Location/Qualifiers
source                  1..884
                        mol_type = protein
                        organism = Homo sapiens
SEQUENCE: 415
MLQTKDLIWT LFFLGTAVSL QVDIVPSQGE ISVGESKFFL CQVAGDAKDK DISWFSPNGE     60
KLTPNQQRIS VVWNDDSSST LTIYNANIDD AGIYKCVVTG EDGSESEATV NVKIFQKLMF    120
KNAPTPQEFR EGEDAVIVCD VVSSLPPTII WKHKGRDVIL KKDVRFIVLS NNYLQIRGIK    180
KTDEGTYRCE GRILARGEIN FKDIQVIVNV PPTIQARQNI VNATANLGQS VTLVCDAEGF    240
PEPTMSWTKD GEQIEQEEDD EKYIFSDDSS QLTIKKVDKN DEAEYICIAE NKAGEQDATI    300
HLKVFAKPKI TYVENQTAME LEEQVTLTCE ASGDPIPSIT WRTSTRNISS EEKASWTRPE    360
KQEVHAPWNW QVGRQKGQAG SAGFPGSHET LDGHMVVRSH ARVSSLTLKS IQYTDAGEYI    420
CTASNTIGQD SQSMYLEVQY APKLQGPVAV YTWEGNQVNI TCEVFAYPSA TISWFRDGQL    480
LPSSNYSNIK IYNTPSASYL EVTPDSENDF GNYNCTAVNR IGQESLEFIL VQADTPSSPS    540
IDQVEPYSST AQVQFDEPEA TGGVPILKYK AEWRAVGEEV WHSKWYDAKE ASMEGIVTIV    600
GLKPETTYAV RLAALNGKGL GEISAASEFK TQPVQGEPSA PKLEGQMGED GNSIKVNLIK    660
QDDGGSPIRH YLVRYRALSS EWKPEIRLPS GSDHVMLKSL DWNAEYEVYV VAENQQGKSK    720
AAHFVFRTSA QPTAIPANGS PTSGLSTGAI VGILIVIFVL LLVVVDITCY FLNKCGLFMC    780
IAVNLCGKAG PGAKGKDMEE GKAAFSKDES KEPIVEVRTE EERTPNHDGG KHTEPNETTP    840
LTEPEKGPVE AKPECQETET KPAPAEVKTV PNDATQTKEN ESKA                    884

SEQ ID NO: 416          moltype = AA  length = 136
FEATURE                 Location/Qualifiers
```

```
source                    1..136
                          mol_type = protein
                          organism = Homo sapiens
SEQUENCE: 416
MLQTKDLIWT LFFLGTAGEP SAPKLEGQMG EDGNSIKVNL IKQDDGGSPI RHYLVRYRAL    60
SSEWKPEIRL PSGSDHVMLK SLDWNAEYEV YVVAENQQGK SKAAHFVFRT SAQPTAIPAN   120
GSPTSGLSTG AIVGIL                                                   136

SEQ ID NO: 417            moltype = AA  length = 726
FEATURE                   Location/Qualifiers
source                    1..726
                          mol_type = protein
                          organism = Homo sapiens
SEQUENCE: 417
MLQTKDLIWT LFFLGTAVSL QVDIVPSQGE ISVGESKFFL CQVAGDAKDK DISWFSPNGE    60
KLTPNQQRIS VVWNDDSSST LTIYNANIDD AGIYKCVVTG EDGSESEATV NVKIFQKLMF   120
KNAPTPQEFR EGEDAVIVCD VVSSLPPTII WKHKGRDVIL KKDVRFIVLS NNYLQIRGIK   180
KTDEGTYRCE GRILARGEIN FKDIQVIVNV PPTIQARQNI VNATANLGQS VTLVCDAEGF   240
PEPTMSWTKD GEQIEQEEDD EKYIFSDDSS QLTIKKVDKN DEAEYICIAE NKAGEQDATI   300
HLKVFAKPKI TYVENQTAME LEEQVTLTCE ASGDPIPSIT WRTSTRNISS EEKTLDGHMV   360
VRSHARVSSL TLKSIQYTDA GEYICTASNT IGQDSQSMYL EVQYAPKLQG PVAVYTWEGN   420
QVNITCEVFA YPSATISWFR DGQLLPSSNY SNIKIYNTPS ASYLEVTPDS ENDFGNYNCT   480
AVNRIGQESL EFILVQADTP SSPSIDQVEP YSSTAQVQFD EPEATGGVPI LKYKAEWRAV   540
GEEVWHSKWY DAKEASMEGI VTIVGLKPET TYAVRLAALN GKGLGEISAA SEFKTQPVQG   600
EPSAPKLEGQ MGEDGNSIKV NLIKQDDGGS PIRHYLVRYR ALSSEWKPEI RLPSGSDHVM   660
LKSLDWNAEY EVYVVAENQQ GKSKAAHFVF RTSAQPTAIP ATLGGNSASY TFVSLLFSAV   720
TLLLLC                                                              726

SEQ ID NO: 418            moltype = AA  length = 761
FEATURE                   Location/Qualifiers
source                    1..761
                          mol_type = protein
                          organism = Homo sapiens
SEQUENCE: 418
MLQTKDLIWT LFFLGTAVSL QVDIVPSQGE ISVGESKFFL CQVAGDAKDK DISWFSPNGE    60
KLTPNQQRIS VVWNDDSSST LTIYNANIDD AGIYKCVVTG EDGSESEATV NVKIFQKLMF   120
KNAPTPQEFR EGEDAVIVCD VVSSLPPTII WKHKGRDVIL KKDVRFIVLS NNYLQIRGIK   180
KTDEGTYRCE GRILARGEIN FKDIQVIVNV PPTIQARQNI VNATANLGQS VTLVCDAEGF   240
PEPTMSWTKD GEQIEQEEDD EKYIFSDDSS QLTIKKVDKN DEAEYICIAE NKAGEQDATI   300
HLKVFAKPKI TYVENQTAME LEEQVTLTCE ASGDPIPSIT WRTSTRNISS EEKTLDGHMV   360
VRSHARVSSL TLKSIQYTDA GEYICTASNT IGQDSQSMYL EVQYAPKLQG PVAVYTWEGN   420
QVNITCEVFA YPSATISWFR DGQLLPSSNY SNIKIYNTPS ASYLEVTPDS ENDFGNYNCT   480
AVNRIGQESL EFILVQADTP SSPSIDQVEP YSSTAQVQFD EPEATGGVPI LKYKAEWRAV   540
GEEVWHSKWY DAKEASMEGI VTIVGLKPET TYAVRLAALN GKGLGEISAA SEFKTQPVHS   600
PPPPASASSS TPVPLSPPDT TWPLPALATT EPATGEPSAP KLEGQMGEDG NSIKVNLIKQ   660
DDGGSPIRHY LVRYRALSSE WKPEIRLPSG SDHVMLKSLD WNAEYEVYVV AENQQGKSKA   720
AHFVFRTSAQ PTAIPATLGG NSASYTFVSL LFSAVTLLLL C                       761

SEQ ID NO: 419            moltype = AA  length = 761
FEATURE                   Location/Qualifiers
source                    1..761
                          mol_type = protein
                          organism = Homo sapiens
SEQUENCE: 419
MLQTKDLIWT LFFLGTAVSL QVDIVPSQGE ISVGESKFFL CQVAGDAKDK DISWFSPNGE    60
KLTPNQQRIS VVWNDDSSST LTIYNANIDD AGIYKCVVTG EDGSESEATV NVKIFQKLMF   120
KNAPTPQEFR EGEDAVIVCD VVSSLPPTII WKHKGRDVIL KKDVRFIVLS NNYLQIRGIK   180
KTDEGTYRCE GRILARGEIN FKDIQVIVNV PPTIQARQNI VNATANLGQS VTLVCDAEGF   240
PEPTMSWTKD GEQIEQEEDD EKYIFSDDSS QLTIKKVDKN DEAEYICIAE NKAGEQDATI   300
HLKVFAKPKI TYVENQTAME LEEQVTLTCE ASGDPIPSIT WRTSTRNISS EEKTLDGHMV   360
VRSHARVSSL TLKSIQYTDA GEYICTASNT IGQDSQSMYL EVQYAPKLQG PVAVYTWEGN   420
QVNITCEVFA YPSATISWFR DGQLLPSSNY SNIKIYNTPS ASYLEVTPDS ENDFGNYNCT   480
AVNRIGQESL EFILVQADTP SSPSIDQVEP YSSTAQVQFD EPEATGGVPI LKYKAEWRAV   540
GEEVWHSKWY DAKEASMEGI VTIVGLKPET TYAVRLAALN GKGLGEISAA SEFKTQPVHS   600
PPPPASASSS TPVPLSPPDT TWPLPALATT EPAKGEPSAP KLEGQMGEDG NSIKVNLIKQ   660
DDGGSPIRHY LVRYRALSSE WKPEIRLPSG SDHVMLKSLD WNAEYEVYVV AENQQGKSKA   720
AHFVFRTSAQ PTAIPATLGG NSASYTFVSL LFSAVTLLLL C                       761

SEQ ID NO: 420            moltype = AA  length = 88
FEATURE                   Location/Qualifiers
source                    1..88
                          mol_type = protein
                          organism = Homo sapiens
SEQUENCE: 420
MSDILRELLC VSEKAANIAR ACRQQEALFQ LLIEEKKEGE KNKKFAVDFK TLADVLVQEV    60
IKQNMENKFP GLEKNIFGEE SNEFTNDW                                       88

SEQ ID NO: 421            moltype = AA  length = 190
FEATURE                   Location/Qualifiers
```

| | | |
|---|---|---|
| source | 1..190<br>mol_type = protein<br>organism = Homo sapiens | |
| SEQUENCE: 421 | | |

```
MSDILRELLC VSEKAANIAR ACRQQEALFQ LLIEEKKEGE KNKKFAVDFK TLADVLVQEV   60
IKQNMENKFP GLEKNIFGEE SNEFTNDWGE KITLRLCSTE EETAELLSKV LNGNKVASEA  120
LARVVHQDVA FTDPTLDSTE INVPQDILGI WVDPIDSTYQ YIKGSADIKS NQGIFPCGLQ  180
CVTILIGVYD                                                        190
```

| | | |
|---|---|---|
| SEQ ID NO: 422 | moltype = AA length = 30 | |
| FEATURE | Location/Qualifiers | |
| source | 1..30<br>mol_type = protein<br>organism = Homo sapiens | |
| SEQUENCE: 422 | | |

```
MSDILRELLC VSEKAANIAR ACRQQEALFQ                                   30
```

| | | |
|---|---|---|
| SEQ ID NO: 423 | moltype = AA length = 68 | |
| FEATURE | Location/Qualifiers | |
| source | 1..68<br>mol_type = protein<br>organism = Homo sapiens | |
| SEQUENCE: 423 | | |

```
MSDILRELLC VSEKAANIAR ACRQQEALFQ LLIEEKKEGE KNKKFAVDFK TLADVLVQEV   60
IKQNMENK                                                           68
```

| | | |
|---|---|---|
| SEQ ID NO: 424 | moltype = AA length = 831 | |
| FEATURE | Location/Qualifiers | |
| source | 1..831<br>mol_type = protein<br>organism = Homo sapiens | |
| SEQUENCE: 424 | | |

```
MSKKGRSKGE KPEMETDAVQ MANEELRAKL TSIQIEFQQE KSKVGKLRER LQEAKLEREQ   60
EQRRHTAYIS ELKAKLHEEK TKELQALREG LIRQHEQEAA RTAKIKEGEL QRLQATLNVL  120
RDGAADKVKT ALLTEAREEA RRAFDGERLR LQQEILELKA ARKQAEEALS NCMQADKTKA  180
ADLRAAYQAH QDEVHRIKRE CERDIRRLMD EIKGKDRVIL ALEKELGVQA GQTQKLLLQK  240
EALDEQLVQV KEAERHHSSP KRELPPGIGD MVELMGVQDQ HMDERDVRRF QLKIAELNSV  300
IRKLEDRNTL LADERNELLK RSRETEVQLK PLVEKNKRMN KKNEDLLQSI QRMEEKIKNL  360
TRENVEMKEK LSAQASLKRH TSLNDLSLTR DEQEIEFLRL QVLEQQHVID DLSLERERLL  420
RSKRHRGKSL KPPPKHVVET FFGFDEESVD SETLSETSYN TDRTDRTPAT PEEDLDDATA  480
REEADLRFCQ LTREYQALQR AYALLQEQVG GTLDAEREAR TREQLQADLL RCQAKIEDLE  540
KLLVEKGQDS KWVEEKQLLI RTNQDLLEKI YRLEMEENQL KNEMQDAKDQ NELLEFRVLE  600
LEERERRSPA FNLQITTFPE NHSSALQLFC HQEGVKDVNV SELMKKLDIL GDNGNLRNEE  660
QVAIIQAGTV LALCEKWLKQ IEGTEAALTQ KMLDLEKEKD LFSRQKGYLE EELDYRKQAL  720
DQAYLKIQDL EATLYTALQQ EPGRRAGEAL SEGQREDLQA AVEKVRRQIL RQSREFDSQI  780
LRERMELLQQ AQQRIRELED KLEFQKRHLK ELEEKFLFLF LFFSLAFILW P           831
```

| | | |
|---|---|---|
| SEQ ID NO: 425 | moltype = AA length = 646 | |
| FEATURE | Location/Qualifiers | |
| source | 1..646<br>mol_type = protein<br>organism = Homo sapiens | |
| SEQUENCE: 425 | | |

```
MSKKGRSKGE KPEMETDAVQ MANEELRAKL TSIQIEFQQE KSKMDEIKGK DRVILALEKE   60
LGVQAGQTQK LLLQKEALDE QLVQVKEAER HHSSPKRELP PGIGDMVELM GVQDQHMDER  120
DVRRFQLKIA ELNSVIRKLE DRNTLLADER NELLKRSRET EVQLKPLVEK NKRMNKKNED  180
LLQSIQRMEE KIKNLTRENV EMKEKLSAQA SLKRHTSLND LSLTRDEQEI EFLRLQVLEQ  240
QHVIDDLSLK HVVETFFGFD EESVDSETLS ETSYNTDRTD RTPATPEEDL DDATAREEAD  300
LRFCQLTREY QALQRAYALL QEQVGGTLDA EREARTREQL QADLLRCQAK IEDLEKLLVE  360
KGQDSKWVEE KQLLIRTNQD LLEKIYRLEM EENQLKNEMQ DAKDQNELLE FRVLELEERE  420
RRSPAFNLQI TTFPENHSSA LQLFCHQEGV KDVNVSELMK KLDILGDNGN LRNEEQVAII  480
QAGTVLALCE KWLKQIEGTE AALTQKMLDL EKEKDLFSRQ KGYLEEELDY RKQALDQAYL  540
KIQDLEATLY TALQQEPGRR AGEALSEGQR EDLQAAVEKV RRQILRQSRE FDSQILRERM  600
ELLQQAQQRI RELEDKLEFQ KRHLKELEEK FLFLFLFFSL AFILWP                 646
```

| | | |
|---|---|---|
| SEQ ID NO: 426 | moltype = AA length = 66 | |
| FEATURE | Location/Qualifiers | |
| source | 1..66<br>mol_type = protein<br>organism = Homo sapiens | |
| SEQUENCE: 426 | | |

```
MAAIRKKLVI VGDGACGKTC LLIVFSKDQF PEVYVPTVFE NYIADIEVDG KQTGSVTWAE   60
SLCLWV                                                             66
```

| | | |
|---|---|---|
| SEQ ID NO: 427 | moltype = AA length = 66 | |
| FEATURE | Location/Qualifiers | |
| source | 1..66<br>mol_type = protein<br>organism = Homo sapiens | |

```
SEQUENCE: 427
MAAIRKKLVI VGDGACGKTC LLIVFSKDQF PEVYVPTVFE NYIADIEVDG KQTGSVTWAE   60
SLCLWV                                                              66

SEQ ID NO: 428         moltype = AA   length = 66
FEATURE                Location/Qualifiers
source                 1..66
                       mol_type = protein
                       organism = Homo sapiens
SEQUENCE: 428
MAAIRKKLVI VGDGACGKTC LLIVFSKDQF PEVYVPTVFE NYIADIEVDG KQTGSVTWAE   60
SLCLWV                                                              66

SEQ ID NO: 429         moltype = AA   length = 500
FEATURE                Location/Qualifiers
source                 1..500
                       mol_type = protein
                       organism = Homo sapiens
SEQUENCE: 429
MPPAVGGPVG YTPPDGGWGW AVVIGAFISI GFSYAFPKSI TVFFKEIEGI FHATTSEVSW   60
ISSIMLAVMY GGGPISSILV NKYGSRIVMI VGGCLSGCGL IAASFCNTVQ QLYVCIGVIG  120
GLGLAFNLNP ALTMIGKYFY KRRPLANGLA MAGSPVFLCT LAPLNQVFFG IFGWRGSFLI  180
LGGLLLNCCV AGALMRPIGP KPTKAGKDKS KASLEKAGKS GVKKDLHDAN TDLIGRHPKQ  240
EKRSVFQTIN QFLDLTLFTH RGFLLYLSGN VIMFFGLFAP LVFLSSYGKS QHYSSEKSAF  300
LLSILAFVDM VARPSMGLVA NTKPIRPRIQ YFFAASVVAN GVCHMLAPLS TTYVGFCVYA  360
GFFGFAFGWL SSVLFETLMD LVGPQRFSSA VGLVTIVECC PVLLGPPLLG RLNDMYGDYK  420
YTYWACGVVL IISGIYLFIG MGINYRLLAK EQKANEQKKE SKEEETSIDV AGKPNEVTKA  480
AESPDQKDTD GGPKEEESPV                                              500

SEQ ID NO: 430         moltype = AA   length = 215
FEATURE                Location/Qualifiers
source                 1..215
                       mol_type = protein
                       organism = Homo sapiens
SEQUENCE: 430
MPPAVGGPVG YTPPDGGWGW AVVIGAFISI GFSYAFPKSI TVFFKEIEGI FHATTSEVSW   60
ISSIMLAVMY GGGPISSILV NKYGSRIVMI VGGCLSGCGL IAASFCNTVQ QLYVCIGVIG  120
GLGLAFNLNP ALTMIGKYFY KRRPLANGLA MAGSPVFLCT LAPLNQVFFG IFGWRGSFLI  180
LGGLLLNCCV AGALMRPIGP KPTKAGKDKS KASLE                             215

SEQ ID NO: 431         moltype = AA   length = 296
FEATURE                Location/Qualifiers
source                 1..296
                       mol_type = protein
                       organism = Homo sapiens
SEQUENCE: 431
MPPAVGGPVG YTPPDGGWGW AVVIGAFISI GFSYAFPKSI TVFFKEIEGI FHATTSEVSW   60
ISSIMLAVMY GGGPISSILV NKYGSRIVMI VGGCLSGCGL IAASFCNTVQ QLYVCIGVIG  120
GLGLAFNLNP ALTMIGKYFY KRRPLANGLA MAGSPVFLCT LAPLNQVFFG IFGWRGSFLI  180
LGGLLLNCCV AGALMRPIGP KPTKAGKDKS KASLEKAGKS GVKKDLHDAN TDLIGRHPKQ  240
EKRSVFQTIN QFLDLTLFTH RGFLLYLSGN VIMFFGLFAP LVFLSSYGKS QHYSSE      296

SEQ ID NO: 432         moltype = AA   length = 456
FEATURE                Location/Qualifiers
source                 1..456
                       mol_type = protein
                       organism = Homo sapiens
SEQUENCE: 432
MPPAVGGPVG YTPPDGGWGW AVVIGAFISI GFSYAFPKSI TVFFKEIEGI FHATTSEVSW   60
ISSIMLAVMY GGGPISSILV NKYGSRIVMI VGGCLSGCGL IAASFCNTVQ QLYVCIGVIG  120
GLGLAFNLNP ALTMIGKYFY KRRPLANGLA MAGSPVFLCT LAPLNQVFFG IFGWRGSFLI  180
LGGLLLNCCV AGALMRPIGP KPTKAGKDKS KASLEKAGKS GVKKDLHDAN TDLIGRHPKQ  240
EKRSVFQTIN QFLDLTLFTH RGFLLYLSGN VIMFFGLFAP LVFLSSYGKS QHYSSEKSAF  300
LLSILAFVDM VARPSMGLVA NTKPIRPRIQ YFFAASVVAN GVCHMLAPLS TTYVGFCVYA  360
GFFGFAFGWL SSVLFETLMD LVGPQRFSSA VGLVTIVECC PVLLGPPLLG RLNDMYGDYK  420
YTYWACGVVL IISGIYLFIG MGINYRLLAK EQKANE                            456

SEQ ID NO: 433         moltype = AA   length = 500
FEATURE                Location/Qualifiers
source                 1..500
                       mol_type = protein
                       organism = Homo sapiens
SEQUENCE: 433
MPPAVGGPVG YTPPDGGWGW AVVIGAFISI GFSYAFPKSI TVFFKEIEGI FHATTSEVSW   60
ISSIMLAVMY GGGPISSILV NKYGSRIVMI VGGCLSGCGL IAASFCNTVQ QLYVCIGVIG  120
GLGLAFNLNP ALTMIGKYFY KRRPLANGLA MAGSPVFLCT LAPLNQVFFG IFGWRGSFLI  180
LGGLLLNCCV AGALMRPIGP KPTKAGKDKS KASLEKAGKS GVKKDLHDAN TDLIGRHPKQ  240
EKRSVFQTIN QFLDLTLFTH RGFLLYLSGN VIMFFGLFAP LVFLSSYGKS QHYSSEKSAF  300
LLSILAFVDM VARPSMGLVA NTKPIRPRIQ YFFAASVVAN GVCHMLAPLS TTYVGFCVYA  360
```

```
GFFGFAFGWL  SSVLFETLMD  LVGPQRFSSA  VGLVTIVECC  PVLLGPPLLG  RLNDMYGDYK   420
YTYWACGVVL  IISGIYLFIG  MGINYRLLAK  EQKANEQKKE  SKEEETSIDV  AGKPNEVTKA   480
AESPDQKDTD  GGPKEEESPV                                                  500

SEQ ID NO: 434            moltype = AA   length = 109
FEATURE                   Location/Qualifiers
source                    1..109
                          mol_type = protein
                          organism = Homo sapiens
SEQUENCE: 434
MKFISTSLLL  MLLVSSLSPV  QGVLEVYYTS  LRCRCVQESS  VFIPRRFIDR  IQILPRGNGC    60
PRKEIIVWKK  NKSIVCVDPQ  AEWIQRMMEV  LRKRSSSTLP  VPVFKRKIP               109

SEQ ID NO: 435            moltype = AA   length = 729
FEATURE                   Location/Qualifiers
source                    1..729
                          mol_type = protein
                          organism = Homo sapiens
SEQUENCE: 435
MDDLTLLDLL  ECPVCFEKLD  VTAKVLPCQH  TFCKPCLQRV  FKAHKELRCP  ECRTPVFSNI    60
EALPANLLLV  RLLDGVRSGQ  SSGRGGSFRR  PGTMTLQDGR  KSRTNPRRLQ  ASPFRLVPNV   120
RIHMDGVPRA  KALCNYRGQN  PGDLRFNKGD  IILLRRQLDE  NWYQGEINGI  SGNFPASSVE   180
VIKQLPQPPP  LCRALYNFDL  RGKDKSENQD  CLTFLKDDII  TVISRVDENW  AEGKLGDKVG   240
IFPILFVEPN  LTARHLLEKN  KGRQSSRTKN  LSLVSSSSRG  NTSTLRRPG   SRRKVPGQFS   300
ITTALNTLNR  MVHSPSGRHM  VEISTPVLIS  SSNPSVITQP  MEKADVPSSC  VGQVSTYHPA   360
PVSPGHSTAV  VSLPGSQQHL  SANMFVALHS  YSAHGPDELD  LQKGEGVRVL  GKCQDGWLRG   420
VSLVTGRVGI  FPNNYVIPIF  RKTSSFPDSR  SPGLYTTWTL  STSSVSSQGS  ISEGDPRQSR   480
PPFKSVFVPTA IVNPVRSTAG  PGTLGQGSLR  KGRSSMRKNG  SLQRPLQSGI  PTLVVGSLRR   540
SPTMVLRPQQ  FQFYQPQGIP  SSPSAVVVEM  GSKPALTGEP  ALTCISRGSE  AWIHSAASSL   600
IMEDKEIPIK  SEPLPKPPAS  APPSILVKPE  NSRNGIEKQV  KTVRFQNYSP  PPTKHYTSHP   660
TSGKPEQPAT  LKASQPEAAS  LGPEMTVLFA  HRSGCHSGQQ  TDLRRKSALG  KATTLVSTAS   720
GTQTVFPSK                                                              729

SEQ ID NO: 436            moltype = AA   length = 729
FEATURE                   Location/Qualifiers
source                    1..729
                          mol_type = protein
                          organism = Homo sapiens
SEQUENCE: 436
MDDLTLLDLL  ECPVCFEKLD  VTAKVLPCQH  TFCKPCLQRV  FKAHKELRCP  ECRTPVFSNI    60
EALPANLLLV  RLLDGVRSGQ  SSGRGGSFRR  PGTMTLQDGR  KSRTNPRRLQ  ASPFRLVPNV   120
RIHMDGVPRA  KALCNYRGQN  PGDLRFNKGD  IILLRRQLDE  NWYQGEINGI  SGNFPASSVE   180
VIKQLPQPPP  LCRALYNFDL  RGKDKSENQD  CLTFLKDDII  TVISRVDENW  AEGKLGDKVG   240
IFPILFVEPN  LTARHLLEKN  KGRQSSRTKN  LSLVSSSSRG  NTSTLRRPG   SRRKVPGQFS   300
ITTALNTLNR  MVHSPSGRHM  VEISTPVLIS  SSNPSVITQP  MEKADVPSSC  VGQVSTYHPA   360
PVSPGHSTAV  VSLPGSQQHL  SANMFVALHS  YSAHGPDELD  LQKGEGVRVL  GKCQDGWLRG   420
VSLVTGRVGI  FPNNYVIPIF  RKTSSFPDSR  SPGLYTTWTL  STSSVSSQGS  ISEGDPRQSR   480
PPFKSVFVPTA IVNPVRSTAG  PGTLGQGSLR  KGRSSMRKNG  SLQRPLQSGI  PTLVVGSLRR   540
SPTMVLRPQQ  FQFYQPQGIP  SSPSAVVVEM  GSKPALTGEP  ALTCISRGSE  AWIHSAASSL   600
IMEDKEIPIK  SEPLPKPPAS  APPSILVKPE  NSRNGIEKQV  KTVRFQNYSP  PPTKHYTSHP   660
TSGKPEQPAT  LKASQPEAAS  LGPEMTVLFA  HRSGCHSGQQ  TDLRRKSALG  KATTLVSTAS   720
GTQTVFPSK                                                              729

SEQ ID NO: 437            moltype = AA   length = 398
FEATURE                   Location/Qualifiers
source                    1..398
                          mol_type = protein
                          organism = Homo sapiens
SEQUENCE: 437
MSGSSLPSAL  ALSLLLVSGS  LLPGPGAAQN  AGFVKSPMSE  TKLTGDAFEL  YCDVVGSPTP    60
EIQWWYAEVN  RAESFRQLWD  GARKRRVTVN  TAYGSNGVSV  LRITRLTLED  SGTYECRASN   120
DPKRNDLRQN  PSITWIRAQA  TISVLQKPRI  VTSEEVIIRD  SPVLPVTLQC  NLTSSSHTLT   180
YSYWTKNGVE  LSATRKNASN  MEYRINKPRA  EDSGEYHCVY  HFVSAPKANA  TIEVKAAPDI   240
TGHKRSENKN  EGQDATMYCK  SVGYPHPDWI  WRKKENGMPM  DIVNTSGRFF  IINKENYTEL   300
NIVNLQITED  PGEYECNATN  AIGSASVVTV  LRVRSHLAPL  WPFLGILAEI  IILVVIIVVY   360
EKRKRPDEVP  DDDEPAGPMK  TNSTNNHKDK  NLRQRNTN                            398

SEQ ID NO: 438            moltype = AA   length = 282
FEATURE                   Location/Qualifiers
source                    1..282
                          mol_type = protein
                          organism = Homo sapiens
SEQUENCE: 438
MSGSSLPSAL  ALSLLLVSGS  LLPGPGAAQN  EPRIVTSEEV  IIRDSPVLPV  TLQCNLTSSS    60
HTLTYSYWTK  NGVELSATRK  NASNMEYRIN  KPRAEDSGEY  HCVYHFVSAP  KANATIEVKA   120
APDITGHKRS  ENKNEGQDAT  MYCKSVGYPH  PDWIWRKKEN  GMPMDIVNTS  GRFFIINKEN   180
YTELNIVNLQ  ITEDPGEYEC  NATNAIGSAS  VVTVLRVRSH  LAPLWPFLGI  LAEIIILVVI   240
IVVYEKRKRP  DEVPDDDEPA  GPMKTNSTNN  HKDKNLRQRN  TN                      282
```

```
SEQ ID NO: 439            moltype = AA  length = 278
FEATURE                   Location/Qualifiers
source                    1..278
                          mol_type = protein
                          organism = Homo sapiens
SEQUENCE: 439
MSGSSLPSAL ALSLLLVSGS LLPGPGAAQN EPRIVTSEEV IIRDSPVLPV TLQCNLTSSS    60
HTLTYSYWTK NGVELSATRK NASNMEYRIN KPRAEDSGEY HCVYHFVSAP KANATIEVKA   120
APDITGHKRS ENKNEGQDAT MYCKSVGYPH PDWIWRKKEN GMPMDIVNTS GRFFIINKEN   180
YTELNIVNLQ ITEDPGEYEC NATNAIGSAS VVTVLRVRSH LAPLWPFLGI LAEIIILVVI   240
IVVYEKRKRP DEVPDAGPMK TNSTNNHKDK NLRQRNTN                          278

SEQ ID NO: 440            moltype = AA  length = 394
FEATURE                   Location/Qualifiers
source                    1..394
                          mol_type = protein
                          organism = Homo sapiens
SEQUENCE: 440
MSGSSLPSAL ALSLLLVSGS LLPGPGAAQN AGFVKSPMSE TKLTGDAFEL YCDVVGSPTP    60
EIQWWYAEVN RAESFRQLWD GARKRRVTVN TAYGSNGVSV LRITRLTLED SGTYECRASN   120
DPKRNDLRQN PSITWIRAQA TISVLQKPRI VTSEEVIIRD SPVLPVTLQC NLTSSSHTLT   180
YSYWTKNGVE LSATRKNASN MEYRINKPRA EDSGEYHCVY HFVSAPKANA TIEVKAAPDI   240
TGHKRSENKN EGQDATMYCK SVGYPHPDWI WRKKENGMPM DIVNTSGRFF IINKENYTEL   300
NIVNLQITED PGEYECNATN AIGSASVVTV LRVRSHLAPL WPFLGILAEI IILVVIIVVY   360
EKRKRPDEVP DAGPMKTNST NNHKDKNLRQ RNTN                              394

SEQ ID NO: 441            moltype = AA  length = 184
FEATURE                   Location/Qualifiers
source                    1..184
                          mol_type = protein
                          organism = Homo sapiens
SEQUENCE: 441
MSGSSLPSAL ALSLLLVSGS LLPGPGAAQN AAPDITGHKR SENKNEGQDA TMYCKSVGYP    60
HPDWIWRKKE NGMPMDIVNT SGRFFIINKE NYTELNIVNL QITEDPGEYE CNATNAIGSA   120
SVVTVLRVRS HLAPLWPFLG ILAEIIILVV IIVVYEKRKR PDEVPDDDEP AGPMKTNSTN   180
NHKD                                                               184

SEQ ID NO: 442            moltype = AA  length = 518
FEATURE                   Location/Qualifiers
source                    1..518
                          mol_type = protein
                          organism = Homo sapiens
SEQUENCE: 442
XRKWSRQFLL SFWCTVCSAH QGTIFLSLKI QFADQKQEFN KRPTKIGRRS LSRSISQSST    60
DSYSSAASYT DSSDDETSPR DKQQKNSKGS SDFCVKNIKQ AEFGRREIEI AEQEMPALMA   120
LRKRAQGEKP LAGAKIVGCT HITAQTAVLM ETLGALGAQC RWAACNIYST LNEVAAALAE   180
SGFPVFAWKG ESEDDFWWCI DRCVNVEGWQ PNMILDDGLK LTHWIYKKYP NMFKKIKGIV   240
EESVTGVHRL YQLSKAGKLC VPAMNVNDSV TKQKFDNLYC CRESILDGLK RTTDMMFGGK   300
QVVVCGYGEV GKGCCAALKA MGSIVYVTEI DPICALQACM DGFRLVKLNE VIRQVDIVIT   360
CTGNKNVVTR EHLDRMKNSC IVCNMGHSNT EIDVASLRTP ELTWERVRSQ VDHVIWPDGK   420
RIVLLAEGRL LNLSCSTVPT FVLSITATTQ ALALIELYNA PEGRYKQDVY LLPKKMDEYV   480
ASLHLPTFDA HLTELTDEQA KYLGLNKNGP FKPNYYRY                          518

SEQ ID NO: 443            moltype = AA  length = 386
FEATURE                   Location/Qualifiers
source                    1..386
                          mol_type = protein
                          organism = Homo sapiens
SEQUENCE: 443
MADSCRNLTY VRGSVGPATS TLMFVAGVVG NGLALGILSA RRPARPSAFA VLVTGLAATD    60
LLGTSFLSPA VFVAYARNSS LLGLARGGPA LCDAFAFAMT FFGLASMLIL FAMAVERCLA   120
LSHPYLYAQL DGPRCARLAL PAIYAFCVLF CALPLLGLGQ HQQYCPGSWC FLRMRWAQPG   180
GAAFSLAYAG LVALLVAAIF LCNGSVTLSL CRMYRQQKRH QGSLGPRPRT GEDEVDHLIL   240
LALMTVVMAV CSLPLTIRCF TQAVAPDSSS EMGDLLAFRF YAFNPILDPW VFILPRKAVF   300
QRLKLWVCCL CLGPAHGDSQ TPLSQLASGR RDPRAPSAPV GKEGSCVPLS AWGEGQVEPL   360
PPTQQSSGSA VGTSSKAEAS VACSLC                                       386

SEQ ID NO: 444            moltype = AA  length = 143
FEATURE                   Location/Qualifiers
source                    1..143
                          mol_type = protein
                          organism = Homo sapiens
SEQUENCE: 444
MTVVMAVCSL PLTIRCFTQA VAPDSSSEMG DLLAFRFYAF NPILDPWVFI LFRKAVFQRL    60
KLWVCCLCLG PAHGDSQTPL SQLASGRRDP RAPSAPVGKE GSCVPLSAWG EGQVEPLPPT   120
QQSSGSAVGT SSKAEASVAC SLC                                          143

SEQ ID NO: 445            moltype = AA  length = 296
FEATURE                   Location/Qualifiers
```

```
source                          1..296
                                mol_type = protein
                                organism = Homo sapiens
SEQUENCE: 445
MADSCRNLTY VRGSVGPATS TLMFVAGVVG NGLALGILSA RRPARPSAFA VLVTGLAATD    60
LLGTSFLSPA VFVAYARNSS LLGLARGGPA LCDAFAFAMT FFGLASMLIL FAMAVERCLA   120
LSHPYLYAQL DGPRCARLAL PAIYAFCVLF CALPLLGLGQ HQQYCPGSWC FLRMRWAQPG   180
GAAFSLAYAG LVALLVAAIF LCNGSVTLSL CRMYRQQKRH QGSLGPRPRT GEDEVDHLIL   240
LALMTVVMAV CSLPLTHVER PRQDRMRWLT PVIPALWEAE AGGSFEVRSS RPVWPT      296

SEQ ID NO: 446                  moltype = AA  length = 115
FEATURE                         Location/Qualifiers
source                          1..115
                                mol_type = protein
                                organism = Homo sapiens
SEQUENCE: 446
MGDLLAFRFY AFNPILDPWV FILFRKAVFQ RLKLWVCCLC LGPAHGDSQT PLSQLASGRR    60
DPRAPSAPVG KEGSCVPLSA WGEGQVEPLP PTQQSSGSAV GTSSKAEASV ACSLC       115

SEQ ID NO: 447                  moltype = AA  length = 174
FEATURE                         Location/Qualifiers
source                          1..174
                                mol_type = protein
                                organism = Homo sapiens
SEQUENCE: 447
MYRQQKRHQG SLGPRPRTGE DEVDHLILLA LMTVVMAVCS LPLTIRCFTQ AVAPDSSSEM    60
GDLLAFRFYA FNPILDPWVF ILFRKAVFQR LKLWVCCLCL GPAHGDSQTP LSQLASGRRD   120
PRAPSAPVGK EGSCVPLSAW GEGQVEPLPP TQQSSGSAVG TSSKAEASVA CSLC        174

SEQ ID NO: 448                  moltype = AA  length = 454
FEATURE                         Location/Qualifiers
source                          1..454
                                mol_type = protein
                                organism = Homo sapiens
SEQUENCE: 448
MGENDPPAVE APFSFRSLFG LDDLKISPVA PDADAVAAQI LSLLPLKFFP IIVIGIIALI    60
LALAIGLGIH FDCSGKYRCR SSFKCIELIA RCDGVSDCKD GEDEYRCVRV GGQNAVLQVF   120
TAASWKTMCS DDWKGHYANV ACAQLGFPSY VSSDNLRVSS LEGQFREEFV SIDHLLPDDK   180
VTALHHSVYV REGCASGHVV TLQCTACGHR RGYSSRIVGG NMSLLSQWPW QASLQFQGYH   240
LCGGSVITPL WIITAAHCVY DLYLPKSWTI QVGLVSLLDN PAPSHLVEKI VYHSKYKPKR   300
LGNDIALMKL AGPLTFNEMI QPVCLPNSEE NFPDGKVCWT SGWGATEDGA GDASPVLNHA   360
AVPLISNKIC NHRDVYGGII SPSMLCAGYL TGGVDSCQGD SGGPLVCQER RLWKLVGATS   420
FGIGCAEVNK PGVYTRVTSF LDWIHEQMER DLKT                              454

SEQ ID NO: 449                  moltype = AA  length = 344
FEATURE                         Location/Qualifiers
source                          1..344
                                mol_type = protein
                                organism = Homo sapiens
SEQUENCE: 449
MGENDPPAVE APFSFRSLFG LDDLKISPVA PDADAVAAQI LSLLPLKFFP IIVIGIIALI    60
LALAIGLGIH FDCSGKYRCR SSFKCIELIA RCDGVSDCKD GEDEYRCVRV GGQNAVLQVF   120
TAASWKTMCS DDWKGHYANV ACAQLGFPSY VSSDNLRVSS LEGQFREEFV SIDHLLPDDK   180
VTALHHSVYV REGCASGHVV TLQCTACGHR RGYSSRIVGG NMSLLSQWPW QASLQFQGYH   240
LCGGSVITPL WIITAAHCVY DLYLPKSWTI QVGLVSLLDN PAPSHLVEKI VYHSKYKPKR   300
LGNDIALMKL AGPLTFNGTS GSLCGSAALP LFQEDLQLLI EAFL                   344

SEQ ID NO: 450                  moltype = AA  length = 451
FEATURE                         Location/Qualifiers
source                          1..451
                                mol_type = protein
                                organism = Homo sapiens
SEQUENCE: 450
MGENDPPAVE APFSFRSLFG LDDLKISPVA PDAVAAQILS LLPLKFFPII VIGIIALILA    60
LAIGLGIHFD CSGKYRCRSS FKCIELIARC DGVSDCKDGE DEYRCVRVGG QNAVLQVFTA   120
ASWKTMCSDD WKGHYANVAC AQLGFPSYVS SDNLRVSSLE GQFREEFVSI DHLLPDDKVT   180
ALHHSVYVRE GCASGHVVTL QCTACGHRRG YSSRIVGGNM SLLSQWPWQA SLQFQGYHLC   240
GGSVITPLWI ITAAHCVYDL YLPKSWTIQV GLVSLLDNPA PSHLVEKIVY HSKYKPKRLG   300
NDIALMKLAG PLTFNEMIQP VCLPNSEENF PDGKVCWTSG WGATEDGGDA SPVLNHAAVP   360
LISNKICNHR DVYGGIISPS MLCAGYLTGG VDSCQGDSGG PLVCQERRLW KLVGATSFGI   420
GCAEVNKPGV YTRVTSFLDW IHEQMERDLK T                                 451

SEQ ID NO: 451                  moltype = AA  length = 453
FEATURE                         Location/Qualifiers
source                          1..453
                                mol_type = protein
                                organism = Homo sapiens
SEQUENCE: 451
MGENDPPAVE APFSFRSLFG LDDLKISPVA PDADAVAAQI LSLLPLKFFP IIVIGIIALI    60
```

```
LALAIGLGIH FDCSGKYRCR SSFKCIELIA RCDGVSDCKD GEDEYRCVRV GGQNAVLQVF  120
TAASWKTMCS DDWKGHYANV ACAQLGFPSY VSSDNLRVSS LEGQFREEFV SIDHLLPDDK  180
VTALHHSVYV REGCASGHVV TLQCTACGHR RGYSSRIVGG NMSLLSQWPW QASLQFQGYH  240
LCGGSVITPL WIITAAHCVY DLYLPKSWTI QVGLVSLLDN PAPSHLVEKI VYHSKYKPKR  300
LGNDIALMKL AGPLTFNEMI QPVCLPNSEE NFPDGKVCWT SGWGATEDGG DASPVLNHAA  360
VPLISNKICN HRDVYGGIIS PSMLCAGYLT GGVDSCQGDS GGPLVCQERR LWKLVGATSF  420
GIGCAEVNKP GVYTRVTSFL DWIHEQMERD LKT                              453

SEQ ID NO: 452           moltype = AA  length = 734
FEATURE                  Location/Qualifiers
source                   1..734
                         mol_type = protein
                         organism = Homo sapiens
SEQUENCE: 452
MLLWLLLLIL TPGREQSGVA PKAVLLLNPP WSTAFKGEKV ALICSSISHS LAQGDTYWYH   60
DEKLLKIKHD KIQITEPGNY QCKTRGSSLS DAVHVEFSPD WLILQALHPV FEGDNVILRC  120
QGKDNKNTHQ KVYYKDGKQL PNSYNLEKIT VNSVSRDNSK YHCTAYRKFY ILDIEVTSKP  180
LNIQVQELFL HPVLRASSST PIEGSPMTLT CETQLSPQRP DVQLQFSLFR DSQTLGLGWS  240
RSPRLQIPAM WTEDSGSYWC EVETVTHSIK KRSLRSQIRV QRVPVSNVNL EIRPTGGQLI  300
EGENMVLICS VAQGSGTVTF SWHKEGRVRS LGRKTQRSLL AELHVLTVKE SDAGRYYCAA  360
DNVHSPILST WIRVTVRIPV SHPVLTFRAP RAHTVVGDLL ELHCESLRGS PPILYRFYHE  420
DVTLGNSSAP SGGGASFNLS LTAEHSGNYS CDADNGLGAQ HSHGVSLRVT VPVSRPVLTL  480
RAPGAQAVVG DLLELHCESL RGSFPILYWF YHEDDTLGNI SAHSGGGASF NLSLTTEHSG  540
NYSCEADNGL GAQHSKVVTL NVTGTSRNRT GLTAAGITGL VLSILVLAAA AALLHYARAR  600
RKPGGLSATG TSSHSPSECQ EPSSSRPSRI DPQEPTHSKP LAPMELEPMY SNVNPGDSNP  660
IYSQIWSIQH TKENSANCPM MHQEHEELTV LYSELKKTHP DDSAGEASSR GRAHEEDDEE  720
NYENVPRVLL ASDH                                                   734

SEQ ID NO: 453           moltype = AA  length = 742
FEATURE                  Location/Qualifiers
source                   1..742
                         mol_type = protein
                         organism = Homo sapiens
SEQUENCE: 453
MLLWLLLLIL TPGREQSGVA PKAVLLLNPP WSTAFKGEKV ALICSSISHS LAQGDTYWYH   60
DEKLLKIKHD KIQITEPGNY QCKTRGSSLS DAVHVEFSPD WLILQALHPV FEGDNVILRC  120
QGKDNKNTHQ KVYYKDGKQL PNSYNLEKIT VNSVSRDNSK YHCTAYRKFY ILDIEVTSKP  180
LNIQVQELFL HPVLRASSST PIEGSPMTLT CETQLSPQRP DVQLQFSLFR DSQTLGLGWS  240
RSPRLQIPAM WTEDSGSYWC EVETVTHSIK KRSLRSQIRV QRVPVSNVNL EIRPTGGQLI  300
EGENMVLICS VAQGSGTVTF SWHKEGRVRS LGRKTQRSLL AELHVLTVKE SDAGRYYCAA  360
DNVHSPILST WIRVTVRIPV SHPVLTFRAP RAHTVVGDLL ELHCESLRGS PPILYRFYHE  420
DVTLGNSSAP SGGGASFNLS LTAEHSGNYS CDADNGLGAQ HSHGVSLRVT VPVSRPVLTL  480
RAPGAQAVVG DLLELHCESL RGSFPILYWF YHEDDTLGNI SAHSGGGASF NLSLTTEHSG  540
NYSCEADNGL GAQHSKVVTL NVTGTSRNRT GLTAAGITGL VLSILVLAAA AALLHYARAR  600
RKPGGLSATG TSSHSPSECQ EPSSSRPSRI DPQEPTHSKP LAPMELEPMY SNVNPGDSNP  660
IYSQIWSIQH TKENSANCPM MHQEHEELTV LYSELKKTHP DDSAGEASSR GRAHEEDDEE  720
NYENILNPRK NKVQDFPCLC NT                                          742

SEQ ID NO: 454           moltype = AA  length = 639
FEATURE                  Location/Qualifiers
source                   1..639
                         mol_type = protein
                         organism = Homo sapiens
SEQUENCE: 454
MLLWLLLLIL TPGREQSGVA PKAVLLLNPP WSTAFKGEKV ALICSSISHS LAQGDTYWYH   60
DEKLLKIKHD KIQITEPGNY QCKTRGSSLS DAVHVEFSPD WLILQALHPV FEGDNVILRC  120
QGKDNKNTHQ KVYYKDGKQL PNSYNLEKIT VNSVSRDNSK YHCTAYRKFY ILDIEVTSKP  180
LNIQVQGPV SNVNLEIRPT GGQLIEGENM VLICSVAQGS GTVTFSWHKE GRVRSLGRKT  240
QRSLLAELHV LTVKESDAGR YYCAADNVHS PILSTWIRVT VRIPVSHPVL TFRAPRAHTV  300
VGDLLELHCE SLRGSPPILY RFYHEDVTLG NSSAPSGGGA SFNLSLTAEH SGNYSCDADN  360
GLGAQHSHGV SLRVTVPVSR PVLTRAPGA QAVVGDLLEL HCESLRGSFP ILYWFYHEDD  420
TLGNISAHSG GGASFNLSLT TEHSGNYSCE ADNGLGAQHS KVVTLNVTGT SRNRTGLTAA  480
GITGLVLSIL VLAAAAALLH YARARRKPGG LSATGTSSHS PSECQEPSSS RPSRIDPQEP  540
THSKPLAPME LEPMYSNVNP GDSNPIYSQI WSIQHTKENS ANCPMMHQEH EELTVLYSEL  600
KKTHPDDSAG EASSRGRAHE EDDEENYENV PRVLLASDH                        639

SEQ ID NO: 455           moltype = AA  length = 734
FEATURE                  Location/Qualifiers
source                   1..734
                         mol_type = protein
                         organism = Homo sapiens
SEQUENCE: 455
MLLWLLLLIL TPGREQSGVA PKAVLLLNPP WSTAFKGEKV ALICSSISHS LAQGDTYWYH   60
DEKLLKIKHD KIQITEPGNY QCKTRGSSLS DAVHVEFSPD WLILQALHPV FEGDNVILRC  120
QGKDNKNTHQ KVYYKDGKQL PNSYNLEKIT VNSVSRDNSK YHCTAYRKFY ILDIEVTSKP  180
LNIQVQELFL HPVLRASSST PIEGSPMTLT CETQLSPQRP DVQLQFSLFR DSQTLGLGWS  240
RSPRLQIPAM WTEDSGSYWC EVETVTHSIK KRSLRSQIRV QRVPVSNVNL EIRPTGGQLI  300
EGENMVLICS VAQGSGTVTF SWHKEGRVRS LGRKTQRSLL AELHVLTVKE SDAGRYYCAA  360
DNVHSPILST WIRVTVRIPV SHPVLTFRAP RAHTVVGDLL ELHCESLRGS PPILYRFYHE  420
```

```
DVTLGNSSAP SGGGASFNLS LTAEHSGNYS CDADNGLGAQ HSHGVSLRVT VPVSRPVLTL    480
RAPGAQAVVG DLLELHCESL RGSFPILYWF YHEDDTLGNI SAHSGGGASF NLSLTTEHSG    540
NYSCEADNGL GAQHSKVVTL NVTGTSRNRT GLTAAGITGL VLSILVLAAA AALLHYARAR    600
RKPGGLSATG TSSHSPSECQ EPSSSRPSRI DPQEPTHSKP LAPMELEPMY SNVNPGDSNP    660
IYSQIWSIQH TKENSANCPM MHQEHEELTV LYSELKKTHP DDSAGEASSR GRAHEEDDEE    720
NYENVPRVLL ASDH                                                    734

SEQ ID NO: 456          moltype = AA  length = 740
FEATURE                 Location/Qualifiers
source                  1..740
                        mol_type = protein
                        organism = Homo sapiens
SEQUENCE: 456
MLLWLLLLIL TPGREQSGVA PKAVLLLNPP WSTAFKGEKV ALICSSISHS LAQGDTYWYH     60
DEKLLKIKHD KIQITEPGNY QCKTRGSSLS DAVHVEFSPD WLILQALHPV FEGDNVILRC    120
QGKDNKNTHQ KVYYKDGKQL PNSYNLEKIT VNSVSRDNSK YHCTAYRKFY ILDIEVTSKP    180
LNIQVQELFL HPVLRASSST PIEGSPMTLT CETQLSPQRP DVQLQFSLFR DSQTLGLGWS    240
RSPRLQIPAM WTEDSGSYWC EVETVTHSIK KRSLRSQIRV QRVPVSNVNL EIRPTGGQLI    300
EGENMVLICS VAQGSGTVTF SWHKEGRVRS LGRKTQRSLL AELHVLTVKE SDAGRYYCAA    360
DNVHSPILST WIRVTVRTLL SPSVPVSHPV LTFRAPRAHT VVGDLLELHC ESLRGSPPIL    420
YRFYHEDVTL GNSSAPSGGG ASFNLSLTAE HSGNYSCDAD NGLGAQHSHG VSLRVTVPVS    480
RPVLTLRAPG AQAVVGDLLE LHCESLRGSF PILYWFYHED DTLGNISAHS GGGASFNLSL    540
TTEHSGNYSC EADNGLGAQH SKVVTLNVTG TSRNRTGLTA AGITGLVLSI LVLAAAAALL    600
HYARARRKPG GLSATGTSSH SPSECQEPSS SRPSRIDPQE PTHSKPLAPM ELEPMYSNVN    660
PGDSNPIYSQ IWSIQHTKEN SANCPMMHQE HEELTVLYSE LKKTHPDDSA GEASSRGRAH    720
EEDDEENYEN VPRVLLASDH                                               740

SEQ ID NO: 457          moltype = AA  length = 256
FEATURE                 Location/Qualifiers
source                  1..256
                        mol_type = protein
                        organism = Homo sapiens
SEQUENCE: 457
MLLWLLLLIL TPGREQSGVA PKAVLLLNPP WSTAFKGEKV ALICSSISHS LAQGDTYWYH     60
DEKLLKIKHD KIQITEPGNY QCKTRGSSLS DAVHVEFSPD WLILQALHPV FEGDNVILRC    120
QGKDNKNTHQ KVYYKDGKQL PNSYNLEKIT VNSVSRDNSK YHCTAYRKFY ILDIEVTSKP    180
LNIQVQELFL HPVLRASSST PIEGSPMTLT CETQLSPQRP DVQLQFSLFR DSQTLGLGWS    240
RSPRLQIPAM WTEDSG                                                   256

SEQ ID NO: 458          moltype = AA  length = 234
FEATURE                 Location/Qualifiers
source                  1..234
                        mol_type = protein
                        organism = Homo sapiens
SEQUENCE: 458
MAFLAGPRLL DWASSPPHLQ FNKFVLTGYR PASSGSGCLR SLFYLHNELG NIYTHGSVLY     60
HLFMCHQGGS AVYARLLALD MCGVCLVNTL GALPIIHCTL ACRPWLRPAA LVGYTVLSGV    120
AGWRALTAPS TSARLRAFGW QAAARLLVFG ARGVGLGSGA PGSLPCYLRM DALALLGGLV    180
NVARLPERWG PGRFDYWGNS HQIMHLLSVG SILQLHAGVV PDLLWAAHHA CPRD          234

SEQ ID NO: 459          moltype = AA  length = 273
FEATURE                 Location/Qualifiers
source                  1..273
                        mol_type = protein
                        organism = Homo sapiens
SEQUENCE: 459
MAFLAGPRLL DWASSPPHLQ FNKFVLTGYR PASSGSGCLR SLFYLHNELG NIYTHGLALL     60
GFLVLVPMTM PWGQLGKDGW LGGTHCVACL APPAGSVLYH LFMCHQGGSA VYARLLALDM    120
CGVCLVNTLG ALPIIHCTLA CRPWLRPAAL VGYTVLSGVA GWRALTAPST SARLRAFGWQ    180
AAARLLVFGA RGVGLGSGAP GSLPCYLRMD ALALLGGLVN VARLPERWGP GRFDYWGNSH    240
QIMHLLSVGS ILQLHAGVVP DLLWAAHHAC PRD                                 273

SEQ ID NO: 460          moltype = AA  length = 199
FEATURE                 Location/Qualifiers
source                  1..199
                        mol_type = protein
                        organism = Homo sapiens
SEQUENCE: 460
MAFLAGPRLL DWASSPPHLQ FNKFVLTGYR PASSGSGCLR SLFYLHNELG NIYTHGALPI     60
IHCTLACRPW LRPAALVGYT VLSGVAGWRA LTAPSTSARL RAFGWQAAAR LLVFGARGVG    120
LGSGAPGSLP CYLRMDALAL LGGLVNVARL PERWGPGRFD YWGNSHQIMH LLSVGSILQL    180
HAGVVPDLLW AAHHACPRD                                                199

SEQ ID NO: 461          moltype = AA  length = 206
FEATURE                 Location/Qualifiers
source                  1..206
                        mol_type = protein
                        organism = Homo sapiens
SEQUENCE: 461
```

```
MTMPWGQLGK DGWLGGTHCV ACLAPPAGSV LYHLFMCHQG GSAVYARLLA LDMCGVCLVN    60
TLGALPIIHC TLACRPWLRP AALVGYTVLS GVAGWRALTA PSTSARLRAF GWQAAARLLV   120
FGARGVGLGS GAPGSLPCYL RMDALALLGG LVNVARLPER WGPGRFDYWG NSHQIMHLLS   180
VGSILQLHAG VVPDLLWAAH HACPRD                                       206

SEQ ID NO: 462          moltype = AA   length = 206
FEATURE                 Location/Qualifiers
source                  1..206
                        mol_type = protein
                        organism = Homo sapiens
SEQUENCE: 462
MTMPWGQLGK DGWLGGTHCV ACLAPPAGSV LYHLFMCHQG GSAVYARLLA LDMCGVCLVN    60
TLGALPIIHC TLACRPWLRP AALVGYTVLS GVAGWRALTA PSTSARLRAF GWQAAARLLV   120
FGARGVGLGS GAPGSLPCYL RMDALALLGG LVNVARLPER WGPGRFDYWG NSHQIMHLLS   180
VGSILQLHAG VVPDLLWAAH HACPRD                                       206

SEQ ID NO: 463          moltype = AA   length = 208
FEATURE                 Location/Qualifiers
source                  1..208
                        mol_type = protein
                        organism = Homo sapiens
SEQUENCE: 463
MGAQGAQESI KAMWRVPGTT RRPVTGESPG MHRPEAMLLL LTLALLGGPT WAGKMYGPGG    60
GKYFSTTEDY DHEITGLRVS VGLLLVKSVQ VKLGDSWDVK LGALGGNTQE VTLQPGEYIT   120
KVFVAFQAFL RGMVMYTSKD RYFYFGKLDG QISSAYPSQE GQVLVGIYGQ YQLLGIKSIG   180
FEWNYPLEEP TTEPPVNLTY SANSPVGR                                     208

SEQ ID NO: 464          moltype = AA   length = 95
FEATURE                 Location/Qualifiers
source                  1..95
                        mol_type = protein
                        organism = Homo sapiens
SEQUENCE: 464
XAQGAQESIK AMWRVPGTTR RPVTGESPGM HRPEAMLLLL TLALLGGPTW AGKMYGPGGG    60
KYFSTTEDYD HEITGLRVSV GLLLVKRFLE GVIYE                              95

SEQ ID NO: 465          moltype = AA   length = 69
FEATURE                 Location/Qualifiers
source                  1..69
                        mol_type = protein
                        organism = Homo sapiens
SEQUENCE: 465
XRRPVTGESP GMHRPEAMLL LLTLALLGGP TWAGKMYGPG GGKYFSTTED YDHEITGLRV    60
SVGLLLVKR                                                           69

SEQ ID NO: 466          moltype = AA   length = 178
FEATURE                 Location/Qualifiers
source                  1..178
                        mol_type = protein
                        organism = Homo sapiens
SEQUENCE: 466
MHRPEAMLLL LTLALLGGPT WAGKMYGPGG GKYFSTTEDY DHEITGLRVS VGLLLVKSVQ    60
VKLGDSWDVK LGALGGNTQE VTLQPGEYIT KVFVAFQAFL RGMVMYTSKD RYFYFGKLDG   120
QISSAYPSQE GQVLVGIYGQ YQLLGIKSIG FEWNYPLEEP TTEPPVNLTY SANSPVGR    178

SEQ ID NO: 467          moltype = AA   length = 399
FEATURE                 Location/Qualifiers
source                  1..399
                        mol_type = protein
                        organism = Homo sapiens
SEQUENCE: 467
MAELLRSLQD SQLVARFQRR CGLFPAPDEG PRENGADPTE RAARVPGVEH LPAANGKGGE    60
APANGLRRAA APEAYVQKYV VKNYFYYYLF QFSAALGQEV FYITFLPFTH WNIDPYLSRR   120
LIIIWVLVMY IGQVAKDVLK WPRPSSPPVV KLEKRLIAEY GMPSTHAMAA TAIAFTLLIS   180
TMDRYQYPFV LGLVMAVVFS TLVCLSRLYT GMHTVLDVLG GVLITALLIV LTYPAWTFID   240
CLDSASPLFP VCVIVVPFFL CYNYPVSDYY SPTRADTTTI LAAGAGVTIG FWINHFFQLV   300
SKPAESLPVI QNIPPLTTYM LVLGLTKFAV GIVLILLVRQ LVQNLSLQVL YSWFKVVTRN   360
KEARRRLEIE VPYKFVTYTS VGICATTFVP MLHRFLGLP                          399

SEQ ID NO: 468          moltype = AA   length = 128
FEATURE                 Location/Qualifiers
source                  1..128
                        mol_type = protein
                        organism = Homo sapiens
SEQUENCE: 468
MDVYGTTKAI ELLDPTASRL PTPMPWDLSN KAVPEPKGFG PKDLALPTGN LKATWHLCLR    60
EHLPTLHTRR GVCHLLLSRC QHPPCALRPH ILLQILCLAG LQRYGQVPCV PLADRGGSPC   120
AGPSCSEG                                                           128
```

| SEQ ID NO: 469 | moltype = AA length = 104 |
| --- | --- |
| FEATURE | Location/Qualifiers |
| source | 1..104 |
| | mol_type = protein |
| | organism = Homo sapiens |

SEQUENCE: 469
```
MDVYGTTKAI ELLDPTASRL PTPMPWDLSN KAVPEPKATP GEECAICFYH AANTRLVPCG   60
HTYFCRYCAW RVFSDTAKCP VCRWQIEAVA PAQGPPALRV EEGS                   104
```

| SEQ ID NO: 470 | moltype = AA length = 83 |
| --- | --- |
| FEATURE | Location/Qualifiers |
| source | 1..83 |
| | mol_type = protein |
| | organism = Homo sapiens |

SEQUENCE: 470
```
MAPGCKIMKV MPSKFLCEFV LLQKDLGQLM ESRTYAYLCC PPRVSGCTPT LSPRPSRLIM   60
LQMWIPLRNL YSQLWLKALW SLA                                          83
```

| SEQ ID NO: 471 | moltype = AA length = 438 |
| --- | --- |
| FEATURE | Location/Qualifiers |
| source | 1..438 |
| | mol_type = protein |
| | organism = Homo sapiens |

SEQUENCE: 471
```
MPCTCTWRNW RQWIRPLVAV IYLVSIVVAV PLCVWELQKL EVGIHTKAWF IAGIFLLLTI   60
PISLWVILQH LVHYTQPELQ KPIIRILWMV PIYSLDSWIA LKYPGIAIYV DTCRECYEAY  120
VIYNFMGFLT NYLTNRYPNL VLILEAKDQQ KHFPPLCCCP PWAMGEVLLF RCKLGVLQYT  180
VVRPFTTIVA LICELLGIYD EGNFSFSNAW TYLVIINNMS QLFAMYCLLL FYKVLKEELS  240
PIQPVGKFLC VKLVVFVSFW QAVVIALLVK VGVISEKHTW EWQTVEAVAT GLQDFIICIE  300
MFLAAIAHHY TFSYKPYVQE AEEGSCFDSF LAMWDVSDIR DDISEQVRHV GRTVRGHPRK  360
KLFPEDQDQN EHTSLLSSSS QDAISIASSM PPSPMGHYQG FGHTVTPQTT PTTAKISDEI  420
LSDTIGEKKE PSDKSVDS                                                438
```

| SEQ ID NO: 472 | moltype = AA length = 72 |
| --- | --- |
| FEATURE | Location/Qualifiers |
| source | 1..72 |
| | mol_type = protein |
| | organism = Homo sapiens |

SEQUENCE: 472
```
LGIYDEGNFS FSNAWTYLVI INNMSQLFAM YCLLLFYKVL KEELSPIQPV GKFLCVKLVV   60
FVSFCIRGNG KL                                                      72
```

| SEQ ID NO: 473 | moltype = AA length = 261 |
| --- | --- |
| FEATURE | Location/Qualifiers |
| source | 1..261 |
| | mol_type = protein |
| | organism = Homo sapiens |

SEQUENCE: 473
```
MPCTCTWRNW RQWIRPLVAV IYLVSIVVAV PLCVWELQKL EVGIHTKAWF IAGIFLLLTI   60
PISLWVILQH LVHYTQPELQ KPIIRILWMV PIYSLDSWIA LKYPGIAIYV DTCRECYEAY  120
VIYNFMGFLT NYLTNRYPNL VLILEAKDQQ KHFPPLCCCP PWAMGEVLLF RCKLGVLQYT  180
VVRPFTTIVA LICELLGIYD EGNFSFSNAW TYLVIINNMS QLFAMYCLLL FYKVLKEELS  240
PIQPVGKFLC VKLVVFVSFW P                                            261
```

| SEQ ID NO: 474 | moltype = AA length = 115 |
| --- | --- |
| FEATURE | Location/Qualifiers |
| source | 1..115 |
| | mol_type = protein |
| | organism = Homo sapiens |

SEQUENCE: 474
```
MLWFQGNSMQ LARSSFGLFL RNCSASKTTL PVLTLFTKDP CPLCDEAKEV LKPYENRFIL   60
QEVNITLPEN SVWYERYKFD IPVFHLNGQF LMMHRVNTSK LEKQLLKLEQ QSTGG       115
```

| SEQ ID NO: 475 | moltype = AA length = 55 |
| --- | --- |
| FEATURE | Location/Qualifiers |
| source | 1..55 |
| | mol_type = protein |
| | organism = Homo sapiens |

SEQUENCE: 475
```
MLWFQGNSMQ LARSSFGLFL RNCSASKTTL PVLTLFTKEF LSTRSLFACC HPCKM        55
```

| SEQ ID NO: 476 | moltype = AA length = 59 |
| --- | --- |
| FEATURE | Location/Qualifiers |
| source | 1..59 |
| | mol_type = protein |
| | organism = Homo sapiens |

SEQUENCE: 476
```
MLWFQGNSMQ LARSSFGLFL RNCSASKTTL PVLTLFTKDP CPLCDEAKEV LKPYENRVI    59
```

```
SEQ ID NO: 477            moltype = AA  length = 138
FEATURE                   Location/Qualifiers
source                    1..138
                          mol_type = protein
                          organism = Homo sapiens
SEQUENCE: 477
MLWFQGNSMQ LARSSFGLFL RNCSASKTTL PVLTLFTKDP CPLCDEAKEV LKPYENRQPY   60
KDQKLPGTRR RRSPSSPSHP HMASQSGKRY NLTLNQVLSF DYDMGLDAPK TISSDCGAFY  120
CLRMFKSPDM TCCFYPKQ                                                138

SEQ ID NO: 478            moltype = AA  length = 57
FEATURE                   Location/Qualifiers
source                    1..57
                          mol_type = protein
                          organism = Homo sapiens
SEQUENCE: 478
KTTLPVLTLF TKDPCPLCDE AKEVLKPYEN RFLMMHRVNT SKLEKQLLKL EQQSTGG      57

SEQ ID NO: 479            moltype = AA  length = 138
FEATURE                   Location/Qualifiers
source                    1..138
                          mol_type = protein
                          organism = Homo sapiens
SEQUENCE: 479
MLWFQGNSMQ LARSSFGLFL RNCSASKTTL PVLTLFTKDP CPLCDEAKEV LKPYENRQPY   60
KDQKLPGTRR RRSPSSPSHP HMASQSGKRY NLTLNQVLSF DYDMGLDAPK TISSDCGAFY  120
CLRMFKSPDM TCCFYPKQ                                                138

SEQ ID NO: 480            moltype = AA  length = 89
FEATURE                   Location/Qualifiers
source                    1..89
                          mol_type = protein
                          organism = Homo sapiens
SEQUENCE: 480
MLWFQGNSMQ LARSSFGLFL RNCSASKTTL PVLTLFTKDP CPLCDEAKEV LKPYENRRST   60
SQSLGNAIYR KKVLHSCCCP GGLNFLMKE                                     89

SEQ ID NO: 481            moltype = AA  length = 215
FEATURE                   Location/Qualifiers
source                    1..215
                          mol_type = protein
                          organism = Homo sapiens
SEQUENCE: 481
MKDYDELLKY YELHETIGTG GFAKVKLACH ILTGEMVAIK IMDKNTLGSD LPRIKTEIEA   60
LKNLRHQHIC QLYHVLETAN KIFMVLEENL LFDEYHKLKL IDFGLCAKPK GNKDYHLQTC  120
CGSLAYAAPE LIQGKSYLGS EADVWSMGIL LYVLMCGFLP FDDDNVMALY KKIMRGKYDV  180
PKWLSPSSIL LLQQMLQVDP KKRISMKNLL NHPWI                             215

SEQ ID NO: 482            moltype = AA  length = 580
FEATURE                   Location/Qualifiers
source                    1..580
                          mol_type = protein
                          organism = Homo sapiens
SEQUENCE: 482
MMNFSNIMNY MKLLGQYCPG GELFDYIISQ DRLSEEETRV VFRQIVSAVA YVHSQGYAHR   60
DLKPENLLFD EYHKLKLIDF GLCAKPKGNK DYHLQTCCGS LAYAAPELIQ GKSYLGSEAD  120
VWSMGILLYV LMCGFLPFDD DNVMALYKKI MRGKYDVPKW LSPSSILLLQ QMLQVDPKKR  180
ISMKNLLNHP WIMQDYNYPV EWQSKNPFIH LDDDCVTELS VHHRNNRQTM EDLISLWQYD  240
HLTATYLLLL AKKARGKPVR LRLSSFSCGQ ASATPFTDIK SNNWSLEDVT ASDKNYVAGL  300
IDYDWCEDDL STGAATPRTS QFTKYWTESN GVESKSLTPA LCRTPANKLK NKENVYTPKS  360
AVKNEEYFMF PEPKTPVNKN QHKREILTTP NRYTTPSKAR NQCLKETPIK IPVNSTGTDK  420
LMTGVISPER RCRSVELDLN QAHMEETPKR KGAKVFGSLE RGLDKVITVL TRSKRKGSAR  480
DGPRRLKLHY NVTTTRLVNP DQLLNEIMSI LPKKHVDFVQ KGYTLKCQTQ SDFGKVTMQF  540
ELEVCQLQKP DVVGIRRQRL KGDAWVYKRL VEDILSSCKV                        580

SEQ ID NO: 483            moltype = AA  length = 520
FEATURE                   Location/Qualifiers
source                    1..520
                          mol_type = protein
                          organism = Homo sapiens
SEQUENCE: 483
MVLEENLLFD EYHKLKLIDF GLCAKPKGNK DYHLQTCCGS LAYAAPELIQ GKSYLGSEAD   60
VWSMGILLYV LMCGFLPFDD DNVMALYKKI MRGKYDVPKW LSPSSILLLQ QMLQVDPKKR  120
ISMKNLLNHP WIMQDYNYPV EWQSKNPFIH LDDDCVTELS VHHRNNRQTM EDLISLWQYD  180
HLTATYLLLL AKKARGKPVR LRLSSFSCGQ ASATPFTDIK SNNWSLEDVT ASDKNYVAGL  240
IDYDWCEDDL STGAATPRTS QFTKYWTESN GVESKSLTPA LCRTPANKLK NKENVYTPKS  300
AVKNEEYFMF PEPKTPVNKN QHKREILTTP NRYTTPSKAR NQCLKETPIK IPVNSTGTDK  360
LMTGVISPER RCRSVELDLN QAHMEETPKR KGAKVFGSLE RGLDKVITVL TRSKRKGSAR  420
DGPRRLKLHY NVTTTRLVNP DQLLNEIMSI LPKKHVDFVQ KGYTLKCQTQ SDFGKVTMQF  480
```

```
ELEVCQLQKP DVVGIRRQRL KGDAWVYKRL VEDILSSCKV                          520

SEQ ID NO: 484          moltype = AA   length = 619
FEATURE                 Location/Qualifiers
source                  1..619
                        mol_type = protein
                        organism = Homo sapiens
SEQUENCE: 484
MMNFSNIMNY MKLLGQSDLP RIKTEIEALK NLRHQHICQL YHVLETANKI FMVLEYCPGG    60
ELFDYIISQD RLSEEETRVV FRQIVSAVAY VHSQGYAHRD LKPENLLFDE YHKLKLIDFG   120
LCAKPKGNKD YHLQTCCGSL AYAAPELIQG KSYLGSEADV WSMGILLYVL MCGFLPFDDD   180
NVMALYKKIM RGKYDVPKWL SPSSILLLQQ MLQVDPKKRI SMKNLLNHPW IMQDYNYPVE   240
WQSKNPFIHL DDDCVTELSV HHRNNRQTME DLISLWQYDH LTATYLLLLA KKARGKPVRL   300
RLSSFSCGQA SATPFTDIKS NNWSLEDVTA SDKNYVAGLI DYDWCEDDLS TGAATPRTSQ   360
FTKYWTESNG VESKSLTPAL CRTPANKLKN KENVYTPKSA VKNEEYFMFP EPKTPVNKNQ   420
HKREILTTPN RYTTPSKARN QCLKETPIKI PVNSTGTDKL MTGVISPERR CRSVELDLNQ   480
AHMEETPKRK GAKVFGSLER GLDKVITVLT RSKRKGSARD GPRRLKLHYN VTTTRLVNPD   540
QLLNEIMSIL PKKHVDFVQK GYTLKCQTQS DFGKVTMQFE LEVCQLQKPD VVGIRRQRLK   600
GDAWVYKRLV EDILSSCKV                                                619

SEQ ID NO: 485          moltype = AA   length = 129
FEATURE                 Location/Qualifiers
source                  1..129
                        mol_type = protein
                        organism = Homo sapiens
SEQUENCE: 485
MVLEYCPGGE LFDYIISQDR LSEEETRVVF RQIVSAVAYV HSQGYAHRDL KPENLLFDEY    60
HKLKLIDFGL CAKPKGNKDY HLQTCCGSLA YAAPELIQGK SYLGSEMFGA WAYCYMFLCV   120
DFYHLMMIM                                                           129

SEQ ID NO: 486          moltype = AA   length = 532
FEATURE                 Location/Qualifiers
source                  1..532
                        mol_type = protein
                        organism = Homo sapiens
SEQUENCE: 486
MAPSFTARIQ LFLLRALGFL IGLVGRAALV LGGPKFASKT PRPVTEPLLL LSGMQLAKLI    60
RQRKVKCIDV VQAYINRIKD VNPMINGIVK YRFEEAMKEA HAVDQKLAEK QEDEATLENK   120
WPFLGVPLTV KEAFQLQGMP NSSGLMNRRD AIAKTDATVV ALLKGAGAIP LGITNCSELC   180
MWYESSNKIY GRSNNPYDLQ HIVGGSSGGE GCTLAAACSV IGVGSDIGGS IRMPAFFNGI   240
FGHKPSPGVV PNKGQFPLAV GAQELFLCTG PMCRYAEDLA PMLKVMAGPG IKRLKLDTKV   300
HLKDLKFYWM EHDGGSFLMS KVDQDLIMTQ KKVVVHLETI LGASVQHVKL KKMKYSFQLW   360
IAMMSAKGHD GKEPVKFVDL LGDHGKHVSP LWELIKWCLG LSVYTIPSIG LALLEEKLRY   420
SNEKYQKFKA VEESLRKELV DMLGDDGVFL YPSHPTVAPK HHVPLTRPFN FAYTGVFSAL   480
GLPVTQCPLG LNAKGLPLGI QVVAGPFNDH LTLAVAQYLE KTFGGWVCPG KF           532

SEQ ID NO: 487          moltype = AA   length = 563
FEATURE                 Location/Qualifiers
source                  1..563
                        mol_type = protein
                        organism = Homo sapiens
SEQUENCE: 487
MGLQACLLGL FALILSGKCS YSPEPDQRRT LPPGWVSLGR ADPEEELSLT FALRQQNVER    60
LSELVQAVSD PSSPQYGKYL TLENVADLVR PSPLTLHTVQ KWLLAAGAQK CHSVITQDFL   120
TCWLSIRQAE LLLPGAEFHH YVGGPTETHV VRSPHPYQLP QALAPHVDFV GGLHRFPPTS   180
SLRQRPEPQV TGTVGLHLGV TPSVIRKRYN LTSQDVGSGT SNNSQACAQF LEQYFHDSDL   240
AQFMRLFGGN FAHQASVARV VGQQRGRAG IEASLDVQYL MSAGANISTW VYSSPGRHEG    300
QEPFLQWLML LSNESALPHV HTVSYGDDED SLSSAYIQRV NTELMKAAAR GLTLLFASGD   360
SGAGCWSVSG RHQFRPTFPA SSPYVTTVGG TSFQEPFLIT NEIVDYISGG PSNVFPRPS    420
YQEEAVTKFL SSSPHLPPSS YFNASGRAYP DVAALSDGYW VVSNRVPIPW VSGTSASTPV   480
FGGILSLINE HRILSGRPPL GFLNPRLYQQ HGAGLFDVTR GCHESCLDEE VEGQGFCSGP   540
GWDPVTGWGT PNFPALLKTL LNP                                           563

SEQ ID NO: 488          moltype = AA   length = 177
FEATURE                 Location/Qualifiers
source                  1..177
                        mol_type = protein
                        organism = Homo sapiens
SEQUENCE: 488
MGLQACLLGL FALILSGKCS YSPEPDQRRT LPPGWVSLGR ADPEEELSLT FALRQQNVER    60
LSELVQAVSD PSSPQYGKYL TLENVADLVR PSPLTLHTVQ KWLLAAGAQK CHSVITQDFL   120
TCWLSIRQAE LLLPGAEFHH YVGGPTETHV AGMRDRSPSC SGSCCSVMSQ PCHMCIL      177

SEQ ID NO: 489          moltype = AA   length = 39
FEATURE                 Location/Qualifiers
source                  1..39
                        mol_type = protein
                        organism = Homo sapiens
SEQUENCE: 489
```

```
MGLQACLLGL FALILSGKCS YSPEPDQRRT KIPDPRECG                           39

SEQ ID NO: 490            moltype = AA   length = 30
FEATURE                   Location/Qualifiers
source                    1..30
                          mol_type = protein
                          organism = Homo sapiens
SEQUENCE: 490
MGLQACLLGL FALILSGKCS YSPEPDQRRT                                    30

SEQ ID NO: 491            moltype = AA   length = 387
FEATURE                   Location/Qualifiers
source                    1..387
                          mol_type = protein
                          organism = Homo sapiens
SEQUENCE: 491
MREPLEAFKL ADLDFRKSSL ASGWRMASGA FTMDQFPESV TENFEYDDLA EACYIGDIVV    60
FGTVFLSIFY SVIFAIGLVG NLLVVFALTN SKKPKSVTDI YLLNLALSDL LFVATLPFWT   120
HYLINEKGLH NAMCKFTTAF FFIGFFGSIF FITVISIDRY LAIVLAANSM NNRTVQHGVT   180
ISLGVWAAAI LVAAPQFMFT KQKENECLGD YPEVLQEIWP VLRNVETNFL GFLLPLLIMS   240
YCYFRIIQTL FSCKNHKKAK AIKLILLVVI VFFLFWTPYN VMIFLETLKL YDFFPSCDMR   300
KDLRLALSVT ETVAFSHCCL NPLIYAFAGE KFRRYLYHLY GKCLAVLCGR SVHVDFSSSE   360
SQRSRHGSVL SSNFTYHTSD GDALLLL                                      387

SEQ ID NO: 492            moltype = AA   length = 355
FEATURE                   Location/Qualifiers
source                    1..355
                          mol_type = protein
                          organism = Homo sapiens
SEQUENCE: 492
MDQFPESVTE NFEYDDLAEA CYIGDIVVFG TVFLSIFYSV IFAIGLVGNL LVVFALTNSK    60
KPKSVTDIYL LNLALSDLLF VATLPFWTHY LINEKGLHNA MCKFTTAFFF IGFFGSIFFI   120
TVISIDRYLA IVLAANSMNN RTVQHGVTIS LGVWAAAILV AAPQFMFTKQ KENECLGDYP   180
EVLQEIWPVL RNVETNFLGF LLPLLIMSYC YFRIIQTLFS CKNHKKAKAI KLILLVVIVF   240
FLFWTPYNVM IFLETLKLYD FFPSCDMRKD LRLALSVTET VAFSHCCLNP LIYAFAGEKF   300
RRYLYHLYGK CLAVLCGRSV HVDFSSSESQ RSRHGSVLSS NFTYHTSDGD ALLLL        355

SEQ ID NO: 493            moltype = AA   length = 106
FEATURE                   Location/Qualifiers
source                    1..106
                          mol_type = protein
                          organism = Homo sapiens
SEQUENCE: 493
MDQFPESVTE NFEYDDLAEA CYIGDIVVFG TVFLSIFYSV IFAIGLVGNL LVVFALTNSK    60
KPKSVTDIYL LNLALSDLLF VATLPFWTHY LINEKGLHNA MCKFTT                  106

SEQ ID NO: 494            moltype = AA   length = 166
FEATURE                   Location/Qualifiers
source                    1..166
                          mol_type = protein
                          organism = Homo sapiens
SEQUENCE: 494
MDQFPESVTE NFEYDDLAEA CYIGDIVVFG TVFLSIFYSV IFAIGLVGNL LVVFALTNSK    60
KPKSVTDIYL LNLALSDLLF VATLPFWTHY LINEKGLHNA MCKFTTAFFF IGFFGSIFFI   120
TVISIDRYLA IVLAANSMNN RTVQHGVTIS LGVWAAAILV AAPQFM                  166

SEQ ID NO: 495            moltype = AA   length = 355
FEATURE                   Location/Qualifiers
source                    1..355
                          mol_type = protein
                          organism = Homo sapiens
SEQUENCE: 495
MDQFPESVTE NFEYDDLAEA CYIGDIVVFG TVFLSIFYSV IFAIGLVGNL LVVFALTNSK    60
KPKSVTDIYL LNLALSDLLF VATLPFWTHY LINEKGLHNA MCKFTTAFFF IGFFGSIFFI   120
TVISIDRYLA IVLAANSMNN RTVQHGVTIS LGVWAAAILV AAPQFMFTKQ KENECLGDYP   180
EVLQEIWPVL RNVETNFLGF LLPLLIMSYC YFRIIQTLFS CKNHKKAKAI KLILLVVIVF   240
FLFWTPYNVM IFLETLKLYD FFPSCDMRKD LRLALSVTET VAFSHCCLNP LIYAFAGEKF   300
RRYLYHLYGK CLAVLCGRSV HVDFSSSESQ RSRHGSVLSS NFTYHTSDGD ALLLL        355

SEQ ID NO: 496            moltype = AA   length = 355
FEATURE                   Location/Qualifiers
source                    1..355
                          mol_type = protein
                          organism = Homo sapiens
SEQUENCE: 496
MDQFPESVTE NFEYDDLAEA CYIGDIVVFG TVFLSIFYSV IFAIGLVGNL LVVFALTNSK    60
KPKSVTDIYL LNLALSDLLF VATLPFWTHY LINEKGLHNA MCKFTTAFFF IGFFGSIFFI   120
TVISIDRYLA IVLAANSMNN RTVQHGVTIS LGVWAAAILV AAPQFMFTKQ KENECLGDYP   180
EVLQEIWPVL RNVETNFLGF LLPLLIMSYC YFRIIQTLFS CKNHKKAKAI KLILLVVIVF   240
```

```
FLFWTPYNVM IFLETLKLYD FFPSCDMRKD LRLALSVTET VAFSHCCLNP LIYAFAGEKF  300
RRYLYHLYGK CLAVLCGRSV HVDFSSSESQ RSRHGSVLSS NFTYHTSDGD ALLLL      355

SEQ ID NO: 497          moltype = AA  length = 268
FEATURE                 Location/Qualifiers
source                  1..268
                        mol_type = protein
                        organism = Homo sapiens
SEQUENCE: 497
MSGKHYKGPE VSCCIKYFIF GFNVIFWFLG ITFLGIGLWA WNEKGVLSNI SSITDLGGFD  60
PVWLFLVVGG VMFILGFAGC IGALRENTFL LKFFSVFLGI IFFLELTAGV LAFVFKDWIK  120
DQLYFFINNN IRAYRDDIDL QNLIDFTQEY WQCCGAFGAD DWNLNIYFNC TDSNASRERC  180
GVPFSCCTKD PAEDVINTQC GYDARQKPEV DQQIVIYTKG CVPQFEKWLQ DNLTIVAGIF  240
IGIALLQIFG ICLAQNLVSD IEAVRASW                                    268

SEQ ID NO: 498          moltype = AA  length = 197
FEATURE                 Location/Qualifiers
source                  1..197
                        mol_type = protein
                        organism = Homo sapiens
SEQUENCE: 498
MFILGFAGCI GALRENTFLL KFFSVFLGII FFLELTAGVL AFVFKDWIKD QLYFFINNNI  60
RAYRDDIDLQ NLIDFTQEYW QCCGAFGADD WNLNIYFNCT DSNASRERCG VPFSCCTKDP  120
AEDVINTQCG YDARQKPEVD QQIVIYTKGC VPQFEKWLQD NLTIVAGIFI GIALLQIFGI  180
CLAQNLVSDI EAVRASW                                                197

SEQ ID NO: 499          moltype = AA  length = 193
FEATURE                 Location/Qualifiers
source                  1..193
                        mol_type = protein
                        organism = Homo sapiens
SEQUENCE: 499
MSGKHYKGPE VSCCIKYFIF GFNVIFWFLG ITFLGIGLWA WNEKGVLSNI SSITDLGGFD  60
PVWLFLVVGG VMFILGFAGC IGALRENTFL LKFFSVFLGI IFFLELTAGV LAFVFKDWIK  120
DQLYFFINNN IRAYRDDIDL QNLIDFTQEY IPMQVESDVA FHSPAALKIP QKMSSTLSVA  180
MMPGKNQKLT SRL                                                    193

SEQ ID NO: 500          moltype = AA  length = 60
FEATURE                 Location/Qualifiers
source                  1..60
                        mol_type = protein
                        organism = Homo sapiens
SEQUENCE: 500
MFILGFAGCI GALRENTFLL KFFSVFLGII FFLELTAGVL AFVFKDWIKD QLYFFINNNI  60

SEQ ID NO: 501          moltype = AA  length = 38
FEATURE                 Location/Qualifiers
source                  1..38
                        mol_type = protein
                        organism = Homo sapiens
SEQUENCE: 501
MFILGFAGCI GALRENTFLL KFLKSPVLTE QAENYTFL                          38

SEQ ID NO: 502          moltype = AA  length = 110
FEATURE                 Location/Qualifiers
source                  1..110
                        mol_type = protein
                        organism = Homo sapiens
SEQUENCE: 502
MFILGFAGCI GALRENTFLL KFFSVFLGII FFLELTAGVL AFVFKDWIKD QLYFFINNNI  60
RAYRDDIDLQ NLIDFTQEYW QCCGAFGADD WNLNIYFNCT DSNASRERCG            110

SEQ ID NO: 503          moltype = AA  length = 87
FEATURE                 Location/Qualifiers
source                  1..87
                        mol_type = protein
                        organism = Homo sapiens
SEQUENCE: 503
XVSCCIKYFI FGFNVIFWFL GITFLGIGLW AWNEKGVLSN ISSITDLGGF DPVWLFLVVG  60
GVMFILGFAG CIGALRENTF LLKFDKQ                                     87

SEQ ID NO: 504          moltype = AA  length = 29
FEATURE                 Location/Qualifiers
source                  1..29
                        mol_type = protein
                        organism = Homo sapiens
SEQUENCE: 504
SFASLKSGTC ACTQTGRAGE AGGLRKAGS                                    29
```

| | | |
|---|---|---|
| SEQ ID NO: 505 | moltype = AA   length = 37 | |
| FEATURE | Location/Qualifiers | |
| source | 1..37 | |
| | mol_type = protein | |
| | organism = Homo sapiens | |
| SEQUENCE: 505 | | |

MLLYPAGFSF ASLKSGTCAC TQTGRAGEAG GLRKAGS                                              37

| | | |
|---|---|---|
| SEQ ID NO: 506 | moltype = AA   length = 677 | |
| FEATURE | Location/Qualifiers | |
| source | 1..677 | |
| | mol_type = protein | |
| | organism = Homo sapiens | |
| SEQUENCE: 506 | | |

MPGFLVRILP LLLVLLLLGP TRGLRNATQR MFEIDYSRDS FLKDGQPFRY ISGSIHYSRV    60
PRFYWKDRLL KMKMAGLNAI QTYVPWNFHE PWPGQYQFSE DHDVEYFLRL AHELGLLVIL   120
RPGPYICAEW EMGGLPAWLL EKESILLRSS DPDYLAAVDK WLGVLLPKMK PLLYQNGGPV   180
ITVQVENEYG SYFACDFDYL RFLQKRFRHH LGDDVVLFTT DGAHKTFLKC GALQGLYTTV   240
DFGTGSNITD AFLSQRKCEP KGPLINSEFY TGWLDHWGQP HSTIKTEAVA SSLYDILARG   300
ASVNLYMFIG GTNFAYWNGA NSPYAAQPTS YDYDAPLSEA GDLTEKYFAL RNIIQKFEKV   360
PEGPIPPSTP KFAYGKVTLE KLKTVGAALD ILCPSGPIKS LYPLTFIQVK QHYGFVLYRT   420
TLPQDCSNPA PLSSPLNGVH DRAYVAVDGI PQGVLERNNV ITLNITGKAG ATLDLLVENM   480
GRVNYGAYIN DFKGLVSNLT LSSNILTDWT IFPLDTEDAV CSHLGGWGHR DSGHHDEAWA   540
HNSSNYTLPA FYMGNFSIPS GIPDLPQDTF IQFPGWTKGQ VWINGFNLGR YWPARGPQLT   600
LFVPQHILMT SAPNTITVLE LEWAPCSSDD PELCAVTFVD RPVIGSSVTY DHPSKPVEKR   660
LMPPPPQKNK DSWLDHV                                                 677

| | | |
|---|---|---|
| SEQ ID NO: 507 | moltype = AA   length = 546 | |
| FEATURE | Location/Qualifiers | |
| source | 1..546 | |
| | mol_type = protein | |
| | organism = Homo sapiens | |
| SEQUENCE: 507 | | |

MPGFLVRILP LLLVLLLLGP TRGLRNATQR MFEIDYSRDS FLKDGQPFRY ISGSIHYSRV    60
PRFYWKDRLL KMKMAGLNAI QTLPGSCGQV VGSPSAQDEA SPLSEWRASY NSAGSNITDA   120
FLSQRKCEPK GPLINSEFYT GWLDHWGQPH STIKTEAVAS SLYDILARGA SVNLYMFIGG   180
TNFAYWNGAN SPYAAQPTSY DYDAPLSEAG DLTEKYFALR NIIQKFEKVP EGPIPPSTPK   240
FAYGKVTLEK LKTVGAALDI LCPSGPIKSL YPLTFIQVKQ HYGFVLYRTT LPQDCSNPAP   300
LSSPLNGVHD RAYVAVDGIP QGVLERNNVI TLNITGKAGA TLDLLVENMG RVNYGAYIND   360
FKGLVSNLTL SSNILTDWTI FPLDTEDAVC SHLGGWGHRD SGHHDEAWAH NSSNYTLPAF   420
YMGNFSIPSG IPDLPQDTFI QFPGWTKGQV WINGFNLGRY WPARGPQLTL FVPQHILMTS   480
APNTITVLEL EWAPCSSDDP ELCAVTFVDR PVIGSSVTYD HPSKPVEKRL MPPPPQKNKD   540
SWLDHV                                                             546

| | | |
|---|---|---|
| SEQ ID NO: 508 | moltype = AA   length = 647 | |
| FEATURE | Location/Qualifiers | |
| source | 1..647 | |
| | mol_type = protein | |
| | organism = Homo sapiens | |
| SEQUENCE: 508 | | |

MFEIDYSRDS FLKDGQPFRY ISGSIHYSRV PRFYWKDRLL KMKMAGLNAI QTYVPWNFHE    60
PWPGQYQFSE DHDVEYFLRL AHELGLLVIL RPGPYICAEW EMGGLPAWLL EKESILLRSS   120
DPDYLAAVDK WLGVLLPKMK PLLYQNGGPV ITVQVENEYG SYFACDFDYL RFLQKRFRHH   180
LGDDVVLFTT DGAHKTFLKC GALQGLYTTV DFGTGSNITD AFLSQRKCEP KGPLINSEFY   240
TGWLDHWGQP HSTIKTEAVA SSLYDILARG ASVNLYMFIG GTNFAYWNGA NSPYAAQPTS   300
YDYDAPLSEA GDLTEKYFAL RNIIQKFEKV PEGPIPPSTP KFAYGKVTLE KLKTVGAALD   360
ILCPSGPIKS LYPLTFIQVK QHYGFVLYRT TLPQDCSNPA PLSSPLNGVH DRAYVAVDGI   420
PQGVLERNNV ITLNITGKAG ATLDLLVENM GRVNYGAYIN DFKGLVSNLT LSSNILTDWT   480
IFPLDTEDAV CSHLGGWGHR DSGHHDEAWA HNSSNYTLPA FYMGNFSIPS GIPDLPQDTF   540
IQFPGWTKGQ VWINGFNLGR YWPARGPQLT LFVPQHILMT SAPNTITVLE LEWAPCSSDD   600
PELCAVTFVD RPVIGSSVTY DHPSKPVEKR LMPPPPQKNK DSWLDHV                 647

| | | |
|---|---|---|
| SEQ ID NO: 509 | moltype = AA   length = 185 | |
| FEATURE | Location/Qualifiers | |
| source | 1..185 | |
| | mol_type = protein | |
| | organism = Homo sapiens | |
| SEQUENCE: 509 | | |

MPGFLVRILP LLLVLLLLGP TRGLRVENEY GSYFACDFDY LRFLQKRFRH HLGDDVVLFT    60
TDGAHKTFLK CGALQGLYTT VDFGTGSNIT DAFLSQRKCE PKGPLINSEF YTGWLDHWGQ   120
PHSTIKTEAV ASSLYDILAR GASVNLYMFI GGTNFAYWNG ANSPYAAQPT SYDYDAPLSE   180
AGDLT                                                              185

| | | |
|---|---|---|
| SEQ ID NO: 510 | moltype = AA   length = 147 | |
| FEATURE | Location/Qualifiers | |
| source | 1..147 | |
| | mol_type = protein | |
| | organism = Homo sapiens | |
| SEQUENCE: 510 | | |

```
MPGFLVRILP LLLVLLLLGP TRGLRSRFLP WAFHLPRQAP KSQLPLHKRG TKTAPNEHAS    60
SNRSGRRRRR QQWNATQRMF EIDYSRDSFL KDGQPFRYIS GSIHYSRVPR FYWKDRLLKM   120
KMAGLNAIQT YVPWNFHEPW PGQYQFS                                      147

SEQ ID NO: 511          moltype = AA   length = 41
FEATURE                 Location/Qualifiers
source                  1..41
                        mol_type = protein
                        organism = Homo sapiens
SEQUENCE: 511
MPGFLVRILP LLLVLLLLGP TRGLRITWQL WTSGWESFCP R                       41

SEQ ID NO: 512          moltype = AA   length = 114
FEATURE                 Location/Qualifiers
source                  1..114
                        mol_type = protein
                        organism = Homo sapiens
SEQUENCE: 512
MGGLPAWLLE KESILLRSSD PDYLAAVDKW LGVLLPKMKP LLYQNGGPVI TVQVENEYGS    60
YFACDFDYLR FLQKRFRHHL GDDVVLFTTD GAHKTFLKCG ALQGLYTTVD FGTG         114

SEQ ID NO: 513          moltype = AA   length = 84
FEATURE                 Location/Qualifiers
source                  1..84
                        mol_type = protein
                        organism = Homo sapiens
SEQUENCE: 513
MFEIDYSRDS FLKDGQPFRY ISGSIHYSRV PRFYWKDRLL KMKMAGLNAI QTLPGSCGQV    60
VGSPSAQDEA SPLSEWRASY NSAG                                          84

SEQ ID NO: 514          moltype = AA   length = 102
FEATURE                 Location/Qualifiers
source                  1..102
                        mol_type = protein
                        organism = Homo sapiens
SEQUENCE: 514
MFEIDYSRDS FLKDGQPFRY ISGSIHYSRV PRFYWKDRLL KMKMAGLNAI QTYVPWNFHE    60
PWPGQYQFSE DHDVEYFLRL AHELGLLVIL RPGPYICAEW EM                     102

SEQ ID NO: 515          moltype = AA   length = 150
FEATURE                 Location/Qualifiers
source                  1..150
                        mol_type = protein
                        organism = Homo sapiens
SEQUENCE: 515
XLGWSKAGSG SVCLALDQLR DVIESQEELI HQLRNVMVLQ DENFVSKEEF QAVEKKLVEE    60
KAAHAKTKVL LAKEEEKLQF ALGEVEVLSK QLEKEKLAFE KALSSVKSKV LQESSKKDQL   120
ITKCNGITCL TSGSRSSRRA TWPRCWTRSI                                   150

SEQ ID NO: 516          moltype = AA   length = 63
FEATURE                 Location/Qualifiers
source                  1..63
                        mol_type = protein
                        organism = Homo sapiens
SEQUENCE: 516
MAASGEPQRQ WQEEVAAVVV VGSCMTDLVR RMCMRICYVH FCCQPTPQLQ NCSSLCVITC    60
QEN                                                                 63

SEQ ID NO: 517          moltype = AA   length = 518
FEATURE                 Location/Qualifiers
source                  1..518
                        mol_type = protein
                        organism = Homo sapiens
SEQUENCE: 517
MALERLCSVL KVLLITVLVV EGIAVAQKTQ DGQNIGIKHI PATQCGIWVR TSNGGHFASP    60
NYPDSYPPNK ECIYILEAAP RQRIELTFDE HYYIEPSFEC RFDHLEVRDG PFGFSPLIDR   120
YCGVKSPPLI RSTGRFMWIK FSSDEELEGL GFRAKYSFIP DPDFTYLGDC QFELSGADGI   180
VRSSQVEQEE KTKPGQAVDC IWTIKATPKA KIYLRFLDYQ MEHSNECKRN FVAVYDGSSS   240
IENLKAKFCS TVANDVMLKT GIGVIRMWAD EGSRLSRFRM LFTSFVEPPC TSSTFFCHSN   300
MCINNSLVCN GVQNCAYPWD ENHCKEKKKA GVFEQITKTH GTIIGITSGI VLVLLIISIL   360
VQVKQPRKKV MACKTAFNKT GFQEVFDPPH YELFSLRDKE ISADLADLSE ELDNYQKMRR   420
SSTASRCIHD HHCGSQASSV KQSRTNLSSM ELPFRNDFAQ PQPMKTFNST FKKSSYTFKQ   480
GHECPEQALE DRVMEEIPCE IYVRGREDSA QASISIDF                          518

SEQ ID NO: 518          moltype = AA   length = 525
FEATURE                 Location/Qualifiers
source                  1..525
                        mol_type = protein
                        organism = Homo sapiens
```

```
SEQUENCE: 518
MALERLCSVL KVLLITVLVV EGIAVAQKTQ DGQNIGIKHI PATQCGIWVR TSNGGHFASP   60
NYPDSYPPNK ECIYILEAAP RQRIELTFDE HYYIEPSFEC RFDHLEVRDG PFGFSPLIDR  120
YCGVKSPPLI RSTGRFMWIK FSSDEELEGL GFRAKYSFIP DPDFTYLGGI LNPIPDCQFE  180
LSGADGIVRS SQVEQEEKTK PGQAVDCIWT IKATPKAKIY LRFLDYQMEH SNECKRNFVA  240
VYDGSSSIEN LKAKFCSTVA NDVMLKTGIG VIRMWADEGS RLSRFRMLFT SFVEPPCTSS  300
TFFCHSNMCI NNSLVCNGVQ NCAYPWDENH CKEKKKAGVF EQITKTHGTI IGITSGIVLV  360
LLIISILVQV KQPRKKVMAC KTAFNKTGFQ EVFDPPHYEL FSLRDKEISA DLADLSEELD  420
NYQKMRRSST ASRCIHDHHC GSQASSVKQS RTNLSSMELP FRNDFAQPQP MKTFNSTFKK  480
SSYTFKQGHE CPEQALEDRV MEEIPCEIYV RGREDSAQAS ISIDF                 525

SEQ ID NO: 519          moltype = AA   length = 365
FEATURE                 Location/Qualifiers
source                  1..365
                        mol_type = protein
                        organism = Homo sapiens
SEQUENCE: 519
XLIDRYCGVK SPPLIRSTGR FMWIKFSSDE ELEGLGFRAK YSFIPDPDFT YLGDCQFELS   60
GADGIVRSSQ VEQEEKTKPG QAVDCIWTIK ATPKAKIYLR FLDYQMEHSN ECKRNFVAVY  120
DGSSSIENLK AKFCSTVAND VMLKTGIGVI RMWADEGSRL SRFRMLFTSF VEQKKKAGVF  180
EQITKTHGTI IGITSGIVLV LLIISILVQV KQPRKKVMAC KTAFNKTGFQ EVFDPPHYEL  240
FSLRDKEISA DLADLSEELD NYQKMRRSST ASRCIHDHHC GSQASSVKQS RTNLSSMELP  300
FRNDFAQPQP MKTFNSTFKK SSYTFKQGHE CPEQALEDRV MEEIPCEIYV RGREDSAQAS  360
ISIDF                                                              365

SEQ ID NO: 520          moltype = AA   length = 194
FEATURE                 Location/Qualifiers
source                  1..194
                        mol_type = protein
                        organism = Homo sapiens
SEQUENCE: 520
XTYLGGILNP IPDCQFELSG ADGIVRSSQV EQEEKTKPGQ AVDCIWTIKA TPKAKIYLRF   60
LDYQMEHSNE CKRNFVAVYD GSSSIENLKA KFCSTVANDV MLKTGIGVIR MWADEGSRLS  120
RFRMLFTSFV EQKKKAGVFE QITKTHGTII GITSGIVLVL LIISILVQVK QPRKKVMACK  180
TAFNKTGFQE VFDP                                                    194

SEQ ID NO: 521          moltype = AA   length = 228
FEATURE                 Location/Qualifiers
source                  1..228
                        mol_type = protein
                        organism = Homo sapiens
SEQUENCE: 521
XSSSIENLKA KFCSTVANDV MLKTGIGVIR MWADEEKKKA GVFEQITKTH GTIIGITSGI   60
VLVLLIISIL VQVKQPRKKV MACKTAFNKT GFQEVFDPPH YELFSLRDKE ISADLADLSE  120
ELDNYQKMRR SSTASRCIHD HHCGSQASSV KQSRTNLSSM ELPFRNDFAQ PQPMKTFNST  180
FKKSSYTFKQ GHECPEQALE DRVMEEIPCE IYVRGREDSA QASISIDF               228

SEQ ID NO: 522          moltype = AA   length = 347
FEATURE                 Location/Qualifiers
source                  1..347
                        mol_type = protein
                        organism = Homo sapiens
SEQUENCE: 522
MSSWSRQRPK SPGGIQPHVS RTLFLLLLLA ASAWGVTLSP KDCQVFRSDH GSSISCQPPA   60
EIPGYLPADT VHLAVEFFNL THLPANLLQG ASKLQELHLS SNGLESLSPE FLRPVPQLRV  120
LDLTRNALTG LPPGLFQASA TLDTLVLKEN QLEVLEVSWL HGLKALGHLD LSGNRLRKLP  180
PGLLANFTLL RTLDLGENQL ETLPPDLLRG PLQLERLHLE GNKLQVLGKD LLLPQPDLRY  240
LFLNGNKLAR VAAGAFQGLR QLDMLDLSNN SLASVPEGLW ASLGQPNWDM RDGFDISGNP  300
WICDQNLSDL YRWLQAQKDK MFSQNDTRCA GPEAVKGQTL LAVAKSQ                347

SEQ ID NO: 523          moltype = AA   length = 330
FEATURE                 Location/Qualifiers
source                  1..330
                        mol_type = protein
                        organism = Homo sapiens
SEQUENCE: 523
MRGPEPGPQP TMEGDVLDTL EALGYKGPLL EEQALTKAAE GGLSSPEFSE LCIWLGSQIK   60
SLCNLEESIT SAGRDDLESF QLEISGFLKE MACPYSVLIS GDIKDRLKKK EDCLKLLLFL  120
STELQASQIL QNKKHKNSQL DKNSEVYQEV QAMFDTLGIP KSTTSDIPHM LNQVESKVKD  180
ILSKVQKNHV GKPLLKMDLN SEQAEQLERI NDALSCEYEC RRRMLMKRLD VTVQSFGWSD  240
RAKVKTDDIA RIYQPKRYAL SPKTTITMAH LLAAREDLSK IIRTSSGTSR EKTACAINKV  300
GVSFSTVENE LMISYLMFLQ ILVYFSFMSW                                   330

SEQ ID NO: 524          moltype = AA   length = 101
FEATURE                 Location/Qualifiers
source                  1..101
                        mol_type = protein
                        organism = Homo sapiens
SEQUENCE: 524
```

```
ISGDIKDRLK KKEDCLKLLL FLSTELQASQ ILQNKKHKNS QLDKNSEVYQ EVQAMFDTLG    60
IPKSTTSDIP HMLNQVESKV KDILSKIHME EVVVVVVVV  E                      101

SEQ ID NO: 525          moltype = AA  length = 352
FEATURE                 Location/Qualifiers
source                  1..352
                        mol_type = protein
                        organism = Homo sapiens
SEQUENCE: 525
MKPALLEVMR MNRICRMVLA TCLGSFILVI FYFQSMLHPV MRRNPFGVDI CCRKGSRSPL    60
QELYNPIQLE LSNTAVLHQM RRDQVTDTCR ANSATSRKRR VLTPNDLKHL VVDEDHELIY   120
CYVPKVACTN WKRLMMVLTG RGKYSDPMEI PANEAHVSAN LKTLNQYSIP EINHRLKSYM   180
KFLFVREPFE RLVSAYRNKF TQKYNISFHK RYGTKIIKRQ RKNATQEALR KGDDVKFEEF   240
VAYLIDPHTQ REEPFNEHWQ TVYSLCHPCH IHYDLVGKYE TLEEDSNYVL QLAGVGSYLK   300
FPTYAKSTRT TDEMTTEFFQ NISSEHQTQL YEVYKLDFLM FNYSVPSYLK LE           352

SEQ ID NO: 526          moltype = AA  length = 72
FEATURE                 Location/Qualifiers
source                  1..72
                        mol_type = protein
                        organism = Homo sapiens
SEQUENCE: 526
MKPALLEVMR MNRICRMVLA TCLGSFILVI FYFQIMRRNP FGVDICCRKG SRSPLQELYN    60
PIQVSFKHSV SM                                                       72

SEQ ID NO: 527          moltype = AA  length = 77
FEATURE                 Location/Qualifiers
source                  1..77
                        mol_type = protein
                        organism = Homo sapiens
SEQUENCE: 527
MKPALLEVMR MNRICRMVLA TCLGSFILVI FYFQSMLHPV MRRNPFGVDI CCRKGSRSPL    60
QELYNPIQVS FKHSVSM                                                  77

SEQ ID NO: 528          moltype = AA  length = 347
FEATURE                 Location/Qualifiers
source                  1..347
                        mol_type = protein
                        organism = Homo sapiens
SEQUENCE: 528
MKPALLEVMR MNRICRMVLA TCLGSFILVI FYFQIMRRNP FGVDICCRKG SRSPLQELYN    60
PIQLELSNTA VLHQMRRDQV TDTCRANSAT SRKRRVLTPN DLKHLVVDED HELIYCYVPK   120
VACTNWKRLM MVLTGRGKYS DPMEIPANEA HVSANLKTLN QYSIPEINHR LKSYMKFLFV   180
REPFERLVSA YRNKFTQKYN ISFHKRYGTK IIKRQRKNAT QEALRKGDDV KFEEFVAYLI   240
DPHTQREEPF NEHWQTVYSL CHPCIHYDL VGKYETLEED SNYVLQLAGV GSYLKFPTYA    300
KSTRTTDEMT TEFFQNISSE HQTQLYEVYK LDFLMFNYSV PSYLKLE                 347

SEQ ID NO: 529          moltype = AA  length = 775
FEATURE                 Location/Qualifiers
source                  1..775
                        mol_type = protein
                        organism = Homo sapiens
SEQUENCE: 529
MEPPYSLTAH YDEFQEVKYV SRCGAGGARG ASLPPGFPLG AARSATGARS GLPRWNRREV    60
CLLSGLVFAA GLCAILAAML ALKYLGPVAA GGGACPEGCP ERKAFARAAR FLAANLDASI   120
DPCQDFYSFA CGGWLRRHAI PDDKLTYGTI AAIGEQNEER LRRLLARPGG GPGGAAQRKV   180
RAFFRSCLDM REIERLGPRP MLEVIEDCGG WDLGGAEERP GVAARWDLNR LLYKAQGVYS   240
AAALFSLTVS LDDRNSSRYV IRIDQDGLTL PERTLYLAQD EDSEKILAAY RVFMERVLSL   300
LGADAVEQKA QEILQVEQQL ANITVSEHDD LRRDVSSMYN KVTLGQLQKI TPHLRWKWLL   360
DQIFQEDFSE EEEVVLLATD YMQQVSQLIR STPHRVLHNY LVWRVVVLS EHLSPPFREA    420
LHELAQEMEG SDKPQELARV CLGQANRHFG MALGALFVHE HFSAASKAKV QQLVEDIKYI   480
LGQRLEELDW MDAETRAAAR AKLQYMMVMV GYPDFLLKPD AVDKEYEFEV HEKTYFKNIL   540
NSIRFSIQLS VKKIRQEVDK STWLLPPQAL NAYYLPNKNQ MVFPPAGILQP TLYDPDFPQS   600
LNYGGIGTII GHELTHGYDD WGGQYDRSGN LLHWWTEASY SRFLRKAECI VRLYDNFTVY   660
NQRVNGKHTL GENIADMGGL KLAYHAYQKW VREHGPEHPL PRLKYTHDQL FFIAFAQNWC   720
IKRRSQSIYL QVLTDKHAPE HYRVLGSVSQ FEEFGRAFHC PKDSPMNPAH KCSVW        775

SEQ ID NO: 530          moltype = AA  length = 773
FEATURE                 Location/Qualifiers
source                  1..773
                        mol_type = protein
                        organism = Homo sapiens
SEQUENCE: 530
MEPPYSLTAH YDEFQEVKYV SRCGAGGARG ASLPPGFPLG AARSATGARS GLPRWNRREV    60
CLLSGLVFAA GLCAILAAML ALKYLGPVAA GGGACPEGCP ERKAFARAAR FLAANLDASI   120
DPCQDFYSFA CGGWLRRHAI PDDKLTYGTI AAIGEQNEER LRRLLARPGG GPGGAAQRKV   180
RAFFRSCLDM REIERLGPRP MLEVIEDCGG WDLGGAEERP GVAARWDLNR LLYKAQGVYS   240
AAALFSLTVS LDDRNSSRYV IRIDQDGLTL PERTLYLAQD EDSEKILAAY RVFMERVLSL   300
LGADAVEQKA QEILQVEQQL ANITVSEHDD LRRDVSSMYN KVTLGQLQKI TPHLRWKWLL   360
```

```
DQIFQEDFSE EEEVVLLATD YMQQVSQLIR STPHRVLHNY LVWRVVVLS  EHLSPPFREA    420
LHELAQEMEG SDKPQELARV CLGQANRHFG MALGALFVHE HFSAASKAKV  QQLVEDIKYI    480
LGQRLEELDW MDAETRAAAR AKLQYMMVMV GYPDFLLKPD AVDKEYEFEV  HEKTYFKNIL    540
NSIRFSIQLS VKKIRQEVDK WLLPPQALNA YYLPNKNQMV FPAGILQPTL  YDPDFPQSLN    600
YGGIGTIIGH ELTHGYDDWG GQYDRSGNLL HWWTEASYSR FLRKAECIVR  LYDNFTVYNQ    660
RVNGKHTLGE NIADMGGLKL AYHAYQKWVR EHGPEHPLPR LKYTHDQLFF  IAFAQNWCIK    720
RRSQSIYLQV LTDKHAPEHY RVLGSVSQFE EFGRAFHCPK DSPMNPAHKC  SVW           773

SEQ ID NO: 531          moltype = AA   length = 233
FEATURE                 Location/Qualifiers
source                  1..233
                        mol_type = protein
                        organism = Homo sapiens
SEQUENCE: 531
MSQSNRELVV DFLSYKLSQK GYSWSQFSDV EENRTEAPEG TESEMETPSA INGNPSWHLA     60
DSPAVNGATG HSSSLDAREV IPMAAVKQAL REAGDEFELR YRRAFSDLTS QLHITPGTAY    120
QSFEQVVNEL FRDGVNWGRI VAFFSFGGAL CVESVDKEMQ VLVSRIAAWM ATYLNDHLEP    180
WIQENGGWDT FVELYGNNAA AESRKGQERF NRWFLTGMTV AGVVLLGSLF SRK           233

SEQ ID NO: 532          moltype = AA   length = 170
FEATURE                 Location/Qualifiers
source                  1..170
                        mol_type = protein
                        organism = Homo sapiens
SEQUENCE: 532
MSQSNRELVV DFLSYKLSQK GYSWSQFSDV EENRTEAPEG TESEMETPSA INGNPSWHLA     60
DSPAVNGATG HSSSLDAREV IPMAAVKQAL REAGDEFELR YRRAFSDLTS QLHITPGTAY    120
QSFEQDTFVE LYGNNAAAES RKGQERFNRW FLTGMTVAGV VLLGSLFSRK               170

SEQ ID NO: 533          moltype = AA   length = 233
FEATURE                 Location/Qualifiers
source                  1..233
                        mol_type = protein
                        organism = Homo sapiens
SEQUENCE: 533
MSQSNRELVV DFLSYKLSQK GYSWSQFSDV EENRTEAPEG TESEMETPSA INGNPSWHLA     60
DSPAVNGATG HSSSLDAREV IPMAAVKQAL REAGDEFELR YRRAFSDLTS QLHITPGTAY    120
QSFEQVVNEL FRDGVNWGRI VAFFSFGGAL CVESVDKEMQ VLVSRIAAWM ATYLNDHLEP    180
WIQENGGWDT FVELYGNNAA AESRKGQERF NRWFLTGMTV AGVVLLGSLF SRK           233

SEQ ID NO: 534          moltype = AA   length = 813
FEATURE                 Location/Qualifiers
source                  1..813
                        mol_type = protein
                        organism = Homo sapiens
SEQUENCE: 534
MSLLGDPLQA LPPSAAPTGP LLAPPAGATL NRLREPLLRR LSELLDQAPE GRGWRRLAEL     60
AGSRGRLRLS CLDLEQCSLK VLEPEGSPSL CLLKLMGEKG CTVTELSDFL QAMEHTEVLQ    120
LLSPPGIKIT VNPESKAVLA GQFVKLCCRA TGHPFVQYQW FKMNKEIPNG NTSELIFNAV    180
HVKDAGFYVC RVNNNFTFEF SQWSQLDVCD IPESFQRSVD GVSESKLQIC VEPTSQKLMP    240
GSTLVLQCVA VGSPIPHYQW FKNELPLTHE TKKLYMVPYV DLEHQGTYWC HVYNDRDSQD    300
SKKVEIIIDE LNNLGHPDNK EQTTDQPLAK DKVALLIGNM NYREHPKLKA PLVDVYELTN    360
LLRQLDFKVV SLLDLTEYEM RNAVDEFLLL LDKGVYGLLY YAGHGYENFG NSFMVPVDAP    420
NPYRSENCLC VQNILKLMQE KETGLNVFLL DMCRKRNDYD DTIPILDALK VTANIVFGYA    480
TCQGAEAFEI QHSGLANGIF MKFLKDRLLE DKKITVLLDE VAEDMGKCHL TKGKQALEIR    540
SSLSEKRALT DPIQGTEYSA ESLVRNLQWA KAHELPESMC LKFDCGVQIQ LGFAAEFSNV    600
MIIYTSIVYK PPEIIMCDAY VTDFPLDLDI DPKDANKGTP EETGSYLVSK DLPKHCLYTR    660
LSSLQKLKEH LVFTVCLSYQ YSGLEDTVED KQEVNVGKPL IAKLDMHRGL GRKTCFQTCL    720
MSNGPYQSSA ATSGGAGHYH SLQDPFHGVY HSHPGNPSNV TPADSCHCSR TPDAFISSFA    780
HHASCHFSRS NVPVETTDEI PFSFSDRLRI SEK                                 813

SEQ ID NO: 535          moltype = AA   length = 824
FEATURE                 Location/Qualifiers
source                  1..824
                        mol_type = protein
                        organism = Homo sapiens
SEQUENCE: 535
MSLLGDPLQA LPPSAAPTGP LLAPPAGATL NRLREPLLRR LSELLDQAPE GRGWRRLAEL     60
AGSRGRLRLS CLDLEQCSLK VLEPEGSPSL CLLKLMGEKG CTVTELSDFL QAMEHTEVLQ    120
LLSPPGIKIT VNPESKAVLA GQFVKLCCRA TGHPFVQYQW FKMNKEIPNG NTSELIFNAV    180
HVKDAGFYVC RVNNNFTFEF SQWSQLDVCD IPESFQRSVD GVSESKLQIC VEPTSQKLMP    240
GSTLVLQCVA VGSPIPHYQW FKNELPLTHE TKKLYMVPYV DLEHQGTYWC HVYNDRDSQD    300
SKKVEIIIGR TDEAVECTED ELNNLGHPDN KEQTTDQPLA KDKVALLIGN MNYREHPKLK    360
APLVDVYELT NLLRQLDFKV VSLLDLTEYE MRNAVDEFLL LLDKGVYGLL YYAGHGYENF    420
GNSFMVPVDA PNPYRSENCL CVQNILKLMQ EKETGLNVFL LDMCRKRNDY DDTIPILDAL    480
KVTANIVFGY ATCQGAEAFE IQHSGLANGI FMKFLKDRLL EDKKITVLLD EVAEDMGKCH    540
LTKGKQALEI RSSLSEKRAL TDPIQGTEYS AESLVRNLQW AKAHELPESM CLKFDCGVQI    600
QLGFAAEFSN VMIIYTSIVY KPPEIIMCDA YVTDFPLDLD IDPKDANKGT PEETGSYLVS    660
KDLPKHCLYT RLSSLQKLKE HLVFTVCLSY QYSGLEDTVE DKQEVNVGKP LIAKLDMHRG    720
```

| | | | | | | |
|---|---|---|---|---|---|---|
| LGRKTCFQTC | LMSNGPYQSS | AATSGGAGHY | HSLQDPFHGV | YHSHPGNPSN | VTPADSCHCS | 780 |
| RTPDAFISSF | AHHASCHFSR | SNVPVETTDE | IPFSFSDRLR | ISEK | | 824 |

SEQ ID NO: 536    moltype = AA  length = 119
FEATURE    Location/Qualifiers
source    1..119
    mol_type = protein
    organism = Homo sapiens
SEQUENCE: 536

| | | | | | | |
|---|---|---|---|---|---|---|
| MGEKGCTVTE | LSDFLQAMEH | TEVLQLLSPP | GIKITVNPES | KAVLAGQFVK | LCCRATGHPF | 60 |
| VQYQWFKMNK | EIPNGNTSEL | IFNAVHVKDA | GFYVCRVNNN | FTFEFSQWSQ | LDVCDIPES | 119 |

SEQ ID NO: 537    moltype = AA  length = 506
FEATURE    Location/Qualifiers
source    1..506
    mol_type = protein
    organism = Homo sapiens
SEQUENCE: 537

| | | | | | | |
|---|---|---|---|---|---|---|
| MAGEVSAATG | RFSLERLGLP | GLALAAALLL | LALCLLVRRT | RRPGEPPLIK | GWLPYLGVVL | 60 |
| NLRKDPLRFM | KTLQKQHGDT | FTVLLGGKYI | TFILDPFQYQ | LVIKNHKQLS | FRVFSNKLLE | 120 |
| KAFSISQLQK | NHDMNDELHL | CYQFLQGKSL | DILLESMMQN | LKQVFEPQLL | KTTSWDTAEL | 180 |
| YPFCSSIIFE | ITFTTIYGKV | IVCDNNKFIS | ELRDDFKFD | DKFAYLVSNI | PIELLGNVKS | 240 |
| IREKIIKCFS | SEKLAKMQGW | SEVFQSRQDV | LEKYYVHEDL | EIGAHHLGFL | WASVANTIPT | 300 |
| MFWAMYLLR | HPEAMAAVRD | EIDRLLQSTG | QKKGSGFPIH | LTREQLDSLI | CLESSIFEAL | 360 |
| RLSSYSTTIR | FVEEDDTLSS | ETGDYCVRKG | DLVAIFPPVL | HGDPEIFEAP | EEFRYDRFIE | 420 |
| DGKKKTTFFK | RGKKLKCYLM | PFGTGTSKCP | GRFFALMEIK | QLLVILLTYF | DLEIIDDKPI | 480 |
| GLNYSRLLFG | IQYPDSDVLF | RYKVKS | | | | 506 |

SEQ ID NO: 538    moltype = AA  length = 543
FEATURE    Location/Qualifiers
source    1..543
    mol_type = protein
    organism = Homo sapiens
SEQUENCE: 538

| | | | | | | |
|---|---|---|---|---|---|---|
| MLLRSKPALP | PPLMLLLLGP | LGPLSPGALP | RPAQAQDVVD | LDFFTQEPLH | LVSPSFLSVT | 60 |
| IDANLATDPR | FLILLGSPKL | RTLARGLSPA | YLRFGGTKTD | FLIFDPKKES | TFEERSYWQS | 120 |
| QVNQDICKYG | SIPPDVEEKL | RLEWPYQEQL | LLREHYQKKF | KNSTYSRSSV | DVLYTFANCS | 180 |
| GLDLIFGLNA | LLRTADLQWN | SSNAQLLLDY | CSSKGYNISW | ELGNEPNSFL | KKADIFINGS | 240 |
| QLGEDFIQLH | KLLRKSTFKN | AKLYGPDVGQ | PRRKTAKMLK | SFLKAGGEVI | DSVTWHHYYL | 300 |
| NGRTATKEDF | LNPDVLDIFI | SSVQKVFQVV | ESTRPGKKVW | LGETSSAYGG | GAPLLSDTFA | 360 |
| AGFMWLDKLG | LSARMGIEVV | MRQVFFGAGN | YHLVDENFDP | LPDYWLSLLF | KKLVGTKVLM | 420 |
| ASVQGSKRRK | LRVYLHCTNT | DNPRYKEGDL | TLYAINLHNV | TKYLRLPYPF | SNKQVDKYLL | 480 |
| RPLGPHGLLS | KSVQLNGLTL | KMVDDQTLPP | LMEKPLRPGS | SLGLPAFSYS | FFVIRNAKVA | 540 |
| ACI | | | | | | 543 |

SEQ ID NO: 539    moltype = AA  length = 543
FEATURE    Location/Qualifiers
source    1..543
    mol_type = protein
    organism = Homo sapiens
SEQUENCE: 539

| | | | | | | |
|---|---|---|---|---|---|---|
| MLLRSKPALP | PPLMLLLLGP | LGPLSPGALP | RPAQAQDVVD | LDFFTQEPLH | LVSPSFLSVT | 60 |
| IDANLATDPR | FLILLGSPKL | RTLARGLSPA | YLRFGGTKTD | FLIFDPKKES | TFEERSYWQS | 120 |
| QVNQDICKYG | SIPPDVEEKL | RLEWPYQEQL | LLREHYQKKF | KNSTYSRSSV | DVLYTFANCS | 180 |
| GLDLIFGLNA | LLRTADLQWN | SSNAQLLLDY | CSSKGYNISW | ELGNEPNSFL | KKADIFINGS | 240 |
| QLGEDFIQLH | KLLRKSTFKN | AKLYGPDVGQ | PRRKTAKMLK | SFLKAGGEVI | DSVTWHHYYL | 300 |
| NGRTATKEDF | LNPDVLDIFI | SSVQKVFQVV | ESTRPGKKVW | LGETSSAYGG | GAPLLSDTFA | 360 |
| AGFMWLDKLG | LSARMGIEVV | MRQVFFGAGN | YHLVDENFDP | LPDYWLSLLF | KKLVGTKVLM | 420 |
| ASVQGSKRRK | LRVYLHCTNT | DNPRYKEGDL | TLYAINLHNV | TKYLRLPYPF | SNKQVDKYLL | 480 |
| RPLGPHGLLS | KSVQLNGLTL | KMVDDQTLPP | LMEKPLRPGS | SLGLPAFSYS | FFVIRNAKVA | 540 |
| ACI | | | | | | 543 |

SEQ ID NO: 540    moltype = AA  length = 226
FEATURE    Location/Qualifiers
source    1..226
    mol_type = protein
    organism = Homo sapiens
SEQUENCE: 540

| | | | | | | |
|---|---|---|---|---|---|---|
| MLLRSKPALP | PPLMLLLLGP | LGPLSPGALP | RPAQAQDVVD | LDFFTQEPLH | LVSPSFLSVT | 60 |
| IDANLATDPR | FLILLGSPKL | RTLARGLSPA | YLRFGGTKTD | FLIFDPKKES | TFEERSYWQS | 120 |
| QVNQDICKYG | SIPPDVEEKL | RLEWPYQEQL | LLREHYQKKF | KNSTYSRSSV | DVLYTFANCS | 180 |
| GLDLIFGLNA | LLRTADLQWN | SSNAQLLLDY | CSSKGYNISW | ELGNAS | | 226 |

SEQ ID NO: 541    moltype = AA  length = 168
FEATURE    Location/Qualifiers
source    1..168
    mol_type = protein
    organism = Homo sapiens
SEQUENCE: 541

```
MLLRSKPALP PPLMLLLLGP LGPLSPGALP RPAQAQDVVD LDFFTQEPLH LVSPSFLSVT    60
IDANLATDPR FLILLGSPKL RTLARGLSPA YLRFGGTKTD FLIFDPKKES TFEERSYWQS   120
QVNQDICKYG SIPPDVEEKL RLEWPYQEQL LLREHYQKKF KNSTYSTS                168

SEQ ID NO: 542            moltype = AA   length = 380
FEATURE                   Location/Qualifiers
source                    1..380
                          mol_type = protein
                          organism = Homo sapiens
SEQUENCE: 542
MLLRSKPALP PPLMLLLLGP LGPLSPGALP RPAQAQDVVD LDFFTQEPLH LVSPSFLSVT    60
IDANLATDPR FLILLGSPKL RTLARGLSPA YLRFGGTKTD FLIFDPKKES TFEERSYWQS   120
QVNQDICKYG SIPPDVEEKL RLEWPYQEQL LLREHYQKKF KNSTYSRSSV DVLYTFANCS   180
GLDLIFGLNA LLRTADLQWN SSNAQLLLDY CSSKGYNISW ELGNEPNSFL KKADIFINGS   240
QLGEDFIQLH KLLRKSTFKN AKLYGPDVGQ PRRKTAKMLK SFLKAGGEVI DSVTWHHYYL   300
NGRTATKEDF LNPDVLDIFI SSVQKVFQVV ESTRPGKKVW LGETSSAYGG GAPLLSDTFA   360
AGFMIIGYLF CSRNWWAPRC                                               380

SEQ ID NO: 543            moltype = AA   length = 469
FEATURE                   Location/Qualifiers
source                    1..469
                          mol_type = protein
                          organism = Homo sapiens
SEQUENCE: 543
MLLRSKPALP PPLMLLLLGP LGPLSPGALP RPAQAQDVVD LDFFTQEPLH LVSPSFLSVT    60
IDANLATDPR FLILLGSPKL RTLARGLSPA YLRFGGTKTD FLIFDPKKES TFEERSYWQS   120
QVNQDICKYG SIPPDVEEKL RLEWPYQEQL LLREHYQKKF KNSTYSRSSV DVLYTFANCS   180
GLDLIFGLNA LLRTADLQWN SSNAQLLLDY CSSKGYNISW ELGNEPNSFL KKADIFINGS   240
QLGEDFIQLH KLLRKSTFKN AKLYGPDVGQ PRRKTAKMLK SFLKAGGEVI DSVTWHHYYL   300
NGRTATKEDF LNPDVLDIFI SSVQKVFQDY WLSLLFKKLV GTKVLMASVQ GSKRRKLRVY   360
LHCTNTDNPR YKEGDLTLYA INLHNVTKYL RLPYPFSNKQ VDKYLLRPLG PHGLLSKSVQ   420
LNGLTLKMVD DQTLPPLMEK PLRPGSSLGL PAFSYSFFVI RNAKVAACI               469

SEQ ID NO: 544            moltype = AA   length = 485
FEATURE                   Location/Qualifiers
source                    1..485
                          mol_type = protein
                          organism = Homo sapiens
SEQUENCE: 544
MLLRSKPALP PPLMLLLLGP LGPLSPGALP RPAQAQDVVD LDFFTQEPLH LVSPSFLSVT    60
IDANLATDPR FLILLGSPKL RTLARGLSPA YLRFGGTKTD FLIFDPKKES TFEERSYWQS   120
QVNQDICKYG SIPPDVEEKL RLEWPYQEQL LLREHYQKKF KNSTYSKPNS FLKKADIFIN   180
GSQLGEDFIQ LHKLLRKSTF KNAKLYGPDV GQPRRKTAKM LKSFLKAGGE VIDSVTWHHY   240
YLNGRTATKE DFLNPDVLDI FISSVQKVFQ VVESTRPGKK VWLGETSSAY GGGAPLLSDT   300
FAAGFMWLDK LGLSARMGIE VVMRQVFFGA GNYHLVDENF DPLPDYWLSL LFKKLVGTKV   360
LMASVQGSKR RKLRVYLHCT NTDNPRYKEG DLTLYAINLH NVTKYLRLPY PFSNKQVDKY   420
LLRPLGPHGL LSKSVQLNGL TLKMVDDQTL PPLMEKPLRP GSSLGLPAFS YSFFVIRNAK   480
VAACI                                                               485

SEQ ID NO: 545            moltype = AA   length = 524
FEATURE                   Location/Qualifiers
source                    1..524
                          mol_type = protein
                          organism = Homo sapiens
SEQUENCE: 545
MDTESTYSGY SYYSSHSKKS HRQGERTRER HKSPRNKDGR GSEKSVTIQP PTGEPLLGND    60
STRTEEVQDD NWGETTTAIT GTSEHSISQE DIARISKDME DSVGLDCKRY LGLTVASFLG   120
LLVFLTPIAF ILLPPILWRD ELEPCGTICE GLFISMAFKL LILLIGTWAL FFRKRRADMP   180
RVFVFRALLL VLIFLFVVSY WLFYGVRILD SRDRNYQGIV QYAVSLVDAL LFIHYLAIVL   240
LELRQLQPMF TLQVVRSTDG ESRFYSLGHL SIQRAALVVL ENYYKDFTIY NPNLLTASKF   300
RAAKHMAGLK VYNVDGPSNN ATGQSRAMIA AAARRRDSSH NELYYEEAEH ERRVKKRKAR   360
LVVAVEEAFI HIQRLQAEEQ QKAPGEVMDP REAAQAIFPS MARALQKYLR ITRQQNYHSM   420
ESILQHLAFC ITNGMTPKAF LERYLSAGPT LQYDKDRWLS TQWRLVSDEA VTNGLRDGIV   480
FVLKCLDFSL VVNVKKIPFI ILSEEFIDPK SHKFVLRLQS ETSV                    524

SEQ ID NO: 546            moltype = AA   length = 524
FEATURE                   Location/Qualifiers
source                    1..524
                          mol_type = protein
                          organism = Homo sapiens
SEQUENCE: 546
MDTESTYSGY SYYSSHSKKS HRQGERTRER HKSPRNKDGR GSEKSVTIQP PTGEPLLGND    60
STRTEEVQDD NWGETTTAIT GTSEHSISQE DIARISKDME DSVGLDCKRY LGLTVASFLG   120
LLVFLTPIAF ILLPPILWRD ELEPCGTICE GLFISMAFKL LILLIGTWAL FFRKRRADMP   180
RVFVFRALLL VLIFLFVVSY WLFYGVRILD SRDRNYQGIV QYAVSLVDAL LFIHYLAIVL   240
LELRQLQPMF TLQVVRSTDG ESRFYSLGHL SIQRAALVVL ENYYKDFTIY NPNLLTASKF   300
RAAKHMAGLK VYNVDGPSNN ATGQSRAMIA AAARRRDSSH NELYYEEAEH ERRVKKRKAR   360
LVVAVEEAFI HIQRLQAEEQ QKAPGEVMDP REAAQAIFPS MARALQKYLR ITRQQNYHSM   420
ESILQHLAFC ITNGMTPKAF LERYLSAGPT LQYDKDRWLS TQWRLVSDEA VTNGLRDGIV   480
```

```
FVLKCLDFSL VVNVKKIPFI ILSEEFIDPK SHKFVLRLQS ETSV              524

SEQ ID NO: 547          moltype = AA  length = 524
FEATURE                 Location/Qualifiers
source                  1..524
                        mol_type = protein
                        organism = Homo sapiens
SEQUENCE: 547
MDTESTYSGY SYYSSHSKKS HRQGERTRER HKSPRNKDGR GSEKSVTIQP PTGEPLLGND  60
STRTEEVQDD NWGETTTAIT GTSEHSISQE DIARISKDME DSVGLDCKRY LGLTVASFLG 120
LLVFLTPIAF ILLPPILWRD ELEPCGTICE GLFISMAFKL LILLIGTWAL FFRKRRADMP 180
RVFVFRALLL VLIFLFVVSY WLFYGVRILD SRDRNYQGIV QYAVSLVDAL LFIHYLAIVL 240
LELRQLQPMF TLQVVRSTDG ESRFYSLGHL SIQRAALVVL ENYYKDFTIY NPNLLTASKF 300
RAAKHMAGLK VYNVDGPSNN ATGQSRAMIA AAARRRDSSH NELYYEEAEH ERRVKKRKAR 360
LVVAVEEAFI HIQRLQAEEQ QKAPGEVMDP REAAQAIFPS MARALQKYLR ITRQQNYHSM 420
ESILQHLAFC ITNGMTPKAF LERYLSAGPT LQYDKDRWLS TQWRLVSDEA VTNGLRDGIV 480
FVLKCLDFSL VVNVKKIPFI ILSEEFIDPK SHKFVLRLQS ETSV              524

SEQ ID NO: 548          moltype = AA  length = 522
FEATURE                 Location/Qualifiers
source                  1..522
                        mol_type = protein
                        organism = Homo sapiens
SEQUENCE: 548
MDTESTYSGY SYYSSHSKKS HRQGERTRER HKSPRNKDGR GSEKSVTIQP PTGEPLLGND  60
STRTEEDDNW GETTTAITGT SEHSISQEDI ARISKDMEDS VGLDCKRYLG LTVASFLGLL 120
VFLTPIAFIL LPPILWRDEL EPCGTICEGL FISMAFKLLI LLIGTWALFF RKRRADMPRV 180
FVFRALLLVL IFLFVVSYWL FYGVRILDSR DRNYQGIVQY AVSLVDALLF IHYLAIVLLE 240
LRQLQPMFTL QVVRSTDGES RFYSLGHLSI QRAALVVLEN YYKDFTIYNP NLLTASKFRA 300
AKHMAGLKVY NVDGPSNNAT GQSRAMIAAA ARRRDSSHNE LYYEEAEHER RVKKRKARLV 360
VAVEEAFIHI QRLQAEEQQK APGEVMDPRE AAQAIFPSMA RALQKYLRIT RQQNYHSMES 420
ILQHLAFCIT NGMTPKAFLE RYLSAGPTLQ YDKDRWLSTQ WRLVSDEAVT NGLRDGIVFV 480
LKCLDFSLVV NVKKIPFIIL SEEFIDPKSH KFVLRLQSET SV                522

SEQ ID NO: 549          moltype = AA  length = 240
FEATURE                 Location/Qualifiers
source                  1..240
                        mol_type = protein
                        organism = Homo sapiens
SEQUENCE: 549
MAGPPRLLLL PLLLALARGL PGALAAQEVQ QSPHCTTVPV GASVNITCST SGGLRGIYLR  60
QLGPQPQDII YYEDGVVPTT DRRFRGRIDF SGSQDNLTIT MHRLQLSDTG TYTCQAITEV 120
NVYGSGTLVL VTEEQSQGWH RCSDAPPRAS ALPAPPTGSA LPDPQTASAL PDPPAASALP 180
AALAVISFLL GLGLGVACVL ARTQIKKLCS WRDKNSAACV VYEDMSHSRC NTLSSPNQYQ 240

SEQ ID NO: 550          moltype = AA  length = 121
FEATURE                 Location/Qualifiers
source                  1..121
                        mol_type = protein
                        organism = Homo sapiens
SEQUENCE: 550
MHRLQLSDTG TYTCQAITEV NVYGSGTLVL VTEEQSQGWH RCSDAPPRAS ALPAPPTGSA  60
LPDPQTASAL PDPPAASALP AALAVISFLL GLGLGVACVL ARTQVSVSPS CHLHPKDCSL 120
S                                                            121

SEQ ID NO: 551          moltype = AA  length = 35
FEATURE                 Location/Qualifiers
source                  1..35
                        mol_type = protein
                        organism = Homo sapiens
SEQUENCE: 551
MAGPPRLLLL PLLLALARGL PGALAAQAGA CVGST                         35

SEQ ID NO: 552          moltype = AA  length = 160
FEATURE                 Location/Qualifiers
source                  1..160
                        mol_type = protein
                        organism = Homo sapiens
SEQUENCE: 552
MAGPPRLLLL PLLLALARGL PGALAAQGRT FSVLLARLMV TAQVLPRGAA VSPLHDCPRG  60
SLRQHHLLHQ RGPAWDLPEA ARATAPRHHL LRGRGGAHYG QTVPGPHRLL RVPGQPDYHH 120
APPAAVGHWH LHLPGHHGGQ CLRLRHPGPG DRGTVPRMAQ                   160

SEQ ID NO: 553          moltype = AA  length = 140
FEATURE                 Location/Qualifiers
source                  1..140
                        mol_type = protein
                        organism = Homo sapiens
SEQUENCE: 553
```

```
MHRLQLSDTG TYTCQAITEV NVYGSGTLVL VTEEQSQGWH RCSDAPPRAS ALPAPPTGSA    60
LPDPQTASAL PDPPAASALP AALAVISFLL GLGLGVACVL ARTQIKKLCS WRDKNSAACV   120
VYEDMSHSRC NTLSSPNQYQ                                              140

SEQ ID NO: 554          moltype = AA   length = 221
FEATURE                 Location/Qualifiers
source                  1..221
                        mol_type = protein
                        organism = Homo sapiens
SEQUENCE: 554
MAGPPRLLLL PLLLALARGL PGALAAQEVQ QSPHCTTVPV GASVNITCST SGGLRGIYLR    60
QLGPQPQDII YYEDGVVPTT DRRFRGRIDF SGSQDNLTIT MHRLQLSDTG TYTCQAITEV   120
NVYGSGTLVL VTEEQSQGWH RCSDAPPRAS ALPAPPTGSA LPDPQTASAL PDPPAASALP   180
AALAVISFLL GLGLGVACVL ARTQVSVSPS CHLHPKDCSL S                      221

SEQ ID NO: 555          moltype = AA   length = 40
FEATURE                 Location/Qualifiers
source                  1..40
                        mol_type = protein
                        organism = Homo sapiens
SEQUENCE: 555
XNYEMPRGDT SSLRAPAEDL RWVEKTLSLL YSPQVAGSSR                          40

SEQ ID NO: 556          moltype = AA   length = 107
FEATURE                 Location/Qualifiers
source                  1..107
                        mol_type = protein
                        organism = Homo sapiens
SEQUENCE: 556
MQCQGYVALL GSDDQSWGWN LVDNNLLHNG EVNGSFPQCN NAPKYQIGER IRVILDMEDK    60
TLAFERGYEF LGVAFRGLPK VCLYPAVSAV YGNTEVTLVY LGKPLDG                107

SEQ ID NO: 557          moltype = AA   length = 530
FEATURE                 Location/Qualifiers
source                  1..530
                        mol_type = protein
                        organism = Homo sapiens
SEQUENCE: 557
MSRSPQRALP PGALPRLLQA APAAAPRALL PQWPRRPGRR WPASPLGMKV FRRKALVLCA    60
GYALLLVLTM LNLLDYKWHK EPLQQCNPDG PLGAAAGAAG GSWGRPGPPP AGPPRAHARL   120
DLRTPYRPPA AAVGAAPAAA AGMAGVAAPP GNGTRGTGGV GDKRQLVYVF TTWRSGSSFF   180
GELFNQNPEV FFLYEPVWHV WQKLYPGDAV SLQGAARDML SALYRCDLSV FQLYSPAGSG   240
GRNLTTLGIF GAATNKVVCS SPLCPAYRKE VVGLVDDRVC KKCPPQRLAR FEEECRKYRT   300
LVIKGVRVFD VAVLAPLLRD PALDLKVIHL VRDPRAVASS RIRSRHGLIR ESLQVVRSRD   360
PRAHRMPFLE AAGHKLGAKK EGVGGPADYH ALGAMEVICN SMAKTLQTAL QPPDWLQGHY   420
LVVRYEDLVG DPVKTLRRVY DFVGLLVSPE MEQFALNMTS GSGSSSKPFV VSARNATQAA   480
NAWRTALTFQ QIKQVEEFCY QPMAVLGYER VNSPEEVKDL SKTLLRKPRL              530

SEQ ID NO: 558          moltype = AA   length = 84
FEATURE                 Location/Qualifiers
source                  1..84
                        mol_type = protein
                        organism = Homo sapiens
SEQUENCE: 558
MKQTQVGSLF SLGIRNPEPG PVSGTAVPRQ LAWKSGKYVM VMGVVQACSP EPCLQAVKMT    60
DLSDNPIHES MWELEVEDLH RNIP                                          84

SEQ ID NO: 559          moltype = AA   length = 313
FEATURE                 Location/Qualifiers
source                  1..313
                        mol_type = protein
                        organism = Homo sapiens
SEQUENCE: 559
MALLVDRVRG HWRIAAGLLF NLLVSICIVF LNKWIYVYHG FPNMSLTLVH FVVTWLGLYI    60
CQKLDIFAPK SLPPSRLLLL ALSFCGFVVF TNLSLQNNTI GTYQLAKAMT TPVIIAIQTF   120
CYQKTFSTRI QLTLIPITLG VILNSYYDVK FNFLGMVFAA LGVLVTSLYQ VWVGAKQHEL   180
QVNSMQLLYY QAPMSSAMLL VAVPFFEPVF GEGGIFGPWS VSALLMVLLS GVIAFMVNLS   240
IYWIIGNTSP VTYNMFGHFK FCITLFGGYV LFKDPLSINQ ALGILCTLFG ILAYTHFKLS   300
EQEGSRSKLA QRP                                                     313

SEQ ID NO: 560          moltype = AA   length = 125
FEATURE                 Location/Qualifiers
source                  1..125
                        mol_type = protein
                        organism = Homo sapiens
SEQUENCE: 560
QAPMSSAMLL VAVPFFEPVF GEGGIFGPWS VSALSTRLEC SGTIMAHCSL SLLGSSNPPA    60
STSPVAGTTG AHQHTWLIFI FFVETEFCHV AQADLKLLSS SHLSASASRS AGITGLSHHT   120
WPVIS                                                              125
```

```
SEQ ID NO: 561         moltype = AA  length = 34
FEATURE                Location/Qualifiers
source                 1..34
                       mol_type = protein
                       organism = Homo sapiens
SEQUENCE: 561
MTVMSLSRDL KDDFHSDTVL SILNEQRIRG ILCD                                 34

SEQ ID NO: 562         moltype = AA  length = 193
FEATURE                Location/Qualifiers
source                 1..193
                       mol_type = protein
                       organism = Homo sapiens
SEQUENCE: 562
MAEAEESPGD PGTASPRPLM RDLKAVGKKF MHVLYPRKSN TLLRDWDLWG PLILCVTLAL      60
MLQRDSADSE KDGGPQFAEV FVIVWFGAVT ITLNSKLLGG NISFFQSLCV LGYCILPLTV     120
AMLICRLVLL ADPGPVNFMV RLFVVIVMFA WSIVASTAFL ADSQPPNRRA LAVYPVFLFY     180
FVISWMILTF TPQ                                                       193

SEQ ID NO: 563         moltype = AA  length = 188
FEATURE                Location/Qualifiers
source                 1..188
                       mol_type = protein
                       organism = Homo sapiens
SEQUENCE: 563
MAEAEESPGD PGTASPRPLM RDLKAVGKKF MHVLYPRKSN TLLRDWDLWG PLILCVTLAL      60
MLQRDSADSE KDGGPQFAEV FVIVWFGAVT ITLNSKLLGG NISFFQSLCV LGYCILPLTV     120
AMLICRLVLL ADPGPVNFMV RLFVVIVMFA WSIVASTAFL ADSQPPNRRA LAVYPVFLFY     180
FVISWMIL                                                             188

SEQ ID NO: 564         moltype = AA  length = 236
FEATURE                Location/Qualifiers
source                 1..236
                       mol_type = protein
                       organism = Homo sapiens
SEQUENCE: 564
MAEAEESPGD PGTASPRPLF AGLSDISISQ DIPVEGEITI PMRSRIREFD SSTLNESVRN      60
TIMRDLKAVG KKFMHVLYPR KSNTLLRDWD LWGPLILCVT LALMLQRDSA DSEKDGGPQF     120
AEVFVIVWFG AVTITLNSKL LGGNISFFQS LCVLGYCILP LTVAMLICRL VLLADPGPVN     180
FMVRLFVVIV MFAWSIVAST AFLADSQPPN RRALAVYPVF LFYFVISWMI LTFTPQ         236

SEQ ID NO: 565         moltype = AA  length = 520
FEATURE                Location/Qualifiers
source                 1..520
                       mol_type = protein
                       organism = Homo sapiens
SEQUENCE: 565
MEVLESGEQG VLQWDRKLSE LSEPGDGEAL MYHTHFSELL DEFSQNVLGQ LLNDPFLSEK      60
SVSMEVEPSP TSPAPLIQAE HSYSLCEEPR AQSPFTHITT SDSFNDDEVE SEKWYLSTDF     120
PSTSIKTEPV TDEPPPGLVP SVTLTITAIS TPLEKEEPPL EMNTGVDSSC QTIIPKIKLE     180
PHEVDQFLNF SPKEAPVDHL HLPPTPPSSH GSDSEGSLSP NPRLHPFSLP QTHSPSRAAP     240
RAPSALSSSP LLTAPHKLQG SGPLVLTEEE KRTLIAEGYP IPTKLPLSKS EEKALKKIRR     300
KIKNKISAQE SRRKKKEYMD SLEKKVESCS TENLELRKKV EVLENTNRTL LQQLQKLQTL     360
VMGKVSRTCK LAGTQTGTCL MVVVLCFAVA FGSFFQGYGP YPSATKMALP SQHSLQEPYT     420
ASVVRSRNLL IYEEHSPPEE SSSPGSAGEL GGWDRGSSLL RVSGLESRPD VDLPHFIISN     480
ETSLEKSVLL ELQQHLVSAK LEGNETLKVV ELDRRVNTTF                          520

SEQ ID NO: 566         moltype = AA  length = 240
FEATURE                Location/Qualifiers
source                 1..240
                       mol_type = protein
                       organism = Homo sapiens
SEQUENCE: 566
NLPRRPRRLS SRLSTATPCA RSLGPSRPSP TLPPVTASMT ICYINSKWMY GPPSLCLGFA      60
SYEYCIFNPR LFEKNLLVSG PAWFKTRVVQ GPTAYVFFSY EVESEKWYLS TDFPSTSIKT     120
EPVTDEPPPG LVPSVTLTIT AISTPLEKEE PPLEMNTGVD SSCQTIIPKI KLEPHEVDQF     180
LNFSPKEGLS ALPVSLWVMD MVSGSTEREY GERAGMSLYH RCCSWLYEIA LFLKNKNFAS     240

SEQ ID NO: 567         moltype = AA  length = 460
FEATURE                Location/Qualifiers
source                 1..460
                       mol_type = protein
                       organism = Homo sapiens
SEQUENCE: 567
MEVLESGEQG VLQWDRKLSE LSEPGDGEAL MYHTHFSELL DEFSQNVLGQ LLNDPFLSEK      60
SVSMEVEPSP TSPAPLIQAE HSYSLCEEPR AQSPFTHITT SDSFNDDEVE SEKWYLSTDF     120
PSTSIKTEPV TDEPPPGLVP SVTLTITAIS TPLEKEEPPL EMNTGVDSSC QTIIPKIKLE     180
PHEVDQFLNF SPKEAPVDHL HLPPTPPSSH GSDSEGSLSP NPRLHPFSLP QTHSPSRAAP     240
```

```
RAPSALSSSP LLTAPHKLQG SGPLVLTEEE KRTLIAEGYP IPTKLPLSKS EEKALKKIRR   300
KIKNKISAQE SRRKKKEYMD SLEKKVESCS TENLELRKKV EVLENTNRTL LQQLQKLQTL   360
VMGKVSRTCK LAGTQTGTCL MVVVLCFAVA FGSFFQGYGP YPSATKMALP SQHSLQEPYT   420
ASVGKTACGK LGRVLFYFPR AGFLSLPKGI FCESPMFKKW                        460

SEQ ID NO: 568         moltype = AA   length = 449
FEATURE                Location/Qualifiers
source                 1..449
                       mol_type = protein
                       organism = Homo sapiens
SEQUENCE: 568
MDRVYEIPEE PNVDPVSSLE EDVIRGANPR FTFPPFSILFS TFLYCGEAAS ALYMVRIYRK    60
NSETYWMTYT FSFFMFSSIM VQLTLIFVHR DLAKDKPLSL FMHLILLGPV IRCLEAMIKY   120
LTLWKKEEQE EPYVSLTRKK MLIDGEEVLI EWEVGHSIRT LAMHRNAYKR MSQIQAFLGS   180
VPQLTYQLYV SLISAEVPLG RVVLMVFSLV SVTYGATLCN MLAIQIKYDD YKIRLGPLEV   240
LCITIWRTLE ITSRLLILVL FSATLKLKAV PFLVLNFLII LFEPWIKFWR SGAQMPNNIE   300
KNFSRVGTLV VLISVTILYA GINFSCWSAL QLRLADRDLV DKGQNWGHMG LHYSVRLVEN   360
VIMVLVFKFF GVKVLLNYCH SLIALQLIIA YLISIGFMLL FFQYLHPLRS LFTHNVVDYL   420
HCVCCHQHPR TRVENSEPPF ETEARQSVV                                    449

SEQ ID NO: 569         moltype = AA   length = 139
FEATURE                Location/Qualifiers
source                 1..139
                       mol_type = protein
                       organism = Homo sapiens
SEQUENCE: 569
MDRVYEIPEE PNVDPVSSLE EDVIRGANPR FTFPPFSILFS TFLYCGEAAS ALYMVRIYRK    60
NSETYWMTYT FSFFMFSSIM VQLTLIFVHR DLAKDKPLSL FMHLILLGPV ISCANGIFPG   120
ICHLWGHPLQ YVGYPDQVR                                               139

SEQ ID NO: 570         moltype = AA   length = 471
FEATURE                Location/Qualifiers
source                 1..471
                       mol_type = protein
                       organism = Homo sapiens
SEQUENCE: 570
MASVVLPSGS QCAAAAAAAA PPGLRLRLLL LLFSAAALIP TGDGQNLFTK DVTVIEGEVA    60
TISCQVNKSD DSVIQLLNPN RQTIYFRDFR PLKDSRFQLL NFSSSELKVS LTNVSISDEG   120
RYFCQLYTDP PQESYTTITV LVPPRNLMID IQKDTAVEGE EIEVNCTAMA SKPATTIRWF   180
KGNTELKGKS EVEEWSDMYT VTSQLMLKVH KEDDGVPVIC QVEHPAVTGN LQTQRYLEVQ   240
YKPQVHIQMT YPLQGLTREG DALELTCEAI GKPQPVMVTW VRVDDEMPQH AVLSGPNLFI   300
NNLNKTDNGT YRCEASNIVG KAHSDYMLYV YDPPTTIPPP TTTTTTTTTT TTTILTIITD   360
TTATTEPAVH GLTQLPNSAE ELDSEDLSDS RAGEEGSIRA VDHAVIGGVV AVVVFAMLCL   420
LIILGRYFAR HKGTYFTHEA KGADDAADAD TAIINAEGGQ NNSEEKKEYF I            471

SEQ ID NO: 571         moltype = AA   length = 442
FEATURE                Location/Qualifiers
source                 1..442
                       mol_type = protein
                       organism = Homo sapiens
SEQUENCE: 571
MASVVLPSGS QCAAAAAAAA PPGLRLRLLL LLFSAAALIP TGDGQNLFTK DVTVIEGEVA    60
TISCQVNKSD DSVIQLLNPN RQTIYFRDFR PLKDSRFQLL NFSSSELKVS LTNVSISDEG   120
RYFCQLYTDP PQESYTTITV LVPPRNLMID IQKDTAVEGE EIEVNCTAMA SKPATTIRWF   180
KGNTELKGKS EVEEWSDMYT VTSQLMLKVH KEDDGVPVIC QVEHPAVTGN LQTQRYLEVQ   240
YKPQVHIQMT YPLQGLTREG DALELTCEAI GKPQPVMVTW VRVDDEMPQH AVLSGPNLFI   300
NNLNKTDNGT YRCEASNIVG KAHSDYMLYV YDPPTTIPPP TTTTTTTTTT TTTILTIITD   360
SRAGEEGSIR AVDHAVIGGV VAVVVFAMLC LLIILGRYFA RHKGTYFTHE AKGADDAADA   420
DTAIINAEGG QNNSEEKKEY FI                                           442

SEQ ID NO: 572         moltype = AA   length = 443
FEATURE                Location/Qualifiers
source                 1..443
                       mol_type = protein
                       organism = Homo sapiens
SEQUENCE: 572
MASVVLPSGS QCAAAAAAAA PPGLRLRLLL LLFSAAALIP TGDGQNLFTK DVTVIEGEVA    60
TISCQVNKSD DSVIQLLNPN RQTIYFRDFR PLKDSRFQLL NFSSSELKVS LTNVSISDEG   120
RYFCQLYTDP PQESYTTITV LVPPRNLMID IQKDTAVEGE EIEVNCTAMA SKPATTIRWF   180
KGNTELKGKS EVEEWSDMYT VTSQLMLKVH KEDDGVPVIC QVEHPAVTGN LQTQRYLEVQ   240
YKPQVHIQMT YPLQGLTREG DALELTCEAI GKPQPVMVTW VRVDDEMPQH AVLSGPNLFI   300
NNLNKTDNGT YRCEASNIVG KAHSDYMLYV YDTTATTEPA VHGLTQLPNS AEELDSEDLS   360
DSRAGEEGSI RAVDHAVIGG VVAVVVFAML CLLIILGRYF ARHKGTYFTH EAKGADDAAD   420
ADTAIINAEG GQNNSEEKKE YFI                                          443

SEQ ID NO: 573         moltype = AA   length = 453
FEATURE                Location/Qualifiers
source                 1..453
                       mol_type = protein
```

```
                                    organism = Homo sapiens
SEQUENCE: 573
MASVVLPSGS QCAAAAAAAA PPGLRLRLLL LLFSAAALIP TGDGQNLFTK DVTVIEGEVA    60
TISCQVNKSD DSVIQLLNPN RQTIYFRDFR PLKDSRFQLL NFSSSELKVS LTNVSISDEG   120
RYFCQLYTDP PQESYTTITV LVPPRNLMID IQKDTAVEGE EIEVNCTAMA SKPATTIRWF   180
KGNTELKGKS EVEEWSDMYT VTSQLMLKVH KEDDGVPVIC QVEHPAVTGN LQTQRYLEVQ   240
YKPQVHIQMT YPLQGLTREG DALELTCEAI GKPQPVMVTW VRVDDEMPQH AVLSGPNLFI   300
NNLNKTDNGT YRCEASNIVG KAHSDYMLYV YDPPTTIPPP TTTTTTTTTT TTTILTIITD   360
TTATTEPAVH DSRAGEEGSI RAVDHAVIGG VVAVVVFAML CLLIILGRYF ARHKGTYFTH   420
EAKGDADDAAD ADTAIINAEG GQNNSEEKKE YFI                              453

SEQ ID NO: 574         moltype = AA  length = 67
FEATURE                Location/Qualifiers
source                 1..67
                       mol_type = protein
                       organism = Homo sapiens
SEQUENCE: 574
MASVVLPSGS QCAAAAAAAA PPGLRLRLLL LLFSAAALIP TGLTSSPRLE CGGTISAHCS    60
LGLPVLR                                                              67

SEQ ID NO: 575         moltype = AA  length = 414
FEATURE                Location/Qualifiers
source                 1..414
                       mol_type = protein
                       organism = Homo sapiens
SEQUENCE: 575
MASVVLPSGS QCAAAAAAAA PPGLRLRLLL LLFSAAALIP TGDGQNLFTK DVTVIEGEVA    60
TISCQVNKSD DSVIQLLNPN RQTIYFRDFR PLKDSRFQLL NFSSSELKVS LTNVSISDEG   120
RYFCQLYTDP PQESYTTITV LVPPRNLMID IQKDTAVEGE EIEVNCTAMA SKPATTIRWF   180
KGNTELKGKS EVEEWSDMYT VTSQLMLKVH KEDDGVPVIC QVEHPAVTGN LQTQRYLEVQ   240
YKPQVHIQMT YPLQGLTREG DALELTCEAI GKPQPVMVTW VRVDDEMPQH AVLSGPNLFI   300
NNLNKTDNGT YRCEASNIVG KAHSDYMLYV YDSRAGEEGS IRAVDHAVIG GVVAVVVFAM   360
LCLLIILGRY FARHKGTYFT HEAKGADDAA DADTAIINAE GGQNNSEEKK EYFI         414

SEQ ID NO: 576         moltype = AA  length = 111
FEATURE                Location/Qualifiers
source                 1..111
                       mol_type = protein
                       organism = Homo sapiens
SEQUENCE: 576
MIDIQKDTAV EGEEIEVNCT AMASKPATTI RWFKGNTELK GKSEVEEWSD MYTVTSQLML    60
KVHKEDDGVP VICQVEHPAV TGNLQTQRYL EVQYKPQVHI QMTYPLQGLT R            111

SEQ ID NO: 577         moltype = AA  length = 79
FEATURE                Location/Qualifiers
source                 1..79
                       mol_type = protein
                       organism = Homo sapiens
SEQUENCE: 577
MIDIQKDTAV EGEEIEVNCT AMASKPATTI RWFKGNTELK GKSEVEEWSD MYTVTSQLML    60
KVHKEDDGVP VICQVEHPA                                                 79

SEQ ID NO: 578         moltype = AA  length = 413
FEATURE                Location/Qualifiers
source                 1..413
                       mol_type = protein
                       organism = Homo sapiens
SEQUENCE: 578
XSVVLPSGSQ CAAAAAAAAP PGLRLRLLLL LFSAAALIPT GDGQNLFTKD VTVIEGEVAT    60
ISCQVNKSDD SVIQLLNPNR QTIYFRDFRP LKDSRFQLLN FSSSELKVSL TNVSISDEGR   120
YFCQLYTDPP QESYTTITVL VPPRNLMIDI QKDTAVEGEE IEVNCTAMAS KPATTIRWFK   180
GNTELKGKSE VEEWSDMYTV TSQLMLKVHK EDDGVPVICQ VEHPAVTGNL QTQRYLEVQY   240
KPQVHIQMTY PLQGLTREGD ALELTCEAIG KPQPVMVTWV RVDDEMPQHA VLSGPNLFIN   300
NLNKTDNGTY RCEASNIVGK AHSDYMLYVY DSRAGEEGSI RAVDHAVIGG VVAVVVFAML   360
CLLIILGRYF ARHKGTYFTH EAKGADDAAD ADTAIINAEG GQNNSEEKKE YFI          413

SEQ ID NO: 579         moltype = AA  length = 346
FEATURE                Location/Qualifiers
source                 1..346
                       mol_type = protein
                       organism = Homo sapiens
SEQUENCE: 579
GDGQNLFTKD VTVIEGEVAT ISCQVNKSDD SVIQLLNPNR QTIYFRDFRP LKDSRFQLLN    60
FSSSELKVSL TNVSISDEGR YFCQLYTDPP QESYTTITVL VPPRNLMIDI QKDTAVEGEE   120
IEVNCTAMAS KPATTIRWFK GNTELKGKSE VEEWSDMYTV TSQLMLKVHK EDDGVPVICQ   180
VEHPAVTGNL QTQRYLEVQY KPQVHIQMTY PLQGLTREGD ALELTCEAIG KPQPVMVTWV   240
RVDDEMPQHA VLSGPNLFIN NLNKTDNGTY RCEASNIVGK AHSDYMLYVY DSRAGEEGSI   300
RAVDHAVIGG VVAVVVFAML CLLIILGRYF ARHKGLFSLT SSPRIK                  346
```

```
SEQ ID NO: 580              moltype = AA  length = 373
FEATURE                     Location/Qualifiers
source                      1..373
                            mol_type = protein
                            organism = Homo sapiens
SEQUENCE: 580
GDGQNLFTKD VTVIEGEVAT ISCQVNKSDD SVIQLLNPNR QTIYFRDFRP LKDSRFQLLN    60
FSSSELKVSL TNVSISDEGR YFCQLYTDPP QESYTTITVL VPPRNLMIDI QKDTAVEGEE   120
IEVNCTAMAS KPATTIRWFK GNTELKGKSE VEEWSDMYTV TSQLMLKVHK EDDGVPVICQ   180
VEHPAVTGNL QTQRYLEVQY KPQVHIQMTY PLQGLTREGD ALELTCEAIG KPQPVMVTWV   240
RVDDEMPQHA VLSGPNLFIN NLNKTDNGTY RCEASNIVGK AHSDYMLYVY DSRAGEEGSI   300
RAVDHAVIGG VVAVVVFAML CLLIILGRYF ARHKGTYFTH EAKGADDAAD ADTAIINAEG   360
GQNNSEEKKE YFI                                                     373

SEQ ID NO: 581              moltype = AA  length = 412
FEATURE                     Location/Qualifiers
source                      1..412
                            mol_type = protein
                            organism = Homo sapiens
SEQUENCE: 581
GDGQNLFTKD VTVIEGEVAT ISCQVNKSDD SVIQLLNPNR QTIYFRDFRP LKDSRFQLLN    60
FSSSELKVSL TNVSISDEGR YFCQLYTDPP QESYTTITVL VPPRNLMIDI QKDTAVEGEE   120
IEVNCTAMAS KPATTIRWFK GNTELKGKSE VEEWSDMYTV TSQLMLKVHK EDDGVPVICQ   180
VEHPAVTGNL QTQRYLEVQY KPQVHIQMTY PLQGLTREGD ALELTCEAIG KPQPVMVTWV   240
RVDDEMPQHA VLSGPNLFIN NLNKTDNGTY RCEASNIVGK AHSDYMLYVY DPPTTIPPPT   300
TTTTTTTTT TTILTIITDT TATTEPAVHD SRAGEEGSIR AVDHAVIGGV VAVVVFAMLC   360
LLIILGRYFA RHKGTYFTHE AKGADDAADA DTAIINAEGG QNNSEEKKEY FI          412

SEQ ID NO: 582              moltype = AA  length = 430
FEATURE                     Location/Qualifiers
source                      1..430
                            mol_type = protein
                            organism = Homo sapiens
SEQUENCE: 582
GDGQNLFTKD VTVIEGEVAT ISCQVNKSDD SVIQLLNPNR QTIYFRDFRP LKDSRFQLLN    60
FSSSELKVSL TNVSISDEGR YFCQLYTDPP QESYTTITVL VPPRNLMIDI QKDTAVEGEE   120
IEVNCTAMAS KPATTIRWFK GNTELKGKSE VEEWSDMYTV TSQLMLKVHK EDDGVPVICQ   180
VEHPAVTGNL QTQRYLEVQY KPQVHIQMTY PLQGLTREGD ALELTCEAIG KPQPVMVTWV   240
RVDDEMPQHA VLSGPNLFIN NLNKTDNGTY RCEASNIVGK AHSDYMLYVY DPPTTIPPPT   300
TTTTTTTTT TTILTIITDT TATTEPAVHG LTQLPNSAEE LDSEDLSDSR AGEEGSIRAV   360
DHAVIGGVVA VVVFAMLCLL IILGRYFARH KGTYFTHEAK GADDAADADT AIINAEGGQN   420
NSEEKKEYFI                                                         430

SEQ ID NO: 583              moltype = AA  length = 401
FEATURE                     Location/Qualifiers
source                      1..401
                            mol_type = protein
                            organism = Homo sapiens
SEQUENCE: 583
GDGQNLFTKD VTVIEGEVAT ISCQVNKSDD SVIQLLNPNR QTIYFRDFRP LKDSRFQLLN    60
FSSSELKVSL TNVSISDEGR YFCQLYTDPP QESYTTITVL VPPRNLMIDI QKDTAVEGEE   120
IEVNCTAMAS KPATTIRWFK GNTELKGKSE VEEWSDMYTV TSQLMLKVHK EDDGVPVICQ   180
VEHPAVTGNL QTQRYLEVQY KPQVHIQMTY PLQGLTREGD ALELTCEAIG KPQPVMVTWV   240
RVDDEMPQHA VLSGPNLFIN NLNKTDNGTY RCEASNIVGK AHSDYMLYVY DPPTTIPPPT   300
TTTTTTTTT TTILTIITDS RAGEEGSIRA VDHAVIGGVV AVVVFAMLCL LIILGRYFAR   360
HKGTYFTHEA KGADDAADAD TAIINAEGGQ NNSEEKKEYF I                      401

SEQ ID NO: 584              moltype = AA  length = 200
FEATURE                     Location/Qualifiers
source                      1..200
                            mol_type = protein
                            organism = Homo sapiens
SEQUENCE: 584
MASSLTCTGV IWALLSFLCA ATSCVGFFMP YWLWGSQLGK PVSFGTFRRC SYPVHDESRQ    60
MMVMVEECGR YASFQGIPSA EWRICTIVTG LGCGLLLLVA LTALMGCCVS DLISRTVGRV   120
AGGIQFLGGL LIGAGCALYP LGWDSEEVRQ TCGYTSGQFD LGKCEIGWAY YCTGAGATAA   180
MLLCTWLACF SGKKQKHYPY                                              200

SEQ ID NO: 585              moltype = AA  length = 554
FEATURE                     Location/Qualifiers
source                      1..554
                            mol_type = protein
                            organism = Homo sapiens
SEQUENCE: 585
MTAPGAAGRC PPTTWLGSLL LLVCLLASRS ITEEVSEYCS HMIGSGHLQS LQRLIDSQME    60
TSCQITFEFV DQEQLKDPVC YLKKAFLLVQ DIMEDTMRFR DNTPNAIAIV QLQELSLRLK   120
SCFTKDYEEH DKACVRTFYE TPLQLLEKVK NVFNETKNLL DKDWNIFSKN CNNSFAECSS   180
QDVVTKPDCN CLYPKAIPSS DPASVSPHQP LAPSMAPVAG LTWEDSEGTE GSSLLPGEQP   240
LHTVDPGSAK QRPPRSTCQS FEPPETPVVK DSTIGGSPQP RPSVGAFNPG MEDILDSAMG   300
```

```
TNWVPEEASG EASEIPVPQG TELSPSRPGG GSMQTEPARP SNFLSASSPL PASAKGQQPA    360
DVTGTALPRV GPVRPTGQDW NHTPQKTDHP SALLRDPPEP GSPRISSLRP QGLSNPSTLS    420
AQPQLSRSHS SGSVLPLGEL EGRRSTRDRR SPAEPEGGPA SEGAARPLPR FNSVPLTDTG    480
HERQSEGSFS PQLQESVFHL LVPSVILVLL AVGGLLFYRW RRRSHQEPQR ADSPLEQPEG    540
SPLTQDDRQV ELPV                                                     554

SEQ ID NO: 586          moltype = AA   length = 119
FEATURE                 Location/Qualifiers
source                  1..119
                        mol_type = protein
                        organism = Homo sapiens
SEQUENCE: 586
MTAPGAAGRC PPTTWLGSLL LLVCLLASRS ITEEVSEYCS HMIGSGHLQS LQRLIDSQME    60
TSCQITFEFV DQEQLKDPVC YLKKAFLLVQ DIMEDTMRFR DNTPNAIAIV QLQELSLRL    119

SEQ ID NO: 587          moltype = AA   length = 438
FEATURE                 Location/Qualifiers
source                  1..438
                        mol_type = protein
                        organism = Homo sapiens
SEQUENCE: 587
MTAPGAAGRC PPTTWLGSLL LLVCLLASRS ITEEVSEYCS HMIGSGHLQS LQRLIDSQME    60
TSCQITFEFV DQEQLKDPVC YLKKAFLLVQ DIMEDTMRFR DNTPNAIAIV QLQELSLRLK   120
SCFTKDYEEH DKACVRTFYE TPLQLLEKVK NVFNETKNLL DKDWNIFSKN CNNSFAECSS   180
QDVVTKPDCN CLYPKAIPSS DPASVSPHQP LAPSMAPVAG LTWEDSEGTE GSSLLPGEQP   240
LHTVDPGSAK QRPPRSTCQS FEPPETPVVK DSTIGGSPQP RPSVGAFNPG MEDILDSAMG   300
TNWVPEEASG EASEIPVPQG TELSPSRPGG GSMQTEPARP SNFLSASSPL PASAKGQQPA   360
DVTGHERQSE GSFSPQLQES VFHLLVPSVI LVLLAVGGLL FYRWRRRSHQ EPQRADSPLE   420
QPEGSPLTQD DRQVELPV                                                 438

SEQ ID NO: 588          moltype = AA   length = 554
FEATURE                 Location/Qualifiers
source                  1..554
                        mol_type = protein
                        organism = Homo sapiens
SEQUENCE: 588
MTAPGAAGRC PPTTWLGSLL LLVCLLASRS ITEEVSEYCS HMIGSGHLQS LQRLIDSQME    60
TSCQITFEFV DQEQLKDPVC YLKKAFLLVQ DIMEDTMRFR DNTPNAIAIV QLQELSLRLK   120
SCFTKDYEEH DKACVRTFYE TPLQLLEKVK NVFNETKNLL DKDWNIFSKN CNNSFAECSS   180
QDVVTKPDCN CLYPKAIPSS DPASVSPHQP LAPSMAPVAG LTWEDSEGTE GSSLLPGEQP   240
LHTVDPGSAK QRPPRSTCQS FEPPETPVVK DSTIGGSPQP RPSVGAFNPG MEDILDSAMG   300
TNWVPEEASG EASEIPVPQG TELSPSRPGG GSMQTEPARP SNFLSASSPL PASAKGQQPA   360
DVTGTALPRV GPVRPTGQDW NHTPQKTDHP SALLRDPPEP GSPRISSLRP QGLSNPSTLS   420
AQPQLSRSHS SGSVLPLGEL EGRRSTRDRR SPAEPEGGPA SEGAARPLPR FNSVPLTDTG   480
HERQSEGSFS PQLQESVFHL LVPSVILVLL AVGGLLFYRW RRRSHQEPQR ADSPLEQPEG   540
SPLTQDDRQV ELPV                                                     554

SEQ ID NO: 589          moltype = AA   length = 256
FEATURE                 Location/Qualifiers
source                  1..256
                        mol_type = protein
                        organism = Homo sapiens
SEQUENCE: 589
MTAPGAAGRC PPTTWLGSLL LLVCLLASRS ITEEVSEYCS HMIGSGHLQS LQRLIDSQME    60
TSCQITFEFV DQEQLKDPVC YLKKAFLLVQ DIMEDTMRFR DNTPNAIAIV QLQELSLRLK   120
SCFTKDYEEH DKACVRTFYE TPLQLLEKVK NVFNETKNLL DKDWNIFSKN CNNSFAECSS   180
QGHERQSEGS FSPQLQESVF HLLVPSVILV LLAVGGLLFY RWRRRSHQEP QRADSPLEQP   240
EGSPLTQDDR QVELPV                                                   256

SEQ ID NO: 590          moltype = AA   length = 285
FEATURE                 Location/Qualifiers
source                  1..285
                        mol_type = protein
                        organism = Homo sapiens
SEQUENCE: 590
MTAPGAAGRC PPTIDSQMET SCQITFEFVD QEQLKDPVCY LKKAFLLVQD IMEDTMRFRD    60
NTPNAIAIVQ LQELSLRLKS CFTKDYEEHD KACVRTFYET PLQLLEKVKN VFNETKNLLD   120
KDWNIFSKNC NNSFAECSSQ DVVTKPDCNC LYPKAIPSSD PASVSPHQPL APSMAPVAGL   180
TWEDSEGTEG SSLLPGEQPL HTVDPGSAKQ RPPRSTCQSF EPPETPVVKD STIGGSPQPR   240
PSVGAFNPGM EDILDSAMGT NWVPEEASGE ASEIPVPQGT ELSPS                   285

SEQ ID NO: 591          moltype = AA   length = 113
FEATURE                 Location/Qualifiers
source                  1..113
                        mol_type = protein
                        organism = Homo sapiens
SEQUENCE: 591
MIGSGHLQSL QRLIDSQMET SCQITFEFVD QEQLKDPVCY LKKAFLLVQD IMEDTMRFRD    60
NTPNAIAIVQ LQELSLRLKS CFTKDYEEHD KACVRTFYET PLQLLEKVKN VFN          113
```

-continued

```
SEQ ID NO: 592          moltype = AA  length = 150
FEATURE                 Location/Qualifiers
source                  1..150
                        mol_type = protein
                        organism = Homo sapiens
SEQUENCE: 592
MGWGRLQRIS LPSQCLSLLS TWLGSLLLLV CLLASRSITE EVSEYCSHMI GSGHLQSLQR  60
LIDSQMETSC QITFEFVDQE QLKDPVCYLK KAFLLVQDIM EDTMRFRDNT PNAIAIVQLQ  120
ELSLRLKSCF TKDYEEHDKA CVRTFYETPL                                  150

SEQ ID NO: 593          moltype = AA  length = 173
FEATURE                 Location/Qualifiers
source                  1..173
                        mol_type = protein
                        organism = Homo sapiens
SEQUENCE: 593
MARMNRPAPV EVSYKHMRFL ITHNPTNATL STFIEDLKKY GATTVVRVCE VTYDKTPLEK  60
DGITVVDWPF DDGAPPPGKV VEDWLSLVKA KFCEAPGSCV AVHCVAGLGR APVLVALALI  120
ESGMKYEDAI QFIRQKRRGA INSKQLTYLE KYRPKQRLRF KDPHTHKTRC CVM         173

SEQ ID NO: 594          moltype = AA  length = 148
FEATURE                 Location/Qualifiers
source                  1..148
                        mol_type = protein
                        organism = Homo sapiens
SEQUENCE: 594
MARMNRPAPV EVSYKHMRFL ITHNPTNATL STFIEDLKKY GATTVVRVCE VTYDKTPLEK  60
DGITVVDWPF DDGAPPPGKV VEDWLSLVKA KFCEAPGSCV AVHCVAGLGR KRRGAINSKQ  120
LTYLEKYRPK QRLRFKDPHT HKTRCCVM                                    148

SEQ ID NO: 595          moltype = AA  length = 148
FEATURE                 Location/Qualifiers
source                  1..148
                        mol_type = protein
                        organism = Homo sapiens
SEQUENCE: 595
MARMNRPAPV EVSYKHMRFL ITHNPTNATL STFIEDLKKY GATTVVRVCE VTYDKTPLEK  60
DGITVVDWPF DDGAPPPGKV VEDWLSLVKA KFCEAPGSCV AVHCVAGLGR KRRGAINSKQ  120
LTYLEKYRPK QRLRFKDPHT HKTRCCVM                                    148

SEQ ID NO: 596          moltype = AA  length = 173
FEATURE                 Location/Qualifiers
source                  1..173
                        mol_type = protein
                        organism = Homo sapiens
SEQUENCE: 596
MARMNRPAPV EVSYKHMRFL ITHNPTNATL STFIEDLKKY GATTVVRVCE VTYDKTPLEK  60
DGITVVDWPF DDGAPPPGKV VEDWLSLVKA KFCEAPGSCV AVHCVAGLGR APVLVALALI  120
ESGMKYEDAI QFIRQKRRGA INSKQLTYLE KYRPKQRLRF KDPHTHKTRC CVM         173

SEQ ID NO: 597          moltype = AA  length = 70
FEATURE                 Location/Qualifiers
source                  1..70
                        mol_type = protein
                        organism = Homo sapiens
SEQUENCE: 597
MARMNRPAPV EVSYKHMRFL ITHNPTNATL STFIEDLKKY GATTVVRVCE VTYDKTPLEK  60
DGITVVDWPF                                                        70

SEQ ID NO: 598          moltype = AA  length = 87
FEATURE                 Location/Qualifiers
source                  1..87
                        mol_type = protein
                        organism = Homo sapiens
SEQUENCE: 598
MARMNRPAPV EVSYKHMRFL ITHNPTNATL STFIESGMKY EDAIQFIRQK RRGAINSKQL  60
TYLEKYRPKQ RLRFKDPHTH KTRCCVM                                     87

SEQ ID NO: 599          moltype = AA  length = 25
FEATURE                 Location/Qualifiers
source                  1..25
                        mol_type = protein
                        organism = Homo sapiens
SEQUENCE: 599
MINACRDFLE LAEIHSRKWQ RALQY                                       25

SEQ ID NO: 600          moltype = AA  length = 244
FEATURE                 Location/Qualifiers
```

```
source                    1..244
                          mol_type = protein
                          organism = Homo sapiens
SEQUENCE: 600
MELTIFILRL AIYILTFPLY LLNFLGLWSW ICKKWFPYFL VRFTVIYNEQ MASKKRELFS   60
NLQEFAGPSG KLSLLEVGCG TGANFKFYPP GCRVTCIDPN PNFEKFLIKS IAENRHLQFE  120
RFVVAAGENM HQVADGSVDV VVCTLVLCSV KNQERILREV CRVLRPGGAF YFMEHVAAEC  180
STWNYFWQQV LDPAWHLLFD GCNLTRESWK ALERASFSKL KLQHIQAPLS WELVRPHIYG  240
YAVK                                                               244

SEQ ID NO: 601            moltype = AA  length = 244
FEATURE                   Location/Qualifiers
source                    1..244
                          mol_type = protein
                          organism = Homo sapiens
SEQUENCE: 601
MELTIFILRL AIYILTFPLY LLNFLGLWSW ICKKWFPYFL VRFTVIYNEQ MASKKRELFS   60
NLQEFAGPSG KLSLLEVGCG TGANFKFYPP GCRVTCIDPN PNFEKFLIKS IAENRHLQFE  120
RFVVAAGENM HQVADGSVDV VVCTLVLCSV KNQERILREV CRVLRPGGAF YFMEHVAAEC  180
STWNYFWQQV LDPAWHLLFD GCNLTRESWK ALERASFSKL KLQHIQAPLS WELVRPHIYG  240
YAVK                                                               244

SEQ ID NO: 602            moltype = AA  length = 244
FEATURE                   Location/Qualifiers
source                    1..244
                          mol_type = protein
                          organism = Homo sapiens
SEQUENCE: 602
MELTIFILRL AIYILTFPLY LLNFLGLWSW ICKKWFPYFL VRFTVIYNEQ MASKKRELFS   60
NLQEFAGPSG KLSLLEVGCG TGANFKFYPP GCRVTCIDPN PNFEKFLIKS IAENRHLQFE  120
RFVVAAGENM HQVADGSVDV VVCTLVLCSV KNQERILREV CRVLRPGGAF YFMEHVAAEC  180
STWNYFWQQV LDPAWHLLFD GCNLTRESWK ALERASFSKL KLQHIQAPLS WELVRPHIYG  240
YAVK                                                               244

SEQ ID NO: 603            moltype = AA  length = 244
FEATURE                   Location/Qualifiers
source                    1..244
                          mol_type = protein
                          organism = Homo sapiens
SEQUENCE: 603
XELTIFILRL AIYILTFPLY LLNFLGLWSW ICKKWFPYFL VRFTVIYNEQ MASKKRELFS   60
NLQEFAGPSG KLSLLEVGCG TGANFKFYPP GCRVTCIDPN PNFEKFLIKS IAENRHLQFE  120
RFVVAAGENM HQVADGSVDV VVCTLVLCSV KNQERILREV CRVLRPGGAF YFMEHVAAEC  180
STWNYFWQQV LDPAWHLLFD GCNLTRESWK ALERASFSKL KLQHIQAPLS WELVRPHIYG  240
YAVK                                                               244

SEQ ID NO: 604            moltype = AA  length = 180
FEATURE                   Location/Qualifiers
source                    1..180
                          mol_type = protein
                          organism = Homo sapiens
SEQUENCE: 604
MELTIFILRL AIYILTFPLY LLNFLGLWSW ICKKWFPYFL VRFTVIYNEQ MASKKRELFS   60
NLQEFAGPSG KLSLLEVGCG TGANFKFYPP GCRVTCIDPN PNFEKFLIKS IAENRHLQFE  120
RFVVAAGENM HQVADGSVDV VVCTLVLCSV KNQERILREV CRVLRPGGAF YFMEHVAAEC  180

SEQ ID NO: 605            moltype = AA  length = 811
FEATURE                   Location/Qualifiers
source                    1..811
                          mol_type = protein
                          organism = Homo sapiens
SEQUENCE: 605
MLLLFHSKRM PVAEAPQVAG GQGDGGDGEE AEPEGMFKAC EDSKRKARGY LRLVPLFVLL   60
ALLVLASAGV LLWYFLGYKA EVMVSQVYSG SLRVLNRHFS QDLTRRESSA FRSETAKAQK  120
MLKELITSTR LGTYYNSSSV YSFGEGPLTC FFWFILQIPE HRRLMLSPEV VQALLVEELL  180
STVNSSAAVP YRAEYEVDPE GLVILEASVK DIAALNSTLG CYRYSVVGQG QVLRLKGPDH  240
LASSCLWHLQ GPKDLMLKLR LEWTLAECRD RLAMYDVAGP LEKRLITSVY GCSRQEPVVE  300
VLASGAIMAV VWKKGLHSYY DPFVLSVQPV VFQQACEVNLGT LDNRLDSQGV LSTPYFPSYY  360
SPQTHCSWHL TVPSLDYGLA LWFDAYALRR QKYDLPCTQG QWTIQNRRLC GLRILQPYAE  420
RIPVVATAGI TINFTSQISL TGPGVRVHYG LYNQSDPCPG EFLCSVNGLC VPACDGVKDC  480
PNGLDERNCV CRATFQCKED STCISLPKVC DGQPDCLNGS DEEQCQEGVP CGTFTFQCED  540
RSCVKKPNPQ CDGRPDCRDG SDEEHCDCGL QGPSSRIVGG AVSSEGEWPW QASLQVRGRH  600
ICGGALIADR WVITAAHCFQ EDSMASTVLW TVFLGKVWQN SRWPGEVSFK VSRLLLHPYH  660
EEDSHDYDVA LLQLDHPVVR SAAVRPVCLP ARSHFFEPGL HCWITGWGAL REGGPISNAL  720
QKVDVQLIPQ DLCSEVYRYQ VTPRMLCAGY RKGKKDACQG DSGGPLVCKA LSGRWFLAGL  780
VSWGLGCGRP NYFGVYTRIT GVISWIQQVV T                                 811

SEQ ID NO: 606            moltype = AA  length = 824
FEATURE                   Location/Qualifiers
```

```
                        source               1..824
                                             mol_type = protein
                                             organism = Homo sapiens
SEQUENCE: 606
MPVAEAPQVA  GGQGDGGDGE  EAEPEGMFKA  CEDSKRKARG  YLRLVPLFVL  LALLVLASAG   60
VLLWYFLGYK  AEVMVSQVYS  GSLRVLNRHF  SQDLTRRESS  AFRSETAKAQ  KMLKELITST  120
RLGTYYNSSS  VYSFGEGPLT  CFFWFILQIP  EHRRLMLSPE  VVQALLVEEL  LSTVNSSAAV  180
PYRAEYEVDP  EGLVILEASV  KDIAALNSTL  GCYRYSYVGQ  GQVLRLKGPD  HLASSCLWHL  240
QGPKDLMLKL  RLEWTLAECR  DRLAMYDVAG  PLEKRLITSV  YGCSRQEPVV  EVLASGAIMA  300
VVWKKGLHSY  YDPFVLSVQP  VVFQACEVNL  TLDNRLDSQG  VLSTPYFPSY  YSPQTHCSWH  360
LTVPSLDYGL  ALWFDAYALR  RQKYDLPCTQ  GQWTIQNRRL  CGLRILQPYA  ERIPVVATAG  420
ITINFTSQIS  LTGPGVRVHY  GLYNQSDPCP  GEFLCSVNGL  CVPACDGVKD  CPNGLDERNC  480
VCRATFQCKE  DSTCISLPKV  CDGQPDCLNG  SDEEQCQEGV  PCGTFTFQCE  DRSCVKKPNP  540
QCDGRPDCRD  GSDEEHCDCG  LQGPSSRIVG  GAVSSEGEWP  WQASLQVRGR  HICGGALIAD  600
RWVITAAHCF  QEDSMASTVL  WTVFLGKVWQ  NSRWPGEVSF  KVSRLLLHPY  HEEDSHDYDV  660
ALLQLDHPVV  RSAAVRPVCL  PARSHFFEPG  LHCWITGWGA  LREGALRADA  VALFYGWRNQ  720
GSETCCCPIS  NALQKVDVQL  IPQDLCSEVY  RYQVTPRMLC  AGYRKGKKDA  CQGDSGGPLV  780
CKALSGRWFL  AGLVSWGLGC  GRPNYFGVYT  RITGVISWIQ  QVVT        824

SEQ ID NO: 607          moltype = AA  length = 802
FEATURE                 Location/Qualifiers
source                  1..802
                        mol_type = protein
                        organism = Homo sapiens
SEQUENCE: 607
MPVAEAPQVA  GGQGDGGDGE  EAEPEGMFKA  CEDSKRKARG  YLRLVPLFVL  LALLVLASAG   60
VLLWYFLGYK  AEVMVSQVYS  GSLRVLNRHF  SQDLTRRESS  AFRSETAKAQ  KMLKELITST  120
RLGTYYNSSS  VYSFGEGPLT  CFFWFILQIP  EHRRLMLSPE  VVQALLVEEL  LSTVNSSAAV  180
PYRAEYEVDP  EGLVILEASV  KDIAALNSTL  GCYRYSYVGQ  GQVLRLKGPD  HLASSCLWHL  240
QGPKDLMLKL  RLEWTLAECR  DRLAMYDVAG  PLEKRLITSV  YGCSRQEPVV  EVLASGAIMA  300
VVWKKGLHSY  YDPFVLSVQP  VVFQACEVNL  TLDNRLDSQG  VLSTPYFPSY  YSPQTHCSWH  360
LTVPSLDYGL  ALWFDAYALR  RQKYDLPCTQ  GQWTIQNRRL  CGLRILQPYA  ERIPVVATAG  420
ITINFTSQIS  LTGPGVRVHY  GLYNQSDPCP  GEFLCSVNGL  CVPACDGVKD  CPNGLDERNC  480
VCRATFQCKE  DSTCISLPKV  CDGQPDCLNG  SDEEQCQEGV  PCGTFTFQCE  DRSCVKKPNP  540
QCDGRPDCRD  GSDEEHCDCG  LQGPSSRIVG  GAVSSEGEWP  WQASLQVRGR  HICGGALIAD  600
RWVITAAHCF  QEDSMASTVL  WTVFLGKVWQ  NSRWPGEVSF  KVSRLLLHPY  HEEDSHDYDV  660
ALLQLDHPVV  RSAAVRPVCL  PARSHFFEPG  LHCWITGWGA  LREGGPISNA  LQKVDVQLIP  720
QDLCSEVYRY  QVTPRMLCAG  YRKGKKDACQ  GDSGGPLVCK  ALSGRWFLAG  LVSWGLGCGR  780
PNYFGVYTRI  TGVISWIQQV  VT          802

SEQ ID NO: 608          moltype = AA  length = 824
FEATURE                 Location/Qualifiers
source                  1..824
                        mol_type = protein
                        organism = Homo sapiens
SEQUENCE: 608
MPVAEAPQVA  GGQGDGGDGE  EAEPEGMFKA  CEDSKRKARG  YLRLVPLFVL  LALLVLASAG   60
VLLWYFLGYK  AEVMVSQVYS  GSLRVLNRHF  SQDLTRRESS  AFRSETAKAQ  KMLKELITST  120
RLGTYYNSSS  VYSFGEGPLT  CFFWFILQIP  EHRRLMLSPE  VVQALLVEEL  LSTVNSSAAV  180
PYRAEYEVDP  EGLVILEASV  KDIAALNSTL  GCYRYSYVGQ  GQVLRLKGPD  HLASSCLWHL  240
QGPKDLMLKL  RLEWTLAECR  DRLAMYDVAG  PLEKRLITSV  YGCSRQEPVV  EVLASGAIMA  300
VVWKKGLHSY  YDPFVLSVQP  VVFQACEVNL  TLDNRLDSQG  VLSTPYFPSY  YSPQTHCSWH  360
LTVPSLDYGL  ALWFDAYALR  RQKYDLPCTQ  GQWTIQNRRL  CGLRILQPYA  ERIPVVATAG  420
ITINFTSQIS  LTGPGVRVHY  GLYNQSDPCP  GEFLCSVNGL  CVPACDGVKD  CPNGLDERNC  480
VCRATFQCKE  DSTCISLPKV  CDGQPDCLNG  SDEEQCQEGV  PCGTFTFQCE  DRSCVKKPNP  540
QCDGRPDCRD  GSDEEHCDCG  LQGPSSRIVG  GAVSSEGEWP  WQASLQVRGR  HICGGALIAD  600
RWVITAAHCF  QEDSMASTVL  WTVFLGKVWQ  NSRWPGEVSF  KVSRLLLHPY  HEEDSHDYDV  660
ALLQLDHPVV  RSAAVRPVCL  PARSHFFEPG  LHCWITGWGA  LREGALRADA  VALFYGWRNQ  720
GSETCCCPIS  NALQKVDVQL  IPQDLCSEVY  RYQVTPRMLC  AGYRKGKKDA  CQGDSGGPLV  780
CKALSGRWFL  AGLVSWGLGC  GRPNYFGVYT  RITGVISWIQ  QVVT        824

SEQ ID NO: 609          moltype = AA  length = 141
FEATURE                 Location/Qualifiers
source                  1..141
                        mol_type = protein
                        organism = Homo sapiens
SEQUENCE: 609
MPVAEAPQVA  GGQGDGGDGE  EAEPEGMFKA  CEDSKRKARG  YLRLVPLFVL  LALLVLASAG   60
VLLWYFLGYK  AEVMVSQVYS  GSLRVLNRHF  SQDLTRRESS  AFRSETAKAQ  KMLKELITST  120
RLGTYYNSSS  VYSFGEGPLT  C            141

SEQ ID NO: 610          moltype = AA  length = 71
FEATURE                 Location/Qualifiers
source                  1..71
                        mol_type = protein
                        organism = Homo sapiens
SEQUENCE: 610
LTLDNRLDSQ  GVLSTPYFPS  YYSPQTHCSW  HLTVPSLDYG  LALWFDAYAL  RRQKYDLPCT   60
QGQWTIQNRR  V           71
```

```
SEQ ID NO: 611           moltype = AA   length = 461
FEATURE                  Location/Qualifiers
source                   1..461
                         mol_type = protein
                         organism = Homo sapiens
SEQUENCE: 611
MLLLFHSKRM PVAEAPQVAG GQGDGGDGEE AEPEGMFKAC EDSKRKARGY LRLVPLFVLL    60
ALLVLASAGV LLWYFLGYKA EVMVSQVYSG SLRVLNRHFS QDLTRRESSA FRSETAKAQK   120
MLKELITSTR LGTYYNSSSV YSFGEGPLTC FFWFILQIPE HRRLMLSPEV VQALLVEELL   180
STVNSSAAVP YRAEYEVDPE GLVILEASVK DIAALNSTLG CYRYSYVGQG QVLRLKGPDH   240
LASSCLWHLQ GPKDLMLKLR LEWTLAECRD RLAMYDVAGP LEKRLITSVY GCSRQEPVVE   300
VLASGAIMAV VWKKGLHSYY DPFVLSVQPV VFQACEVNLT LDNRLDSQGV LSTPYFPSYY   360
SPQTHCSWHL TVPSLDYGLA LWFDAYALRR QKYDLPCTQG QWTIQNRRYH FLSSLWLPFL   420
PPPPSLPSSI VTPSLEAQVP NLRGAARGAS RGWGWCQACC P                      461

SEQ ID NO: 612           moltype = AA   length = 428
FEATURE                  Location/Qualifiers
source                   1..428
                         mol_type = protein
                         organism = Homo sapiens
SEQUENCE: 612
MLRTLLRRRL FSYPTKYYFM VLVLSLITFS VLRIHQKPEF VSVRHLELAG ENPSSDINCT    60
KVLQGDVNEI QKVKLEILTV KFKKRPRWTP DDYINMTSDC SSFIKRRKYI VEPLSKEEAE   120
FPIAYSIVVH HKIEMLDRLL RAIYMPQNFY CIHVDTKSED SYLAAVMGIA SCFSNVFVAS   180
RLESVVYASW SRVQADLNCM KDLYAMSANW KYLINLCGMD FPIKTNLEIV RKLKLLMGEN   240
NLETERMPSH KEERWKKRYE VVNGKLTNTG TVKMLPPLET PLFSGSAYFV VSREYVGYVL   300
QNEKIQKLME WAQDTYSPDE YLWATIQRIP EVPGSLPASH KYDLSDMQAV ARFVKWQYFE   360
GDVSKGAPYP PCDGVHVRSV CIFGAGDLNW MLRKHHLFAN KFDVDVDLFA IQCLDEHLRH   420
KALETLKH                                                           428

SEQ ID NO: 613           moltype = AA   length = 428
FEATURE                  Location/Qualifiers
source                   1..428
                         mol_type = protein
                         organism = Homo sapiens
SEQUENCE: 613
MLRTLLRRRL FSYPTKYYFM VLVLSLITFS VLRIHQKPEF VSVRHLELAG ENPSSDINCT    60
KVLQGDVNEI QKVKLEILTV KFKKRPRWTP DDYINMTSDC SSFIKRRKYI VEPLSKEEAE   120
FPIAYSIVVH HKIEMLDRLL RAIYMPQNFY CIHVDTKSED SYLAAVMGIA SCFSNVFVAS   180
RLESVVYASW SRVQADLNCM KDLYAMSANW KYLINLCGMD FPIKTNLEIV RKLKLLMGEN   240
NLETERMPSH KEERWKKRYE VVNGKLTNTG TVKMLPPLET PLFSGSAYFV VSREYVGYVL   300
QNEKIQKLME WAQDTYSPDE YLWATIQRIP EVPGSLPASH KYDLSDMQAV ARFVKWQYFE   360
GDVSKGAPYP PCDGVHVRSV CIFGAGDLNW MLRKHHLFAN KFDVDVDLFA IQCLDEHLRH   420
KALETLKH                                                           428

SEQ ID NO: 614           moltype = AA   length = 428
FEATURE                  Location/Qualifiers
source                   1..428
                         mol_type = protein
                         organism = Homo sapiens
SEQUENCE: 614
MLRTLLRRRL FSYPTKYYFM VLVLSLITFS VLRIHQKPEF VSVRHLELAG ENPSSDINCT    60
KVLQGDVNEI QKVKLEILTV KFKKRPRWTP DDYINMTSDC SSFIKRRKYI VEPLSKEEAE   120
FPIAYSIVVH HKIEMLDRLL RAIYMPQNFY CIHVDTKSED SYLAAVMGIA SCFSNVFVAS   180
RLESVVYASW SRVQADLNCM KDLYAMSANW KYLINLCGMD FPIKTNLEIV RKLKLLMGEN   240
NLETERMPSH KEERWKKRYE VVNGKLTNTG TVKMLPPLET PLFSGSAYFV VSREYVGYVL   300
QNEKIQKLME WAQDTYSPDE YLWATIQRIP EVPGSLPASH KYDLSDMQAV ARFVKWQYFE   360
GDVSKGAPYP PCDGVHVRSV CIFGAGDLNW MLRKHHLFAN KFDVDVDLFA IQCLDEHLRH   420
KALETLKH                                                           428

SEQ ID NO: 615           moltype = AA   length = 219
FEATURE                  Location/Qualifiers
source                   1..219
                         mol_type = protein
                         organism = Homo sapiens
SEQUENCE: 615
MPRGRKSRRR RNARAAEENR NNRKIQASEA SETPMAASVV ASTPEDDLSG PEEDPSTPEE    60
ASTTPEEASS TAQAQKPSVP RSNFQGTKKS LLMSILALIF IMGNSAKEAL VWKVLGKLGM   120
QPGRQHSIFG DPKKIVTEEF VRRGYLIYKP VPRSSPVEYE FFWGPRAHVE SSKLKVMHFV   180
ARVRNRCSKD WPCNYDWDSD DDAEVEAILN SGARGYSAP                         219

SEQ ID NO: 616           moltype = AA   length = 85
FEATURE                  Location/Qualifiers
source                   1..85
                         mol_type = protein
                         organism = Homo sapiens
SEQUENCE: 616
MGPRQGRWWL LLWLPPLATL PVRGEAAAAA LSVRRCKALK EKDLIRTSES DCYCYNQNSQ    60
```

```
VEWKYIWSTM QGDCVLLCGA CQEDI                                               85

SEQ ID NO: 617          moltype = AA   length = 417
FEATURE                 Location/Qualifiers
source                  1..417
                        mol_type = protein
                        organism = Homo sapiens
SEQUENCE: 617
MGPRQGRWWL LLWLPPLATL PVRGEAAAAA LSVRRCKALK EKDLIRTSES DCYCYNQNSQ          60
VEWKYIWSTM QVKITSPGLF RIVYIAERHN CQYPENILSF IKCVIHNFWI PKESNEITII         120
INPYRETVCF SVEPVKKIFN YMIHVNRNIM DFKLFLVFVA GVFLFFYART LSQSPTFYYS         180
SGTVLGVLMT LVFVLLLVKR FIPKYSTFWA LMVGCWFASV YIVCQLMEDL KWLWYENRIY         240
VLGYVLIVGF FSFVVCYKHG PLADDRSRSL LMWMLRLLSL VLVYAGVAVP QFAYAAIILL         300
MSSWSLHYPL RACSYMRWKM EQWFTSKELV VKYLTEDEYR EQADAETNSA LEELRRACRK         360
PDFPSWLVVS RLHTPSKFAD FVLGGSHLSP EEISLHEEQY GLGGAFLEEQ LFNPSTA            417

SEQ ID NO: 618          moltype = AA   length = 138
FEATURE                 Location/Qualifiers
source                  1..138
                        mol_type = protein
                        organism = Homo sapiens
SEQUENCE: 618
MQVKITSPGL FRIVYIAERH NCQYPENILS FIKCVIHNFW IPKESNEITI IINPYRETVC          60
FSVEPVKKIF NYMIHVNRNI MDFKLFLVFV AGVFLFFYAR TLSQSPTFYY SSGTVLGVLM         120
TLVFVLLLVK RFIPKAMS                                                      138

SEQ ID NO: 619          moltype = AA   length = 24
FEATURE                 Location/Qualifiers
source                  1..24
                        mol_type = protein
                        organism = Homo sapiens
SEQUENCE: 619
MQVKITSPGL FRIVYIAERH NCQY                                                24

SEQ ID NO: 620          moltype = AA   length = 35
FEATURE                 Location/Qualifiers
source                  1..35
                        mol_type = protein
                        organism = Homo sapiens
SEQUENCE: 620
DCYCYNQNSQ VEWKYIWSTM QGDCVLLCGA CQEDI                                    35

SEQ ID NO: 621          moltype = AA   length = 422
FEATURE                 Location/Qualifiers
source                  1..422
                        mol_type = protein
                        organism = Homo sapiens
SEQUENCE: 621
MLHLLALFLH CLPLASGDYD ICKSWVTTDE GPTWEFYACQ PKVMRLKDYV KVKVEPSGIT          60
CGDPPERFCS HENPYLCSNE CDASNPDLAH PPRLMFDKEE EGLATYWQSI TWSRYPSPLE         120
ANITLSWNKT VELTDDVVMT FEYGRPTVMV LEKSLDNGRT WQPYQFYAED CMEAFGMSAR         180
RARDMSSSSA HRVLCTEEYS RWAGSKKEKH VRFEVRDRFA IFAGPDLRNM DNLYTRLESA         240
KGLKEFFTLT DLRMRLLRPA LGGTYVQREN LYKYFYAISN IEVIGRCKCN LHANLCSMRE         300
GSLQCECEHN TTGPDCGKCK KNFRTRSWRA GSYLPLPHGS PNACATAGSF GTLQTPPPGR         360
SPSALRGSRR GLANVKEPAG SRPQISEMLL GCTVTLHQGS VGPHIPPKLS LPDPGGPWLG         420
SQ                                                                       422

SEQ ID NO: 622          moltype = AA   length = 530
FEATURE                 Location/Qualifiers
source                  1..530
                        mol_type = protein
                        organism = Homo sapiens
SEQUENCE: 622
MLHLLALFLH CLPLASGDYD ICKSWVTTDE GPTWEFYACQ PKVMRLKDYV KVKVEPSGIT          60
CGDPPERFCS HENPYLCSNE CDASNPDLAH PPRLMFDKEE EGLATYWQSI TWSRYPSPLE         120
ANITLSWNKT VELTDDVVMT FEYGRPTVMV LEKSLDNGRT WQPYQFYAED CMEAFGMSAR         180
RARDMSSSSA HRVLCTEEYS RWAGSKKEKH VRFEVRDRFA IFAGPDLRNM DNLYTRLESA         240
KGLKEFFTLT DLRMRLLRPA LGGTYVQREN LYKYFYAISN IEVIGRCKCN LHANLCSMRE         300
GSLQCECEHN TTGPDCGKCK KNFRTRSWRA GSYLPLPHGS PNACATAGSF GNCECYGHSN         360
RCSYIDFLNV VTCVSCKHNT RGQHCQHCRL GYYRNGSAEL DDENVCIECN CNQIGSVHDR         420
CNETGFCECR EGAAGPKCDD CLPTHYWRQG CYPNVCDDDQ LLCQNGGTCL QNQRCACPRG         480
YTGVRCEQPR CDPADDDGGL DCDRAPGAAP RPATLLGCLL LLGLAARLGR                    530

SEQ ID NO: 623          moltype = AA   length = 211
FEATURE                 Location/Qualifiers
source                  1..211
                        mol_type = protein
                        organism = Homo sapiens
SEQUENCE: 623
```

```
MRTLACLLLL GCGYLAHVLA EEAEIPREVI ERLARSQIHS IRDLQRLLEI DSVGSEDSLD    60
TSLRAHGVHA TKHVPEKRPL PIRRKRSIEE AVPAVCKTRT VIYEIPRSQV DPTSANFLIW   120
PPCVEVKRCT GCCNTSSVKC QPSRVHHRSV KVAKVEYVRK KPKLKEVQVR LEEHLECACA   180
TTSLNPDYRE EDTGRPRESG KKRKRKRLKP T                                 211

SEQ ID NO: 624          moltype = AA   length = 205
FEATURE                 Location/Qualifiers
source                  1..205
                        mol_type = protein
                        organism = Homo sapiens
SEQUENCE: 624
QRQAAALGSQ SPSPAGLRAG AVPPARACLQ EAEIPREVIE RLARSQIHSI RDLQRLLEID    60
SVGSEDSLDT SLRAHGVHAT KHVPEKRPLP IRRKRSIEEA VPAVCKTRTV IYEIPRSQVD   120
PTSANFLIWP PCVEVKRCTG CCNTSSVKCQ PSRVHHRSVK VAKVEYVRKK PKLKEVQVRL   180
EEHLECACAT TSLNPDYREE DTDVR                                        205

SEQ ID NO: 625          moltype = AA   length = 196
FEATURE                 Location/Qualifiers
source                  1..196
                        mol_type = protein
                        organism = Homo sapiens
SEQUENCE: 625
MRTLACLLLL GCGYLAHVLA EEAEIPREVI ERLARSQIHS IRDLQRLLEI DSVGSEDSLD    60
TSLRAHGVHA TKHVPEKRPL PIRRKRSIEE AVPAVCKTRT VIYEIPRSQV DPTSANFLIW   120
PPCVEVKRCT GCCNTSSVKC QPSRVHHRSV KVAKVEYVRK KPKLKEVQVR LEEHLECACA   180
TTSLNPDYRE EDTDVR                                                  196

SEQ ID NO: 626          moltype = AA   length = 86
FEATURE                 Location/Qualifiers
source                  1..86
                        mol_type = protein
                        organism = Homo sapiens
SEQUENCE: 626
MRTLACLLLL GCGYLAHVLA EEAEIPREVI ERLARSQIHS IRDLQRLLEI DSVGSEDSLD    60
TSLRAHGVHA TKHVPEKRPL PIRRKR                                        86

SEQ ID NO: 627          moltype = AA   length = 273
FEATURE                 Location/Qualifiers
source                  1..273
                        mol_type = protein
                        organism = Homo sapiens
SEQUENCE: 627
MIFLLLMLSL ELQLHQIAAL FTVTVPKELY IIEHGSNVTL ECNFDTGSHV NLGAITASLQ    60
KVENDTSPHR ERATLLEEQL PLGKASFHIP QVQVRDEGQY QCIIIYGVAW DYKYLTLKVK   120
ASYRKINTHI LKVPETDEVE LTCQATGYPL AEVSWPNVSV PANTSHSRTP EGLYQVTSVL   180
RLKPPPGRNF SCVFWNTHVR ELTLASIDLQ SQMEPRTHPT WLLHIFIPFC IIAFIFIATV   240
IALRKQLCQK LYSSKDTTKR PVTTTKREVN SAI                                273

SEQ ID NO: 628          moltype = AA   length = 423
FEATURE                 Location/Qualifiers
source                  1..423
                        mol_type = protein
                        organism = Homo sapiens
SEQUENCE: 628
MDRGQPSLEP AAAAPRASGR CVIAPVRAVL RLRRRVCVLR KRRLLQPGGG PDVGTGAPRP    60
GCSPRAPRAD LDQPKFFTFD SPAELPSRTP RKKRRRSRLV LYPETSRKYR PRVEHRSRAQ   120
RCLLLLVAIV GFQVLNAIEN LDDNAQRYDL DGLEKALQRA VFGQPAAVSR IVALMRDYLA   180
THVHSRPLLL ALHGPSGVGK SHVGRLLARH FRSVLEDSAL VLQYHARHHC PEARAAQDCR   240
EELARRVADV VAREAEAEKT PLLVLDDDVE LMPRPLLDELH GFLQPQRSHH FHNAIYVLLS   300
GAGGAEVTRF VLQNASRALP LRPDGFRSAE AAAAQAEEDL RASLLAVLSR EHPLWQAAAI   360
VPFLLLDKRD VVSCFRDEMA GEGFFPDQAR AENLAAQLSF YRVAGREFAV TGCKQVVATV   420
NLL                                                                423

SEQ ID NO: 629          moltype = AA   length = 69
FEATURE                 Location/Qualifiers
source                  1..69
                        mol_type = protein
                        organism = Homo sapiens
SEQUENCE: 629
XISEAEKAKQ KIAPVFFREE YMLNNAVGSC QKPYVALIHG ITMGGDCSLM WVEVISCHDS    60
KENLVTSLH                                                           69

SEQ ID NO: 630          moltype = AA   length = 52
FEATURE                 Location/Qualifiers
source                  1..52
                        mol_type = protein
                        organism = Homo sapiens
SEQUENCE: 630
DVGGGYFLPR LQGKLGYFLA LTGFRLKGRD VYRAGIATHF VDSEKNGDDT IT            52
```

```
SEQ ID NO: 631          moltype = AA  length = 793
FEATURE                 Location/Qualifiers
source                  1..793
                        mol_type = protein
                        organism = Homo sapiens
SEQUENCE: 631
MLRGGRRGQL GWHSWAAGPG SLLAWLILAS AGAAPCPDAC CPHGSSGLRC TRDGALDSLH   60
HLPGAENLTE LYIENQQHLQ HLELRDLRGL GELRNLTIVK SGLRFVAPDA FHFTPRLSRL  120
NLSFNALESL SWKTVQGLSL QELVLSGNPL HCSCALRWLQ RWEEEGLGGV PEQKLQCHGQ  180
GPLAHMPNAS CGVPTLKVQV PNASVDVGDD VLLRCQVEGR GLEQAGWILT ELEQSATVMK  240
SGGLPSLGLT LANVTSDLNR KNVTCWAEND VGRAEVSVQV NVSFPASVQL HTAVEMHHWC  300
IPFSVDGQPA PSLRWLFNGS VLNETSFIFT EFLEPAANET VRHGCLRLNQ PTHVNNGNYT  360
LLAANPFGQA SASIMAAFMD NPFEFNPEDP IPDTNSTSGD PVEKKDETPF GVSAVAVGLAV  420
FACLFLSTLL LVLNKCGRRN KFGINRPAVL APEDGLAMSL HFMTLGGSSL SPTEGKGSGL  480
QGHIIENPQY FSDASPSGVH HIKRRDIVLK WELGEGAFGK VFLAECHNLL PEQDKMLVAV  540
KALKEASESA RQDFQREAEL LTMLQHQHIV RFFGVCTEGR PLLMVFEYMR HGDLNRFLRS  600
HGPDAKLLAG GEDVAPGPLG LGQLLAVASQ VAAGMVYLAG LHFVHRDLAT RNCLVGQGLV  660
VKIGDFGMSR DIYSTDYYRV GGRTMLPIRW MPPESILYRK FTTESDVWSF GVVLWEIFTY  720
GKQPWYQLSN TEAIDCITQG RELERPRACP PEVYAIMRGC WQREPQQRHS IKDVHARLQA  780
LAQAPPVYLD VLG                                                    793

SEQ ID NO: 632          moltype = AA  length = 790
FEATURE                 Location/Qualifiers
source                  1..790
                        mol_type = protein
                        organism = Homo sapiens
SEQUENCE: 632
MLRGGRRGQL GWHSWAAGPG SLLAWLILAS AGAAPCPDAC CPHGSSGLRC TRDGALDSLH   60
HLPGAENLTE LYIENQQHLQ HLELRDLRGL GELRNLTIVK SGLRFVAPDA FHFTPRLSRL  120
NLSFNALESL SWKTVQGLSL QELVLSGNPL HCSCALRWLQ RWEEEGLGGV PEQKLQCHGQ  180
GPLAHMPNAS CGVPTLKVQV PNASVDVGDD VLLRCQVEGR GLEQAGWILT ELEQSATVMK  240
SGGLPSLGLT LANVTSDLNR KNVTCWAEND VGRAEVSVQV NVSFPASVQL HTAVEMHHWC  300
IPFSVDGQPA PSLRWLFNGS VLNETSFIFT EFLEPAANET VRHGCLRLNQ PTHVNNGNYT  360
LLAANPFGQA SASIMAAFMD NPFEFNPEDP IPDTNSTSGD PVEKKDETPF GVSAVAVGLAV  420
FACLFLSTLL LVLNKCGRRN KFGINRPAVL APEDGLAMSL HFMTLGGSSL SPTEGKGSGL  480
QGHIIENPQY FSDACVHHIK RRDIVLKWEL GEGAFGKVFL AECHNLLPEQ DKMLVAVKAL  540
KEASESARQD FQREAELLTM LQHQHIVRFF GVCTEGRPLL MVFEYMRHGD LNRFLRSHGP  600
DAKLLAGGED VAPGPLGLGQ LLAVASQVAA GMVYLAGLHF VHRDLATRNC LVGQGLVVKI  660
GDFGMSRDIY STDYYRVGGR TMLPIRWMPP ESILYRKFTT ESDVWSFGVV LWEIFTYGKQ  720
PWYQLSNTEA IDCITQGREL ERPRACPPEV YAIMRGCWQR EPQQRHSIKD VHARLQALAQ  780
APPVYLDVLG                                                        790

SEQ ID NO: 633          moltype = AA  length = 760
FEATURE                 Location/Qualifiers
source                  1..760
                        mol_type = protein
                        organism = Homo sapiens
SEQUENCE: 633
MKEAALICLA PSVPPILTVK SWDTMQLRAA RSRCTNLLAA SYIENQQHLQ HLELRDLRGL   60
GELRNLTIVK SGLRFVAPDA FHFTPRLSRL NLSFNALESL SWKTVQGLSL QELVLSGNPL  120
HCSCALRWLQ RWEEEGLGGV PEQKLQCHGQ GPLAHMPNAS CGVPTLKVQV PNASVDVGDD  180
VLLRCQVEGR GLEQAGWILT ELEQSATVMK SGGLPSLGLT LANVTSDLNR KNVTCWAEND  240
VGRAEVSVQV NVSFPASVQL HTAVEMHHWC IPFSVDGQPA PSLRWLFNGS VLNETSFIFT  300
EFLEPAANET VRHGCLRLNQ PTHVNNGNYT LLAANPFGQA SASIMAAFMD NPFEFNPEDP  360
IPDTNSTSGD PVEKKDETPF GVSAVAVGLAV FACLFLSTLL LVLNKCGRRN KFGINRPAVL  420
APEDGLAMSL HFMTLGGSSL SPTEGKGSGL QGHIIENPQY FSDACVHHIK RRDIVLKWEL  480
GEGAFGKVFL AECHNLLPEQ DKMLVAVKAL KEASESARQD FQREAELLTM LQHQHIVRFF  540
GVCTEGRPLL MVFEYMRHGD LNRFLRSHGP DAKLLAGGED VAPGPLGLGQ LLAVASQVAA  600
GMVYLAGLHF VHRDLATRNC LVGQGLVVKI GDFGMSRDIY STDYYRVGGR TMLPIRWMPP  660
ESILYRKFTT ESDVWSFGVV LWEIFTYGKQ PWYQLSNTEA IDCITQGREL ERPRACPPEV  720
YAIMRGCWQR EPQQRHSIKD VHARLQALAQ APPVYLDVLG                        760

SEQ ID NO: 634          moltype = AA  length = 388
FEATURE                 Location/Qualifiers
source                  1..388
                        mol_type = protein
                        organism = Homo sapiens
SEQUENCE: 634
MKEAALICLA PSVPPILTVK SWDTMQLRAA RSRCTNLLAA SYIENQQHLQ HLELRDLRGL   60
GELRNLTIVK SGLRFVAPDA FHFTPRLSRL NLSFNALESL SWKTVQGLSL QELVLSGNPL  120
HCSCALRWLQ RWEEEGLGGV PEQKLQCHGQ GPLAHMPNAS CGVPTLKVQV PNASVDVGDD  180
VLLRCQVEGR GLEQAGWILT ELEQSATVMS RPVCSCTRRW RCTTGASPSL WMGSRHRLCA  240
GSSMAPCSMR PASSSLSSWS RQPMRPCGTG VCASTSPPTS TTATTRCWLP TPSARPPPPS  300
WLPSWTTLSS STPRTPSLTL TAHLETRWRR RTKHLLGSRW LWAWPSLPAS SFLRCSLCST  360
NVDGETSLGS TARLCWLQRM GWPCPCIS                                    388

SEQ ID NO: 635          moltype = AA  length = 796
FEATURE                 Location/Qualifiers
```

```
source                    1..796
                          mol_type = protein
                          organism = Homo sapiens
SEQUENCE: 635
MLRGGRRGQL GWHSWAAGPG SLLAWLILAS AGAAPCPDAC CPHGSSGLRC TRDGALDSLH    60
HLPGAENLTE LYIENQQHLQ HLELRDLRGL GELRNLTIVK SGLRFVAPDA FHFTPRLSRL   120
NLSFNALESL SWKTVQGLSL QELVLSGNPL HCSCALRWLQ RWEEEGLGGV PEQKLQCHGQ   180
GPLAHMPNAS CGVPTLKVQV PNASVDVGDD VLLRCQVEGR GLEQAGWILT ELEQSATVMK   240
SGGLPSLGLT LANVTSDLNR KNVTCWAEND VGRAEVSVQV NVSFPASVQL HTAVEMHHWC   300
IPFSVDGQPA PSLRWLFNGS VLNETSFIFT EFLEPAANET VRHGCLRLNQ PTHVNNGNYT   360
LLAANPFGQA SASIMAAFMD NPFEFNPEDP IPVSFSPVDT NSTSGDPVEK KDETPFGVSV   420
AVGLAVFACL FLSTLLLVLN KCGRRNKFGI NRPAVLAPED GLAMSLHFMT LGGSSLSPTE   480
GKGSGLQGHI IENPQYFSDA CVHHIKRRDI VLKWELGEGA FGKVFLAECH NLLPEQDKML   540
VAVKALKEAS ESARQDFQRE AELLTMLQHQ HIVRFFGVCT EGRPLLMVFE YMRHGDLNRF   600
LRSHGPDAKL LAGGEDVAPG PLGLGQLLAV ASQVAAGMVY LAGLHFVHRD LATRNCLVGQ   660
GLVVKIGDFG MSRDIYSTDY YRVGGRTMLP IRWMPPESIL YRKFTTESDV WSFGVVLWEI   720
FTYGKQPWYQ LSNTEAIDCI TQGRELERPR ACPPEVYAIM RGCWQREPQQ RHSIKDVHAR   780
LQALAQAPPV YLDVLG                                                   796

SEQ ID NO: 636            moltype = AA  length = 131
FEATURE                   Location/Qualifiers
source                    1..131
                          mol_type = protein
                          organism = Homo sapiens
SEQUENCE: 636
MSKRYLQKAT KGKLLIIIFI VTLWGKVVSS ANHHKAHHVK TGTCEVVALH RCCNKNKIEE    60
RSQTVKCSCF PGQVAGTTRA APSCVDASIV EQKWWCHMQP CLEGEECKVL PDRKGWSCSS   120
GNKVKTTRVT H                                                        131

SEQ ID NO: 637            moltype = AA  length = 87
FEATURE                   Location/Qualifiers
source                    1..87
                          mol_type = protein
                          organism = Homo sapiens
SEQUENCE: 637
MMSKRYLQKA TKGKLLIIIF IVTLWGKVVS SANHHKAHHV KTGTCEVVAL HRCCNKNKIE    60
ERSQTVKCSC FPGQVAGTTR AAPSCVD                                        87

SEQ ID NO: 638            moltype = AA  length = 131
FEATURE                   Location/Qualifiers
source                    1..131
                          mol_type = protein
                          organism = Homo sapiens
SEQUENCE: 638
MSKRYLQKAT KGKLLIIIFI VTLWGKVVSS ANHHKAHHVK TGTCEVVALH RCCNKNKIEE    60
RSQTVKCSCF PGQVAGTTRA APSCVDASIV EQKWWCHMQP CLEGEECKVL PDRKGWSCSS   120
GNKVKTTRAN V                                                        131

SEQ ID NO: 639            moltype = AA  length = 101
FEATURE                   Location/Qualifiers
source                    1..101
                          mol_type = protein
                          organism = Homo sapiens
SEQUENCE: 639
MVTPITRMSK RYLQKATKGK LLIIIFIVTL WGKVVSSANH HKAHHVKTGT CEVVALHRCC    60
NKNKIEERSQ TVKCSCFPGQ VAGTTRAAPS CVDASIVEQK W                       101

SEQ ID NO: 640            moltype = AA  length = 34
FEATURE                   Location/Qualifiers
source                    1..34
                          mol_type = protein
                          organism = Homo sapiens
SEQUENCE: 640
MQPCLEGEEC KVLPDRKGWS CSSGNKVKTT RVTH                                 34

SEQ ID NO: 641            moltype = AA  length = 49
FEATURE                   Location/Qualifiers
source                    1..49
                          mol_type = protein
                          organism = Homo sapiens
SEQUENCE: 641
MSKRYLQKAT KGKLLIIIFI VTLWGKVVSS ANHHKGNPLT QEKSSDPQG                 49

SEQ ID NO: 642            moltype = AA  length = 131
FEATURE                   Location/Qualifiers
source                    1..131
                          mol_type = protein
                          organism = Homo sapiens
SEQUENCE: 642
```

```
MSKRYLQKAT KGKLLIIIFI VTLWGKVVSS ANHHKAHHVK TGTCEVVALH RCCNKNKIEE   60
RSQTVKCSCF PGQVAGTTRA APSCVDASIV EQKWWCHMQP CLEGEECKVL PDRKGWSCSS  120
GNKVKTTRVT H                                                      131

SEQ ID NO: 643         moltype = AA   length = 110
FEATURE                Location/Qualifiers
source                 1..110
                       mol_type = protein
                       organism = Homo sapiens
SEQUENCE: 643
MMSKRYLQKA TKGKLLIIIF IVTLWGKVVS SANHHKAHHV KTGTCEVVAL HRCCNKNKIE   60
ERSQTVKCSC FPGQVAGTTR AAPSCVDASI VEQKWWCHMQ PCLEGEECKV            110

SEQ ID NO: 644         moltype = AA   length = 2229
FEATURE                Location/Qualifiers
source                 1..2229
                       mol_type = protein
                       organism = Homo sapiens
SEQUENCE: 644
MFPGCPRLWV LVVLGTSWVG WGSQGTEAAQ LRQFYVAAQG ISWSYRPEPT NSSLNLSVTS   60
FKKIVYREYE PYFKKEKPQS TISGLLGPTL YAEVGDIIKV HFKNKADKPL SIHPQGIRYS  120
KLSEGASYLD HTFPAEKMDD AVAPGREYTY EWSISEDSGP THDDPPCLTH IYYSHENLIE  180
DFNSGLIGPL LICKKGTLTE GGTQKTFDKQ IVLLFAVFDE SKSWSQSSSL MYTVNGYVNG  240
TMPDITVCAH DHISWHLLGM SSGPELFSIH FNGQVLEQNH HKVSAITLVS ATSTTANMTV  300
GPEGKWIISS LTPKHLQAGM QAYIDIKNCP KKTRNLKKIT REQRRHMKRW EYFIAAEEVI  360
WDYAPVIPAN MDKKYRSQHL DNFSNQIGKH YKKVMYTQYE DESFTKHTVN PNMKEDGILG  420
PIIRAQVRDT LKIVFKNMAS RPYSIYPHGV TFSPYEDEVN SSFTSGRNNT MIRAVQPGET  480
YTYKWNILEF DEPTENDAQC LTRPYYSDVD IMRDIASGLI GLLLICKSRS LDRRGIQRAA  540
DIEQQAVFAV FDENKSWYLE DNINKFCENP DEVKRDDPKF YESNIMSNFT LSAINGYVPE  600
SITTLGFCFD DTVQWHFCSV GTQNEILTIH FTGHSFIYGK RHEDTLTLFP MRGESVTVTM  660
DNVGTWMLTS MNSSPRSKKL RLKFRDVKCI PDDDEDSYEI FEPPESTVMA TRKMHDRLEP  720
EDEESDADYD YQNRLAAALG IRSFRNSSLN QEEEEFNLTA LALENGTEFV SSNTDIIVGS  780
NYSSPSNISK FTVNNLAEPQ KAPSHQQATT AGSPLRHLIG KNSVLNSSTA EHSSPYSEDP  840
IEDPLQPDVT GIRLLSLGAG EFKSQEHAKH KGPKVERDQA AKHRFSWMKL LAHKVGRHLS  900
QDTGSPSGMR PWEDLPSQDT GSPSRMRPWK DPPSDLLLLK QSNSSKILVG RWHLASEKGS  960
YEIIQDTDED TAVNNWLISP QNASRAWGES TPLANKPGKQ SGHPKFPVR HKSLQVRQDG  1020
GKSRLKKSQF LIKTRKKKKE KHTHHAPLSP RTFHPLRSEA YNTFSERRLK HSLVLHKSNE 1080
TSLPTDLNQT LPSMDFGWIA SLPDHNQNSS NDTGQASCPP GLYQTVPPEE HYQTFPIQDP 1140
DQMHSTSDPS HRSSSPELSE MLEYDRSHKS FPTDISQMSP SSEHEVWQTV ISPDLSQVTL 1200
SPELSQTNLS PDLSHTTLSP ELIQRNLSPA LGQMPISPDL SHTTLSPDLS HTTLSLDLSQ 1260
TNLSPELSQT NLSPALGQMP LSPDLSHTTL SLDFSQTNLS PELSHMTLSP ELSQTNLSPA 1320
LGQMPISPDL SHTTLSLDFS QTNLSPELSQ TNLSPALGQM PLSPDLSHTT LSLDLSQTNL 1380
SPELSQTNLS PDLSEMPLFA DLSQIPLTPD LDQMTLSPDL PQMSLSPDLSQ 1440
VTLSPDISDT TLLPDLSQIS PPPDLDQIFY PSESSQSLLL QEFNESFPYP DLGQMPSPSS 1500
PTLNDTFLSK EFNPLVIVGL SKDGTDYIEI IPKEEVQSSE DDYAEIDYVP YDDPYKTDVR 1560
TNINSSRDPD NIAAWYLRSN NGNRRNYYIA AEEISWDYSE FVQRETDIED SDDIPEDTTY 1620
KKVVFRKYLD STFTKRDPRG EYEEHLGILG PIIRAEVDDV IQVRFKNLAS RPYSLHAHGL 1680
SYEKSSEGKT YEDDSPEWFK EDNAVQPNSS YTYVWHATER SGPESPGSAC RAWAYYSAVN 1740
PEKDIHSGLI GPLLICQKGI LHKDSNMPMD MREFVLLFMT FDEKKSWYYE KKSRSSWRLT 1800
SSEMKKSHEF HAINGMIYSL PGLKMYEQEW VRLHLLNIGG SQDIHVVFH GQTLLENGNK 1860
QHQLGVWPLL PGSFKTLEMK ASKPGWWLLN TEVGENQRAG MQTPFLIMDR DCRMPMGLST 1920
GIIISDSQIKA SEFLGYWEPR LARLNNGGSY NAWSVEKLAA EFASKPWIQV DMQKEVIITG 1980
IQTQGAKHYL KSCYTTEFYV AYSSNQINWQ IFKGNSTRNV MYFNGNSDAS TIKENQFDPP 2040
IVARYIRISP TRAYNRPTLR LELQGCEVNG CSTPLGMENG KIENKQITAS FKKSWWGDY  2100
WEPFRARLNA QGRVNAWQAK ANNNKQWLEI DLLKIKKITA IITQGCKSLS SEMYVKSYTI 2160
HYSEQGVEWK PYRLKSSMVD KIFEGNTNTK GHVKNFFNPP IISRFIRVIP KTWNQSIALR 2220
LELFGCDIY                                                        2229

SEQ ID NO: 645         moltype = AA   length = 2224
FEATURE                Location/Qualifiers
source                 1..2224
                       mol_type = protein
                       organism = Homo sapiens
SEQUENCE: 645
MFPGCPRLWV LVVLGTSWVG WGSQGTEAAQ LRQFYVAAQG ISWSYRPEPT NSSLNLSVTS   60
FKKIVYREYE PYFKKEKPQS TISGLLGPTL YAEVGDIIKV HFKNKADKPL SIHPQGIRYS  120
KLSEGASYLD HTFPAEKMDD AVAPGREYTY EWSISEDSGP THDDPPCLTH IYYSHENLIE  180
DFNSGLIGPL LICKKGTLTE GGTQKTFDKQ IVLLFAVFDE SKSWSQSSSL MYTVNGYVNG  240
TMPDITVCAH DHISWHLLGM SSGPELFSIH FNGQVLEQNH HKVSAITLVS ATSTTANMTV  300
GPEGKWIISS LTPKHLQAGM QAYIDIKNCP KKTRNLKKIT REQRRHMKRW EYFIAAEEVI  360
WDYAPVIPAN MDKKYRSQHL DNFSNQIGKH YKKVMYTQYE DESFTKHTVN PNMKEDGILG  420
PIIRAQVRDT LKIVFKNMAS RPYSIYPHGV TFSPYEDEVN SSFTSGRNNT MIRAVQPGET  480
YTYKWNILEF DEPTENDAQC LTRPYYSDVD IMRDIASGLI GLLLICKSRS LDRRGIQRAA  540
DIEQQAVFAV FDENKSWYLE DNINKFCENP DEVKRDDPKF YESNIMSTIN GYVPESITTL  600
GFCFDDTVQW HFCSVGTQNE ILTIHFTGHS FIYGKRHEDT LTLFPMRGES VTVTMDNVGT  660
WMLTSMNSSP RSKKLRLKFR DVKCIPDDDE DSYEIFEPPE STVMATRKMH DRLEPEDEES  720
DADYDYQNRL AAALGIRSFR NSSLNQEEEE FNLTALALEN GTEFVSSNTD IIVGSNYSSP  780
SNISKFTVNN LAEPQKAPSH QQATTAGSPL RHLIGKNSVL NSSTAEHSSP YSEDPIEDPL  840
QPDVTGIRLL SLGAGEFKSQ EHAKHKGPKV ERDQAAKHRF SWMKLLAHKV GRHLSQDTGS  900
```

```
PSGMRPWEDL PSQDTGSPSR MRPWKDPPSD LLLLKQSNSS KILVGRWHLA SEKGSYEIIQ  960
DTDEDTAVNN WLISPQNASR AWGESTPLAN KPGKQSGHPK FPRVRHKSLQ VRQDGGKSRL 1020
KKSQFLIKTR KKKKEKHTHH APLSPRTFHP LRSEAYNTFS ERRLKHSLVL HKSNETSLPT 1080
DLNQTLPSMD FGWIASLPDH NQNSSNDTGQ ASCPPGLYQT VPPEEHYQTF PIQDPDQMHS 1140
TSDPSHRSSS PELSEMLEYD RSHKFSPTDI SQMSPSSEHE VWQTVISPDL SQVTLSPELS 1200
QTNLSPDLSH TTLSPELIQR NLSPALGQMP ISPDLSHTTL SPDLSHTTLS LDLSQTNLSP 1260
ELSQTNLSPA LGQMPLSPDL SHTTLSLDFS QTNLSPELSH MTLSPELSQT NLSPALGQMP 1320
ISPDLSHTTL SLDFSQTNLS PELSQTNLSP ALGQMPLSPD PSHTTLSLDL SQTNLSPELS 1380
QTNLSPDLSE MPLFADLSQI PLTPDLDQMT LSPDLGETDL SPNFGQMSLS PDLSQVTLSP 1440
DISDTTLLPD LSQISPPPDL DQIFYPSESS QSLLLQEFNE SFPYPDLGQM PSPSSPTLND 1500
TFLSKEFNPL VIVGLSKDGT DYIEIIPKEE VQSSEDDYAE IDYVPYDDPY KTDVRTNINS 1560
SRDPDNIAAW YLRSNNGNRR NYYIAAEEIS WDYSEFVQRE TDIEDSDDIP EDTTYKKVVF 1620
RKYLDSTFTK RDPRGEYEEH LGILGPIIRA EVDDVIQVRF KNLASRPYSL HAHGLSYEKS 1680
SEGKTYEDDS PEWFKEDNAV QPNSSYTYVW HATERSGPES PGSACRAWAY YSAVNPEKDI 1740
HSGLIGPLLI CQKGILHKDS NMPMDMREFV LLFMTFDEKK SWYYEKKSRS SWRLTSSEMK 1800
KSHEFHAING MIYSLPGLKM YEQEWVRLHL LNIGGSQDIH VVHFHGQTLL ENGNKQHQLG 1860
VWPLLPGSFK TLEMKASKPG WWLLNTEVGE NQRAGMQTPF LIMDRDCRMP MGLSTGIISD 1920
SQIKASEFLG YWEPRLARLN NGGSYNAWSV EKLAAEFASK PWIQVDMQKE VIITGIQTQG 1980
AKHYLKSCYT TEFYVAYSSN QINWQIFKGN STRNVMYFNG NSDASTIKEN QFDPPIVARY 2040
IRISPTRAYN RPTLRLELQG CEVNGCSTPL GMENGKIENK QITASSFKKS WWGDYWEPFR 2100
ARLNAQGRVN AWQAKANNNK QWLEIDLLKI KKITAIITQG CKSLSSEMYV KSYTIHYSEQ 2160
GVEWKPYRLK SSMVDKIFEG NTNTKGHVKN FFNPPIISRF IRVIPKTWNQ SIALRLELFG 2220
CDIY                                                             2224

SEQ ID NO: 646          moltype = AA  length = 553
FEATURE                 Location/Qualifiers
source                  1..553
                        mol_type = protein
                        organism = Homo sapiens
SEQUENCE: 646
MAASKKAVLG PLVGAVDQGT SSTRFLVFNS KTAELLSHHQ VEIKQEFPRE GWVEQDPKEI  60
LHSVYECIEK TCEKLGQLNI DISNIKAIGV SNQRETTVVW DKITGEPLYN AVVWLDLRTQ 120
STVESLSKRI PGNNNFVKSK TGLPLSTYFS AVKLRWLLDN VRKVQAVEE KRALFGTIDS 180
WLIWSLTGGV NGGVHCTDVT NASRTMLFNI HSLEWDKQLC EFFGIPMEIL PNVRSSSEIY 240
GLMKAGALEG VPISGCLGDQ SAALVGQMCF QIGQAKNTYG TGCFLLCNTG HKCVFSDHGL 300
LTTVAYKLGR DKPVYYALEG SVAIAGAVIR WLRDNLGIIK TSEEIEKLAK EVGTSYGCYF 360
VPAFSGLYAP YWEPSARGII CGLTQFTNKC HIAFAALEAV CFQTREILDA MNRDCGIPLS 420
HLQVDGGMTS NKILMQLQAD ILYIPVVKPS MPETTALGAA MAAGAAEGVG VWSLEPEDLS 480
AVTMERFEPQ INAEESEIRY STWKKAVMKS MGWVTTQSPE SGDPSIFCSL PLGFFIVSSM 540
VMLIGARYIS GIP                                                   553

SEQ ID NO: 647          moltype = AA  length = 559
FEATURE                 Location/Qualifiers
source                  1..559
                        mol_type = protein
                        organism = Homo sapiens
SEQUENCE: 647
MAASKKAVLG PLVGAVDQGT SSTRFLVFNS KTAELLSHHQ VEIKQEFPRE GWVEQDPKEI  60
LHSVYECIEK TCEKLGQLNI DISNIKAIGV SNQRETTVVW DKITGEPLYN AVVWLDLRTQ 120
STVESLSKRI PGNNNFVKSK TGLPLSTYFS AVKLRWLLDN VRKVQAVEE KRALFGTIDS 180
WLIWSLTGGV NGGVHCTDVT NASRTMLFNI HSLEWDKQLC EFFGIPMEIL PNVRSSSEIY 240
GLMKISHSVK AGALEGVPIS GCLGDQSAAL VGQMCFQIGQ AKNTYGTGCF LLCNTGHKCV 300
FSDHGLLTTV AYKLGRDKPV YYALEGSVAI AGAVIRWLRD NLGIIKTSEE IEKLAKEVGT 360
SYGCYFVPAF SGLYAPYWEP SARGIICGLT QFTNKCHIAF AALEAVCFQT REILDAMNRD 420
CGIPLSHLQV DGGMTSNKIL MQLQADILYI PVVKPSMPET TALGAAMAAG AAEGVGVWSL 480
EPEDLSAVTM ERFEPQINAE ESEIRYSTWK KAVMKSMGWV TTQSPESGDP SIFCSLPLGF 540
FIVSSMVMLI GARYISGIP                                             559

SEQ ID NO: 648          moltype = AA  length = 41
FEATURE                 Location/Qualifiers
source                  1..41
                        mol_type = protein
                        organism = Homo sapiens
SEQUENCE: 648
SARVAKFRCC LIPDSDSITC IPLKPAFSGM APDVAYSTPT S                      41

SEQ ID NO: 649          moltype = AA  length = 57
FEATURE                 Location/Qualifiers
source                  1..57
                        mol_type = protein
                        organism = Homo sapiens
SEQUENCE: 649
MRLHYRYKEA SGYFHTLRAV MRNPEEDGKD TLQCIAEMLQ ITKQAMGSDL PIIEKKL      57

SEQ ID NO: 650          moltype = AA  length = 183
FEATURE                 Location/Qualifiers
source                  1..183
                        mol_type = protein
                        organism = Homo sapiens
```

```
SEQUENCE: 650
MPRSHRPPPT AQRAATAAAA EPKSEGVVAM TFKIFLLFAG LMVKVPVGLY FSCKLLLFQS    60
LMLMSPEDSG FYATIVAVVG LHVQQFSECT LIDATHRDVD VLLLLSNSAY YVAYYDDEVD   120
KVNQYQRLSL ENLEKIEIGP EPTLFGKPKF SCMRLHYRYK EASGYFHTLR AVMRNPEEDG   180
KDT                                                                183

SEQ ID NO: 651           moltype = AA  length = 145
FEATURE                  Location/Qualifiers
source                   1..145
                         mol_type = protein
                         organism = Homo sapiens
SEQUENCE: 651
MSAVLLLALL GFILPLPGVQ ALLCQFGTVQ HVWKVSDLPR QWTPKNTSCD SGLGCQDTLM    60
LIESGPQVSL VLSKGCTEAK DQEPRVTEHR MGPGLSLISY TFVCRQEDFC NNLVNSLPLW   120
APQPPADPMM GAAEGPFGKA EQVDS                                        145

SEQ ID NO: 652           moltype = AA  length = 139
FEATURE                  Location/Qualifiers
source                   1..139
                         mol_type = protein
                         organism = Homo sapiens
SEQUENCE: 652
MSAVLLLALL GFILPLPGVQ ALLCQFGTVQ HVWKVSDLPR QWTPKNTSCD SGLGCQDTLM    60
LIESGPQVSL VLSKGCTEAK DQEPRVTEHR MGPGLSLISY TFVCRQEDFC NNLVNSLPLW   120
APQPPAGACG RVGRRGRGC                                               139

SEQ ID NO: 653           moltype = AA  length = 437
FEATURE                  Location/Qualifiers
source                   1..437
                         mol_type = protein
                         organism = Homo sapiens
SEQUENCE: 653
MSAVLLLALL GFILPLPGVQ ALLCQFGTVQ HVWKVSDLPR QWTPKNTSCD SGLGCQDTLM    60
LIESGPQVSL VLSKGCTEAK DQEPRVTEHR MGPGLSLISY TFVCRQEDFC NNLVNSLPLW   120
APQPPADPGS LRCPVCLSME GCLEGTTEEI CPKGTTHCYD GLLRLRGGGI FSNLRVQGCM   180
PQPVCNLLNG TQEIGPVGMT ENCDMKDFLT CHRGTTIMTH GNLAQEPTDW TTSNTEMCEV   240
GQVCQETLLL LDVGLTSTLV GTKGCSTVGA QNSQKTTIHS APPGVLVASY THFCSSDLCN   300
SASSSSVLLN SLPPQAAPVP GDRQCPTCVQ PLGTCSSGSP RMTCPRGATH CYDGYIHLSG   360
GGLSTKMSIQ GCVAQPSSFL LNHTRQIGIF SAREKRDVQP PASQHEGGGA EGLESLTWGV   420
GLALAPALWW GVVCPSC                                                 437

SEQ ID NO: 654           moltype = AA  length = 131
FEATURE                  Location/Qualifiers
source                   1..131
                         mol_type = protein
                         organism = Homo sapiens
SEQUENCE: 654
MAGVKALVAL SFSGAIGLTF LMLGCALEDY GVYWPLFVLI FHAISPIPHF IAKRVTYDSD    60
ATSSACRELA YFFTTGIVVS AFGFPVILAR VAVIKWGACG LVLAGNAVIF LTIQGFFLIF   120
GRGDDFSWEQ W                                                       131

SEQ ID NO: 655           moltype = AA  length = 140
FEATURE                  Location/Qualifiers
source                   1..140
                         mol_type = protein
                         organism = Homo sapiens
SEQUENCE: 655
MRDGKGFLQG FLYFALVALS FSGAIGLTFL MLGCALEDYG VYWPLFVLIF HAISPIPHFI    60
AKRVTYDSDA TSSACRELAY FFTTGIVVSA FGFPVILARV AVIKWGACGL VLAGNAVIFL   120
TIQGFFLIFG RGDDFSWEQW                                              140

SEQ ID NO: 656           moltype = AA  length = 140
FEATURE                  Location/Qualifiers
source                   1..140
                         mol_type = protein
                         organism = Homo sapiens
SEQUENCE: 656
MQFGELLAAV RKAQANVMLF LEEKEQAALS QANGIKAHLE YRSAEMEKSK QELERMAAIS    60
NTVQFLEMRM TSRLTRTQHT SISGCRRRTA RSPTPRPGSI PTRTSPAGSC TGGRCCPSRV   120
CTCTGTILRW RSSGQAPMLA                                              140

SEQ ID NO: 657           moltype = AA  length = 205
FEATURE                  Location/Qualifiers
source                   1..205
                         mol_type = protein
                         organism = Homo sapiens
SEQUENCE: 657
MTPPERLFLP RVCGTTLHLL LLGLLLVLLP GAQGLPGVGL TPSAAQTARQ HPKMHLAHST    60
LKPAAHLIGD PSKQNSLLWR ANTDRAFLQD GFSLSNNSLL VPTSGIYFVY SQVVFSGKAY   120
```

```
SPKATSSPLY LAHEVQLFSS QYPFHVPLLS SQKMVYPGLQ EPWLHSMYHG AAFQLTQGDQ    180
LSTHTDGIPH LVLSPSTVFF GAFAL                                         205

SEQ ID NO: 658             moltype = AA  length = 205
FEATURE                    Location/Qualifiers
source                     1..205
                           mol_type = protein
                           organism = Homo sapiens
SEQUENCE: 658
MTPPERLFLP RVCGTTLHLL LLGLLLVLLP GAQGLPGVGL TPSAAQTARQ HPKMHLAHST    60
LKPAAHLIGD PSKQNSLLWR ANTDRAFLQD GFSLSNNSLL VPTSGIYFVY SQVVFSGKAY    120
SPKATSSPLY LAHEVQLFSS QYPFHVPLLS SQKMVYPGLQ EPWLHSMYHG AAFQLTQGDQ    180
LSTHTDGIPH LVLSPSTVFF GAFAL                                         205

SEQ ID NO: 659             moltype = AA  length = 1015
FEATURE                    Location/Qualifiers
source                     1..1015
                           mol_type = protein
                           organism = Homo sapiens
SEQUENCE: 659
MLTALAPPAL PGIPRQLPTA PARRQDSSGS SGSYYTAPGS PEPPDVGPDA KGPANWPWVA    60
PGRGAGAQPR LSVSAQNSRQ RHGPLPPGFPR GPGSGPRPPQ PQLRTLPSGE MEVIFGVGPL   120
FGCSGADDRE AQQQFTEPAF ISPLPPGPAS PAAVPRQSQV PDGGSRWATY LELRPRGPSP    180
AAPAQFECVE VALEEGAAPA RPRTVPKRQI ELRPRPQSPP RAAGAPRPRL LLRTGSLDES    240
LGPLQAAAGF VQTALARKLS PEAPAPSSAT FGSTGRSEPE TRETARSTHV VLEKAKSRPL    300
RVRDNSAPAK APRPWPSLRE RAIRRDKPAP GTEPLGPVSS SIFLQSEEKI QEARKTRFPR    360
EAPDRTVQRA RSPPFECRIP SEVPSRAVRP RSPSPPRQTP NGAVRGPRCP SPQNLSPWDR    420
TTRRVSSPLF PEASSEWENQ NPAVEETVSR RSPSPPILSQ WNQCVAGERS PSLEAPSLWE    480
IPHSAVADAV EPRSSPSPPA FFPWEAPDRP IGTWGPSPQE TWDPMGPGSS IAFTQEAQNG    540
LTQEELAPPT PSAPGTPEPT EMQSPSTREI SDLAFGGSQG SPEVAAPEPP GSHPVGTLDA    600
DKCPEVLGPG EAASGRPRMA IPRPRDVRKL VKTTYAPGFP AGAQGSGLPA PPADPCGEEG    660
GESKTQEPPA LGPPAPAHYT SVFIKDFLPV VPHPYEPPEP SFDTVARDAS QPNGVLRRRA    720
ENSTAKPFKR TEIRLPGALA LGRRPEVTSR VRARGPGGEN RDVEAQRLVP DGDGRTSPLG    780
GARSSSQRSP VGPAGVRSPR PGSPQMQASP SPGIAPKPKT PPTAPEPAAA VQAPLPREPL    840
ALAGRTAPAQ PRAASAPPTD RSPQSPSQGA RRQPGAAPLG KVLVDPESGR YYFVEAPRQP    900
RLRVLFDPES GQYVEVLLPP SSPGPPHRVY TPLALGLGLY PPAYGPIPSL SLPPSPGPQA    960
LGSPQLPWVS EAGPLDGTYY LPVSGTPNPA PPLLLCAPPS SSGPTQPGKG SLFPL        1015

SEQ ID NO: 660             moltype = AA  length = 418
FEATURE                    Location/Qualifiers
source                     1..418
                           mol_type = protein
                           organism = Homo sapiens
SEQUENCE: 660
MDMLHPSSVS TTSEPENASS AWPPDATLGN VSAGPSPAGL AVSGVLIPLV YLVVCVVGLL    60
GNSLVIYVVL RHTASPSVTN VYILNLALAD ELFMLGLPFL AAQNALSYWP FGSLMCRLVM   120
AVDGINQFTS IFCLTVMSVD RYLAVVHPTR SARWRTAPVA RTVSAAVWVA SAVVVLPVVV   180
FSGVPRGMST CHMQWPEPAA AWRAGFIIYT AALGFFGPLL VICLCYLLIV VKVRSAGRRV   240
WAPSCQRRRR SERRVTRMVV AVVALFVLCW MPFYVLNIVN VVCPLPEEPA FFGLYFLVVA   300
LPYANSCANP ILYGFLSYRF KQGFRRVLLR PSRRVRSQEP TVGPPEKTEE EDEEEEDGEE   360
SREGGKGKEM NGRVSQITQP GTSGQERPPS RVASKEQQLL PQEASTGEKS STMRISYL     418

SEQ ID NO: 661             moltype = AA  length = 418
FEATURE                    Location/Qualifiers
source                     1..418
                           mol_type = protein
                           organism = Homo sapiens
SEQUENCE: 661
MDMLHPSSVS TTSEPENASS AWPPDATLGN VSAGPSPAGL AVSGVLIPLV YLVVCVVGLL    60
GNSLVIYVVL RHTASPSVTN VYILNLALAD ELFMLGLPFL AAQNALSYWP FGSLMCRLVM   120
AVDGINQFTS IFCLTVMSVD RYLAVVHPTR SARWRTAPVA RTVSAAVWVA SAVVVLPVVV   180
FSGVPRGMST CHMQWPEPAA AWRAGFIIYT AALGFFGPLL VICLCYLLIV VKVRSAGRRV   240
WAPSCQRRRR SERRVTRMVV AVVALFVLCW MPFYVLNIVN VVCPLPEEPA FFGLYFLVVA   300
LPYANSCANP ILYGFLSYRF KQGFRRVLLR PSRRVRSQEP TVGPPEKTEE EDEEEEDGEE   360
SREGGKGKEM NGRVSQITQP GTSGQERPPS RVASKEQQLL PQEASTGEKS STMRISYL     418

SEQ ID NO: 662             moltype = AA  length = 526
FEATURE                    Location/Qualifiers
source                     1..526
                           mol_type = protein
                           organism = Homo sapiens
SEQUENCE: 662
MGHLSAPLHR VRVPWQGLLL TASLLTFWNP PTTAQLTTES MPFNVAEGKE VLLLVHNLPQ    60
QLFGYSWYKG ERVDGNRQIV GYAIGTQQAT PGPANSGRET IYPNASLLIQ NVTQNDTGFY   120
TLQVIKSDLV NEEATGQFHV YPELPKPSIS SNNSNPVEDK DAVAFTCEPE TQDTTYLWWI   180
NNQSLPVSPR LQLSNGNRTL TLLSVTRNDT GPYECEIQNP VSANRSDPVT LNVTYGPDTP   240
TISPSDTYYR PGANLSLSCY AASNPPAQYS WLINGTFQQS TQELFIPNIT VNNSGSYTCH   300
ANNSVTGCNR TTVKTIIVTE LSPVVAKPQI KASKTTVTGD KDSVNLTCST NDTGISIRWF   360
FKNQSLPSSE RMKLSQGNTT LSINPVKRED AGTYWCEVFN PISKNQSDPI MLNVNYNALP   420
```

```
QENGLSPGAI AGIVIGVVAL VALIAVALAC FLHFGKTGRA SDQRDLTEHK PSVSNHTQDH    480
SNDPPNKMNE VTYSTLNFEA QQPTQPTSAS PSLTATEIIY SEVKKQ                  526

SEQ ID NO: 663            moltype = AA  length = 430
FEATURE                   Location/Qualifiers
source                    1..430
                          mol_type = protein
                          organism = Homo sapiens
SEQUENCE: 663
MGHLSAPLHR VRVPWQGLLL TASLLTFWNP PTTAQLTTES MPFNVAEGKE VLLLVHNLPQ    60
QLFGYSWYKG ERVDGNRQIV GYAIGTQQAT PGPANSGRET IYPNASLLIQ NVTQNDTGFY    120
TLQVIKSDLV NEEATGQFHV YPELPKPSIS SNNSNPVEDK DAVAFTCEPE TQDTTYLWWI    180
NNQSLPVSPR LQLSNGNRTL TLLSVTRNDT GPYECEIQNP VSANRSDPVT LNVTYGPDTP    240
TISPSDTYYR PGANLSLSCY AASNPPAQYS WLINGTFQQS TQELFIPNIT VNNSGSYTCH    300
ANNSVTGCNR TTVKTIIVTD NALPQENGLS PGAIAGIVIG VVALVALIAV ALACFLHFGK    360
TGRASDQRDL TEHKPSVSNH TQDHSNDPPN KMNEVTYSTL NFEAQQPTQP TSASPSLTAT    420
EIIYSEVKKQ                                                          430

SEQ ID NO: 664            moltype = AA  length = 461
FEATURE                   Location/Qualifiers
source                    1..461
                          mol_type = protein
                          organism = Homo sapiens
SEQUENCE: 664
MGHLSAPLHR VRVPWQGLLL TASLLTFWNP PTTAQLTTES MPFNVAEGKE VLLLVHNLPQ    60
QLFGYSWYKG ERVDGNRQIV GYAIGTQQAT PGPANSGRET IYPNASLLIQ NVTQNDTGFY    120
TLQVIKSDLV NEEATGQFHV YPELPKPSIS SNNSNPVEDK DAVAFTCEPE TQDTTYLWWI    180
NNQSLPVSPR LQLSNGNRTL TLLSVTRNDT GPYECEIQNP VSANRSDPVT LNVTYGPDTP    240
TISPSDTYYR PGANLSLSCY AASNPPAQYS WLINGTFQQS TQELFIPNIT VNNSGSYTCH    300
ANNSVTGCNR TTVKTIIVTE RQNLTMLPRL DSNSWAQAIL PSVSQSAEIT DNALPQENGL    360
SPGAIAGIVI GVVALVALIA VALACFLHFG KTGRASDQRD LTEHKPSVSN HTQDHSNDPP    420
NKMNEVTYST LNFEAQQPTQ PTSASPSLTA TEIIYSEVKK Q                       461

SEQ ID NO: 665            moltype = AA  length = 464
FEATURE                   Location/Qualifiers
source                    1..464
                          mol_type = protein
                          organism = Homo sapiens
SEQUENCE: 665
MGHLSAPLHR VRVPWQGLLL TASLLTFWNP PTTAQLTTES MPFNVAEGKE VLLLVHNLPQ    60
QLFGYSWYKG ERVDGNRQIV GYAIGTQQAT PGPANSGRET IYPNASLLIQ NVTQNDTGFY    120
TLQVIKSDLV NEEATGQFHV YPELPKPSIS SNNSNPVEDK DAVAFTCEPE TQDTTYLWWI    180
NNQSLPVSPR LQLSNGNRTL TLLSVTRNDT GPYECEIQNP VSANRSDPVT LNVTYGPDTP    240
TISPSDTYYR PGANLSLSCY AASNPPAQYS WLINGTFQQS TQELFIPNIT VNNSGSYTCH    300
ANNSVTGCNR TTVKTIIVTE LSPVVAKPQI KASKTTVTGD KDSVNLTCST NDTGISIRWF    360
FKNQSLPSSE RMKLSQGNTT LSINPVKRED AGTYWCEVFN PISKNQSDPI MLNVNYNALP    420
QENGLSPGAI AGIVIGVVAL VALIAVALAC FLHFGKTGSS GPLQ                    464

SEQ ID NO: 666            moltype = AA  length = 368
FEATURE                   Location/Qualifiers
source                    1..368
                          mol_type = protein
                          organism = Homo sapiens
SEQUENCE: 666
MGHLSAPLHR VRVPWQGLLL TASLLTFWNP PTTAQLTTES MPFNVAEGKE VLLLVHNLPQ    60
QLFGYSWYKG ERVDGNRQIV GYAIGTQQAT PGPANSGRET IYPNASLLIQ NVTQNDTGFY    120
TLQVIKSDLV NEEATGQFHV YPELPKPSIS SNNSNPVEDK DAVAFTCEPE TQDTTYLWWI    180
NNQSLPVSPR LQLSNGNRTL TLLSVTRNDT GPYECEIQNP VSANRSDPVT LNVTYGPDTP    240
TISPSDTYYR PGANLSLSCY AASNPPAQYS WLINGTFQQS TQELFIPNIT VNNSGSYTCH    300
ANNSVTGCNR TTVKTIIVTD NALPQENGLS PGAIAGIVIG VVALVALIAV ALACFLHFGK    360
TGSSGPLQ                                                            368

SEQ ID NO: 667            moltype = AA  length = 94
FEATURE                   Location/Qualifiers
source                    1..94
                          mol_type = protein
                          organism = Homo sapiens
SEQUENCE: 667
MPFNVAEGKE VLLLVHNLPQ QLFGYSWYKG ERVDGNRQIV GYAIGTQQAT PGPANSGRET    60
IYPNASLLIQ NVTQNDTGFY TLQVIKSDLV NEEA                               94

SEQ ID NO: 668            moltype = AA  length = 399
FEATURE                   Location/Qualifiers
source                    1..399
                          mol_type = protein
                          organism = Homo sapiens
SEQUENCE: 668
MGHLSAPLHR VRVPWQGLLL TASLLTFWNP PTTAQLTTES MPFNVAEGKE VLLLVHNLPQ    60
QLFGYSWYKG ERVDGNRQIV GYAIGTQQAT PGPANSGRET IYPNASLLIQ NVTQNDTGFY    120
```

```
TLQVIKSDLV NEEATGQFHV YPELPKPSIS SNNSNPVEDK DAVAFTCEPE TQDTTYLWWI    180
NNQSLPVSPR LQLSNGNRTL TLLSVTRNDT GPYECEIQNP VSANRSDPVT LNVTYGPDTP    240
TISPSDTYYR PGANLSLSCY AASNPPAQYS WLINGTFQQS TQELFIPNIT VNNSGSYTCH    300
ANNSVTGCNR TTVKTIIVTE MAFHHVAKAG LKLLSSSNPP ASTSQSAKIT DNALPQENGL    360
SPGAIAGIVI GVVALVALIA VALACFLHFG KTGSSGPLQ                          399

SEQ ID NO: 669           moltype = AA   length = 99
FEATURE                  Location/Qualifiers
source                   1..99
                         mol_type = protein
                         organism = Homo sapiens
SEQUENCE: 669
MPFNVAEGKE VLLLVHNLPQ QLFGYSWYKG ERVDGNRQIV GYAIGTQQAT PGPANSGRET     60
IYPNASLLIQ NVTQNDTGFY TLQVIKSDLV NEEATGQFH                           99

SEQ ID NO: 670           moltype = AA   length = 174
FEATURE                  Location/Qualifiers
source                   1..174
                         mol_type = protein
                         organism = Homo sapiens
SEQUENCE: 670
MACLGFQRHK AQLNLATRTW PCTLLFFLLF IPVFCKAMHV AQPAVVLASS RGIASFVCEY     60
ASPGKATEVR VTVLRQADSQ VTEVCAATYM MGNELTFLDD SICTGTSSGN QVNLTIQGLR    120
AMDTGLYICK VELMYPPPYY LGIGNGTQIY VIAKEKKPSY NRGLCENAPN RARM          174

SEQ ID NO: 671           moltype = AA   length = 223
FEATURE                  Location/Qualifiers
source                   1..223
                         mol_type = protein
                         organism = Homo sapiens
SEQUENCE: 671
MACLGFQRHK AQLNLATRTW PCTLLFFLLF IPVFCKAMHV AQPAVVLASS RGIASFVCEY     60
ASPGKATEVR VTVLRQADSQ VTEVCAATYM MGNELTFLDD SICTGTSSGN QVNLTIQGLR    120
AMDTGLYICK VELMYPPPYY LGIGNGTQIY VIDPEPCPDS DFLLWILAAV SSGLFFYSFL    180
LTAVSLSKML KKRSPLTTGV YVKMPPTEPE CEKQFQPYFI PIN                     223

SEQ ID NO: 672           moltype = AA   length = 137
FEATURE                  Location/Qualifiers
source                   1..137
                         mol_type = protein
                         organism = Homo sapiens
SEQUENCE: 672
MHVAQPAVVL ASSRGIASFV CEYASPGKAT EVRVTVLRQA DSQVTEVCAA TYMMGNELTF     60
LDDSICTGTS SGNQVNLTIQ GLRAMDTGLY ICKVELMYPP PYYLGIGNGT QIYVIAKEKK    120
PSYNRGLCEN APNRARM                                                  137

SEQ ID NO: 673           moltype = AA   length = 79
FEATURE                  Location/Qualifiers
source                   1..79
                         mol_type = protein
                         organism = Homo sapiens
SEQUENCE: 673
MACLGFQRHK AQLNLATRTW PCTLLFFLLF IPVFCKAMHV AQPAVVLASS RGIASFVSKE     60
KKPSYNRGLC ENAPNRARM                                                 79

SEQ ID NO: 674           moltype = AA   length = 244
FEATURE                  Location/Qualifiers
source                   1..244
                         mol_type = protein
                         organism = Homo sapiens
SEQUENCE: 674
MRWCLLLIWA QGLRQAPLAS GMMTGTIETT GNISAEKGGS IILQCHLSST TAQVTQVNWE     60
QQDQLLAICN ADLGWHISPS FKDRVAPGPG LGLTLQSLTV NDTGEYFCIY HTYPDGTYTG    120
RIFLEVLESS VAEHGARFQI PLLGAMAATL VVICTAVIVV VALTRKKKAL RIHSVEGDLR    180
RKSAGQEEWS PSAPSPPGSC VQAEAAPAGL CGEQRGEDCA ELHDYFNVLS YRSLGNCSFF    240
TETG                                                                244

SEQ ID NO: 675           moltype = AA   length = 169
FEATURE                  Location/Qualifiers
source                   1..169
                         mol_type = protein
                         organism = Homo sapiens
SEQUENCE: 675
MMTGTIETTG NISAEKGGSI ILQCHLSSTT AQVTQVNWEQ QDQLLAICNA DLGWHISPSF     60
KDRVAPGPGL GLTLQSLTVN DTGEYFCIYH TYPDGTYTGR IFLEVLESSV AEHGARFQIP    120
LLGAMAATLV VICTAVIVVV ALTRKKKALR IHSVEGDLRR KSAGQEEWS               169

SEQ ID NO: 676           moltype = AA   length = 311
FEATURE                  Location/Qualifiers
```

```
source                       1..311
                             mol_type = protein
                             organism = Homo sapiens
SEQUENCE: 676
MAFLVAHPMQ FVYLLTTLCV FNMVFAKLGF SETVFSQRLS FTVLSAVGYF QWQKRPHLLP    60
VGPLGRSMRW CLLLIWAQGL RQAPLASGMM TGTIETTGNI SAEKGGSIIL QCHLSSTTAQ   120
VTQVNWEQQD QLLAICNADL GWHISPSFKD RVAPGPGLGL TLQSLTVNDT GEYFCIYHTY   180
PDGTYTGRIF LEVLESSVAE HGARFQIPLL GAMAATLVVI CTAVIVVVAL TRKKKALRIH   240
SVEGDLRRKS AGQEEWSPSA PSPPGSCVQA EAAPAGLCGE QRGEDCAELH DYFNVLSYRS   300
LGNCSFFTET G                                                       311

SEQ ID NO: 677               moltype = AA  length = 163
FEATURE                      Location/Qualifiers
source                       1..163
                             mol_type = protein
                             organism = Homo sapiens
SEQUENCE: 677
MMTGTIETTG NISAEKGGSI ILQCHLSSTT AQVTQVNWEQ QDQLLAICNA DLGWHISPSF    60
KDRVAPGPGL GLTLQSLTVN DTGEYFCIYH TYPDGTYTGR IFLEVLESSV AEHGARFQIP   120
LLGAMAATLV VICTAVIVVV ALTRKKKALR IHSVEGDLRR KSA                     163

SEQ ID NO: 678               moltype = AA  length = 244
FEATURE                      Location/Qualifiers
source                       1..244
                             mol_type = protein
                             organism = Homo sapiens
SEQUENCE: 678
MRWCLLLIWA QGLRQAPLAS GMMTGTIETT GNISAEKGGS IILQCHLSST TAQVTQVNWE    60
QQDQLLAICN ADLGWHISPS FKDRVAPGPG LGLTLQSLTV NDTGEYFCIY HTYPDGTYTG   120
RIFLEVLESS VAEHGARFQI PLLGAMAATL VVICTAVIVV VALTRKKKAL RIHSVEGDLR   180
RKSAGQEEWS PSAPSPPGSC VQAEAAPAGL CGEQRGEDCA ELHDYFNVLS YRSLGNCSFF   240
TETG                                                               244

SEQ ID NO: 679               moltype = AA  length = 263
FEATURE                      Location/Qualifiers
source                       1..263
                             mol_type = protein
                             organism = Homo sapiens
SEQUENCE: 679
MDSYLLMWGL LTFIMVPGCQ AELCDDDPPE IPHATFKAMA YKEGTMLNCE CKRGFRRIKS    60
GSLYMLCTGN SSHSSWDNQC QCTSSATRNT TKQVTPQPEE QKERKTTEMQ SPMQPVDQAS   120
LPGHCREPPP WENEATERIY HFVVGQMVYY QCVQGYRALH RGPAESVCKM THGKTRWTQP   180
QLICTGEEKP QASPEGRPES ETSCLVTTTD FQIQTEMAAT METSIFTTEY QVAVAGCVFL   240
LISVLLLSGL TWQRRQRKSR RTI                                          263

SEQ ID NO: 680               moltype = AA  length = 200
FEATURE                      Location/Qualifiers
source                       1..200
                             mol_type = protein
                             organism = Homo sapiens
SEQUENCE: 680
MDSYLLMWGL LTFIMVPGCQ AELCDDDPPE IPHATFKAMA YKEGTMLNCE CKRGFRRIKS    60
GSLYMLCTGN SSHSSWDNQC QCTSSATRNT TKQVTPQPEE QKERKTTEMQ SPMQPVDQAS   120
LPGEEKPQAS PEGRPESETS CLVTTTDFQI QTEMAATMET SIFTTEYQVA VAGCVFLLIS   180
VLLLSGLTWQ RRQRKSRRTI                                              200

SEQ ID NO: 681               moltype = AA  length = 272
FEATURE                      Location/Qualifiers
source                       1..272
                             mol_type = protein
                             organism = Homo sapiens
SEQUENCE: 681
MDSYLLMWGL LTFIMVPGCQ AELCDDDPPE IPHATFKAMA YKEGTMLNCE CKRGFRRIKS    60
GSLYMLCTGN SSHSSWDNQC QCTSSATRNT TKQVTPQPEE QKERKTTEMQ SPMQPVDQAS   120
LPGHCREPPP WENEATERIY HFVVGQMVYY QCVQGYRALH RGPAESVCKM THGKTRWTQP   180
QLICTGEMET SQFPGEEKPQ ASPEGRPESE TSCLVTTTDF QIQTEMAATM ETSIFTTEYQ   240
VAVAGCVFLL ISVLLLSGLT WQRRQRKSRR TI                                 272

SEQ ID NO: 682               moltype = AA  length = 510
FEATURE                      Location/Qualifiers
source                       1..510
                             mol_type = protein
                             organism = Homo sapiens
SEQUENCE: 682
MEDTKESNVK TFCSKNILAI LGFSSIIAVI ALLAVGLTQN KALPENVKYG IVLDAGSSHT    60
SLYIYKWPAE KENDTGVVHQ VEECRVKGPG ISKFVQKVNE IGIYLTDCME RAREVIPRSQ   120
HQETPVYLGA TAGMRLLRME SEELADRVLD VVERSLSNYP FDFQGARIIT GQEEGAYGWI   180
TINYLLGKFS QKTRWFSIVP YETNNQETFG ALDLGGASTQ VTFVPQNQTI ESPDNALQFR   240
LYGKDYNVYT HSFLCYGKDQ ALWQKLAKDI QVASNEILRD PCFHPGYKKV VNVSDLYKTP   300
```

```
CTKRFEMTLP FQQFEIQGIG NYQQCHQSIL ELFNTSYCPY SQCAFNGIFL PPLQGDFGAF    360
SAFYFVMKFL NLTSEKVSQE KVTEMMKKFC AQPWEEIKTS YAGVKEKYLS EYCFSGTYIL    420
SLLLQGYHFT ADSWEHIHFI GKIQGSDAGW TLGYMLNLTN MIPAEQPLST PLSHSTYVFL    480
MVLFSLVLFT VAIIGLLIFH KPSYFWKDMV                                    510

SEQ ID NO: 683             moltype = AA   length = 522
FEATURE                    Location/Qualifiers
source                     1..522
                           mol_type = protein
                           organism = Homo sapiens
SEQUENCE: 683
MGREELFLTF SFSSGFQESN VKTFCSKNIL AILGFSSIIA VIALLAVGLT QNKALPENVK    60
YGIVLDAGSS HTSLYIYKWP AEKENDTGVV HQVEECRVKG PGISKFVQKV NEIGIYLTDC    120
MERAREVIPR SQHQETPVYL GATAGMRLLR MESEELADRV LDVVERSLSN YPFDFQGARI    180
ITGQEEGAYG WITINYLLGK FSQKTRWFSI VPYETNNQET FGALDLGGAS TQVTFVPQNQ    240
TIESPDNALQ FRLYGKDYNV YTHSFLCYGK DQALWQKLAK DIQVASNEIL RDPCFHPGYK    300
KVVNVSDLYK TPCTKRFEMT LPFQQFEIQG IGNYQQCHQS ILELFNTSYC PYSQCAFNGI    360
FLPPLQGDFG AFSAYFVMK FLNLTSEKVS QEKVTEMMKK FCAQPWEEIK TSYAGVKEKY    420
LSEYCFSGTY ILSLLLQGYH FTADSWEHIH FIGKIQGSDA GWTLGYMLNL TNMIPAEQPL    480
STPLSHSTYV FLMVLFSLVL FTVAIIGLLI FHKPSYFWKD MV                      522

SEQ ID NO: 684             moltype = AA   length = 517
FEATURE                    Location/Qualifiers
source                     1..517
                           mol_type = protein
                           organism = Homo sapiens
SEQUENCE: 684
MKGTKDLTSQ QKESNVKTFC SKNILAILGF SSIIAVIALL AVGLTQNKAL PENVKYGIVL    60
DAGSSHTSLY IYKWPAEKEN DTGVVHQVEE CRVKGPGISK FVQKVNEIGI YLTDCMERAR    120
EVIPRSQHQE TPVYLGATAG MRLLRMESEE LADRVLDVVE RSLSNYPPDF QGARIITGQE    180
EGAYGWITIN YLLGKFSQKT RWFSIVPYET NNQETFGALD LGGASTQVTF VPQNQTIESP    240
DNALQFRLYG KDYNVYTHSF LCYGKDQALW QKLAKDIQVA SNEILRDPCF HPGYKKVVNV    300
SDLYKTPCTK RFEMTLPFQQ FEIQGIGNYQ QCHQSILELF NTSYCPYSQC AFNGIFLPPL    360
QGDFGAFSAF YFVMKFLNLT SEKVSQEKVT EMMKKFCAQP WEEIKTSYAG VKEKYLSEYC    420
FSGTYILSLL LQGYHFTADS WEHIHFIGKI QGSDAGWTLG YMLNLTNMIP AEQPLSTPLS    480
HSTYVFLMVL FSLVLFTVAI IGLLIFHKPS YFWKDMV                            517

SEQ ID NO: 685             moltype = AA   length = 63
FEATURE                    Location/Qualifiers
source                     1..63
                           mol_type = protein
                           organism = Homo sapiens
SEQUENCE: 685
MERAREVIPR SQHQETPVYL GATAGMRLLR VPGSLLAKRK VPMAGLLSTI CWANSVRKQG    60
GSA                                                                 63

SEQ ID NO: 686             moltype = AA   length = 402
FEATURE                    Location/Qualifiers
source                     1..402
                           mol_type = protein
                           organism = Homo sapiens
SEQUENCE: 686
MERAREVIPR SQHQETPVYL GATAGMRLLR MESEELADRV LDVVERSLSN YPFDFQGARI    60
ITGQEEGAYG WITINYLLGK FSQKTRWFSI VPYETNNQET FGALDLGGAS TQVTFVPQNQ    120
TIESPDNALQ FRLYGKDYNV YTHSFLCYGK DQALWQKLAK DIQVASNEIL RDPCFHPGYK    180
KVVNVSDLYK TPCTKRFEMT LPFQQFEIQG IGNYQQCHQS ILELFNTSYC PYSQCAFNGI    240
FLPPLQGDFG AFSAYFVMK FLNLTSEKVS QEKVTEMMKK FCAQPWEEIK TSYAGVKEKY    300
LSEYCFSGTY ILSLLLQGYH FTADSWEHIH FIGKIQGSDA GWTLGYMLNL TNMIPAEQPL    360
STPLSHSTYV FLMVLFSLVL FTVAIIGLLI FHKPSYFWKD MV                      402

SEQ ID NO: 687             moltype = AA   length = 51
FEATURE                    Location/Qualifiers
source                     1..51
                           mol_type = protein
                           organism = Homo sapiens
SEQUENCE: 687
MEDTKESNVK TFCSKNILAI LGFSSIIAVI ALLAVGLTQN KALPENVKDG K             51

SEQ ID NO: 688             moltype = AA   length = 199
FEATURE                    Location/Qualifiers
source                     1..199
                           mol_type = protein
                           organism = Homo sapiens
SEQUENCE: 688
MKSGLWYFFL FCLRIKVLTG EINGSANYEM FIFHNGGVQI LCKYPDIVQQ FKMQLLKGGQ    60
ILCDLTKTKG SGNTVSIKSL KFCHSQLSNN SVSFFLYNLD HSHANYYPCN LSIFDPPPFK    120
VTLTGGYLHI YESQLCCQLK FWLPIGCAAF VVVCILGCIL ICWLTKKKYS SSVHDPNGEY    180
MFMRAVNTAK KSRLTDVTL                                                199
```

```
SEQ ID NO: 689          moltype = AA   length = 168
FEATURE                 Location/Qualifiers
source                  1..168
                        mol_type = protein
                        organism = Homo sapiens
SEQUENCE: 689
MKSGLWYFFL FCLRIKVLTG EINGSANYEM FIFHNGGVQI LCKYPDIVQQ FKMQLLKGGQ      60
ILCDLTKTKG SGNTVSIKSL KFCHSQLSNN SVSFFLYNLD HSHANYYFCN LSIFDPPPFK     120
VTLTGGYLHI YESQLCCQLK FWLPIGCAAF VVVCILGCIL ICWLTKKM                  168

SEQ ID NO: 690          moltype = AA   length = 277
FEATURE                 Location/Qualifiers
source                  1..277
                        mol_type = protein
                        organism = Homo sapiens
SEQUENCE: 690
MCVGARRLGR GPCAALLLLG LGLSTVTGLH CVGDTYPSND RCCHECRPGN GMVSRCSRSQ      60
NTVCRPCGPG FYNDVVSSKP CKPCTWCNLR SGSERKQLCT ATQDTVCRCR AGTQPLDSYK     120
PGVDCAPCPP GHFSPGDNQA CKPWTNCTLA GKHTLQPASN SSDAICEDRD PPATQPQETQ     180
GPPARPITVQ PTEAWPRTSQ GPSTRPVEVP GGRAVAAILG LGLVLGLLGP LAILLALYLL     240
RRDQRLPPDA HKPPGGGSFR TPIQEEQADA HSTLAKI                              277

SEQ ID NO: 691          moltype = AA   length = 255
FEATURE                 Location/Qualifiers
source                  1..255
                        mol_type = protein
                        organism = Homo sapiens
SEQUENCE: 691
MAQHGAMGAF RALCGLALLC ALSLGQRPTG GPGCGPGRLL LGTGTDARCC RVHTTRCCRD      60
YPGEECCSEW DCMCVQPEFH CGDPCCTTCR HHPCPPGQGV QSQGKFSFGF QCIDCASGTF     120
SGGHEGHCKP WTDCCWRCRR RPKTPEAASS PRKSGASDRQ RRRGGWETCG CEPGRPPGPP     180
TAASPSPGAP QAAGALRSAL GRALLPWQQK WVQEGGSDQR PGPCSSAAAA GPCRRERETQ     240
SWPPSSLAGP DGVGS                                                     255

SEQ ID NO: 692          moltype = AA   length = 234
FEATURE                 Location/Qualifiers
source                  1..234
                        mol_type = protein
                        organism = Homo sapiens
SEQUENCE: 692
MAQHGAMGAF RALCGLALLC ALSLGQRPTG GPGCGPGRLL LGTGTDARCC RVHTTRCCRD      60
YPGEECCSEW DCMCVQPEFH CGDPCCTTCR HHPCPPGQGV QSQGKFSFGF QCIDCASGTF     120
SGGHEGHCKP WTDCTQFGFL TVFPGNKTHN AVCVPGSPPA EPLGWLTVVL LAVAACVLLL     180
TSAQLGLHIW QLRKTQLLLE VPPSTEDARS CQFPEEERGE RSAEEKGRLG DLWV           234

SEQ ID NO: 693          moltype = AA   length = 241
FEATURE                 Location/Qualifiers
source                  1..241
                        mol_type = protein
                        organism = Homo sapiens
SEQUENCE: 693
MAQHGAMGAF RALCGLALLC ALSLGQRPTG GPGCGPGRLL LGTGTDARCC RVHTTRCCRD      60
YPGEECCSEW DCMCVQPEFH CGDPCCTTCR HHPCPPGQGV QSQGKFSFGF QCIDCASGTF     120
SGGHEGHCKP WTDCTQFGFL TVFPGNKTHN AVCVPGSPPA EPLGWLTVVL LAVAACVLLL     180
TSAQLGLHIW QLRSQCMWPR ETQLLLEVPP STEDARSCQF PEEERGERSA EEKGRLGDLW     240
V                                                                    241

SEQ ID NO: 694          moltype = AA   length = 169
FEATURE                 Location/Qualifiers
source                  1..169
                        mol_type = protein
                        organism = Homo sapiens
SEQUENCE: 694
MCVQPEFHCG DPCCTTCRHH PCPPGQGVQS QGKFSFGFQC IDCASGTFSG GHEGHCKPWT      60
DCTQFGFLTV FPGNKTHNAV CVPGSPPAEP LGWLTVVLLA VAACVLLLTS AQLGLHIWQL    120
RSQCMWPRET QLLLEVPPST EDARSCQFPE EERGERSAEE KGRLGDLWV                 169

SEQ ID NO: 695          moltype = AA   length = 595
FEATURE                 Location/Qualifiers
source                  1..595
                        mol_type = protein
                        organism = Homo sapiens
SEQUENCE: 695
MRVLLAALGL LFLGALRAFP QDRPFEDTCH GNPSHYYDKA VRRCCYRCPM GLFPTQQCPQ      60
RPTDCRKQCE PDYYLDEADR CTACVTCSRD DLVEKTPCAW NSSRVCECRP GMFCSTSAVN     120
SCARCFFHSV CPAGMIVKFP GTAQKNTVCE PASPGVSPAC ASPENCKEPS SGTIPQAKPT     180
PVSPATSSAS TMPVRGGTRL AQEAASKLTR APDSPSSVGR PSSDPGLSPT QPCPEGSGDC     240
RKQCEPDYYL DEAGRCTACV SCSRDDLVEK TPCAWNSSRT CECRPGMICA TSATNSCARC     300
VPYPICAAET VTKPQDMAEK DTTFEAPPLG TQPDCNPTPE NGEAPASTSP TQSLLVDSQA     360
```

```
SKTLPIPTSA PVALSSTGKP VLDAGPVLFW VILVLVVVG SSAFLLCHRR ACRKRIRQKL    420
HLCYPVQTSQ PKLELVDSRP RRSSTQLRSG ASVTEPVAEE RGLMSQPLME TCHSVGAAYL    480
ESLPLQDASP AGGPSSPRDL PEPRVSTEHT NNKIEKIYIM KADTVIVGTV KAELPEGRGL    540
AGPAEPELEE ELEADHTPHY PEQETEPPLG SCSDVMLSVE EEGKEDPLPT AASGK         595

SEQ ID NO: 696              moltype = AA   length = 483
FEATURE                     Location/Qualifiers
source                      1..483
                            mol_type = protein
                            organism = Homo sapiens
SEQUENCE: 696
MFCSTSAVNS CARCFFHSVC PAGMIVKFPG TAQKNTVCEP ASPGVSPACA SPENCKEPSS     60
GTIPQAKPTP VSPATSSAST MPVRGGTRLA QEAASKLTRA PDSPSSVGRP SSDPGLSPTQ    120
PCPEGSGDCR KQCEPDYYLD EAGRCTACVS CSRDDLVEKT PCAWNSSRTC ECRPGMICAT    180
SATNSCARCV PYPICAAETV TKPQDMAEKD TTFEAPPLGT QPDCNPTPEN GEAPASTSPT    240
QSLLVDSQAS KTLPIPTSAP VALSSTGKPV LDAGPVLFWV ILVLVVVGS SAFLLCHRRA     300
CRKRIRQKLH LCYPVQTSQP KLELVDSRPR RSSTLRSGAS VTEPVAEERG LMSQPLMETC    360
HSVGAAYLES LPLQDASPAG GPSSPRDLPE PRVSTEHTNK IEKIYIMKA DTVIVGTVKA     420
ELPEGRGLAG PAEPELEEEL EADHTPHYPE QETEPPLGSC SDVMLSVEEE GKEDPLPTAA    480
SGK                                                                  483

SEQ ID NO: 697              moltype = AA   length = 55
FEATURE                     Location/Qualifiers
source                      1..55
                            mol_type = protein
                            organism = Homo sapiens
SEQUENCE: 697
MRVLLAALGL LFLGALRAFP QGCSRHSSAH RGLLTAGSSV SLTTTWMRPT AVQPA          55

SEQ ID NO: 698              moltype = AA   length = 176
FEATURE                     Location/Qualifiers
source                      1..176
                            mol_type = protein
                            organism = Homo sapiens
SEQUENCE: 698
MRIFAVFIFM TYWHLLNAPY NKINQRILVV DPVTSEHELT CQAEGYPKAE VIWTSSDHQV     60
LSGKTTTTNS KREEKLFNVT STLRINTTTN EIFYCTFRRL DPEENHTAEL VIPELPLAHP    120
PNERTHLVIL GAILLCLGVA LTFIFRLRKG RMMDVKKCGI QDTNSKKQSD THLEET        176

SEQ ID NO: 699              moltype = AA   length = 290
FEATURE                     Location/Qualifiers
source                      1..290
                            mol_type = protein
                            organism = Homo sapiens
SEQUENCE: 699
MRIFAVFIFM TYWHLLNAFT VTVPKDLYVV EYGSNMTIEC KFPVEKQLDL AALIVYWEME     60
DKNIIQFVHG EEDLKVQHSS YRQRARLLKD QLSLGNAALQ ITDVKLQDAG VYRCMISYGG    120
ADYKRITVKV NAPYNKINQR ILVVDPVTSE HELTCQAEGY PKAEVIWTSS DHQVLSGKTT    180
TTNSKREEKL FNVTSTLRIN TTTNEIFYCT FRRLDPEENH TAELVIPELP LAHPPNERTH    240
LVILGAILLC LGVALTFIFR LRKGRMMDVK KCGIQDTNSK KQSDTHLEET              290

SEQ ID NO: 700              moltype = AA   length = 551
FEATURE                     Location/Qualifiers
source                      1..551
                            mol_type = protein
                            organism = Homo sapiens
SEQUENCE: 700
MAAPALSWRL PLLILLLPLA TSWASAAVNG TSQFTCFYNS RANISCVWSQ DGALQDTSCQ     60
VHAWPDRRRW NQTCELLPVS QASWACNLIL GAPDSQKLTT VDIVTLRVLC REGVRWRVMA    120
IQDFKPFENL RLMAPISLQV VHVETHRCNI SWEISQASHY FERHLEFEAR TLSPGHTWEE    180
APLLTLKQKQ EWICLETLTP DTQYEFQVRV KPLQGEFTTW SPWSQPLAFR TKPAALGKDT    240
IPWLGHLLVG LSGAFGFIIL VYLLINCRNT GPWLKKVLKC NTPDPSKFFS QLSSEHGGDV    300
QKWLSSPFPS SSFSPGGLAP EISPLEVLER DKVTQLLLQQ DKVPEPASLS SNHSLTSCFT    360
NQGYFFFHLP DALEIEACQV YFTYDPYSEE DPDEGVAGAP TGSSPQPLQP LSGEDDAYCT    420
FPSRDDLLLF SPSLLGGPSP PSTAPGGSGA GEERMPPSLQ ERVPRDWDPQ PLGPPTPGVP    480
DLVDFQPPPE LVLREAGEEV PDAGPREGVS FPWSRPPGQG EFRALNARLP LNTDAYLSLQ    540
ELQGQDPTHL V                                                         551

SEQ ID NO: 701              moltype = AA   length = 146
FEATURE                     Location/Qualifiers
source                      1..146
                            mol_type = protein
                            organism = Homo sapiens
SEQUENCE: 701
MAAPALSWRL PLLILLLPLA TSWASAAVNG TSQFTCFYNS RANISCVWSQ DGALQDTSCQ     60
VHAWPDRRRW NQTCELLPVS QASWACNLIL GAPDSQKLTT VDIVTLRVLC REGVRWRVMA    120
IQDFKPFENL RLMAPISLQV VHVETH                                        146

SEQ ID NO: 702              moltype = AA   length = 88
```

| FEATURE | Location/Qualifiers |
|---|---|
| source | 1..88<br>mol_type = protein<br>organism = Homo sapiens |

SEQUENCE: 702
```
MAAPALSWRL PLLILLLPLA TSWASAAVNG TSQFTCFYNS RANISCVWSQ DGALQDTSCQ    60
VHAWPDRRRW NQTCELLPVS QASWACNL                                      88
```

SEQ ID NO: 703     moltype = AA   length = 188
| FEATURE | Location/Qualifiers |
|---|---|
| source | 1..188<br>mol_type = protein<br>organism = Homo sapiens |

SEQUENCE: 703
```
MAAPALSWRL PLLILLLPLA TSWASAAVNG TSQFTCFYNS RANISCVWSQ DGALQDTSCQ    60
VHAWPDRRRW NQTCELLPVS QASWACNLIL GAPDSQKLTT VDIVTLRVLC REGVRWRVMA   120
IQDFKPFENL RLMAPISLQV VHVETHRCNI SWEISQASHY FERHLEFEAR TLSPGHTWEE   180
APLLTLKQ                                                           188
```

SEQ ID NO: 704     moltype = AA   length = 255
| FEATURE | Location/Qualifiers |
|---|---|
| source | 1..255<br>mol_type = protein<br>organism = Homo sapiens |

SEQUENCE: 704
```
MGNSCYNIVA TLLLVLNFER TRSLQDPCSN CPAGTFCDNN RNQICSPCPP NSFSSAGGQR    60
TCDICRQCKG VFRTRKECSS TSNAECDCTP GFHCLGAGCS MCEQDCKQGQ ELTKKGCKDC   120
CFGTFNDQKR GICRPWTNCS LDGKSVLVNG TKERDVVCGP SPADLSPGAS SVTPPAPARE   180
PGHSPQIISF FLALTSTALL FLLFFLTLRF SVVKRGRKKL LYIFKQPFMR PVQTTQEEDG   240
CSCRFPEEEE GGCEL                                                   255
```

SEQ ID NO: 705     moltype = AA   length = 87
| FEATURE | Location/Qualifiers |
|---|---|
| source | 1..87<br>mol_type = protein<br>organism = Homo sapiens |

SEQUENCE: 705
```
ERDVVCGPSP ADLSPGASSV TPPAPAREPG HSPQIISFFL ALTSTALLFL LFFLTLRFSV    60
VKRGRKKLLY IFKQHGSSGD TFTILES                                       87
```

SEQ ID NO: 706     moltype = AA   length = 255
| FEATURE | Location/Qualifiers |
|---|---|
| source | 1..255<br>mol_type = protein<br>organism = Homo sapiens |

SEQUENCE: 706
```
MGNSCYNIVA TLLLVLNFER TRSLQDPCSN CPAGTFCDNN RNQICSPCPP NSFSSAGGQR    60
TCDICRQCKG VFRTRKECSS TSNAECDCTP GFHCLGAGCS MCEQDCKQGQ ELTKKGCKDC   120
CFGTFNDQKR GICRPWTNCS LDGKSVLVNG TKERDVVCGP SPADLSPGAS SVTPPAPARE   180
PGHSPQIISF FLALTSTALL FLLFFLTLRF SVVKRGRKKL LYIFKQPFMR PVQTTQEEDG   240
CSCRFPEEEE GGCEL                                                   255
```

SEQ ID NO: 707     moltype = AA   length = 92
| FEATURE | Location/Qualifiers |
|---|---|
| source | 1..92<br>mol_type = protein<br>organism = Homo sapiens |

SEQUENCE: 707
```
MHCTLTMETE AIDGYITCDN ELSPEREHSN MAIDLTSSTP NGQHASPSHM TSSKSSFYDF    60
FLCVCVSPAT DFNLLGLWGP LTLWYSYCYR FC                                 92
```

SEQ ID NO: 708     moltype = DNA   length = 660
| FEATURE | Location/Qualifiers |
|---|---|
| source | 1..660<br>mol_type = genomic DNA<br>organism = Homo sapiens |

SEQUENCE: 708
```
atgcctcggg gacgaaagag tcggcgccgc cgtaatgcga gagccgcaga agagaaccgc    60
aacaatcgca aaatccaggc ctcagaggcg tccgagaccc ctatggccgc ctctgtggta   120
gcgagcaccc ccgaagacga cctgagcggc cccgaggaag acccgagcac tccagaggag   180
gcctctacca cccctgaaga agcctcgagc actgcccaag cacaaaagcc ttcagtgccc   240
cggagcaatt tcagggcac caagaaaagt ctcctgatgt ctatattagc gctcatcttc   300
atcatggca acagcgccaa ggaagctctg gtctggaaag tgctgggaa gttaggaatg   360
cagcctggac gtcagcacag catctttgga gatccgaaga agatcgtcac agaagagttt   420
gtgcgcagag ggtacctgat ttataaaccg gtgccccgta gcagtccggt ggagtatgag   480
ttcttctggg ggccccgagc acacgtggaa tcgagcaaac tgaaagtcat gcattttgtg   540
gcaagggttc gtaaccgatg ctctaaagac tggccttgta attatgactg ggattcggac   600
gatgatgcag aggttgaggc tatcctcaat tcaggtgcta ggggttattc cgccccttaa   660
```

| SEQ ID NO: 709 | moltype = AA length = 219 |
| --- | --- |
| FEATURE | Location/Qualifiers |
| source | 1..219 |
| | mol_type = protein |
| | organism = Homo sapiens |

SEQUENCE: 709
```
MPRGRKSRRR RNARAAEENR NNRKIQASEA SETPMAASVV ASTPEDDLSG PEEDPSTPEE   60
ASTTPEEASS TAQAQKPSVP RSNFQGTKKS LLMSILALIF IMGNSAKEAL VWKVLGKLGM  120
QPGRQHSIFG DPKKIVTEEF VRRGYLIYKP VPRSSPVEYE FFWGPRAHVE SSKLKVMHFV  180
ARVRNRCSKD WPCNYDWDSD DDAEVEAILN SGARGYSAP                        219
```

| SEQ ID NO: 710 | moltype = DNA length = 64 |
| --- | --- |
| FEATURE | Location/Qualifiers |
| misc_feature | 1..64 |
| | note = Adapter sequence |
| source | 1..64 |
| | mol_type = other DNA |
| | organism = synthetic construct |

SEQUENCE: 710
```
agatcggaag agcacacgtc tgaactccag tcacnnnnnn atctcgtatg ccgtcttctg   60
cttg                                                                64
```

| SEQ ID NO: 711 | moltype = DNA length = 58 |
| --- | --- |
| FEATURE | Location/Qualifiers |
| misc_feature | 1..58 |
| | note = Adapter sequence |
| source | 1..58 |
| | mol_type = other DNA |
| | organism = synthetic construct |

SEQUENCE: 711
```
agatcggaag agcgtcgtgt agggaaagag tgtagatctc ggtggtcgcc gtatcatt     58
```

| SEQ ID NO: 712 | moltype = AA length = 116 |
| --- | --- |
| FEATURE | Location/Qualifiers |
| source | 1..116 |
| | mol_type = protein |
| | organism = Homo sapiens |

SEQUENCE: 712
```
MLRLQMTDGH ISCTAVEFSY MSKISLNTPP GTKVKLSGIV DIKNGFLLLN DSNTTVLGGE   60
VEHLIEKWEL QRSLSKHNRS NIGTEGGPPP FVPFGQFGRR NSQDKRKCEV LWCDPC      116
```

| SEQ ID NO: 713 | moltype = AA length = 651 |
| --- | --- |
| FEATURE | Location/Qualifiers |
| source | 1..651 |
| | mol_type = protein |
| | organism = Homo sapiens |

SEQUENCE: 713
```
MLRLQMTDGH ISCTAVEFSY MSKISLNTPP GTKVKLSGIV DIKNGFLLLN DSNTTVLGGE   60
VEHLIEKWEL QRSLSKHNRS NIGTEGGPPP FVPFGQKCVS HVQVDSRELD RRKTLQVTMP  120
VKPTNDNEF EKQRTAAIAE VAKSKETKTF GGGGGGARSN LNMNAAGNRN REVLQKEKST   180
KSEGKHEGVY RELVDEKALK HITEMGFSKE ASRQALMDNG NNLEAALNVL LTSNKQKPVM  240
GPPLRGRGKG RGRIRSEDEE DLGNARPSAP STLFDFLESK MGTLNVEEPK SQPQQLHQGQ  300
YRSSNTEQNG VKDNNHLRHP PRNDTRQPRN EKPPRFQRDS QNSKSVLEGS GLPRNRGSER  360
PSTSSVSEVW AEDRIKCDRP YSRYDRTKDT SYPLGSQHSD GAFKKRDNSM QSRSGKGPSF  420
AEAKENPLPQ GSVDYNNQKR GKRESQTSIP DYFYDRKSQT INNEAFSGIK IEKHFNVNTD  480
YQNPVRSNSF IGVPNGEVEM PLKGRRIGPI KPAGPVTAVP CDDKIFYNSG PKRRSGPIKP  540
EKILESSIPM EYAKMWKPGD ECFALYWEDN KFYRAEVEAL HSSGMTAVVK FIDYGNYEEV  600
LLSNIKPIQT EAWEEEGTYD QTLEFRRGGD GQPRRSTRPT QQFYQPPRAR N          651
```

| SEQ ID NO: 714 | moltype = AA length = 651 |
| --- | --- |
| FEATURE | Location/Qualifiers |
| source | 1..651 |
| | mol_type = protein |
| | organism = Homo sapiens |

SEQUENCE: 714
```
MLRLQMTDGH ISCTAVEFSY MSKISLNTPP GTKVKLSGIV DIKNGFLLLN DSNTTVLGGE   60
VEHLIEKWEL QRSLSKHNRS NIGTEGGPPP FVPFGQKCVS HVQVDSRELD RRKTLQVTMP  120
VKPTNDNEF EKQRTAAIAE VAKSKETKTF GGGGGGARSN LNMNAAGNRN REVLQKEKST   180
KSEGKHEGVY RELVDEKALK HITEMGFSKE ASRQALMDNG NNLEAALNVL LTSNKQKPVM  240
GPPLRGRGKG RGRIRSEDEE DLGNARPSAP STLFDFLESK MGTLNVEEPK SQPQQLHQGQ  300
YRSSNTEQNG VKDNNHLRHP PRNDTRQPRN EKPPRFQRDS QNSKSVLEGS GLPRNRGSER  360
PSTSSVSEVW AEDRIKCDRP YSRYDRTKDT SYPLGSQHSD GAFKKRDNSM QSRSGKGPSF  420
AEAKENPLPQ GSVDYNNQKR GKRESQTSIP DYFYDRKSQT INNEAFSGIK IEKHFNVNTD  480
YQNPVRSNSF IGVPNGEVEM PLKGRRIGPI KPAGPVTAVP CDDKIFYNSG PKRRSGPIKP  540
EKILESSIPM EYAKMWKPGD ECFALYWEDN KFYRAEVEAL HSSGMTAVVK FIDYGNYEEV  600
LLSNIKPIQT EAWEEEGTYD QTLEFRRGGD GQPRRSTRPT QQFYQPPRAR N          651
```

| SEQ ID NO: 715 | moltype = AA length = 129 |
| --- | --- |
| FEATURE | Location/Qualifiers |

```
source                  1..129
                        mol_type = protein
                        organism = Homo sapiens
SEQUENCE: 715
MLRLQMTDGH ISCTAVEFSY MSKISLNTPP GTKVKLSGIV DIKNGFLLLN DSNTTVLGGE    60
VEHLIEKWEL QRSLSKHNRS NIGTEGGPPP FVPFGQKCVS HVQVDSRELD RRKTLQVTMP   120
VKPTNDNDE                                                           129

SEQ ID NO: 716          moltype = AA  length = 744
FEATURE                 Location/Qualifiers
source                  1..744
                        mol_type = protein
                        organism = Homo sapiens
SEQUENCE: 716
MAQVAGAALS QAGWYLSDEG IEACTSSPDK VNVNDIILIA LNTDLRTIGK KFLPSDINSG    60
KVEKLEGPCV LQIQKIRNVA APKDNEESQA APRMLRLQMT DGHISCTAVE FSYMSKISLN   120
TPPGTKVKLS GIVDIKNGFL LLNDSNTTVL GGEVEHLIEK WELQRSLSKH NRSNIGTEGG   180
PPPFVPFGQK CVSHVQVDSR ELDRRKTLQV TMPVKPTNDN DEFEKQRTAA IAEVAKSKET   240
KTFGGGGGGA RSNLNMNAAG NRNREVLQKE KSTKSEGKHE GVYRELVDEK ALKHITEMGF   300
SKEASRQALM DNGNNLEAAL NVLLTSNKQK PVMGPPLRGR GKGRGRIRSE DEEDLGNARP   360
SAPSTLFDFL ESKMGTLNVE EPKSQPQQLH QGQYRSSNTE QNGVKDNNHL RHPPRNDTRQ   420
PRNEKPPRFQ RDSQNSKSVL EGSGLPRNRG SERPSTSSVS EVWAEDRIKC DRPYSRYDRT   480
KDTSYPLGSQ HSDGAFKKRD NSMQSRSGKG PSFAEAKENP LPQGSVDYNN QKRGKRESQT   540
SIPDYFYDRK SQTINNEAFS GIKIEKHFNV NTDYQNPVRS NSFIGVPNGE VEMPLKGRRI   600
GPIKPAGPVT AVPCDDKIFY NSGPKRRSGP IKPEKILESS IPMEYAKMWK PGDECFALYW   660
EDNKFYRAEV EALHSSGMTA VVKFIDYGNY EEVLLSNIKP IQTEAWEEEG TYDQTLEFRR   720
GGDGQPRRST RPTQQFYQPP RARN                                          744

SEQ ID NO: 717          moltype = AA  length = 651
FEATURE                 Location/Qualifiers
source                  1..651
                        mol_type = protein
                        organism = Homo sapiens
SEQUENCE: 717
MLRLQMTDGH ISCTAVEFSY MSKISLNTPP GTKVKLSGIV DIKNGFLLLN DSNTTVLGGE    60
VEHLIEKWEL QRSLSKHNRS NIGTEGGPPP FVPFGQKCVS HVQVDSRELD RRKTLQVTMP   120
VKPTNDNDEF EKQRTAAIAE VAKSKETKTF GGGGGGARSN LNMNAAGNRN REVLQKEKST   180
KSEGKHEGVY RELVDEKALK HITEMGFSKE ASRQALMDNG NNLEAALNVL LTSNKQKPVM   240
GPPLRGRGKG RGRIRSEDEE DLGNARPSAP STLFDFLESK MGTLNVEEPK SQPQQLHQGQ   300
YRSSNTEQNG VKDNNHLRHP PRNDTRQPRN EKPPRFQRDS QNSKSVLEGS GLPRNRGSER   360
PSTSSVSEVW AEDRIKCDRP YSRYDRTKDT SYPLGSQHSD GAFKKRDNSM QSRSGKGPSF   420
AEAKENPLPQ GSVDYNNQKR GKRESQTSIP DYFYDRKSQT INNEAFSGIK IEKHFNVNTD   480
YQNPVRSNSF IGVPNGEVEM PLKGRRIGPI KPAGPVTAVP CDDKIFYNSG PKRRSGPIKP   540
EKILESSIPM EYAKMWKPGD ECFALYWEDN KFYRAEVEAL HSSGMTAVVK FIDYGNYEEV   600
LLSNIKPIQT EAWEEEGTYD QTLEFRRGGD GQPRRSTRPT QQFYQPPRAR N            651

SEQ ID NO: 718          moltype = AA  length = 650
FEATURE                 Location/Qualifiers
source                  1..650
                        mol_type = protein
                        organism = Homo sapiens
SEQUENCE: 718
MLRLQMTDGH ISCTAVEFSY MSKISLNTPP GTKVKLSGIV DIKNGFLLLN DSNTTVLGGE    60
VEHLIEKWEL QRSLSKHNRS NIGTEGGPPP FVPFGQCVSH VQVDSRELDR RKTLQVTMPV   120
KPTNDNDEFE KQRTAAIAEV AKSKETKTFG GGGGARSNLN MNAAGNRNRE VLQKEKSTKS   180
EGKHEGVYRE LVDEKALKHI TEMGFSKEAS RQALMDNGNN LEAALNVLLT SNKQKPVMGP   240
PLRGRGKGRG RIRSEDEEDL GNARPSAPST LFDFLESKMG TLNVEEPKSQ PQQLHQGQYR   300
SSNTEQNGVK DNNHLRHPPR NDTRQPRNEK PPRFQRDSQN SKSVLEGSGL PRNRGSERPS   360
TSSVSEVWAE DRIKCDRPYS RYDRTKDTSY PLGSQHSDGA FKKRDNSMQS RSGKGPSFAE   420
AKENPLPQGS VDYNNQKRGK RESQTSIPDY FYDRKSQTIN NEAFSGIKIE KHFNVNTDYQ   480
NPVRSNSFIG VPNGEVEMPL KGRRIGPIKP AGPVTAVPCD DKIFYNSGPK RRSGPIKPEK   540
ILESSIPMEY AKMWKPGDEC FALYWEDNKF YRAEVEALHS SGMTAVVKFI DYGNYEEVLL   600
SNIKPIQTEA WEEEGTYDQT LEFRRGGDGQ PRRSTRPTQQ FYQPPRARN               650

SEQ ID NO: 719          moltype = AA  length = 832
FEATURE                 Location/Qualifiers
source                  1..832
                        mol_type = protein
                        organism = Homo sapiens
SEQUENCE: 719
MSEAGGAGPG GCGAGAGAGA GPGALPPQPA ALPPAPPQGS PCAAAAGGSG ACGPATAVAA    60
AGTAEGPGGG GSARIAVKKA QLRSAPRAKK LEKLGVYSAC KAEESCKCNG WKNPNPSPTP   120
PRADLQQIIV SLTESCRSCS HALAAHVSHL ENVSEEEMNR LLGIVLDVYL LFTCVHKEED   180
ADTKQVYFYL FKLLRKSILQ RGKPVVEGSL EKKPPFEKPS IEQGVNNFVQ YKFSHLPAKE   240
RQTIVELAKM FLNRINYWHL EAPSQRRLRS PNDDISGYKE NYTRWLCYCN VPQFCDSLPR   300
YETTQVFGRT LLRSVPTVMR RQLLEQARQE KDKLPLEKRT LILTHFPKFL SMLEEEVYSQ   360
NSPIWDQDFL SASSRTSQLG IQTVINPPPV AGTISYNSTS SSLEQPNAGS SSPACKASSG   420
LEANPGEKRK MTDSHVLEEA KKPRVMGDIP MELINEVMST ITDPAAMLGP ETNFLSAHSA   480
RDEAARLEER RGVIEFHVVG NSLNQKPNKK ILMWLVGLQN VFSHQLPRMP KEYITRLVFD   540
```

```
PKHKTLALIK DGRVIGGICF RMFPSQGFTE IVFCAVTSNE QVKGYGTHLM NHLKEYHIKH    600
DILNFLTYAD EYAIGYFKKQ GFSKEIKIPK TKYVGYIKDY EGATLMGCEL NPRIPYTEFS    660
VIIKKQKEII KKLIERKQAQ IRKVYPGLSC FKDGVRQIPI ESIPGIRETG WKPSGKEKSK    720
EPRDPDQLYS TLKSILQQVK SHQSAWPFME PVKRTEAPGY YEVIRFPMDL KTMSERLKNR    780
YYVSKKLFMA DLQRVFTNCK EYNPPESEYY KCANILEKFF FSKIKEAGLI DK            832

SEQ ID NO: 720          moltype = AA   length = 472
FEATURE                 Location/Qualifiers
source                  1..472
                        mol_type = protein
                        organism = Homo sapiens
SEQUENCE: 720
MLGTVKMEGH ETSDWNSYYA DTQEAYSSVP VSNMNSGLGS MNSMNTYMTM NTMTTSGNMT    60
PASFNMSYAN PGLGAGLSPG AVAGMPGGSA GAMNSMTAAG VTAMGTALSP SGMGAMGAQQ    120
AASMNGLGPY AAAMNPCMSP MAYAPSNLGR SRAGGGGDAK TFKRSYPHAK PPYSYISLIT    180
MAIQQAPSKM LTLSEIYQWI MDLFPYYRQN QQRWQNSIRH SLSFNDCFVK VARSPDKPGK    240
GSYWTLHPDS GNMFENGCYL RRQKRFKCEK QPGAGGGGGS GSGGSGAKGG PESRKDPSGA    300
SNPSADSPLH RGVHGKTGQL EGAPAPGPAA SPQTLDHSGA TATGGASELK TPASSTAPPI    360
SSGPGALASV PASHPAHGLA PHESQLHLKG DPHYSFNHPF SINNLMSSSE QQHKLDFKAY    420
EQALQYSPYG STLPASLPLG SASVTTRSPI EPSALEPAYY QGVYSRPVLN TS            472

SEQ ID NO: 721          moltype = AA   length = 36
FEATURE                 Location/Qualifiers
source                  1..36
                        mol_type = protein
                        organism = Homo sapiens
SEQUENCE: 721
MLGTVKMEGH ETSDWNSYYA DTQELAITLQ KFNYHY                              36

SEQ ID NO: 722          moltype = AA   length = 531
FEATURE                 Location/Qualifiers
source                  1..531
                        mol_type = protein
                        organism = Homo sapiens
SEQUENCE: 722
MVDVGKWPIF TLLSPQEIAS IRKACVFGTS ASEALYVTDN DEVFVFGLNY SNCLGTGDNQ    60
STLVPKKLEG LCGKKIKSLS YGSGPHVLLS TEDGVVYAWG HNGYSQLGNG TTNQGIAPVQ    120
VCTNLLIKQV VEVACGSHHS MALAADGEVF AWGYNNCGQV GSGSTANQPT PRKVTNCLHI    180
KRVVGIACGQ TSSMAVLDNG EVYGWGYNGN GQLGLGNNGN QLTPVRVAAL HSVCVNQIVC    240
GYAHTLALTD EGLLYAWGAN TYGQLGTGNK NNLLSPAHIM VEKERVVEIA ACHSAHTSAA    300
KTQGGHVYMW GQCRGQSVIL PHLTHFSCTD DVFACFATPA VSWRLLSVEH EDFLTVAESL    360
KKEFDSPETA DLKFRIDGKY IHVHKAVLKI RCEHFRSMFQ SYWNEDMKEV IEIDQFSYPV    420
YRAFLQYLYT DTVDLPPEDA IGLLDLATSY CENRLKKLCQ HIIKRGITVE NAFSLFSAAV    480
RYDAEDLEEF CFKFCINHLT EVTQTAAFWQ MDGPLLKEFI AKASKCGAFK N             531

SEQ ID NO: 723          moltype = AA   length = 531
FEATURE                 Location/Qualifiers
source                  1..531
                        mol_type = protein
                        organism = Homo sapiens
SEQUENCE: 723
MVDVGKWPIF TLLSPQEIAS IRKACVFGTS ASEALYVTDN DEVFVFGLNY SNCLGTGDNQ    60
STLVPKKLEG LCGKKIKSLS YGSGPHVLLS TEDGVVYAWG HNGYSQLGNG TTNQGIAPVQ    120
VCTNLLIKQV VEVACGSHHS MALAADGEVF AWGYNNCGQV GSGSTANQPT PRKVTNCLHI    180
KRVVGIACGQ TSSMAVLDNG EVYGWGYNGN GQLGLGNNGN QLTPVRVAAL HSVCVNQIVC    240
GYAHTLALTD EGLLYAWGAN TYGQLGTGNK NNLLSPAHIM VEKERVVEIA ACHSAHTSAA    300
KTQGGHVYMW GQCRGQSVIL PHLTHFSCTD DVFACFATPA VSWRLLSVEH EDFLTVAESL    360
KKEFDSPETA DLKFRIDGKY IHVHKAVLKI RCEHFRSMFQ SYWNEDMKEV IEIDQFSYPV    420
YRAFLQYLYT DTVDLPPEDA IGLLDLATSY CENRLKKLCQ HIIKRGITVE NAFSLFSAAV    480
RYDAEDLEEF CFKFCINHLT EVTQTAAFWQ MDGPLLKEFI AKASKCGAFK N             531

SEQ ID NO: 724          moltype = AA   length = 420
FEATURE                 Location/Qualifiers
source                  1..420
                        mol_type = protein
                        organism = Homo sapiens
SEQUENCE: 724
MSGRPRTTSF AESCKPVQQP SAFGSMKVSR DKDGSKVTTV VATPGQGPDR PQEVSYTDTK    60
VIGNGSFGVV YQAKLCDSGE LVAIKKVLQD KRFKNRELQI MRKLDHCNIV RLRYFFYSSG    120
EKKDEVYLNL VLDYVPETVY RVARHYSRAK QTLPVIYVKL YMYQLFRSLA YIHSFGICHR    180
DIKPQNLLLD PDTAVLKLCD FGSAKQLVRG EPNVSYICSR YYRAPELIFG ATDYTSSIDV    240
WSAGCVLAEL LLGQPIFPGD SGVDQLVEII KVLGTPTREQ IREMNPNYTE FKFPQIKAHP    300
WTKVFRPRTP PEAIALCSRL LEYTPTARLT PLEACAHSFF DELRDPNVKL PNGRDTPALF    360
NFTTQELSSN PPLATILIPP HARIQAAAST PTNATAASDA NTGDRGQTNN AASASASNST    420

SEQ ID NO: 725          moltype = AA   length = 433
FEATURE                 Location/Qualifiers
source                  1..433
                        mol_type = protein
```

```
                     organism = Homo sapiens
SEQUENCE: 725
MSGRPRTTSF AESCKPVQQP SAFGSMKVSR DKDGSKVTTV VATPGQGPDR PQEVSYTDTK    60
VIGNGSFGVV YQAKLCDSGE LVAIKKVLQD KRFKNRELQI MRKLDHCNIV RLRYFFYSSG   120
EKKDEVYLNL VLDYVPETVY RVARHYSRAK QTLPVIYVKL YMYQLFRSLA YIHSFGICHR   180
DIKPQNLLLD PDTAVLKLCD FGSAKQLVRG EPNVSYICSR YYRAPELIFG ATDYTSSIDV   240
WSAGCVLAEL LLGQPIFPGD SGVDQLVEII KVLGTPTREQ IREMNPNYTE FKFPQIKAHP   300
WTKDSSGTGH FTSGVRVFRP RTPPEAIALC SRLLEYTPTA RLTPLEACAH SFFDELRDPN   360
VKLPNGRDTP ALFNFTTQEL SSNPPLATIL IPPHARIQAA ASTPTNATAA SDANTGDRGQ   420
TNNAASASAS NST                                                    433

SEQ ID NO: 726         moltype = AA  length = 326
FEATURE                Location/Qualifiers
source                 1..326
                       mol_type = protein
                       organism = Homo sapiens
SEQUENCE: 726
MEKDGLCRAD QQYECVAEIG EGAYGKVFKA RDLKNGGRFV ALKRVRVQTG EEGMPLSTIR    60
EVAVLRHLET FEHPNVVRLF DVCTVSRTDR ETKLTLVFEH VDQDLTTYLD KVPEPGVPTE   120
TIKDMMFQLL RGLDFLHSHR VVHRDLKPQN ILVTSSGQIK LADFGLARIY SFQMALTSVV   180
VTLWYRAPEV LLQSSYATPV DLWSVGCIFA EMFRRKPLFR GSSDVDQLGK ILDVIGLPGE   240
EDWPRDVALP RQAFHSKSAQ PIEKFVTDID ELGKDLLLKC LTFNPAKRIS AYSALSHPYF   300
QDLERCKENL DSHLPPSQNT SELNTA                                      326

SEQ ID NO: 727         moltype = AA  length = 326
FEATURE                Location/Qualifiers
source                 1..326
                       mol_type = protein
                       organism = Homo sapiens
SEQUENCE: 727
MEKDGLCRAD QQYECVAEIG EGAYGKVFKA RDLKNGGRFV ALKRVRVQTG EEGMPLSTIR    60
EVAVLRHLET FEHPNVVRLF DVCTVSRTDR ETKLTLVFEH VDQDLTTYLD KVPEPGVPTE   120
TIKDMMFQLL RGLDFLHSHR VVHRDLKPQN ILVTSSGQIK LADFGLARIY SFQMALTSVV   180
VTLWYRAPEV LLQSSYATPV DLWSVGCIFA EMFRRKPLFR GSSDVDQLGK ILDVIGLPGE   240
EDWPRDVALP RQAFHSKSAQ PIEKFVTDID ELGKDLLLKC LTFNPAKRIS AYSALSHPYF   300
QDLERCKENL DSHLPPSQNT SELNTA                                      326

SEQ ID NO: 728         moltype = AA  length = 113
FEATURE                Location/Qualifiers
source                 1..113
                       mol_type = protein
                       organism = Homo sapiens
SEQUENCE: 728
MRSLGQNPTE AELQDMINEV DADGNGTIDF PEFLTMMARK MKDTDSEEEI REAFRVFDKD    60
GNGYISAAEL RHVMTNLGEK LTDEEVDEMI READIDGDGQ VNYEEFVQMM TAK          113

SEQ ID NO: 729         moltype = AA  length = 149
FEATURE                Location/Qualifiers
source                 1..149
                       mol_type = protein
                       organism = Homo sapiens
SEQUENCE: 729
MADQLTEEQI AEFKEAFSLF DKDGDGTITT KELGTVMRSL GQNPTEAELQ DMINEVDADG    60
NGTIDFPEFL TMMARKMKDT DSEEEIREAF RVFDKDGNGY ISAAELRHVM TNLGEKLTDE   120
EVDEMIREAD IDGDGQVNYE EFVQMMTAK                                   149

SEQ ID NO: 730         moltype = AA  length = 83
FEATURE                Location/Qualifiers
source                 1..83
                       mol_type = protein
                       organism = Homo sapiens
SEQUENCE: 730
MADQLTEEQI AEFKEAFSLF DKDGDGTITT KELGTVMRSL GQNPTEAELQ DMINEVDEMI    60
READIDGDGQ VNYEEFVQMM TAK                                          83

SEQ ID NO: 731         moltype = AA  length = 113
FEATURE                Location/Qualifiers
source                 1..113
                       mol_type = protein
                       organism = Homo sapiens
SEQUENCE: 731
MRSLGQNPTE AELQDMINEV DADGNGTIDF PEFLTMMARK MKDTDSEEEI REAFRVFDKD    60
GNGYISAAEL RHVMTNLGEK LTDEEVDEMI READIDGDGQ VNYEEFVQMM TAK          113

SEQ ID NO: 732         moltype = AA  length = 113
FEATURE                Location/Qualifiers
source                 1..113
                       mol_type = protein
                       organism = Homo sapiens
```

```
SEQUENCE: 732
MRSLGQNPTE AELQDMINEV DADGNGTIDF PEFLTMMARK MKDTDSEEEI REAFRVFDKD    60
GNGYISAAEL RHVMTNLGEK LTDEEVDEMI READIDGDGQ VNYEEFVQMM TAK          113

SEQ ID NO: 733           moltype = AA  length = 113
FEATURE                  Location/Qualifiers
source                   1..113
                         mol_type = protein
                         organism = Homo sapiens
SEQUENCE: 733
MRSLGQNPTE AELQDMINEV DADGNGTIDF PEFLTMMARK MKDTDSEEEI REAFRVFDKD    60
GNGYISAAEL RHVMTNLGEK LTDEEVDEMI READIDGDGQ VNYEEFVQMM TAK          113

SEQ ID NO: 734           moltype = AA  length = 149
FEATURE                  Location/Qualifiers
source                   1..149
                         mol_type = protein
                         organism = Homo sapiens
SEQUENCE: 734
MADQLTEEQI AEFKEAFSLF DKDGDGTITT KELGTVMRSL GQNPTEAELQ DMINEVDADG    60
NGTIDFPEFL TMMARKMKDT DSEEEIREAF RVFDKDGNGY ISAAELRHVM TNLGEKLTDE   120
EVDEMIREAD IDGDGQVNYE EFVQMMTAK                                    149

SEQ ID NO: 735           moltype = AA  length = 474
FEATURE                  Location/Qualifiers
source                   1..474
                         mol_type = protein
                         organism = Homo sapiens
SEQUENCE: 735
MVQQTNNAEN TEALLAGESS DSGAGLELGI ASSPTPGSTA STGGKADDPS WCKTPSGHIK    60
RPMNAFMVWS QIERRKIMEQ SPDMHNAEIS KRLGKRWKLL KDSDKIPFIR EAERLRLKHM   120
ADYPDYKYRP RKKVKSGNAN SSSSAAASSK PGEKGDKVGG SGGGGHGGGG GGGSSNAGGG   180
GGGASGGGAN SKPAQKKSCG SKVAGGAGGG VSKPHAKLIL AGGGGGGKAA AAAAASFAAE   240
QAGAAALLPL GAAADHHSLY KARTPSASAS ASSAASASAA LAAPGKHLAE KKVKRVYLFG   300
GLGTSSSPVG GVGAGADPSD PLGLYEEEGA GCSPDAPSLS GRSSAASSPA AGRSPADHRG   360
YASLRAASPA PSSAPSHASS SASSHSSSSS SSGSSSSDDE FEDDLLDLNP SSNFESMSLG   420
SFSSSSALDR DLDFNFEPGS GSHFEFPDYC TPEVSEMISG DWLESSISNL VFTY         474

SEQ ID NO: 736           moltype = AA  length = 680
FEATURE                  Location/Qualifiers
source                   1..680
                         mol_type = protein
                         organism = Homo sapiens
SEQUENCE: 736
MKMKKFQIPV SFQDLTVNFT QEEWQQLDPA QRLLYRDVML ENYSNLVSVG YHVSKPDVIF    60
KLEQGEEPWI VEEFSNQNYP DIDDALEKNK EIQDKHLTQT VFFSNKTLIT ERENVFGKTL   120
NLGMNSVPSR KMPYKCNPGG NSLKTNSEVI VAKKSKENRK IPDGYSGFGK HEKSHLGMKK   180
YRYNPMRKAS NQNENLILHQ NIQILKQPFD YNKCGKTFFK RAILITQKGR QTERKPNECN   240
ECRKTFSKRS TLIVHQRIHT GEKPYVCSDC RKTFRVKTSL TRHRRIHTGE RPYECSECRK   300
TFIDKSALIV HQKIHGGEKS YECNECGKTF FRKSALAEHF RSHTGEKPYE CKECGNAFSK   360
KSYLVVHQRT HRGEKPNECK ECGKTFFCQS ALTAHQRIHT GEKPYECSEC EKTFFCQSAL   420
NVHRRSHTGE KPYECSQCGK FLCTKSALIA HQITHRGKKS YECNECGKFF CHKSTLTIHQ   480
RTHTGEKHGV FNKCGRISIV KSNCSQCKRM NTKENLYECS EHGHAVSKNS HLIVHQRTIW   540
ERPYECNECG RTYCRKSALT HHQRTHTGQR PYECNECGKT FCQKFSFVEH QRTHTGEKPY   600
ECNECGKSFC HKSAFRVHRR IHTGEKPYEC NQCGKTYRRL WTLTEHQKIH TGEKPYECNK   660
CEKTFRHKSN FLLHQKSHKE                                              680

SEQ ID NO: 737           moltype = AA  length = 642
FEATURE                  Location/Qualifiers
source                   1..642
                         mol_type = protein
                         organism = Homo sapiens
SEQUENCE: 737
MLENYSNLVS VGYHVSKPDV IFKLEQGEEP WIVEEFSNQN YPDIDDALEK NKEIQDKHLT    60
QTVFFSNKTL ITERENVFGK TLNLGMNSVP SRKMPYKCNP GGNSLKTNSE VIVAKKSKEN   120
RKIPDGYSGF GKHEKSHLGM KKYRYNPMRK ASNQNENLIL HQNIQILKQP FDYNKCGKTF   180
FKRAILITQK GRQTERKPNE CNECRKTFSK RSTLIVHQRI HTGEKPYVCS DCRKTFRVKT   240
SLTRHRRIHT GERPYECSEC RKTFIDKSAL IVHQKIHGGE KSYECNECGK TFFRKSALAE   300
HFRSHTGEKP YECKECGNAF SKKSYLVVHQ RTHRGEKPNE CKECGKTFFC QSALTAHQRI   360
HTGEKPYECS ECEKTFFCQS ALNVHRRSHT GEKPYECSQC GKFLCTKSAL IAHQITHRGK   420
KSYECNECGK FFCHKSTLTI HQRTHTGEKH GVFNKCGRIS IVKSNCSQCK RMNTKENLYE   480
CSEHGHAVSK NSHLIVHQRT IWERPYECNE CGRTYCRKSA LTHHQRTHTG QRPYECNECG   540
KTFCQKFSFV EHQRTHTGEK PYECNECGKS FCHKSAFRVH RRIHTGEKPY ECNQCGKTYR   600
RLWTLTEHQK IHTGEKPYEC NKCEKTFRHK SNFLLHQKSK E                      642

SEQ ID NO: 738           moltype = AA  length = 703
FEATURE                  Location/Qualifiers
source                   1..703
                         mol_type = protein
```

```
                          organism = Homo sapiens
SEQUENCE: 738
MCVFLHLLSY IKDTSFIPGP DCELHPRGMA ATGPCSEAPV QGCDAGELQQ LGLCGVSDVQ    60
RSWSKFCNFP LTGYHVSKPD VIFKLEQGEE PWIVEEFSNQ NYPDIDDALE KNKEIQDKHL   120
TQTVFFSNKT LITERENVFG KTLNLGMNSV PSRKMPYKCN PGGNSLKTNS EVIVAKKSKE   180
NRKIPDGYSG FGKHEKSHLG MKKYRYNPMR KASNQNENLI LHQNIQILKQ PFDYNKCGKT   240
FFKRAILITQ KGRQTERKPN ECNECRKTFS KRSTLIVHQR IHTGEKPYVC SDCRKTFRVK   300
TSLTRHRRIH TGERPYECSE CRKTFIDKSA LIVHQKIHGG EKSYECNECG KTFFRKSALA   360
EHFRSHTGEK PYECKECGNA FSKKSYLVVH QRTHRGEKPN ECKECGKTFF CQSALTAHQR   420
IHTGEKPYEC SECEKTFFCQ SALNVHRRSH TGEKPYECSQ CGKFLCTKSA LIAHQITHRG   480
KKSYECNECG KFFCHKSTLT IHQRTHTGEK HGVFNKCGRI SIVKSNCSQC KRMNTKENLY   540
ECSEHGHAVS KNSHLIVHQR TIWERPYECN ECGRTYCRKS ALTHHQRTHT GQRPYECNEC   600
GKTFCQKFSF VEHQRTHTGE KPYECNECGK SFCHKSAFRV HRRIHTGEKP YECNQCGKTY   660
RRLWTLTEHQ KIHTGEKPYE CNKCEKTFRH KSNFLLHQKS HKE                    703

SEQ ID NO: 739          moltype = AA  length = 679
FEATURE                 Location/Qualifiers
source                  1..679
                        mol_type = protein
                        organism = Homo sapiens
SEQUENCE: 739
MENEKEIPVS FQDLTVNFTQ EEWQQLDPAQ RLLYRDVMLE NYSNLVSVGY HVSKPDVIFK    60
LEQGEEPWIV EEFSNQNYPD IDDALEKNKE IQDKHLTQTV FFSNKTLITE RENVFGKTLN   120
LGMNSVPSRK MPYKCNPGGN SLKTNSEVIV AKKSKENRKI PDGYSGFGKH EKSHLGMKKY   180
RYNPMRKASN QNENLILHQN IQILKQPFDY NKCGKTFFKR AILITQKGRQ TERKPNECNE   240
CRKTFSKRST LIVHQRIHTG EKPYVCSDCR KTFRVKTSLT RHRRIHTGER PYECSECRKT   300
FIDKSALIVH QKIHGGEKSY ECNECGKTFF RKSALAEHFR SHTGEKPYEC KECGNAFSKK   360
SYLVVHQRTH RGEKPNECKE CGKTFFCQSA LTAHQRIHTG EKPYECSECE KTFFCQSALN   420
VHRRSHTGEK PYECSQCGKF LCTKSALIAH QITHRGKKSY ECNECGKFFC HKSTLTIHQR   480
THTGEHGVF NKCGRISIVK SNCSQCKRMN TKENLYECSE HGHAVSKNSH LIVHQRTIWE   540
RPYECNECGR TYCRKSALTH HQRTHTGQRP YECNECGKTF CQKFSFVEHQ RTHTGEKPYE   600
CNECGKSFCH KSAFRVHRRI HTGEKPYECN QCGKTYRRLW TLTEHQKIHT GEKPYECNKC   660
EKTFRHKSNF LLHQKSHKE                                                679

SEQ ID NO: 740          moltype = AA  length = 173
FEATURE                 Location/Qualifiers
source                  1..173
                        mol_type = protein
                        organism = Homo sapiens
SEQUENCE: 740
MLENYSNLVS VGYHVSKPDV IFKLEQGEEP WIVEEFSNQN YPDIDDALEK NKEIQDKHLT    60
QTVFFSNKTL ITERENVFGK TLNLGMNSVP SRKMPYKCNP GGNSLKTNSE VIVAKKSKEN   120
RKIPDGYSGF GKHEKSHLGM KKYRYNPMRK ASNQNENLIL HQNIQILKQP FDY          173

SEQ ID NO: 741          moltype = AA  length = 679
FEATURE                 Location/Qualifiers
source                  1..679
                        mol_type = protein
                        organism = Homo sapiens
SEQUENCE: 741
MENEKEIPVS FQDLTVNFTQ EEWQQLDPAQ RLLYRDVMLE NYSNLVSVGY HVSKPDVIFK    60
LEQGEEPWIV EEFSNQNYPD IDDALEKNKE IQDKHLTQTV FFSNKTLITE RENVFGKTLN   120
LGMNSVPSRK MPYKCNPGGN SLKTNSEVIV AKKSKENRKI PDGYSGFGKH EKSHLGMKKY   180
RYNPMRKASN QNENLILHQN IQILKQPFDY NKCGKTFFKR AILITQKGRQ TERKPNECNE   240
CRKTFSKRST LIVHQRIHTG EKPYVCSDCR KTFRVKTSLT RHRRIHTGER PYECSECRKT   300
FIDKSALIVH QKIHGGEKSY ECNECGKTFF RKSALAEHFR SHTGEKPYEC KECGNAFSKK   360
SYLVVHQRTH RGEKPNECKE CGKTFFCQSA LTAHQRIHTG EKPYECSECE KTFFCQSALN   420
VHRRSHTGEK PYECSQCGKF LCTKSALIAH QITHRGKKSY ECNECGKFFC HKSTLTIHQR   480
THTGEHGVF NKCGRISIVK SNCSQCKRMN TKENLYECSE HGHAVSKNSH LIVHQRTIWE   540
RPYECNECGR TYCRKSALTH HQRTHTGQRP YECNECGKTF CQKFSFVEHQ RTHTGEKPYE   600
CNECGKSFCH KSAFRVHRRI HTGEKPYECN QCGKTYRRLW TLTEHQKIHT GEKPYECNKC   660
EKTFRHKSNF LLHQKSHKE                                                679

SEQ ID NO: 742          moltype = AA  length = 1455
FEATURE                 Location/Qualifiers
source                  1..1455
                        mol_type = protein
                        organism = Homo sapiens
SEQUENCE: 742
MGGACSSFTT SSSPTIYSTS VTDSKAMQVE SCSSAVGVSN RGVSEKQLTS NTVQQHPSTP    60
KRHTVLYISP PPEDLLDNSR MSCQDEGCGL ESEQSCSMWM EDSPSNFSNM STSSYNDNTE   120
VPRKSRKRNP KQRPGVKRRD CEESNMDIFD ADSAKAPHYV LSQLTTDNKG NSKAGNGTLE   180
NQKGTGVKKS PMLCGQYPVK SEGKELKIVV QPETQHRARY LTEGSRGSVK DRTQQGFPTV   240
KLEGHNEPVV LQVFVGNDSG RVKPHGFYQA CRVTGRNTTP CKEVDIEGTT VIEVGLDPSN   300
NMTLAVDCVG ILKLRNADVE ARIGIAGSKK KSTRARLVFR VNIMRKDGST LTLQTPSSPI   360
LCTQPAGVPE ILKKSLHSCS VKGEEEVFLI GKNFLKGTKV IFQENVSDEN SWKSEAEIDM   420
ELFHQNHLIV KVPPYHDQHI TLPVSVGIYV VTNAGRSHDV QPFTYTPDPA AAGALNVNVK   480
KEISSPARPC SFEEAMKAMK TTGCNLDKVN IIPNALMTPL IPSSMIKSED VTPMEVTAEK   540
RSSTIFKTTK SVGSTQQTLE NISNIAGNGS FSSPSSSHLP SENEKQQQIQ PKAYNPETLT   600
```

```
TIQTQDISQP GTFPAVSASS QLPNSDALLQ QATQFQTRET QSREILQSDG TVVNLSQLTE    660
ASQQQQQSPL QEQAQTLQQQ ISSNIFPSPN SVSQLQNTIQ QLQAGSFTGS TASGSSGSVD    720
LVQQVLEAQQ QLSSVLFSAP DGNENVQEQL SADIFQQVSQ IQSGVSPGMF SSTEPTVHTR    780
PDNLLPGRAE SVHPQSENTL SNQQQQQQQQ QQVMESSAAM VMEMQQSICQ AAAQIQSELF    840
PSTASANGNL QQSPVYQQTS HMMSALSTNE DMQMQCELFS SPPAVSGNET STTTTQQVAT    900
PGTTMFQTSS SGDGEETGTQ AKQIQNSVFQ TMVQMQHSGD NQPQVNLFSS TKSMMSVQNS    960
GTQQQGNGLF QQGNEMMSLQ SGNFLQQSSH SQAQLFHPQN PIADAQNLSQ ETQGSLFHSP   1020
NPIVHSQTST TSSEQMQPPM FHSQSTIAVL QGSSVPQDQQ STNIFLSQSP MNNLQTNTVA   1080
QEAFFAAPNS ISPLQSTSNS EQQAAFQQQA PISHIQTPML SQEQAQPPQQ GLFQPQVALG   1140
SLPPNPMPQS QQGTMFQSQH SIVAMQSNSP SQEQQQQQQQ QQQQQQQQQQ SILFSNQNTM   1200
ATMASPKQPP PNMIFNPNQN PMANQEQQNQ SIFHQQSNMA PMNQEQQPMQ FQSQSTVSSL   1260
QNPGPTQSES SQTPLFHSSP QIQLVQGSPS SQEQQVTLFL SPASMSALQT SINQQDMQQS   1320
PLYSPQNNMP GIQGATSSPQ PQATLFHNTA GGTMNQLQNS PGSSQQTSGM FLFGIQNNCS   1380
QLLTSGPATL PDQLMAISQP GQPQNEGQPP VTTLLSQQMP ENSPLASSIN TNQNIEKIDL   1440
LVSLQNQGNN LTGSF                                                   1455

SEQ ID NO: 743           moltype = AA  length = 70
FEATURE                  Location/Qualifiers
source                   1..70
                         mol_type = protein
                         organism = Homo sapiens
SEQUENCE: 743
XIIPTLPSDK LSKIQTLKLA ARYIDFLYQV LQSDELDSKM ASCSYVAHER LSYAFSVWRM    60
EGAWSMSASH                                                          70

SEQ ID NO: 744           moltype = AA  length = 135
FEATURE                  Location/Qualifiers
source                   1..135
                         mol_type = protein
                         organism = Homo sapiens
SEQUENCE: 744
XPAQGKRGKK SAGCGGGGGA GGGGGSSSGG GSPQSYEELQ TQRVMANVRE RQRTQSLNEA    60
FAALRKIIPT LPSDKLSKIQ TLKLAARYID FLYQVLQSDE LDSKMASCSY VAHERLSYAF   120
SVWRMEGAWS MSASH                                                   135

SEQ ID NO: 745           moltype = AA  length = 202
FEATURE                  Location/Qualifiers
source                   1..202
                         mol_type = protein
                         organism = Homo sapiens
SEQUENCE: 745
MMQDVSSSPV SPADDSLSNS EEEPDRQQPP SGKRGGRKRR SSRRSAGGGA GPGGAAGGGV    60
GGGDEPGSPA QGKRGKKSAG CGGGGGAGGG GGSSSGGGSP QSYEELQTQR VMANVRERQR   120
TQSLNEAFAA LRKIIPTLPS DKLSKIQTLK LAARYIDFLY QVLQSDELDS KMASCSYVAH   180
ERLSYAFSVW RMEGAWSMSA SH                                           202

SEQ ID NO: 746           moltype = AA  length = 636
FEATURE                  Location/Qualifiers
source                   1..636
                         mol_type = protein
                         organism = Homo sapiens
SEQUENCE: 746
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVKKRRHG DEDTYYLQVR   360
GRENFEILMK LKESLELMEL VPQPLVDSYR QQQQLLQRPS HLQPPSYGPV LSPMNKVHGG   420
MNKLPSVNQL VGQPPPHSSA ATPNLGPVGP GMLNNHGHAV PANGEMSSSH SAQSMVSGSH   480
CTPPPPYHAD PSLVSFLTGL GCPNCIEYFT SQGLQSIYHL QNLTIEDLGA LKIPEQYRMT   540
IWRGLQDLKQ GHDYSTAQQL LRSSNAATIS IGGSGELQRQ RVMEAVHFRV RHTITIPNRG   600
GPGGGPDEWA DFGFDLPDCK ARKQPIKEEF TEAEIH                             636

SEQ ID NO: 747           moltype = AA  length = 403
FEATURE                  Location/Qualifiers
source                   1..403
                         mol_type = protein
                         organism = Homo sapiens
SEQUENCE: 747
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVKKRRHG DEDTYYLQVR   360
GRENFEILMK LKESLELMEL VPQPLVDSYR QQQQLLQRPT WGP                     403

SEQ ID NO: 748           moltype = AA  length = 499
```

| FEATURE | Location/Qualifiers |
|---|---|
| source | 1..499 |
| | mol_type = protein |
| | organism = Homo sapiens |

SEQUENCE: 748

```
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVKKRRHG DEDTYYLQVR   360
GRENFEILMK LKESLELMEL VPQPLVDSYR QQQQLLQRPS HLQPPSYGPV LSPMNKVHGG   420
MNKLPSVNQL VGQPPPHSSA ATPNLGPVGP GMLNNHGHAV PANGEMSSSH SAQSMVSGSH   480
CTPPPPYHAD PSLVRTWGP                                               499
```

| SEQ ID NO: 749 | moltype = AA  length = 555 |
|---|---|
| FEATURE | Location/Qualifiers |
| source | 1..555 |
| | mol_type = protein |
| | organism = Homo sapiens |

SEQUENCE: 749

```
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVKKRRHG DEDTYYLQVR   360
GRENFEILMK LKESLELMEL VPQPLVDSYR QQQQLLQRPP RDAQQPWPRS ASQRRDEQQP   420
QRPVHGLGVP LHSATPLPRR PQPRQDLGAL KIPEQYRMTI WRGLQDLKQG HDYSTAQQLL   480
RSSNAATISI GGSGELQRQR VMEAVHFRVR HTITIPNRGG PGGGPDEWAD FGFDLPDCKA   540
RKQPIKEEFT EAEIH                                                   555
```

| SEQ ID NO: 750 | moltype = AA  length = 540 |
|---|---|
| FEATURE | Location/Qualifiers |
| source | 1..540 |
| | mol_type = protein |
| | organism = Homo sapiens |

SEQUENCE: 750

```
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVKKRRHG DEDTYYLQVR   360
GRENFEILMK LKESLELMEL VPQPLVDSYR QQQQLLQRPF LTGLGCPNCI EYFTSQGLQS   420
IYHLQNLTIE DLGALKIPEQ YRMTIWRGLQ DLKQGHDYST AQQLLRSSNA ATISIGGSGE   480
LQRQRVMEAV HFRVRHTITI PNRGGPGGGP DEWADFGFDL PDCKARKQPI KEEFTEAEIH   540
```

| SEQ ID NO: 751 | moltype = AA  length = 450 |
|---|---|
| FEATURE | Location/Qualifiers |
| source | 1..450 |
| | mol_type = protein |
| | organism = Homo sapiens |

SEQUENCE: 751

```
MLYVGDPARH LATAQFNLLS STMDQMSSRA ASASPYTPEH AASVPTHSPY AQPSSTFDTM    60
SPAPVIPSNT DYPGPHHFEV TFQQSSTAKS ATWTYSPLLK KLYCQIAKTC PIQIKVSTPP   120
PPGTAIRAMP VYKKAEHVTD VVKRCPNHEL GRDFNEGQSA PASHLIRVEG NNLSQYVDDP   180
VTGRQSVVVP YEPPQVGTEF TTILYNFMCN SSCVGGMNRR PILIIITLEM RDGQVLGRRS   240
FEGRICACPG RDRKADEDHY REQQALNESS AKNGAASKRA FKQSPPAVPA LGAGVKKRRH   300
GDEDTYYLQV RGRENFEILM KLKESLELME LVPQPLVDSY RQQQQLLQRP SHLQPPSYGP   360
VLSPMNKVHG GMNKLPSVNQ LVGQPPPHSS AATPNLGPVG PGMLNNHGHA VPANGEMSSS   420
HSAQSMVSGS HCTPPPPYHA DPSLVRTWGP                                   450
```

| SEQ ID NO: 752 | moltype = AA  length = 426 |
|---|---|
| FEATURE | Location/Qualifiers |
| source | 1..426 |
| | mol_type = protein |
| | organism = Homo sapiens |

SEQUENCE: 752

```
MLYVGDPARH LATAQFNLLS STMDQMSSRA ASASPYTPEH AASVPTHSPY AQPSSTFDTM    60
SPAPVIPSNT DYPGPHHFEV TFQQSSTAKS ATWTYSPLLK KLYCQIAKTC PIQIKVSTPP   120
PPGTAIRAMP VYKKAEHVTD VVKRCPNHEL GRDFNEGQSA PASHLIRVEG NNLSQYVDDP   180
VTGRQSVVVP YEPPQVGTEF TTILYNFMCN SSCVGGMNRR PILIIITLEM RDGQVLGRRS   240
FEGRICACPG RDRKADEDHY REQQALNESS AKNGAASKRA FKQSPPAVPA LGAGVKKRRH   300
GDEDTYYLQV RGRENFEILM KLKESLELME LVPQPLVDSY RQQQQLLQRP PRDAQQPWPR   360
SASQRRDEQQ PQRPVHGLGV PLHSATPLPR RPQPRQFFNR IGVSKLHRVF HLPRVTEHLP   420
PAEPDH                                                             426
```

| SEQ ID NO: 753 | moltype = AA  length = 587 |
|---|---|

| FEATURE | Location/Qualifiers | |
|---|---|---|
| source | 1..587 | |
| | mol_type = protein | |
| | organism = Homo sapiens | |

SEQUENCE: 753
```
MLYVGDPARH LATAQFNLLS STMDQMSSRA ASASPYTPEH AASVPTHSPY AQPSSTFDTM   60
SPAPVIPSNT DYPGPHHFEV TFQQSSTAKS ATWTYSPLLK KLYCQIAKTC PIQIKVSTPP  120
PPGTAIRAMP VYKKAEHVTD VVKRCPNHEL GRDFNEGQSA PASHLIRVEG NNLSQYVDDP  180
VTGRQSVVVP YEPPQVGTEF TTILYNFMCN SSCVGGMNRR PILIIITLEM RDGQVLGRRS  240
FEGRICACPG RDRKADEDHY REQQALNESS AKNGAASKRA FKQSPPAVPA LGAGVKKRRH  300
GDEDTYYLQV RGRENFEILM KLKESLELME LVPQPLVDSY RQQQQLLQRP SHLQPPSYGP  360
VLSPMNKVHG GMNKLPSVNQ LVGQPPPHSS AATPNLGPVG PGMLNNHGHA VPANGEMSSS  420
HSAQSMVSGS HCTPPPPYHA DPSLVSFLTG LGCPNCIEYF TSQGLQSIYH LQNLTIEDLG  480
ALKIPEQYRM TIWRGLQDLK QGHDYSTAQQ LLRSSNAATI SIGGSGELQR QRVMEAVHFR  540
VRHTITIPNR GGPGGGPDEW ADFGFDLPDC KARKQPIKEE FTEAEIH            587
```

| SEQ ID NO: 754 | moltype = AA  length = 565 | |
|---|---|---|
| FEATURE | Location/Qualifiers | |
| source | 1..565 | |
| | mol_type = protein | |
| | organism = Homo sapiens | |

SEQUENCE: 754
```
MDQMSSRAAS ASPYTPEHAA SVPTHSPYAQ PSSTFDTMSP APVIPSNTDY PGPHHFEVTF   60
QQSSTAKSAT WTYSPLLKKL YCQIAKTCPI QIKVSTPPPP GTAIRAMPVY KKAEHVTDVV  120
KRCPNHELGR DFNEGQSAPA SHLIRVEGNN LSQYVDDPVT GRQSVVVPYE PPQVGTEFTT  180
ILYNFMCNSS CVGGMNRRPI LIIITLEMRD GQVLGRRSFE GRICACPGRD RKADEDHYRE  240
QQALNESSAK NGAASKRAFK QSPPAVPALG AGVKKRRHGD EDTYYLQVRG RENFEILMKL  300
KESLELMELV PQPLVDSYRQ QQQLLQRPSH LQPPSYGPVL SPMNKVHGGM NKLPSVNQLV  360
GQPPPHSSAA TPNLGPVGPG MLNNHGHAVP ANGEMSSSHS AQSMVSGSHC TPPPPYHADP  420
SLVSFLTGLG CPNCIEYFTS QGLQSIYHLQ NLTIEDLGAL KIPEQYRMTI WRGLQDLKQG  480
HDYSTAQQLL RSSNAATISI GGSGELQRQR VMEAVHFRVR HTITIPNRGG PGGGPDEWAD  540
FGFDLPDCKA RKQPIKEEFT EAEIH                                     565
```

| SEQ ID NO: 755 | moltype = AA  length = 555 | |
|---|---|---|
| FEATURE | Location/Qualifiers | |
| source | 1..555 | |
| | mol_type = protein | |
| | organism = Homo sapiens | |

SEQUENCE: 755
```
MAQSTATSPD GGTTFEHLWS SLEPDSTYFD LPQSSRGNNE VVGGTDSSMD VFHLEGMTTS   60
VMAQFNLLSS TMDQMSSRAA SASPYTPEHA ASVPTHSPYA QPSSTFDTMS PAPVIPSNTD  120
YPGPHHFEVT FQQSSTAKSA TWTYSPLLKK LYCQIAKTCP IQIKVSTPPP PGTAIRAMPV  180
YKKAEHVTDV VKRCPNHELG RDFNEGQSAP ASHLIRVEGN NLSQYVDDPV TGRQSVVVPY  240
EPPQVGTEFT TILYNFMCNS SCVGGMNRRP ILIIITLEMR DGQVLGRRSF EGRICACPGR  300
DRKADEDHYR EQQALNESSA KNGAASKRAF KQSPPAVPAL GAGVKKRRHG DEDTYYLQVR  360
GRENFEILMK LKESLELMEL VPQPLVDSYR QQQQLLQRPP RDAQQPWPRS ASQRRDEQQP  420
QRPVHGLGVP LHSATPLPRR PQPRQDLGAL KIPEQYRMTI WRGLQDLKQG HDYSTAQQLL  480
RSSNAATISI GGSGELQRQR VMEAVHFRVR HTITIPNRGG PGGGPDEWAD FGFDLPDCKA  540
RKQPIKEEFT EAEIH                                                555
```

| SEQ ID NO: 756 | moltype = AA  length = 540 | |
|---|---|---|
| FEATURE | Location/Qualifiers | |
| source | 1..540 | |
| | mol_type = protein | |
| | organism = Homo sapiens | |

SEQUENCE: 756
```
MAQSTATSPD GGTTFEHLWS SLEPDSTYFD LPQSSRGNNE VVGGTDSSMD VFHLEGMTTS   60
VMAQFNLLSS TMDQMSSRAA SASPYTPEHA ASVPTHSPYA QPSSTFDTMS PAPVIPSNTD  120
YPGPHHFEVT FQQSSTAKSA TWTYSPLLKK LYCQIAKTCP IQIKVSTPPP PGTAIRAMPV  180
YKKAEHVTDV VKRCPNHELG RDFNEGQSAP ASHLIRVEGN NLSQYVDDPV TGRQSVVVPY  240
EPPQVGTEFT TILYNFMCNS SCVGGMNRRP ILIIITLEMR DGQVLGRRSF EGRICACPGR  300
DRKADEDHYR EQQALNESSA KNGAASKRAF KQSPPAVPAL GAGVKKRRHG DEDTYYLQVR  360
GRENFEILMK LKESLELMEL VPQPLVDSYR QQQQLLQRPP LTGLGCPNCI EYFTSQGLQS  420
IYHLQNLTIE DLGALKIPEQ YRMTIWRGLQ DLKQGHDYST AQQLLRSSNA ATISIGGSGE  480
LQRQRVMEAV HFRVRHTITI PNRGGPGGGP DEWADFGFDL PDCKARKQPI KEEFTEAEIH  540
```

| SEQ ID NO: 757 | moltype = AA  length = 602 | |
|---|---|---|
| FEATURE | Location/Qualifiers | |
| source | 1..602 | |
| | mol_type = protein | |
| | organism = Homo sapiens | |

SEQUENCE: 757
```
MAAEEEAAAG GKVLREENQC IAPVVSSRVS PGTRPTAMGS FSSHMTEFPR KRKGSDSDPS   60
QVEDGEHQVK MKAFREAHSQ TEKRRRDKMN NLIEELSAMI PQCNPMARKL DKLTVLRMAV  120
QHLRSLKGLT NSYVGSNYRP SFLQDNELRH LILKTAEGFL FVVGCERGKI LFVSKSVSKI  180
LNYDQASLTG QSLFDPLHPK DVAKVKEQLS SFDISPREKL IDAKTGLQVH SNLHAGRTRV  240
YSGSRRSFFC RIKSCKISVK EEHGCLPNSK KKEHRKFYTI HCTGYLRSWP PNIVGMEEER  300
NSKKDNSNFT CLVAIGRLQP YIVPQNSGEI NVKPTEFITR FAVNGKFVYV DQRATAILGY  360
LPQELLGTSC YEYFHQDDHN NLTDKHKAVL QSKEKILTDS YKFRAKDGSF VTLKSQWFSF  420
```

```
TNPWTKELEY IVSVNTLVLG HSEPGEASFL PCSSQSSEES SRQSCMSVPG MSTGTVLGAG    480
SIGTDIANEI LDLQRLQSSS YLDDSSPTGL MKDTHTVNCR SMSNKELFPP SPSEMGELEA    540
TRQNQSTVAV HSHEPLLSDG AQLDFDALCD NDDTAMAAFM NYLEAEGGLG DPGDFSDIQW    600
TL                                                                   602

SEQ ID NO: 758          moltype = AA   length = 599
FEATURE                 Location/Qualifiers
source                  1..599
                        mol_type = protein
                        organism = Homo sapiens
SEQUENCE: 758
MAAEEEAAAG GEVAGGEATA PGKVLREENQ CIAPVVSSRV SPGTRPTAMG SFSSHMTEFP     60
RKRKGSDSDP SQEAHSQTEK RRRDKMNNLI EELSAMIPQC NPMARKLDKL TVLRMAVQHL    120
RSLKGLTNSY VGSNYRPSFL QDNELRHLIL KTAEGFLFVV GCERGKILFV SKSVSKILNY    180
DQASLTGQSL FDFLHPKDVA KVKEQLSSFD ISPREKLIDA KTGLQVHSNL HAGRTRVYSG    240
SRRSFFCRIK SCKISVKEEH GCLPNSKKKE HRKFYTIHCT GYLRSWPPNI VGMEEERNSK    300
KDNSNFTCLV AIGRLQPYIV PQNSGEINVK PTEFITRFAV NGKFVYVDQR ATAILGYLPQ    360
ELLGTSCYEY FHQDDHNNLT DKHKAVLQSK EKILTDSYKF RAKDGSFVTL KSQWFSFTNP    420
WTKELEYIVS VNTLVLGHSE PGEASFLPCS SQSSEESSRQ SCMSVPGMST GTVLGAGSIG    480
TDIANEILDL QRLQSSSYLD DSSPTGLMKD THTVNCRSMS NKELFPPSPS EMGELEATRQ    540
NQSTVAVHSH EPLLSDGAQL DFDALCDNDD TAMAAFMNYL EAEGGLGDPG DFSDIQWTL    599

SEQ ID NO: 759          moltype = AA   length = 540
FEATURE                 Location/Qualifiers
source                  1..540
                        mol_type = protein
                        organism = Homo sapiens
SEQUENCE: 759
MAAEEEAAAG GEVAGGEATA PGKVLREENQ CIAPVVSSRV SPGTRPTAMG SFSSHMTEFP     60
RKRKGSDSDP SQEAHSQTEK RRRDKMNNLI EELSAMIPQC NPMARKLDKL TVLRMAVQHL    120
RSLKGLTNSY VGSNYRPSFL QDNELRHLIL KTAEGFLFVV GCERGKILFV SKSVSKILNY    180
DQASLTGQSL FDFLHPKDVA KVKEQLSSFD ISPREKLIDA KTGLQVHSNL HAGRTRVYSG    240
SRRSFFCRIK SCKISVKEEH GCLPNSKKKE HRKFYTIHCT GYLRSWPPNI VGMEEERNSK    300
KDNSNFTCLV AIGRLQPYIV PQNSGEINVK PTEFITRFAV NGKFVYVDQR ATAILGYLPQ    360
ELLGTSCYEY FHQDDHNNLT DKHKAVLQSK EKILTDSYKF RAKDGSFVTL KSQWFSFTNP    420
WTKELEYIVS VNTLVLGHSE PGEASFLPCS SQSSEESSRQ SCMSVPGMST GTVLGAGSIG    480
TDIANEILDL QRLQSSSYLD DSSPTGLMKD THTVNCRSVM VHSWISMPYV TMMTQPWLHL    540

SEQ ID NO: 760          moltype = AA   length = 622
FEATURE                 Location/Qualifiers
source                  1..622
                        mol_type = protein
                        organism = Homo sapiens
SEQUENCE: 760
MAAEEEAAAG GKVLREENQC IAPVVSSRVS PGTRPTAMGS FSSHMTEFPR KRKGSDSDPS     60
QSGIMTEKVV EKLSQNPLTY LLSTRIEISA SSGSREAHSQ TEKRRRDKMN NLIEELSAMI    120
PQCNPMARKL DKLTVLRMAV QHLRSLKGLT NSYVGSNYRP SFLQDNELRH LILKTAEGFL    180
FVVGCERGKI LFVSKSVSKI LNYDQASLTG QSLFDFLHPK DVAKVKEQLS SFDISPREKL    240
IDAKTGLQVH SNLHAGRTRV YSGSRRSFFC RIKSCKISVK EEHGCLPNSK KKEHRKFYTI    300
HCTGYLRSWP PNIVGMEEER NSKKDNSNFT CLVAIGRLQP YIVPQNSGEI NVKPTEFITR    360
FAVNGKFVYV DQRATAILGY LPQELLGTSC YEYFHQDDHN NLTDKHKAVL QSKEKILTDS    420
YKFRAKDGSF VTLKSQWFSF TNPWTKELEY IVSVNTLVLG HSEPGEASFL PCSSQSSEES    480
SRQSCMSVPG MSTGTVLGAG SIGTDIANEI LDLQRLQSSS YLDDSSPTGL MKDTHTVNCR    540
SMSNKELFPP SPSEMGELEA TRQNQSTVAV HSHEPLLSDG AQLDFDALCD NDDTAMAAFM    600
NYLEAEGGLG DPGDFSDIQW TL                                              622

SEQ ID NO: 761          moltype = AA   length = 588
FEATURE                 Location/Qualifiers
source                  1..588
                        mol_type = protein
                        organism = Homo sapiens
SEQUENCE: 761
MAAEEEAAAG GKVLREENQC IAPVVSSRVS PGTRPTAMGS FSSHMTEFPR KRKGSDSDPS     60
QEAHSQTEKR RRDKMNNLIE ELSAMIPQCN PMARKLDKLT VLRMAVQHLR SLKGLTNSYV    120
GSNYRPSFLQ DNELRHLILK TAEGFLFVVG CERGKILFVS KSVSKILNYD QASLTGQSLF    180
DFLHPKDVAK VKEQLSSFDI SPREKLIDAK TGLQVHSNLH AGRTRVYSGS RRSFFCRIKS    240
CKISVKEEHG CLPNSKKKEH RKFYTIHCTG YLRSWPPNIV GMEEERNSKK DNSNFTCLVA    300
IGRLQPYIVP QNSGEINVKP TEFITRFAVN GKFVYVDQRA TAILGYLPQE LLGTSCYEYF    360
HQDDHNNLTD KHKAVLQSKE KILTDSYKFR AKDGSFVTLK SQWFSFTNPW TKELEYIVSV    420
NTLVLGHSEP GEASFLPCSS QSSEESSRQS CMSVPGMSTG TVLGAGSIGT DIANEILDLQ    480
RLQSSSYLDD SSPTGLMKDT HTVNCRSMSN KELFPPSPSE MGELEATRQN QSTVAVHSHE    540
PLLSDGAQLD FDALCDNDDT AMAAFMNYLE AEGGLGDPGD FSDIQWTL                 588

SEQ ID NO: 762          moltype = AA   length = 636
FEATURE                 Location/Qualifiers
source                  1..636
                        mol_type = protein
                        organism = Homo sapiens
SEQUENCE: 762
```

```
MAAEEEAAAG GKVLREENQC IAPVVSSRVS PGTRPTAMGS FSSHMTEFPR KRKGSDSDPS    60
QSGIMTEKVV EKLSQNPLTY LLSTRIEISA SSGSRVEDGE HQVKMKAFRE AHSQTEKRRR   120
DKMNNLIEEL SAMIPQCNPM ARKLDKLTVL RMAVQHLRSL KGLTNSYVGS NYRPSFLQDN   180
ELRHLILKTA EGFLFVVGCE RGKILFVSKS VSKILNYDQA SLTGQSLFDF LHPKDVAKVK   240
EQLSSFDISP REKLIDAKTG LQVHSNLHAG RTRVYSGSRR SFFCRIKSCK ISVKEEHGCL   300
PNSKKKEHRK FYTIHCTGYL RSWPPNIVGM EEERNSKKDN SNFTCLVAIG RLQPYIVPQN   360
SGEINVKPTE FITRFAVNGK FVYVDQRATA ILGYLPQELL GTSCYEYFHQ DDHNNLTDKH   420
KAVLQSKEKI LTDSYKFRAK DGSFVTLKSQ WFSFTNPWTK ELEYIVSVNT LVLGHSEPGE   480
ASFLPCSSQS SEESSRQSCM SVPGMSTGTV LGAGSIGTDI ANEILDLQRL QSSSYLDDSS   540
PTGLMKDTHT VNCRSMSNKE LFPPSPSEMG ELEATRQNQS TVAVHSHEPL LSDGAQLDFD   600
ALCDNDDTAM AAFMNYLEAE GGLGDPGDFS DIQWTL                             636

SEQ ID NO: 763         moltype = AA   length = 588
FEATURE                Location/Qualifiers
source                 1..588
                       mol_type = protein
                       organism = Homo sapiens
SEQUENCE: 763
XPVVSSRVSP GTRPTAMGSF SSHMTEFPRK RKGSDSDPSH QNPLTYLLST RIEISASSGS    60
REAHSQTEKR RRDKMNNLIE ELSAMIPQCN PMARKLDKLT VLRMAVQHLR SLKGLTNSYV   120
GSNYRPSFLQ DNELRHLILK TAEGFLFVVG CERGKILFVS KSVSKILNYD QASLTGQSLF   180
DFLHPKDVAK VKEQLSSFDI SPREKLIDAK TGLQVHSNLH AGRTRVYSGS RRSFFCRIKS   240
CKISVKEEHG CLPNSKKKEH RKFYTIHCTG YLRSWPPNIV GMEEERNSKK DNSNFTCLVA   300
IGRLQPYIVP QNSGEINVKP TEFITRFAVN GKFVYVDQRA TAILGYLPQE LLGTSCYEYF   360
HQDDHNNLTD KHKAVLQSKE KILTDSYKFR AKDGSFVTLK SQWFSFTNPW TKELEYIVSV   420
NTLVLGHSEP GEASFLPCSS QSSEESSRQS CMSVPGMSTG TVLGAGSIGT DIANEILDLQ   480
RLQSSSYLDD SSPTGLMKDT HTVNCRSMSN KELFPPSPSE MGELEATRQN QSTVAVHSHE   540
PLLSDGAQLD FDALCDNDDT AMAAFMNYLE AEGGLGDPGD FSDIQWTL                588

SEQ ID NO: 764         moltype = AA   length = 551
FEATURE                Location/Qualifiers
source                 1..551
                       mol_type = protein
                       organism = Homo sapiens
SEQUENCE: 764
MGSFSSHMTE FPRKRKGSDS DPSQEAHSQT EKRRRDKMNN LIEELSAMIP QCNPMARKLD    60
KLTVLRMAVQ HLRSLKGLTN SYVGSNYRPS FLQDNELRHL ILKTAEGFLF VVGCERGKIL   120
FVSKSVSKIL NYDQASLTGQ SLFDFLHPKD VAKVKEQLSS FDISPREKLI DAKTGLQVHS   180
NLHAGRTRVY SGSRRSFFCR IKSCKISVKE EHGCLPNSKK KEHRKFYTIH CTGYLRSWPP   240
NIVGMEEERN SKKDNSNFTC LVAIGRLQPY IVPQNSGEIN VKPTEFITRF AVNGKFVYVD   300
QRATAILGYL PQELLGTSCY EYFHQDDHNN LTDKHKAVLQ SKEKILTDSY KFRAKDGSFV   360
TLKSQWFSFT NPWTKELEYI VSVNTLVLGH SEPGEASFLP CSSQSSEESS RQSCMSVPGM   420
STGTVLGAGS IGTDIANEIL DLQRLQSSSY LDDSSPTGLM KDTHTVNCRS MSNKELFPPS   480
PSEMGELEAT RQNQSTVAVH SHEPLLSDGA QLDFDALCDN DDTAMAAFMN YLEAEGGLGD   540
PGDFSDIQWT L                                                       551

SEQ ID NO: 765         moltype = AA   length = 125
FEATURE                Location/Qualifiers
source                 1..125
                       mol_type = protein
                       organism = Homo sapiens
SEQUENCE: 765
MPHSSDSSDS SFSRSPPPGK QDSSDDVRRV QRREKNRIAA QKSRQRQTQK ADTLHLESED    60
LEKQNAALRK EIKQLTEELK YFTSVLNSHE PLCSVLAAST PSPPEVVYSA HAFHQPHVSS   120
PRFQP                                                               125

SEQ ID NO: 766         moltype = AA   length = 73
FEATURE                Location/Qualifiers
source                 1..73
                       mol_type = protein
                       organism = Homo sapiens
SEQUENCE: 766
MPHSSDSSDS SFSRSPPPGK QDSSDDVRRV QRREKNRIAA QKSRQRQTQK SIKKDAQVPW    60
HRARRAGNGY FSK                                                      73

SEQ ID NO: 767         moltype = AA   length = 202
FEATURE                Location/Qualifiers
source                 1..202
                       mol_type = protein
                       organism = Homo sapiens
SEQUENCE: 767
MATLIYVDKE NGEPGTRVVA KDGLKLGSGP SIKALDGRSQ VSTPRFGKTF DAPPALPKAT    60
RKALGTVNRA TEKSVKTKGP LKQKQPSFSA KKMTEKTVKA KSSVPASDDA YPEIEKFFPF   120
NPLDFESFDL PEEHQIAHLP LSGVPLMILD EERELEKLFQ LGPPSPVKMP SPPWESNLLQ   180
SPSSILSTLD VELPPVCCDI DI                                            202

SEQ ID NO: 768         moltype = AA   length = 121
FEATURE                Location/Qualifiers
source                 1..121
```

```
                      mol_type =  protein
                      organism =  Homo sapiens
SEQUENCE: 768
MPLPKVGGGF GGERSSLYTQ YLSCTGILLL EYSYGKTFSS AIKALDGRSQ VSTPRFGKTF    60
DAPPALPKAT RKALGTVNRA TEKSVKTKGP LKQKQPSFSA KKMTEKTVKA KSSVPASDDA   120
Y                                                                  121

SEQ ID NO: 769        moltype =  AA   length =  202
FEATURE               Location/Qualifiers
source                1..202
                      mol_type =  protein
                      organism =  Homo sapiens
SEQUENCE: 769
MATLIYVDKE NGEPGTRVVA KDGLKLGSGP SIKALDGRSQ VSTPRFGKTF DAPPALPKAT    60
RKALGTVNRA TEKSVKTKGP LKQKQPSFSA KKMTEKTVKA KSSVPASDDA YPEIEKFFPF   120
NPLDFESFDL PEEHQIAHLP LSGVPLMILD EERELEKLFQ LGPPSPVKMP SPPWESNLLQ   180
SPSSILSTLD VELPPVCCDI DI                                           202

SEQ ID NO: 770        moltype =  AA   length =  202
FEATURE               Location/Qualifiers
source                1..202
                      mol_type =  protein
                      organism =  Homo sapiens
SEQUENCE: 770
MATLIYVDKE NGEPGTRVVA KDGLKLGSGP SIKALDGRSQ VSTPRFGKTF DAPPALPKAT    60
RKALGTVNRA TEKSVKTKGP LKQKQPSFSA KKMTEKTVKA KSSVPASDDA YPEIEKFFPF   120
NPLDFESFDL PEEHQIAHLP LSGVPLMILD EERELEKLFQ LGPPSPVKMP SPPWESNLLQ   180
SPSSILSTLD VELPPVCCDI DI                                           202

SEQ ID NO: 771        moltype =  AA   length =  2406
FEATURE               Location/Qualifiers
source                1..2406
                      mol_type =  protein
                      organism =  Homo sapiens
SEQUENCE: 771
MDPEQSVKGT KKAEGSPRKR LTKGEAIQTS VSSSVPYPGS GTAATQESPA QELLAPQPFP    60
GPSSVLREGS QEKTGQQQKP PKRPPIEASV HISQLPQHPL TPAFMSPGKP EHLLEGSTWQ   120
LVDPMRPGPS GSFVAPGLHP QSQLLPSHAS IIPPEDLPGV PKVFVPRPSQ VSLKPTEEAH   180
KKERKPQKPG KYICQYCSRP CAKPSVLQKH IRSHTGERPY PCGPCGFSFK TKSNLYKHRK   240
SHAHRIKAGL ASGMGGEMYP HGLEMERIPG EEFEEPTEGE STDSEEETSA TSGHPAELSP   300
RPKQPLLSSG LYSSGSHSSS HERCSLSQSS TAQSLEDPPP FVEPSSEHPL SHKPEDTHTI   360
KQKLALRLSE RKKVIDEQAF LSPGSKGSTE SGYFSRSESA EQQVSPPNTN AKSYAEIIFG   420
KCGRIGQRTA MLTATSTQPL LPLSTEDKPS LVPLSVPRTQ VIEHITKLIT INEAVVDTSE   480
IDSVKPRRSS LSRRSSMESP KSSLYREPLS SHSEKTKPEQ SLLSLQHPPS TAPPVPLLRS   540
HSMPSAACTI STPHHPFRGS YSFDDHITDS EALSHSSHVF TSHPRMLKRQ PAIELPLGGE   600
YSSEEPGPSS KDTASKPSDE VEPKESELTK KTKKGLKTKG VIYECNICGA RYKKRDNYEA   660
HKKYYCSELQ IAKPISAGTH TSPEAEKSQI EHEPWSQMMH YKLGTTLELT PLRKRRKEKS   720
LGDEEEPPAF ESTKSQFGSP GPSDAARNLP LESTKSPAEP SKSVPSLEGP TGFQPRTPKP   780
GSGSESGKER RTTSKEISVI QHTSSFEKDS SLEQPSGLEG EDKPLAQFPS PPPAPHGRSA   840
HSLQPKLVRQ PNIQVPEILV TEEPDRPDTE PEPPPKEPEK TEEFQWPQRS QTLAQLPAEK   900
LPPKKKRLRL AEMAQSSGES SFESSVPLSR SPSQESNVSL SGGSSRSASFE RDDHGKAEAP   960
SPSSDMRPKP LGTHMLTVPS HHPHAREMRR SASEQSPNVS HSAHMTETRS KSFDYGSLSL  1020
TGPSAPAPVA PPARVAPPER RKCFLVRQAS LSRPPESELE VAPKGRQESE EPQPSSSKPS  1080
AKSSLSQISS AATSHGGPPG GKGPGQDRPP LGPTVPYTEA LQVFHHPVAQ TPLHEKPYLP  1140
PPVSLFSFQH LVQHEPGQSP EFFSTQAMSS LLSSPYSMPP LPPSLFQAPP LPLQPTVLHP  1200
GQLHLPQLMP HPANIPFRQP PSFLPMPYPT SSALSSGFFL PLQSQFALQL PGDVESHLPQ  1260
IKTSLAPLAT GSAGLSPSTE YSSDIRLPPV APPASSSAPT SAPPLALPAC PDTMVSLVVP  1320
VRVQTNMPSY GSAMYTTLSQ ILVTQSQGSS ATVALPKFEE PPSKGTTVCG ADVHEVGPGP  1380
SGLSEGSRA FPTPYLRVPV TLPERKGTSL SSESILSLEG SSSTAGGSKR VLSPAGSLEL  1440
TMETQQQKRV KEEEASKADE KLELVKPCSV VLTSTEDGKR PEKSHLGNQG QGRRELEMLS  1500
SLSSDPSDTK EIPPLPHPAL SHGTAPGSEA LKEYPQPSGK PHRRGLTPLS VKKEDSKEQP  1560
DLPSLAPPSS LPLSETSSRP AKSQEGTDSK KVLQFPSLHT TTNVSWCYLN YIKPNHIQHA  1620
DRRSSVYAGW CISLYNPNLP GVSTKAALSL LRSKQKVSKE TYTMATAPHP EAGRLVPSSS  1680
RKPRMTEVHL PSLVSPEGQK DLARVEKEEE RRGEPEEDAP ASQRGEPARI KIFEGGYKSN  1740
EEYVYVRGRG RGKYVCEECG IRCKKPSMLK KHIRTHTDVR PYVCKHCHFA FKTKGNLTKH  1800
MKSKAHSKKC QETGVLEELE AEEGTSDDLF QDSEGREGSE AVEEHQFSDL EDSDSDSDLD  1860
EDEDEDEEES QDELSRPSSE APPPGPPHAL RADSSPILGP QPPDAPASGT EATRGSSVSE  1920
AERLTASSCS MSSQSMPGLP WLGPAPLGSV EKDTGSALSY KPVSPRRPWS PSKEAGSRPP  1980
LARKHSLTKN DSSPQRCSPA REPQASAPSP PGLHVDPGRG MGALPCGSPR LQLSPLTLCP  2040
LGRELAPRAH VLSKLEGTTD PGLPRYSPTR RWSPGQAESP PRSAPPGKWA LAGPGSPSAG  2100
EHGPGLGLDP RVLFPPAPLP HKLLSRSPET CASPWQKAES RSPSCSPGPA HPLSSRPFSA  2160
LHDFHGHILA RTEENIFSHL PLHSQHLTRA PCPLIPIGGI QMVQARPGAH PTLLPGPTAA  2220
WVSGFSGGGS DLTGAREAQE RGRWSPTESS SASVSPAKV SKFTLSSELE GGDYPKERER  2280
TGGGPGRPPD WTPHGTGAPA EPTPTHSPCT PPDTLPRPPQ GRRAAQSWSP RLESPRAPTN  2340
PEPSATPPLD RSSSVGCLAE ASARFPARTR NLSGEPRTRQ DSPKPSGSGE PRAHPHQPED  2400
RVPPNA                                                            2406

SEQ ID NO: 772        moltype =  AA   length =  2405
FEATURE               Location/Qualifiers
```

| source | 1..2405 |
| --- | --- |
| | mol_type = protein |
| | organism = Homo sapiens |

SEQUENCE: 772

| MDPEQSVKGT | KKAEGSPRKR | LTKGEAIQTS | VSSSVPYPGS | GTAATQESPA | QELLAPQPFP | 60 |
| --- | --- | --- | --- | --- | --- | --- |
| GPSSVLREGS | QEKTGQQQKP | PKRPPIEASV | HISQLPQHPL | TPAFMSPGKP | EHLLEGSTWQ | 120 |
| LVDPMRPGPS | GSFVAPGLHP | QSQLLPSHAS | IIPPEDLPGV | PKVFVPRPSQ | VSLKPTEEAH | 180 |
| KKERKPQKPG | KYICQYCSRP | CAKPSVLQKH | IRSHTGERPY | PCGPCGFSFK | TKSNLYKHRK | 240 |
| SHAHRIKAGL | ASGMGGEMYP | HGLEMERIPG | EEFEEPTEGE | STDSEEETSA | TSGHPAELSP | 300 |
| RPKQPLLSSG | LYSSGSHSSS | HERCSLSQSS | TAQSLEDPPP | FVEPSSEHPL | SHKPEDTHTI | 360 |
| KQKLALRLSE | RKKVIDEQAF | LSPGSKGSTE | SGYFSRSESA | EQQVSPPNTN | AKSYAEIIFG | 420 |
| KCGRIGQRTA | MLTATSTQPL | LPLSTEDKPS | LVPLSVPRTQ | VIEHITKLIT | INEAVVDTSE | 480 |
| IDSVKPRRSS | LSRRSSMESP | KSSLYREPLS | SHSEKTKPEQ | SLLSLQHPPS | TAPPVPLLRS | 540 |
| HSMPSAACTI | STPHHPFRGS | YSFDDHITDS | EALSHSSHVF | TSHPRMLKRQ | PAIELPLGGE | 600 |
| YSSEEPGPSS | KDTASKPSDE | VEPKESELTK | KTKKGLKTKG | VIYECNICGA | RYKKRDNYEA | 660 |
| HKKYYCSELQ | IAKPISAGTH | TSPEAEKSQI | EHEPWSQMMH | YKLGTTLELT | PLRKRRKEKS | 720 |
| LGDEEEPPAF | ESTKSQFGSP | GPSDAARNLP | LESTKSPAEP | SKSVPSLEGP | TGFQPRTPKP | 780 |
| GSGSESGKER | RTTSKEISVI | QHTSSFEKSD | SLEQPSGLEG | EDKPLAQFPS | PPPAPHGRSA | 840 |
| HSLQPKLVRQ | PNIQVPEILV | TEEPDRPDTE | PEPPPKEPEK | TEEFQWPQRS | QTLAQLPAEK | 900 |
| LPPKKKRLRL | AEMAQSSGES | SFESSVPLSR | SPSQESNVSL | SGGSRSASFE | RDDHGKAEAP | 960 |
| SPSSDMRPKP | LGTHMLTVPS | HHPHAREMRR | SASEQSPNVS | HSAHMTETRS | KSFDYGSLSL | 1020 |
| TGPSAPAPVA | PPARVAPPER | RKCFLVRQAS | LSRPPESELE | VAPKGRQESE | EPQPSSSKPS | 1080 |
| AKSSLSQISS | AATSHGGPPG | GKGPGQDRPP | LGPTVPYTEA | LQVFHHPVAQ | TPLHEKPYLP | 1140 |
| PPVSLFSFQH | LVQHEPGQSP | EFFSTQAMSS | LLSSPYSMPP | LPPSLFQAPP | LPLQPTVLHP | 1200 |
| GQLHLPQLMP | HPANIPFRQP | PSFLPMPYPT | SSALSSGFFL | PLQSQFALQL | PGDVESHLPQ | 1260 |
| IKTSLAPLAT | GSAGLSPSTE | YSSDIRLPPV | APPASSSAPT | SAPPLALPAC | PDTMVSLVVP | 1320 |
| VRVQTNMPSY | GSAMYTTLSQ | ILVTQSQGSS | ATVALPKFEE | PPSKGTTVCG | ADVHEVGPGP | 1380 |
| SGLSEEQSRA | FPTPYLRVPV | TLPERKGTSL | SSESILSLEG | SSSTAGGSKR | VLSPAGSLEL | 1440 |
| TMETQQQKRV | KEEEASKADE | KLELVKPCSV | VLTSTEDGKR | PEKSHLGNQG | QGRRELEMLS | 1500 |
| SLSSDPSDTK | EIPPLPHPAL | SHGTAPGSEA | LKEYPQPSGK | PHRRGLTPLS | VKKEDSKEQP | 1560 |
| DLPSLAPPSS | LPLSETSSRP | AKSQEGTDSK | KVLQFPSLHT | TTNVSWCYLN | YIKPNHIQHA | 1620 |
| DRRSSVYAGW | CISLYNPNLP | GVSTKAALSL | LRSKQKVSKE | TYTMATAPHP | EAGRLVPSSS | 1680 |
| RKPRMTEVHL | PSLVSPEGQK | DLARVEKEEE | RRGEPEEDAP | ASQRGEPARI | KIFEGGYKSN | 1740 |
| EEYVYVRGRG | RGKYVCEECG | IRCKKPSMLK | KHIRTHTDYR | PYVCKHCHFA | FKTKGNLTKH | 1800 |
| MKSKAHSKKC | QETGVLEELE | AEEGTSDDLF | QDSEGREGSE | AVEEHQFSDL | EDSDSDSDLD | 1860 |
| EDEDEDEEES | QDELSRPSSE | APPPGPPHAL | RADSSPILGP | QPPDAPSGT | EATRGSSVSE | 1920 |
| AERLTASSCS | MSSQSMPGLP | WLGPAPLGSV | EKDTGSALSY | KPVSPRRPWS | PSKEAGSRPP | 1980 |
| LARKHSLTKN | DSSPQRCSPA | REPQASAPSP | PGLHVDPGPR | MGALPCGSPR | LQLSPLTLCP | 2040 |
| LGRELAPRAH | VLSKLEGTTD | PGLPRYSPTR | RWSPGQAESP | PRSAPPGKWA | LAGPGSPSAG | 2100 |
| EHGPGLGLDP | RVLFPPAPLP | HKLLSRSPET | CASPWKAESR | SPSCSPGPAH | PLSSRPFSAL | 2160 |
| HDFHGHILAR | TEENIFSHLP | LHSQHLTRAP | CPLIPIGGIQ | MVQARPGAHP | TLLPGPTAAW | 2220 |
| VSGFSGGGSD | LTGAREAQER | GRWSPTESSS | ASVSPVAKVS | KFTLSSELEG | GDYPKERERT | 2280 |
| GGGPGRPPDW | TPHGTGAPAE | PTPTHSPCTP | PDTLPRPPQG | RRAAQSWSPR | LESPRAPTNP | 2340 |
| EPSATPPLDR | SSSVGCLAEA | SARFPARTRN | LSGEPRTRQD | SPKPSGSGEP | RAHPHQPEDR | 2400 |
| VPPNA | | | | | | 2405 |

| SEQ ID NO: 773 | moltype = AA length = 801 |
| --- | --- |
| FEATURE | Location/Qualifiers |
| source | 1..801 |
| | mol_type = protein |
| | organism = Homo sapiens |

SEQUENCE: 773

| MKTSPRRPLI | LKRRRLPLPV | QNAPSETSEE | EPKRSPAQQE | SNQAEASKEV | AESNSCKFPA | 60 |
| --- | --- | --- | --- | --- | --- | --- |
| GIKIINHPTM | PNTQVVAIPN | NANIHSIITA | LTAKGKESGS | SGPNKFILIS | CGGAPTQPPG | 120 |
| LRPQTQTSYD | AKRTEVTLET | LGPKPAARDV | NLPRPPGALC | EQKRETCADG | EAAGCTINNS | 180 |
| LSNIQWLRKM | SSDGLGSRSI | KQEMEEKENC | HLEQRQVKVE | EPSRPSASWQ | NSVSERPPYS | 240 |
| YMAMIQFAIN | STERKRMTLK | DIYTWIEDHF | PYFKHIAKPG | WKNSIRHNLS | LHDMFVRETS | 300 |
| ANGKVSFWTI | HPSANRYLTL | DQVFKPLDPG | SPQLPEHLES | QQKRPNPELR | RNMTIKTELP | 360 |
| LGARRKMKPL | LPRVSSYLVP | IQFPVNQSLV | LQPSVKVPLA | LAASLMSSEL | ARHSKRVRIA | 420 |
| PKVFGEQVVF | GYMSKFFSGD | LRDFGTPITS | LFNFIFLCLS | VLLAEEGIAP | LSSAGPGKEE | 480 |
| KLLFGEGFSP | LLPVQTIKEE | EIQPGEEMPH | LARPIKVESP | PLEEWPSPAP | SFKEESSHSW | 540 |
| EDSSQSPTPR | PKKSYSGLRS | PTRCVSEMLV | IQHRERRERS | RSRRKQHLLP | PCVDEPELLF | 600 |
| SEGPSTSRWA | AELPFPADSS | DPASQLSYSQ | EVGGPFKTPI | KETLPISSTP | SKSVLPRTPE | 660 |
| SWRLTPPAKV | GGLDFSPVQT | SQGASDPLPD | PLGLMDLSTT | PLQSAPPLES | PQRLLSSEPL | 720 |
| DLISVPFGNS | SPSDIDVPKP | GSPEPQVSGL | AANRSLTEGL | VLDTMNDSLS | KILLDISFPG | 780 |
| LDEDPLGPDN | INWSQFIPEL | Q | | | | 801 |

| SEQ ID NO: 774 | moltype = AA length = 748 |
| --- | --- |
| FEATURE | Location/Qualifiers |
| source | 1..748 |
| | mol_type = protein |
| | organism = Homo sapiens |

SEQUENCE: 774

| MKTSPRRPLI | LKRRRLPLPV | QNAPSETSEE | EPKRSPAQQE | SNQAEASKEV | AESNSCKFPA | 60 |
| --- | --- | --- | --- | --- | --- | --- |
| GIKIINHPTM | PNTQVVAIPN | NANIHSIITA | LTAKGKESGS | SGPNKFILIS | CGGAPTQPPG | 120 |
| LRPQTQTSYD | AKRTEVTLET | LGPKPAARDV | NLPRPPGALC | EQKRETCADG | EAAGCTINNS | 180 |
| LSNIQWLRKM | SSDGLGSRSI | KQEMEEKENC | HLEQRQVKVE | EPSRPSASWQ | NSVSERPPYS | 240 |
| YMAMIQFAIN | STERKRMTLK | DIYTWIEDHF | PYFKHIAKPG | WKNSIRHNLS | LHDMFVRETS | 300 |
| ANGKVSFWTI | HPSANRYLTL | DQVFKQQKRP | NPELRRNMTI | KTELPLGARR | KMKPLLPRVS | 360 |

```
SYLVPIQFPV NQSLVLQPSV KVPLPLAASL MSSELARHSK RVRIAPKVLL AEEGIAPLSS     420
AGPGKEEKLL FGEGFSPLLP VQTIKEEEIQ PGEEMPHLAR PIKVESPPLE EWPSPAPSFK     480
EESSHSWEDS SQSPTPRPKK SYSGLRSPTR CVSEMLVIQH RERRERSRSR RKQHLLPPCV     540
DEPELLFSEG PSTSRWAAEL PFPADSSDPA SQLSYSQEVG GPFKTPIKET LPISSTPSKS     600
VLPRTPESWR LTPPAKVGGL DFSPVQTSQG ASDPLPDPLG LMDLSTTPLQ SAPPLESPQR     660
LLSSEPLDLI SVPFGNSSPS DIDVPKPGSP EPQVSGLAAN RSLTEGLVLD TMNDSLSKIL     720
LDISFPGLDE DPLGPDNINW SQFIPELQ                                       748

SEQ ID NO: 775              moltype = AA   length = 763
FEATURE                     Location/Qualifiers
source                      1..763
                            mol_type = protein
                            organism = Homo sapiens
SEQUENCE: 775
MKTSPRRPLI LKRRRLPLPV QNAPSETSEE EPKRSPAQQE SNQAEASKEV AESNSCKFPA      60
GIKIINHPTM PNTQVVAIPN NANIHSIITA LTAKGKESGS SGPNKFILIS CGGAPTQPPG     120
LRPQTQTSYD AKRTEVTLET LGPKPAARDV NLPRPPGALC EQKRETCADG EAAGCTINNS     180
LSNIQWLRKM SSDGLGSRSI KQEMEEKENC HLEQRQVKVE EPSRPSASWQ NSVSERPPYS     240
YMAMIQFAIN STERKRMTLK DIYTWIEDHF PYFKHIAKPG WKNSIRHNLS LHDMFVRETS     300
ANGKVSFWTI HPSANRYLTL DQVFKPLDPG SPQLPEHLES QQKRPNPELR RNMTIKTELP     360
LGARRKMKPL LPRVSSYLVP IQFPVNQSLV LQPSVKVPLP LAASLMSSEL ARHSKRVRIA     420
PKVLLAEEGI APLSSAGPGK EEKLLFGEGF SPLLPVQTIK EEEIQPGEEM PHLARPIKVE     480
SPPLEEWPSP APSFKEESSH SWEDSSQSPT PRPKKSYSGL RSPTRCVSEM LVIQHRERRE     540
RSRSRRKQHL LPPCVDEPEL LFSEGPSTSR WAAELPFPAD SSDPASQLSY SQEVGGPFKT     600
PIKETLPISS TPSKSVLPRT PESWRLTPPA KVGGLDFSPV QTSQGASDPL PDPLGLMDLS     660
TTPLQSAPPL ESPQRLLSSE PLDLISVPFG NSSPSDIDVP KPGSPEPQVS GLAANRSLTE     720
GLVLDTMNDS LSKILLDISF PGLDEDPLGP DNINWSQFIP ELQ                       763

SEQ ID NO: 776              moltype = AA   length = 206
FEATURE                     Location/Qualifiers
source                      1..206
                            mol_type = protein
                            organism = Homo sapiens
SEQUENCE: 776
XAKPGWKNSI RHNLSLHDMF VRETSANGKV SFWTIHPSAN RYLTLDQVFK PLDPGSPQLP      60
EHLESQQKR PNPELRRNMT IKTELPLGAR RKMKPLLPRV SSYLVPIQFP VNQSLVLQPS      120
VKVPLPLAAS LMSSELARHS KRVRIAPKVL LAEEGIAPLS SAGPGKEEKL LFGEGFSPLL     180
PVQTIKEEEI QPGEEMPHLA RPIKVE                                         206

SEQ ID NO: 777              moltype = AA   length = 80
FEATURE                     Location/Qualifiers
source                      1..80
                            mol_type = protein
                            organism = Homo sapiens
SEQUENCE: 777
TALTAKGKES GSSGPNKFIL ISCGGAPTQP PGLRPQTQTS YDAKRTEVTL ETLGPKPAAR      60
DVNLPRPPGA LCEQKRETCG                                                 80

SEQ ID NO: 778              moltype = AA   length = 748
FEATURE                     Location/Qualifiers
source                      1..748
                            mol_type = protein
                            organism = Homo sapiens
SEQUENCE: 778
MKTSPRRPLI LKRRRLPLPV QNAPSETSEE EPKRSPAQQE SNQAEASKEV AESNSCKFPA      60
GIKIINHPTM PNTQVVAIPN NANIHSIITA LTAKGKESGS SGPNKFILIS CGGAPTQPPG     120
LRPQTQTSYD AKRTEVTLET LGPKPAARDV NLPRPPGALC EQKRETCDGE AAGCTINNSL     180
SNIQWLRKMS SDGLGSRSIK QEMEEKENCH LEQRQVKVEE PSRPSASWQN SVSERPPYSY     240
MAMIQFAINS TERKRMTLKD IYTWIEDHFP YFKHIAKPGW KNSIRHNLSL HDMFVRETSA     300
NGKVSFWTIH PSANRYLTLD QVFKQQQKRP NPELRRNMTI KTELPLGARR KMKPLLPRVS     360
SYLVPIQFPV NQSLVLQPSV KVPLPLAASL MSSELARHSK RVRIAPKVLL AEEGIAPLSS     420
AGPGKEEKLL FGEGFSPLLP VQTIKEEEIQ PGEEMPHLAR PIKVESPPLE EWPSPAPSFK     480
EESSHSWEDS SQSPTPRPKK SYSGLRSPTR CVSEMLVIQH RERRERSRSR RKQHLLPPCV     540
DEPELLFSEG PSTSRWAAEL PFPADSSDPA SQLSYSQEVG GPFKTPIKET LPISSTPSKS     600
VLPRTPESWR LTPPAKVGGL DFSPVQTSQG ASDPLPDPLG LMDLSTTPLQ SAPPLESPQR     660
LLSSEPLDLI SVPFGNSSPS DIDVPKPGSP EPQVSGLAAN RSLTEGLVLD TMNDSLSKIL     720
LDISFPGLDE DPLGPDNINW SQFIPELQ                                       748

SEQ ID NO: 779              moltype = AA   length = 432
FEATURE                     Location/Qualifiers
source                      1..432
                            mol_type = protein
                            organism = Homo sapiens
SEQUENCE: 779
MSELKDCPLQ FHDFKSVDHL KVCPRYTAVL ARSEDDGIGI EELDTLQLEL ETLLSSASRR      60
LRVLEAETQI LTDWQDKKGD RRFLKLGRDH ELGAPPKHGK PKKQKLEGKA GHGPGPGPGR     120
PKSKNLQPKI QEYEFTDDPI DVPRIPKNDA PNRFWASVEP YCADITSEEV RTLEELLKPP     180
EDEAEHYKIP PLGKHYSQRW AQEDLLEEQK DGARAAAVAD KKKGLMGPLT ELDTKDVDAL     240
LKKSEAQHEQ PEDGCPFGAL TQRLLQALVE ENIISPMEDS PIPDMSGKES GADGASTSPR     300
```

```
NQNKPFSVPH TKSLESRIKE ELIAQGLLES EDRPAEDSED EVLAELRKRQ AELKALSAHN  360
RTKKHDLLRL AKEEVSRQEL RQRVRMADNE VMDAFRKIMA ARQKKRTPTK KEKDQAWKTL  420
KERESILKLL DG                                                    432

SEQ ID NO: 780          moltype = AA  length = 432
FEATURE                 Location/Qualifiers
source                  1..432
                        mol_type = protein
                        organism = Homo sapiens
SEQUENCE: 780
MSELKDCPLQ FHDFKSVDHL KVCPRYTAVL ARSEDDGIGI EELDTLQLEL ETLLSSASRR  60
LRVLEAETQI LTDWQDKKGD RRFLKLGRDH ELGAPPKHGK PKKQKLEGKA GHGPGPGPGR  120
PKSKNLQPKI QEYEFTDDPI DVPRIPKNDA PNRFWASVEP YCADITSEEV RTLEELLKPP  180
EDEAEHYKIP PLGKHYSQRW AQEDLLEEQK DGARAAAVAD KKKGLMGPLT ELDTKDVDAL  240
LKKSEAQHEQ PEDGCPFGAL TQRLLQALVE ENIISPMEDS PIPDMSGKES GADGASTSPR  300
NQNKPFSVPH TKSLESRIKE ELIAQGLLES EDRPAEDSED EVLAELRKRQ AELKALSAHN  360
RTKKHDLLRL AKEEVSRQEL RQRVRMADNE VMDAFRKIMA ARQKKRTPTK KEKDQAWKTL  420
KERESILKLL DG                                                    432

SEQ ID NO: 781          moltype = AA  length = 369
FEATURE                 Location/Qualifiers
source                  1..369
                        mol_type = protein
                        organism = Homo sapiens
SEQUENCE: 781
MSELKDCPLQ FHDFKSVDHL KVCPRYTAVL ARSEDDGIGI EELDTLQLEL ETLLSSASRR  60
LRVLEAETQI LTDWQDKKGD RRFLKLGRDH ELGAPPKHGK PKKQKLEGKA GHGPGPGPGR  120
PKSKNLQPKI QEYEFTDDPI DVPRIPKNDA PNRFWASVEP YCADITSEEV RTLEELLKPP  180
EDEAEHYKIP PLGKHYSQRW AQEDLLEEQK DGARAAAVAD KKKGLMGPLT ELDTKDVDAL  240
LKKSEAQHEQ PEDGCPFGAL TQRLLQALVE ENIISPMEDS PIPDMSGKES GADGASTSPR  300
NQNKPFSVPH TKSLESRIKE ELIAQGLLES EDRPAEDSED EVLAELRKRQ AELKALSAHN  360
RTKKHDLLR                                                        369

SEQ ID NO: 782          moltype = AA  length = 95
FEATURE                 Location/Qualifiers
source                  1..95
                        mol_type = protein
                        organism = Homo sapiens
SEQUENCE: 782
MSELKDCPLQ FHDFKSVDHL KVCPRYTAVL ARSEDDGIGI EELDTLQLEL ETLLSSASRR  60
LRVLEAETQI LTDWQDKKGD RRFLKLGRDH ELGAP                            95

SEQ ID NO: 783          moltype = AA  length = 99
FEATURE                 Location/Qualifiers
source                  1..99
                        mol_type = protein
                        organism = Homo sapiens
SEQUENCE: 783
MPSDFISLLS ADLDLESPKS LYSRDSLKLH PSQNFHRAGL LEESVYDLLP KELQLPPSRE  60
TSVASMSQTS GGEAGSPPPA VVAAGFASEA GSVCIKNDL                        99

SEQ ID NO: 784          moltype = AA  length = 1531
FEATURE                 Location/Qualifiers
source                  1..1531
                        mol_type = protein
                        organism = Homo sapiens
SEQUENCE: 784
MPSDFISLLS ADLDLESPKS LYSRESVYDL LPKELQLPPS RETSVASMSQ TSGGEAGSPP  60
PAVVAADASS APSSSMGGA CSSFTTSSSP TIYSTSVTDS KAMQVESCSS AVGVSNRGVS  120
EKQLTSNTVQ QHPSTPKRHT VLYISPPPED LLDNSRMSCQ DEGCGLESEQ SCSMWMEDSP  180
SNFSNMSTSS YNDNTEVPRK SRKRNPKQRP GVKRRDCEES NMDIFDADSA KAPHYVLSQL  240
TTDNKGNSKA GNGTLENQKG TGVKKSPMLC GQYPVKSEGK ELKIVVQPET QHRARYLTEG  300
SRGSVKDRTQ QGFPTVKLEG HNEPVVLQVF VGNDSGRVKV HGFYQACRVT GRNTTPCKEV  360
DIEGTTVIEV GLDPSNNMTL AVDCVGILKK RNADVEARIG IAGSKKKSTR ARLVPRVNIM  420
RKDGSTLTLQ TPSSPILCTQ PAGVPEILKK SLHSCSVKGE EEVFLIGKNF LKGTKVIFQE  480
NVSDENSWKS EAEIDMELFH QNHLIVKVPP YHDQHITLPV SVGIYVVTNA GRSHDVQPFT  540
YTPDPAAAGA LNVNVKKEIS SPARPCSFEE AMKAMKTTGC NLDKVNIIPN ALMTPLIPSS  600
MIKSEDVTPM EVTAEKRSST IFKTTKSVGS TQQTLENISN IAGNGSFSSP SSSHLPSENE  660
KQQQIQPKAY NPETLTTIQT QDISQPGTFP AVSASSQLPN SDALLQQATQ FQTRETQSRE  720
ILQSDGTVVN LSQLTEASQQ QQQSPLQEQA QTLQQQISSN IFPSPNSVSQ LQNTIQQLQA  780
GSFTGSTASG SSGSVDLVQQ VLEAQQQLSS VLFSAPDGNE NVQEQLSADI FQQVSQIQSG  840
VSPGMFSSTE PTVHTRPDNL LPGRAESVHP QSENTLSNQQ QQQQQQQQVM ESSAAMVMEM  900
QQSICQAAAQ IQSELFPSTA SANGNLQQSP VYQQTSHMMS ALSTNEDMQM QCELFSSPPA  960
VSGNETSTTT TQQQVATPGTT MFQTSSSGDG EETGTQAKQI QNSVFQTMVQ MQHSGDNQPQ  1020
VNLFSSTKSM MSVQNSGTQQ QGNGLFQQGN EMMSLQSGNF LQQSSHSQAQ LFHPQNPIAD  1080
AQNLSQETQG SLFHSPNPIV HSQTSTTSSE QMQPPMFHSQ STIAVLQGSS VPDQQSTNI   1140
FLSQSPMNNL QTNTVAQEAF FAAPNSISPL QSTSNSEQQA AFQQQAPISH IQTPMLSQEQ  1200
AQPPQQGLFQ PQVALGSLPP NPMPQSQQGT MFQSQHSIVA MQSNSPSEQ QQQQQQQQQQ  1260
QQQQQQSILF SNQNTMATMA SPKQPPPNMI FNPNQNPMAN QEQQNQSIFH QQSNMAPMNQ  1320
```

```
EQQPMQFQSQ STVSSLQNPG PTQSESSQTP LFHSSPQIQL VQGSPSSQEQ QVTLFLSPAS  1380
MSALQTSINQ QDMQQSPLYS PQNNMPGIQG ATSSPQPQAT LFHNTAGGTM NQLQNSPGSS  1440
QQTSGMFLFG IQNNCSQLLT SGPATLPDQL MAISQPGQPQ NEGQPPVTTL LSQQMPENSP  1500
LASSINTNQN IEKIDLLVSL QNQGNNLTGS F                                1531

SEQ ID NO: 785          moltype = AA   length = 119
FEATURE                 Location/Qualifiers
source                  1..119
                        mol_type = protein
                        organism = Homo sapiens
SEQUENCE: 785
MPSDFISLLS ADLDLESPKS LYSRDSLKLH PSQNFHRAGL LEESVYDLLP KELQLPPSRE  60
TSVASMSQTS GGEAGSPPPA VVAAGIPEMF ILCILMCMIL RFKKGFASEA GSVCIKNDL   119

SEQ ID NO: 786          moltype = AA   length = 1548
FEATURE                 Location/Qualifiers
source                  1..1548
                        mol_type = protein
                        organism = Homo sapiens
SEQUENCE: 786
MPSDFISLLS ADLDLESPKS LYSRDSLKLH PSQNFHRAGL LEESVYDLLP KELQLPPSRE  60
TSVASMSQTS GGEAGSPPPA VVAADASSAP SSSSMGGACS SFTTSSSPTI YSTSVTDSKA  120
MQVESCSSAV GVSNRGVSEK QLTSNTVQQH PSTPKRHTVL YISPPPEDLL DNSRMSCQDE  180
GCGLESEQSC SMWMEDSPSN FSNMSTSSYN DNTEVPRKSR KRNPKQRPGV KRRDCEESNM  240
DIFDADSAKA PHYVLSQLTT DNKGNSKAGN GTLENQKGTG VKKSPMLCGQ YPVKSEGKEL  300
KIVVQPETQH RARYLTEGSR GSVKDRTQQG FPTVKLEGHN EPVVLQVFVG NDSGRVKPHG  360
FYQACRVTGR NTTPCKEVDI EGTTVIEVGL DPSNNMTLAV DCVGILKLRN ADVEARIGIA  420
GSKKKSTRAR LVFRVNIMRK DGSTLTLQTP SSPILCTQPA GVPEILKKSL HSCSVKGEEE  480
VFLIGKNFLK GTKVIFQENV SDENSWKSEA EIDMELFHQN HLIVKVPPYH DQHITLPVSV  540
GIYVVTNAGR SHDVQPFTYT PDPAAGALNV NVKKEISSPA RPCSFEEAMK AMKTTGCNLD  600
KVNIIPNALM TPLIPSSMIK SEDVTPMEVT AEKRSSTIFK TTKSVGSTQQ TLENISNIAG  660
NGSFSSPSSS HLPSENEKQQ QIQPKAYNPE TLTTIQTQDI SQPGTFPAVS ASSQLPNSDA  720
LLQQATQFQT RETQSREILQ SDGTVVNLSQ LTEASQQQQQ SPLQEAQTL QQQISSNIFP   780
SPNSVSQLQN TIQQLQAGSF TGSTASGSSG SVDLVQQVLE AQQQLSSVLF SAPDGNENVQ  840
EQLSADIFQQ VSQIQSGVSP GMFSSTEPTV HTRPDNLLPG RAESVHPQSE NTLSNQQQQQ  900
QQQQQVMESS AAMVMEMQQS ICQAAAQIQS ELFPSTASAN GNLQQSPVYQ QTSHMMSALS  960
TNEDMQMQCE LFSSPPAVSG NETSTTTTQQ VATPGTTMFQ TSSSGDGEET GTQAKQIQNS  1020
VFQTMVQMQH SGDNQPQVNL FSSTKSMMSV QNSGTQQQGN GLFQQGNEMM SLQSGNFLQQ  1080
SSHSQAQLFH PQNPIADAQN LSQETQGSLF HSPNPIVHSQ TSTTSSEQMQ PPMFHSQSTI  1140
AVLQGSSVPQ DQQSTNIFLS QSPMNNLQTN TVAQEAFFAA PNSISPLQST SNEQQAAFQ   1200
QQAPISHIQT PMLSQEAQP PQQGLFQPQV ALGSLPPNPM PQSQQGTMFQ SQHSIVAMQS   1260
NSPSQEQQQQ QQQQQQQQQQ QQQSILFSNQ NTMATMASPK QPPPNMIFNP NQNPMANQEQ  1320
QNQSIFHQQS NMAPMNQEQQ PMQFQSQSTV SSLQNPGPTQ SESSQTPLFH SSPQIQLVQG  1380
SPSSQEQQVT LFLSPASMSA LQTSINQQDM QQSPLYSPQN NMPGIQGATS SPQPQATLFH  1440
NTAGGTMNQL QNSPGSSQQT SGMFLFGIQN NCSQLLTSGP ATLPDQLMAI SQPGQPQNEG  1500
QPPVTTLLSQ QMPENSPLAS SINTNQNIEK IDLLVSLQNQ GNNLTGSF               1548

SEQ ID NO: 787          moltype = AA   length = 1549
FEATURE                 Location/Qualifiers
source                  1..1549
                        mol_type = protein
                        organism = Homo sapiens
SEQUENCE: 787
MPSDFISLLS ADLDLESPKS LYSRDSLKLH PSQNFHRAGL LEESVYDLLP KELQLPPSRE  60
TSVASMSQTS GGEAGSPPPA VVAADASSAP SSSSMGGACS SFTTSSSPTI YSTSVTDSKA  120
MQVESCSSAV GVSNRGVSEK QLTSNTVQQH PSTPKRHTVL YISPPPEDLL DNSRMSCQDE  180
GCGLESEQSC SMWMEDSPSN FSNMSTSSYN DNTEVPRKSR KRNPKQRPGV KRRDCEESNM  240
DIFDADSAKA PHYVLSQLTT DNKGNSKAGN GTLENQKGTG VKKSPMLCGQ YPVKSEGKEL  300
KIVVQPETQH RARYLTEGSR GSVKDRTQQG FPTVKLEGHN EPVVLQVFVG NDSGRVKPHG  360
FYQACRVTGR NTTPCKEVDI EGTTVIEVGL DPSNNMTLAV DCVGILKLRN ADVEARIGIA  420
GSKKKSTRAR LVFRVNIMRK DGSTLTLQTP SSPILCTQPA GVPEILKKSL HSCSVKGEEE  480
VFLIGKNFLK GTKVIFQENV SDENSWKSEA EIDMELFHQN HLIVKVPPYH DQHITLPVSV  540
GIYVVTNAGR SHDVQPFTYT PDPAAAGALN VNVKKEISSP ARPCSFEEAM KAMKTTGCNL  600
DKVNIIPNAL MTPLIPSSMI KSEDVTPMEV TAEKRSSTIF KTTKSVGSTQ QTLENISNIA  660
GNGSFSSPSS SHLPSENEKQ QQIQPKAYNP ETLTTIQTQD ISQPGTFPAV SASSQLPNSD  720
ALLQQATQFQ TRETQSREIL QSDGTVVNLS QLTEASQQQQ QSPLQEAQTL QQQISSNIF   780
PSPNSVSQLQ NTIQQLQAGS FTGSTASGSS GSVDLVQQVL EAQQQLSSVL FSAPDGNENV  840
QEQLSADIFQ QVSQIQSGVS PGMFSSTEPT VHTRPDNLLP GRAESVHPQS ENTLSNQQQQ  900
QQQQQQVMES SAAMVMEMQQ SICQAAAQIQ SELFPSTASA NGNLQQSPVY QQTSHMMSAL  960
STNEDMQMQC ELFSSPPAVS GNETSTTTTQ QVATPGTTMF QTSSSGDGEE TGTQAKQIQN  1020
SVFQTMVQMQ HSGDNQPQVN LFSSTKSMMS VQNSGTQQQG NGLFQQGNEM MSLQSGNFLQ  1080
QSSHSQAQLF HPQNPIADAQ NLSQETQGSL FHSPNPIVHS QTSTTSSEQM QPPMFHSQST  1140
IAVLQGSSVP QDQQSTNIFL SQSPMNNLQT NTVAQEAFFA APNSISPLQS TSNEQQAAFQ  1200
QQAPISHIQT PMLSQEAQ PPQQGLFQPQ VALGSLPPNP MPQSQQGTMF QSQHSIVAMQ   1260
SNSPSQEQQQ QQQQQQQQQQ QQQSILFSNQ NTMATMASP KQPPPNMIFN PNQNPMANQE   1320
QQNQSIFHQQ SNMAPMNQEQ QPMQFQSQST VSSLQNPGPT QSESSQTPLF HSSPQIQLVQ  1380
GSPSSQEQQV TLFLSPASMS ALQTSINQQD MQQSPLYSPQ NNMPGIQGAT SSPQPQATLF  1440
HNTAGGTMNQ LQNSPGSSQQ TSGMFLFGIQ NNCSQLLTSG PATLPDQLMA ISQPGQPQNE  1500
GQPPVTTLLS QQMPENSPLA SSINTNQNIE KIDLLVSLQN QGNNLTGSF              1549
```

```
SEQ ID NO: 788         moltype = AA   length = 1455
FEATURE                Location/Qualifiers
source                 1..1455
                       mol_type = protein
                       organism = Homo sapiens
SEQUENCE: 788
MGGACSSFTT SSSPTIYSTS VTDSKAMQVE SCSSAVGVSN RGVSEKQLTS NTVQQHPSTP     60
KRHTVLYISP PPEDLLDNSR MSCQDEGCGL ESEQSCSMWM EDSPSNFSNM STSSYNDNTE    120
VPRKSRKRNP KQRPGVKRRD CEESNMDIFD ADSAKAPHYV LSQLTTDNKG NSKAGNGTLE    180
NQKGTGVKKS PMLCGQYPVK SEGKELKIVV QPETQHRARY LTEGSRGSVK DRTQQGFPTV    240
KLEGHNEPVV LQVFVGNDSG RVKPHGFYQA CRVTGRNTTP CKEVDIEGTT VIEVGLDPSN    300
NMTLAVDCVG ILKLRNADVE ARIGIAGSKK KSTRARLVFR VNIMRKDGST LTLQTPSSPI    360
LCTQPAGVPE ILKKSLHSCS VKGEEEVFLI GKNFLKGTKV IFQENVSDEN SWKSEAEIDM    420
ELFHQNHLIV KVPPYHDQHI TLPVSVGIYV VTNAGRSHDV QPFTYTPDPA AAGALNVNVK    480
KEISSPARPC SFEEAMKAMK TTGCNLDKVN IIPNALMTPL IPSSMIKSED VTPMEVTAEK    540
RSSTIFKTTK SVGSTQQTLE NISNIAGNGS FSSPSSSHLP SENEKQQQIQ PKAYNPETLT    600
TIQTQDISQP GTFPAVSASS QLPNSDALLQ QATQFQTRET QSREILQSDG TVVNLSQLTE    660
ASQQQQQSPL QEQAQTLQQQ ISSNIFPSPN SVSQLQNTIQ QLQAGSFTGS TASGSSGSVD    720
LVQQVLEAQQ QLSSVLFSAP DGNENVQEQL SADIFQQVSQ IQSGVSPGMF SSTEPTVHTR    780
PDNLLPGRAE SVHPQSENTL SNQQQQQQQQ QQVMESSAAM VMEMQQSICQ AAAQIQSELF    840
PSTASANGNL QQSPVYQQTS HMMSALSTNE DMQMQCELFS SPPAVSGNET STTTTQQVAT    900
PGTTMFQTSS SGDGEETGTQ AKQIQNSVFQ TMVQMQHSGD NQPQVNLFSS TKSMMSVQNS    960
GTQQQGNGLF QQGNEMMSLQ SGNFLQQSSH SQAQLFHPQN PIADAQNLSQ ETQGSLFHSP   1020
NPIVHSQTST TSSEQMQPPM FHSQSTIAVL QGSSVPQDQQ STNIFLSQSP MNNLQTNTVA   1080
QEAFFAAPNS ISPLQSTSNS EQQAAFQQQA PISHIQTPML SQEAQPPQQ GLFQPQVALG    1140
SLPPNPMPQS QQGTMFQSQH SIVAMQSNSP SQEQQQQQQQ QQQQQQQQQQ SILFSNQNTM   1200
ATMASPKQPP PNMIFNPNQN PMANQEQQNQ SIFHQQSNMA PMNQEQQPMQ FQSQSTVSSL   1260
QNPGPTQSES SQTPLFHSSP QIQLVQGSPS SQEQQVTLFL SPASMSALQT SINQQDMQQS   1320
PLYSPQNNMP GIQGATSSPQ PQATLFHNTA GGTMNQLQNS PGSSQQTSGM FLFGIQNNCS   1380
QLLTSGPATL PDQLMAISQP GQPQNEGQPP VTTLLSQQMP ENSPLASSIN TNQNIEKIDL   1440
LVSLQNQGNN LTGSF                                                   1455

SEQ ID NO: 789         moltype = AA   length = 1455
FEATURE                Location/Qualifiers
source                 1..1455
                       mol_type = protein
                       organism = Homo sapiens
SEQUENCE: 789
MGGACSSFTT SSSPTIYSTS VTDSKAMQVE SCSSAVGVSN RGVSEKQLTS NTVQQHPSTP     60
KRHTVLYISP PPEDLLDNSR MSCQDEGCGL ESEQSCSMWM EDSPSNFSNM STSSYNDNTE    120
VPRKSRKRNP KQRPGVKRRD CEESNMDIFD ADSAKAPHYV LSQLTTDNKG NSKAGNGTLE    180
NQKGTGVKKS PMLCGQYPVK SEGKELKIVV QPETQHRARY LTEGSRGSVK DRTQQGFPTV    240
KLEGHNEPVV LQVFVGNDSG RVKPHGFYQA CRVTGRNTTP CKEVDIEGTT VIEVGLDPSN    300
NMTLAVDCVG ILKLRNADVE ARIGIAGSKK KSTRARLVFR VNIMRKDGST LTLQTPSSPI    360
LCTQPAGVPE ILKKSLHSCS VKGEEEVFLI GKNFLKGTKV IFQENVSDEN SWKSEAEIDM    420
ELFHQNHLIV KVPPYHDQHI TLPVSVGIYV VTNAGRSHDV QPFTYTPDPA AAGALNVNVK    480
KEISSPARPC SFEEAMKAMK TTGCNLDKVN IIPNALMTPL IPSSMIKSED VTPMEVTAEK    540
RSSTIFKTTK SVGSTQQTLE NISNIAGNGS FSSPSSSHLP SENEKQQQIQ PKAYNPETLT    600
TIQTQDISQP GTFPAVSASS QLPNSDALLQ QATQFQTRET QSREILQSDG TVVNLSQLTE    660
ASQQQQQSPL QEQAQTLQQQ ISSNIFPSPN SVSQLQNTIQ QLQAGSFTGS TASGSSGSVD    720
LVQQVLEAQQ QLSSVLFSAP DGNENVQEQL SADIFQQVSQ IQSGVSPGMF SSTEPTVHTR    780
PDNLLPGRAE SVHPQSENTL SNQQQQQQQQ QQVMESSAAM VMEMQQSICQ AAAQIQSELF    840
PSTASANGNL QQSPVYQQTS HMMSALSTNE DMQMQCELFS SPPAVSGNET STTTTQQVAT    900
PGTTMFQTSS SGDGEETGTQ AKQIQNSVFQ TMVQMQHSGD NQPQVNLFSS TKSMMSVQNS    960
GTQQQGNGLF QQGNEMMSLQ SGNFLQQSSH SQAQLFHPQN PIADAQNLSQ ETQGSLFHSP   1020
NPIVHSQTST TSSEQMQPPM FHSQSTIAVL QGSSVPQDQQ STNIFLSQSP MNNLQTNTVA   1080
QEAFFAAPNS ISPLQSTSNS EQQAAFQQQA PISHIQTPML SQEAQPPQQ GLFQPQVALG    1140
SLPPNPMPQS QQGTMFQSQH SIVAMQSNSP SQEQQQQQQQ QQQQQQQQQQ SILFSNQNTM   1200
ATMASPKQPP PNMIFNPNQN PMANQEQQNQ SIFHQQSNMA PMNQEQQPMQ FQSQSTVSSL   1260
QNPGPTQSES SQTPLFHSSP QIQLVQGSPS SQEQQVTLFL SPASMSALQT SINQQDMQQS   1320
PLYSPQNNMP GIQGATSSPQ PQATLFHNTA GGTMNQLQNS PGSSQQTSGM FLFGIQNNCS   1380
QLLTSGPATL PDQLMAISQP GQPQNEGQPP VTTLLSQQMP ENSPLASSIN TNQNIEKIDL   1440
LVSLQNQGNN LTGSF                                                   1455

SEQ ID NO: 790         moltype = AA   length = 141
FEATURE                Location/Qualifiers
source                 1..141
                       mol_type = protein
                       organism = Homo sapiens
SEQUENCE: 790
AMQVESCSSA VGNNMPGIQG ATSSPQPQAT LFHNTAGGTM NQLQNSPGSS QQTSGMFLFG     60
IQNNCSQLLT SGPATLPDQL MAISQPGQPQ NEGPPVTTL LSQQMPENSP LASSINTNQN    120
IEKIDLLVSL QNQGNNLTGS F                                             141

SEQ ID NO: 791         moltype = AA   length = 143
FEATURE                Location/Qualifiers
source                 1..143
                       mol_type = protein
```

```
                    organism = Homo sapiens
SEQUENCE: 791
XTLENQKGTG VKKSPMLCGQ YPVKSEGKEL KIVVQPETQH RARYLTEGSR GSVKDRTQQG    60
FPTVKLEGHN EPVVLQVFVG NDSGRVKPHG FYQACRVTGR NTTPCKEVDI EGTTVIEVGL   120
DPSNNMTLAS ASRSARNLKE KLA                                          143
```

MARKERS SELECTIVELY DEREGULATED IN TUMOR-INFILTRATING REGULATORY T CELLS

RELATED APPLICATIONS

This application is a continuation of U.S. application Ser. No. 16/301,805, filed Nov. 15, 2018, which is a national stage filing under 35 U.S.C. § 371 of International Application Serial No. PCT/EP2017/061642, filed May 15, 2017, the contents of each of which is incorporated herein by reference in its entirety.

REFERENCE TO AN ELECTRONIC SEQUENCE LISTING

The contents of the electronic sequence listing (C158570000US01-SEQ-JRV.xml; Size: 953,138 bytes; and Date of Creation: Apr. 5, 2023) is herein incorporated by reference in its entirety.

FIELD OF THE INVENTION

The present invention relates to a molecule able to modulate the expression and/or function of at least one marker that is selectively deregulated in tumor-infiltrating regulatory T cell or to a molecule capable of specifically binding to at least one marker that is selectively deregulated in tumor-infiltrating regulatory T cell and inducing antibody-dependent cell-mediated cytotoxicity (ADCC) for use in the prevention and/or treatment of cancer or for use in a method for in vivo depleting tumor-infiltrating regulatory T cell in a subject or for use in a method to enhance tumor immunity in a subject and relative pharmaceutical composition.

BACKGROUND OF THE INVENTION

The combination of genetic mutations and epigenetic modifications that are peculiar to all tumors generate antigens that T and B lymphocytes can use to specifically recognize tumor cells (Jamal-Hanjani et al., 2013). It is increasingly clear that T lymphocytes recognizing tumor derived peptides presented by major histocompatibility complex (MHC) molecules play a central role in immunotherapy and in conventional chemo-radiotherapy of cancer (Galluzzi et al., 2015). In fact, anti-tumor T cell responses arise in cancer patients but are disabled upon tumor progression by suppressive mechanisms triggered by the interplay between malignant cells and the tumor microenvironment (Munn and Bronte, 2015). The tumor-dependent immunosuppressive mechanisms depend on the integrated action of infiltrating leukocytes and lymphocytes that upregulate a range of modulatory molecules, collectively called immune checkpoints, whose function is only partially characterized (Pardoll, 2012). Therefore, the search for agonists of co-stimulatory complexes or antagonists of inhibitory molecules to potentiate antigen-specific T cell responses is a primary goal of current anti-tumor research (Sharma and Allison, 2015; Zitvogel et al., 2013). Indeed, clinical trials have unequivocally shown that the blockade of immune checkpoints unleashes the spontaneous anti-tumor immune responses in such a powerful way that it has created a paradigm shift in cancer therapy (Sledzinska et al., 2015; Topalian et al., 2015).

Amongst the immune checkpoints targeted by blocking strategies, CTLA-4 has been one of the first to be translated into therapeutic applications.

Anti-CTLA-4 monoclonal antibodies (mAb) showed remarkable success in metastatic melanoma, and more recently in non-small-cell lung cancer, prostate cancer, renal cell carcinoma, urothelial carcinoma and ovarian cancer (Carthon et al., 2010; Hodi et al., 2010; van den Eertwegh et al., 2012; Yang et al., 2007). However, the fraction of patients that do not respond remains high, prompting a deeper investigation of the mechanisms underpinning the modulation of immune responses by tumors. Recent experimental evidence showed that anti-CTLA-4 mAb efficacy depends on FcγR mediated depletion of CD4$^+$ regulatory T cells (Treg cells) within the tumor microenvironment (Peggs et al., 2009; Selby et al., 2013; Simpson et al., 2013; Twyman-Saint Victor et al., 2015). Treg cells, which are physiologically engaged in the maintenance of immunological self-tolerance and immune homeostasis (Josefowicz et al., 2012; Sakaguchi et al., 2008), are potent suppressors of effector cells and are found at high frequencies in various types of cancers (Fridman et al., 2012; Nishikawa and Sakaguchi, 2010). Interestingly, Treg cells adapt their transcriptional program to the various cytokines to which they are exposed in the inflammatory milieu (Campbell and Koch, 2011). This versatility is controlled by transcription factors generally associated with the differentiation of other effector CD4$^+$ T cell subsets, resulting in various Treg cell populations with unique features and immunomodulatory functions (Duhen et al., 2012; Geginat et al., 2014). Moreover, Treg cells infiltrating non-lymphoid tissues are reported to exhibit unique phenotypes and transcriptional signatures, as they can display functions beyond their well-established suppressive roles, such as metabolic modulation in adipose tissue (Cipolletta et al., 2012) or regulation of tissue repair in skeletal muscle (Burzyn et al., 2013) and in lung tissue (Arpaia et al., 2015).

Treg cells depletion has been reported to increase anti-tumor specific immune responses and to reduce tumor burden (Marabelle et al., 2013; Teng et al., 2010; Walter et al., 2012). Although promising clinical results have been achieved with Treg cell depleting strategies, some relevant issues are to be addressed, for a safer, more effective and wider clinical application of these therapies. First, severe autoimmunity can occur following systemic Treg cells depletion (Nishikawa and Sakaguchi, 2010), which could be avoided if selective depletion of tumor infiltrating Treg cells were feasible. A second issue concerns the specificity of targeting, indeed Treg cells share with effector lymphocytes most of the molecules targeted for therapy, which can possibly deplete also the tumor-specific effector cells. Therefore, the molecular characterization of Treg cells at different tumor sites should help to better define therapeutic targets through a better description of their signature molecules and of the network that regulates Treg cell functions in the tumor microenvironment.

Non-small-cell lung cancer (NSCLC) and colorectal cancer (CRC) are the two most frequent cancers in both genders (Torre et al., 2015). NSCLC has the worst prognosis due to its high mortality rate even in early stages. Although CRC survival rate is highly dependent on the tumor stage at diagnosis, about 50% of patients will progress to metastatic cancer (Gonzalez-Pons and Cruz-Correa, 2015). Both tumors have been targeted with therapies based on monoclonal antibodies to checkpoint inhibitors, but the outcomes were different. While remarkable clinical success has been obtained in NSCLC, evidence of durable response in CRC is scarce with the exception of mismatch repair-deficient CRC lesions (Jacobs et al., 2015; Kroemer et al., 2015; Le et al., 2015). Then there is still need for agents that target tumor infiltrating Treg cells for the treatment and/or prevention of cancer.

SUMMARY OF THE INVENTION

Tumor-infiltrating regulatory T lymphocytes (Treg) can suppress effector T cells specific for tumor antigens. Since new anti-cancer immunotherapies aim at unleashing effector T cells by targeting immune-checkpoints, deeper molecular definitions of tumor-infiltrating-lymphocytes could offer new therapeutic opportunities. Transcriptomes of T helper 1(Th1), Th17 and Treg cells infiltrating colorectal or non-small-cell lung cancers were compared to transcriptomes of the same subsets from normal tissues, and validated at the single cell level. The inventors found tumor-infiltrating Treg cells are highly suppressive, upregulate several immune-checkpoints, and express on the cell surface specific signature molecules such as interleukin-1 receptor 2 (IL1R2), programmed death (PD)-1 Ligand1, PD-1 Ligand2, and CCR8 chemokine which were not previously described on Treg cells. Remarkably, high expression in whole tumor samples of Treg signature genes, such as LAYN, MAGEH1 or CCR8, correlated with poor prognosis. The invention provides new insights into the molecular identity and functions of human tumor-infiltrating Treg cells, and define new potential targets for tumor immunotherapy.

In the present invention, the inventors provide a comprehensive transcriptome analysis of human CD4+ Treg cells and effector cells (Th1 and Th17) infiltrating NSCLC or CRC and their matched normal tissues.

Inventors defined molecular signatures of tumor-infiltrating Treg cells in these two cancer types and confirmed the relevance of these signatures by single-cell analyses. These data could help a better understanding of Treg functional role at tumor sites and pave the way to the identification of therapeutic targets for more specific and safer modulation of Treg cells in cancer therapy.

The inventors' findings provide new insights on the inhibitory mechanisms of Treg cells and offer precise targets for cancer immunotherapy.

Then the present invention provides a molecule able to modulate the expression and/or function of at least one marker that is selectively deregulated in tumor-infiltrating regulatory T cells for use in the prevention and/or treatment of said tumor.

Preferably, the molecule according to the invention is capable of specifically binding to said at least one marker and inducing antibody-dependent cell-mediated cytotoxicity (ADCC).

Said molecule is preferably able to selectively deplete tumor-infiltrating regulatory T cells.

Said molecule is preferably selected from the group consisting of:
a) an antibody or a fragment thereof;
b) a polypeptide;
c) a small molecule;
d) a polynucleotide coding for said antibody or polypeptide or a functional derivative thereof;
e) a polynucleotide, such as antisense construct, antisense oligonucleotide, RNA interference construct or siRNA,
e) a vector comprising or expressing the polynucleotide as defined in d) or e);
f) a host cell genetically engineered expressing said polypeptide or antibody or comprising the polynucleotide as defined in d) or e).

Preferably, the marker is selected from the group consisting of at least one marker disclosed in the following Table VIII.

TABLE VIII

| MARKER NAME | ENSEMBL_release87 | ENTREZ_ID release108 |
|---|---|---|
| FUCA2 | ENSG00000001036 | 2519 |
| ICA1 | ENSG00000003147 | 3382 |
| TTC22 | ENSG00000006555 | 55001 |
| COX10 | ENSG00000006695 | 1352 |
| IL32 | ENSG00000008517 | 9235 |
| ETV7 | ENSG00000010030 | 51513 |
| ATP2C1 | ENSG00000017260 | 27032 |
| FAS | ENSG00000026103 | 355 |
| ARNTL2 | ENSG00000029153 | 56938 |
| IKZF2 | ENSG00000030419 | 22807 |
| PEX3 | ENSG00000034693 | 8504 |
| MAT2B | ENSG00000038274 | 27430 |
| TSPAN17 | ENSG00000048140 | 26262 |
| COL9A2 | ENSG00000049089 | 1298 |
| TNFRSF9 | ENSG00000049249 | 3604 |
| FOXP3 | ENSG00000049768 | 50943 |
| NFE2L3 | ENSG00000050344 | 9603 |
| LIMA1 | ENSG00000050405 | 51474 |
| TNIP3 | ENSG00000050730 | 79931 |
| LY75 | ENSG00000054219 | 4065 |
| ZNF280C | ENSG00000056277 | 55609 |
| YIPF1 | ENSG00000058799 | 54432 |
| NFYC | ENSG00000066136 | 4802 |
| ISOC1 | ENSG00000066583 | 51015 |
| PHKA1 | ENSG00000067177 | 5255 |
| ACSL4 | ENSG00000068366 | 2182 |
| MAST4 | ENSG00000069020 | 375449 |
| LMCD1 | ENSG00000071282 | 29995 |
| TFRC | ENSG00000072274 | 7037 |
| PANX2 | ENSG00000073150 | 56666 |
| FNDC3B | ENSG00000075420 | 64778 |
| REXO2 | ENSG00000076043 | 25996 |
| TP73 | ENSG00000078900 | 7161 |
| LXN | ENSG00000079257 | 56925 |
| CEACAM1 | ENSG00000079385 | 634 |
| IL12RB2 | ENSG00000081985 | 3595 |
| GSK3B | ENSG00000082701 | 2932 |
| TDRD3 | ENSG00000083544 | 81550 |
| RRAGB | ENSG00000083750 | 10325 |
| STARD7 | ENSG00000084090 | 56910 |
| SSH1 | ENSG00000084112 | 54434 |
| NCOA1 | ENSG00000084676 | 8648 |
| MGST2 | ENSG00000085871 | 4258 |
| ACOX3 | ENSG00000087008 | 8310 |
| AURKA | ENSG00000087586 | 6790 |
| TPX2 | ENSG00000088325 | 22974 |
| ANKRD10 | ENSG00000088448 | 55608 |
| FKBP1A | ENSG00000088832 | 2280 |
| SIRPG | ENSG00000089012 | 55423 |
| BIRC5 | ENSG00000089685 | 332 |
| RGS1 | ENSG00000090104 | 5996 |
| DPYSL2 | ENSG00000092964 | 1808 |
| WHRN | ENSG00000095397 | 25861 |
| CENPM | ENSG00000100162 | 79019 |
| SEPT3 | ENSG00000100167 | 55964 |
| NCF4 | ENSG00000100365 | 4689 |
| CSF2RB | ENSG00000100368 | 1439 |
| IL2RB | ENSG00000100385 | 3560 |
| CNIH1 | ENSG00000100528 | 10175 |
| ZMYND8 | ENSG00000101040 | 23613 |
| MAP1LC3A | ENSG00000101460 | 84557 |
| PIGU | ENSG00000101464 | 128869 |
| NXT2 | ENSG00000101888 | 55916 |
| SMS | ENSG00000102172 | 6611 |
| NDFIP2 | ENSG00000102471 | 54602 |
| ACP5 | ENSG00000102575 | 54 |
| NFAT5 | ENSG00000102908 | 10725 |
| CYB5B | ENSG00000103018 | 80777 |
| IL21R | ENSG00000103522 | 50615 |
| LAPTM4B | ENSG00000104341 | 55353 |
| IL7 | ENSG00000104432 | 3574 |
| NCALD | ENSG00000104490 | 83988 |

TABLE VIII-continued

| MARKER NAME | ENSEMBL_release87 | ENTREZ_ID release108 |
|---|---|---|
| ERI1 | ENSG00000104626 | 90459 |
| EBI3 | ENSG00000105246 | 10148 |
| PLA2G4C | ENSG00000105499 | 8605 |
| CDK6 | ENSG00000105810 | 1021 |
| HOXA1 | ENSG00000105991 | 3198 |
| GLCCI1 | ENSG00000106415 | 113263 |
| MINPP1 | ENSG00000107789 | 9562 |
| ACTA2 | ENSG00000107796 | 59 |
| WSB1 | ENSG00000109046 | 26118 |
| CLNK | ENSG00000109684 | 116449 |
| HTATIP2 | ENSG00000109854 | 10553 |
| CTSC | ENSG00000109861 | 1075 |
| VWA5A | ENSG00000110002 | 4013 |
| DCPS | ENSG00000110063 | 28960 |
| SLC35F2 | ENSG00000110660 | 54733 |
| FOXM1 | ENSG00000111206 | 2305 |
| RAD51AP1 | ENSG00000111247 | 10635 |
| RASAL1 | ENSG00000111344 | 8437 |
| VDR | ENSG00000111424 | 7421 |
| FAM184A | ENSG00000111879 | 79632 |
| DNPH1 | ENSG00000112667 | 10591 |
| KIF20A | ENSG00000112984 | 10112 |
| SEC24A | ENSG00000113615 | 10802 |
| KAT2B | ENSG00000114166 | 8850 |
| PPM1G | ENSG00000115241 | 5496 |
| IL1R2 | ENSG00000115590 | 7850 |
| IL1R1 | ENSG00000115594 | 3554 |
| IL1RL2 | ENSG00000115598 | 8808 |
| IL1RL1 | ENSG00000115602 | 9173 |
| UXS1 | ENSG00000115652 | 80146 |
| SLC25A12 | ENSG00000115840 | 8604 |
| THADA | ENSG00000115970 | 63892 |
| PARK7 | ENSG00000116288 | 11315 |
| LEPR | ENSG00000116678 | 3953 |
| GADD45A | ENSG00000116717 | 1647 |
| KIF14 | ENSG00000118193 | 9928 |
| MREG | ENSG00000118242 | 55686 |
| HSDL2 | ENSG00000119471 | 84263 |
| FLVCR2 | ENSG00000119686 | 55640 |
| CD274 | ENSG00000120217 | 29126 |
| SOCS2 | ENSG00000120833 | 8835 |
| TNFRSF8 | ENSG00000120949 | 943 |
| RDH10 | ENSG00000121039 | 157506 |
| LAX1 | ENSG00000122188 | 54900 |
| TWIST1 | ENSG00000122691 | 7291 |
| ZWINT | ENSG00000122952 | 11130 |
| CIT | ENSG00000122966 | 11113 |
| ACOT9 | ENSG00000123130 | 23597 |
| IKZF4 | ENSG00000123411 | 64375 |
| HJURP | ENSG00000123485 | 55355 |
| METTL8 | ENSG00000123600 | 79828 |
| TOX2 | ENSG00000124191 | 84969 |
| GTSF1L | ENSG00000124196 | 149699 |
| SOX4 | ENSG00000124766 | 6659 |
| TM9SF2 | ENSG00000125304 | 9375 |
| HS3ST3B1 | ENSG00000125430 | 9953 |
| EML2 | ENSG00000125746 | 24139 |
| MGME1 | ENSG00000125871 | 92667 |
| IGFLR1 | ENSG00000126246 | 79713 |
| DLGAP5 | ENSG00000126787 | 9787 |
| HIVEP3 | ENSG00000127124 | 59269 |
| LRRC61 | ENSG00000127399 | 65999 |
| TST | ENSG00000128311 | 7263 |
| STRIP2 | ENSG00000128578 | 57464 |
| MYO5C | ENSG00000128833 | 55930 |
| FOXA1 | ENSG00000129514 | 3169 |
| ITFG1 | ENSG00000129636 | 81533 |
| KLHDC7B | ENSG00000130487 | 113730 |
| TRAF3 | ENSG00000131323 | 7187 |
| MCCC2 | ENSG00000131844 | 64087 |
| GRSF1 | ENSG00000132463 | 2926 |
| SYT11 | ENSG00000132718 | 23208 |
| SLC41A1 | ENSG00000133065 | 254428 |
| ATP13A3 | ENSG00000133657 | 79572 |
| MICAL2 | ENSG00000133816 | 9645 |
| IL2RA | ENSG00000134460 | 3559 |
| CABLES1 | ENSG00000134508 | 91768 |
| RFK | ENSG00000135002 | 55312 |
| HAVCR2 | ENSG00000135077 | 84868 |
| CGA | ENSG00000135346 | 1081 |
| FAIM2 | ENSG00000135472 | 23017 |
| EGLN1 | ENSG00000135766 | 54583 |
| ARHGEF4 | ENSG00000136002 | 50649 |
| SLC41A2 | ENSG00000136052 | 84102 |
| FLNB | ENSG00000136068 | 2317 |
| RCBTB1 | ENSG00000136144 | 55213 |
| TMOD1 | ENSG00000136842 | 7111 |
| TPMT | ENSG00000137364 | 7172 |
| CASP1 | ENSG00000137752 | 834 |
| NUSAP1 | ENSG00000137804 | 51203 |
| ADAM10 | ENSG00000137845 | 102 |
| ZNF280D | ENSG00000137871 | 54816 |
| HADHB | ENSG00000138029 | 3032 |
| CEP55 | ENSG00000138180 | 55165 |
| ENTPD1 | ENSG00000138185 | 953 |
| NAB1 | ENSG00000138386 | 4664 |
| HECW2 | ENSG00000138411 | 57520 |
| CD27 | ENSG00000139193 | 939 |
| CDH24 | ENSG00000139880 | 64403 |
| RAB15 | ENSG00000139998 | 376267 |
| ETFA | ENSG00000140374 | 2108 |
| KSR1 | ENSG00000141068 | 8844 |
| PCTP | ENSG00000141179 | 58488 |
| SECTM1 | ENSG00000141574 | 6398 |
| EVA1B | ENSG00000142694 | 55194 |
| WDTC1 | ENSG00000142784 | 23038 |
| CTTNBP2NL | ENSG00000143079 | 55917 |
| CASQ1 | ENSG00000143318 | 844 |
| SNAP47 | ENSG00000143740 | 116841 |
| STAC | ENSG00000144681 | 6769 |
| ARL6IP5 | ENSG00000144746 | 10550 |
| ADPRH | ENSG00000144843 | 141 |
| PAM | ENSG00000145730 | 5066 |
| RNF145 | ENSG00000145860 | 153830 |
| TTBK1 | ENSG00000146216 | 84630 |
| TMEM140 | ENSG00000146859 | 55281 |
| CHST7 | ENSG00000147119 | 56548 |
| CHRNA6 | ENSG00000147434 | 8973 |
| MKI67 | ENSG00000148773 | 4288 |
| PTPRJ | ENSG00000149177 | 5795 |
| ZC3H12C | ENSG00000149289 | 85463 |
| NCAM1 | ENSG00000149294 | 4684 |
| INPP1 | ENSG00000151689 | 3628 |
| JAKMIP1 | ENSG00000152969 | 152789 |
| GTF3C6 | ENSG00000155115 | 112495 |
| RHOC | ENSG00000155366 | 389 |
| SLC16A1 | ENSG00000155380 | 6566 |
| BATF | ENSG00000156127 | 10538 |
| CXCL13 | ENSG00000156234 | 10563 |
| SH3RF2 | ENSG00000156463 | 153769 |
| NPTN | ENSG00000156642 | 27020 |
| CCNB2 | ENSG00000157456 | 9133 |
| RNF207 | ENSG00000158286 | 388591 |
| AHCYL2 | ENSG00000158467 | 23382 |
| PTGIR | ENSG00000160013 | 5739 |
| CALM3 | ENSG00000160014 | 808 |
| TMPRSS3 | ENSG00000160183 | 64699 |
| FCRL3 | ENSG00000160856 | 115352 |
| PAQR4 | ENSG00000162073 | 124222 |
| ZG16B | ENSG00000162078 | 124220 |
| JAK1 | ENSG00000162434 | 3716 |
| DIRAS3 | ENSG00000162595 | 9077 |
| ACTG2 | ENSG00000163017 | 72 |
| SGPP2 | ENSG00000163082 | 130367 |
| NEURL3 | ENSG00000163121 | 93082 |
| CTLA4 | ENSG00000163599 | 1493 |
| ICOS | ENSG00000163600 | 29851 |
| RYBP | ENSG00000163602 | 23429 |
| KIF15 | ENSG00000163808 | 56992 |
| TMEM184C | ENSG00000164168 | 55751 |
| C5orf63 | ENSG00000164241 | 401207 |
| PTTG1 | ENSG00000164611 | 9232 |
| MELK | ENSG00000165304 | 9833 |
| FAAH2 | ENSG00000165591 | 158584 |

TABLE VIII-continued

| MARKER NAME | ENSEMBL_release87 | ENTREZ_ID release108 |
|---|---|---|
| PRDX3 | ENSG00000165672 | 10935 |
| HPRT1 | ENSG00000165704 | 3251 |
| CACNB2 | ENSG00000165995 | 783 |
| TPP1 | ENSG00000166340 | 1200 |
| AKIP1 | ENSG00000166452 | 56672 |
| ACAA2 | ENSG00000167315 | 10449 |
| GNG8 | ENSG00000167414 | 94235 |
| GNG4 | ENSG00000168243 | 2786 |
| CX3CR1 | ENSG00000168329 | 1524 |
| AHCYL1 | ENSG00000168710 | 10768 |
| TSPAN5 | ENSG00000168785 | 10098 |
| PGM2 | ENSG00000169299 | 55276 |
| CRADD | ENSG00000169372 | 8738 |
| UGP2 | ENSG00000169764 | 7360 |
| ZNF282 | ENSG00000170265 | 8427 |
| GLB1 | ENSG00000170266 | 2720 |
| SMAD1 | ENSG00000170365 | 4086 |
| SPATA24 | ENSG00000170469 | 202051 |
| PRKCDBP | ENSG00000170955 | 112464 |
| TADA3 | ENSG00000171148 | 10474 |
| RBKS | ENSG00000171174 | 64080 |
| NETO2 | ENSG00000171208 | 81831 |
| LRG1 | ENSG00000171236 | 116844 |
| FAM98B | ENSG00000171262 | 283742 |
| CHST11 | ENSG00000171310 | 50515 |
| ECEL1 | ENSG00000171551 | 9427 |
| BCL2L1 | ENSG00000171552 | 598 |
| MALT1 | ENSG00000172175 | 10892 |
| ZMAT3 | ENSG00000172667 | 64393 |
| CORO1B | ENSG00000172725 | 57175 |
| CYP7B1 | ENSG00000172817 | 9420 |
| HPSE | ENSG00000173083 | 10855 |
| VANGL1 | ENSG00000173218 | 81839 |
| GLRX | ENSG00000173221 | 2745 |
| TRIB1 | ENSG00000173334 | 10221 |
| CD7 | ENSG00000173762 | 924 |
| HAP1 | ENSG00000173805 | 9001 |
| FBXO45 | ENSG00000174013 | 200933 |
| CHST2 | ENSG00000175040 | 9435 |
| RMI2 | ENSG00000175643 | 116028 |
| SLC35E3 | ENSG00000175782 | 55508 |
| ZBTB38 | ENSG00000177311 | 253461 |
| ZBED2 | ENSG00000177494 | 79413 |
| PARD6G | ENSG00000178184 | 84552 |
| GLDC | ENSG00000178445 | 2731 |
| AKAP5 | ENSG00000179841 | 9495 |
| CCR8 | ENSG00000179934 | 1237 |
| PAK2 | ENSG00000180370 | 5062 |
| YIPF6 | ENSG00000181704 | 286451 |
| TIGIT | ENSG00000181847 | 201633 |
| CREB3L2 | ENSG00000182158 | 64764 |
| XKRX | ENSG00000182489 | 402415 |
| CADM1 | ENSG00000182985 | 23705 |
| LHFP | ENSG00000183722 | 10186 |
| CSF1 | ENSG00000184371 | 1435 |
| PTP4A3 | ENSG00000184489 | 11156 |
| CDCA2 | ENSG00000184661 | 157313 |
| OSBP2 | ENSG00000184792 | 23762 |
| METTL7A | ENSG00000185432 | 25840 |
| SPATC1 | ENSG00000186583 | 375686 |
| TNFRSF4 | ENSG00000186827 | 7293 |
| TNFRSF18 | ENSG00000186891 | 8784 |
| TMPRSS6 | ENSG00000187045 | 164656 |
| GCNT1 | ENSG00000187210 | 2650 |
| MAGEH1 | ENSG00000187601 | 28986 |
| NHS | ENSG00000188158 | 4810 |
| IL17REL | ENSG00000188263 | 400935 |
| ADAT2 | ENSG00000189007 | 134637 |
| NEMP2 | ENSG00000189362 | 100131211 |
| SPATS2L | ENSG00000196141 | 26010 |
| NTNG2 | ENSG00000196358 | 84628 |
| MYL6B | ENSG00000196465 | 140465 |
| ARHGEF12 | ENSG00000196914 | 23365 |
| MAP3K5 | ENSG00000197442 | 4217 |
| PDGFA | ENSG00000197461 | 5154 |
| PDCD1LG2 | ENSG00000197646 | 80380 |
| TOR4A | ENSG00000198113 | 54863 |
| HIBCH | ENSG00000198130 | 26275 |
| ZNF334 | ENSG00000198185 | 55713 |
| NTRK1 | ENSG00000198400 | 4914 |
| TMA16 | ENSG00000198498 | 55319 |
| WDHD1 | ENSG00000198554 | 11169 |
| FAM19A2 | ENSG00000198673 | 338811 |
| F5 | ENSG00000198734 | 2153 |
| GK | ENSG00000198814 | 2710 |
| INPP5F | ENSG00000198825 | 22876 |
| LAYN | ENSG00000204381 | 143903 |
| CARD16 | ENSG00000204397 | 114769 |
| TBC1D8 | ENSG00000204634 | 11138 |
| CD177 | ENSG00000204936 | 57126 |
| LEPROT | ENSG00000213625 | 54741 |
| SEC14L6 | ENSG00000214491 | 730005 |
| TRIM16 | ENSG00000221926 | 10626 |
| LTA | ENSG00000226979 | 4049 |
| PROB1 | ENSG00000228672 | 389333 |
| AF165138.7 | ENSG00000243440 | NA |
| USP51 | ENSG00000247746 | 158880 |
| CARD17 | ENSG00000255221 | 440068 |
| DOC2B | ENSG00000272636 | 8447 |
| C17orf96 | ENSG00000273604 | 100170841 |
| SSTR3 | ENSG00000278195 | 6753 |
| AC019206.1 | ENSG00000279229 | NA | wherein each of said marker name is characterized by "Ensembl gene id" and includes all of therein disclosed isoform protein sequences.

Each gene of table VIII is characterized by its Ensembl Gene accession number (ENSG), retrievable in the public database EnsEMBL (http://www.ensembl.org) and by its Entrez Gene ID, retrievable in the public database NCBI (https://www.ncbi.nlm.nih.gov/), if present.

Preferably the marker is selected from the group consisting of: a transmembrane protein, a cytokine, an epigenetic factor, a kinase phosphatase or a transcription factor.

More preferably, the marker is a transmembrane protein selected from the group of SEQ ID NO:1-661, even more preferably, the marker is selected from the group consisting of: LAYN (SEQ ID NOs:1-9), CCR8 (SEQ ID Nos:10-11), IL21R (SEQ ID Nos: 12-14), IL1 R2 (SEQ ID Nos:206-209), LY75 (SEQ ID NO: 78), SIRPG (SEQ ID Nos:122-126), CD177 (SEQ ID Nos:651-653), CD7 (SEQ ID Nos: 549-554), FCRL3 (SEQ ID Nos:452-457), CADM1 (SEQ ID Nos: 570-583), NTNG2 (SEQ ID Nos:621-622), CSF2RB (SEQ ID Nos:134-137), SECTM1 (SEQ ID Nos: 349-356), TSPAN5 (SEQ ID Nos:497-503), TMPRSS3 (SEQ ID Nos:448-451), TMPRSS6 (SEQ ID Nos:605-611), METTL7A (SEQ ID Nos:600-604), THADA (SEQ ID Nos: 237), NDFIP2 (SEQ ID Nos:148-151), CHRNA6 (SEQ ID Nos:392-394), or from the group consisting of:

```
LAYN (SEQ ID NOS: 1-9
[>ENSG00000204381_ENST00000375614_ENSP00000364764_LAYN

MRPGTALQAVLLAVLLVGLRAATGRLLSGQPVCRGGTQRPCYKVIYFHDTSRRLNFEEAKEACR

RDGGQLVSIESEDEQKLIEKFIENLLPSDGDFWIGLRRREEKQSNSTACQDLYAWTDGSISQFRN
```

-continued

WYVDEPSCGSEVCVVMYHQPSAPAGIGGPYMFQWNDDRCNMKNNFICKYSDEKPAVPSREAE

GEETELTTPVLPEETQEEDAKKTFKESREAALNLAYILIPSIPLLLLLVVTTVVCWVWICRKRKRE

QPDPSTKKQHTIWPSPHQGNSPDLEVYNVIRKQSEADLAETRPDLKNISFRVCSGEATPDDMSCD

YDNMAVNPSESGFVTLVSVESGFVTNDIYEFSPDQMGRSKESGWVENEIYGY* (SEQ ID NO: 1)

>ENSG00000204381_ENST00000375615_ENSP00000364765_LAYN

MRPGTALQAVLLAVLLVGLRAATGRLLSASDLDLRGGQPVCRGGTQRPCYKVIYFHDTSRRLNF

EEAKEACRRDGGQLVSIESEDEQKLIEKFIENLLPSDGDFWIGLRRREEKQSNSTACQDLYAWTD

GSISQFRNWYVDEPSCGSEVCVVMYHQPSAPAGIGGPYMFQWNDDRCNMKNNFICKYSDEKPA

VPSREAEGEETELTTPVLPEETQEEDAKKTFKESREAALNLAYILIPSIPLLLLLVVTTVVCWVWIC

RKRKREQPDPSTKKQHTIWPSPHQGNSPDLEVYNVIRKQSEADLAETRPDLKNISFRVCSGEATP

DDMSCDYDNMAVNPSESGFVTLVSVESGFVTNDIYEFSPDQMGRSKESGWVENEIYGY*

(SEQ ID NO: 2)

>ENSG00000204381_ENST00000436913_ENSP00000392942_LAYN

MVTSGLGSGGVRRNKAIAQPARTFMLGLMAAYHNLEKPAVPSREAEGEETELTTPVLPEETQEE

DAKKTFKESREAALNLAYILIPSIPLLLLLVVTTVVCWVWICRKRKREQPDPSTKKQHTIWPSPHQ

GNSPDLEVYNVIRKQSEADLAETRPDLKNISFRVCSGEATPDDMSCDYDNMAVNPSESGFVTLV

SVESGFVTNDIYEFSPDQMGRSKESGWVENEIYGY* (SEQ ID NO: 3)

>ENSG00000204381_ENST00000525126_ENSP00000434328_LAYN

MRPGTALQAVLLAVLLVGLRAATGRLLSASDLDLRGGQPVCRGGTQRPCYKVIYFHDTSRRLNF

EEAKEACRRDGGQLVSIESEDEQKLIEKFIENLLPSDGDFWIGLRRREEKQSNSTACQDLYAWTD

GSISQFRNWYVDEPSCGSEVCVVMYHQPSAPAGIGGPYMFQWNDDRCNMKNNFICKYSDEKPA

VPSREAEGEETELTTPVLPEETQEEDAKKTFKESREAALNLAYILIPSIPLLLLLVVTTVVCWVWIC

RKRQKTGAARP* (SEQ ID NO: 4)

>ENSG00000204381_ENST00000525866_ENSP00000434300_LAYN

MRPGTALQAVLLAVLLVGLRAATGRLLSGQPVCRGGTQRPCYKVIYFHDTSRRLNFEEAKEACR

RDGGQLVSIESEDEQKLIEKFIENLLPSDGDFWIGLRRREEKQSNSTACQDLYAWTDGSISQFRET

SSSF* (SEQ ID NO: 5)

>ENSG00000204381_ENST00000528924_ENSP00000486561_LAYN

MVTSGLGSGGVRRNKAIAQPARTFMLGLMAAYHNLEKPAVPSREAEGEETELTTPVLPEETQEE

DAKKTFKESREAALNLAYILIPSIPLLLLLVVTTVVCWVWICRK (SEQ ID NO: 6)

>ENSG00000204381_ENST00000530962_ENSP00000431627_LAYN

MYHQPSAPAGIGGPYMFQWNDDRCNMKNNFICKYSDEKPAVPSREAEGEETELTTPVLPEETQE

EDAKKTFKESREAALNLAYILIPSIPLLLLLVVTTVVCWVWICRK (SEQ ID NO: 7)

>ENSG00000204381_ENST00000533265_ENSP00000434972_LAYN

MRPGTALQAVLLAVLLVGLRAATGRLLSGQPVCRGGTQRPCYKVIYFHDTSRRLNFEEAKEACR

RDGGQLVSIESEDEQKLIEKFIENLLPSDGDFWIGLRRREEKQSNSTACQDLYAWTDGSISQFRN

WYVDEPSCGSEVCVVMYHQPSAPAGIGGPYMFQWNDDRCNMKNNFICKYSDEKPAVPSREAE

GEETELTTPVLPEETQEEDAKKTFKESREAALNLAYILIPSIPLLLLLVVTTVVCWVWICRKRQKT

-continued

GAARP* (SEQ ID NO: 8)

>ENSG00000204381_ENST00000533999_ENSP00000432434_LAYN

MYHQPSAPAGIGGPYMFQWNDDRCNMKNNFICKYSDEKPAVPSREAEGE (SEQ ID NO: 9)]),

CCR8 (SEQ ID Nos:10-11

[>ENSG00000179934_ENST00000326306_ENSP00000326432_CCR8

MDYTLDLSVTTVTDYYYPDIFSSPCDAELIQTNGKLLLAVFYCLLFVFSLLGNSLVILVLVVCKKL

RSITDVYLLNLALSDLLFVFSFPFQTYYLLDQWVFGTVMCKVVSGFYYIGFYSSMFFITLMSVDR

YLAVVHAVYALKVRTIRMGTTLCLAVWLTAIMATIPLLVFYQVASEDGVLQCYSFYNQQTLKW

KIFTNFKMNILGLLIPFTIFMFCYIKILHQLKRCQNHNKTKAIRLVLIVVIASLLFWVPFNVVLFLTS

LHSMHILDGCSISQQLTYATHVTEIISFTHCCVNPVIYAFVGEKFKKHLSEIFQKSCSQIFNYLGRQ

MPRESCEKSSSCQQHSSRSSSVDYIL* (SEQ ID NO: 10)

>ENSG00000179934_ENST00000414803_ENSP00000390104_CCR8

MDYTLDLSVTTVTDYYYPDIFSSPCDAELIQTNDLLSAGPVGVWDCNVQSGVWLLLHWLLQQH

VFHHPHECGQVPGCCPCRVCPKGEDDQDGHNAVPGSMANRHYGYHPIASVLPSGL* (SEQ ID

NO: 11)]),

IL21R (SEQ ID Nos: 12-14

[>ENSG00000103522_ENST00000337929_ENSP00000338010_IL21R

MPRGWAAPLLLLLLQGGWGCPDLVCYTDYLQTVICILEMWNLHPSTLTLTWQDQYEELKDEAT

SCSLHRSAHNATHATYTCHMDVFHFMADDIFSVNITDQSGNYSQECGSFLLAESIKPAPPFNVTV

TFSGQYNISWRSDYEDPAFYMLKGKLQYELQYRNRGDPWAVSPRRKLISVDSRSVSLLPLEFRK

DSSYELQVRAGPMPGSSYQGTWSEWSDPVIFQTQSEELKEGWNPHLLLLLLLVIVFIPAFWSLKT

HPLWRLWKKIWAVPSPERFFMPLYKGCSGDFKKWVGAPFTGSSLELGPWSPEVPSTLEVYSCHP

PRSPAKRLQLTELQEPAELVESDGVPKPSFWPTAQNSGGSAYSEERDRPYGLVSIDTVTVLDAEG

PCTWPCSCEDDGYPALDLDAGLEPSPGLEDPLLDAGTTVLSCGCVSAGSPGLGGPLGSLLDRLKP

PLADGEDWAGGLPWGGRSPGGVSESEAGSPLAGLDMDTFDSGFVGSDCSSPVECDFTSPGDEGP

PRSYLRQWVVIPPPLSSPGPQAS* (SEQ ID NO: 12)

>ENSG00000103522_ENST00000395754_ENSP00000379103_IL21R

MPRGWAAPLLLLLLQGGWGCPDLVCYTDYLQTVICILEMWNLHPSTLTLTWQDQYEELKDEAT

SCSLHRSAHNATHATYTCHMDVFHFMADDIFSVNITDQSGNYSQECGSFLLAESIKPAPPFNVTV

TFSGQYNISWRSDYEDPAFYMLKGKLQYELQYRNRGDPWAVSPRRKLISVDSRSVSLLPLEFRK

HPLWRLWKKIWAVPSPERFFMPLYKGCSGDFKKWVGAPFTGSSLELGPWSPEVPSTLEVYSCHP

PRSPAKRLQLTELQEPAELVESDGVPKPSFWPTAQNSGGSAYSEERDRPYGLVSIDTVTVLDAEG

PCTWPCSCEDDGYPALDLDAGLEPSPGLEDPLLDAGTTVLSCGCVSAGSPGLGGPLGSLLDRLKP

PLADGEDWAGGLPWGGRSPGGVSESEAGSPLAGLDMDTFDSGFVGSDCSSPVECDFTSPGDEGP

PRSYLRQWVVIPPPLSSPGPQAS* (SEQ ID NO: 13)

>ENSG00000103522_ENST00000564089_ENSP00000456707_IL21R

MPRGWAAPLLLLLLQGGWGCPDLVCYTDYLQTVICILEMWNLHPSTLTLTWQDQYEELKDEAT

SCSLHRSAHNATHATYTCHMDVFHFMADDIFSVNITDQSGNYSQECGSFLLAESIKPAPPFNVTV

TFSGQYNISWRSDYEDPAFYMLKGKLQYELQYRNRGDPWAVSPRRKLISVDSRSVSLLPLEFRK

DSSYELQVRAGPMPGSSYQGTWSEWSDPVIFQTQSEELKEGWNPHLLLLLLLVIVFIPAFWSLKT

HPLWRLWKKIWAVPSPERFFMPLYKGCSGDFKKWVGAPFTGSSLELGPWSPEVPSTLEVYSCHP

-continued

```
PRSPAKRLQLTELQEPAELVESDGVPKPSFWPTAQNSGGSAYSEERDRPYGLVSIDTVTVLDAEG

PCTWPCSCEDDGYPALDLDAGLEPSPGLEDPLLDAGTTVLSCGCVSAGSPGLGGPLGSLLDRLKP

PLADGEDWAGGLPWGGRSPGGVSESEAGSPLAGLDMDTFDSGFVGSDCSSPVECDFTSPGDEGP

PRSYLRQWVVIPPPLSSPGPQAS* (SEQ ID NO: 14)]).
```

Said cytokine is preferably selected from the group of consisting of: IL32 (SEQ ID Nos: 19-30), IL7 (SEQ ID Nos: 168-174), EBI3 (SEQ ID NO: 175), SECTM1 (SEQ ID Nos: 349-356), CSF1 (SEQ ID Nos: 585-592) and LTA (SEQ ID Nos: 657-658).

Said epigenetic factor is preferably selected from the group of consisting of: TDRD3 (SEQ ID NO: 712-718), KAT2B (SEQ ID NO:719), FOXA1 (SEQ ID Nos: 720-721) and RCBTB1 (SEQ ID Nos: 722-723).

Said kinase phosphatase is preferably selected from the group of consisting of: GSK3B (SEQ ID Nos: 724-725), SSH1 (SEQ ID NOS:111-112), CDK6 (SEQ ID Nos: 726-727), MINPP1 (SEQ ID Nos:181-183), PTPRJ (SEQ ID Nos: 395-400), CALM3 (SEQ ID Nos: 728-734) and PTP4A3 (SEQ ID Nos: 593-598).

Said transcription factor is preferably selected from the group of consisting of:

VDR (SEQ ID NO:204), ZNF334 (SEQ ID Nos: 736-741), CREB3L2 (SEQ ID Nos: 565-567), ETV7 (SEQ ID NO:31 or 32), SOX4 (SEQ ID NO:735), TWIST1 (SEQ ID Nos: 743-745), TP73 (SEQ ID Nos: 746-756), FOXP3, NFE2L3 (SEQ ID NO:76), ARNTL2 (SEQ ID Nos: 757-764), BATF (SEQ ID Nos: 765-766), PTTG1 (SEQ ID Nos: 767-770), HIVEP3 (SEQ ID Nos: 771-772), FOXA1 (SEQ ID Nos: 720-721), ZBTB38 (SEQ ID NO:561), FOXM1 (SEQ ID Nos: 773-778), TADA3 (SEQ ID Nos: 779-782), NFAT5 (SEQ ID NO:160, 783-791, 742).

In a preferred embodiment, the marker is MAGEH1 (SEQ ID NO: 708 or 709)

In the present invention, the tumor is preferably a solid or liquid tumor. Preferably, the solid tumor is selected from the group consisting of: non-small cell lung cancer, colorectal cancer, breast cancer, gastric cancer.

In a preferred embodiment of the invention, the tumor is a metastasis, preferably a bone, a brain or a liver metastasis.

Preferably, the metastasis derives from colon rectal cancer or non-small-cell lung cancer.

Another object of the invention is the above defined molecule for use in a method for in vivo depleting tumor-infiltrating regulatory T cells in a subject or for use in a method to enhance tumor immunity in a subject.

Another object of the invention is a pharmaceutical composition comprising the molecule as defined above and at least one pharmaceutically acceptable carrier.

A further object of the invention is a pharmaceutical composition comprising the molecule as above defined, for use in the prevention and/or treatment of tumor or for use in a method for in vivo depleting tumor-infiltrating regulatory T cell in a subject or for use in a method to enhance tumor immunity in a subject.

The pharmaceutical composition according to the invention may further comprise a therapeutic agent, preferably the therapeutic agent in an anti-tumoral agent.

Another object of the invention is an in vitro method for diagnosing and/or assessing the risk of developing and/or prognosing and/or for monitoring the progression and/or for monitoring the efficacy of a therapeutic treatment and/or for

```
[MAGEH1_Entrez:28986_ENSG00000187601_ENST00000342972_ENSP00000343706

ATGCCTCGGGGACGAAAGAGTCGGCGCCGCCGTAATGCGAGAGCCGCAGAAGAGAACCGC

AACAATCGCAAAATCCAGGCCTCAGAGGCCTCCGAGACCCCTATGGCCGCCTCTGTGGTAGC

GAGCACCCCCGAAGACGACCTGAGCGGCCCCGAGGAAGACCCGAGCACTCCAGAGGAGGC

CTCTACCACCCCTGAAGAAGCCTCGAGCACTGCCCAAGCACAAAAGCCTTCAGTGCCCCGGA

GCAATTTTCAGGGCACCAAGAAAAGTCTCCTGATGTCTATATTAGCGCTCATCTTCATCATG

GGCAACAGCGCCAAGGAAGCTCTGGTCTGGAAAGTGCTGGGGAAGTTAGGAATGCAGCCTG

GACGTCAGCACAGCATCTTTGGAGATCCGAAGAAGATCGTCACAGAAGAGTTTGTGCGCAG

AGGGTACCTGATTTATAAACCGGTGCCCCGTAGCAGTCCGGTGGAGTATGAGTTCTTCTGGG

GGCCCCGAGCACACGTGGAATCGAGCAAACTGAAAGTCATGCATTTTGTGGCAAGGGTTCG

TAACCGATGCTCTAAAGACTGGCCTTGTAATTATGACTGGGATTCGGACGATGATGCAGAGG

TTGAGGCTATCCTCAATTCAGGTGCTAGGGGTTATTCCGCCCCTTAA (SEQ ID NO: 708)

MPRGRKSRRRRNARAAEENRNNRKIQASEASETPMAASVVASTPEDDLSGPEEDPSTPEEASTTP

EEASSTAQAQKPSVPRSNFQGTKKSLLMSILALIFIMGNSAKEALVWKVLGKLGMQPGRQHSIFG

DPKKIVTEEFVRRGYLIYKPVPRSSPVEYEFFWGPRAHVESSKLKVMHFVARVRNRCSKDWPCN

YDWDSDDDAEVEAILNSGARGYSAP* (SEQ ID NO: 709)].
``` the screening of a therapeutic treatment of a tumour in a subject comprising the steps of:
   a) detecting at least one of the marker as above defined in an isolated biological sample obtained from the subject and
   b) comparing with respect to a proper control.

Another object of the invention is an in vitro or ex-vivo method for diagnosing and/or assessing the risk of developing and/or prognosing and/or for monitoring the progression and/or for monitoring the efficacy of a therapeutic treatment and/or for the screening of a therapeutic treatment of a tumour in a subject as above defined, wherein the marker to be detected is at least one of the marker selected from the group consisting of: LAYN, MAGEH1 and CCR8.

Preferably the above method is for prognosing of colorectal cancer or non-small cell lung cancer in a subject and comprises the steps of:
   a) detecting at least one of the marker selected from the group consisting of:
   LAYN, MAGEH1 and CCR8
   in an isolated biological sample obtained from the subject and
   b) comparing with respect to a proper control,
wherein an amount of said at least one marker in the isolated biological sample obtained from the subject higher than the control amount indicates that the subject has a poor prognosis.

In the above method, preferably step a) comprises measuring the amount of the marker or of fragments thereof or of the polynucleotide coding for said protein (DNA or mRNA) or of fragments thereof in said isolated biological sample obtained from the subject and step b) comprises comparing the measured amount of step a) with a proper control amount.

Preferably, the in vitro method for monitoring the progression and/or for monitoring the efficacy of a therapeutic treatment of a tumour, as above defined, comprises the steps of:
   a) measuring the alteration of the amount or the alteration of the activity of the above markers or of fragments thereof or of the polynucleotide coding for said protein or fragments thereof in said isolated biological sample obtained from the subject and
   b) comparing the measured alteration of step a) with a proper control alteration.

Another object of the invention is a method for the treatment and/or prevention of tumor comprising administering to a subject the molecule as above defined.

A further object is a method for identifying a molecule acting as an anti-tumoral, comprising the steps of:
   assaying candidate molecules for their binding specificity to the at least one marker as above defined;
   selecting molecules having a specific binding activity to the at least one marker as above defined;
   testing such specific binding molecules for their capacity of inhibiting proliferation and/or inducing an apoptotic response in a cell system,
   preferably by selectively depleting tumor-infiltrating regulatory T cell, more preferably by inducing antibody-dependent cell-mediated cytotoxicity (ADCC).

Preferably, the biological sample is a fluid, a cell or a tissue sample, more preferably said sample is plasma or serum.

The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like.

A "sample" in the context of the present teachings refers to any biological sample that is isolated from a subject. A sample can include, without limitation an aliquot of body fluid, whole blood, serum, plasma, solid tissue samples such as tissue biopsies, or tissue cultures or cells derived therefrom and the progeny thereof, synovial fluid, lymphatic fluid, ascites fluid, and interstitial or extracellular fluid. The term "sample" also encompasses the fluid in spaces between cells, including gingival crevicular fluid, bone marrow, cerebrospinal fluid (CSF), saliva, mucous, sputum, semen, sweat, urine, or any other bodily fluids. "Blood sample" can refer to whole blood or any fraction thereof, including serum and plasma. Samples can be obtained from a subject by means including but not limited to venipuncture, excretion, ejaculation, massage, biopsy, needle aspirate, lavage, scraping, surgical incision, or intervention or other means known in the art. The definition also includes samples that have been manipulated in any way after their procurement, such as by treatment with reagents; washed; or enrichment for certain cell populations, such as cancer cells or samples in which regulatory T cells, are isolated and then analyzed. The definition also includes sample that have been enriched for particular types of molecules, e.g., nucleic acids, polypeptides, etc.

Another object of the invention is a kit for carrying out the above methods, comprising
   means to measure the amount or the activity of the above markers or of fragments thereof and/or means to measure the amount of the polynucleotide coding for said protein or of fragments thereof and optionally,
   control means.

Any combination of the above markers is comprised within the present invention.

Preferred combinations of markers are LAYN and MAGEH1; LAYN and CCR8; CCR8 and MAGEH1; LAYN, MAGEH1 and CCR8.

Preferably, the above polynucleotide is an RNAi inhibitor, preferably selected from the group consisting of: siRNA, miRNA, shRNA, stRNA, snRNA, and antisense nucleic acid, or a functional derivative thereof.

A comparative analysis of gene expression arrays from $CD4^+$ T cells infiltrating NSCLC and CRC revealed Treg-specific expression of 328 markers as listed in Table IV Manipulation of Treg cells via these markers can therefore be used to enhance immunotherapy of cancer.

The expression "molecule able to modulate" and "modulator" are herein interchangeable.

By the term "modulator" it is meant a molecule that effects a change in the expression and/or function of at least one marker as above defined.

The change is relative to the normal or baseline level of expression and/or function in the absence of the modulator, but otherwise under similar conditions, and it may represent an increase (e.g. by using an inducer or activator) or a decrease (e.g. by using a suppressor or inhibitor) in the normal/baseline expression and/or function. In the context of the present invention, a "modulator" is a molecule which may suppress or inhibit the expression and/or function of at least one marker that is selectively deregulated in tumor-infiltrating regulatory T cell for use in the prevention and/or treatment of cancer.

By the term "suppressor or inhibitor" or a "molecule which (selectively) suppresses or inhibits" it is meant a molecule that effects a change in the expression and/or function of the target.

In the context of the present invention, a "modulator" is a molecule which may induce or activate the expression and/or function of at least one marker that is selectively deregulated in tumor-infiltrating regulatory T cell for use in the prevention and/or treatment of cancer.

The change is relative to the normal or baseline level of expression and/or function in the absence of the modulator, but otherwise under similar conditions, and it may represent an increase (e.g. by using an inducer or activator) or a decrease (e.g. by using a suppressor or inhibitor) in the normal/baseline expression and/or function.

The suppression or inhibition of the expression and/or function of the target may be assessed by any means known to the skilled in the art. The assessment of the expression level or of the presence of the target is preferably performed using classical molecular biology techniques such as (real time Polymerase Chain Reaction) qPCR, microarrays, bead arrays, RNAse protection analysis or Northern blot analysis or cloning and sequencing.

The assessment of target function is preferably performed by in vitro suppression assay, whole transcriptome analysis, mass spectrometry analysis to identify proteins interacting with the target.

In the context of the present invention, the target (or the marker) may be the gene, the mRNA, the cDNA, or the encoded protein thereof, including fragments, derivatives, variants, isoforms, etc. Preferably, the marker is characterized by its Accession numbers (i.e. NCBI Entrez ID; Ensembl Gene accession number (ENSG), Ensembl transcript accession number (ENST) and Ensembl protein accession number (ENSP), retrievable in the public database EnsEMBL (http://www.ensembl.org) and/or amino acid and nucleotide sequences, herein disclosed.

In the context of the present invention, the term "treat" (or "treated", "treatment", etc.) when referred to CD4+ T cell, means e.g. the exposure of the cell to an exogenous modulator as above defined. The overexpression may be obtained e.g. by infecting the cells with a viral vector expressing the molecule of the invention. The inhibition of marker expression may e.g. by obtained by transfection with polynucleotide, as e.g. with siRNAs.

The term "treat" may also mean that the cells are manipulated in order to overexpress or silence the marker. The overexpression or the silencing may be obtained e.g. by genetically modifying the cells.

Control means can be used to compare the amount or the increase of amount of the marker defined to a proper control. The proper control may be obtained for example, with reference to known standard, either from a normal subject or from normal population, or from T cells different from tumour infiltrating regulatory T cells or regulatory T cells.

The means to measure the amount of at least one marker as above defined are preferably at least one antibody, functional analogous or derivatives thereof. Said antibody, functional analogous or derivatives thereof are specific for said marker.

In the context of the present invention, the antibody is preferably selected from the group consisting of an intact immunoglobulin, a Fv, a scFv (single chain Fv fragment), a Fab, a F(ab')2, an "antibody-like" domain, an "antibody-mimetic domain", a single antibody domain (VH domain or VL domains), a multimeric antibody, recombinant or synthetic antigen-binding fragments, a peptide or a proteolytic fragment containing the epitope binding region. The terms "antibody" and "immunoglobulin" can be used interchangeably and are herein used in the broadest sense and encompass various antibodies and antibody mimetics structures, including but not limited to monoclonal antibodies, polyclonal antibodies, multispecific antibodies (e.g., bispecific antibodies), chimeric antibodies, nanobodies, antibody derivatives, antibody fragments, anticalins, DARPins, affibodies, affilins, affimers, affitins, alphabodies, avimers, fynomers, monobodies and other binding domains, so long as they exhibit the desired antigen-binding activity.

The term immunoglobulin also includes "conjugate" thereof. In the context of the present invention "conjugate" in relation to the antibody of the invention includes antibodies (or fragments thereof) conjugated with a substance (a compound, etc.) having a therapeutic activity, e.g. anti-tumor activity and/or cell-killing activity or a cytotoxic agents such as various A chain toxins, ribosomes inactivating proteins, and ribonucleases; bispecific antibodies designed to induce cellular mechanisms for killing tumors (see, for example, U.S. Pat. Nos. 4,676,980 and 4,954,617). The conjugate may be formed by previously preparing each of the aforementioned antibody molecule and the aforementioned substance having anti-tumor activity and/or cell-killing activity, separately, and then combining them (immunoconjugate) or by ligating a protein toxin used as such a substance having anti-tumor activity and/or cell-killing activity to an antibody gene on a gene according to a genetic recombination technique, so as to allow it to express as a single protein (a fusion protein) (immunotoxin).

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. VH or VL Fvs are also called "Nanobodies".

The term "antibody mimetics" refers to those organic compounds or binding domains that are not antibody derivatives but that can bind specifically an antigen like antibodies do. They include anticalins, DARPins, affibodies, affilins, affimers, affitins, alphabodies, avimers, fynomers, monobodies and others.

The term "chimeric" antibody refers to an antibody in which a portion of the heavy and/or light chain is derived from a particular source or species, while the remainder of the heavy and/or light chain is derived from a different source or species.

The terms "full length antibody," "intact antibody," and "whole antibody" are used herein interchangeably to refer to an antibody having a structure substantially similar to a native antibody structure or having heavy chains that contain an Fc region as defined herein.

In a preferred embodiment, the kit of the invention comprises:
a solid phase adhered antibody specific for said compound;
detection means of the ligand specific-marker complex.

Alternatively, the reagents can be provided as a kit comprising reagents in a suspension or suspendable form, e.g. reagents bound to beads suitable for flow cytometry, preferably magnetic beads coated with antibody capture. The instructions may comprise instructions for conducting an antibody-based flow cytometry assay.

Detection means are preferably means able to detect and/or measure the amount of the described markers, e.g. means able to detect the complex antigen-antibody, as enzyme conjugated secondary antibodies, luminescent substrates, magnetic beads coated with antibody capture, customized dried antibody cocktails and/or columns with size filter cartridges and/or combined with specific antibody filter (SAF).

In an embodiment, the method further comprises selecting a therapeutic regimen based on the analysis. In an embodiment, the method further comprises determining a treatment course for the subject based on the analysis. Other means may be e.g. specific primers and probes for RT PCR. The kits according to the invention can further comprise customary auxiliaries, such as buffers, carriers, markers, etc. and/or instructions for use.

In the context of the present invention the term "detecting" may be intended also as "measuring the amount" or "measuring the alteration". In the case of a method or a kit for assessing the risk and/or diagnosing and/or prognosing of a tumour, the proper control may be a sample taken from a healthy patient or from a patient affected by another disorder or pathology, and the proper control amount or activity may be the amount or activity of the same protein or polynucleotide measured in a sample taken from a healthy patient or from a patient affected by another disorder or pathology.

In the case of a method or a kit for monitoring the progression of a tumour, the progress of the cancer is monitored and the proper control may be a sample taken from the same subject at various times or from another patient, and the proper control amount or activity may by the amount or activity of the same protein or polynucleotide measured in a sample taken from the same subject at various times or from another patient.

In the case of a method or a kit for monitoring the efficacy of a therapeutic treatment, the proper control may by a sample taken from the same subject before initiation of the therapy or taken at various times during the course of the therapy and the proper control amount or activity may be the amount or activity of the same protein or polynucleotide measured in a sample taken from the same subject before initiation of the therapy or taken at various times during the course of the therapy.

In the case of a method or a kit for the screening of a therapeutic treatment, the proper control may be a sample taken from subjects without treatment and from subjects treated with a substance that is to be assayed or from subjects treated with a reference treatment and the proper control amount or activity may be the average of the amounts or activity of the same protein or polynucleotide measured in samples taken from subjects without treatment and from subjects treated with a substance that is to be assayed or from subjects treated with a reference treatment. In this case, if the amount or activity of MAGEH1 and/or LAYN and/or CCR8 or polynucleotides thereof in the isolated biological sample obtained from the subject is lower or equal than the control amount or activity, it may indicate that the tested substance is effective for the treatment of the tumour.

In the present invention, the expression "measuring the amount" can be intended as measuring the amount (or the activity) or concentration or level of the respective protein and/or mRNA thereof and/or DNA thereof, preferably semi-quantitative or quantitative. Measurement of a protein can be performed directly or indirectly. Direct measurement refers to the amount or concentration measure of the marker, based on a signal obtained directly from the protein, and which is directly correlated with the number of protein molecules present in the sample. This signal—which can also be referred to as intensity signal—can be obtained, for example, by measuring an intensity value of a chemical or physical property of the marker. Indirect measurements include the measurement obtained from a secondary component (e.g., a different component from the gene expression product) and a biological measurement system (e.g. the measurement of cellular responses, ligands, "tags" or enzymatic reaction products).

The term "amount", as used in the description refers but is not limited to the absolute or relative amount of proteins and/or mRNA thereof and/or DNA thereof, and any other value or parameter associated with the same or which may result from these. Such values or parameters comprise intensity values of the signal obtained from either physical or chemical properties of the protein, obtained by direct measurement, for example, intensity values in an immunoassay, mass spectroscopy or a nuclear magnetic resonance.

Additionally, these values or parameters include those obtained by indirect measurement, for example, any of the measurement systems described herein. Methods of measuring mRNA and DNA in samples are known in the art. To measure nucleic acid levels, the cells in a test sample can be lysed, and the levels of mRNA in the lysates or in RNA purified or semi-purified from lysates can be measured by any variety of methods familiar to those in the art. Such methods include hybridization assays using detectably labeled DNA or RNA probes (i.e., Northern blotting) or quantitative or semi-quantitative RT-PCR methodologies using appropriate oligonucleotide primers. Alternatively, quantitative or semi-quantitative in situ hybridization assays can be carried out using, for example, tissue sections, or unlysed cell suspensions, and detectably labeled (e.g., fluorescent, or enzyme-labeled) DNA or RNA probes. Additional methods for quantifying mRNA include RNA protection assay (RPA), cDNA and oligonucleotide microarrays, representation difference analysis (RDA), differential display, EST sequence analysis, and serial analysis of gene expression (SAGE).

If by comparing the measured amount or activity of the above markers or of the polynucleotide coding for said protein with the amount or activity obtained from a control sample, the amount or the activity of said marker in the sample isolated from the subject corresponds to a higher value, the subject may present cancer or go towards an aggravation of said disease.

If by comparing the measured amount or activity of the above markers or of the polynucleotide coding for said protein with the amount or the activity obtained from a control sample, the amount or the activity of said marker in the sample isolated from the subject corresponds to a similar or lower value, the subject may be not affected by cancer or go toward an amelioration of cancer, respectively.

Alternatively, the expression "detecting" or "measuring the amount" is intended as measuring the alteration of the molecule. Said alteration can reflect an increase or a decrease in the amount or activity of the molecules as above defined. An increase of the protein or of the activity of the marker or of the polynucleotide coding for said marker can be correlated to an aggravation of cancer. A decrease of the protein or of the activity of said marker or of the polynucleotide coding for said protein can be correlated to an amelioration of cancer or to recovery of the subject.

The expression "marker" is intended to include also the corresponding protein encoded from said marker orthologous or homologous genes, functional mutants, functional derivatives, functional fragments or analogues, isoforms, splice variants thereof.

When the expression "marker" is referred to genes, it is intended to include also the corresponding orthologous or homologous genes, functional mutants, functional derivatives, functional fragments or analogues, isoforms thereof.

As used herein "fragments" refers to polynucleotides having preferably a length of at least 1000 nucleotides, 1100 nucleotide, 1200 nucleotides, 1300 nucleotides, 1400 nucleotides, 1500 nucleotides.

As used herein "fragments" refers to polypeptides having preferably a length of at least 10 amino acids, more preferably at least 15, at least 17 amino acids or at least 20 amino acids, even more preferably at least 25 amino acids or at least 37 or 40 amino acids, and more preferably of at least 50, or 100, or 150 or 200 or 250 or 300 or 350 or 400 or 450 or 500 amino acids.

The term "polynucleotide" also refers to modified polynucleotides.

As used herein, the term "vector" refers to an expression vector, and may be for example in the form of a plasmid, a viral particle, a phage, etc. Such vectors may include bacterial plasmids, phage DNA, baculovirus, yeast plasmids, vectors derived from combinations of plasmids and phage DNA, viral DNA such as vaccinia, adenovirus, lentivirus, fowl pox virus, and pseudorabies. Large numbers of suitable vectors are known to those of skill in the art and are commercially available.

The polynucleotide sequence, preferably the DNA sequence in the vector is operatively linked to an appropriate expression control sequence(s) (promoter) to direct mRNA synthesis. As representative examples of such promoters, one can mention prokaryotic or eukaryotic promoters such as CMV immediate early, HSV thymidine kinase, early and late SV40, LTRs from retrovirus, and mouse metallothionein-I. The expression vector may also contain a ribosome binding site for translation initiation and a transcription vector. The vector may also include appropriate sequences for amplifying expression. In addition, the vectors preferably contain one or more selectable marker genes to provide a phenotypic trait for selection of transformed host cells such as dihydro folate reductase or neomycin resistance for eukaryotic cell culture, or such as tetracycline or ampicillin resistance in $E.$ $coli$.

As used herein, the term "host cell genetically engineered" relates to host cells which have been transduced, transformed or transfected with the polynucleotide or with the vector described previously. As representative examples of appropriate host cells, one can cite bacterial cells, such as $E.$ $coli$, $Streptomyces$, $Salmonella$ $typhimurium$, fungal cells such as yeast, insect cells such as Sf9, animal cells such as CHO or COS, plant cells, etc. The selection of an appropriate host is deemed to be within the scope of those skilled in the art from the teachings herein. Preferably, said host cell is an animal cell, and most preferably a human cell.

The introduction of the polynucleotide or of the vector described previously into the host cell can be effected by method well known from one of skill in the art such as calcium phosphate transfection, DEAE-Dextran mediated transfection, electroporation, lipofection, microinjection, viral infection, thermal shock, transformation after chemical permeabilisation of the membrane or cell fusion.

The polynucleotide may be a vector such as for example a viral vector.

The polynucleotides as above defined can be introduced into the body of the subject to be treated as a nucleic acid within a vector which replicates into the host cells and produces the polynucleotides or the proteins.

Suitable administration routes of the pharmaceutical composition of the invention include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). An additional suitable administration route includes chemoembolization. Other suitable administration methods include injection, viral transfer, use of liposomes, e.g. cationic liposomes, oral intake and/or dermal application.

In certain embodiments, a pharmaceutical composition of the present invention is administered in the form of a dosage unit (e.g., tablet, capsule, bolus, etc.).

For pharmaceutical applications, the composition may be in the form of a solution, e.g. an injectable solution, emulsion, suspension or the like. The carrier may be any suitable pharmaceutical carrier. Preferably, a carrier is used which is capable of increasing the efficacy of the RNA molecules to enter the target cells. Suitable examples of such carriers are liposomes.

The modulator as above defined is administered in a pharmaceutically effective dosage, which in the case of polynucleotides may be in the range of 0.001 pg/kg body weight to 10 mg/kg body weight depending on the route of administration and the type or severity of the disease.

The term "pharmaceutical composition" refers to a preparation which is in such form as to permit the biological activity of an active ingredient contained therein to be effective, and which contains no additional components which are unacceptably toxic to a subject to which the formulation would be administered. In the present invention the term "effective amount" shall mean an amount which achieves a desired effect or therapeutic effect as such effect is understood by those of ordinary skill in the art. In the present invention, the antibody may be administered simultaneously or sequentially with another therapeutic treatment, that may be a chemotherapy or radiotherapy. The invention provides formulations comprising a therapeutically effective amount of an antibody as disclosed herein, a buffer maintaining the pH in the range from about 4.5 to about 8.5, and, optionally, a surfactant. The formulations are typically for an antibody as disclosed herein, recombinant or synthetic antigen-binding fragments thereof of the invention as active principle concentration from about 0.1 mg/ml to about 100 mg/ml. In certain embodiments, the antibody, recombinant or synthetic antigen-binding fragments thereof concentration is from about 0.1 mg/ml to 1 mg/ml; preferably from 1 mg/ml to 10 mg/ml, preferably from 10 to 100 mg/ml.

Therapeutic formulations of the antibody/antibodies can be prepared by mixing the antibody having the desired degree of purity with optional physiologically acceptable carriers, excipients or stabilizers (Remington's Pharmaceutical Sciences 16th edition, Osol, A. Ed., 1980), in the form of lyophilized formulations or aqueous solutions.

Pharmaceutical compositions containing the antibody of the present invention may be manufactured by processes well known in the art, e.g., using a variety of well-known mixing, dissolving, granulating, levigating, emulsifying, encapsulating, entrapping or lyophilizing processes. Proper formulation is dependent upon the route of administration chosen. Parenteral routes are preferred in many aspects of the invention.

For injection, including, without limitation, intravenous, intramusclular and subcutaneous injection, the compounds of the invention may be formulated in aqueous solutions, preferably in physiologically compatible buffers such as physiological saline buffer or polar solvents including, without limitation, a pyrrolidone or dimethylsulfoxide.

Formulations for injection may be presented in unit dosage form, e.g. in ampoules or in multi-dose containers.

Useful compositions include, without limitation, suspensions, solutions or emulsions in oily or aqueous vehicles, and may contain adjuncts such as suspending, stabilizing and/or dispersing agents. Pharmaceutical compositions for parenteral administration include aqueous solutions of a water soluble form, such as, without limitation, a salt of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions. Alternatively, the active ingredient may be in powder form for constitution with a suitable vehicle, e.g., sterile, pyrogen-free water, before use. For administration by inhalation, the antibody of the present invention can conveniently be delivered in the form of an aerosol spray using a pressurized pack or a nebulizer and a suitable propellant. The antibody may also be formulated in rectal compositions such as suppositories or retention enemas, using, e.g., conventional suppository bases such as cocoa butter or other glycerides. In addition to the formulations described previously, the antibody may also be formulated as depot preparations. Such long acting formulations may be administered by implantation (for example, subcutaneously or intramuscularly) or by intramuscular injection. The compounds of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt. Additionally, the antibody may be delivered using a sustained-release system, such as semi-permeable matrices of solid hydrophobic polymers containing the therapeutic agent. Other delivery systems such as liposomes and emulsions can also be used.

A therapeutically effective amount refers to an amount of compound effective to prevent, alleviate or ameliorate cancer or cancer recurrence symptoms. Determination of a therapeutically effective amount is well within the capability of those skilled in the art, especially in light of the disclosure herein. For any antibody used in the invention, the therapeutically effective amount can be estimated initially from in vitro assays. Then, the dosage can be formulated for use in animal models so as to achieve a circulating concentration range that includes the effective dosage. Such information can then be used to more accurately determine dosages useful in patients. The amount of the composition that is administered will depend upon the parent molecule included therein.

Generally, the amount used in the treatment methods is that amount which effectively achieves the desired therapeutic result in mammals. Naturally, the dosages of the various compounds can vary somewhat depending upon the compound, rate of in vivo hydrolysis, etc. In addition, the dosage, of course, can vary depending upon the dosage form and route of administration. The range set forth above is illustrative and those skilled in the art will determine the optimal dosing of the compound selected based on clinical experience and the treatment indication. Moreover, the exact formulation, route of administration and dosage can be selected by the individual physician in view of the patient's condition and of the most effective route of administration (e.g., intravenous, subcutaneous, intradermal). Additionally, toxicity and therapeutic efficacy of the antibody and other therapeutic agent described herein can be determined by standard pharmaceutical procedures in cell cultures or experimental animals using methods well-known in the art.

It is contemplated that the treatment will be given for one or more cycles until the desired clinical and biological result is obtained. The exact amount, frequency and period of administration of the compound of the present invention will vary, of course, depending upon the sex, age and medical condition of the patient as well as the severity and type of the disease as determined by the attending clinician.

The modulator of the present invention may comprise a single type of modulator or a plurality of different modulators.

The function of a regulatory T-cell may be inhibited by inhibiting markers activity and/or expression or by decreasing the number of cells positive for such markers in a T-cell population (for example by binding at least one of the above marker and inducing antibody-dependent cell-mediated cytotoxicity (ADCC)). Inhibiting the function of regulatory T-cells in an organism may be used to enhance the immune T-cell response in those circumstances where such a response is desirable, such as in a patient suffering from cancer.

When treating a cancer patient with an inhibitory agent that binds to marker protein or mRNA, one may optionally co-administer an anti-tumor vaccine or therapy. Such vaccines may be directed to isolated antigens or to groups of antigens or to whole tumor cells. It may be desirable to administer the inhibitory agent with chemotherapeutic agents or together with radiotherapy.

Treatment with multiple agents need not be done using a mixture of agents but may be done using separate pharmaceutical preparations. The preparations need not be delivered at the same exact time, but may be coordinated to be delivered to a patient during the same period of treatment, i.e. within a week or a month or each other.

Thus a composition comprising two active ingredients may be constituted in the body of the patient. Any suitable anti-tumor treatment can be coordinated with the treatments of the present invention targeted to the markers. Similarly, if treating patients with infections, other anti-infection agents can be coordinated with the treatment of the present invention targeted to the markers. Such agents may be small molecule drugs, vaccines, antibodies, etc.

The number of marker+ cells in a T-cell population can be modified by using an antibody or other agent that selectively binds to the marker. marker+ cells represent an enriched population of regulatory T-cells that can be introduced back into the original source of the T-cells or into another compatible host to enhance regulatory T-cell function. Alternatively, the marker-cells represent a population of T-cells deficient in regulatory T-cell activity that can be reintroduced into the original source of the T-cells or another compatible host to inhibit or reduce regulatory T-cell function while retaining general T-cell activity.

Any desired means for either increasing or decreasing (modulating) marker activity can be used in the methods of the invention. This includes directly modulating the function of marker protein, modulating marker signal transduction, and modulating expression of marker in T-cells by modulating either transcription or translation or both. Those means which selectively modulate marker activity are preferred over nonselective modulators. Also, those inhibitory means which create a transient marker deficiency in a population of T-cells which then return to normal levels of marker activity may be preferred for treating a temporary T-cell deficiency. The transiently deficient T-cells may be used to reconstitute a diminished T-cell population with T-cells that will be genetically normal with respect to the marker. Modulation of marker activity can be performed on cells in vitro or in whole animals, in vivo. Cells which are treated in vitro can be administered to a patient, either the original source of the cells or an unrelated individual.

To inhibit the function of the marker (antagonist), marker antibodies or small molecule inhibitors can be used. Antibodies or antibody fragments that are useful for this purpose will be those that can bind to the marker and block its ability to function. Such antibodies may be polyclonal antibodies, monoclonal antibodies, chimeric antibodies, humanized antibodies, single-chain antibodies, soluble MHC class II molecules, antibody fragments, etc.

Antibodies generated against marker polypeptides can be obtained by direct injection of the marker polypeptides into an animal or by administering marker polypeptides to an animal, preferably a nonhuman. The antibody so obtained will then bind the marker polypeptides itself. In this manner, even a sequence encoding only a fragment of the marker polypeptide can be used to generate antibodies binding the whole native marker polypeptide.

For preparation of monoclonal antibodies, any technique which provides antibodies produced by continuous cell line cultures can be used. Examples include the hybridoma technique (Kohler and Milstein, 1975, Nature, 256: 495-497), the trioma technique, the human B-cell hybridoma technique (Kozbor et al., 1983, Immunology Today 4: 72), and the EBV-hybridoma technique to produce human monoclonal antibodies (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be readily used to produce single chain antibodies to marker polypeptides. Also, transgenic mice may be used to express humanized antibodies to immunogenic marker polypeptides. To enhance or activate the function of the marker, any agent which increases the level of the marker or the activity of existing marker in the T-cell may be used. Such agents may be identified using the screening assays described below.

Expression vectors encoding the marker can also be administered to increase the gene dosage. The expression vectors can be plasmid vectors or viral vectors, as are known in the art. Any vector can be chosen by the skilled in the art for particularly desirable properties. In the context of the present invention, the term "polynucleotide" includes DNA molecules (e.g., cDNA or genomic DNA) and RNA molecules (e.g., mRNA, siRNA, shRNA) and analogues of the DNA or RNA generated using nucleotide analogues. The polynucleotide may be single-stranded or double-stranded. The polynucleotide may be synthesized using oligonucleotide analogues or derivatives (e.g., inosine or phosphorothioate nucleotides).

The RNAi inhibitors as above defined are preferably capable of hybridizing to all or part of specific target sequence. Therefore, RNAi inhibitors may be fully or partly complementary to all of or part of the target sequence The RNAi inhibitors may hybridize to the specified target sequence under conditions of medium to high stringency.

An RNAi inhibitors may be defined with reference to a specific sequence identity to the reverse complement of the sequence to which it is intended to target. The antisense sequences will typically have at least about 75%, preferably at least about 80%, at least about 85%, at least about 90%, at least about 95% or at least about 99% sequence identity with the reverse complements of their target sequences.

The term polynucleotide and polypeptide also includes derivatives and functional fragments thereof.

In the context of the present invention, the at least one gene or marker as above defined is preferably characterized by at least one of the sequence identified by its Ensembl Gene ID or NCBI Accession Numbers, as disclosed in Tables VIII or VI, or by at least one of the SEQ ID No. 1-709.

The term gene herein also includes corresponding orthologous or homologous genes, isoforms, variants, allelic variants, functional derivatives, functional fragments thereof.

The expression "protein" is intended to include also the corresponding protein encoded from a corresponding orthologous or homologous genes, functional mutants, functional derivatives, functional fragments or analogues, isoforms thereof.

The term "analogue" as used herein referring to a protein means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide.

A "derivative" may be a nucleic acid molecule, as a DNA molecule, coding the polynucleotide as above defined, or a nucleic acid molecule comprising the polynucleotide as above defined, or a polynucleotide of complementary sequence. In the context of the present invention the term "derivatives" also refers to longer or shorter polynucleotides and/or polypeptides having e.g. a percentage of identity of at least 41%, 50%, 60%, 65%, 70% or 75%, more preferably of at least 85%, as an example of at least 90%, and even more preferably of at least 95% or 100% with the sequences herein mentioned or with their complementary sequence or with their DNA or RNA corresponding sequence. The term "derivatives" and the term "polynucleotide" also include modified synthetic oligonucleotides. The modified synthetic oligonucleotides are preferably LNA (Locked Nucleic Acid), phosphoro-thiolated oligos or methylated oligos, morpholinos, 2'-O-methyl, 2'-O-methoxyethyl oligonucleotides and cholesterol-conjugated 2'-O-methyl modified oligonucleotides (antagomirs).

The term "derivative" may also include nucleotide analogues, i.e. a naturally occurring ribonucleotide or deoxyribonucleotide substituted by a non-naturally occurring nucleotide.

The term "derivatives" also includes nucleic acids or polypeptides that may be generated by mutating one or more nucleotide or amino acid in their sequences, equivalents or precursor sequences. The term "derivatives" also includes at least one functional fragment of the polynucleotide.

In the context of the present invention "functional" is intended for example as "maintaining their activity".

In the context of the present invention, the vector as above defined is preferably selected from the group consisting of: plasmids, viral vectors and phages, more preferably the viral vector is a lentiviral vector.

In the context of the present invention, the host cell as above defined is preferably selected from the group consisting of: bacterial cells, fungal cells, insect cells, animal cells, plant cells, preferably being an animal cell.

Compositions comprising a mixture of antibodies which specifically bind to the marker(s); and an anti-cancer vaccine can be made in vitro. Preferably the composition is made under conditions which render it suitable for use as a pharmaceutical composition.

Pharmaceutical compositions may be sterile and pyrogen-free. The components of the composition can also be administered separately to a patient within a period of time such that they are both within the patient's body at the same time. Such a time-separated administration leads to formation of the mixture of antibodies and vaccine within the patient's body. If the antibody and vaccine are to be administered in a time-separated fashion, they may be supplied together in a kit. Within the kit the components may be separately packaged or contained. Other components such as excipients, carriers, other immune modulators or adjuvants, instructions for administration of the antibody and the vaccine, and injection devices can be supplied in the kit as well. Instructions can be in a written, video, or audio form, can be contained on paper, an electronic medium, or even as a reference to another source, such as a website or reference manual.

Anti-marker antibodies of the invention can be used to increase the magnitude of anti-cancer response of the cancer patient to the anti-cancer vaccine or anti-cancer therapy. It can also be used to increase the number of responders in a population of cancer patients. Thus the antibodies can be used to overcome immune suppression found in patients refractory to anti-cancer vaccines or treatment. The anti-cancer vaccines can be any that are known in the art, including, but not limited to whole tumor cell vaccines, isolated tumor antigens or polypeptides comprising one or more epitopes of tumor antigens.

Expression of marker in T-cells can be modulated at the transcriptional or translational level. Agents which are capable of such modulation can be identified using the screening assays described below.

Translation of marker mRNA can be inhibited by using ribozymes, antisense molecules, small interference RNA (siRNA; See Elbashir, S. M. et al., "Duplexes of 21-nucleotide RNAs mediate RNA interference in cultured mammalian cells", Nature 411: 494-498 (2001)) or small molecule inhibitors of this process which target marker mRNA.

Antisense technology can be used to control gene expression through triple-helix formation or antisense DNA or RNA, both of which methods are based on binding of a polynucleotide to DNA or RNA. For example, the 5'coding portion of the polynucleotide sequence, which codes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6: 3073 (1979); Cooney et al, Science, 241: 456 (1988); and Dervan et al., Science, 251: 1360 (1991)), thereby preventing transcription and the production of the marker. The antisense RNA oligonucleotide hybridizes to the mRNA in vivo and blocks translation of the mRNA molecule into the marker polypeptide (Antisense—Okano, J. Neurochem., 56: 560 (1991); Oligodeoxynucleotides as Antisense Inhibitors of Gene Expression, CRC Press, Boca Raton, Fla. (1988)). The oligonucleotides described above can also be delivered to cells by antisense expression constructs such that the antisense RNA or DNA may be expressed in vivo to inhibit production of the marker. Such constructs are well known in the art. Antisense constructs, antisense oligonucleotides, RNA interference constructs or siRNA duplex RNA molecules can be used to interfere with expression of the marker.

Typically, at least 15, 17, 19, or 21 nucleotides of the complement of marker mRNA sequence are sufficient for an antisense molecule. Typically at least 19, 21, 22, or 23 nucleotides of marker are sufficient for an RNA interference molecule. Preferably an RNA interference molecule will have a 2 nucleotide 3'overhang. If the RNA interference molecule is expressed in a cell from a construct, for example from a hairpin molecule or from an inverted repeat of the desired marker sequence, then the endogenous cellular machinery will create the overhangs. siRNA molecules can be prepared by chemical synthesis, in vitro transcription, or digestion of long dsRNA by Rnase III or Dicer. These can be introduced into cells by transfection, electroporation, or other methods known in the art. (See Hannon, G J, 2002, RNA Interference, Nature 418:244-251; Bernstein E et al., 2002, The rest is silence. RNA 7:1509-1521; Hutvagner G et aL 9 RNAi: Nature harbors a double-strand. Curr. Opin. Genetics & Development 12: 225-232, 2002, A system for stable expression of short interfering RNAs in mammalian cells. Science 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. Nature Biotechnol. 20: 500-505; Miyagishi M, and Taira K. (2002). U6-promoter-driven siRNAs with four uridine 3'overhangs efficiently suppress targeted gene expression in mammalian cells. Nature Biotechnol. 20: 497-500; Paddison P J, Caudy A A, Bernstein E, Hannon G J, and Conklin D S. (2002). Short hairpin RNAs (shRNAs) induce sequence-specific silencing in mammalian cells. Genes & Dev. 16: 948-958; Paul C P, Good P D, Winer I, and Engelke D R. (2002). Effective expression of small interfering RNA in human cells. Nature Biotechnol. 20: 505-508; Sui G, Soohoo C, Affar E-B, Gay F, Shi Y, Forester W C, and Shi Y. (2002). A DNA vector-based RNAi technology to suppress gene expression in mammalian cells. Proc. Natl. Acad. Sci. USA 99 (6): 5515-5520; Yu J-Y, DeRuiter S L, and Turner D L. (2002). RNA interference by expression of short-interfering RNAs and hairpin RNAs in mammalian cells. Proc. Natl. Acad. Sci. USA 99 (9): 6047-6052).

In addition to known modulators, additional modulators of markers activity that are useful in the methods of the invention can be identified using two-hybrid screens, conventional biochemical approaches, and cell-based screening techniques, such as screening candidate molecules for an ability to bind to marker or screening for compounds which inhibit marker activity in cell culture.

This provides a simple in vitro assay system to screen for marker activity modulators.

The method may identify agents that directly interact with and modulate the marker, as well as agents that indirectly modulate marker activity by affecting a step in the marker signal transduction pathway.

Cell-based assays employing cells which express the marker can employ cells which are isolated from mammals and which naturally express the marker. Alternatively, cells which have been genetically engineered to express the marker can be used. Preferably the genetically engineered cells are T-cells.

Agents which modulate the marker activity by modulating the marker gene expression can be identified in cell based screening assays by measuring amounts of the marker protein in the cells in the presence and absence of candidate agents. The marker protein can be detected and measured, for example, by flow cytometry using anti-marker specific monoclonal antibodies. Marker mRNA can also be detected and measured using techniques known in the art, including but not limited to Northern blot, RT-PCR, and array hybridization.

In accordance with the teachings of the invention, marker inhibitors may be administered to an organism to increase the number of T-cells in the organism. This method may be useful for treating organisms suffering from conditions resulting in a low T-cell population. Such conditions include disorders involving unwanted cellular invasion or growth, such as tumor growth or cancer. Marker inhibitors may also be useful when administered in combination with conventional therapeutics to treat T-cell proliferation sensitive disorders. For instance, a tumor, which is a T-cell proliferation sensitive disorder, is conventionally treated with a chemotherapeutic agent which functions by killing rapidly dividing cells. The marker inhibitors of the invention when administered in conjunction with a chemotherapeutic agent enhance the tumoricidal effect of the chemotherapeutic agent by stimulating T-cell proliferation to enhance the immunological rejection of the tumor cells.

In accordance with the teachings of the invention, marker activators (agonists) or expression enhancers may be administered to an organism to decrease the number of T-cells, in particular tumor-infiltrating regulatory T cells, in the organism and thereby decrease deleterious T-cell activity. The methods of the invention may be applied to any organism which contains T-cells that express the marker. This includes, but is not limited to, any mammal and particularly includes humans and mice.

When methods of the invention are carried out in vivo, the effective amount of the marker modulator used will vary with the particular modulator being used, the particular condition being treated, the age and physical condition of the subject being treated, the severity of the condition, the duration of the treatment, the nature of the concurrent therapy (if any), the specific route of administration and similar factors within the knowledge and expertise of the health practitioner. For example, an effective amount can depend upon the degree to which an individual has abnormally depressed levels of T cells.

When administered, the pharmaceutical preparations of the invention are applied in pharmaceutically-acceptable amounts and in pharmaceutically-acceptably compositions.

Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. Marker modulators may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the anti-inflammatory agent, which is preferably isotonic with the blood of the recipient. This aqueous preparation may be formulated according to known methods using suitable dispersing or wetting agents and suspending agents.

The sterile injectable preparation also may be a sterile injectable solution or suspension in a non-toxic parenterally-acceptable diluent or solvent, for example, as a solution in butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes.

The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred because of the convenience to the patient as well as the dosing schedule. The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active agent into association with a liquid carrier, a finely divided solid carrier, or both, and then, if necessary, shaping the product. Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the active agent, increasing convenience to the subject and the physician.

Many types of release delivery systems are available and known to those of ordinary skill in the art. They include polymer base systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and triglycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to deliver therapeutic levels of the active ingredient for at least 30 days, and preferably 60 days. Long-term sustained release implants are well-known to those of ordinary skill in the art and include some of the release systems described above. While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

The invention will be illustrated by means of non-limiting examples in reference to the following figures.

FIG. 1. Purification, functional characterization and expression of immune checkpoints in tumor infiltrating cells.
  (A) Representation of the sorting strategy of Treg cells infiltrating tumor or normal tissue.
  (B) Representative flow cytometry plots showing suppressive activity of Treg cells isolated from tumor (NSCLC or CRC), normal lung and blood of the same patient. $4 \times 10^5$ carboxyfluorescein diacetate succinimidyl ester (CFSE)-labeled CD4+ naïve T cells from healthy donors were cocultured with an equal number of Treg cells for 4 days with a CD3-specific mAb and CD1c+CD11c+ dendritic cells. Percentage of proliferating cells are indicated. Data are representative of three independent experiments.
  (C) Z-score normalized RNA-seq expression values of immune checkpoints genes are represented as a heatmap. Cell populations are reported in the upper part of the graph, while gene names have been assigned to heatmap rows. Hierarchical clustering results are shown as a dendrogram drawn on the left side of the matrix. Colon tissues are indicated as C, lung tissues as L and peripheral blood as B. See also FIG. 6.

Figure 2:
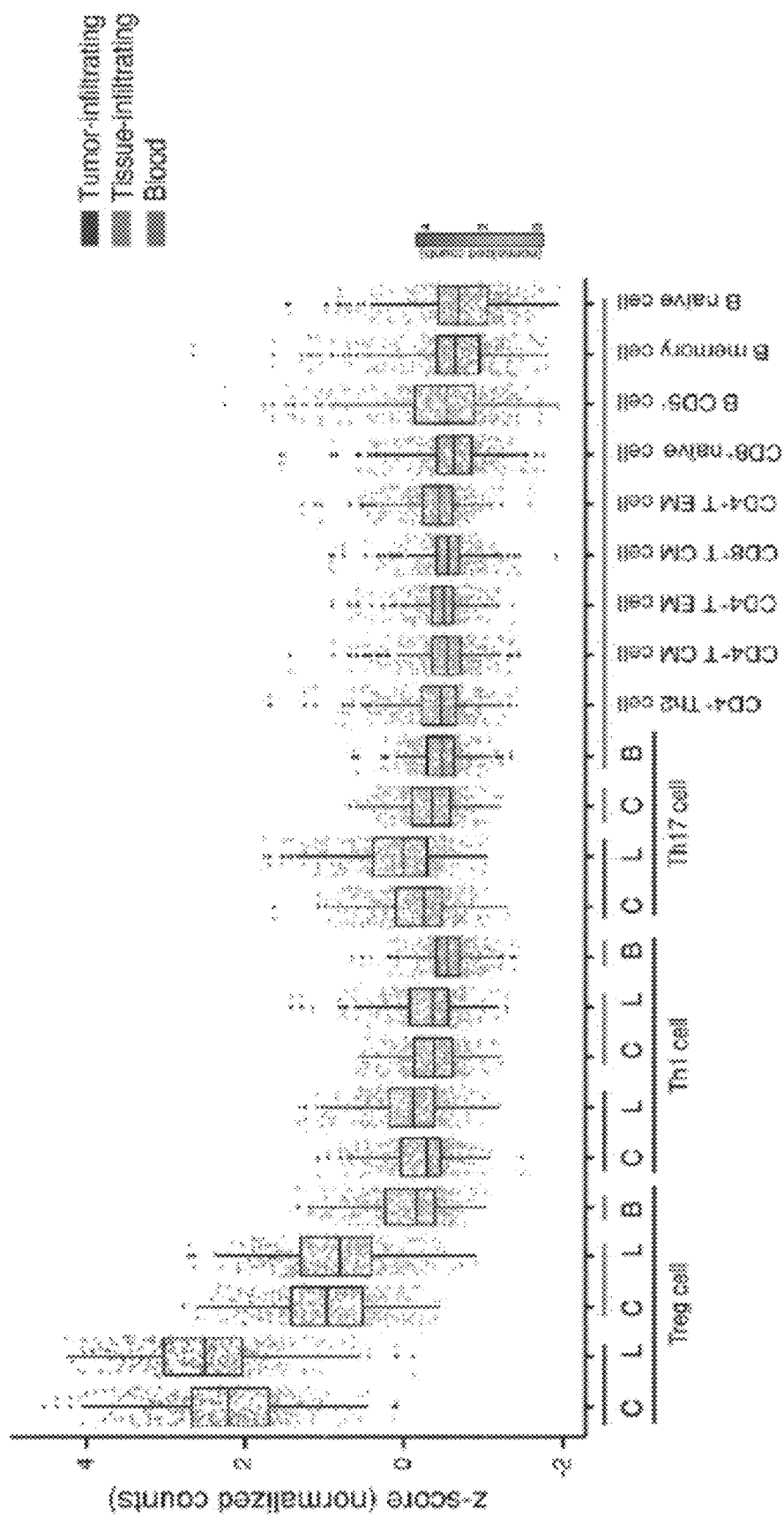

FIG. 2. Differential expression analysis identifies co-regulated genes in tumor infiltrating Treg cells
  Z-score normalized expression values of genes that are preferentially expressed in tumor-infiltrating Tregs (Wilcoxon Mann Whitney test p<2.2×10-16) over the listed cell subsets are represented as boxed plots. Colon tissues are indicated as C, lung tissues as L and peripheral blood as B.

Figure 3:
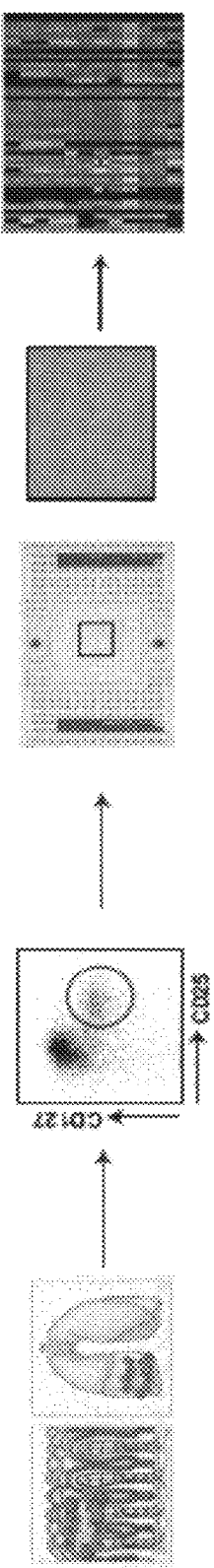
Figure 3:
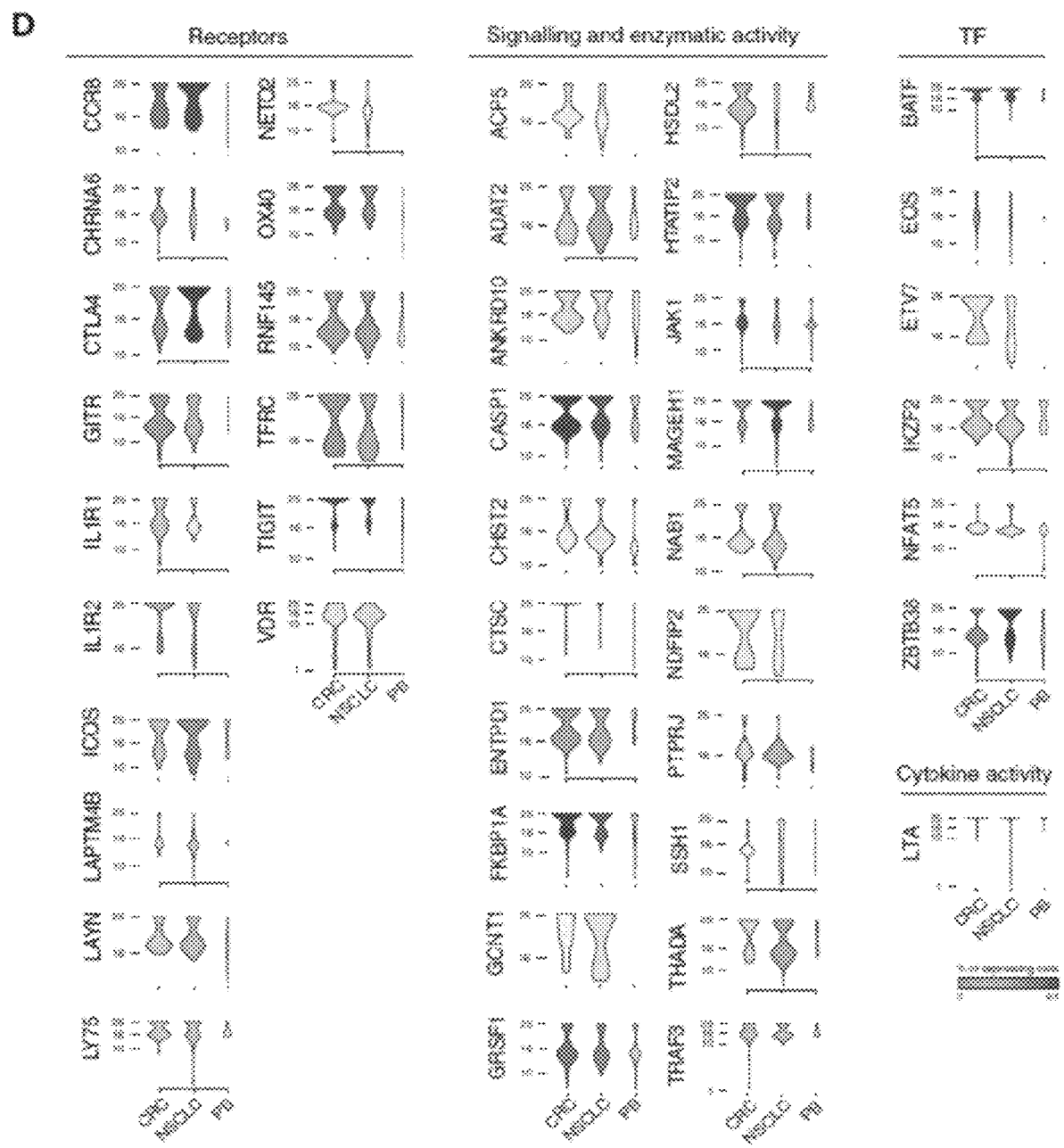
Figure 3:
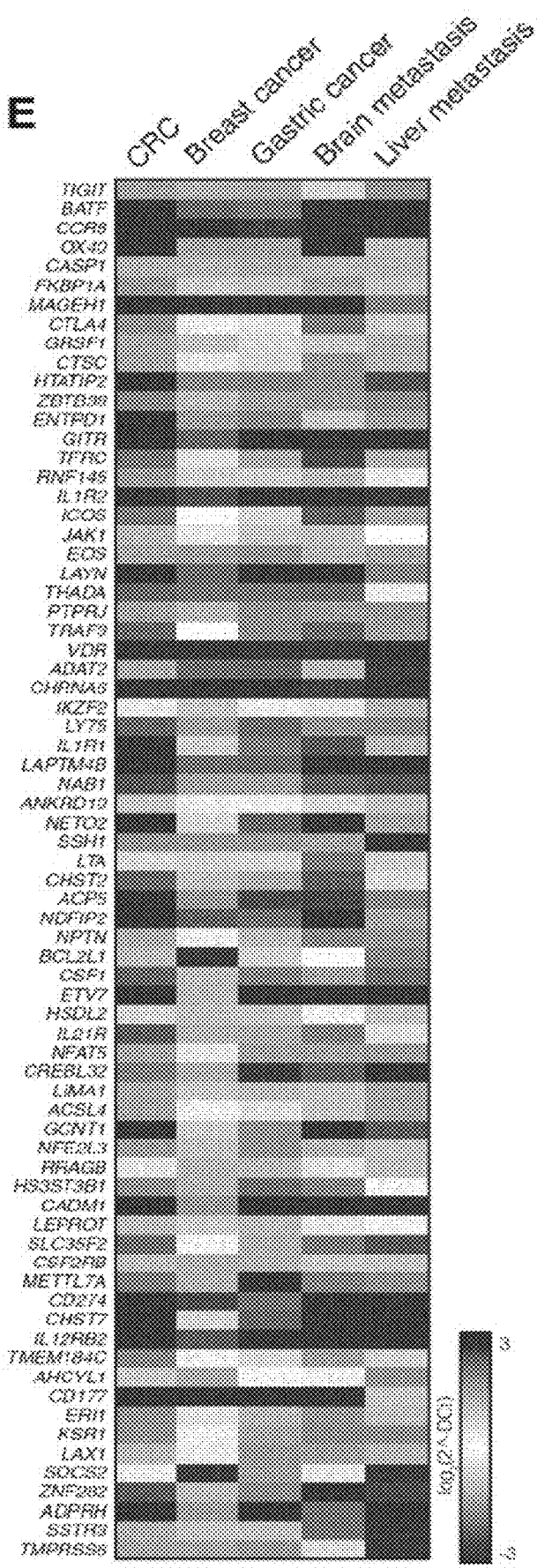

FIG. 3. Single cell analysis of tumor infiltrating Treg cells
  (A) Schematic representation of the experimental workflow. Experiments were performed on Treg cells infiltrating CRC, NSCLC, or isolated from peripheral blood of healthy donors (PB); five samples were collected for each tissue.
  (B) Percentage of co-expression of signature genes with FOXP3 and IL2RA is depicted.
  (C) Expression levels of the signature genes classified by the percentage of co-expression are represented as box plot.
  (D) Expression distribution (violin plots) in Treg cells infiltrating CRC, NSCLC or PB. Plots representing the ontology classes of receptors, signaling and enzymatic activity, cytokine activity and transcription factors are shown (Wilcoxon Mann Whitney test p<0.05). Gray scale gradient indicates the percentage of cells expressing each gene in Treg cells isolated from the three compartments.
  (E) Gene expression analysis of tumor Treg signature genes in different tumor types. Expression values are expressed as log 2 (2^-DCt).

Figure 4:
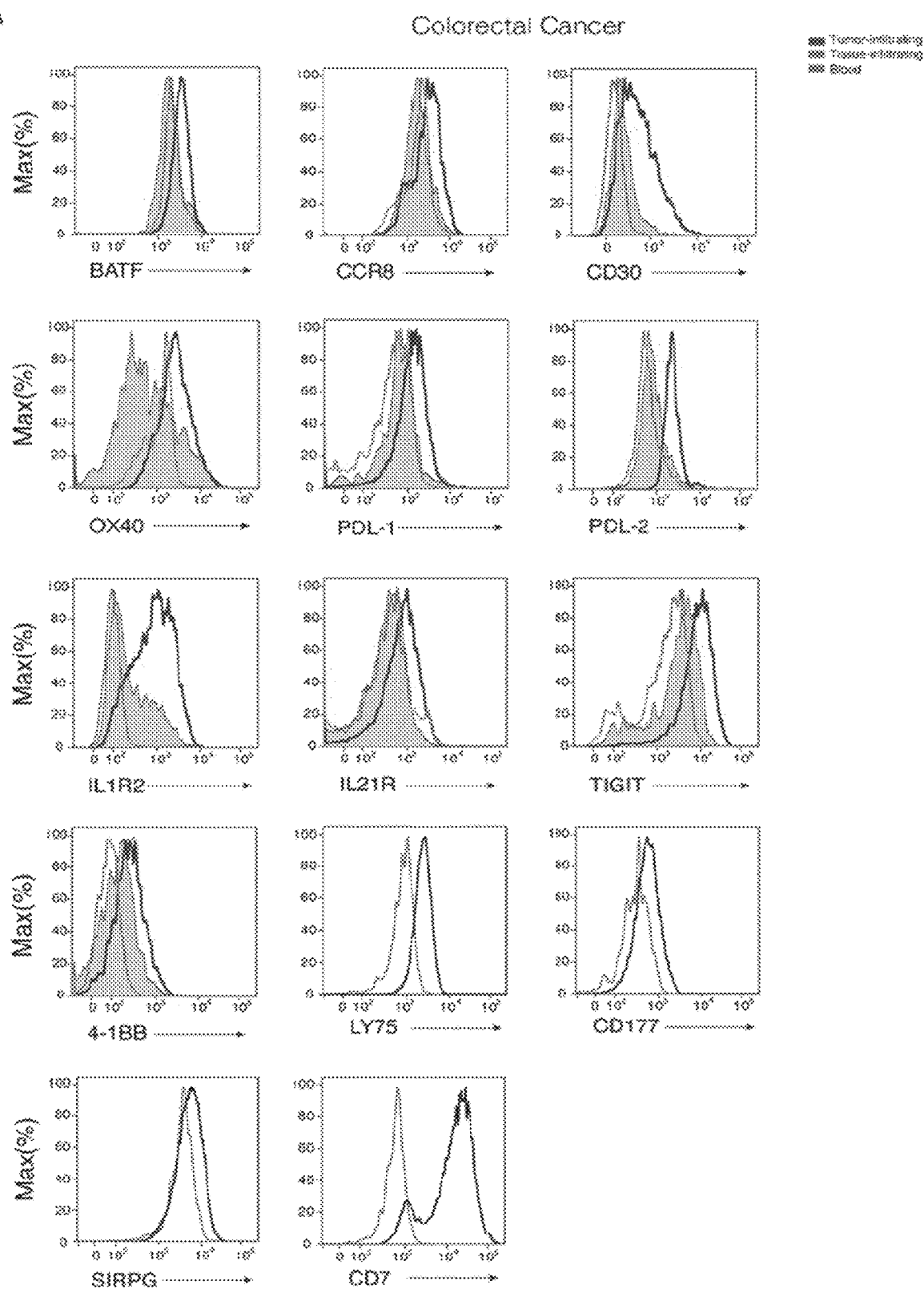
Figure 4:
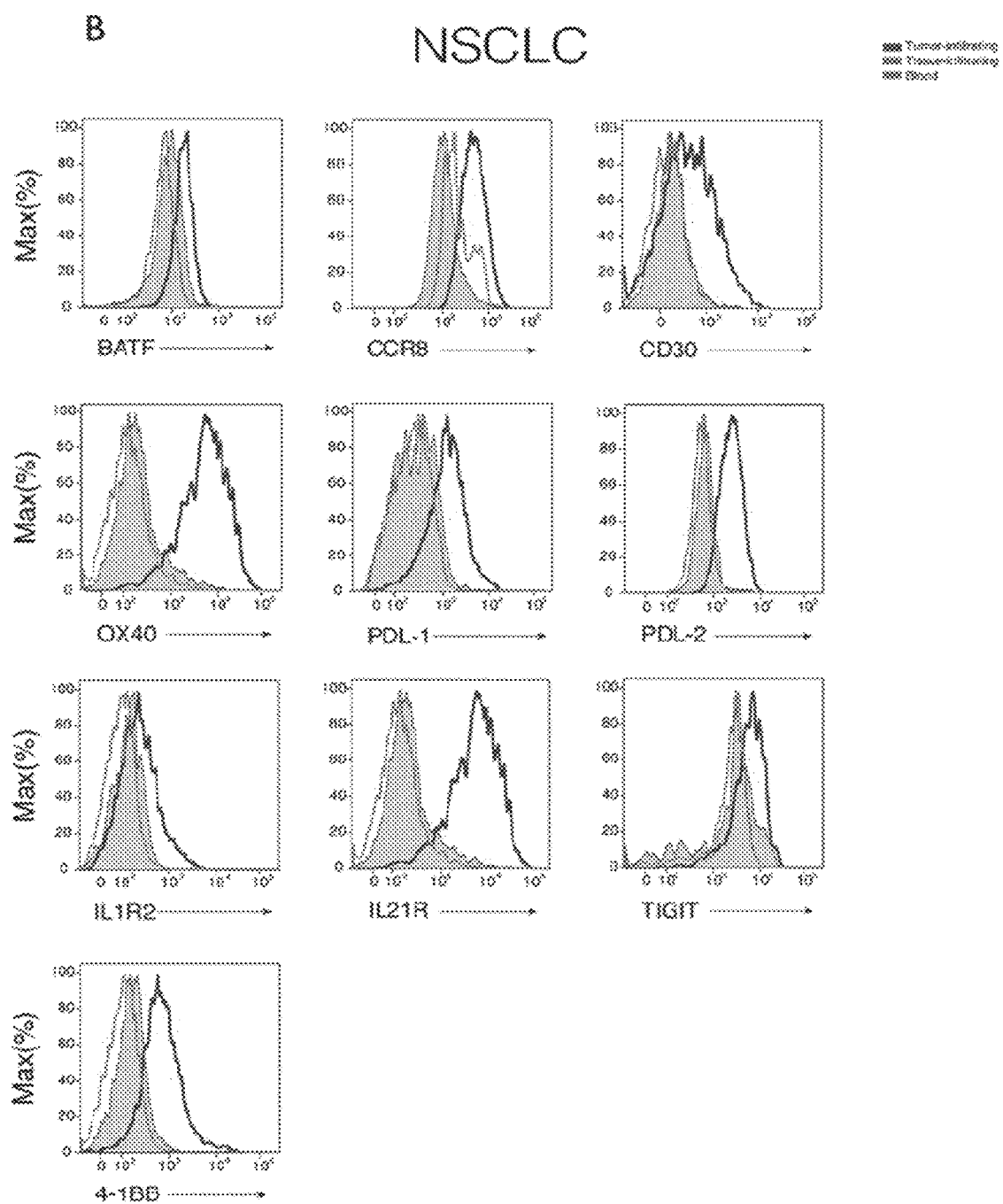

FIG. 4. Expression of tumor-infiltrating Treg cells protein signatures in CRC and NSCLC samples.
  (A and B) Representative flow cytometry plots for tumor normal tissue infiltrating Treg cells and peripheral blood Treg cells anlayzed for the expression of the indicated proteins.

Figure 5:
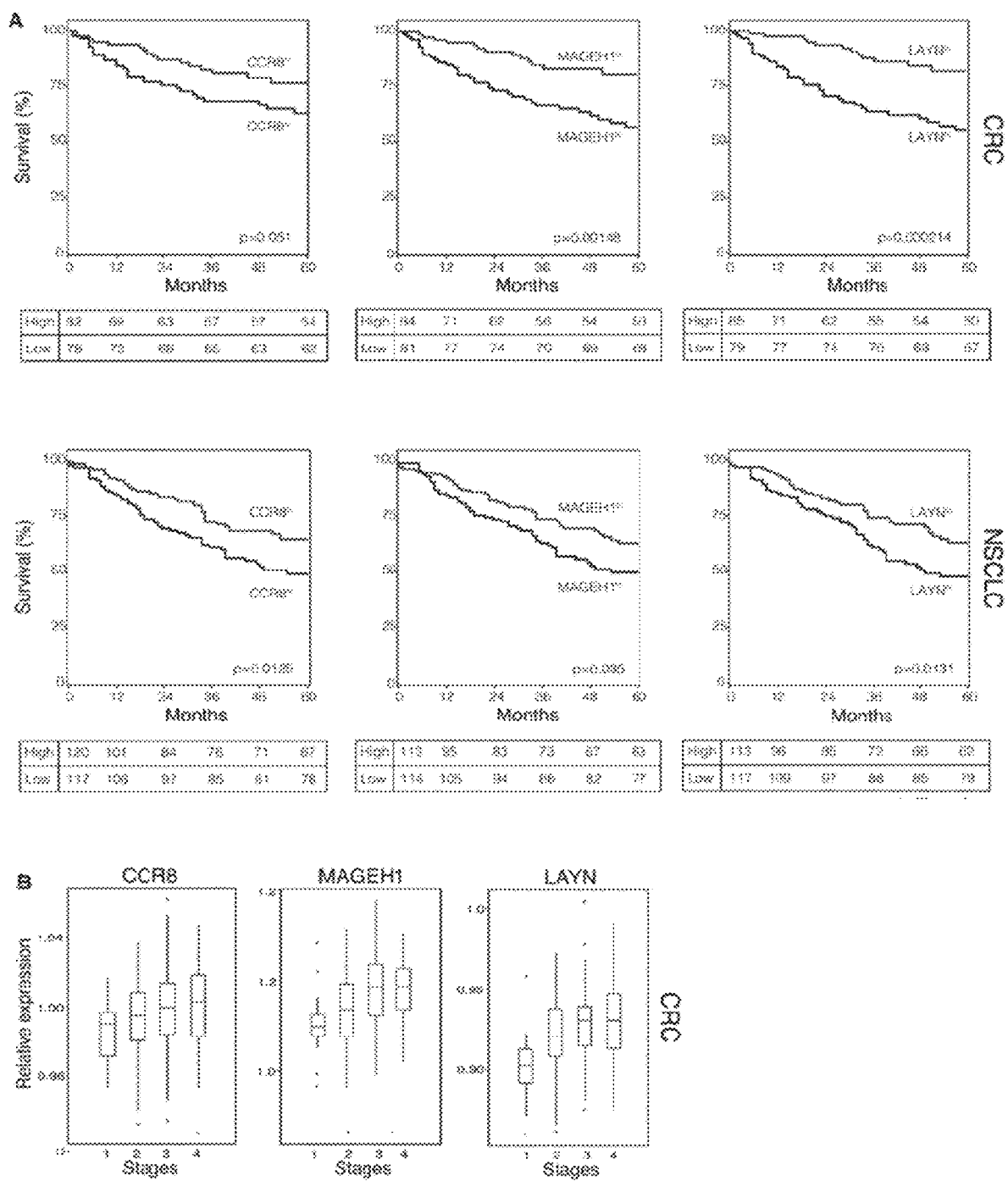

FIG. 5. Prognostic value of signature transcripts of tumor infiltrating Treg cells.
  (A) Kaplan-Meier survival curve comparing the high and low expression of the tumor Treg signature transcripts (CCR8, MAGEH1, LAYN) normalized to the CD3G for the CRC (n=177) and NSCLC (n=263) studies. Univariate analysis confirmed a significant difference in overall survival curve comparing patients with high and low expression. Statistical significance was determined by the log-rank test. (CRC: p=0.05 for CCR8, p=1.48×10-3 for MAGEH1, p=2.1×10-4 for LAYN; NSCLC: p=0.0125 for CCR8, p=0.035 for MAGEH1, p=0.0131 for LAYN) Each table depicts the Kaplan Meier estimates at the specified time points. (B) Expression distributions of CCR8, MAGEH1 and LAYN according to tumor staging at the time of surgery in the cohort of CRC patients. See also FIG. 9.

Figure 6:
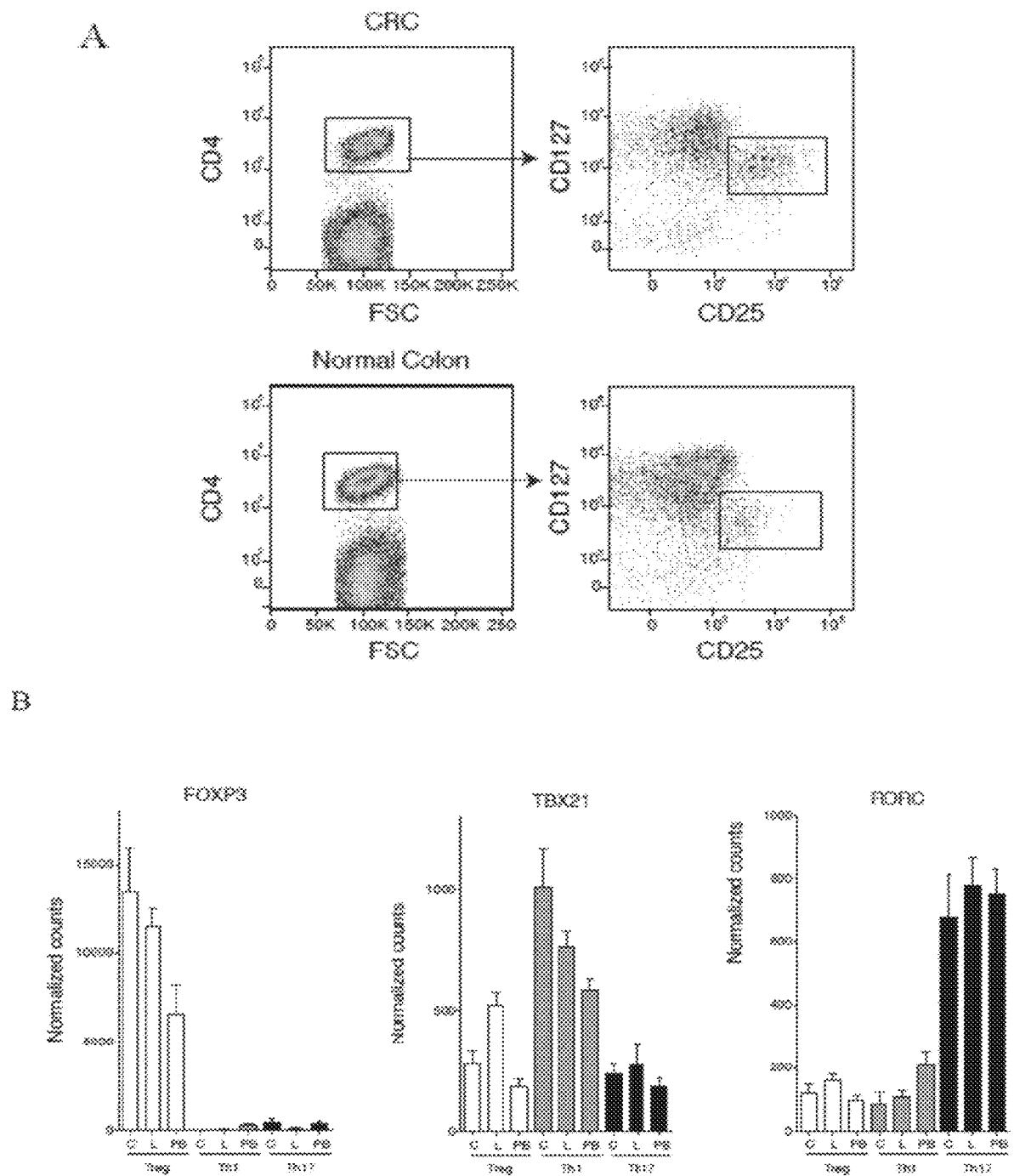
Figure 6:
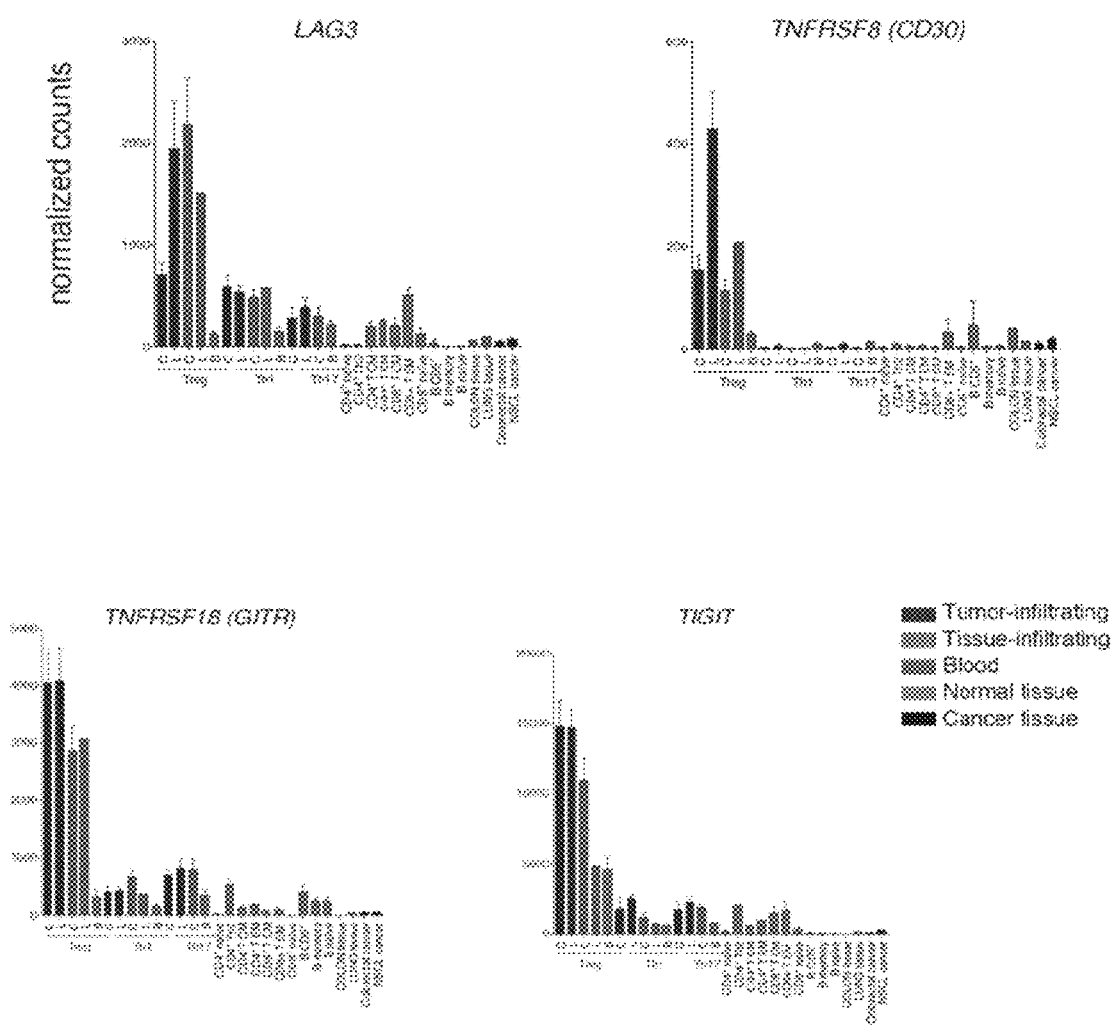
Figure 6:
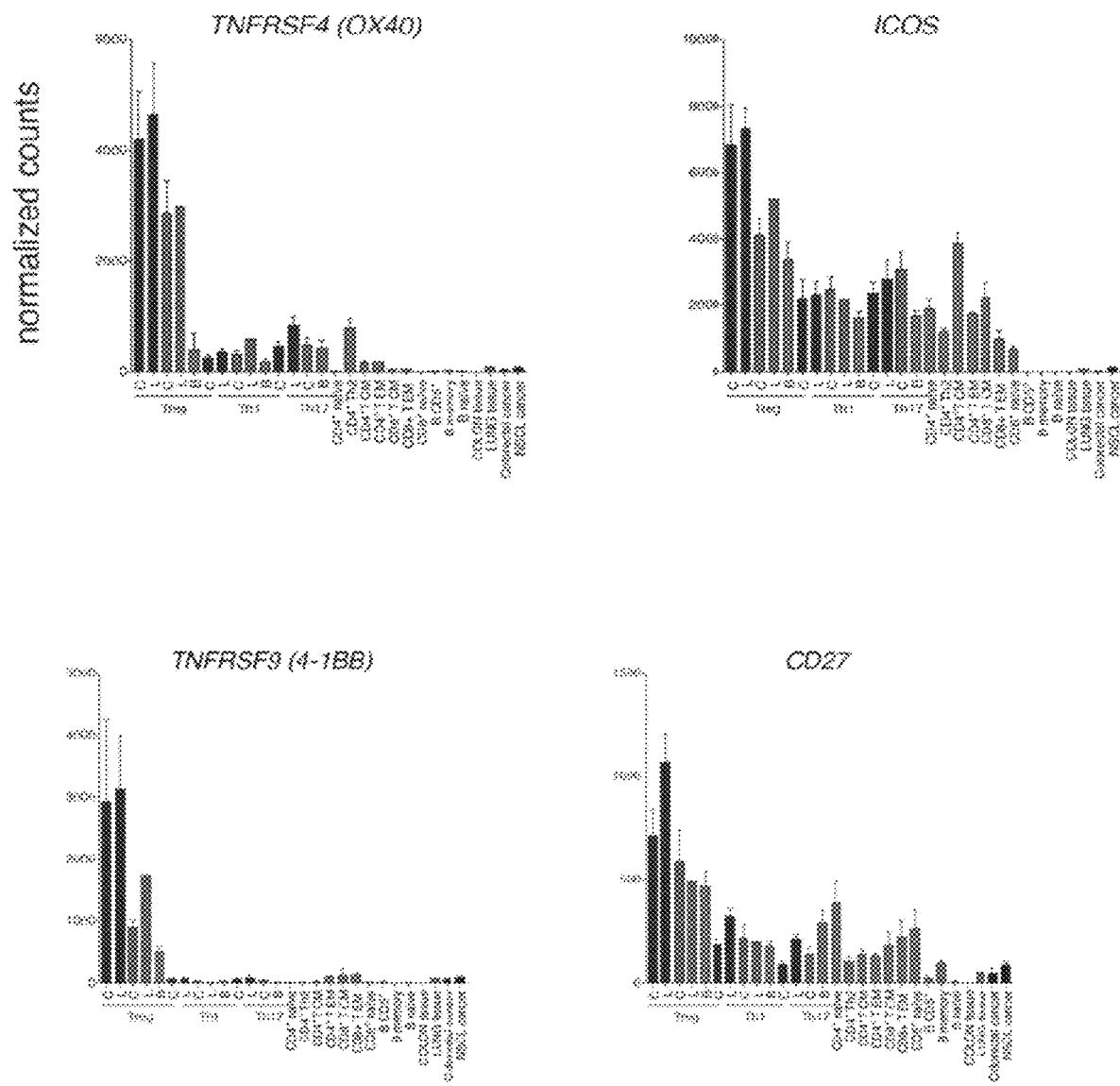
Figure 6:
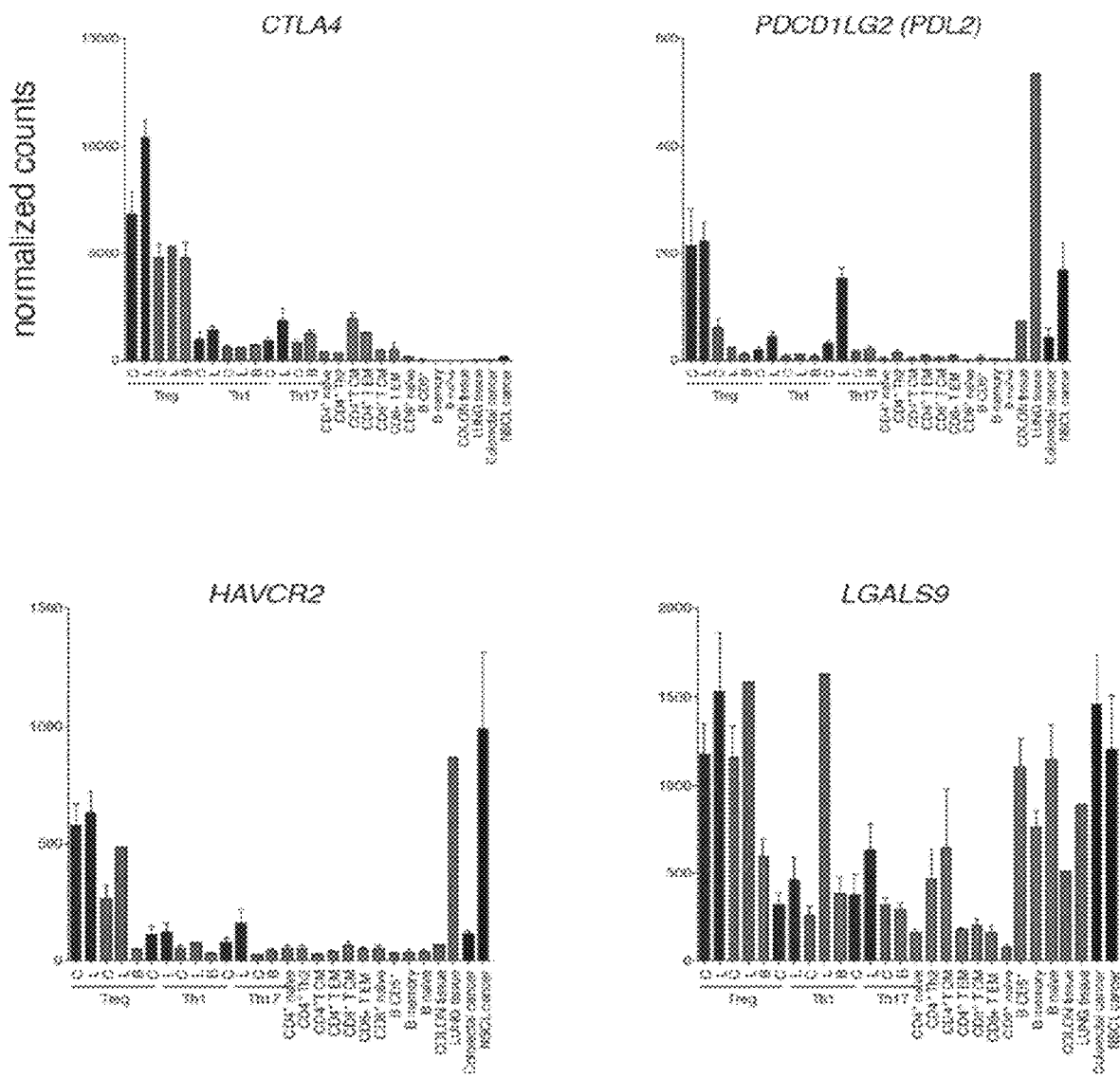
Figure 6:
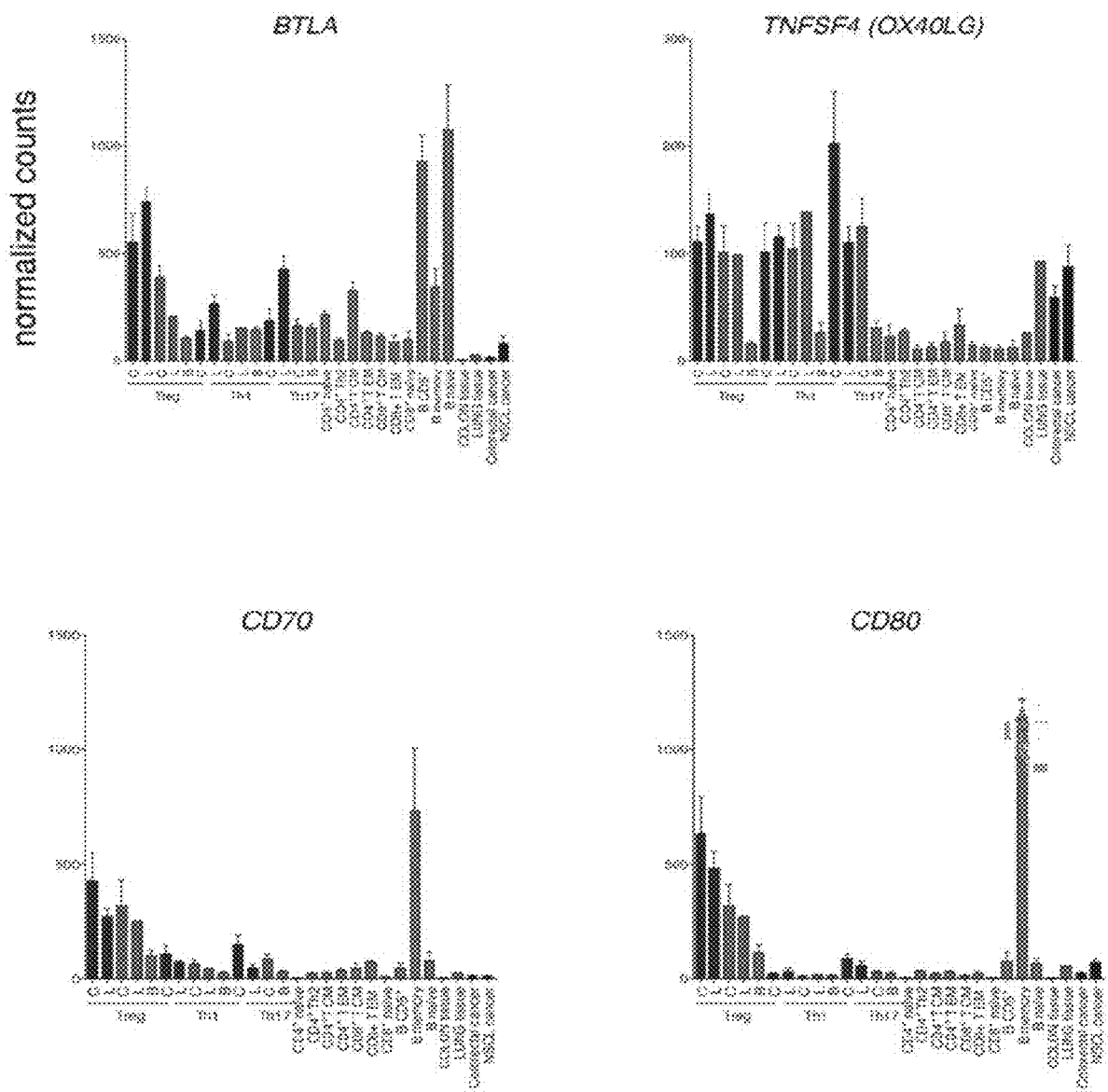

FIG. 6 related to FIG. 1. Transcriptome analysis of tumor infiltrating lymphocytes.
  (A) Representation of the sorting strategy of Treg cells infiltrating colorectal tumor or normal tissue.
  (B) RNA-seq expression values (normalized counts) of FOXP3, TBX21 and RORC in CD4+ Th1, Th17 and Treg cells from CRC (C), NSCLC (L) or peripheral blood (PB) of healthy donors.
  (C) RNA-seq normalized counts data for selected immune checkpoints and their ligands are shown as histogram plot. Cell population names are reported in the lower part of each graph, while gene names are shown in the upper part.

Figure 7:
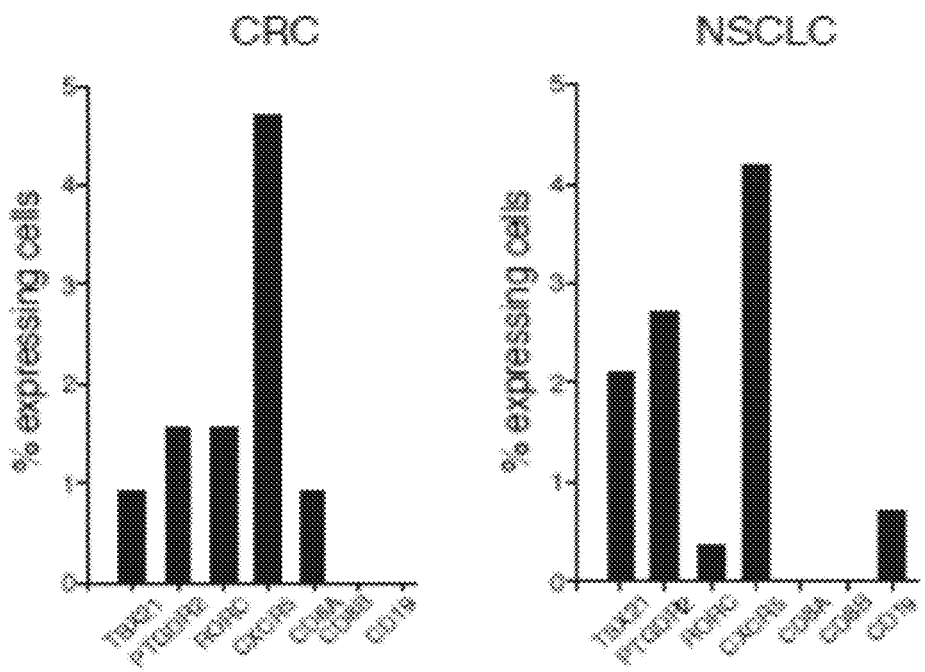

FIG. 7 related to FIG. 3. Single-cell analysis of tumor infiltrating Treg cells.
  Assessment of CD4+ Treg, Th1, Th17, Th2, CD8+ T cells and B cell markers expression (percentage of expressing cells) in single Treg cells purified from NSCLC and CRC.

Figure 8:
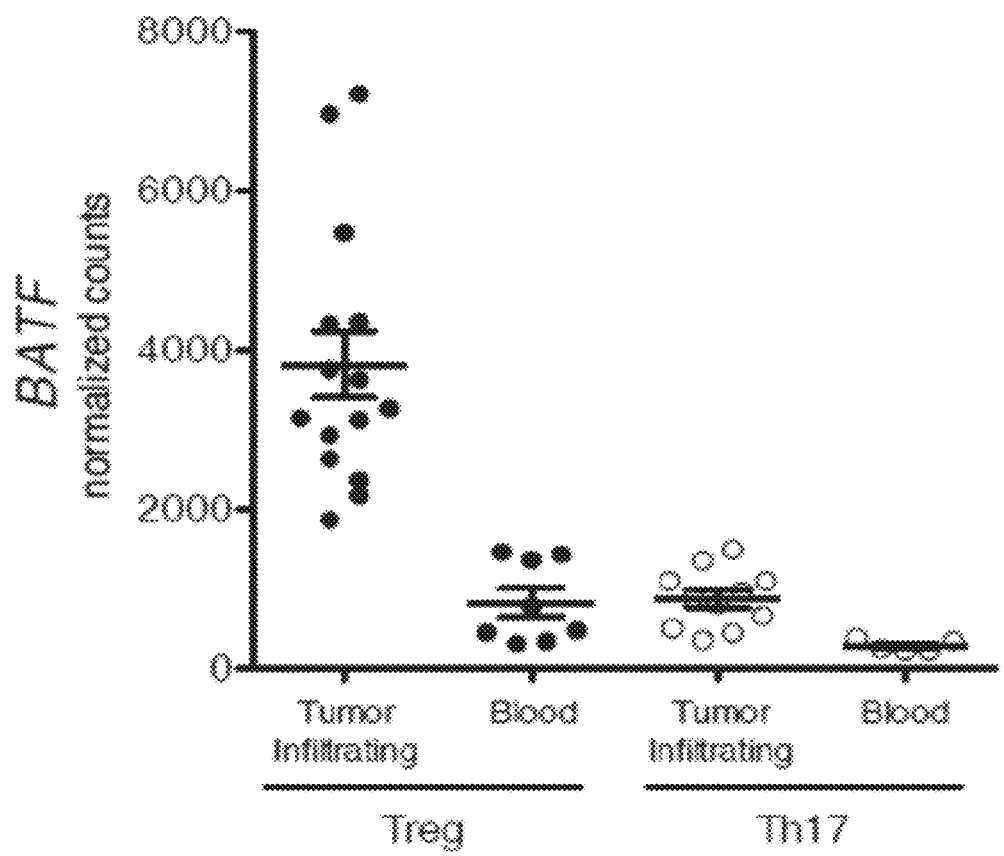

FIG. 8 related to FIG. 4. Comparison of BATF expression in CD4+ Treg vs Th17 cells.

Figure 9:
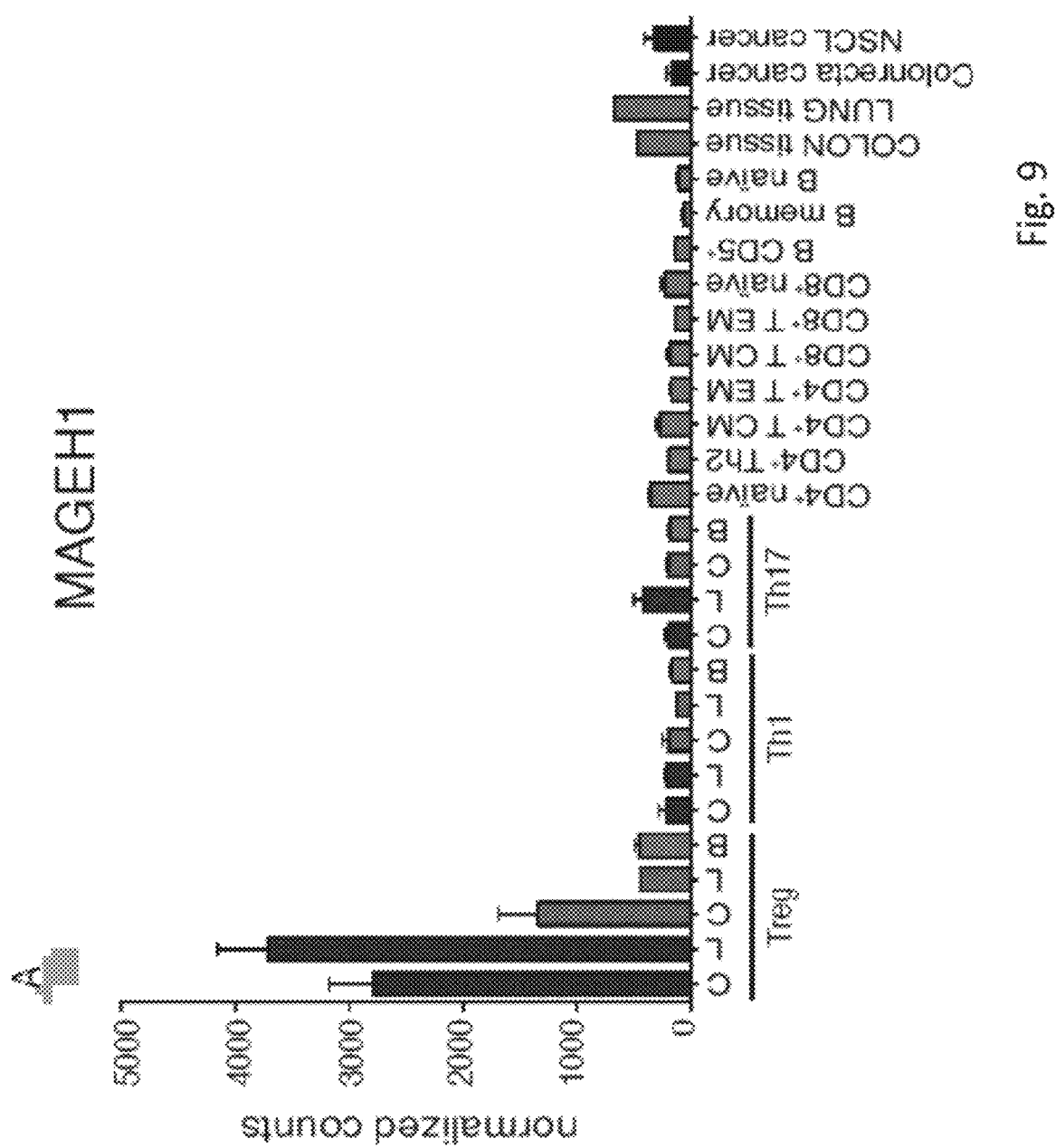
Figure 9:
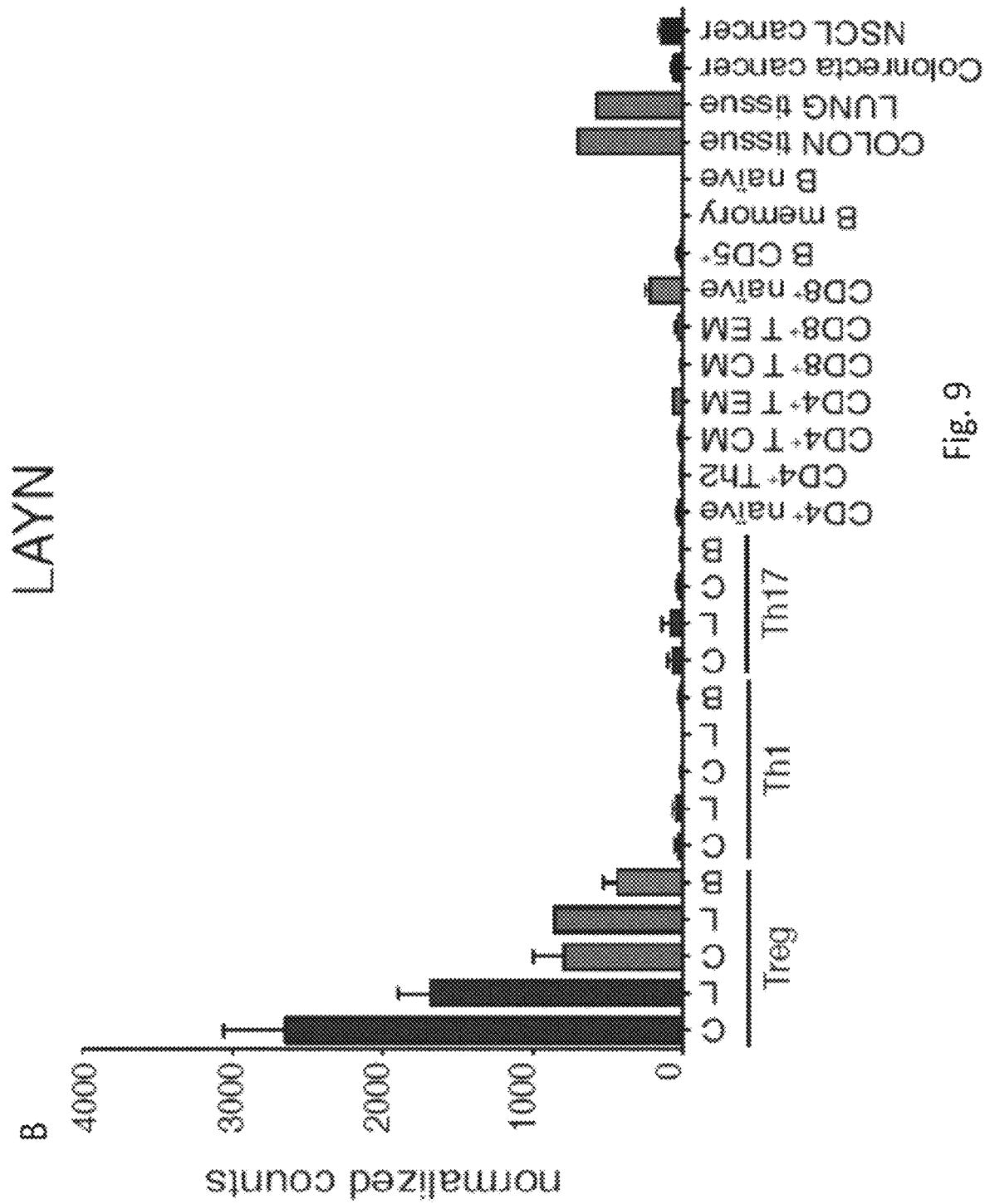
Figure 9:
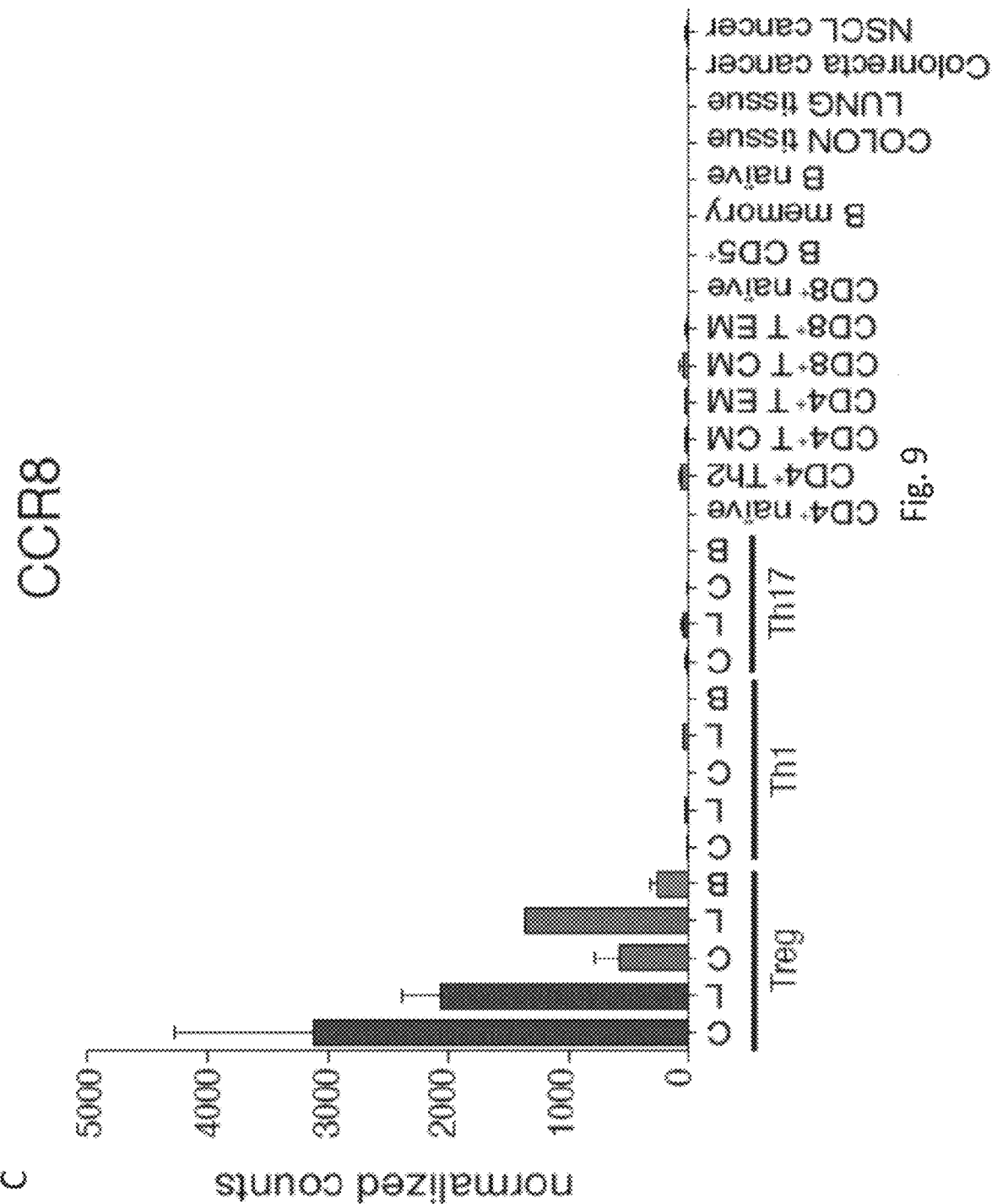

BATF expression levels (RNA-seq normalized counts data) in CD4+ Treg and Th17 subsets isolated from tumor tissue or peripheral blood FIG. 9 related to FIG. 5. Expression levels of tumour-infiltrating Treg signature genes.

RNA-seq normalized counts data of three tumour-infiltrating Treg signature genes (MAGEH1 (panel A), LAYN (panel B) and CCR8 (panel C)) across listed cell populations.

Figure 10:
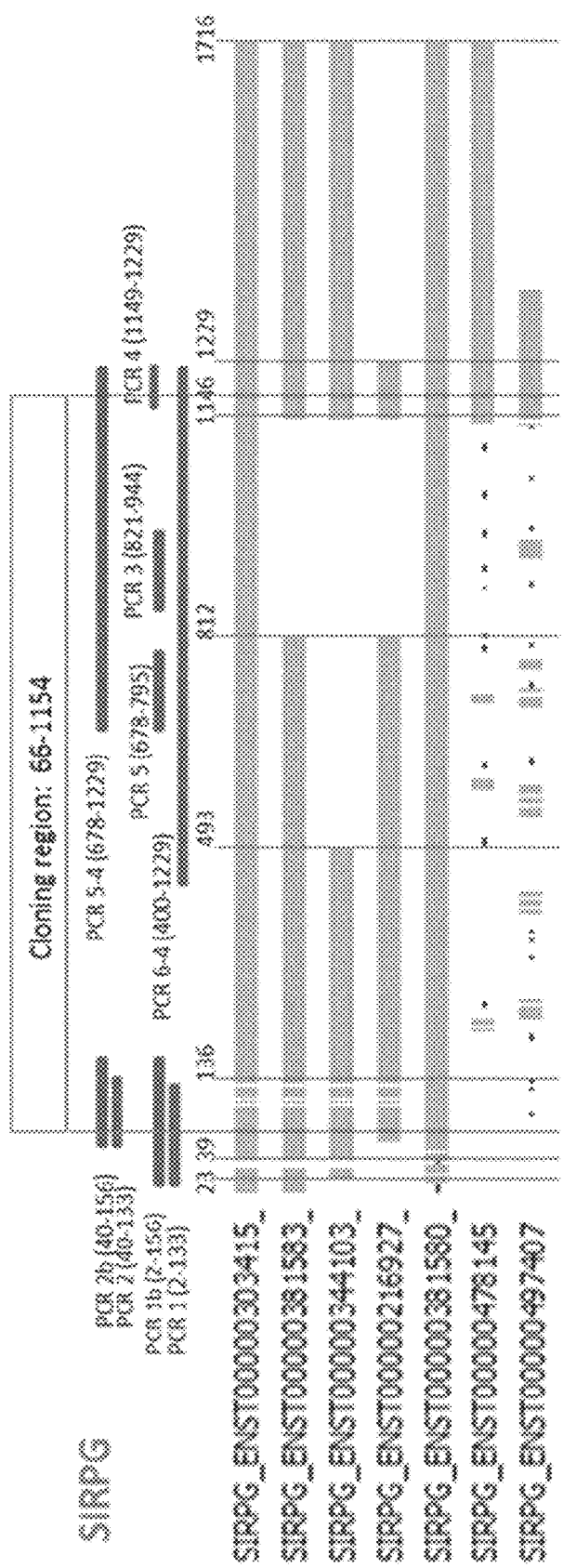
Figure 10:
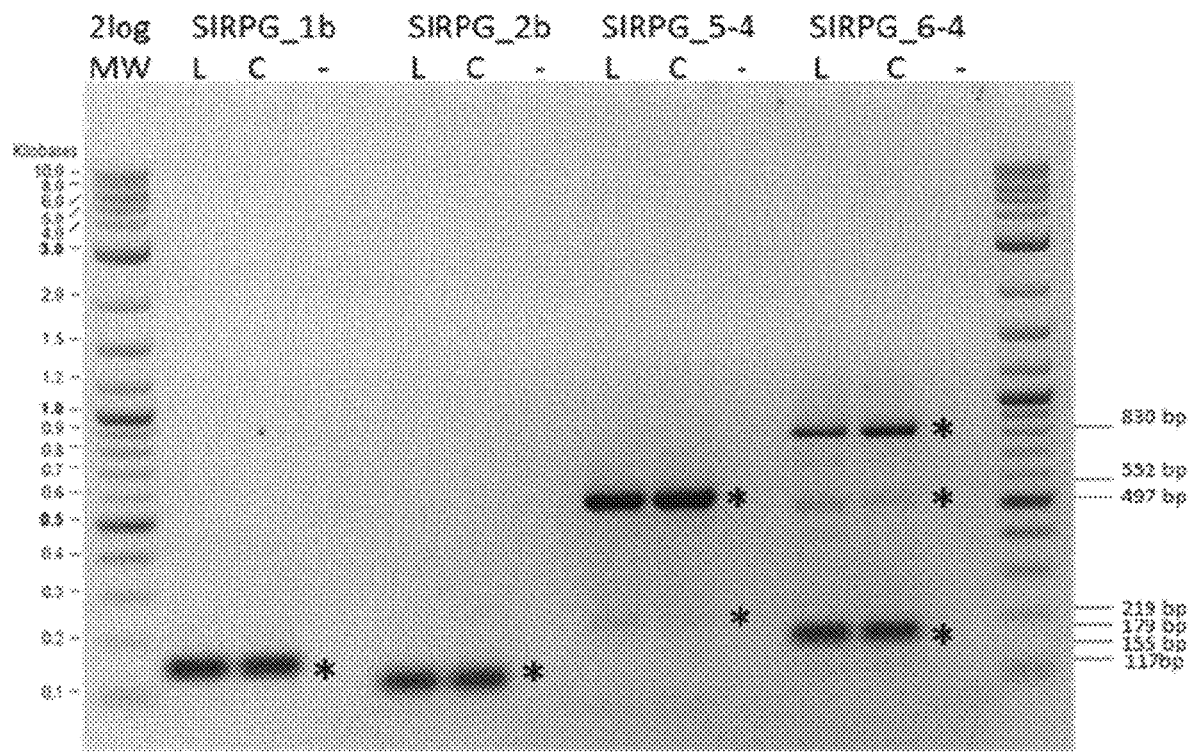

FIG. 10. Results of RT-PCR analysis done on cDNA from Tumor infiltrating Treg cells (L=NSCLC, C=CRC, -=ntc) with specific primers able to discriminate the different transcript isoforms annotated for SIRPG.

DETAILED DESCRIPTION OF THE INVENTION

Experimental Procedures

Human Primary Tissues

Primary human lung or colorectal tumors and non-neoplastic counterparts were obtained respectively from fifteen and fourteen patients who underwent surgery for therapeutic purposes at Fondazione IRCCS Ca' Granda, Policlinico or San Gerardo Hospitals (Italy). Records were available for all cases and included patients' age at diagnosis, gender, smoking habit (for lung cancer patients), clinicopathological staging (Sobin et al., 2009), tumor histotype and grade (Table II). No patient received palliative surgery or neoadjuvant chemo- and/or radiotherapy. Informed consent was obtained from all patients, and the study was approved by the Institutional Review Board of the Fondazione IRCCS Ca' Granda (approval n. 30/2014).

Non-small-cell lung cancer (NSCLC) were cut into pieces and single-cell suspensions were prepared by using the Tumor Dissociation Kit, human and the gentleMACS™ Dissociator (Miltenyi Biotech cat. 130-095-929) according to the accompanying standard protocol. Cell suspensions were than isolated by ficoll-hypaque density-gradient centrifugation (Amersham Bioscience). Colorectal cancer (CRC) specimens were cut into pieces and incubated in DTT 0.1 mM (Sigma-Aldrich) for 10 min, then extensively washed in HBSS (Thermo Scientific) and incubated in 1 mM EDTA (Sigma-Aldrich) for 50 min at 37° C. in the presence of 5% CO2. They were then washed and incubated in type D collagenase solution 0.5 mg/mL (Roche Diagnostic) for 4 h at 37° C. Supernatants containing tumor infiltrating lymphocytes were filtered through 100 µm cell strainer, centrifuged and fractionated 1800×g for 30 min at 4° C. on a four-step gradient consisting of 100%, 60%, and 40% and 30% Percoll solutions (Pharmacia). The T cell fraction was recovered from the inter-face between the 60% and 40% Percoll layers.

CD4 T cell subsets were purified by FACS sorting using the following fluorochrome conjugated antibodies: anti-CD4 APC/Cy7 (Biolegend clone OKT4), anti-CD27 Pacific Blue (Biolegend, clone M-T271), anti-IL7R PE (Milteniy, clone MB15-18C9), anti-CD25 PE/Cy7 (eBioscience, clone BC96), anti-CXCR3 PE/Cy5 (BD, clone 1C6/CXCR3), anti-CCR6 APC (Biolegend, clone G034E3) and anti-CCRS FITC (Biolegend, clone j418F1) using a FACSAria II (BD).

Flow Cytometry

To validate surface marker expression cells were directly stained with the following fluorochrome-conjugated antibodies and analyzed by flow cytometry: anti-CD4 (Biolegend, clone OKT4); anti-PD-L2 (Biolegend, Clone CL24F.10C12); anti-CD127 (eBioscience, clone RDR5); anti-BATF (eBioscience, clone MBM7C7), anti-GITR (eBioscience, clone eBIOAITR), anti-CD25 (Miltenyi, clone 4E3) and anti 4-1B (eBioscience clone 4B4) anti CCR8 (Biolegend clone L263G8) anti CD30 (eBioscience, clone Ber-H2) anti PD-L1 (Biolegend clone 29E.2A3) anti TIGIT (eBioscience, clone MBSA43) anti IL1 R2 (R and D clone 34141) IL21R (Biolegend clone 2G1-K12) anti OX40 (Biolegend clone Ber-ACT35). Intracellular staining was performed using eBioscience Foxp3 staining kit according to the manufactured's protocol (eBioscience cat 00-5523-00). Briefly cells were harvested and fixed for 30 min in fixation/permeabilization buffer at 4° C., and than stained with anti-FOXP3 antibody (eBioscience, clone 236A/E7) and anti-BATF (eBioscience clone MBM7C7) in permeabilisation buffer for 30 min at 4° C. Cells were then washed two times, resuspended in FACS washing buffer and analyzed by flow cytometry.

Suppression Assay.

$4 \times 10^4$ carboxyfluorescein diacetate succinimidyl ester (CFSE)-labeled (1 µM) responders Naive+ T cells from healthy donors were cocultured with different E/T ratio with unlabeled CD127-CD25$^{low}$CD4+ T cells sorted from TILs or PBMCs of patients with CRC or NSCLC, using FACS Aria II (BD Biosciences), in the presence of CD11c+CD1c+ dentritic cells as antigen-presenting cells and 0.5 mg/ml anti-CD3 (OKT3) mAb. Proliferation of CFSE-labeled cells was assessed by flow cytometry after 96 hr culture.

RNA Isolation and RNA Sequencing

RNA from tumor-infiltrating lymphocytes was isolated using mirVana Isolation Kit. Residual contaminating genomic DNA was removed from the total RNA fraction using Turbo DNA-free (Thermo Fisher). The RNA yields were quantified using the QuantiFluor RNA System (Promega) and the RNA quality was assessed by the Agilent 2100 Bioanalyzer (Agilent). Libraries for Illumina sequencing were constructed from 50 ng of total RNA with the Illumina TruSeq RNA Sample Preparation Kit v2 (Set A). The generated libraries were loaded on to the cBot (Illumina) for clustering on a HiSeq Flow Cell v3. The flow cell was then sequenced using a HiSeq 2500 in High Output mode (Illumina). A paired-end (2×125) run was performed.

RNA-Seq Data Analysis

Raw .fastq files were analyzed using FastQC v0.11.3, and adapter removal was performed using cutadapt 1.8. Cutadapt is run both for reverse and forward sequences with default parameters [- -anywhere <adapter1>- -anywhere <adapter2>- -overlap 10- -times 2- -mask-adapter]. Adapter sequences used for libraries preparation are

```
Adapter1:
                                   (SEQ ID NO: 710)
AGATCGGAAGAGCACACGTCTGAACTCCAGTCACNNNNNNNATCTCGTATG

CCGTCTTCTGCTTG

Adapter2:
                                   (SEQ ID NO: 711)
AGATCGGAAGAGCGTCGTGTAGGGAAAGAGTGTAGATCTCGGTGGTCGCC

GTATCATT
```

Trimming was performed on raw reads using Trimmomatic (Bolger et al., 2014): standard parameters for phred33 encoding were used: ILLUMINACLIP (LEADING:3 TRAILING:3 SLIDINGWINDOW:4:15), MINLEN parameter was set to 50.

Mapping and quantification: reads mapping to the reference genome (GRCh38) was performed on quality-checked and trimmed reads using STAR 2.4.1c: [STAR—genomeDir <index_star>—runThreadN<cpu_number>—readFilesIn <trimmed>_Rtfastq.gz<trimmed>_R2_P.fastq.gz—readFilesCommand zcat]. The reference annotation is Ensembl v80. The overlap of reads with annotation features found in the reference .gtf was calculated using HT-seq v0.6.1. The output computed for each sample (raw read counts) was then used as input for DESeq2 analysis. Raw counts were normalized using DESeq2's function 'rlog', and normalized counts were used to perform and visualize Principal Component Analysis (PCA) results (using DESeq2's 'plotPCA' function).

Differential expression analysis: differential expression analyses of tumor-infiltrating CD4+ Treg/Th1/Th17 subsets vs. CD4+ Treg/Th1/Th17 from PBMC were performed using DESeq2. Upregulated/downregulated genes were selected for subsequent analyses if their expression values were found to exceed the threshold of 0.05 FDR (Benjamini-Hochberg correction).

Capturing of Single Cells, Preparation of cDNA and Single-Cell PCR

Treg cells from 5 CRC and 5 NSCLC specimens were isolated as previously described (See also Table II). Single cells were captured on a microfluidic chip on the C1 System (Fluidigm) and whole-transcriptome amplified. cDNA was prepared on chip using the SMARTer Ultra Low RNA kit (Clontech). Cells were loaded onto the chip at a concentration of 3-5E5 cells/ml, stained for viability (LIVE/DEAD cell viability assay; Thermo Fisher) and imaged by phase-contrast and fluorescence microscopy to assess the number and viability of cells per capture site. Only single, live cells were included in the analysis. For qPCR experiments, harvested cDNA was pre-amplified using a 0.2×pool of primers prepared from the same gene expression assays to be used for qPCR.

Pre-amplification allows for multiplex sequence-specific amplification 78 targets. In detail, a 1.25 µl aliquot of single cell cDNA was pre-amplified in a final volume of 5 µl using 1 µl of PreAmp Master Mix (Fluidigm) and 1.25 µl pooled TaqMan assay mix (0.2×). cDNA went through amplification by denaturing at 95° C. for 15 s, and annealing and amplification at 60° C. for 4 min for 20 cycles. After cycling, pre-amplified cDNA was diluted 1:5 by adding 20 µl TE Buffer to the final 5 µl reaction volume for a total volume of 25 µl.

Single-cell gene expression experiments were performed using the 96×96 quantitative PCR (qPCR) DynamicArray microfluidic chips (Fluidigm). A 2.25 µl aliquot of amplified cDNA was mixed with 2.5 µl of TaqMan Fast Advanced Master Mix (Thermo Fisher) and 0.25 µl of Fluidigm's "sample loading agent," then inserted into one of the chip "sample" inlets. A 2.5 µl aliquot of each 20×TaqMan assay was mixed with 2.5 µl of Fluidigm's "assay loading agent" and individually inserted into one of the chip "assay" inlets. Samples and probes were loaded into 96×96 chips using an IFC Controller HX (Fluidigm), then transferred to a BioMark real-time PCR reader (Fluidigm) following manufacturer's instructions. A list of the 78 TaqMan assays used in this study is provided below.

TABLE V

Related to FIG. 3.
List of TaqMan Probes and assay number used in RT-qPCR single-cell experiments
Taqman Assays Numbers

| Gene Name | Assay Number | Gene Name | Assay Number |
|---|---|---|---|
| BCL2L1 | Hs00235329_m1 | ACP5 | Hs00356261_m1 |
| EOS | Hs00223842_m1 | BATF | Hs00232390_m1 |
| AHCYL1 | Hs00198382_m1 | SLC35F2 | Hs00233850_m1 |
| NFE2L3 | Hs00852569_m1 | LAX1 | Hs00214948_m1 |
| IL12RB2 | Hs00155486_m1 | CCR8 | Hs00174764_m1 |
| CD177 | Hs00360669_m1 | ADPRH | Hs00153890_m1 |
| OX40 | HS00937194_g1 | IKZF2 | Hs00212361_m1 |
| METTL7A | Hs00204042_m1 | C5F2RB | Hs00166144_m1 |
| ENTPD1 | HS00969339_m1 | NDFIP2 | Hs00324851_m1 |
| NFAT5 | Hs00232437_m1 | CADM1 | Hs00942508_m1 |
| CT9C | Hs00175188_m1 | ICOS | Hs00359999_m1 |
| SSH1 | Hs00368014_m1 | COL9A2 | Hs00156712_m1 |
| TMEM184C | Hs00217311_m1 | LTA | Hs00236874_m1 |
| HTATIP2 | Hs03091727_m1 | MAGEH1 | Hs00371974_s1 |
| HSDL2 | Hs00953689_m1 | IL21R | Hs00222310_m1 |
| FOXP3 | Hs01085834_m1 | S6TR3 | Hs01066399_m1 |
| IL2RA | Hs00907778_m1 | RNF145 | Hs01066399_m1 |
| LIMA1 | Hs01033646_m1 | LAPTM4B | Hs00363282_m1 |
| NAB1 | Hs00428619_m1 | GRSF1 | Hs00909877_m1 |
| ACSL4 | Hs00244871_m1 | ANKRD10 | Hs00214321_m1 |
| ERI1 | Hs00405251_m1 | NPTN | Hs01033353_m1 |
| FKEP1A | Hs00356621_g1 | HS3ST3B1 | Hs00797512_s1 |
| LEPROT | Hs00956627_s1 | TRAF3 | Hs00936781_m1 |
| NETO2 | Hs00983152_m1 | RRAGB | Hs01099787_m1 |
| VDR | Hs00172113_m1 | ZBT3S | Hs00257315_s1 |
| CSF1 | Hs00174164_m1 | TIGIT | Hs00545087_m1 |
| GITR | Hs00188346_m1 | TFRC | Hs00951083_m1 |
| IL1R2 | Hs01030384_m1 | JAK1 | Hs01026982_m1 |
| IL1R1 | Hs00991010_m1 | KSR1 | Hs00300134_m1 |
| LAYN | Hs00379511_m1 | ZNF202 | Hs00411965_m1 |
| THADA | Hs00736554_m1 | PTPRJ | Hs01119326_m1 |
| CTLA4 | Hs00175480_m1 | CHRNA6 | Hs02563909_s1 |
| CHST2 | Hs01921028_s1 | IL2RB | Hs01081597_m1 |
| CHST7 | Hs00219871_m1 | TBX21 | Hs00203436_m1 |
| LRBA | Hs01032231_m1 | RORC | Hs01076112_m1 |
| ETV7 | Hs00903229_m1 | CXCR5 | Hs00540548_s1 |
| LY75 | Hs00982383_m1 | CD8A | Hs00233520_m1 |
| ADAT2 | Hs00699339_m1 | CD8B | Hs00174762_m1 |
| GCNT1 | Hs00155243_m1 | PTGDR2 | Hs00173717_m1 |
| CASP1 | Hs00354836_m1 | CD19 | Hs01047410_g1 |

Single-cell data analysis: The Quality Threshold in the BioMark™ Analysis software is a qualitative tool designed to measure the "quality" of each amplification curve. Basically, each amplification curve is compared to an ideal exponential curve and as the quality score approaches 1 the closer it is to ideal. The further the curve is from ideal, its quality score approaches 0. The default cutoff of 0.65 is an arbitrary value set by Fluidigm. Any curve above 0.65 passes. Any curve below, fails. Baseline correction was set on Linear (Derivative)[default]. Ct Threshold Method was set on Auto (Detectors). This method independently calculates a threshold for each detector on a chip. For clustering and downstream analysis, raw Cts have been converted to Log 2Exp by using a Limit of Detection (LOD) of 35, which corresponds to the last PCR cycle. Co-expression analysis has been performed by considering both CRC and NSCLC samples on those genes for which both FOXP3 and IL2RA were co-expressed at least to 2%. Gene's levels above the background were depicted as violin plots after log 2 scale transformation by ggplot2 (v. 2.1.10). The violin color gradient is the percentage of cells that are expressing the gene of interest and the upper bound of the color scale is the maximum percentage of cells that express a gene of the whole geneset.

Procedure for the removal of transcripts whose expression values are affected by the 'dropout' effect. Single-cell qPCR data are inherently noisy, and due the limitations of current technologies the expression patterns of a certain number of genes may be affected by the 'dropout effect'. Inventors performed a gene selection procedure in order to take into account this 'dropout' effect and discard those genes whose expression values cannot be reliably used in a binary comparison (tumor-peripheral vs blood).

Inventors fitted a number of parametric distributions to the ratios of detected genes on the total number of tumor cells (both NSCLC and CRC) and selected the reciprocal inverse Gaussian continuous random variable as best fit.

Inventors then calculated the median value of the fitted distribution and discarded those genes whose detection ratio is less than this threshold value (at least 8.4% of detection).

Inventors reasoned that these genes are more likely to be affected by the 'dropout' effect. With this threshold inventors selected 45 genes for which a non-parametric T-test (Wilcoxon Mann Whitney test p<0.05) has been performed (by comparing tumor vs. peripheral blood samples).

Meta Analysis Kaplan-Meier and Stage Correlation

Statistical analysis was performed by using the R survival package (Therneau T. 2013). Survival times were calculated as the number of days from initial pathological diagnosis to death, or the number of days from initial pathological diagnosis to the last time the patient was reported to be alive. The Kaplan-Meier (KM) was used to compare the high and low expression levels of the tumor-Treg cell signature transcripts in either CRC (GSE17536) and NSCLC (GSE41271) patients. For both studies annotation was normalized to four tumor stages (1,2,3,4). For study GSE41271 five patients were excluded due to incomplete or inaccurate annotation (GSM1012883, GSM1012884, GSM1012885, GSM1013100, GSM1012888), retaining a total of two hundred and sixty three patients. Patients from both studies were labeled as 'High' 'Low' whether or not their relative expression values exceeded a decision boundary (mean of the samples). Inventors define $\tilde{x}_{ij}$ to denote the relative expression of the gene i for the n samples of the study normalized to the CD3 level:

$$\tilde{x}_{i,j} = \frac{x_{i,j}}{x_{CDBG,j}}; i = (CCR8, MAGEH1, LAYN) \; j = 1, 2, \ldots, n \text{ samples}$$

To classify a patient, a threshold on the is required and defined as $$T_{(Upper,Lower)} = \text{median}(\tilde{x}_{i,j}) \pm \frac{\sigma(\tilde{x}_{i,j})}{10}$$

where $T_{(Upper,Lower)}$ represent the upper and lower extreme of the decision boundary:

$$\begin{cases} \tilde{x}_{i,j} > T_{Upper} & \text{High} \\ \tilde{x}_{i,j} < T_{Lower} & \text{Low} \\ T_{Upper} \leq \tilde{x}_{i,j} \leq T_{Lower} & \text{excluded} \end{cases}$$

Inventors examined the prognostic significance of tumor Treg cells transcripts by using log-rank statistics; a p-value of less than 0.05 was considered statistically significant. Since the log-rank test resulted in a p-value of less than 0.05, a post stage comparison by means of box plot representation was performed in order to evaluate the correlation degree between the expression level of the transcripts and tumor stages in the cohort of CRC patients. The annotation was normalized to four tumor stages (1,2,3,4).

ACCESSION NUMBERS

The accession numbers for the present data are as follows: ENA: PRJEB11844 for RNA-seq tumor and tissue infiltrating lymphocytes; ArrayExpress: E-MTAB-2319 for RNA-seq human lymphocytes datasets; ArrayExpress: E-MTAB-513 for Illumina Human BodyMap 2.0 project; GEO: GSE50760 for RNA-seq datasets CRC; GEO: GSE40419 for RNA-seq datasets NSCLC; GEO: GSE17536 for CRC expression profiling by array; and GEO: GSE41271 for NSCLC expression profiling by array.

Prediction of Surface-Exposed and Membrane-Associated Proteins

The probability of surface exposure of the proteins encoded by the genes of interest was determined by a combination of four different cell localization prediction algorithms: Yloc (Briesemeister et al, 2010), TMHMM (http://www.cbs.dtu.dk/services/TMHMM/), SignalP (http://www.cbs.dtu.dk/services/SignalP/) and Phobius (Kali et. al, 2007). In particular Yloc is a interpretable system offering multiple predictive models in animal version; inventors used both YLoc-LowRes predicting into 4 location (nucleus, cytoplasm, mitochodrion, secretory pathway) and Yloc-HighRes predicting into 9 locations (extracellular space, plasma membrane, nucleus, cytoplasm, mitochodrion, endoplasmic reticulum, peroxisome, Golgi apparatus, and lysosome).

TMHMM and SignalP were developed by the bioinformatic unit of the technical University of Denmark for the prediction of transmembrane helices and the presence and location of signal peptide cleavage sites in amino acid sequences, respectively. Phobius is a combined transmembrane topology and signal peptide predictor.

RT-PCR Analysis of Transcript Isoforms Expressed by Tumor-Infiltrating Regulatory T Cells (Treg Cells)

Total RNA was extracted from tumor Treg cells (NSCLC or CRC) using miRCURY RNA isolation kit (Exiqon) and 1 µg was reverse transcribed with iScript reverse transcription supermix (BIORAD). Afterwards, 25 ng of cDNA were amplified with DreamTaq Green PCR Master Mix (ThermoScientific) using multiple gene-specific primers able to discriminate the different isoforms. PCR products were run on agarose gel. The expression of specific transcripts was assessed based on the expected band size.

Results

Tumor Infiltrating Tregs Cells Upregulate Immune Checkpoints and are Highly Suppressive To assess the gene expression landscape of tumor infiltrating $CD4^+$ T cells, the inventors isolated different $CD4^+$ lymphocytes subsets from two different tumors, NSCLC and CRC, from the adjacent normal tissues, and from peripheral blood samples. From all these tissues, the inventors purified by flow cytometry (FIGS. 1A and 6A and 6B) $CD4^+$ Treg (36 samples from 18 individuals), Th1 (30 samples from 21 individuals) and Th17 (22 samples from 14 individuals) cells (Table I and Table II).

TABLE 1

Purification and RNA-Sequencing of Human Primary Lymphocyte Subsets

| Tissue | Subset | Sorting Phenotype | Number of Samples | Mapped Reads (M) |
|---|---|---|---|---|
| NSCLC | CD4+ Treg | CD4+ CD127− CD25+ | 8 | 587 |
|  | CD4+ Th1 | CD4+ CXCR3+ CCR6− | 8 | 409 |
|  | CD4+ Th17 | CD4+ CCR6+ CXCR3− | 6 | 206 |
| CRC | CD4+ Treg | CD4+ CD127− CD25+ | 7 | 488 |
|  | CD4+ Th1 | CD4+ CXCR3+ CCR6− | 5 | 266 |
|  | CD4+ Th17 | CD4+ CCR6+ CXCR3− | 5 | 308 |
| Lung (normal tissue) | CD4+ Treg | CD4+ CD127− CD25+ | 1 (pool of 6) | 73 |
|  | CD4+ Th1 | CD4+ CXCR3+ CCR6− | 1 (pool of 6) | 76 |
| Colon (normal tissue) | CD4+ Treg | CD4+ CD127− CD25+ | 7 | 404 |
|  | CD4+ Th1 | CD4+ CXCR3+ CCR6− | 6 | 352 |
|  | CD4+ Th17 | CD4+ CCR6+ CXCR3− | 6 | 284 |
| PB (healthy donor) | CD4+ Treg | CD4+ CD127− CD25+ | 8 | 259 |
|  | CD4+ Th1 | CD4+ CXCR3+ CCR6− | 5 | 70 |
|  | CD4+ Th17 | CD4+ CCR6+ CXCR3− | 5 | 77 |

For each cell subsets profiled by RNA-sequencing tissue of origin, surface marker combinations used for sorting, number of profiled samples, as well as number of mapped sequencing reads are indicated. M, million; CRC, colorectal cancer; NSCLC, non-small cell lung cancer; PB, peripheral blood.

TABLE II related to Table I. Patients information and histological analysis. For each cell subset profiled by RNA-sequencing, patient records are shown including: age at diagnosis, gender, smoking habit (for lung cancer patients), clinicopathological staging (TNM classification) tumor histotype and grade. For Treg cell isolated for qPCR experiment the same information are available, including also the number of live cells captured from each tumor and available for single-cell analysis.

| NSCLC PATIENTS LIST (RNA SEQUENCING) | (T)Th1 | (T)Th17 | (T)Treg | (H)Th1 | (H)Th17 | (H)Treg | SMOKE HABIT | STATUS | GENDER |
|---|---|---|---|---|---|---|---|---|---|
| PATIENT1 |  |  | SQ_0342 |  |  |  | PREVIOUS SMOKER > 15 y | ALIVE | M |
| PATIENT2 |  |  | SQ_0339 |  |  |  | PREVIOUS SMOKER < 15 y | ALIVE | M |
| PATIENT3 | SQ_0365 | SQ_0375 |  |  |  |  | PREVIOUS SMOKER < 15 y | ALIVE | M |
| PATIENT4 | SQ_0366 | SQ_0374 | SQ_0341 |  |  |  | PREVIOUS SMOKER > 15 y | ALIVE | M |
| PATIENT5 | SQ_0364 | SQ_0373 |  | SQ_0350 |  | SQ_0351 | SMOKER | DEAD | M |
| PATIENT6 | SQ_0358 |  | SQ_0336 | SQ_0350 |  | SQ_0351 | PREVIOUS SMOKER < 15 y | ALIVE | M |
| PATIENT7 | SQ_0363 | SQ_0376 | SQ_0334 | SQ_0350 |  | SQ_0351 | PREVIOUS SMOKER < 15 y | ALIVE | M |
| PATIENT8 | SQ_0357 |  | SQ_0337 | SQ_0350 |  | SQ_0351 | PREVIOUS SMOKER < 15 y | ALIVE WITH RELAPSE | M |
| PATIENT9 | SQ_0404 | SQ_0408 | SQ_0398 | SQ_0350 |  | SQ_0351 | SMOKER | ALIVE | F |
| PATIENT10 | SQ_0403 | SQ_0407 | SQ_0396 | SQ_0350 |  | SQ_0351 | PREVIOUS SMOKER > 15 y | ALIVE | F |

| NSCLC PATIENTS LIST (RNA SEQUENCING) | AGE(y) | HISTOTYPE MAJOR | ADCA SUBTYPE (PRE-DOMINANT) | GRADE | pTNM: T | pTNM: N | pTNM: M | STAGE |
|---|---|---|---|---|---|---|---|---|
| PATIENT1 | 84 | SCC |  | G3 | 2b | 0 | 0 | IIA |
| PATIENT2 | 83 | SCC |  | G3 | 2a | 0 | 0 | IB |
| PATIENT3 | 72 | SCC |  | G3 | 2 | 2 | 0 | IIIA |
| PATIENT4 | 79 | SCC |  | G3 | 2a | 0 | 0 | IB |
| PATIENT5 | 66 | SCC |  | G3 | 3 | 2 | 0 | IIIA |
| PATIENT6 | 71 | SCC |  | G3 | 4 | 1 | 0 | IIIA |
| PATIENT7 | 78 | SCC |  | G3 | 2b | 1 | 0 | IB |
| PATIENT8 | 77 | ADCA | SOLID | G3 | 2 | 2 | 0 | IIIA |
| PATIENT9 | 69 | ADCA | SOLID | G3 | 1a | 0 | 0 | IA |
| PATIENT10 | 77 | ADCA | ACINAR | G3 | 1a | 0 | 0 | IA |

NSLC = Non Small Cell Lung Cancer
ADC = Adenocarcinoma
SCC = Squamous Cell Carcinoma
(T) = Tumor Sample
(H) = Healthy Tissue TABLE II-continued related to Table I. Patients information and histological analysis.
For each cell subset profiled by RNA-sequencing, patient records are shown including: age at diagnosis, gender, smoking habit (for lung cancer patients), clinicopathological staging (TNM classification) tumor histotype and grade. For Treg cell isolated for qPCR experiment the same information are available, including also the number of live cells captured from each tumor and available for single-cell analysis.

| TUMOR INFILTRATING TREG FROM NSCLC (SINGLE CELL qPCR) | SMOKE HABIT | STATUS | GENDER | AGE(y) | HISTO-TYPE MAJOR | ADCA SUBTYPE PREDOMINANT |
|---|---|---|---|---|---|---|
| PATIENT1 | NEVER SMOKER | ALIVE | F | 65 | ADCA | ACINAR and PAPILLARY |
| PATIENT2 | PREVIOUS SMOKER < 15 y | ALIVE | M | 62 | ADCA | SOLID |
| PATIENT3 | NEVER SMOKER | ALIVE | F | 63 | ADCA | ACINAR |
| PATIENT4 | SMOKER | ALIVE | M | 66 | SCC | |
| PATIENT5 | SMOKER | ALIVE | M | 68 | SCC | |

| TUMOR INFILTRATING TREG FROM NSCLC (SINGLE CELL qPCR | GRADE | pTNM: T | pTNM: N | pTNM: M | STAGE | CAPTURED SINGLE CELLS |
|---|---|---|---|---|---|---|
| PATIENT1 | G2 | 2a | 0 | 0 | IB | 71 |
| PATIENT2 | G2 | 1b | 0 | 0 | IA | 61 |
| PATIENT3 | G1 | 1a | 0 | 0 | IA | 44 |
| PATIENT4 | G2 | 2a | 0 | 0 | IB | 55 |
| PATIENT5 | G3 | 1b | 0 | 0 | IA | 55 |

NSLC = Non Small Cell Lung Cancer
ADC = Adenocarcinoma
SCC = Squamous Cell Carcinoma
(T) = Tumor Sample
(H) = Healthy Tissue

| CRC PATIENTS LIST (RNA SEQUENCING) | (T) Th1 | (T) Th17 | (T) Treg | (H) Th1 | (H) Th17 | (H) Treg | GENDER |
|---|---|---|---|---|---|---|---|
| PATIENT1 | | | SQ_0389 | SQ_0386 | SQ_0387 | SQ_0388 | M |
| PATIENT2 | SQ_0427 | SQ_0434 | | | | SQ_0418 | F |
| PATIENT3 | SQ_0423 | SQ_0436 | SQ_0411 | | | | M |
| PATIENT4 | SQ_0426 | SQ_0437 | SQ_0413 | SQ_0428 | SQ_0439 | SQ_0417 | M |
| PATIENT5 | SQ_0425 | | SQ_0412 | SQ_0429 | SQ_0441 | SQ_0422 | M |
| PATIENT6 | SQ_0424 | | SQ_0415 | SQ_0431 | SQ_0442 | SQ_0421 | M |
| PATIENT7 | | SQ_0435 | SQ_0416 | SQ_0432 | SQ_0438 | SQ_0420 | F |
| PATIENT8 | | | SQ_0414 | | | | F |
| PATIENT9 | | SQ_0433 | | SQ_0430 | SQ_0440 | SQ_0419 | M |

| CRC PATIENTS LIST (RNA SEQUENCING) | AGE(y) | HISTO-TYPE MAJOR | GRADE | pTNM: T | pTNM: N | pTNM: M | STAGE |
|---|---|---|---|---|---|---|---|
| PATIENT1 | 76 | ADC | G2 | 3 | 1A | 0 | IIIB |
| PATIENT2 | 68 | ADC | G2 | 3 | 0 | 0 | IIA |
| PATIENT3 | 80 | ADC | G2 | 4B | 1B | 0 | IIIB |
| PATIENT4 | 79 | ADC | G2 | 3 | 1A | 0 | IIIB |
| PATIENT5 | 78 | ADC | G2 | 3 | 0 | 0 | IIA |
| PATIENT6 | 69 | MUC ADC | — | 3 | 1B | 0 | IIIB |
| PATIENT7 | 84 | ADC | G2 | 4B | 0 | 0 | IIC |
| PATIENT8 | 75 | MUC ADC | — | 3 | 1C | 0 | IIIB |
| PATIENT9 | 54 | ADC | G2 | 2 | 0 | 0 | I |

ADC = Adenocarcinoma
MUC ADC = Mucinous Adenocarcinoma
CRIB ADC = Cribrous Adenocarcinoma
(T) = Subsets purified from Tumor Sample
(H) = Subsets purified from Healthy Tissue TABLE II-continued related to Table I. Patients information and histological analysis.
For each cell subset profiled by RNA-sequencing, patient records are shown including: age at diagnosis,
gender, smoking habit (for lung cancer patients), clinicopathological staging (TNM classification) tumor
histotype and grade. For Treg cell isolated for qPCR experiment the same information are available,
including also the number of live cells captured from each tumor and available for single-cell analysis.

| TUMOR INFILTRATING TREG FROM CRC (SINGLE CELL qPCR) | GENDER | AGE(y) | HISTO-TYPE MAJOR | GRADE | pTNM: T |
|---|---|---|---|---|---|
| PATIENT1 | M | 64 | ADC | 2 | 3 |
| PATIENT2 | M | 59 | CRIB ADC | — | 3 |
| PATIENT3 | F | 75 | MUC ADC | — | 4A |
| PATIENT4 | M | 71 | ADC | 1 | 3 |
| PATIENT5 | M | 64 | ADC | 2 | 3 |

| TUMOR INFILTRATING TREG FROM CRC (SINGLE CELL qPCR) | pTNM: N | pTNM: M | STAGE | CAPTURED SINGLE CELLS |
|---|---|---|---|---|
| PATIENT1 | 0 | 0 | IIA | 62 |
| PATIENT2 | 0 | 0 | IIA | 66 |
| PATIENT3 | 2B | 0 | IIIC | 65 |
| PATIENT4 | 0 | 0 | IIA | 63 |
| PATIENT5 | 0 | 0 | IIA | 64 |

ADC = Adenocarcinoma
MUC ADC = Mucinous Adenocarcinoma
CRIB ADC = Cribrous Adenocarcinoma
(T) = Subsets purified from Tumor Sample
(H) = Subsets purified from Healthy Tissue CRC: colorectal cancer;
NSCLC: non-small cell lung cancer;
(T): Tumor Sample;
(H): Healthy Tissue;
ADC: Adenocarcinoma;
SCC: Squamous Cell Carcinoma;
MUC ADC: Mucinous Adenocarcinoma.

To assess Treg cell function, inventors tested their suppressor activity and showed that Treg cells infiltrating either type of tumor tissues have a remarkably stronger suppressive activity in vitro compared to Treg cells isolated from the adjacent normal tissue and peripheral blood of the same patients (FIG. 1B).

The polyadenylated RNA fraction extracted from the sorted CD4+ Treg, Th1, and Th17 cells was then analyzed by pair-end RNA sequencing obtaining about 4 billion mapped "reads" (Table I). First, inventors interrogated RNA-sequencing data of CD4+ T cells infiltrating both CRC and NSCLC and their matched normal tissues, to quantitate mRNA expression of known immune checkpoints and their ligands. Second, inventors analyzed RNA-seq data of CRC and NSCLC, as well as of normal colon and lung samples.

Inventors found that several immune checkpoints and their ligands transcripts were strikingly upregulated in tumor infiltrating Treg cells compared to both normal tissue and peripheral blood-derived Treg cells, as well as to T and B lymphocyte subsets purified from peripheral blood mononuclear cells (PBMCs) (FIGS. 1C and 6C and Table III).

Table III related to FIG. 1. Expression levels of immune checkpoints genes in all the subsets analyzed.

| GENE NAME | Treg_Tumor_ Infiltrating CRC | Treg_Tumor_ Infiltrating NSCLC | Treg_Tissue_ Infiltrating Colon | Treg_Tissue_ Infiltrating Lung | Treg healthy Peripheral Blood |
|---|---|---|---|---|---|
| ADORA2A | 14.69 | 24.06 | 17.97 | 44.84 | 18.52 |
| BTLA | 554.04 | 742.11 | 389.51 | 208.76 | 108.2 |
| BTNL2 (BTLN2) | 0 | 0.14 | 0.29 | 0 | 0.75 |
| C10orf54 (VISTA) | 779.38 | 872.36 | 555.47 | 1405.63 | 1111.37 |
| CD160 | 58.39 | 38.24 | 51.87 | 34.54 | 36.55 |
| CD200 | 268.39 | 283.21 | 282.05 | 104.64 | 99.59 |
| CD200R1 | 95.89 | 136.08 | 81.36 | 349.99 | 59.03 |
| CD244 | 34.46 | 31.21 | 29.59 | 128.35 | 47.8 |
| CD27 | 710.13 | 1068.55 | 583.58 | 496.38 | 468.93 |
| CD274 (PD-L1) | 1050.94 | 645.66 | 576.59 | 390.71 | 120.19 |

-continued

| GENE NAME | Treg_Tumor_Infiltrating CRC | Treg_Tumor_Infiltrating NSCLC | Treg_Tissue_Infiltrating Colon | Treg_Tissue_Infiltrating Lung | Treg healthy Peripheral Blood |
|---|---|---|---|---|---|
| CD276 | 16.85 | 72.3 | 10.44 | 65.98 | 3.61 |
| CD28 | 4770.41 | 4585.17 | 5446.29 | 3687.01 | 5179.32 |
| CD40 | 112.04 | 161.29 | 80.64 | 93.3 | 34.71 |
| CD40LG | 135.51 | 143.07 | 360.09 | 418.55 | 104.22 |
| CD44 | 13049.36 | 8518.98 | 13513.69 | 19851 | 16013.71 |
| CD48 | 346.61 | 489.78 | 494.58 | 594.83 | 1523.63 |
| CD70 | 426.35 | 269.38 | 318.97 | 249.48 | 101.67 |
| CD80 | 632.12 | 483.34 | 318.48 | 269.06 | 114.41 |
| CD86 | 29.52 | 78.86 | 52.72 | 278.86 | 3.87 |
| CTLA4 | 6798.82 | 10378.3 | 4810.74 | 5340.06 | 4806.23 |
| HAVCR2 (TIM-3) | 577.57 | 633.27 | 265.84 | 487.62 | 49.81 |
| HHLA2 | 3.41 | 3.66 | 4.47 | 9.28 | 12.7 |
| ICOS | 6830.94 | 7339.08 | 4119.2 | 5211.71 | 3398.28 |
| ICOSLG (B7RP1) | 58.02 | 8.86 | 59.13 | 33.5 | 76.5 |
| IDO1 | 3.86 | 83.81 | 9.51 | 5.15 | 2.36 |
| IDO2 | 0.22 | 2.25 | 1.41 | 5.15 | 1.58 |
| KIR3DL1 (KIR) | 0.38 | 0.43 | 0.28 | 4.64 | 0.9 |
| LAG3 | 705.14 | 1956.22 | 2181.52 | 1505.63 | 127.02 |
| LAIR1 | 277.06 | 194.09 | 551.94 | 874.72 | 346.22 |
| LGALS9 (Galectin-9) | 1175.81 | 1530.47 | 1160.89 | 1593.26 | 592.56 |
| NRP1 | 7.38 | 36.24 | 8.89 | 106.7 | 8.59 |
| PDCD1LG2 (PD-L2) | 214.51 | 223.04 | 61.89 | 25.77 | 12.12 |
| PDCD1 (PD1) | 467.22 | 496.56 | 405.01 | 676.27 | 111.26 |
| TIGIT | 14821.45 | 14747.79 | 10986.74 | 4901.41 | 4611.14 |
| TMIGD2 | 28.38 | 16.64 | 78.3 | 75.77 | 71.27 |
| TNFRSF14 (HVEM) | 2230.85 | 2677.32 | 2297.43 | 2675.7 | 2274.82 |
| TNFRSF18 (GITR) | 4038.86 | 4078.14 | 2871.78 | 3071.57 | 333.36 |
| TNFRSF25 | 5236.86 | 4188.61 | 4986.56 | 5111.71 | 3587.58 |
| TNFRSF4 (OX40) | 4222.16 | 4642.56 | 2873.16 | 2992.18 | 400.56 |
| TNFRSF8 (CD30) | 155.59 | 430.23 | 115.57 | 208.24 | 30.89 |
| TNFRSF9 (4-1BB) | 2921.72 | 3128.82 | 898.69 | 1739.13 | 502.86 |
| TNFSF14 (LIGHT) | 148.57 | 183.77 | 223.49 | 421.12 | 105.12 |
| TNFSF15 | 1.58 | 3.75 | 0.89 | 25.77 | 1.23 |
| TNFSF18 | 0.4 | 1.11 | 0.53 | 0 | 0.45 |
| TNFSF4 (OX40LG) | 110.82 | 136.82 | 100.95 | 98.97 | 16.33 |
| TNFSF9 (CD137L) | 26.79 | 19.48 | 19.72 | 29.9 | 7.41 |
| VTCN1 (B7-H4) | 1.12 | 4.49 | 1.48 | 1.55 | 2.65 |

RNA-seq normalized counts data for selected immune checkpoints genes and their ligands in all the subsets analyzed.

These findings highlight the specific expression patterns of immune checkpoints and their ligands in tumor infiltrating Treg and effector cells and suggest that their functional relevance should be investigated directly at tumor sites.

Tumor-Infiltrating Treg Cells Express a Specific Gene Signature

The inventors then asked whether tumor infiltrating Treg cells could be defined by specific gene expression patterns.

To identify signature transcripts of tumor-infiltrating Treg cells, the inventors included in the expression pattern analyses the transcriptome dataset they previously obtained from different T and B lymphocyte subsets purified from PBMCs (Ranzani et al., 2015). In so doing, the inventors obtained a signature of 328 transcripts whose expression is higher in tumor infiltrating Treg cells (Wilcoxon Mann Whitney test p<2.2×10-16) (FIG. 2, and Table IV compared to the other lymphocyte subsets purified from non-tumoral tissues and from PBMCs of healthy or neoplastic patients.

Table IV related to FIG. 2. Expression levels of tumor-infiltrating Treg gene signatures in all the subsets analysed.

Normalized expression values of tumour-infiltrating Treg signature gnees across listed cell populations.

| Gene Name | Treg_Tumor_ Infiltrating CRC | Treg_Tumor_ Infiltrating NSCLC | Treg_Tissue_ Infiltrating Colon | Treg_Tissue_ Infiltrating Lung | Treg healthy Peripheral Blood |
|---|---|---|---|---|---|
| AC019206.1 | 15.41 | 8.72 | 12.89 | 12.04 | 29.46 |
| ACAA2 | 305.76 | 499.02 | 497.41 | 526.58 | 614.28 |
| ACOT9 | 918.3 | 803.71 | 1361.82 | 2180.66 | 1272.07 |
| ACOX3 | 183.48 | 384.73 | 469.06 | 506.97 | 439.27 |
| ACP5 | 267.7 | 837.72 | 859.77 | 1872.29 | 1483.27 |
| ACSL4 | 1154.87 | 1384.88 | 1903.56 | 2170.94 | 2043.91 |
| ACTA2 | 86.65 | 270.74 | 108.76 | 234.86 | 232.15 |
| ACTG2 | 10.69 | 6.16 | 22.68 | 21.11 | 36.14 |
| ADAM10 | 2378.26 | 3051.7 | 2545.29 | 3600.38 | 3167.56 |
| ADAT2 | 927.45 | 1272.17 | 1214.4 | 2094.25 | 3103.21 |
| ADPRH | 136.34 | 460.61 | 352.57 | 836.7 | 718.74 |
| AHCYL1 | 914.19 | 1271.5 | 1269.55 | 1835.94 | 1711.94 |
| AHCYL2 | 305.15 | 570.67 | 525.24 | 790.1 | 856.25 |
| AKAP5 | 174.24 | 264 | 358.75 | 709.28 | 535.97 |
| AKIP1 | 261.47 | 273.85 | 225.25 | 436.84 | 360.48 |
| ANKRD10 | 2251.92 | 3433.73 | 2805.08 | 4192.8 | 4672.81 |
| ARHGEF12 | 1371.05 | 2064.05 | 1536.04 | 3069.77 | 2637.79 |
| ARHGEF4 | 19.42 | 71.47 | 28.87 | 195.02 | 252.84 |
| ARL6IP5 | 3008.69 | 4385.74 | 4051.43 | 4983.16 | 4712.48 |
| ARNTL2 | 20.4 | 201.3 | 281.95 | 560.77 | 445.13 |
| ATP13A3 | 3776.14 | 4020.7 | 4688.02 | 6688.94 | 6967.94 |
| ATP2C1 | 1491.87 | 1399.81 | 1553.57 | 2029.41 | 1819.78 |
| AURKA | 24.56 | 50.12 | 79.89 | 66.37 | 87.07 |
| BATF | 820.97 | 3325.93 | 1698.92 | 5052.64 | 2727.65 |
| BCL2L1 | 212.64 | 478.8 | 537.61 | 554.11 | 892.28 |
| BIRC5 | 14.74 | 20.27 | 20.62 | 25.03 | 44.99 |
| C17orf96 | 19 | 174.31 | 159.79 | 239.88 | 377.03 |
| C5orf63 | 146.45 | 201.44 | 112.88 | 228.2 | 357.09 |
| CABLES1 | 59.04 | 196.68 | 125.77 | 473.94 | 386.73 |
| CACNB2 | 67.43 | 50.49 | 40.21 | 169.83 | 105.62 |
| CADM1 | 113.76 | 602.72 | 115.46 | 1766.12 | 901.32 |
| CALM3 | 2474.48 | 2829.3 | 2675.18 | 2954.03 | 4107.03 |
| CARD16 | 370.31 | 696.36 | 493.29 | 1220.7 | 823.89 |
| CARD17 | 41.87 | 96.94 | 54.12 | 101.19 | 132.95 |
| CASP1 | 925.29 | 1453.84 | 1521.09 | 2028.95 | 1980.45 |
| CASQ1 | 52.11 | 31.21 | 24.74 | 135.08 | 174.95 |
| CCNB2 | 18.28 | 27.62 | 34.02 | 51.57 | 58.08 |
| CCR8 | 255.66 | 578.27 | 1355.63 | 3127.33 | 2069.11 |
| CD177 | 2.36 | 204.74 | 299.99 | 718.58 | 470.27 |
| CD27 | 468.93 | 583.58 | 496.38 | 710.13 | 1068.55 |
| CD274 | 120.19 | 576.59 | 390.71 | 1050.94 | 645.66 |
| CD7 | 1622.12 | 6900.01 | 2829.82 | 9053.96 | 6919.59 |
| CDCA2 | 19.24 | 35.09 | 49.48 | 68.21 | 49.95 |
| CDH24 | 57.67 | 57.11 | 89.69 | 148.93 | 105.02 |
| CDK6 | 602.97 | 2175.36 | 2463.85 | 3580.4 | 3238.58 |
| CEACAM1 | 360.01 | 340.84 | 326.28 | 381.79 | 732.86 |
| CENPM | 43,72 | 39.12 | 61.85 | 72.94 | 61.32 |
| CEP55 | 56.18 | 88.17 | 223.71 | 220.17 | 273.64 |
| CGA | 1.08 | 13.59 | 22.68 | 334.28 | 9.73 |
| CHRNA6 | 14.46 | 218.49 | 67.52 | 336.38 | 504.28 |
| CHST11 | 1822.7 | 2085.92 | 2806.19 | 2790.19 | 2535.23 |
| CHST2 | 75.46 | 218.75 | 156.7 | 458.24 | 604.97 |
| CHST7 | 141.3 | 341.87 | 426.79 | 1087.21 | 333.3 |
| CIT | 89.25 | 105.13 | 155.15 | 150.2 | 262.67 |
| CLNK | 153.06 | 288.36 | 248.96 | 340.12 | 528.54 |
| CNIH1 | 1028.31 | 1005.46 | 935.03 | 2336.95 | 1101.87 |
| COL9A2 | 149.87 | 278.77 | 357.72 | 889.47 | 805.72 |
| CORO1B | 481.34 | 667.37 | 861.83 | 774.65 | 1040.47 |
| COX10 | 305.31 | 399.33 | 397.93 | 447.17 | 612.29 |
| CRADD | 77.04 | 155.66 | 277.31 | 394.31 | 306.61 |
| CREB3L2 | 739.04 | 1289.66 | 1415.94 | 2984.54 | 2590.37 |
| CSF1 | 313.09 | 1629.13 | 1609.75 | 2204.79 | 3288.67 |
| CSF2RB | 1069.75 | 1275.49 | 1290.69 | 2036.76 | 2531.99 |
| CTLA4 | 4806.23 | 4810.74 | 5340.06 | 6798.82 | 10378.3 |
| CTSC | 1026.76 | 2196.93 | 2514.88 | 3030.74 | 2767.27 |
| CTTNBP2NL | 85 | 200.53 | 248.45 | 500.75 | 267.16 |
| CX3CR1 | 9.57 | 63.99 | 123.71 | 341.79 | 293.28 |
| CXCL13 | 1.07 | 255.23 | 1145.33 | 1270.98 | 11433.26 |
| CYB5B | 714.26 | 1129.39 | 947.4 | 1156.4 | 1221.22 |
| CYP7B1 | 9.83 | 210.33 | 29.38 | 186.99 | 161.17 |
| DCPS | 153.25 | 210.26 | 210.82 | 191.31 | 271.71 |
| DFNB31 | 561.87 | 1636.56 | 1727.79 | 4251.83 | 2526.15 |
| DIRAS3 | 1.9 | 4.59 | 3.61 | 26.01 | 35.64 |
| DLGAP5 | 7.89 | 14.46 | 20.62 | 27.41 | 49.7 |
| DNPH1 | 160.15 | 650.05 | 321.13 | 683.55 | 576.77 |
| DOC2B | 10.47 | 3.42 | 5.15 | 14.23 | 238.86 |
| DPYSL2 | 208.98 | 189.08 | 580.4 | 591.32 | 618.42 |

-continued

| Gene Name | Treg_Tumor_Infiltrating CRC | Treg_Tumor_Infiltrating NSCLC | Treg_Tissue_Infiltrating Colon | Treg_Tissue_Infiltrating Lung | Treg healthy Peripheral Blood |
|---|---|---|---|---|---|
| EBI3 | 7.47 | 103.59 | 56.7 | 148.96 | 200.74 |
| ECEL1 | 3.7 | 150.7 | 34.02 | 199.17 | 794.51 |
| EGLN1 | 977.29 | 969.32 | 1021.11 | 1381.2 | 1271.06 |
| EML2 | 861.51 | 1601.25 | 1643.25 | 2156.04 | 1957.43 |
| ENTPD1 | 752.88 | 2078.17 | 1447.38 | 4321.79 | 4162.57 |
| ERI1 | 354.33 | 862.86 | 932.45 | 1200.06 | 1070.15 |
| ETFA | 414.08 | 586.15 | 534.01 | 615.35 | 689.14 |
| ETV7 | 93.62 | 511.26 | 361.85 | 728.85 | 1111.55 |
| EVA1B | 21.39 | 35.63 | 26.8 | 42.86 | 47.36 |
| F5 | 2343.39 | 2346.94 | 2499.41 | 4868.41 | 4729.97 |
| FAAH2 | 244.19 | 431.76 | 209.27 | 737.44 | 699.42 |
| FAIM2 | 15.05 | 33.47 | 57.21 | 69.26 | 117.28 |
| FAM184A | 192.41 | 742.47 | 525.24 | 706.33 | 891.02 |
| FAM19A2 | 311.38 | 204.56 | 302.57 | 264.46 | 748.09 |
| FAM98B | 314.26 | 664.69 | 491.22 | 698.92 | 657.42 |
| FAS | 2337.14 | 5167.46 | 2712.81 | 5982.39 | 3656.21 |
| FBXO45 | 460.56 | 783.06 | 631.43 | 964.13 | 894.23 |
| FCRL3 | 1161.64 | 1997.02 | 938.63 | 3281.36 | 2699.01 |
| FKBP1A | 733.83 | 1240.62 | 1174.19 | 1377.67 | 1578.09 |
| FLNB | 1671.04 | 1363.04 | 1394.81 | 3395.38 | 2307.44 |
| FLVCR2 | 69.84 | 579.55 | 388.13 | 744.8 | 528.01 |
| FNDC3B | 377.47 | 501.27 | 506.17 | 1111.07 | 531.12 |
| FOXA1 | 2.7 | 11.87 | 17.01 | 70.68 | 18.22 |
| FOXM1 | 56.39 | 74.94 | 108.24 | 88.16 | 125.31 |
| FOXP3 | 6586.98 | 10713.12 | 6060.66 | 13483.77 | 11472.41 |
| FUCA2 | 107.56 | 175.46 | 160.82 | 249.54 | 315.45 |
| GADD45A | 745.14 | 1431.9 | 884.51 | 3681.24 | 1396.98 |
| GCNT1 | 99.22 | 632.16 | 608.75 | 1133.62 | 845.83 |
| GK | 637.31 | 1994.73 | 2430.34 | 5200.55 | 2065.35 |
| GLB1 | 563.96 | 819.22 | 873.17 | 1077.84 | 854.94 |
| GLCCI1 | 1557.57 | 3211.73 | 1753.04 | 3189.77 | 2909.06 |
| GLDC | 19.25 | 20.56 | 25.26 | 31.21 | 74.61 |
| GLRX | 1213.06 | 1251.64 | 1512.85 | 1764.61 | 1872 |
| GNG4 | 5.08 | 79.18 | 64.43 | 197.1 | 343.93 |
| GNG8 | 11.94 | 63.28 | 10.82 | 67.63 | 175.16 |
| GRSF1 | 1277.4 | 1725.67 | 1397.9 | 2899.76 | 2343.4 |
| GSK3B | 1099.5 | 1267.18 | 1208.73 | 1333.16 | 1454.67 |
| GTF3C6 | 313.17 | 579.04 | 445.86 | 617.48 | 597.55 |
| GTSF1L | 13.67 | 20.36 | 15.46 | 44.6 | 99.03 |
| HADHB | 1179.61 | 1207.14 | 1287.59 | 1396.89 | 1521.16 |
| HAP1 | 92.39 | 180.51 | 74.22 | 292.97 | 577 |
| HAVCR2 | 49.81 | 265.84 | 487.62 | 577.57 | 633.27 |
| HECW2 | 17.63 | 98.93 | 38.66 | 111.21 | 177.5 |
| HIBCH | 124.32 | 290.04 | 226.8 | 348.34 | 332.88 |
| HIVEP3 | 358.34 | 649.68 | 893.27 | 1091.96 | 1316.89 |
| HJURP | 8.55 | 18.52 | 15.98 | 27.13 | 39.99 |
| HOXA1 | 16.66 | 15.22 | 14.95 | 25.57 | 44.75 |
| HPRT1 | 442.58 | 532.66 | 542.25 | 811.75 | 724.15 |
| HPSE | 248.88 | 676.54 | 515.45 | 674.09 | 754.04 |
| HS3ST3B1 | 1222.43 | 1930.88 | 1980.87 | 2609.49 | 2431.83 |
| HSDL2 | 242.56 | 611.72 | 285.56 | 785.27 | 921.97 |
| HTATIP2 | 567.61 | 1439.29 | 997.4 | 3285.86 | 1576.24 |
| ICA1 | 94.65 | 371.57 | 113.91 | 487.68 | 411.64 |
| ICOS | 3398.28 | 4119.2 | 5211.71 | 6830.94 | 7339.08 |
| IGFLR1 | 67.43 | 78.13 | 92.78 | 108.12 | 185.13 |
| IKZF2 | 6061.48 | 6317.6 | 4919.45 | 9983.52 | 8551.49 |
| IKZF4 | 1422.66 | 2362.49 | 1258.21 | 3745.25 | 3958.19 |
| IL12RB2 | 120.8 | 369.84 | 509.78 | 835.92 | 877.51 |
| IL17REL | 9.74 | 23.21 | 34.02 | 52.62 | 57.04 |
| IL1R1 | 506.51 | 9670.81 | 2766.42 | 7852.18 | 5585.89 |
| IL1R2 | 41.72 | 1225.4 | 526.79 | 2117.34 | 1793.21 |
| IL1RL1 | 17.37 | 135.26 | 44.33 | 715.42 | 71.67 |
| IL1RL2 | 8.65 | 76.53 | 28.35 | 74.81 | 59.47 |
| IL21R | 708.61 | 1355.83 | 1715.93 | 3092.3 | 3514.36 |
| IL2RA | 5244.31 | 9685.38 | 5627.68 | 11454.42 | 12731.31 |
| IL2RB | 6716.4 | 14249.6 | 12502.75 | 17733 | 18564.35 |
| IL32 | 4332.08 | 13202.73 | 9755.92 | 11766.98 | 13883.45 |
| IL7 | 117.66 | 230.78 | 165.97 | 257.71 | 178.1 |
| INPP1 | 124.25 | 497.01 | 312.88 | 458.2 | 487.93 |
| INPP5F | 787.92 | 2172.55 | 830.9 | 2189.48 | 1549.46 |
| ISOC1 | 233.44 | 329.49 | 400.5 | 514.43 | 335.93 |
| ITFG1 | 313.34 | 324.11 | 402.05 | 396.94 | 511.86 |
| JAK1 | 10779.78 | 11919.66 | 10072.4 | 17755.9 | 11521.32 |
| JAKMIP1 | 291.14 | 387.49 | 1063.89 | 756.36 | 953.47 |
| KAT2B | 3145.05 | 3910.01 | 4756.57 | 5520.88 | 4632.76 |

| Gene Name | Treg_Tumor_Infiltrating CRC | Treg_Tumor_Infiltrating NSCLC | Treg_Tissue_Inflitrating Colon | Treg_Tissue_Inflitrating Lung | Treg healthy Peripheral Blood |
|---|---|---|---|---|---|
| KIF14 | 20.18 | 25.43 | 31.96 | 36.73 | 59.61 |
| KIF15 | 20.64 | 29.67 | 51.03 | 41.9 | 68.63 |
| KIF20A | 9.84 | 14.93 | 7.22 | 20.97 | 32.72 |
| KLHDC7B | 131.39 | 211.42 | 188.65 | 245.3 | 394.73 |
| KSR1 | 837.87 | 1569.86 | 1176.77 | 2241.36 | 1847.72 |
| LAPTM4B | 86.42 | 369.78 | 181.44 | 938.88 | 738.38 |
| LAX1 | 1135.24 | 1155.91 | 1406.15 | 1721.7 | 1854.78 |
| LAYN | 441.73 | 796.76 | 859.25 | 2650.24 | 1681.25 |
| LEPR | 58.77 | 130.22 | 129.38 | 137.47 | 237.88 |
| LEPROT | 614.73 | 860.55 | 676.79 | 1044.66 | 1296.13 |
| LHFP | 1.58 | 10.38 | 9.79 | 18.09 | 63.16 |
| LIMA1 | 404.55 | 727.57 | 1017.5 | 1064.46 | 1570.15 |
| LMCD1 | 115.76 | 104.74 | 112.37 | 257.92 | 404.7 |
| LOC388813 | 7.42 | 45.99 | 28.87 | 86.3 | 60.63 |
| LRG1 | 17.67 | 61.54 | 46.39 | 71.6 | 78.3 |
| LRRC61 | 98.78 | 291.45 | 138.66 | 292.51 | 314.79 |
| LTA | 214.07 | 516.57 | 270.61 | 351.26 | 747.01 |
| LXN | 67.37 | 91.06 | 75.77 | 114.23 | 133.43 |
| LY75 | 249.92 | 970.85 | 680.91 | 1302.79 | 1624.82 |
| MAGEH1 | 461.13 | 1349.51 | 448.96 | 2800.36 | 3719.29 |
| MALT1 | 3362.14 | 3568.46 | 2743.74 | 5892.86 | 4776.24 |
| MAP1LC3A | 70,92 | 110,44 | 119,07 | 272,07 | 169,3 |
| MAP3K5 | 1865.12 | 2189.99 | 1787.06 | 2822.55 | 2265.54 |
| MAST4 | 1053.08 | 2239.36 | 2198.39 | 3373.36 | 1855.42 |
| MAT2B | 2305.62 | 4050.5 | 2959.2 | 4435.41 | 4159.25 |
| MCCC2 | 737.75 | 875.78 | 873.69 | 1018.1 | 1245.79 |
| MELK | 28.77 | 50.08 | 83.5 | 72.28 | 83.06 |
| METTL7A | 280.99 | 442.99 | 385.04 | 845.09 | 1671.74 |
| METTL8 | 318.99 | 882.21 | 377.82 | 880.99 | 1413.12 |
| MGME1 | 236.76 | 332.08 | 342.77 | 400.19 | 552.69 |
| MGST2 | 54.22 | 87.18 | 69.59 | 147.04 | 148.13 |
| MICAL2 | 354.6 | 1601.79 | 1813.35 | 1910.22 | 3188.92 |
| MINPP1 | 85.19 | 204.32 | 211.85 | 243.22 | 290.02 |
| MKI67 | 192.68 | 206.77 | 518.03 | 372.61 | 650.04 |
| MREG | 120.75 | 119.91 | 226.28 | 229.41 | 325.33 |
| MYL6B | 122.13 | 182.71 | 107.73 | 174.22 | 252.52 |
| MYO5C | 95.68 | 122.36 | 157.21 | 130.81 | 347.49 |
| NAB1 | 508.21 | 973.74 | 1261.31 | 1831.77 | 1227.51 |
| NCALD | 111.73 | 163.32 | 272.67 | 283.43 | 370.26 |
| NCAM1 | 7.88 | 58.27 | 39.69 | 207.45 | 213.23 |
| NCF4 | 509.63 | 630.55 | 880.39 | 894.67 | 1176.84 |
| NCOA1 | 2088.38 | 2062.57 | 1941.7 | 2367.54 | 2618.11 |
| NDFIP2 | 77.99 | 529.73 | 618.54 | 829.53 | 987.25 |
| NEMP2 | 382.56 | 478.4 | 475.76 | 565.18 | 634.41 |
| NETO2 | 145.84 | 559.95 | 773.69 | 1490.82 | 1137.73 |
| NEURL3 | 4.04 | 29.74 | 12.37 | 24.02 | 35.49 |
| NFAT5 | 2075.17 | 3880.92 | 3923.6 | 4786.04 | 5295.06 |
| NFE2L3 | 279.28 | 590.19 | 560.29 | 743.24 | 1114.26 |
| NFYC | 588.49 | 713.51 | 756.16 | 733.52 | 798.27 |
| NHS | 7.27 | 18.73 | 55.15 | 60.16 | 159.44 |
| NPTN | 525.86 | 838.02 | 897.91 | 1007.87 | 969.1 |
| NTNG2 | 117.04 | 296.81 | 534.52 | 669.43 | 1001.58 |
| NTRK1 | 20.85 | 27.9 | 155.15 | 88.29 | 161.78 |
| NUSAP1 | 199.28 | 266.11 | 445.86 | 635.51 | 365.17 |
| NXT2 | 221.6 | 263.39 | 226.8 | 285.15 | 302.01 |
| OSBP2 | 111.03 | 89.82 | 127.83 | 195.47 | 244.93 |
| PAK2 | 4621.62 | 6173.86 | 5024.6 | 7194.78 | 6376.28 |
| PAM | 582.52 | 904.05 | 1069.56 | 1365.03 | 1631.64 |
| PANX2 | 3.7 | 76.02 | 15.46 | 97.12 | 71.72 |
| PAQR4 | 16.99 | 46.54 | 62.37 | 92.6 | 65.27 |
| PARD6G | 55.86 | 172.18 | 249.99 | 546.52 | 182.4 |
| PARK7 | 1271.06 | 1563.96 | 1283.47 | 1764.8 | 1764.91 |
| PCTP | 49.2 | 173.47 | 163.4 | 253.27 | 270.62 |
| PDCD1LG2 | 12.12 | 61.89 | 25.77 | 214.51 | 223.04 |
| PDGFA | 6.19 | 38.74 | 159.79 | 154.17 | 153.03 |
| PEX3 | 179.31 | 239.78 | 205.66 | 326.61 | 291.17 |
| PGM2 | 316.91 | 419.51 | 454.63 | 471.89 | 487.85 |
| PHKA1 | 8.59 | 19.98 | 28.87 | 107.79 | 109.7 |
| PIGU | 147.54 | 205.18 | 184.53 | 220.25 | 265.12 |
| PLA2G4C | 22.16 | 128.81 | 65.98 | 245.65 | 159.6 |
| PPM1G | 1974.96 | 2324.16 | 2563.85 | 2751.69 | 2598.5 |
| PRDX3 | 466.56 | 854.12 | 745.34 | 890.58 | 1052.67 |
| PRKCDBP | 4.45 | 6.8 | 19.07 | 28.51 | 27.92 |
| PROB1 | 53.7 | 140.39 | 109.79 | 177.19 | 272.89 |
| PTGIR | 96.17 | 147.61 | 107.21 | 214.61 | 449.25 |

| Gene Name | Treg_Tumor_Infiltrating CRC | Treg_Tumor_Infiltrating NSCLC | Treg_Tissue_Infiltrating Colon | Treg_Tissue_Infiltrating Lung | Treg healthy Peripheral Blood |
|---|---|---|---|---|---|
| PTP4A3 | 134.06 | 262.63 | 463.39 | 340.08 | 667.84 |
| PTPRJ | 2654.92 | 3999.84 | 5584.38 | 6101.63 | 7239.3 |
| PTTG1 | 211.97 | 198.56 | 236.59 | 302.53 | 335.68 |
| RAB15 | 160.6 | 470.25 | 302.05 | 420.06 | 519.4 |
| RAD51AP1 | 29.89 | 46.33 | 40.21 | 49.23 | 51.73 |
| RASAL1 | 18.87 | 53.37 | 50 | 87.38 | 238.78 |
| RBKS | 67.62 | 56.45 | 133.5 | 141.16 | 85.46 |
| RCBTB1 | 1154.33 | 1312.01 | 1131.41 | 1960.76 | 1384.84 |
| RDH10 | 194.04 | 311.58 | 467.51 | 658.5 | 1448.57 |
| REXO2 | 487.9 | 832.35 | 648.44 | 852.58 | 987.43 |
| RFK | 378.31 | 396.91 | 292.26 | 460.78 | 452.8 |
| RGS1 | 16547.6 | 15176.27 | 18057.75 | 23425.18 | 17168.17 |
| RHOC | 78.07 | 230.17 | 207.21 | 317.85 | 290.86 |
| RMI2 | 19.46 | 76.58 | 39.69 | 70.44 | 73.47 |
| RNF145 | 1625.11 | 3074.78 | 2117.47 | 4417.29 | 3266.94 |
| RNF207 | 41.75 | 469.3 | 314.94 | 723.56 | 765.87 |
| RRAGB | 281.49 | 274.98 | 196.9 | 384.81 | 506.1 |
| RYBP | 1861.27 | 2273.72 | 2496.32 | 3178.31 | 2818.02 |
| SEC14L6 | 6.42 | 86.23 | 27.32 | 179.47 | 274.97 |
| SEC24A | 718 | 917.25 | 1157.7 | 1259.04 | 1062.95 |
| SECTM1 | 69.01 | 1347.35 | 725.75 | 2354.1 | 1511.04 |
| SEPT3 | 15.6 | 59.23 | 49.48 | 149.11 | 244.4 |
| SGPP2 | 428.14 | 656.73 | 364.94 | 1001.71 | 809.92 |
| SH3RF2 | 20.9 | 18.3 | 65.98 | 98.4 | 196.34 |
| SIRPG | 433.99 | 605.49 | 317 | 575.41 | 1245.12 |
| SLC16A1 | 947.47 | 1385.08 | 1532.43 | 2050.74 | 1460.73 |
| SLC25A12 | 246.72 | 323.6 | 423.18 | 406.15 | 498.91 |
| SLC35E3 | 385.3 | 451.16 | 370.09 | 582.86 | 653.13 |
| SLC35F2 | 378.22 | 795.55 | 688.64 | 1130.81 | 880.5 |
| SLC41A1 | 1194.29 | 1119.86 | 1164.92 | 1401.41 | 1630.88 |
| SLC41A2 | 13.45 | 356.73 | 114.95 | 482.48 | 395.27 |
| SMAD1 | 15.34 | 53.93 | 30.41 | 63.54 | 87.46 |
| SMS | 565.6 | 760.65 | 719.57 | 818.12 | 735.99 |
| SNAP47 | 310.71 | 503.77 | 577.82 | 690.31 | 696.18 |
| SOCS2 | 245.77 | 405.76 | 463.39 | 605.25 | 611.78 |
| SOX4 | 128.76 | 244.57 | 218.04 | 1205.78 | 715.01 |
| SPATA24 | 38.86 | 77.02 | 36.6 | 66.43 | 94.41 |
| SPATC1 | 7.97 | 10.96 | 19.59 | 61.51 | 55.84 |
| SPATS2L | 366.98 | 891.61 | 1172.13 | 1430.11 | 1531.61 |
| SSH1 | 1890.01 | 3432.55 | 2771.06 | 4390.36 | 4552.26 |
| SSTR3 | 230.28 | 248.12 | 341.74 | 240.77 | 901.25 |
| STAC | 11.63 | 48.36 | 39.69 | 75.94 | 71.4 |
| STARD7 | 2415.01 | 3185.95 | 3024.66 | 3809.46 | 3445.47 |
| STRIP2 | 103.39 | 1002.96 | 540.19 | 716.49 | 1192.77 |
| SYT11 | 1078.51 | 1733.37 | 2080.36 | 2110.18 | 2818.39 |
| TADA3 | 677.14 | 893.74 | 852.04 | 880.43 | 1189.01 |
| TBC1D8 | 53.89 | 374.1 | 265.97 | 817.36 | 1087.39 |
| TDRD3 | 461.34 | 383.25 | 520.09 | 584.64 | 643.84 |
| TFRC | 3608.04 | 4612.18 | 5640.05 | 8107.35 | 10082.21 |
| THADA | 1102.51 | 1505.13 | 1467.48 | 3472.21 | 3171.99 |
| TIGIT | 4611.14 | 10986.74 | 4901.41 | 14821.45 | 14747.79 |
| TM9SF2 | 2048.03 | 2689.14 | 2665.91 | 2935.98 | 3358.4 |
| TMA16 | 172.88 | 180.92 | 137.11 | 304.24 | 192.53 |
| TMEM140 | 273.98 | 640.28 | 574.73 | 917.16 | 691 |
| TMEM184C | 520.19 | 508.83 | 599.98 | 1170.37 | 519.43 |
| TMOD1 | 14.75 | 72.22 | 32.47 | 150.93 | 89.62 |
| TMPRSS3 | 70.84 | 352.78 | 321.64 | 540.8 | 1106.85 |
| TMPRSS6 | 113.53 | 548.87 | 265.97 | 698.41 | 985.34 |
| TNFRSF18 | 333.36 | 2871.78 | 3071.57 | 4038.86 | 4078.14 |
| TNFRSF4 | 400.56 | 2873.16 | 2992.18 | 4222.16 | 4642.56 |
| TNFRSF8 | 30.89 | 115.57 | 208.24 | 155.59 | 430.23 |
| TNFRSF9 | 502.86 | 898.69 | 1739.13 | 2921.72 | 3128.82 |
| TNIP3 | 28.73 | 485.83 | 213.91 | 324.53 | 419.8 |
| TOR4A | 141.27 | 291.3 | 346.9 | 358.98 | 326.51 |
| TOX2 | 237.46 | 860.48 | 490.71 | 861.08 | 1264.13 |
| TP73 | 7.86 | 31.27 | 39.69 | 78.27 | 93.99 |
| TPMT | 357.13 | 354.93 | 305.66 | 480.15 | 519.82 |
| TPP1 | 2589.92 | 6024.92 | 4380.81 | 7164.96 | 6236.83 |
| TPX2 | 106.25 | 89.08 | 184.02 | 150.35 | 202.77 |
| TRAF3 | 1140.85 | 3231.25 | 2706.11 | 4078.84 | 3554.01 |
| TRIB1 | 927.27 | 1820.64 | 1482.95 | 2402.58 | 1469.85 |
| TRIM16 | 160.05 | 115.2 | 121.13 | 240.55 | 210.13 |
| TSPAN17 | 709.59 | 1721.26 | 1322.64 | 1685.38 | 1865.69 |
| TSPAN5 | 372.4 | 1167.46 | 723.69 | 1230.67 | 1398.7 |
| TST | 3.8 | 26.32 | 26.8 | 39.78 | 41.65 |

| Gene Name | Treg_Tumor_ Infiltrating CRC | Treg_Tumor_ Infiltrating NSCLC | Treg_Tissue_ Infiltrating Colon | Treg_Tissue_ Infiltrating Lung | Treg healthy Peripheral Blood |
|---|---|---|---|---|---|
| TTBK1 | 13.41 | 164.27 | 99.48 | 380.69 | 460.64 |
| TTC22 | 237.9 | 386.91 | 323.19 | 483.96 | 451.61 |
| TWIST1 | 4.21 | 94.46 | 21.65 | 95.32 | 195.78 |
| UGP2 | 1950.41 | 3283.79 | 2562.82 | 3399.18 | 2864.71 |
| USP51 | 48.1 | 133.95 | 28.87 | 233.48 | 291.46 |
| UXS1 | 1661.1 | 2156.16 | 1600.47 | 2614.66 | 1914.74 |
| VANGL1 | 97.19 | 192.58 | 248.96 | 263.46 | 289.05 |
| VDR | 123 | 992.41 | 1771.6 | 2616.68 | 3656.18 |
| VWA5A | 426.29 | 550.67 | 373.7 | 604.53 | 739.57 |
| WDHD1 | 101.74 | 126.37 | 140.2 | 136.76 | 193.58 |
| WDTC1 | 1220.3 | 3855.35 | 2029.33 | 4398.54 | 3774.61 |
| WSB1 | 2837.49 | 3876.77 | 4697.29 | 5090.18 | 5383.33 |
| XKRX | 16.06 | 71.84 | 90.2 | 115.05 | 101.81 |
| YIPF1 | 310.29 | 351.68 | 285.04 | 354.44 | 456.27 |
| YIPF6 | 342.01 | 687.07 | 705.14 | 1078.09 | 793.2 |
| ZBED2 | 87.53 | 94.86 | 522.15 | 230.51 | 1238.63 |
| ZBTB38 | 1986.89 | 5405.41 | 3134.97 | 6174.05 | 4680.43 |
| ZC3H12C | 123.76 | 159.39 | 518.54 | 1191.95 | 985.54 |
| ZG16B | 3.42 | 17.03 | 15.46 | 32.31 | 32.59 |
| ZMAT3 | 529.91 | 925.46 | 822.66 | 1077.17 | 1234.3 |
| ZMYND8 | 585.94 | 675.31 | 711.84 | 850.29 | 1131.01 |
| ZNF280C | 181.86 | 444.81 | 326.28 | 635.21 | 467.78 |
| ZNF280D | 698.54 | 973.93 | 616.48 | 1061.55 | 1290.04 |
| ZNF282 | 374.36 | 1273.4 | 2253.55 | 2562.43 | 3165.99 |
| ZNF334 | 6.95 | 26.52 | 17.53 | 40.03 | 100.33 |
| ZWINT | 60.55 | 73.28 | 101.03 | 87.1 | 105.4 |

Altogether, the data show that Treg cells display the most pronounced differences in transcripts expression among CD4+ T cell subsets infiltrating normal and tumor tissues. The inventors defined a subset of signature genes that describe the specific gene expression profile of tumor infiltrating Treg cells.

Gene Signature of Tumor-Infiltrating Treg Cells is Present in Primary and Metastatic Human Tumors The inventors then looked at the single cell level for the differential expression profile of signature genes of tumor infiltrating Treg cells. The inventors isolated CD4+ T cells from 5 CRC and 5 NSCLC tumor samples as well as from 5 PBMCs of healthy individuals (Table II), purified Treg cells, and using an automated microfluidic system (C1 Fluidigm) captured single cells (a total of 858 Treg cells: 320 from CRC and 286 from NSCLC; 252 from PBMCs of healthy individuals). The inventors then assessed by high throughput RT-qPCR (Biomark HD, Fluidigm) the expression of 79 genes selected among the highly expressed (>10 FKPM) tumor Treg cell signature genes (FIGS. 3A, 3C and 7).

Notably, it was found that the vast majority (75 over 79; 95%) of the tumor-infiltrating Treg cell signatures were co-expressed with bona fide Treg cell markers (i.e., FOXP3+ and IL2RA) (FIG. 3B). The percentage of co-expression between these Treg cell markers and the 79 genes selected among the tumor-infiltrating-Treg-cell signature genes ranged between 81% of TIGIT and 0.59% of CGA (FIG. 3B). The expression of Treg signature genes in the RNA-seq of the whole Treg cell population correlated with the percentage of single cells expressing the different genes (FIG. 3C). In order to reduce the "drop-out" effect of the single cell data (i.e., events in which a transcript is detected in one cell but not in another one because the transcript is 'missed' during the reverse-transcription step) (Kharchenko et al., 2014), a threshold (median value t=8.4%) was defined based on the expression distribution for each transcript and discarded genes below this threshold. The forty-five signature transcripts of tumor infiltrating Treg cells detected above this threshold were in most cases significantly over-expressed in Treg cells from both tumors (39 over 45, 87%; Wilcoxon Mann Whitney test p<0.05) or in one tumor type (43 over 45, 96%; FIG. 3D). Homogeneity of the purified tissue infiltrating Treg cells can be affected by the carry-over of cells from other lymphocyte subsets. To quantitate this possible contamination, the single cell RT-qPCR analyses of Treg cells was performed including markers specific for other lymphocytes subsets (i.e., Th1, Th2, Th17, Tfh, CD8 T cells, B cells) (FIG. 7). Our data showed that only a very low fraction of the purified single cells displayed markers of lymphocytes subsets different from Treg cells (FIG. 7).

The overlap between the signature genes in the CRC and NSCLC infiltrating Treg cells (FIG. 2) prompted us to assess whether this signature were also enriched in Treg cells infiltrating other tumors. RNA was thus extracted from Treg cells infiltrating breast cancer, gastric cancer, brain metastasis of NSCLC, and liver metastasis of CRC. It was found by RT-qPCR that tumor infiltrating Treg signatures genes were mostly upregulated also in these tumors (FIG. 3E).

Overall these data show that the tumor-infiltrating Treg cell signature genes are co-expressed at single cell level with FOXP3 and IL2RA and that several primary and metastatic human tumors express the tumor-infiltrating Treg cell signature.

Gene Signature of Tumor Infiltrating Treg Cells is Translated in a Protein Signature The inventors then assessed at the single cell level by flow cytometry the protein expression of ten representative signature genes present in CRC and NSCLC infiltrating Treg cells, adjacent normal tissues, and patients PBMCs. Of the ten proteins, two are proteins (OX40 and TIGIT) whose relevance for Treg cells biology has been demonstrated (Joller et al., 2014; Voo et al., 2013), seven are proteins (BATF, CCR8, CD30, IL-1 R2, IL-21R, PDL-1 and PDL-2) whose expression has never been described in tumor-infiltrating Treg cells, and one protein, 4-1BB, is a co-stimulatory receptor expressed on several hematopoietic cells, whose expression on Treg cells has been shown to mark antigen-activated cells (Schoenbrunn et al., 2012). Our findings showed that all these proteins were upregulated (FIGS. 4A and 4B), at different extent, in tumor infiltrating Treg cells compared to the Treg cells resident in normal tissues.

Altogether, our data show there is a molecular signature of tumor infiltrating Treg cells, which can be detected both at the mRNA and at the protein levels.

Expression of Tumor Treg Signature Genes is Negatively Correlated with Patients Survival In an attempt to correlate our findings with clinical outcome, the inventors asked whether the expression of the tumor-Treg signature transcripts correlated with disease prognosis in CRC and NSCLC patients. The inventors therefore interrogated for expression of Treg signature genes transcriptomic datasets obtained from resected tumor tissues of a cohort of 177 CRC patients (GSE17536 (Smith et al., 2010) and of a cohort of 263 NSCLC patients (GSE41271—(Sato et al., 2013), and correlated high and low gene expression levels with the 5-years survival data. Among those genes whose expression is highly enriched in tumor infiltrating Treg cells, LAYN, MAGEH1 and CCR8 were selected as they are the three genes more selectively expressed (FIG. 9A-C). To normalize for differences in T cell densities within the resected tumor tissues, the inventors used the ratio between expression of the selected signature genes and CD3G. Remarkably, it was found that high expression of the three signature genes is in all cases correlated with a significantly reduced survival (FIG. 5A). Interestingly, it was also observed that expressions of the three signature genes increased with tumor staging of CRC patients (FIG. 5B).

In conclusion, high expression in the whole tumor samples of three genes (LAYN, MAGEH1 and CCR8) that are specifically and highly expressed in tumor infiltrating Treg cells, correlates with a poor prognosis in both NSCLC and CRC patients.

Selection of Potential Targets Specifically Over-Expressed on the Surface of Tumor-Infiltrating Treg All annotated protein isoforms encoded by the 328 genes and retrievable in the public database EnsEMBL (http://www.ensembl.org) were simultaneously analysed with the four prediction algorithms and genes encoding at least one isoform predicted to be surface exposed were considered as potential targets.

Out of 328 genes, 193 encode for at least one potential cell surface protein isoform on the basis of at least one of the four predictors. The list of protein isoforms predicted to be membrane-associated is reported in Table VI.

TABLE VI

| Gene name | Description | ENSG ID release87 | ENST ID | ENSP ID | SEQ ID No of the aa sequence of the protein isoform |
|---|---|---|---|---|---|
| LAYN | Layilin | ENSG00000204381 | ENST00000375614 | ENSP00000364764 | 1 |
| | | | ENST00000375615 | ENSP00000364765 | 2 |
| | | | ENST00000436913 | ENSP00000392942 | 3 |
| | | | ENST00000525126 | ENSP00000434328 | 4 |
| | | | ENST00000525866 | ENSP00000434300 | 5 |
| | | | ENST00000528924 | ENSP00000486561 | 6 |
| | | | ENST00000530962 | ENSP00000431627 | 7 |
| | | | ENST00000533265 | ENSP00000434972 | 8 |
| | | | ENST00000533999 | ENSP00000432434 | 9 |
| CCR8 | C—C chemokine receptor type 8 | ENSG00000179934 | ENST00000326306 | ENSP00000326432 | 10 |
| | | | ENST00000414803 | ENSP00000390104 | 11 |
| IL21R | Interleukin-21 receptor | ENSG00000103522 | ENST00000337929 | ENSP00000338010 | 12 |
| | | | ENST00000395754 | ENSP00000379103 | 13 |
| | | | ENST00000564089 | ENSP00000456707 | 14 |
| FUCA2 | Plasma alpha-L-fucosidase | ENSG00000001036 | ENST00000002165 | ENSP00000002165 | 15 |
| | | | ENST00000451668 | ENSP00000398119 | 16 |
| ICA1 | Islet cell autoantigen 1 | ENSG00000003147 | ENST00000407906 | ENSP00000386021 | 17 |
| COX10 | Protoheme IX farnesyltransferase, mit. | ENSG00000006695 | ENST00000261643 | ENSP00000261643 | 18 |
| IL32 | Interleukin-32 | ENSG00000008517 | ENST00000008180 | ENSP00000008180 | 19 |
| | | | ENST00000396890 | ENSP00000380099 | 20 |
| | | | ENST00000525228 | ENSP00000431740 | 21 |
| | | | ENST00000525377 | ENSP00000433866 | 22 |
| | | | ENST00000530890 | ENSP00000433747 | 23 |
| | | | ENST00000534507 | ENSP00000431775 | 24 |
| | | | ENST00000548246 | ENSP00000447979 | 25 |
| | | | ENST00000548476 | ENSP00000449483 | 26 |
| | | | ENST00000548807 | ENSP00000448354 | 27 |
| | | | ENST00000551513 | ENSP00000449147 | 28 |
| | | | ENST00000552356 | ENSP00000446978 | 29 |
| | | | ENST00000552936 | ENSP00000447033 | 30 |
| ETV7 | Transcription factor ETV7 | ENSG00000010030 | ENST00000339796 | ENSP00000342260 | 31 |
| | | | ENST00000627426 | ENSP00000486712 | 32 |
| ATP2C1 | Calcium-transporting ATPase type 2C member 1 | ENSG00000017260 | ENST00000328560 | ENSP00000329664 | 33 |
| | | | ENST00000359644 | ENSP00000352665 | 34 |
| | | | ENST00000422190 | ENSP00000402677 | 35 |
| | | | ENST00000428331 | ENSP00000395809 | 36 |
| | | | ENST00000504381 | ENSP00000425320 | 37 |
| | | | ENST00000504571 | ENSP00000422489 | 38 |
| | | | ENST00000504612 | ENSP00000425228 | 39 |

TABLE VI-continued

| Gene name | Description | ENSG ID release87 | ENST ID | ENSP ID | SEQ ID No of the aa sequence of the protein isoform |
|---|---|---|---|---|---|
| | | | ENST00000504948 | ENSP00000423330 | 40 |
| | | | ENST00000505072 | ENSP00000427625 | 41 |
| | | | ENST00000505330 | ENSP00000423774 | 42 |
| | | | ENST00000507194 | ENSP00000427087 | 43 |
| | | | ENST00000507488 | ENSP00000421326 | 44 |
| | | | ENST00000508297 | ENSP00000421261 | 45 |
| | | | ENST00000508532 | ENSP00000424783 | 46 |
| | | | ENST00000508660 | ENSP00000424930 | 47 |
| | | | ENST00000509662 | ENSP00000426849 | 48 |
| | | | ENST00000510168 | ENSP00000427461 | 49 |
| | | | ENST00000513801 | ENSP00000422872 | 50 |
| | | | ENST00000515854 | ENSP00000422890 | 51 |
| | | | ENST00000533801 | ENSP00000432956 | 52 |
| FAS | Fatty acid synthase | ENSG00000026103 | ENST00000352159 | ENSP00000345601 | 53 |
| | | | ENST00000355279 | ENSP00000347426 | 54 |
| | | | ENST00000355740 | ENSP00000347979 | 55 |
| | | | ENST00000357339 | ENSP00000349896 | 56 |
| | | | ENST00000479522 | ENSP00000424113 | 57 |
| | | | ENST00000484444 | ENSP00000420975 | 58 |
| | | | ENST00000488877 | ENSP00000425159 | 59 |
| | | | ENST00000492756 | ENSP00000422453 | 60 |
| | | | ENST00000494410 | ENSP00000423755 | 61 |
| | | | ENST00000612663 | ENSP00000477997 | 62 |
| PEX3 | Peroxisomal biogenesis factor 3 | ENSG00000034693 | ENST00000367591 | ENSP00000356563 | 63 |
| | | | ENST00000367592 | ENSP00000356564 | 64 |
| TSPAN17 | Tetraspanin-17 | ENSG00000048140 | ENST00000298564 | ENSP00000298564 | 65 |
| | | | ENST00000310032 | ENSP00000309036 | 66 |
| | | | ENST00000503030 | ENSP00000425975 | 67 |
| | | | ENST00000503045 | ENSP00000425212 | 68 |
| | | | ENST00000504168 | ENSP00000423957 | 69 |
| | | | ENST00000507471 | ENSP00000423610 | 70 |
| | | | ENST00000508164 | ENSP00000422053 | 71 |
| | | | ENST00000515708 | ENSP00000426650 | 72 |
| COL9A2 | Collagen alpha-2(IX) chain | ENSG00000049089 | ENST00000372736 | ENSP00000361821 | 73 |
| | | | ENST00000372748 | ENSP00000361834 | 74 |
| | | | ENST00000417105 | ENSP00000388493 | 75 |
| NFE2L3 | Nuclear factor erythroid 2-related factor 3 | ENSG00000050344 | ENST00000056233 | ENSP00000056233 | 76 |
| TNIP3 | TNFAIP3-interacting prot.3 | ENSG00000050730 | ENST00000515036 | ENSP00000424284 | 77 |
| LY75 | Lymphocyte antigen 75 | ENSG00000054219 | ENST00000263636 | ENSP00000263636 | 78 |
| YIPF1 | Protein YIPF1 | ENSG00000058799 | ENST00000072644 | ENSP00000072644 | 79 |
| | | | ENST00000371399 | ENSP00000360452 | 80 |
| | | | ENST00000412288 | ENSP00000416507 | 81 |
| | | | ENST00000464950 | ENSP00000432266 | 82 |
| ISOC1 | Isochrismatase domain-containing protein 1 | ENSG00000066583 | ENST00000173527 | ENSP00000173527 | 83 |
| | | | ENST00000514194 | ENSP00000421273 | 84 |
| ACSL4 | Long-chain-fatty-acid--CoA ligase 4 | ENSG00000068366 | ENST00000340800 | ENSP00000339787 | 85 |
| | | | ENST00000469796 | ENSP00000419171 | 86 |
| | | | ENST00000469857 | ENSP00000423077 | 87 |
| | | | ENST00000502391 | ENSP00000425408 | 88 |
| | | | ENST00000504980 | ENSP00000421425 | 89 |
| | | | ENST00000508092 | ENSP00000425378 | 90 |
| MAST4 | Microtubule-assoc.serine/ threonine-protein kinase 4 | ENSG00000069020 | ENST00000434115 | ENSP00000396765 | 91 |
| LMCD1 | LIM and cysteine-rich domains protein 1 | ENSG00000071282 | ENST00000456506 | ENSP00000405049 | 92 |
| TFRC | Transferrin receptor protein 1 | ENSG00000072274 | ENST00000360110 | ENSP00000353224 | 93 |
| | | | ENST00000392396 | ENSP00000376197 | 94 |
| | | | ENST00000421258 | ENSP00000402839 | 95 |
| | | | ENST00000426789 | ENSP00000414015 | 96 |
| PANX2 | Pannexin-2 | ENSG00000073150 | ENST00000159647 | ENSP00000159647 | 97 |
| | | | ENST00000395842 | ENSP00000379183 | 98 |
| | | | ENST00000402472 | ENSP00000384148 | 99 |
| FNDC3B | Fibronectin type III domain-containing protein 3B | ENSG00000075420 | ENST00000336824 | ENSP00000338523 | 100 |
| | | | ENST00000415807 | ENSP00000411242 | 101 |
| | | | ENST00000416957 | ENSP00000389094 | 102 |
| | | | ENST00000421757 | ENSP00000408496 | 103 |
| | | | ENST00000423424 | ENSP00000392471 | 104 |
| IL12RB2 | Interleukin-12 receptor subunit beta-2 | ENSG00000081985 | ENST00000262345 | ENSP00000262345 | 105 |
| | | | ENST00000371000 | ENSP00000360039 | 106 |
| | | | ENST00000441640 | ENSP00000400959 | 107 |

TABLE VI-continued

| Gene name | Description | ENSG ID release87 | ENST ID | ENSP ID | SEQ ID No of the aa sequence of the protein isoform |
|---|---|---|---|---|---|
| | | | ENST00000541374 | ENSP00000445276 | 108 |
| | | | ENST00000544434 | ENSP00000442443 | 109 |
| STARD7 | StAR-related lipid transfer protein 7, mitochondrial | ENSG00000084090 | ENST00000337288 | ENSP00000338030 | 110 |
| SSH1 | Protein phosphatase Slingshot homolog 1 | ENSG00000084112 | ENST00000546697 | ENSP00000446652 | 111 |
| | | | ENST00000548522 | ENSP00000448586 | 112 |
| MGST2 | Microsomal glutathione S-transferase 2 | ENSG00000085871 | ENST00000265498 | ENSP00000265498 | 113 |
| | | | ENST00000503816 | ENSP00000423008 | 114 |
| | | | ENST00000506797 | ENSP00000424278 | 115 |
| | | | ENST00000616265 | ENSP00000482639 | 116 |
| ACOX3 | Peroxisomal acyl-coenzyme A oxidase 3 | ENSG00000087008 | ENST00000514423 | ENSP00000427321 | 117 |
| ANKRD10 | Ankyrin repeat domain-containing protein 10 | ENSG00000088448 | ENST00000603993 | ENSP00000474638 | 118 |
| FKBP1A | Peptidyl-prolyl cis-trans isomerase FKBP1A | ENSG00000088832 | ENST00000612074 | ENSP00000480846 | 119 |
| | | | ENST00000614856 | ENSP00000482758 | 120 |
| | | | ENST00000618612 | ENSP00000478093 | 121 |
| SIRPG | Signal-regulatory protein gamma | ENSG00000089012 | ENST00000216927 | ENSP00000216927 | 122 |
| | | | ENST00000303415 | ENSP00000305529 | 123 |
| | | | ENST00000344103 | ENSP00000342759 | 124 |
| | | | ENST00000381580 | ENSP00000370992 | 125 |
| | | | ENST00000381583 | ENSP00000370995 | 126 |
| WHRN | Whirlin | ENSG00000095397 | ENST00000374059 | ENSP00000363172 | 127 |
| CENPM | Centromere protein M | ENSG00000100162 | ENST00000215980 | ENSP00000215980 | 128 |
| | | | ENST00000402338 | ENSP00000384731 | 129 |
| | | | ENST00000402420 | ENSP00000384132 | 130 |
| | | | ENST00000404067 | ENSP00000384814 | 131 |
| | | | ENST00000407253 | ENSP00000384743 | 132 |
| NCF4 | Neutrophil cytosol factor 4 | ENSG00000100365 | ENST00000447071 | ENSP00000414958 | 133 |
| CSF2RB | Cytokine receptor common subunit beta | ENSG00000100368 | ENST00000262825 | ENSP00000262825 | 134 |
| | | | ENST00000403662 | ENSP00000384053 | 135 |
| | | | ENST00000406230 | ENSP00000385271 | 136 |
| | | | ENST00000421539 | ENSP00000393585 | 137 |
| CNIH1 | Protein cornichon homolog 1 | ENSG00000100528 | ENST00000216416 | ENSP00000216416 | 138 |
| | | | ENST00000395573 | ENSP00000378940 | 139 |
| | | | ENST00000553660 | ENSP00000452457 | 140 |
| | | | ENST00000554683 | ENSP00000452466 | 141 |
| | | | ENST00000556113 | ENSP00000451142 | 142 |
| | | | ENST00000557659 | ENSP00000451640 | 143 |
| | | | ENST00000557690 | ENSP00000451852 | 144 |
| PIGU | Phosphatidylinositol glycan anchor biosynthesis class U protein | ENSG00000101464 | ENST00000217446 | ENSP00000217446 | 145 |
| | | | ENST00000374820 | ENSP00000363953 | 146 |
| | | | ENST00000438215 | ENSP00000395755 | 147 |
| NDFIP2 | NEDD4 family-interacting protein 2 | ENSG00000102471 | ENST00000218652 | ENSP00000218652 | 148 |
| | | | ENST00000487865 | ENSP00000419200 | 149 |
| | | | ENST00000612570 | ENSP00000480798 | 150 |
| | | | ENST00000620924 | ENSP00000480881 | 151 |
| ACP5 | Tartrate-resistant acid phosphatase type 5 | ENSG00000102575 | ENST00000218758 | ENSP00000218758 | 152 |
| | | | ENST00000412435 | ENSP00000392374 | 153 |
| | | | ENST00000433365 | ENSP00000413456 | 154 |
| | | | ENST00000589792 | ENSP00000468685 | 155 |
| | | | ENST00000590420 | ENSP00000468509 | 156 |
| | | | ENST00000590832 | ENSP00000465127 | 157 |
| | | | ENST00000591319 | ENSP00000464831 | 158 |
| | | | ENST00000592828 | ENSP00000468767 | 159 |
| NFAT5 | Nuclear factor of activated T-cells 5 | ENSG00000102908 | ENST00000567990 | ENSP00000455115 | 160 |
| CYB5B | Cytochrome b5 type B | ENSG00000103018 | ENST00000307892 | ENSP00000308430 | 161 |
| | | | ENST00000512062 | ENSP00000423679 | 162 |
| | | | ENST00000568237 | ENSP00000464102 | 163 |
| LAPTM4B | Lysosomal-associated transmembrane protein 4B | ENSG00000104341 | ENST00000445593 | ENSP00000402301 | 164 |
| | | | ENST00000517924 | ENSP00000429868 | 165 |
| | | | ENST00000521545 | ENSP00000428409 | 166 |
| | | | ENST00000619747 | ENSP00000482533 | 167 |
| IL7 | Interleukin-7 | ENSG00000104432 | ENST00000263851 | ENSP00000263851 | 168 |
| | | | ENST00000379113 | ENSP00000368408 | 169 |
| | | | ENST00000518982 | ENSP00000430272 | 170 |
| | | | ENST00000520215 | ENSP00000428364 | 171 |
| | | | ENST00000520269 | ENSP00000427750 | 172 |

TABLE VI-continued

| Gene name | Description | ENSG ID release87 | ENST ID | ENSP ID | SEQ ID No of the aa sequence of the protein isoform |
|---|---|---|---|---|---|
| | | | ENST00000520317 | ENSP00000427800 | 173 |
| | | | ENST00000541183 | ENSP00000438922 | 174 |
| EBI3 | Interleukin-27 subunit beta | ENSG00000105246 | ENST00000221847 | ENSP00000221847 | 175 |
| PLA2G4C | Cytosolic phospholipase A2 gamma | ENSG00000105499 | ENST00000595161 | ENSP00000469528 | 176 |
| | | | ENST00000595487 | ENSP00000471328 | 177 |
| | | | ENST00000596352 | ENSP00000471759 | 178 |
| | | | ENST00000598488 | ENSP00000468972 | 179 |
| GLCCI1 | Glucocorticoid-induced transcript 1 protein | ENSG00000106415 | ENST00000430798 | ENSP00000396171 | 180 |
| MINPP1 | Multiple inositol polyphosphate phosphatase 1 | ENSG00000107789 | ENST00000371994 | ENSP00000361062 | 181 |
| | | | ENST00000371996 | ENSP00000361064 | 182 |
| | | | ENST00000536010 | ENSP00000437823 | 183 |
| WSB1 | WD repeat and SOCS box-containing protein 1 | ENSG00000109046 | ENST00000581440 | ENSP00000462737 | 184 |
| | | | ENST00000582208 | ENSP00000463621 | 185 |
| | | | ENST00000583193 | ENSP00000462595 | 186 |
| | | | ENST00000583742 | ENSP00000462365 | 187 |
| HTATIP2 | Oxidoreductase HTATIP2 | ENSG00000109854 | ENST00000419348 | ENSP00000392985 | 188 |
| | | | ENST00000530266 | ENSP00000436548 | 189 |
| | | | ENST00000532081 | ENSP00000432107 | 190 |
| | | | ENST00000532505 | ENSP00000432338 | 191 |
| CTSC | Dipeptidyl peptidase 1 | ENSG00000109861 | ENST00000227266 | ENSP00000227266 | 192 |
| | | | ENST00000524463 | ENSP00000432541 | 193 |
| | | | ENST00000527018 | ENSP00000432556 | 194 |
| | | | ENST00000528020 | ENSP00000433229 | 195 |
| | | | ENST00000529974 | ENSP00000433539 | 196 |
| VWA5A | von Willebrand factor A domain-containing protein 5A | ENSG00000110002 | ENST00000392744 | ENSP00000376501 | 197 |
| | | | ENST00000392748 | ENSP00000376504 | 198 |
| | | | ENST00000456829 | ENSP00000407726 | 199 |
| SLC35F2 | Solute carrier family 35 member F2 | ENSG00000110660 | ENST00000375682 | ENSP00000364834 | 200 |
| | | | ENST00000525071 | ENSP00000434307 | 201 |
| | | | ENST00000525815 | ENSP00000436785 | 202 |
| | | | ENST00000532513 | ENSP00000433783 | 203 |
| VDR | Vitamin D3 receptor | ENSG00000111424 | ENST00000547065 | ENSP00000449074 | 204 |
| SEC24A | Protein transport protein Sec24A | ENSG00000113615 | ENST00000398844 | ENSP00000381823 | 205 |
| IL1R2 | Interleukin-1 receptor type 2 | ENSG00000115590 | ENST00000332549 | ENSP00000330959 | 206 |
| | | | ENST00000393414 | ENSP00000377066 | 207 |
| | | | ENST00000441002 | ENSP00000414611 | 208 |
| | | | ENST00000457817 | ENSP00000408415 | 209 |
| IL1R1 | Interleukin-1 receptor type 1 | ENSG00000115594 | ENST00000409288 | ENSP00000386478 | 210 |
| | | | ENST00000409329 | ENSP00000387131 | 211 |
| | | | ENST00000409589 | ENSP00000386555 | 212 |
| | | | ENST00000409929 | ENSP00000386776 | 213 |
| | | | ENST00000410023 | ENSP00000386380 | 214 |
| | | | ENST00000413623 | ENSP00000407017 | 215 |
| | | | ENST00000422532 | ENSP00000390349 | 216 |
| | | | ENST00000424272 | ENSP00000415366 | 217 |
| | | | ENST00000428279 | ENSP00000410461 | 218 |
| | | | ENST00000430171 | ENSP00000408101 | 219 |
| | | | ENST00000442590 | ENSP00000393296 | 220 |
| | | | ENST00000450319 | ENSP00000411627 | 221 |
| | | | ENST00000452403 | ENSP00000401646 | 222 |
| IL1RL2 | Interleukin-1 receptor-like 2 | ENSG00000115598 | ENST00000264257 | ENSP00000264257 | 223 |
| | | | ENST00000421464 | ENSP00000387611 | 224 |
| | | | ENST00000441515 | ENSP00000413348 | 225 |
| IL1RL1 | Interleukin-1 receptor-like 1 | ENSG00000115602 | ENST00000233954 | ENSP00000233954 | 226 |
| | | | ENST00000311734 | ENSP00000310371 | 227 |
| | | | ENST00000404917 | ENSP00000384822 | 228 |
| | | | ENST00000409584 | ENSP00000386618 | 229 |
| | | | ENST00000427077 | ENSP00000391120 | 230 |
| | | | ENST00000447231 | ENSP00000409437 | 231 |
| UXS1 | UDP-glucuronic acid decarboxylase 1 | ENSG00000115652 | ENST00000283148 | ENSP00000283148 | 232 |
| | | | ENST00000409501 | ENSP00000387019 | 233 |
| | | | ENST00000441952 | ENSP00000416656 | 234 |
| | | | ENST00000457835 | ENSP00000399316 | 235 |
| SLC25A12 | Calcium-binding mitochondrial carrier protein Aralar1 | ENSG00000115840 | ENST00000426896 | ENSP00000413968 | 236 |
| THADA | Thyroid adenoma-associated protein | ENSG00000115970 | ENST00000403856 | ENSP00000385469 | 237 |

TABLE VI-continued

| Gene name | Description | ENSG ID release87 | ENST ID | ENSP ID | SEQ ID No of the aa sequence of the protein isoform |
|---|---|---|---|---|---|
| LEPR | Leptin receptor | ENSG00000116678 | ENST00000344610 | ENSP00000340884 | 238 |
|  |  |  | ENST00000349533 | ENSP00000330393 | 239 |
|  |  |  | ENST00000371058 | ENSP00000360097 | 240 |
|  |  |  | ENST00000371059 | ENSP00000360098 | 241 |
|  |  |  | ENST00000371060 | ENSP00000360099 | 242 |
|  |  |  | ENST00000406510 | ENSP00000384025 | 243 |
|  |  |  | ENST00000616738 | ENSP00000483390 | 244 |
| MREG | Melanoregulin | ENSG00000118242 | ENST00000263268 | ENSP00000263268 | 245 |
|  |  |  | ENST00000620139 | ENSP00000484331 | 246 |
| FLVCR2 | Feline leukemia virus subgroup C receptor-related protein 2 | ENSG00000119686 | ENST00000238667 | ENSP00000238667 | 247 |
|  |  |  | ENST00000539311 | ENSP00000443439 | 248 |
|  |  |  | ENST00000553341 | ENSP00000452584 | 249 |
|  |  |  | ENST00000553587 | ENSP00000451603 | 250 |
|  |  |  | ENST00000554580 | ENSP00000451781 | 251 |
|  |  |  | ENST00000555027 | ENSP00000452453 | 252 |
|  |  |  | ENST00000555058 | ENSP00000451104 | 253 |
|  |  |  | ENST00000556856 | ENSP00000452468 | 254 |
| SOCS2 | Suppressor of cytokine signaling 2 | ENSG00000120833 | ENST00000548537 | ENSP00000448709 | 255 |
|  |  |  | ENST00000549510 | ENSP00000474888 | 256 |
| RDH10 | Retinol dehydrogenase 10 | ENSG00000121039 | ENST00000240285 | ENSP00000240285 | 257 |
|  |  |  | ENST00000519380 | ENSP00000428132 | 258 |
|  |  |  | ENST00000521928 | ENSP00000429727 | 259 |
| LAX1 | Lymphocyte transmembrane adapter 1 | ENSG00000122188 | ENST00000367217 | ENSP00000356186 | 260 |
|  |  |  | ENST00000442561 | ENSP00000406970 | 261 |
| ZWINT | ZW10 interactor | ENSG00000122952 | ENST00000489649 | ENSP00000473330 | 262 |
| ACOT9 | Acyl-coenzyme A thioesterase 9, mitochondrial | ENSG00000123130 | ENST00000336430 | ENSP00000336580 | 263 |
|  |  |  | ENST00000379303 | ENSP00000368605 | 264 |
|  |  |  | ENST00000494361 | ENSP00000420238 | 265 |
| TM9SF2 | Transmembrane 9 superfamily member 2 | ENSG00000125304 | ENST00000376387 | ENSP00000365567 | 266 |
| HS3ST3B1 | Heparan sulfate glucosamine 3-O-sulfotransferase 3B1 | ENSG00000125430 | ENST00000360954 | ENSP00000354213 | 267 |
|  |  |  | ENST00000466596 | ENSP00000436078 | 268 |
| EML2 | Echinoderm microtubule-associated protein-like 2 | ENSG00000125746 | ENST00000245925 | ENSP00000245925 | 269 |
|  |  |  | ENST00000586195 | ENSP00000465339 | 270 |
|  |  |  | ENST00000586405 | ENSP00000465885 | 271 |
|  |  |  | ENST00000586770 | ENSP00000465786 | 272 |
|  |  |  | ENST00000587152 | ENSP00000468312 | 273 |
|  |  |  | ENST00000587484 | ENSP00000465994 | 274 |
|  |  |  | ENST00000588272 | ENSP00000466100 | 275 |
|  |  |  | ENST00000588308 | ENSP00000468329 | 276 |
|  |  |  | ENST00000589876 | ENSP00000464789 | 277 |
|  |  |  | ENST00000590018 | ENSP00000468373 | 278 |
|  |  |  | ENST00000590043 | ENSP00000464804 | 279 |
|  |  |  | ENST00000590819 | ENSP00000464950 | 280 |
|  |  |  | ENST00000591721 | ENSP00000468470 | 281 |
|  |  |  | ENST00000592853 | ENSP00000468383 | 282 |
|  |  |  | ENST00000593255 | ENSP00000467941 | 283 |
| MGME1 | Mitochondrial genome maintenance exonuclease 1 | ENSG00000125871 | ENST00000377704 | ENSP00000366933 | 284 |
|  |  |  | ENST00000377709 | ENSP00000366938 | 285 |
|  |  |  | ENST00000377710 | ENSP00000366939 | 286 |
| IGFLR1 | IGF-like family receptor 1 | ENSG00000126246 | ENST00000246532 | ENSP00000246532 | 287 |
|  |  |  | ENST00000588018 | ENSP00000468545 | 288 |
|  |  |  | ENST00000588992 | ENSP00000465962 | 289 |
|  |  |  | ENST00000591277 | ENSP00000468644 | 290 |
|  |  |  | ENST00000591748 | ENSP00000476009 | 291 |
|  |  |  | ENST00000592537 | ENSP00000466181 | 292 |
|  |  |  | ENST00000592693 | ENSP00000474913 | 293 |
|  |  |  | ENST00000592889 | ENSP00000467750 | 294 |
| MYO5C | Unconventional myosin-Vc | ENSG00000128833 | ENST00000261839 | ENSP00000261839 | 295 |
| ITFG1 | T-cell immunomodulatory protein | ENSG00000129636 | ENST00000320640 | ENSP00000319918 | 296 |
|  |  |  | ENST00000544001 | ENSP00000441062 | 297 |
|  |  |  | ENST00000563730 | ENSP00000455630 | 298 |
|  |  |  | ENST00000565262 | ENSP00000457665 | 299 |
|  |  |  | ENST00000565940 | ENSP00000459192 | 300 |
| SYT11 | Synaptotagmin-11 | ENSG00000132718 | ENST00000368324 | ENSP00000357307 | 301 |
| SLC41A1 | Solute carrier family 41 member 1 | ENSG00000133065 | ENST00000367137 | ENSP00000356105 | 302 |

TABLE VI-continued

| Gene name | Description | ENSG ID release87 | ENST ID | ENSP ID | SEQ ID No of the aa sequence of the protein isoform |
|---|---|---|---|---|---|
| ATP13A3 | Probable cation-transporting ATPase 13A3 | ENSG00000133657 | ENST00000256031 | ENSP00000256031 | 303 |
| | | | ENST00000429136 | ENSP00000402550 | 304 |
| | | | ENST00000439040 | ENSP00000416508 | 305 |
| | | | ENST00000446356 | ENSP00000410767 | 306 |
| | | | ENST00000457986 | ENSP00000406234 | 307 |
| | | | ENST00000619199 | ENSP00000482200 | 308 |
| MICAL2 | Protein-methionine sulfoxide oxidase MICAL2 | ENSG00000133816 | ENST00000379612 | ENSP00000368932 | 309 |
| CABLES1 | CDK5 and ABL1 enzyme substrate 1 | ENSG00000134508 | ENST00000256925 | ENSP00000256925 | 310 |
| | | | ENST00000579963 | ENSP00000464435 | 311 |
| HAVCR2 | Hepatitis A virus cellular receptor 2 | ENSG00000135077 | ENST00000307851 | ENSP00000312002 | 312 |
| | | | ENST00000522593 | ENSP00000430873 | 313 |
| CGA | Chromogranin-A | ENSG00000135346 | ENST00000369582 | ENSP00000358595 | 314 |
| | | | ENST00000610310 | ENSP00000482232 | 315 |
| | | | ENST00000625577 | ENSP00000486666 | 316 |
| | | | ENST00000627148 | ENSP00000486024 | 317 |
| | | | ENST00000630630 | ENSP00000487300 | 318 |
| FAIM2 | Protein lifeguard 2 | ENSG00000135472 | ENST00000320634 | ENSP00000321951 | 319 |
| | | | ENST00000547871 | ENSP00000449360 | 320 |
| | | | ENST00000550195 | ENSP00000447715 | 321 |
| | | | ENST00000550635 | ENSP00000449711 | 322 |
| | | | ENST00000550890 | ENSP00000450132 | 323 |
| | | | ENST00000552669 | ENSP00000446771 | 324 |
| | | | ENST00000552863 | ENSP00000449957 | 325 |
| ARHGEF4 | Rho guanine nucleotide exchange factor 4 | ENSG00000136002 | ENST00000392953 | ENSP00000376680 | 326 |
| SLC41A2 | Solute carrier family 41 member 2 | ENSG00000136052 | ENST00000258538 | ENSP00000258538 | 327 |
| | | | ENST00000437220 | ENSP00000391377 | 328 |
| NUSAP1 | Nucleolar and spindle-associated protein 1 | ENSG00000137804 | ENST00000557840 | ENSP00000453428 | 329 |
| | | | ENST00000559046 | ENSP00000452725 | 330 |
| ADAM10 | Disintegrin and metalloproteinase domain-containing protein 10 | ENSG00000137845 | ENST00000260408 | ENSP00000260408 | 331 |
| | | | ENST00000396136 | ENSP00000456542 | 332 |
| | | | ENST00000402627 | ENSP00000386056 | 333 |
| | | | ENST00000439637 | ENSP00000391930 | 334 |
| | | | ENST00000461408 | ENSP00000481779 | 335 |
| | | | ENST00000558004 | ENSP00000452704 | 336 |
| | | | ENST00000559053 | ENSP00000453952 | 337 |
| | | | ENST00000561288 | ENSP00000452639 | 338 |
| HADHB | Trifunctional enzyme subunit beta, mitochondrial | ENSG00000138029 | ENST00000545822 | ENSP00000442665 | 339 |
| CD27 | CD27 antigen | ENSG00000139193 | ENST00000266557 | ENSP00000266557 | 340 |
| CDH24 | Cadherin-24 | ENSG00000139880 | ENST00000267383 | ENSP00000267383 | 341 |
| | | | ENST00000397359 | ENSP00000380517 | 342 |
| | | | ENST00000487137 | ENSP00000434821 | 343 |
| | | | ENST00000554034 | ENSP00000452493 | 344 |
| | | | ENST00000610348 | ENSP00000478078 | 345 |
| ETFA | Electron transfer alpha, mitochondrial flavoprotein subunit | ENSG00000140374 | ENST00000560044 | ENSP00000452942 | 346 |
| | | | ENST00000560309 | ENSP00000453753 | 347 |
| KSR1 | Kinase suppressor of Ras 1 | ENSG00000141068 | ENST00000580163 | ENSP00000463204 | 348 |
| SECTM1 | Secreted and transmembrane protein 1 | ENSG00000141574 | ENST00000269389 | ENSP00000269389 | 349 |
| | | | ENST00000580437 | ENSP00000463904 | 350 |
| | | | ENST00000581691 | ENSP00000463114 | 351 |
| | | | ENST00000581864 | ENSP00000464111 | 352 |
| | | | ENST00000581954 | ENSP00000464385 | 353 |
| | | | ENST00000582290 | ENSP00000462294 | 354 |
| | | | ENST00000582563 | ENSP00000463120 | 355 |
| | | | ENST00000583093 | ENSP00000462563 | 356 |
| EVA1B | Protein eva-1 homolog B | ENSG00000142694 | ENST00000270824 | ENSP00000270824 | 357 |
| CTTNBP2NL | CTTNBP2 N-terminal-like protein | ENSG00000143079 | ENST00000271277 | ENSP00000271277 | 358 |
| | | | ENST00000441739 | ENSP00000390976 | 359 |
| CASQ1 | Calsequestrin-1 | ENSG00000143318 | ENST00000368078 | ENSP00000357057 | 360 |
| ARL6IP5 | PRA1 family protein 3 | ENSG00000144746 | ENST00000273258 | ENSP00000273258 | 361 |
| | | | ENST00000478935 | ENSP00000420138 | 362 |
| | | | ENST00000484921 | ENSP00000419374 | 363 |
| | | | ENST00000485444 | ENSP00000419021 | 364 |
| ADPRH | [Protein ADP-ribosylarginine] hydrolase | ENSG00000144843 | ENST00000357003 | ENSP00000349496 | 365 |
| | | | ENST00000465513 | ENSP00000417430 | 366 |
| | | | ENST00000478399 | ENSP00000420200 | 367 |

TABLE VI-continued

| Gene name | Description | ENSG ID release87 | ENST ID | ENSP ID | SEQ ID No of the aa sequence of the protein isoform |
|---|---|---|---|---|---|
| | | | ENST00000478927 | ENSP00000417528 | 368 |
| | | | ENST00000481816 | ENSP00000419703 | 369 |
| PAM | Peptidyl-glycine alpha-amidating monooxygenase | ENSG00000145730 | ENST00000304400 | ENSP00000306100 | 370 |
| | | | ENST00000345721 | ENSP00000302544 | 371 |
| | | | ENST00000346918 | ENSP00000282992 | 372 |
| | | | ENST00000348126 | ENSP00000314638 | 373 |
| | | | ENST00000438793 | ENSP00000396493 | 374 |
| | | | ENST00000455264 | ENSP00000403461 | 375 |
| | | | ENST00000504691 | ENSP00000424203 | 376 |
| | | | ENST00000505654 | ENSP00000421569 | 377 |
| | | | ENST00000506006 | ENSP00000423611 | 378 |
| | | | ENST00000509832 | ENSP00000423763 | 379 |
| | | | ENST00000511477 | ENSP00000421823 | 380 |
| | | | ENST00000511839 | ENSP00000426448 | 381 |
| | | | ENST00000512073 | ENSP00000420851 | 382 |
| RNF145 | RING finger protein 145 | ENSG00000145860 | ENST00000274542 | ENSP00000274542 | 383 |
| | | | ENST00000424310 | ENSP00000409064 | 384 |
| | | | ENST00000518802 | ENSP00000430955 | 385 |
| | | | ENST00000519865 | ENSP00000430397 | 386 |
| | | | ENST00000520638 | ENSP00000429071 | 387 |
| | | | ENST00000521606 | ENSP00000430753 | 388 |
| | | | ENST00000611185 | ENSP00000482720 | 389 |
| TMEM140 | Transmembrane protein 140 | ENSG00000146859 | ENST00000275767 | ENSP00000275767 | 390 |
| CHST7 | Carbohydrate sulfotransferase 7 | ENSG00000147119 | ENST00000276055 | ENSP00000276055 | 391 |
| CHRNA6 | Neuronal acetylcholine receptor subunit alpha-6 | ENSG00000147434 | ENST00000276410 | ENSP00000276410 | 392 |
| | | | ENST00000533810 | ENSP00000434659 | 393 |
| | | | ENST00000534622 | ENSP00000433871 | 394 |
| PTPRJ | Receptor-type tyrosine-protein phosphatase eta | ENSG00000149177 | ENST00000418331 | ENSP00000400010 | 395 |
| | | | ENST00000440289 | ENSP00000409733 | 396 |
| | | | ENST00000527952 | ENSP00000435618 | 397 |
| | | | ENST00000534219 | ENSP00000432686 | 398 |
| | | | ENST00000613246 | ENSP00000477933 | 399 |
| | | | ENST00000615445 | ENSP00000479342 | 400 |
| NCAM1 | Neural cell adhesion molecule 1 | ENSG00000149294 | ENST00000316851 | ENSP00000318472 | 401 |
| | | | ENST00000401611 | ENSP00000384055 | 402 |
| | | | ENST00000524916 | ENSP00000478072 | 403 |
| | | | ENST00000526322 | ENSP00000479687 | 404 |
| | | | ENST00000528158 | ENSP00000486241 | 405 |
| | | | ENST00000528590 | ENSP00000480269 | 406 |
| | | | ENST00000529356 | ENSP00000482205 | 407 |
| | | | ENST00000531044 | ENSP00000484943 | 408 |
| | | | ENST00000531817 | ENSP00000475074 | 409 |
| | | | ENST00000533073 | ENSP00000486406 | 410 |
| | | | ENST00000613217 | ENSP00000479353 | 411 |
| | | | ENST00000615112 | ENSP00000480797 | 412 |
| | | | ENST00000615285 | ENSP00000479241 | 413 |
| | | | ENST00000618266 | ENSP00000477835 | 414 |
| | | | ENST00000619839 | ENSP00000480132 | 415 |
| | | | ENST00000620046 | ENSP00000482852 | 416 |
| | | | ENST00000621128 | ENSP00000481083 | 417 |
| | | | ENST00000621518 | ENSP00000477808 | 418 |
| | | | ENST00000621850 | ENSP00000480774 | 419 |
| INPP1 | Inositol polyphosphate 1-phosphatase | ENSG00000151689 | ENST00000413239 | ENSP00000391415 | 420 |
| | | | ENST00000444194 | ENSP00000404732 | 421 |
| | | | ENST00000451089 | ENSP00000410662 | 422 |
| | | | ENST00000458193 | ENSP00000412119 | 423 |
| JAKMIP1 | Janus kinase and microtubule-interacting protein 1 | ENSG00000152969 | ENST00000409021 | ENSP00000386711 | 424 |
| | | | ENST00000409371 | ENSP00000387042 | 425 |
| RHOC | Rho-related GTP-binding protein RhoC | ENSG00000155366 | ENST00000468093 | ENSP00000431392 | 426 |
| | | | ENST00000484280 | ENSP00000434310 | 427 |
| | | | ENST00000528831 | ENSP00000432209 | 428 |
| SLC16A1 | Monocarboxylate transporter 1 | ENSG00000155380 | ENST00000369626 | ENSP00000358640 | 429 |
| | | | ENST00000429288 | ENSP00000397106 | 430 |
| | | | ENST00000443580 | ENSP00000399104 | 431 |
| | | | ENST00000458229 | ENSP00000416167 | 432 |
| | | | ENST00000538576 | ENSP00000441065 | 433 |
| CXCL13 | C—X—C motif chemokine 13 | ENSG00000156234 | ENST00000286758 | ENSP00000286758 | 434 |

TABLE VI-continued

| Gene name | Description | ENSG ID release87 | ENST ID | ENSP ID | SEQ ID No of the aa sequence of the protein isoform |
|---|---|---|---|---|---|
| SH3RF2 | Putative E3 ubiquitin-protein ligase SH3RF2 | ENSG00000156463 | ENST00000359120 | ENSP00000352028 | 435 |
| | | | ENST00000511217 | ENSP00000424497 | 436 |
| NPTN | Neuroplastin | ENSG00000156642 | ENST00000345330 | ENSP00000290401 | 437 |
| | | | ENST00000351217 | ENSP00000342958 | 438 |
| | | | ENST00000562924 | ENSP00000456349 | 439 |
| | | | ENST00000563691 | ENSP00000457028 | 440 |
| | | | ENST00000565325 | ENSP00000457470 | 441 |
| AHCYL2 | Adenosylhomocysteinase 3 | ENSG00000158467 | ENST00000466924 | ENSP00000419346 | 442 |
| PTGIR | Prostacyclin receptor | ENSG00000160013 | ENST00000291294 | ENSP00000291294 | 443 |
| | | | ENST00000594275 | ENSP00000469408 | 444 |
| | | | ENST00000596260 | ENSP00000468970 | 445 |
| | | | ENST00000597185 | ENSP00000470566 | 446 |
| | | | ENST00000598865 | ENSP00000470799 | 447 |
| TMPRSS3 | Transmembrane protease serine 4 | ENSG00000160183 | ENST00000291532 | ENSP00000291532 | 448 |
| | | | ENST00000398397 | ENSP00000381434 | 449 |
| | | | ENST00000398405 | ENSP00000381442 | 450 |
| | | | ENST00000433957 | ENSP00000411013 | 451 |
| FCRL3 | Fc receptor-like protein 3 | ENSG00000160856 | ENST00000368184 | ENSP00000357167 | 452 |
| | | | ENST00000368186 | ENSP00000357169 | 453 |
| | | | ENST00000477837 | ENSP00000433430 | 454 |
| | | | ENST00000485028 | ENSP00000434331 | 455 |
| | | | ENST00000492769 | ENSP00000435487 | 456 |
| | | | ENST00000496769 | ENSP00000473680 | 457 |
| PAQR4 | Progestin and adipoQ receptor family member 4 | ENSG00000162073 | ENST00000293978 | ENSP00000293978 | 458 |
| | | | ENST00000318782 | ENSP00000321804 | 459 |
| | | | ENST00000572687 | ENSP00000459418 | 460 |
| | | | ENST00000574988 | ENSP00000458683 | 461 |
| | | | ENST00000576565 | ENSP00000460326 | 462 |
| ZG16B | Zymogen granule protein 16 homolog B | ENSG00000162078 | ENST00000382280 | ENSP00000371715 | 463 |
| | | | ENST00000570670 | ENSP00000460793 | 464 |
| | | | ENST00000571723 | ENSP00000458847 | 465 |
| | | | ENST00000572863 | ENSP00000461740 | 466 |
| SGPP2 | Sphingosine-1-phosphate phosphatase 2 | ENSG00000163082 | ENST00000321276 | ENSP00000315137 | 467 |
| NEURL3 | E3 ubiquitin-protein ligase NEURL1B | ENSG00000163121 | ENST00000310865 | ENSP00000479456 | 468 |
| | | | ENST00000435380 | ENSP00000480933 | 469 |
| KIF15 | Kinesin-like protein KIF15 | ENSG00000163808 | ENST00000438321 | ENSP00000406939 | 470 |
| TMEM184C | Transmembrane protein 184C | ENSG00000164168 | ENST00000296582 | ENSP00000296582 | 471 |
| | | | ENST00000505999 | ENSP00000421159 | 472 |
| | | | ENST00000508208 | ENSP00000425940 | 473 |
| C5ORF63 | Glutaredoxin-like protein C5orf63 | ENSG00000164241 | ENST00000296662 | ENSP00000453964 | 474 |
| | | | ENST00000508527 | ENSP00000475157 | 475 |
| | | | ENST00000509733 | ENSP00000475415 | 476 |
| | | | ENST00000535381 | ENSP00000454153 | 477 |
| | | | ENST00000606042 | ENSP00000475733 | 478 |
| | | | ENST00000606937 | ENSP00000475810 | 479 |
| | | | ENST00000607731 | ENSP00000476160 | 480 |
| MELK | Maternal embryonic leucine zipper kinase | ENSG00000165304 | ENST00000495529 | ENSP00000487536 | 481 |
| | | | ENST00000536329 | ENSP00000443550 | 482 |
| | | | ENST00000536987 | ENSP00000439184 | 483 |
| | | | ENST00000543751 | ENSP00000441596 | 484 |
| | | | ENST00000626154 | ENSP00000486558 | 485 |
| FAAH2 | Fatty-acid amide hydrolase 2 | ENSG00000165591 | ENST00000374900 | ENSP00000364035 | 486 |
| TPP1 | Alpha-tocopherol transfer protein | ENSG00000166340 | ENST00000299427 | ENSP00000299427 | 487 |
| | | | ENST00000436873 | ENSP00000398136 | 488 |
| | | | ENST00000528571 | ENSP00000434647 | 489 |
| | | | ENST00000528657 | ENSP00000435001 | 490 |
| CX3CR1 | CX3C chemokine receptor 1 | ENSG00000168329 | ENST00000358309 | ENSP00000351059 | 491 |
| | | | ENST00000399220 | ENSP00000382166 | 492 |
| | | | ENST00000412814 | ENSP00000408835 | 493 |
| | | | ENST00000435290 | ENSP00000394960 | 494 |
| | | | ENST00000541347 | ENSP00000439140 | 495 |
| | | | ENST00000542107 | ENSP00000444928 | 496 |
| TSPAN5 | Tetraspanin-5 | ENSG00000168785 | ENST00000305798 | ENSP00000307701 | 497 |
| | | | ENST00000505184 | ENSP00000423916 | 498 |
| | | | ENST00000508798 | ENSP00000421808 | 499 |
| | | | ENST00000511651 | ENSP00000426248 | 500 |
| | | | ENST00000511800 | ENSP00000422548 | 501 |
| | | | ENST00000515287 | ENSP00000423504 | 502 |
| | | | ENST00000515440 | ENSP00000422351 | 503 |

TABLE VI-continued

| Gene name | Description | ENSG ID release87 | ENST ID | ENSP ID | SEQ ID No of the aa sequence of the protein isoform |
|---|---|---|---|---|---|
| UGP2 | UTP--glucose-1-uridylyltransferase phosphate | ENSG00000169764 | ENST00000467999<br>ENST00000496334 | ENSP00000418642<br>ENSP00000420760 | 504<br>505 |
| GLB1 | Beta-galactosidase | ENSG00000170266 | ENST00000307363<br>ENST00000307377<br>ENST00000399402<br>ENST00000415454<br>ENST00000436768<br>ENST00000438227<br>ENST00000440656<br>ENST00000446732<br>ENST00000450835 | ENSP00000306920<br>ENSP00000305920<br>ENSP00000382333<br>ENSP00000411813<br>ENSP00000387989<br>ENSP00000401250<br>ENSP00000411769<br>ENSP00000407365<br>ENSP00000403264 | 506<br>507<br>508<br>509<br>510<br>511<br>512<br>513<br>514 |
| SPATA24 | Spermatogenesis-associated protein 24 | ENSG00000170469 | ENST00000514983 | ENSP00000423424 | 515 |
| RBKS | Ribokinase | ENSG00000171174 | ENST00000449378 | ENSP00000413789 | 516 |
| NETO2 | Neuropilin and tolloid-like protein 2 | ENSG00000171208 | ENST00000303155<br>ENST00000562435<br>ENST00000562559<br>ENST00000563078<br>ENST00000564667 | ENSP00000306726<br>ENSP00000455169<br>ENSP00000454213<br>ENSP00000456818<br>ENSP00000457133 | 517<br>518<br>519<br>520<br>521 |
| LRG1 | Leucine-rich alpha-2-glycoprotein | ENSG00000171236 | ENST00000306390 | ENSP00000302621 | 522 |
| FAM98B | Protein FAM98B | ENSG00000171262 | ENST00000491535<br>ENST00000559431 | ENSP00000453166<br>ENSP00000453926 | 523<br>524 |
| CHST11 | Carbohydrate sulfotransferase 11 | ENSG00000171310 | ENST00000303725<br>ENST00000546689<br>ENST00000547956<br>ENST00000549260 | ENSP00000305725<br>ENSP00000448678<br>ENSP00000449093<br>ENSP00000450004 | 525<br>526<br>527<br>528 |
| ECEL1 | Endothelin-converting enzyme-like 1 | ENSG00000171551 | ENST00000304546<br>ENST00000409941 | ENSP00000302051<br>ENSP00000386333 | 529<br>530 |
| BCL2L1 | Bcl-2-like protein 1 | ENSG00000171552 | ENST00000307677<br>ENST00000376055<br>ENST00000376062 | ENSP00000302564<br>ENSP00000365223<br>ENSP00000365230 | 531<br>532<br>533 |
| MALT1 | Mucosa-associated lymphoid tissue lymphoma translocation protein 1 | ENSG00000172175 | ENST00000345724<br>ENST00000348428<br>ENST00000591792 | ENSP00000304161<br>ENSP00000319279<br>ENSP00000467222 | 534<br>535<br>536 |
| CYP7B1 | 25-hydroxycholesterol 7-alpha-hydroxylase | ENSG00000172817 | ENST00000310193 | ENSP00000310721 | 537 |
| HPSE | Heparanase | ENSG00000173083 | ENST00000311412<br>ENST00000405413<br>ENST00000507150<br>ENST00000508891<br>ENST00000509906<br>ENST00000512196<br>ENST00000513463 | ENSP00000308107<br>ENSP00000384262<br>ENSP00000426139<br>ENSP00000421827<br>ENSP00000421038<br>ENSP00000423265<br>ENSP00000421365 | 538<br>539<br>540<br>541<br>542<br>543<br>544 |
| VANGL1 | Vang-like protein 1 | ENSG00000173218 | ENST00000310260<br>ENST00000355485<br>ENST00000369509<br>ENST00000369510 | ENSP00000310800<br>ENSP00000347672<br>ENSP00000358522<br>ENSP00000358523 | 545<br>546<br>547<br>548 |
| CD7 | T-cell antigen CD7 | ENSG00000173762 | ENST00000312648<br>ENST00000578509<br>ENST00000581434<br>ENST00000582480<br>ENST00000583376<br>ENST00000584284 | ENSP00000312027<br>ENSP00000464565<br>ENSP00000464546<br>ENSP00000464182<br>ENSP00000463489<br>ENSP00000463612 | 549<br>550<br>551<br>552<br>553<br>554 |
| HAP1 | Huntingtin-associated protein 1 | ENSG00000173805 | ENST00000455021 | ENSP00000397242 | 555 |
| FBXO45 | F-box/SPRY domain-containing protein 1 | ENSG00000174013 | ENST00000440469 | ENSP00000389868 | 556 |
| CHST2 | Carbohydrate sulfotransferase 2 | ENSG00000175040 | ENST00000309575 | ENSP00000307911 | 557 |
| RM12 | RecQ-mediated genome instability protein 2 | ENSG00000175643 | ENST00000572173 | ENSP00000461206 | 558 |
| SLC35E3 | Solute carrier family 35 member E3 | ENSG00000175782 | ENST00000398004<br>ENST00000431174 | ENSP00000381089<br>ENSP00000403769 | 559<br>560 |
| ZBTB38 | Zinc finger and BTB domain-containing protein 38 | ENSG00000177311 | ENST00000503809 | ENSP00000422051 | 561 |
| YIPF6 | Protein YIPF6 | ENSG00000181704 | ENST00000374622<br>ENST00000451537<br>ENST00000462683 | ENSP00000363751<br>ENSP00000401799<br>ENSP00000417573 | 562<br>563<br>564 |

TABLE VI-continued

| Gene name | Description | ENSG ID release87 | ENST ID | ENSP ID | SEQ ID No of the aa sequence of the protein isoform |
|---|---|---|---|---|---|
| CREB3L2 | Cyclic AMP-responsive element-binding protein 3-like protein 2 | ENSG00000182158 | ENST00000330387 | ENSP00000329140 | 565 |
| | | | ENST00000420629 | ENSP00000402889 | 566 |
| | | | ENST00000456390 | ENSP00000403550 | 567 |
| XKRX | XK-related protein 2 | ENSG00000182489 | ENST00000372956 | ENSP00000362047 | 568 |
| | | | ENST00000468904 | ENSP00000419884 | 569 |
| CADM1 | Cell adhesion molecule 1 | ENSG00000182985 | ENST00000331581 | ENSP00000329797 | 570 |
| | | | ENST00000452722 | ENSP00000395359 | 571 |
| | | | ENST00000536727 | ENSP00000440322 | 572 |
| | | | ENST00000537058 | ENSP00000439817 | 573 |
| | | | ENST00000540951 | ENSP00000445375 | 574 |
| | | | ENST00000542447 | ENSP00000439176 | 575 |
| | | | ENST00000542450 | ENSP00000442001 | 576 |
| | | | ENST00000543540 | ENSP00000439847 | 577 |
| | | | ENST00000545380 | ENSP00000442387 | 578 |
| | | | ENST00000612235 | ENSP00000483648 | 579 |
| | | | ENST00000612471 | ENSP00000483793 | 580 |
| | | | ENST00000616271 | ENSP00000484516 | 581 |
| | | | ENST00000621043 | ENSP00000482840 | 582 |
| | | | ENST00000621709 | ENSP00000482924 | 583 |
| LHFP | Lipoma HMGIC fusion partner | ENSG00000183722 | ENST00000379589 | ENSP00000368908 | 584 |
| CSF1 | Macrophage colony-stimulating factor 1 | ENSG00000184371 | ENST00000329608 | ENSP00000327513 | 585 |
| | | | ENST00000357302 | ENSP00000349854 | 586 |
| | | | ENST00000369801 | ENSP00000358816 | 587 |
| | | | ENST00000369802 | ENSP00000358817 | 588 |
| | | | ENST00000420111 | ENSP00000407317 | 589 |
| | | | ENST00000488198 | ENSP00000433837 | 590 |
| | | | ENST00000525659 | ENSP00000431547 | 591 |
| | | | ENST00000527192 | ENSP00000434527 | 592 |
| PTP4A3 | Protein tyrosine phosphatase type IVA 3 | ENSG00000184489 | ENST00000329397 | ENSP00000332274 | 593 |
| | | | ENST00000349124 | ENSP00000331730 | 594 |
| | | | ENST00000520105 | ENSP00000428758 | 595 |
| | | | ENST00000521578 | ENSP00000428976 | 596 |
| | | | ENST00000523147 | ENSP00000428725 | 597 |
| | | | ENST00000524028 | ENSP00000430332 | 598 |
| OSBP2 | Oxysterol-binding protein 2 | ENSG00000184792 | ENST00000445781 | ENSP00000411497 | 599 |
| METTL7A | Methyltransferase-like protein 7A | ENSG00000185432 | ENST00000332160 | ENSP00000331787 | 600 |
| | | | ENST00000547104 | ENSP00000447542 | 601 |
| | | | ENST00000548553 | ENSP00000448785 | 602 |
| | | | ENST00000550097 | ENSP00000448286 | 603 |
| | | | ENST00000550502 | ENSP00000450239 | 604 |
| TMPRSS6 | Transmembrane protease serine 6 | ENSG00000187045 | ENST00000346753 | ENSP00000334962 | 605 |
| | | | ENST00000381792 | ENSP00000371211 | 606 |
| | | | ENST00000406725 | ENSP00000385453 | 607 |
| | | | ENST00000406856 | ENSP00000384964 | 608 |
| | | | ENST00000423761 | ENSP00000400317 | 609 |
| | | | ENST00000429068 | ENSP00000392433 | 610 |
| | | | ENST00000442782 | ENSP00000397691 | 611 |
| GCNT1 | Beta-1,3-galactosyl-O-glycosyl-glycoprotein beta-1,6-N-acetylglucosaminyltransferase | ENSG00000187210 | ENST00000376730 | ENSP00000365920 | 612 |
| | | | ENST00000442371 | ENSP00000415454 | 613 |
| | | | ENST00000444201 | ENSP00000390703 | 614 |
| MAGEH1 | Melanoma-associated antigen H1 | ENSG00000187601 | ENST00000342972 | ENSP00000343706 | 615 |
| NEMP2 | Nuclear envelope integral membrane protein 2 | ENSG00000189362 | ENST00000343105 | ENSP00000340087 | 616 |
| | | | ENST00000409150 | ENSP00000386292 | 617 |
| | | | ENST00000414176 | ENSP00000404283 | 618 |
| | | | ENST00000421038 | ENSP00000410306 | 619 |
| | | | ENST00000444545 | ENSP00000403867 | 620 |
| NTNG2 | Netrin-G2 | ENSG00000196358 | ENST00000372179 | ENSP00000361252 | 621 |
| | | | ENST00000393229 | ENSP00000376921 | 622 |
| PDGFA | Platelet-derived growth factor subunit A | ENSG00000197461 | ENST00000354513 | ENSP00000346508 | 623 |
| | | | ENST00000400761 | ENSP00000383572 | 624 |
| | | | ENST00000402802 | ENSP00000383889 | 625 |
| | | | ENST00000405692 | ENSP00000384673 | 626 |
| PDCD1LG2 | Programmed cell death 1 ligand 2 | ENSG00000197646 | ENST00000397747 | ENSP00000380855 | 627 |
| TOR4A | Torsin-4A | ENSG00000198113 | ENST00000357503 | ENSP00000350102 | 628 |
| HIBCH | 3-hydroxyisobutyryl-CoA hydrolase, mitochondrial | ENSG00000198130 | ENST00000392333 | ENSP00000376145 | 629 |
| | | | ENST00000414928 | ENSP00000414820 | 630 |

TABLE VI-continued

| Gene name | Description | ENSG ID release87 | ENST ID | ENSP ID | SEQ ID No of the aa sequence of the protein isoform |
|---|---|---|---|---|---|
| NTRK1 | High affinity nerve growth factor receptor | ENSG00000198400 | ENST00000358660 | ENSP00000351486 | 631 |
| | | | ENST00000368196 | ENSP00000357179 | 632 |
| | | | ENST00000392302 | ENSP00000376120 | 633 |
| | | | ENST00000497019 | ENSP00000436804 | 634 |
| | | | ENST00000524377 | ENSP00000431418 | 635 |
| FAM19A2 | Protein FAM19A2 | ENSG00000198673 | ENST00000416284 | ENSP00000393987 | 636 |
| | | | ENST00000548780 | ENSP00000449310 | 637 |
| | | | ENST00000549379 | ENSP00000447584 | 638 |
| | | | ENST00000549958 | ENSP00000447280 | 639 |
| | | | ENST00000550003 | ENSP00000449457 | 640 |
| | | | ENST00000551449 | ENSP00000449632 | 641 |
| | | | ENST00000551619 | ENSP00000447305 | 642 |
| | | | ENST00000552075 | ENSP00000449516 | 643 |
| F5 | Coagulation factor V | ENSG00000198734 | ENST00000367796 | ENSP00000356770 | 644 |
| | | | ENST00000367797 | ENSP00000356771 | 645 |
| GK | Glycerol kinase | ENSG00000198814 | ENST00000378943 | ENSP00000368226 | 646 |
| | | | ENST00000427190 | ENSP00000401720 | 647 |
| | | | ENST00000488296 | ENSP00000419771 | 648 |
| INPP5F | Phosphatidylinositide phosphatase SAC2 | ENSG00000198825 | ENST00000490818 | ENSP00000487706 | 649 |
| | | | ENST00000631572 | ENSP00000488726 | 650 |
| CD177 | CD177 antigen | ENSG00000204936 | ENST00000378012 | ENSP00000367251 | 651 |
| | | | ENST00000607855 | ENSP00000483817 | 652 |
| | | | ENST00000618265 | ENSP00000479536 | 653 |
| LEPROT | Leptin Receptor Overlapping Transcrip | ENSG00000213625 | ENST00000371065 | ENSP00000360104 | 654 |
| | | | ENST00000613538 | ENSP00000483521 | 655 |
| TRIM16 | Tripartite motif-containing protein 16 | ENSG00000221926 | ENST00000579219 | ENSP00000463639 | 656 |
| LTA | Lymphotoxin-alpha | ENSG00000226979 | ENST00000418386 | ENSP00000413450 | 657 |
| | | | ENST00000454783 | ENSP00000403495 | 658 |
| PROB1 | Proline-rich basic protein 1 | ENSG00000228672 | ENST00000434752 | ENSP00000416033 | 659 |
| SSTR3 | Somatostatin receptor type 3 | ENSG00000278195 | ENST00000610913 | ENSP00000480971 | 660 |
| | | | ENST00000617123 | ENSP00000481325 | 661 |
| CEACAM1 | Carcinoembryonic antigen-related cell adhesion molecule 1 | ENSG00000079385 | ENST00000161559 | ENSP00000161559 | 662 |
| | | | ENST00000352591 | ENSP00000244291 | 663 |
| | | | ENST00000358394 | ENSP00000351165 | 664 |
| | | | ENST00000403444 | ENSP00000384709 | 665 |
| | | | ENST00000403461 | ENSP00000384083 | 666 |
| | | | ENST00000471298 | ENSP00000472633 | 667 |
| | | | ENST00000599389 | ENSP00000471918 | 668 |
| | | | ENST00000600172 | ENSP00000471566 | 669 |
| CTLA4 | Cytotoxic T-lymphocyte protein 4 | ENSG00000163599 | ENST00000295854 | ENSP00000295854 | 670 |
| | | | ENST00000302823 | ENSP00000303939 | 671 |
| | | | ENST00000427473 | ENSP00000409707 | 672 |
| | | | ENST00000472206 | ENSP00000417779 | 673 |
| TIGIT | T-cell immunoreceptor with Ig and ITIM domains | ENSG00000181847 | ENST00000383671 | ENSP00000373167 | 674 |
| | | | ENST00000461158 | ENSP00000418917 | 675 |
| | | | ENST00000481065 | ENSP00000420552 | 676 |
| | | | ENST00000484319 | ENSP00000419706 | 677 |
| | | | ENST00000486257 | ENSP00000419085 | 678 |
| IL2RA | Interleukin-2 receptor subunit alpha | ENSG00000134460 | ENST00000256876 | ENSP00000256876 | 679 |
| | | | ENST00000379954 | ENSP00000369287 | 680 |
| | | | ENST00000379959 | ENSP00000369293 | 681 |
| ENTPD1 | Ectonucleoside triphosphate diphosphohydrolase 1 | ENSG00000138185 | ENST00000371205 | ENSP00000360248 | 682 |
| | | | ENST00000371207 | ENSP00000360250 | 683 |
| | | | ENST00000453258 | ENSP00000390955 | 684 |
| | | | ENST00000483213 | ENSP00000489333 | 685 |
| | | | ENST00000543964 | ENSP00000442968 | 686 |
| | | | ENST00000635076 | ENSP00000489250 | 687 |
| ICOS | Inducible T-cell costimulator | ENSG00000163600 | ENST00000316386 | ENSP00000319476 | 688 |
| | | | ENST00000435193 | ENSP00000415951 | 689 |
| TNFRSF4 | Tumor necrosis factor receptor superfamily member 4 | ENSG00000186827 | ENST00000379236 | ENSP00000368538 | 690 |
| TNFRSF18 | Tumor necrosis factor receptor superfamily member 18 | ENSG00000186891 | ENST00000328596 | ENSP00000328207 | 691 |
| | | | ENST00000379265 | ENSP00000368567 | 692 |
| | | | ENST00000379268 | ENSP00000368570 | 693 |
| | | | ENST00000486728 | ENSP00000462735 | 694 |
| TNFRSF8 | Tumor necrosis factor receptor superfamily member 8 | ENSG00000120949 | ENST00000263932 | ENSP00000263932 | 695 |
| | | | ENST00000417814 | ENSP00000390650 | 696 |
| | | | ENST00000514649 | ENSP00000421938 | 697 |
| CD274 | Programmed cell death 1 ligand 1 | ENSG00000120217 | ENST00000381573 | ENSP00000370985 | 698 |
| | | | ENST00000381577 | ENSP00000370989 | 699 |

TABLE VI-continued

| Gene name | Description | ENSG ID release87 | ENST ID | ENSP ID | SEQ ID No of the aa sequence of the protein isoform |
|---|---|---|---|---|---|
| IL2RB | Interleukin-2 receptor subunit beta | ENSG00000100385 | ENST00000216223 | ENSP00000216223 | 700 |
| | | | ENST00000429622 | ENSP00000402685 | 701 |
| | | | ENST00000445595 | ENSP00000401020 | 702 |
| | | | ENST00000453962 | ENSP00000403731 | 703 |
| TNFRSF9 | Tumor necrosis factor receptor superfamily member 9 | ENSG00000049249 | ENST00000377507 | ENSP00000366729 | 704 |
| | | | ENST00000474475 | ENSP00000465272 | 705 |
| | | | ENST00000615230 | ENSP00000478699 | 706 |
| IKZF2 | Zinc finger protein Helios | ENSG00000030419 | ENST00000442445 | ENSP00000390045 | 707 |

Genes of table VI are characterized by their Ensembl Gene accession number (ENSG), retrievable in the public database EnsEMBL (http://www.ensembl.org). Each related protein isoform is characterized by an Ensembl transcript accession number (ENST) and an Ensembl protein accession number (ENSP).

Identification of Transcript Isoforms Expressed by Tumor-Treg Cells

An important aspect to be verified in the selection of potential targets of tumor-T reg is that the protein isoforms predicted to be surface exposed/membrane associated by the cell localization algorithms are indeed expressed in tumor Treg cells. Thus, total RNA was extracted from tumor Treg cells isolated from NSCLC or CRC samples and subjected to RT-PCR using specific primer pairs able to discriminate the different isoforms annotated for each gene. Exemplificative results of protein isoforms predicted to be surface exposed and detected in tumor T reg cells is reported in Table VII. Moreover, an example of RT-PCR analysis carried out for SIRPG is reported in FIG. 10.

TABLE VII

Representative examples of transcripts detected in tumor-infiltrating Treg cells

| GENE SYMBOL | Surface predicted isoform detected in Tumor Treg cells |
|---|---|
| CCR8 | ENST00000326306 |
| LAYN | ENST00000375614 and/or ENST00000533265 and/or ENST00000375615 and/or ENST00000525126 |
| CD7 | ENST00000312648 and/or ENST00000584284 |
| CXCL13 | ENST00000286758 |
| FCRL3 | ENST00000492769 and/or ENST00000368184 and/or ENST00000368186 and/or ENST00000485028 |
| IL1R2 | ENST00000332549 and/or ENST00000393414 |
| IL21R | ENST00000337929 and/or ENST00000395754 and/or ENST00000564089 |
| NTNG2 | ENST00000393229 |
| SIRPG | ENST00000303415 and/or ENST00000216927 and/or ENST00000344103 and/or ENST00000381580 and/or ENST00000381583 |
| TSPAN5 | ENST00000305798 and/or ENST00000505184 |
| TMPRSS3 | ENST00000291532 |
| TMPRSS6 | ENST00000406725 and/or ENST00000406856 |
| NDFIP2 | ENST00000218652 |

DISCUSSION

Diversity of tumor infiltrating Treg cells should be fully elucidated to understand their functional relevance and prognostic significance in different types of cancer, and to possibly improve the therapeutic efficacy of Treg cell modulation through the selective depletion of tumor infiltrating Treg cells. The transcriptome analysis performed on CRC- and NSCLC-infiltrating T cells showed that tumor-infiltrating Treg cells are different from both circulating and normal tissue-infiltrating Tregs, suggesting that the tumor microenvironment influences specific gene expression in Treg cells. Our findings further support the view that Treg cells from different tissues are instructed by environmental factors to display different gene expression profiles (Panduro et al., 2016). Indeed the list of signature genes includes a number of molecules that are consistently upregulated in tumor infiltrating Treg cells isolated from different tumor types, and these signature genes would have not been identified if the inventors had not profiled specifically tumor infiltrating Treg cells. It was found tumor-infiltrating-Treg signature genes are not only largely shared between CRC and NSCLC infiltrating cells, but are also conserved in breast and gastric cancers as well as in CRC and NSCLC metastatic tumors (in liver and brain respectively) suggesting that expression of these genes is a common feature of tumor infiltrating Treg cells that may correlate with Treg cells specific function within the tumor microenvironment. Although our knowledge on the function of immune checkpoints on lymphocytes is still incomplete, agonist or antagonist monoclonal antibodies targeting checkpoints are in clinical development. Interestingly, it has been found that some of these checkpoints (such as GITR, OX40, TIGIT, LAG-3 and TIM-3) and some of their ligands (such as OX40LG, Galectin-9, CD70) are upregulated also in tumor infiltrating Treg cells, and this fact should be taken into account in interpreting clinical results with checkpoint inhibitors. Indeed, it is likely that assessment of the expression of checkpoints and of their ligands on the various subsets of tumor infiltrating lymphocytes will help to elucidate conflicting results and provide the rationale for combination therapies.

Therefore, expression pattern of checkpoints should be evaluated both in tumor infiltrating lymphocytes and in tumor cells. Single-cell analysis on selected tumor Treg signature genes confirmed the whole transcriptomic data and provided information on the expression frequency of these genes. Tumor infiltrating Treg cells express with high frequency genes that are associated with increased suppressor activity, such as the well characterized OX40, CTLA4 and GITR. Moreover, there are a number of interesting and less expected genes the specific expression of which was validated also at the protein level. For example, IL-1R2 upregulation could be another mechanism that tumor resident Treg cells employ to dampen anti-tumor immune responses through the neutralization of IL-1β function on effector cells. PD-L1 and PD-L2 expression has been recently reported on activated T cells or APCs (Boussiotis et al., 2014; Lesterhuis et al., 2011; Messal et al., 2011) but, to the best of our knowledge, neither PD-L2 nor PD-L1 expression has ever been reported in Treg cells, and our finding that they are overexpressed in tumor infiltrating Treg cells adds an additional level of complexity to the PD1/PD-Ls immunomodulatory axis within the tumor microenvironment. BATF is a transcription factor that has been mainly associated to Th17 development and $CD8^+$ T cells differentiation (Murphy et al., 2013). Our findings show that BATF transcript is upregulated in tumor infiltrating Treg cells more than in tumor infiltrating Th17 cells (FIG. 8). Interestingly, expression of BATF in $CD8^+$ T cells is induced by IL-21 (Xin et al., 2015), and it was found that IL21R is highly expressed in tumor-infiltrating Treg cells (FIG. 4).

It was showed that tumor infiltrating Treg cells express high amounts of 4-1 BB (CD137) a marker of TcR mediated activation (Schoenbrunn et al., 2012) and have shown they display very high suppressor function on effector T cell proliferation. It could be that expression of the signature genes correlated with the enhanced suppressive ability and so contributed to the establishment of a strong immunosuppressive environment at tumor sites. A corollary to our findings would have that increased number of Treg cells in the tumor environment should associate with a worst clinical outcome. In fact, when LAYN, MAGEH1 and CCR8 (which represent three of the most enriched genes in tumor infiltrating Treg cells) are highly detected in whole tumor samples there is a significant worsening of the 5 years survival of both CRC and NSCLC patients. Although, the functional roles in Treg cells of LAYN, a transmembrane protein with homology to c-type lectin (Borowsky and Hynes, 1998), and of MAGEH1, a member of the Melanoma Antigen Gene family (Weon and Potts, 2015) are unknown, the high expression of the chemokine receptor CCR8 is instead intriguing. Indeed CCL18, the ligand of CCR8 (Islam et al., 2013), is highly expressed in different tumors including NSCLC (Chen et al., 2011; Schutyser et al., 2005). The high specificity of CCR8 expression on tumor infiltrating Treg cells suggests it could be a new interesting therapeutic target to inhibit Treg cells trafficking to tumor sites, without disturbing recruitment of other effector T cells that do not express CCR8. Considerable efforts have been recently put in the development of sophisticated bioinformatics approaches that exploit lymphocyte gene expression data to understand the immune-modulatory networks at tumor sites, to predict clinical responses to immune-therapies, and to define novel therapeutic targets (Bindea et al., 2013a; Bindea et al., 2013b; Gentles et al., 2015). The data here presented represent the first comprehensive RNA-sequencing analysis performed on tumor-infiltrating human $CD4^+$ Treg, Th1 and Th17 cells. Our findings highlight the relevance of assessing gene expression patterns of lymphocyte at tumor-sites and suggest that generation of more transcriptomic data of tumor-infiltrating lymphocyte subsets purified from different cancer types may contribute to a better understanding of the dynamics underlying immune modulation in the tumor microenvironment. Moreover, our data represent a resource to generate and validate novel hypotheses that will increase our knowledge on tumor infiltrating Treg cell biology and should lead to the identification of new therapeutic targets.

REFERENCES

Arpaia, N., Green, J. A., Moltedo, B., Arvey, A., Hemmers, S., Yuan, S., Treuting, P. M., and Rudensky, A. Y. (2015). A Distinct Function of Regulatory T Cells in Tissue Protection. Cell 162, 1078-1089.

Bindea, G., Galon, J., and Mlecnik, B. (2013a). CluePedia Cytoscape plugin: pathway insights using integrated experimental and in silico data. Bioinformatics 29, 661-663.

Bindea, G., Mlecnik, B., Tosolini, M., Kirilovsky, A., Waldner, M., Obenauf, A. C., Angell, H., Fredriksen, T., Lafontaine, L., Berger, A., et al. (2013b). Spatiotemporal dynamics of intratumoral immune cells reveal the immune landscape in human cancer. Immunity 39, 782-795.

Bolger, A. M., Lohse, M., and Usadel, B. (2014). Trimmomatic: a flexible trimmer for Illumina sequence data. Bioinformatics 30, 2114-2120.

Borowsky, M. L., and Hynes, R. O. (1998). Layilin, a novel talin-binding transmembrane protein homologous with C-type lectins, is localized in membrane ruffles. J Cell Biol 143, 429-442.

Boussiotis, V. A., Chatterjee, P., and Li, L. (2014). Biochemical signaling of PD-1 on T cells and its functional implications. Cancer J 20, 265-271.

Burzyn, D., Kuswanto, W., Kolodin, D., Shadrach, J. L., Cerletti, M., Jang, Y., Sefik, E., Tan, T. G., Wagers, A. J., Benoist, C., et al. (2013). A special population of regulatory T cells potentiates muscle repair. Cell 155, 1282-1295.

Campbell, D. J., and Koch, M. A. (2011). Phenotypical and functional specialization of FOXP3+ regulatory T cells. Nat Rev Immunol 11, 119-130.

Carthon, B. C., Wolchok, J. D., Yuan, J., Kamat, A., Ng Tang, D. S., Sun, J., Ku, G., Troncoso, P., Logothetis, C. J., Allison, J. P., et al. (2010). Preoperative CTLA-4 blockade: tolerability and immune monitoring in the setting of a presurgical clinical trial. Clin Cancer Res 16, 2861-2871.

Chen, J., Yao, Y., Gong, C., Yu, F., Su, S., Chen, J., Liu, B., Deng, H., Wang, F., Lin, L., et al. (2011). CCL18 from tumor-associated macrophages promotes breast cancer metastasis via PITPNM3. Cancer Cell 19, 541-555.

Cipolletta, D., Feuerer, M., Li, A., Kamei, N., Lee, J., Shoelson, S. E., Benoist, C., and Mathis, D. (2012). PPAR-gamma is a major driver of the accumulation and phenotype of adipose tissue Treg cells. Nature 486, 549-553.

Duhen, T., Duhen, R., Lanzavecchia, A., Sallusto, F., and Campbell, D. J. (2012). Functionally distinct subsets of human FOXP3+ Treg cells that phenotypically mirror effector Th cells. Blood 119, 4430-4440.

Fridman, W. H., Pages, F., Sautes-Fridman, C., and Galon, J. (2012). The immune contexture in human tumours: impact on clinical outcome. Nat Rev Cancer 12, 298-306. Galluzzi, L., Buque, A., Kepp, O., Zitvogel, L., and Kroemer, G. (2015). Immunological Effects of Conventional Chemotherapy and Targeted Anticancer Agents. Cancer Cell 28, 690-714.

Geginat, J., Paroni, M., Maglie, S., Alfen, J. S., Kastirr, I., Gruarin, P., De Simone, M., Pagani, M., and Abrignani, S. (2014). Plasticity of human CD4 T cell subsets. Front Immunol 5, 630.

Gentles, A. J., Newman, A. M., Liu, C. L., Bratman, S. V., Feng, W., Kim, D., Nair, V. S., Xu, Y., Khuong, A., Hoang, C. D., et al. (2015). The prognostic landscape of genes and infiltrating immune cells across human cancers. Nat Med 21, 938-945.

Gonzalez-Pons, M., and Cruz-Correa, M. (2015). Colorectal Cancer Biomarkers: Where Are We Now? Biomed Res Int 2015, 149014.

Hodi, F. S., O'Day, S. J., McDermott, D. F., Weber, R. W., Sosman, J. A., Haanen, J. B., Gonzalez, R., Robert, C., Schadendorf, D., Hassel, J. C., et al. (2010). Improved survival with ipilimumab in patients with metastatic melanoma. N Engl J Med 363, 711-723.

Huang da, W., Sherman, B. T., and Lempicki, R. A. (2009). Systematic and integrative analysis of large gene lists using DAVID bioinformatics resources. Nat Protoc 4, 44-57.

Islam, S. A., Ling, M. F., Leung, J., Shreffler, W. G., and Luster, A. D. (2013). Identification of human CCR8 as a CCL18 receptor. J Exp Med 210, 1889-1898.

Jacobs, J., Smits, E., Lardon, F., Pauwels, P., and Deschoolmeester, V. (2015). Immune Checkpoint Modulation in Colorectal Cancer: What's New and What to Expect. J Immunol Res 2015, 158038.

Jamal-Hanjani, M., Thanopoulou, E., Peggs, K. S., Quezada, S. A., and Swanton, C. (2013). Tumour heterogeneity and immune-modulation. Curr Opin Pharmacol 13, 497-503.

Joller, N., Lozano, E., Burkett, P. R., Patel, B., Xiao, S., Zhu, C., Xia, J., Tan, T. G., Sefik, E., Yajnik, V., et al. (2014). Treg cells expressing the coinhibitory molecule TIGIT selectively inhibit proinflammatory Th1 and Th17 cell responses. Immunity 40, 569-581.

Josefowicz, S. Z., Lu, L. F., and Rudensky, A. Y. (2012). Regulatory T cells: mechanisms of differentiation and function. Annu Rev Immunol 30, 531-564.

Kharchenko, P. V., Silberstein, L., and Scadden, D. T. (2014). Bayesian approach to single-cell differential expression analysis. Nat Methods 11, 740-742.

Kroemer, G., Galluzzi, L., Zitvogel, L., and Fridman, W. H. (2015). Colorectal cancer: the first neoplasia found to be under immunosurveillance and the last one to respond to immunotherapy? Oncoimmunology 4, e1058597.

Le, D. T., Uram, J. N., Wang, H., Bartlett, B. R., Kemberling, H., Eyring, A. D., Skora, A. D., Luber, B. S., Azad, N. S., Laheru, D., et al. (2015). PD-1 Blockade in Tumors with Mismatch-Repair Deficiency. N Engl J Med 372, 2509-2520.

Lesterhuis, W. J., Steer, H., and Lake, R. A. (2011). PD-L2 is predominantly expressed by Th2 cells. Mol Immunol 49, 1-3.

Loffler-Wirth, H., Kalcher, M., and Binder, H. (2015). oposSOM: R-package for high-dimensional portraying of genome-wide expression landscapes on bioconductor. Bioinformatics 31, 3225-3227.

Marabelle, A., Kohrt, H., Sagiv-Barfi, I., Ajami, B., Axtell, R. C., Zhou, G., Rajapaksa, R., Green, M. R., Torchia, J., Brody, J., et al. (2013). Depleting tumor-specific Tregs at a single site eradicates disseminated tumors. J Clin Invest 123, 2447-2463.

Messal, N., Serriari, N. E., Pastor, S., Nunes, J. A., and Olive, D. (2011). PD-L2 is expressed on activated human T cells and regulates their function. Mol Immunol 48, 2214-2219.

Munn, D. H., and Bronte, V. (2015). Immune suppressive mechanisms in the tumor microenvironment. Curr Opin Immunol 39, 1-6.

Murphy, T. L., Tussiwand, R., and Murphy, K. M. (2013). Specificity through cooperation: BATF-IRF interactions control immune-regulatory networks. Nat Rev Immunol 13, 499-509.

Nishikawa, H., and Sakaguchi, S. (2010). Regulatory T cells in tumor immunity. Int J Cancer 127, 759-767.

Panduro, M., Benoist, C., and Mathis, D. (2016). Tissue Tregs. Annu Rev Immunol 34, 609-633.

Pardoll, D. M. (2012). The blockade of immune checkpoints in cancer immunotherapy. Nat Rev Cancer 12, 252-264.

Peggs, K. S., Quezada, S. A., Chambers, C. A., Korman, A. J., and Allison, J. P. (2009). Blockade of CTLA-4 on both effector and regulatory T cell compartments contributes to the antitumor activity of anti-CTLA-4 antibodies. J Exp Med 206, 1717-1725.

Ranzani, V., Rossetti, G., Panzeri, I., Arrigoni, A., Bonnal, R. J., Curti, S., Gruarin, P., Provasi, E., Sugliano, E., Marconi, M., et al. (2015). The long intergenic non-coding RNA landscape of human lymphocytes highlights the regulation of T cell differentiation by linc-MAF-4. Nature immunology 16, 318-325.

Ripley, B. D. (1996) Pattern Recognition and Neural Networks. Cambridge: Cambridge University Press. [i, 2, 8, 36, 42, 59, 69, 73, 79, 91, 92]

Sakaguchi, S., Yamaguchi, T., Nomura, T., and Ono, M. (2008). Regulatory T cells and immune tolerance. Cell 133, 775-787.

Sato, M., Larsen, J. E., Lee, W., Sun, H., Shames, D. S., Dalvi, M. P., Ramirez, R. D., Tang, H., DiMaio, J. M., Gao, B., et al. (2013). Human lung epithelial cells progressed to malignancy through specific oncogenic manipulations. Mol Cancer Res 11, 638-650.

Schoenbrunn, A., Frentsch, M., Kohler, S., Keye, J., Dooms, H., Moewes, B., Dong, J., Loddenkemper, C., Sieper, J., Wu, P., et al. (2012). A converse 4-1 BB and CD40 ligand expression pattern delineates activated regulatory T cells (Treg) and conventional T cells enabling direct isolation of alloantigen-reactive natural Foxp3+ Treg. J Immunol 189, 5985-5994.

Schutyser, E., Richmond, A., and Van Damme, J. (2005). Involvement of CC chemokine ligand 18 (CCL18) in normal and pathological processes. J Leukoc Biol 78, 14-26.

Selby, M. J., Engelhardt, J. J., Quigley, M., Henning, K. A., Chen, T., Srinivasan, M., and Korman, A. J. (2013). Anti-CTLA-4 antibodies of IgG2a isotype enhance antitumor activity through reduction of intratumoral regulatory T cells. Cancer Immunol Res 1, 32-42.

Sharma, P., and Allison, J. P. (2015). Immune checkpoint targeting in cancer therapy: toward combination strategies with curative potential. Cell 161, 205-214.

Simpson, T. R., Li, F., Montalvo-Ortiz, W., Sepulveda, M. A., Bergerhoff, K., Arce, F., Roddie, C., Henry, J. Y., Yagita, H., Wolchok, J. D., et al. (2013). Fc-dependent depletion of tumor-infiltrating regulatory T cells co-defines the efficacy of anti-CTLA-4 therapy against melanoma. J Exp Med 210, 1695-1710.

Sledzinska, A., Menger, L., Bergerhoff, K., Peggs, K. S., and Quezada, S. A. (2015). Negative immune checkpoints on T lymphocytes and their relevance to cancer immunotherapy. Mol Oncol.

Smith, J. J., Deane, N. G., Wu, F., Merchant, N. B., Zhang, B., Jiang, A., Lu, P., Johnson, J. C., Schmidt, C., Bailey, C. E., et al. (2010). Experimentally derived metastasis gene expression profile predicts recurrence and death in patients with colon cancer. Gastroenterology 138, 958-968.

Sobin, L. H., Gospodarowicz, M. K., Wittekind, C., International Union against Cancer., and ebrary Inc. (2009). TNM classification of malignant tumours (Chichester, West Sussex, UK; Hoboken, NJ: Wiley-Blackwell), pp. 100-105, 138-146, 7th edition Teng, M. W., Ngiow, S. F., von Scheidt, B., McLaughlin, N., Sparwasser, T., and Smyth, M. J. (2010). Conditional regulatory T-cell depletion releases adaptive immunity preventing carcinogenesis and suppressing established tumor growth. Cancer Res 70, 7800-7809.

Therneau T. 2013. *A package for survival analysis* in S. R package version 2.37-4.

Topalian, S. L., Drake, C. G., and Pardoll, D. M. (2015). Immune checkpoint blockade: a common denominator approach to cancer therapy. Cancer Cell 27, 450-461.

Torre, L. A., Bray, F., Siegel, R. L., Ferlay, J., Lortet-Tieulent, J., and Jemal, A. (2015). Global cancer statistics, 2012. CA Cancer J Clin 65, 87-108.

Twyman-Saint Victor, C., Rech, A. J., Maity, A., Rengan, R., Pauken, K. E., Stelekati, E., Benci, J. L., Xu, B., Dada, H., Odorizzi, P. M., et al. (2015). Radiation and dual checkpoint blockade activate non-redundant immune mechanisms in cancer. Nature 520, 373-377.

van den Eertwegh, A. J., Versluis, J., van den Berg, H. P., Santegoets, S. J., van Moorselaar, R. J., van der Sluis, T. M., Gall, H. E., Harding, T. C., Jooss, K., Lowy, I., et al. (2012). Combined immunotherapy with granulocyte-macrophage colony-stimulating factor-transduced allogeneic prostate cancer cells and ipilimumab in patients with metastatic castration-resistant prostate cancer: a phase 1 dose-escalation trial. Lancet Oncol 13, 509-517.

Voo, K. S., Boyer, L., Harline, M. L., Vien, L. T., Facchinetti, V., Arima, K., Kwak, L. W., and Liu, Y. J. (2013). Antibodies targeting human OX40 expand effector T cells and block inducible and natural regulatory T cell function. J Immunol 191, 3641-3650.

Walter, S., Weinschenk, T., Stenzl, A., Zdrojowy, R., Pluzanska, A., Szczylik, C., Staehler, M., Brugger, W., Dietrich, P. Y., Mendrzyk, R., et al. (2012). Multipeptide immune response to cancer vaccine IMA901 after single-dose cyclophosphamide associates with longer patient survival. Nat Med 18, 1254-1261.

Weon, J. L., and Potts, P. R. (2015). The MAGE protein family and cancer. Curr Opin Cell Biol 37, 1-8.

Wirth, H., von Bergen, M., and Binder, H. (2012). Mining SOM expression portraits: feature selection and integrating concepts of molecular function. BioData Min 5, 18.

Xin, G., Schauder, D. M., Lainez, B., Weinstein, J. S., Dai, Z., Chen, Y., Esplugues, E., Wen, R., Wang, D., Parish, I. A., et al. (2015). A Critical Role of IL-21-Induced BATF in Sustaining CD8-T-Cell-Mediated Chronic Viral Control. Cell Rep 13, 1118-1124.

Yang, J. C., Hughes, M., Kammula, U., Royal, R., Sherry, R. M., Topalian, S. L., Suri, K. B., Levy, C., Allen, T., Mavroukakis, S., et al. (2007). Ipilimumab (anti-CTLA4 antibody) causes regression of metastatic renal cell cancer associated with enteritis and hypophysitis. J Immunother 30, 825-830.

Zitvogel, L., Galluzzi, L., Smyth, M. J., and Kroemer, G. (2013). Mechanism of action of conventional and targeted anticancer therapies: reinstating immunosurveillance. Immunity 39, 74-88.

Sebastian Briesemeister, Jorg RahnenfUhrer, and Oliver Kohlbacher, (2010). Going from where to why—interpretable prediction of protein subcellular localization, Bioinformatics, 26(9):1232-1238.

Lukas Käll, Anders Krogh and Erik L. L. Sonnhammer. Advantages of combined transmembrane topology and signal peptide prediction—the Phobius web server. Nucleic Acids Res., 35:W429-32, July 2007

The invention claimed is:

1. A method for identifying an antibody acting as an anti-tumoral agent that depletes tumor-infiltrating regulatory T cells, comprising the steps of:
   a) assaying candidate antibodies for their binding specificity to LAYN;
   b) selecting antibodies having a specific binding activity to LAYN; and
   c) testing the binding antibodies in a cell system comprising tumor-infiltrating regulatory T cells for their ability to induce antibody-dependent cell-mediated cytotoxicity (ADCC) on the tumor-infiltrating regulatory T cells, thereby identifying an antibody that depletes tumor-infiltrating regulatory T cells.

* * * * *